(12) United States Patent  
Momose et al.

(10) Patent No.: US 7,368,578 B2
(45) Date of Patent: May 6, 2008

(54) FIVE-MEMBERED HETEROCYCLIC COMPOUNDS

(75) Inventors: Yu Momose, Osaka (JP); Nobuyuki Takakura, Osaka (JP); Tsuyoshi Maekawa, Osaka (JP); Hiroyuki Odaka, Osaka (JP); Hiroyuki Kimura, Osaka (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 267 days.

(21) Appl. No.: 10/527,426

(22) PCT Filed: Sep. 9, 2003

(86) PCT No.: PCT/JP03/11511

§ 371 (c)(1),
(2), (4) Date: Mar. 10, 2005

(87) PCT Pub. No.: WO2004/024705

PCT Pub. Date: Mar. 25, 2004

(65) Prior Publication Data

US 2006/0135578 A1   Jun. 22, 2006

(30) Foreign Application Priority Data

Sep. 10, 2002  (JP) .............................. 2002-264703

(51) Int. Cl.
C07D 263/02 (2006.01)
C07D 263/00 (2006.01)
C07D 263/30 (2006.01)
C07D 261/00 (2006.01)
C07D 261/04 (2006.01)
C07D 261/06 (2006.01)
A01N 43/76 (2006.01)
A01N 43/80 (2006.01)

(52) U.S. Cl. ...................... 548/235; 548/215; 548/225; 548/233; 548/243; 548/245; 548/247; 514/374; 514/376; 514/377; 514/378; 514/380

(58) Field of Classification Search ...................... None
See application file for complete search history.

(56) References Cited

U.S. PATENT DOCUMENTS 4,171,365 A   10/1979   Diana et al.
4,996,216 A    2/1991   Leyendecker et al.
6,214,842 B1   4/2001   Malamas et al.

FOREIGN PATENT DOCUMENTS

| GB | 2 110 211 A | 6/1983 |
|---|---|---|
| JP | 63159373 | 7/1988 |
| WO | WO J96/13264 | 5/1996 |
| WO | WO 00/64876 | 11/2000 |
| WO | WO 01/00603 A1 | 1/2001 |
| WO | WO 01/16111 A2 | 3/2001 |
| WO | WO 01/17994 A1 | 3/2001 |
| WO | WO 01/38325 A1 | 5/2001 |
| WO | WO 01-16111 A2 * | 8/2001 |
| WO | WO 02/053547 | 7/2002 |
| WO | WO 02/076959 A1 | 10/2002 |
| WO | WO 03/000685 | 1/2003 |
| WO | WO 03/015774 A1 | 2/2003 |

OTHER PUBLICATIONS http://dictionary.reference.com/browse/prophylaxis, p. 1 of 4.*
Rieusset et al., A New Selective Peroxisome Proliferator-Activated Receptor gamma Antagonist with Antiobesity and Antidiabetic Activity, abstract (pp. 1 and 2 of 6).*
He et al., Adipose-specific peroxisome proliferator-activated receptor (gamma) knockout causes insulin resistance in fat and liver but not in muscle, PNAS, vol. 100, No. 26, pp. 15712-15717.*
Ryan et al., PPAR gamma Agonist Rosiglitazone Improves Vascular Function and Lowers Blood Pressure in Hypertensive Transgenic Mice, abstract (pp. 1 and 2 of 4).*
Hung et al., Rosiglitazone improves insulin sensitivity and glucose tolerance in subjects with impaired glucose tolerance, abstract (pp. 1 and 2 of 3).*

(Continued)

*Primary Examiner*—Rebecca Anderson
*Assistant Examiner*—Sun Jae Y Loewe
(74) *Attorney, Agent, or Firm*—Finnegan, Henderson, Farabow, Garrett & Dunner, LLP

(57) ABSTRACT

The present invention provides a compound represented by the formula:

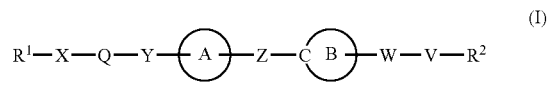

wherein $R^1$ is an optionally substituted 5-membered heterocyclic group; X, Y and V are the same or different and each is a bond, an oxygen atom, a sulfur atom and the like; Q is a divalent hydrocarbon group having 1 to 20 carbon atoms; ring A is an aromatic ring optionally further having 1 to 3 substituents; Z is —$(CH_2)_n$-$Z^1$- or -$Z^1$-$(CH_2)_n$— (n is an integer of 0 to 8, $Z^1$ is a bond, an oxygen atom, a sulfur atom and the like); ring B is a nitrogen-containing heterocycle optionally further having 1 to 3 substituents; W is a bond or a divalent hydrocarbon group having 1 to 20 carbon atoms; $R^2$ is a hydrogen atom, a cyano group, —$PO(OR^9)(OR^{10})$ ($R^9$ and $R^{10}$ are the same or different and each is a hydrogen atom or an optionally substituted hydrocarbon group, and $R^9$ and $R^{10}$ are optionally bonded to form an optionally substituted ring) and the like, or a salt thereof, which has a superior adipose tissue weight decreasing action, a hypoglycemic action and a hypolipidemic action, and which is useful as an agent for the prophylaxis or treatment of obesity, diabetes mellitus, hyperlipidemia, impaired glucose tolerance, hypertension and the like.

12 Claims, No Drawings

OTHER PUBLICATIONS http://diabetes.webmd.com/guide/preventing-type-2-diabetes, pp. 1-2 of 2.*
http://diabetes.webmd.com/tc/Prediabetes-Topic-Overview, p. 2 and 3 of 3.*
http://diabetes.webmd.com/guide/insulin-resistance-syndrome, p. 1 of 1.*
http://www.webmd.com/diet/tc/Obesity-Overview, p. 1-3-2 of 3.*
http://www.webmd.com/hypertension-high-blood-pressure/guide/preventing-high-blood-pressure?page=2, pp. 1-2 of 2.*
http://jcem.endojournals.org/cgi/content/full/90/3/0, pp. 1-4 of 4.*
Farmer et al., "Aza-retinoids as novel retinoid x receptor specific agonists", bioorganic&medicinal chemistry letters, 16, 2006, 2352-2356.*
Rieusset et al, "A new selective peroxisome proliferator-activated receptor antagonist with antiobesity and antidiabetic activity", molecular endocrinology 16 (11), 2628-2644, abstract (2 pages).*
http://www.healthatoz.com/healthatoz/Atoz/common/standard/transform.jsp?requestURI=/healthatoz/Atoz/dc/cen/card/hypr/hypertreat.jsp.*
http://www.medicinenet.com/diabetes_treatment/article.htm.*
http://www.webmd.com/diet/tc/Obesity-Overview.*
Rieusset et al., "A New Selective Peroxisome Proliferator-Activated Receptor g Antagonist with Antiobesity and antidiabetic Activity", Mol. Endocrinology, 16, 11, 2628-2644.*
E. Winkelmann, et al., "Chemotherapeutically Active Nitro Compounds", Arzneim-Forsch./Drug Res. 28(I), Heft 5, (1978), pp. 739-749.
E. Winkelmann, et al., "Chemotherapeutically Active Nitro Compounds", Arzneim-Forsch./Drug Res. 28(I), Heft 3, (1978), pp. 351-366.
Yu Momose, et al., "Novel 5-Substituted-1H-tetrazole Derivatives as Potent Glucose and Lipid Lowering Agents", Chem. Pharm. Bull., (2002), pp. 100-111, vol. 50, No. 1.
John J. Baldwin, et al., "Beta 1-Selective Adrenoceptor Antagonists: Examples of the 2-[4-[3-(Substituted amino)-2-hydroxypropoxy]phenyl]imidazole Class. 2", Journal of Medicinal Chemistry, (1986), pp. j1065-j1080, vol. 29, No. 6.
Yu Momose, et al., "Novel 5-Substituted 2,4-Thiazolidinedione and 2,4-Oxazolidinedione Derivatives as Insuline Sensitizers with Antidiabetic Activities", J. Med. chem., (2002), pp. 1518-1534, vol. 45, No. 7.

* cited by examiner

FIVE-MEMBERED HETEROCYCLIC COMPOUNDS

This application is the National Phase filing of International Patent Application No. PCT/JP2003/011511, filed Sep. 9, 2003.

TECHNICAL FIELD

The present invention relates to a novel 5-membered heterocyclic compound having a superior adipose tissue weight decreasing action, a superior hypoglycemic action and a superior hypolipidemic action, which is useful as an agent for the prophylaxis or treatment of obesity, diabetes mellitus, hyperlipidemia, impaired glucose tolerance, hypertension and the like.

BACKGROUND ART

As a heterocyclic compound, the following compounds are known.

(1) As a PPAR ligand-receptor binder, a compound represented by the formula:

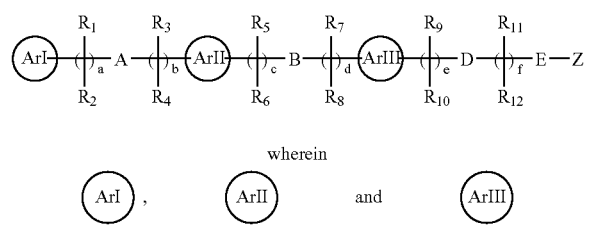

wherein

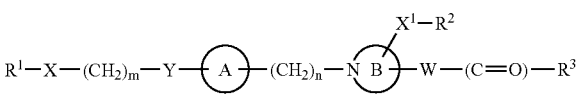

are each independently an aryl and the like; A is —O— and the like; B is —O— and the like; D is —O— and the like; E is a bond or an ethylene group; a, b, c and e are each 0-4; d is 0-5; f is 0-6; $R_1$, $R_3$, $R_5$, $R_7$, $R_9$ and $R_{11}$ are each independently a hydrogen and the like; $R_2$, $R_4$, $R_6$, $R_8$, $R_{10}$ and $R_{12}$ are each independently —(CH)$_q$—X; q is 0-3; X is hydrogen and the like; Z is $R_{21}O_2C$— and the like; $R_{21}$ is hydrogen and the like has been reported (WO 00/64876).

(2) As a compound that acts by binding to PPAR-α, PPAR-γ and PPAR-δ, a compound represented by the formula

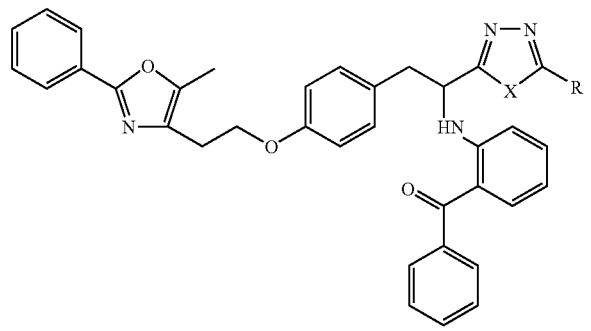

wherein X is O, S or NH and R is methyl, ethyl, n-propyl, i-propyl, cyclopropyl, n-butyl, phenyl or —CH$_2$OCH$_3$, and a compound represented by the formula

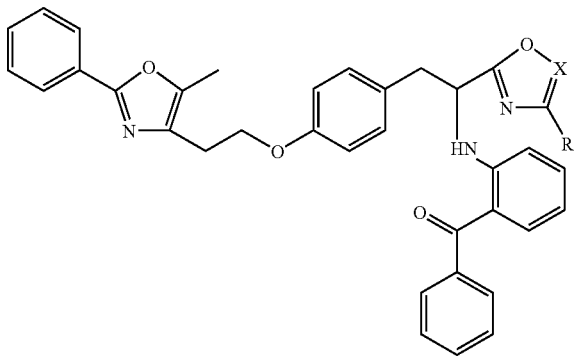

wherein X is C or N and R is methyl, ethyl, n-propyl, i-propyl, —CH$_2$OCH$_3$ or —CO$_2$CH$_3$ have been reported (WO01/17994).

(3) As a retinoid related receptor function regulator, a compound represented by the formula (I)

$$R^1-X-(CH_2)_m-Y-\boxed{A}-(CH_2)_n-N\boxed{B}^{X^1-R^2}-W-(C=O)-R^3$$

wherein $R^1$ is an optionally substituted hydrocarbon group or an optionally substituted heterocyclic group; X is a bond, O, S, —CO—, —CS—, —CR$^4$(OR$^5$)— or —NR$^6$— (R$^4$ and R$^6$ are each a hydrogen atom or an optionally substituted hydrocarbon group and R$^5$ is a hydrogen atom or a hydroxyl-protecting group); m is 0-3; Y is O, S, —SO—, —SO$_2$—, —NR$^7$—, —CONR$^7$— or —NR$^7$CO— (R$^7$ is a hydrogen atom or an optionally substituted hydrocarbon group); ring A is an aromatic ring optionally further have 1 to 3 substituents; n is 1-8; ring B is a nitrogen-containing 5-membered heterocycle optionally further substituted by an alkyl group; X$^1$ is a bond, O, S, —SO—, —SO$_2$—, —O—SO$_2$— or —NR$^{16}$— (R$^{16}$ is a hydrogen atom or an optionally substituted hydrocarbon group); R$^2$ is a hydrogen atom, an optionally substituted hydrocarbon group or an optionally substituted heterocyclic group; W is a bond or a C$_{1-20}$ divalent hydrocarbon residue; and R$^3$ is —OR$^8$ (R$^8$ is a hydrogen atom or an optionally substituted hydrocarbon group) or —NR$^9$R$^{10}$ (R$^9$ and R$^{10}$ are the same or different and each is a hydrogen atom, an optionally substituted hydrocarbon group, an optionally substituted heterocyclic group or an optionally substituted acyl group, or R$^9$ and R$^{10}$ are bonded to each other to form a ring) has been reported (WO01/38325).

(4) As a retinoid related receptor function regulator, a compound represented by the formula (I)

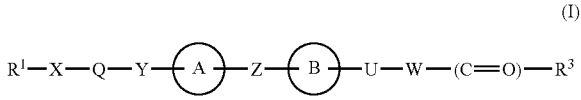

wherein $R^1$ is an optionally substituted 5-membered aromatic heterocyclic group;

X is a bond, an oxygen atom, a sulfur atom, —CO—, —CS—, —CR$^4$(OR$^5$)— or —NR$^6$— (R$^4$ is a hydrogen atom or an optionally substituted hydrocarbon group, R$^5$ is a hydrogen atom or a hydroxyl-protecting group, R$^6$ is a hydrogen atom, an optionally substituted hydrocarbon group or an amino-protecting group);

Q is a divalent hydrocarbon group having 1 to 20 carbon atoms;

Y is a bond, an oxygen atom, a sulfur atom, —SO—, —SO$_2$—, —NR$^7$—, —CONR$^7$— or —NR$^7$CO— (R$^7$ is a hydrogen atom, an optionally substituted hydrocarbon group or an amino-protecting group);

ring A is an aromatic ring optionally further having 1 to 3 substituents;

Z is —(CH$_2$)$_n$-Z$^1$- or -Z$^1$-(CH$_2$)$_n$— (n is an integer of 1 to 8, Z$^1$ is an oxygen atom, a sulfur atom, —SO—, —SO$_2$— or —NR$^{16}$— (R$^{16}$ is a hydrogen atom or an optionally substituted hydrocarbon group));

ring B is a pyridine ring, benzene ring or naphthalene ring, each optionally further having 1 to 3 substituents;

U is a bond, an oxygen atom, a sulfur atom, —SO— or —SO$_2$—;

W is a divalent hydrocarbon group having 1 to 20 carbon atoms; and

R$^3$ is —OR$^8$ (R$^8$ is a hydrogen atom or an optionally substituted hydrocarbon group) or —NR$^9$R$^{10}$ (R$^9$ and R$^{10}$ are the same or different and each is a hydrogen atom, an optionally substituted hydrocarbon group, an optionally substituted heterocyclic group, or an optionally substituted acyl group, or R$^9$ and R$^{10}$ are optionally bonded to form an optionally substituted ring):

provided that, when ring B is a benzene ring optionally further having 1 to 3 substituents, U is a bond has been reported (WO02/53547).

Peroxisome proliferator-activated receptor gamma (PPARγ), a member of the intranuclear hormone receptor superfamily, which is typically exemplified by steroid hormone receptors and thyroid hormone receptors, plays an important role as a master regulator in the differentiation of adipocytes with its expression induced in the very early stage of adipocyte differentiation. PPARγ forms a dimer with the retinoid X receptor (RXR) by binding to a ligand, and binds to a responsive site of the target gene in the nucleus to directly control (activate) transcription efficiency. In recent years, the possibility that 15-deoxy-Δ$^{12.14}$ prostaglandin J$_2$, which is a metabolite of prostaglandin D$_2$, serves as an endogenous ligand for PPARγ, has been suggested, and it has been shown that a class of insulin resistance enhancers, typically exemplified by thiazolidinedione derivatives, possess ligand activity for PPARγ, and that its potency is proportional to its hypoglycemic action or adipocyte differentiation-promoting action (e.g., Cell, vol. 83, p. 803 (1995): The Journal of Biological Chemistry, vol. 270, p. 12953 (1995); Journal of Medicinal Chemistry, vol. 39, p. 655 (1996)).

In recent years, furthermore, it has been shown that 1) PPARγ is expressed in cultured cells of human liposarcoma origin, whose proliferation is ceased by the addition of a PPARγ ligand (Proceedings of the National Academy of Sciences of The United States of America, vol. 94, p. 237 (1997)), 2) nonsteroidal anti-inflammatory drugs, typically exemplified by indomethacin and fenoprofen, have PPARγ ligand activity (e.g., The Journal of Biological Chemistry, vol. 272, p. 3406 (1997)), 3) PPARγ is expressed at high levels in activated macrophages, with the transcription of a gene involved in inflammation inhibited by the addition of a ligand therefor (e.g., Nature, vol. 391, p. 79 (1998)), 4) PPARγ ligands suppress the production of inflammatory cytokines (TNFα, IL-1β, IL-6) by monocytes (e.g., Nature, vol. 391, p. 82 (1998)), 5) adipocyte hypertrophy, fat accumulation and expression of insulin resistance are suppressed in PPARγ hetero deficient mouse (e.g., Molecular Cell (1999), vol. 4, p. 597), 6) PPARγ ligand inhibits differentiation of 10T1/2 cell into adipocyte by PPARγ agonist (e.g., Proceedings of The National Academy of Sciences of The United States of America (1999), vol. 96, p. 6102), 7) PPARγ ligand suppresses differentiation of 3T3-L1 cell into adipocyte by PPARγ agonist (e.g., Molecular Endocrinology (2000), vol. 14, p. 1425) and the like.

DISCLOSURE OF THE INVENTION

The development of a novel compound useful as an agent for the prophylaxis or treatment of obesity, diabetes mellitus, hyperlipidemia, impaired glucose tolerance, hypertension and the like and, having superior properties as a pharmaceutical agent, such as fewer side effects and the like, has been demanded.

Accordingly, the present invention relates to (1) a compound represented by the formula:

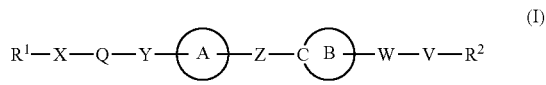

(I)

wherein

R$^1$ is an optionally substituted 5-membered heterocyclic group;

X, Y and V
are the same or different and each is a bond, an oxygen atom, a sulfur atom, —CO—, —CS—, —SO—, —SO$_2$—, —CR$^3$ (OR$^4$)—, —NR$^5$—, —CONR$^6$—, —NR$^6$CO—, —CSNR$^6$—, —NR$^6$CS— or —CONR$^6$NR$^7$— (R$^3$ is a hydrogen atom or an optionally substituted hydrocarbon group, R$^4$ is a hydrogen atom or a hydroxyl-protecting group, R$^5$ is a hydrogen atom, an optionally substituted hydrocarbon group or an amino-protecting group, and R$^6$ and R$^7$ are the same or different and each is a hydrogen atom or an optionally substituted hydrocarbon group);

Q is a divalent hydrocarbon group having 1 to 20 carbon atoms;

ring A is an aromatic ring optionally further having 1 to 3 substituents;

Z is —(CH$_2$)$_n$-Z$^1$- or -Z$^1$-(CH$_2$)$_n$— (n is an integer of 0 to 8 and Z$^1$ is a bond, an oxygen atom, a sulfur atom, —CO—, —CS—, —SO—, —SO$_2$—, —NR$^8$—, —CONR$^8$—, —NR$^8$CO—, —CSNR$^8$— or —NR$^8$CS— (R$^8$ is a hydrogen atom or an optionally substituted hydrocarbon group));

ring B is a nitrogen-containing heterocycle optionally further having 1 to 3 substituents;

W is a bond or a divalent hydrocarbon group having 1 to 20 carbon atoms; and

R$^2$ is a hydrogen atom, a cyano group, —PO(OR$^9$)(OR$^{10}$) (R$^9$ and R$^{10}$ are the same or different and each is a hydrogen atom or an optionally substituted hydrocarbon group, or R$^9$ and R$^{10}$ are optionally bonded to form an optionally substituted ring), —COR$^{11}$ [R$^{11}$ is a hydrogen atom, an optionally substituted hydrocarbon group, an optionally substituted heterocyclic group, —OR$^{12}$ (R$^{12}$ is a hydrogen atom or an optionally substituted hydrocarbon group) or —NR$^{13}$R$^{14}$ (R$^{13}$ and R$^{14}$ are the same or different and each is a hydrogen atom, an optionally substituted hydrocarbon group, an optionally substituted heterocyclic group, an optionally substituted acyl group or an optionally substituted hydroxy group, or R$^{13}$ and R$^{14}$ are optionally bonded to form an optionally substituted ring)], an optionally substituted hydrocarbon group, or an optionally substituted heterocyclic group, provided that 1) —W—V—R$^2$ is not "Wa-(C=O)—R$^a$ [Wa is a saturated divalent hydrocarbon group having 1 to 20 carbon atoms and R$^a$ is —OR$^b$ (R$^b$ is a hydrogen atom or an optionally substituted hydrocarbon group) or —NR$^c$R$^d$ (R$^c$ and R$^d$ are the same or different and each is a hydrogen atom, an optionally substituted hydrocarbon group, an optionally substituted heterocyclic group or an acyl group, and R$^c$ and R$^d$ are optionally bonded to form an optionally substituted ring together with the adjacent nitrogen atom)]",
2) ring A and ring B do not have a substituent represented by the formula: -Wa-(C=O)—R$^a$ (Wa and R$^a$ are as defined above),
3) ring B does not have, on a ring-constituting N atom, a substituent represented by the formula:

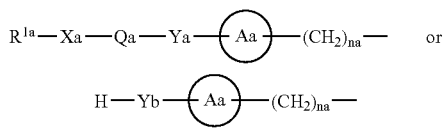

wherein
R$^{1a}$ is an optionally substituted hydrocarbon group or an optionally substituted heterocyclic group;
Xa and Ya
are the same or different and each is a bond, an oxygen atom, a sulfur atom, —CO—, —CS—, —SO—, —SO$_2$—, —CR$^{3a}$(OR$^{4a}$)—, —NR$^{5a}$—, —CONR$^{6a}$— or —NR$^{6a}$CO— (R$^{3a}$ is a hydrogen atom or an optionally substituted hydrocarbon group, R$^{4a}$ is a hydrogen atom or a hydroxyl-protecting group, R$^{5a}$ is a hydrogen atom, an optionally substituted hydrocarbon group or an amino-protecting group, R$^{6a}$ is a hydrogen atom or an optionally substituted hydrocarbon group);
Qa is a divalent hydrocarbon group having 1 to 20 carbon atoms;
ring Aa is an aromatic ring optionally further having 1 to 3 substituents;
na is an integer of 1 to 8; and
Yb is an oxygen atom, a sulfur atom or —NR$^{6a}$— (R$^{6a}$ is as defined above),
4) —X-Q-Y— is not —(CH$_2$)na- (na is an integer of 1 to 8),
5) when the nitrogen-containing heterocycle represented by ring B is a pyridine ring, the ring B does not have a further substituent, W is a divalent hydrocarbon group having 1 to 20 carbon atoms, V is a bond and R$^2$ is —PO(OR$^9$)(OR$^{10}$) or an optionally substituted heterocyclic group,
6) when R$^1$ has a substituent represented by the formula: -Wa-(C=O)—R$^a$ (Wa and R$^a$ are as defined above), W is a divalent hydrocarbon group having 1 to 20 carbon atoms, V is a bond and R$^2$ is —PO(OR$^9$)(OR$^{10}$) or an optionally substituted heterocyclic group, except 5-{2-[4-(5-methyl-2-phenyl-1,3-oxazol-4-yl)methoxyphenyl]ethyl}-4-methoxymethoxymethyl-2-phenyl-1,3-oxazole;
(5-{2-[4-(5-methyl-2-phenyl-1,3-oxazol-4-yl)methoxyphenyl]ethyl}-2-phenyl-1,3-oxazol-4-yl)methanol;
(5-{2-[4-(5-methyl-2-phenyl-1,3-oxazol-4-yl)methoxyphenyl]ethyl}-2-phenyl-1,3-oxazol-4-yl)acetonitrile;
ethyl 2-ethoxycarbonyl-3-(5-{2-[4-(5-methyl-2-phenyl-1,3-oxazol-4-yl)methoxyphenyl]ethyl}-2-phenyl-1,3-oxazol-4-yl)propionate;
methyl 3-(4-{[2-(2-furyl)-5-methyl-1,3-oxazol-4-yl-methoxy]-3-methoxybenzyl}oxy)-1-phenyl-1H-pyrazole-5-carboxylate;
[3-(4-{[2-(2-furyl)-5-methyl-1,3-oxazol-4-ylmethoxy]-3-methoxybenzyl}oxy)-1-phenyl-1H-pyrazol-5-yl]methanol;
3-(4-{[2-(2-furyl)-5-methyl-1,3-oxazol-4-ylmethoxy]-3-methoxybenzyl}oxy)-1-phenyl-1H-pyrazole-5-carbaldehyde; and
[3-(4-{[2-(2-furyl)-5-methyl-1,3-oxazol-4-ylmethoxy]-3-methoxybenzyl}oxy)-1-phenyl-1H-pyrazol-5-yl]acetonitrile, or a salt thereof;
(2) the compound of the aforementioned (1), wherein the 5-membered heterocyclic group for R$^1$ is a 5-membered aromatic heterocyclic group;
(3) the compound of the aforementioned (2), wherein the 5-membered aromatic heterocyclic group is oxazolyl, thiazolyl or triazolyl;
(4) the compound of the aforementioned (1), wherein X is a bond;
(5) the compound of the aforementioned (1), wherein Q is a C$_{1-6}$ alkylene or a C$_{2-6}$ alkenylene;
(6) the compound of the aforementioned (1), wherein Y is an oxygen atom;
(7) the compound of the aforementioned (1), wherein the nitrogen-containing heterocycle represented by ring B is a pyrazole ring, an oxazole ring or a thiazole ring;
(8) the compound of the aforementioned (1), wherein the substituent that ring B may further have is a hydrocarbon group;
(9) the compound of the aforementioned (8), wherein the hydrocarbon group is a C$_{1-10}$ alkyl group, a C$_{7-13}$ aralkyl group or a C$_{6-14}$ aryl group;
(10) the compound of the aforementioned (1), wherein V is a bond;
(11) the compound of the aforementioned (1), wherein R$^2$ is —PO(OR$^9$)(OR$^{10}$) (R$^9$ and R$^{10}$ are the same or different and each is a hydrogen atom or an optionally substituted hydrocarbon group, or R$^9$ and R$^{10}$ are optionally bonded to form an optionally substituted ring) or an optionally substituted heterocyclic group;
(12) the compound of the aforementioned (1), wherein R$^2$ is an optionally substituted heterocyclic group;
(13) the compound of the aforementioned (1), wherein the aromatic ring represented by ring A is a benzene ring;
(14) the compound of the aforementioned (1), wherein Z$^1$ is an oxygen atom;
(15) the compound of the aforementioned (1), wherein W is a C$_{1-6}$ alkylene or a C$_{2-6}$ alkenylene; V is a bond; and R$^2$ is —PO(OR$^9$)(OR$^{10}$) (R$^9$ and R$^{10}$ are the same or different and each is a hydrogen atom or an optionally substituted hydrocarbon group, or R$^9$ and R$^{10}$ are optionally bonded to form an optionally substituted ring) or an optionally substituted heterocyclic group;

(16) a pharmaceutical composition comprising the compound represented by the formula (I) or a salt thereof or a prodrug thereof;
(17) the pharmaceutical composition of the aforementioned (16), which is an agent for the prophylaxis or treatment of diabetes mellitus;
(18) the pharmaceutical composition of the aforementioned (16), which is an agent for the prophylaxis or treatment of hyperlipidemia;
(19) the pharmaceutical composition of the aforementioned (16), which is an agent for the prophylaxis or treatment of impaired glucose tolerance;
(20) the pharmaceutical composition of the aforementioned (16), which is an agent for the prophylaxis or treatment of obesity;
(21) the pharmaceutical composition of the aforementioned (16), which is an agent for the prophylaxis or treatment of hypertension;
(22) a retinoid-related receptor function regulating agent, which comprises the compound represented by the formula (I) or a salt thereof or a prodrug thereof;
(23) the agent of the aforementioned (22), which is a peroxisome proliferator-activated receptor ligand;
(24) the agent of the aforementioned (22), which is a retinoid X receptor ligand;
(25) an agent for improving insulin resistance, which comprises the compound represented by the formula (I) or a salt thereof or a prodrug thereof;
(26) a method for the prophylaxis or treatment of diabetes mellitus in a mammal, which comprises administering the compound represented by the formula (I) or a salt thereof or a prodrug thereof to the mammal;
(27) use of the compound represented by the formula (I) or a salt thereof or a prodrug thereof for the production of an agent for the prophylaxis or treatment of diabetes mellitus;
(28) a method for the prophylaxis or treatment of obesity in a mammal, which comprises administering the compound represented by the formula (I) or a salt thereof or a prodrug thereof to the mammal;
(29) use of the compound represented by the formula (I) or a salt thereof or a prodrug thereof for the production of an agent for the prophylaxis or treatment of obesity; and the like.

In the formula (I), as the "5-membered heterocyclic group" for $R^1$, for example, a 5-membered heterocyclic group containing, as ring-constituting atom(s) besides carbon atoms, 1 to 4 hetero atoms selected from an oxygen atom, a sulfur atom and a nitrogen atom can be mentioned.

As preferable examples of the "5-membered heterocyclic group", 5-membered non-aromatic heterocyclic groups such as pyrrolidinyl (2- or 3-pyrrolidinyl), imidazolidinyl (2- or 4-imidazolidinyl), pyrazolidinyl (2-, 3- or 4-pyrazolidinyl) and the like; 5-membered aromatic heterocyclic groups such as furyl (2- or 3-furyl), thienyl (2- or 3-thienyl), pyrrolyl (1-, 2- or 3-pyrrolyl), imidazolyl (1-, 2-, 4- or 5-imidazolyl), pyrazolyl (1-, 3- or 4-pyrazolyl), isoxazolyl (3-, 4- or 5-isoxazolyl), isothiazolyl (3-, 4- or 5-isothiazolyl), thiazolyl (2-, 4- or 5-thiazolyl) oxazolyl (2-, 4- or 5-oxazolyl), oxadiazolyl (1,2,4-oxadiazol-5-yl, 1,3,4-oxadiazol-2-yl), thiadiazolyl (1,2,4-thiadiazol-5-yl, 1,3,4-thiadiazol-2-yl), triazolyl (1,2,4-triazol-1-yl, 1,2,4-triazol-3-yl, 1,2,3-triazol-1-yl, 1,2,3-triazol-2-yl, 1,2,3-triazol-4-yl), tetrazolyl (tetrazol-1-yl, tetrazol-5-yl) and the like can be mentioned.

The "5-membered heterocyclic group" is preferably a 5-membered aromatic heterocyclic group, which is more preferably oxazolyl, thiazolyl, pyrazolyl, imidazolyl, triazolyl and the like. Of these, oxazolyl, thiazolyl and triazolyl are preferable.

The "5-membered heterocyclic group" for $R^1$ may have 1 to 4, preferably 1 to 3, substituents at substitutable position(s). As such substituents, "a halogen atom", "a nitro group", "an optionally substituted aliphatic hydrocarbon group", "an optionally substituted alicyclic hydrocarbon group", "an optionally substituted aromatic hydrocarbon group", "an optionally substituted heterocyclic group", "an optionally substituted acyl group", "an optionally substituted amino group", "an optionally substituted hydroxy group", "an optionally substituted thiol group" and the like can be mentioned.

As the "halogen atom", fluorine, chlorine, bromine and iodine can be mentioned, with preference given to fluorine and chlorine.

As the aliphatic hydrocarbon group of the "optionally substituted aliphatic hydrocarbon group", a straight-chain or branched $C_{1-15}$ aliphatic hydrocarbon group, such as an alkyl group, an alkenyl group, an alkynyl group and the like can be mentioned.

As preferable examples of the alkyl group, a $C_{1-10}$ alkyl group, such as methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl, 2-ethylbutyl, heptyl, octyl, nonyl, decyl and the like can be mentioned.

As preferable examples of the alkenyl group, a $C_{2-10}$ alkenyl group, such as ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl, 5-hexenyl, 1-heptenyl, 1-octenyl and the like can be mentioned.

As preferable examples of the alkynyl group, a $C_{2-10}$ alkynyl group, such as ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl, 1-heptynyl, 1-octynyl and the like can be mentioned.

As the substituent of the "optionally substituted aliphatic hydrocarbon group", for example, a $C_{3-10}$ cycloalkyl group; a $C_{6-14}$ aryl group (e.g., phenyl, naphthyl); an aromatic heterocyclic group (e.g., thienyl, furyl, pyridyl, oxazolyl, thiazolyl); a non-aromatic heterocyclic group (e.g., tetrahydrofuryl, morpholino, thiomorpholino, piperidino, pyrrolidinyl, piperazinyl); an amino group optionally mono- or di-substituted by a $C_{1-4}$ alkyl group or a $C_{1-6}$ alkyl-carbonyl group; an amidino group; a $C_{1-6}$ alkyl-carbonyl group; a carbamoyl group optionally mono- or di-substituted by a $C_{1-4}$ alkyl group; a sulfamoyl group optionally mono- or di-substituted by a $C_{1-4}$ alkyl group; a carboxyl group; a $C_{1-6}$ alkoxy-carbonyl group; a $C_{1-6}$ alkyl-carbonyloxy group; a $C_{1-6}$ alkylsulfonyloxy group; a hydroxy group; a $C_{1-6}$ alkoxy group optionally substituted by 1 to 3 substituents selected from a halogen atom (e.g., fluorine, chlorine, bromine, iodine), a carboxyl group, a carbamoyl group and a $C_{1-6}$ alkoxy-carbonyl group; a $C_{2-5}$ alkenyloxy group optionally substituted by 1 to 3 substituents selected from a halogen atom (e.g., fluorine, chlorine, bromine, iodine), a carboxyl group, a carbamoyl group and a $C_{1-6}$ alkoxy-carbonyl group; a $C_{3-7}$ cycloalkyloxy group; a $C_{7-9}$ aralkyloxy group; a $C_{6-14}$ aryloxy group (e.g., phenyloxy, naphthyloxy); a thiol group; a $C_{1-6}$ alkylthio group optionally substituted by 1 to 3 halogen atoms (e.g., fluorine, chlorine, bromine, iodine); a $C_{7-9}$ aralkylthio group; a $C_{6-14}$ arylthio group (e.g., phenylthio, naphthylthio); a sulfo group; a cyano group; an azide group; a nitro group; a nitroso group; a halogen atom (e.g., fluorine, chlorine, bromine, iodine) and the like can be mentioned. The number of the substituents is, for example, 1 to 3.

As the alicyclic hydrocarbon group of the "optionally substituted alicyclic hydrocarbon group", a saturated or unsaturated $C_{3-12}$ alicyclic hydrocarbon group such as a cycloalkyl group, a cycloalkenyl group, a cycloalkadienyl group and the like can be mentioned.

As preferable examples of the cycloalkyl group, a $C_{3-10}$ cycloalkyl group, such as cyclopropyl, cyclobutyl, cyclopentyl, cyclohexyl, cycloheptyl, cyclooctyl, bicyclo[2.2.1]heptyl, bicyclo[2.2.2]octyl, bicyclo[3.2.1]octyl, bicyclo[3.2.2]nonyl, bicyclo[3.3.1]nonyl, bicyclo[4.2.1]nonyl, bicyclo[4.3.1]decyl and the like can be mentioned.

As preferable examples of the cycloalkenyl group, a $C_{3-10}$ cycloalkenyl group, such as 2-cyclopenten-1-yl, 3-cyclopenten-1-yl, 2-cyclohexen-1-yl, 3-cyclohexen-1-yl and the like can be mentioned.

As preferable examples of the cycloalkadienyl group, a $C_{4-10}$ cycloalkadienyl group, such as 2,4-cyclopentadien-1-yl, 2,4-cyclohexadien-1-yl, 2,5-cyclohexadien-1-yl and the like can be mentioned.

As preferable examples of the aromatic hydrocarbon group of the "optionally substituted aromatic hydrocarbon group", an aromatic $C_{6-14}$ hydrocarbon group (e.g., an aryl group), such as phenyl, naphthyl, anthryl, phenanthryl, acenaphthylenyl, biphenylyl and the like can be mentioned, with preference given to phenyl, 1-naphthyl, 2-naphthyl and the like.

As the heterocyclic group of the "optionally substituted heterocyclic group", aromatic heterocyclic groups and non-aromatic heterocyclic groups can be mentioned.

As the aromatic heterocyclic group, for example, a monocyclic, bicyclic or tricyclic aromatic heterocyclic group containing, as ring-constituting atom(s) besides carbon atoms, 1 to 5 hetero atoms selected from an oxygen atom, a sulfur atom and a nitrogen atom and the like can be mentioned.

As preferable examples of the monocyclic aromatic heterocyclic group, for example, furyl, thienyl, pyrrolyl, oxazolyl, isoxazolyl, thiazolyl, isothiazolyl, imidazolyl, pyrazolyl, oxadiazolyl (1,2,3-, 1,2,4- or 1,3,4-oxadiazolyl), furazanyl, thiadiazolyl (1,2,3-, 1,2,4- or 1,3,4-thiadiazolyl), triazolyl (1,2,3- or 1,2,4-triazolyl), tetrazolyl, pyridyl, pyrimidinyl, pyridazinyl, pyrazinyl and triazinyl can be mentioned.

As preferable examples of the bicyclic or tricyclic aromatic heterocyclic group, for example, benzofuranyl, isobenzofuranyl, benzo[b]thienyl, indolyl, isoindolyl, 1H-indazolyl, benzimidazolyl, benzoxazolyl, benzothiazolyl, 1H-benzotriazolyl, quinolyl, isoquinolyl, cinnolyl, quinazolyl, quinoxalinyl, phthalazinyl, naphthyridinyl, purinyl, pteridinyl, carbazolyl, α-carbonylyl, β-carbonylyl, γ-carbonylyl, acridinyl, phenoxazinyl, phenothiazinyl, phenazinyl, phenoxathiinyl, thianthrenyl, indolizinyl, pyrrolo[1,2-b]pyridazinyl, pyrazolo[1,5-a]pyridyl, imidazo[1,2-a]pyridyl, imidazo[1,5-a]pyridyl, imidazo[1,2-b]pyridazinyl, imidazo[1,2-a]pyrimidinyl, 1,2,4-triazolo[4,3-a]pyridyl, 1,2,4-triazolo[4,3-b]pyridazinyl and the like can be mentioned.

As the non-aromatic heterocyclic groups, a $C_{2-10}$ non-aromatic heterocyclic group containing, as ring constituting atom(s) besides carbon atoms, 1 to 5 (preferably 1 to 3) hetero atoms selected from an oxygen atom, a sulfur atom and a nitrogen atom and the like can be mentioned. As preferable examples of the non-aromatic heterocyclic group, oxiranyl, azetidinyl, oxetanyl, thietanyl, pyrrolidinyl, tetrahydrofuryl, tetrahydropyranyl, oxazolinyl, oxazolidinyl, dioxooxazolidinyl, thiazolinyl, thiazolidinyl, dioxothiazolidinyl, morpholinyl, thiomorpholinyl, piperazinyl, pyrrolidinyl, piperidino, morpholino, thiomorpholino, oxodihydrooxadiazolyl (5-oxo-4,5-dihydro-1,3,4-oxadiazolyl; 5-oxo-4,5-dihydro-1,2,4-oxadiazolyl), oxodihydrothiadiazolyl (5-oxo-4,5-dihydro-1,3,4-thiadiazolyl; 5-oxo-4,5-dihydro-1,2,4-thiadiazolyl), thioxodihydrooxadiazolyl (5-thioxo-4,5-dihydro-1,3,4-oxadiazolyl; 5-thioxo-4,5-dihydro-1,2,4-oxadiazolyl), thioxodihydrothiadiazolyl(5-thioxo-4,5-dihydro-1,3,4-thiadiazolyl; 5-thioxo-4,5-dihydro-1,2,4-thiadiazolyl), oxideoxathiadiazolyl (2-oxide-3H-1,2,3,5-oxathiadiazolyl) and the like can be mentioned.

As the substituent of the aforementioned "optionally substituted alicyclic hydrocarbon group", "optionally substituted aromatic hydrocarbon group" and "optionally substituted heterocyclic group", for example, a $C_{1-6}$ alkyl group optionally substituted by 1 to 3 substituents selected from a halogen atom (e.g., fluorine, chlorine, bromine, iodine), a carboxyl group, a carbamoyl group, a $C_{1-6}$ alkoxy-carbonyl group, a hydroxy group and a $C_{6-14}$ aryl-carbonyloxy group (e.g., benzoyloxy); a $C_{2-6}$ alkenyl group optionally substituted by 1 to 3 substituents selected from a halogen atom (e.g., fluorine, chlorine, bromine, iodine), a carboxyl group, a carbamoyl group, a $C_{1-6}$ alkoxy-carbonyl group, a hydroxy group and a $C_{6-14}$ aryl-carbonyloxy group (e.g., benzoyloxy); a $C_{3-10}$ cycloalkyl group; a $C_{6-14}$ aryl group (e.g., phenyl, naphthyl); an aromatic heterocyclic group (e.g., thienyl, furyl, pyridyl, oxazolyl, thiazolyl, triazolyl, tetrazolyl); a non-aromatic heterocyclic group (e.g., tetrahydrofuryl, morpholino, thiomorpholino, piperidino, pyrrolidinyl, piperazinyl, oxodihydrooxadiazolyl, oxodihydrothiadiazolyl, thioxodihydrooxadiazolyl, thioxodihydrothiadiazolyl, oxideoxathiadiazolyl) optionally substituted by a $C_{1-6}$ alkoxy-carbonyl group; a $C_{7-9}$ aralkyl group; an amino group optionally mono- or di-substituted by a substituent selected from a $C_{1-4}$ alkyl group, a $C_{1-6}$ alkyl-carbonyl group and a $C_{1-6}$ alkylsulfonyl group; an amidino group optionally substituted a hydroxy group; a $C_{1-6}$ alkyl-carbonyl group; a carbamoyl group optionally mono- or di-substituted by a substituent selected from a $C_{1-4}$ alkyl group and a $C_{1-6}$ alkylsulfonyl; a sulfamoyl group optionally mono- or di-substituted by a $C_{1-4}$ alkyl group; a carboxyl group; a $C_{1-6}$ alkoxy-carbonyl group; a $C_{1-6}$ alkyl-carbonyloxy group; a $C_{1-6}$ alkylsulfonyloxy group; a hydroxy group; a $C_{1-6}$ alkoxy group optionally substituted by 1 to 3 substituents selected from a halogen atom (e.g., fluorine, chlorine, bromine, iodine), a carboxyl group, a carbamoyl group and a $C_{1-6}$ alkoxy-carbonyl group; a $C_{2-5}$ alkenyloxy group optionally substituted by 1 to 3 substituents selected from a halogen atom (e.g., fluorine, chlorine, bromine, iodine), a carboxyl group, a carbamoyl group and a $C_{1-6}$ alkoxy-carbonyl group; a $C_{3-7}$ cycloalkyloxy group; a $C_{7-9}$ aralkyloxy group; a $C_{6-14}$ aryloxy group (e.g., phenyloxy, naphthyloxy); a thiol group; a $C_{1-6}$ alkylthio group optionally substituted by 1 to 3 halogen atoms (e.g., fluorine, chlorine, bromine, iodine); a $C_{7-9}$ aralkylthio group; a $C_{6-14}$ arylthio group (e.g., phenylthio, naphthylthio); a sulfo group; a cyano group; an azide group; a nitro group; a nitroso group; a halogen atom (e.g., fluorine, chlorine, bromine, iodine) and the like can be mentioned. The number of the substituents is, for example, 1 to 3.

As the acyl group of the "optionally substituted acyl group", for example, —COR$^{15}$, —CO—OR$^{15}$, —SO$_2$R$^{15}$, —SOR$^{15}$, —PO(OR$^{15}$)(OR$^{16}$), —CO—NR$^{17}$R$^{18}$, —CS—

NR$^{17}$R$^{18}$ [R$^{15}$ and R$^{16}$ are the same or different and each is a hydrogen atom, a hydrocarbon group or a heterocyclic group, or R$^{15}$ and R$^{16}$ are optionally bonded to form a ring. R$^{17}$ and R$^{18}$ are the same or different and each is a hydrogen atom, a hydrocarbon group or a heterocyclic group or R$^{17}$ and R$^{18}$ optionally form a nitrogen-containing heterocycle, together with the adjacent nitrogen atom) and the like can be mentioned.

As the "hydrocarbon group" represented by R$^{15}$, R$^{16}$, R$^{17}$ and R$^{18}$, an aliphatic hydrocarbon group, an alicyclic hydrocarbon group, an aromatic hydrocarbon group, an alicyclic-aliphatic hydrocarbon group, an aromatic aliphatic hydrocarbon group and the like can be mentioned.

As used herein, as the aliphatic hydrocarbon group, alicyclic hydrocarbon group and aromatic hydrocarbon group, those exemplified as the substituent of R$^1$ can be mentioned.

As the alicyclic-aliphatic hydrocarbon group, those resulting from the binding of the aforementioned alicyclic hydrocarbon group and aliphatic hydrocarbon group (e.g., a cycloalkyl-alkyl group, a cycloalkenyl-alkyl group) can be mentioned, with preference given to a C$_{4-9}$ alicyclic-aliphatic hydrocarbon group. As preferable examples of the alicyclic-aliphatic hydrocarbon group, cyclopropylmethyl, cyclopropylethyl, cyclobutylmethyl, cyclopentylmethyl, 2-cyclopentenylmethyl, 3-cyclopentenylmethyl, cyclohexylmethyl, 2-cyclohexenylmethyl, 3-cyclohexenylmethyl, cyclohexylethyl, cyclohexylpropyl, cycloheptylmethyl and cycloheptylethyl can be mentioned.

As the aromatic aliphatic hydrocarbon group, a C$_{7-13}$ aromatic aliphatic hydrocarbon group (e.g., a C$_{7-13}$ group, a C$_{8-13}$ arylalkenyl group) and the like can be mentioned. As preferable examples of the aromatic aliphatic hydrocarbon group, C$_{7-9}$ phenylalkyls, such as benzyl, phenethyl, 1-phenylethyl, 1-phenylpropyl, 2-phenylpropyl, 3-phenylpropyl and the like; a C$_{11-13}$ naphthylalkyl, such as α-naphthylmethyl, α-naphthylethyl, β-naphthylmethyl, β-naphthylethyl and the like; a C$_{8-10}$ phenylalkenyl, such as styryl; and a C$_{12-13}$ naphthylalkenyl such as 2-(2-naphthylvinyl) and the like can be mentioned.

The hydrocarbon group is preferably a C$_{1-10}$ alkyl group (preferably methyl, ethyl, propyl, butyl, tert-butyl, pentyl, 1-ethylpropyl, 2,2-dimethylpropyl); a C$_{2-10}$ alkynyl group (preferably 2-propynyl); a C$_{3-10}$ cycloalkyl group (preferably cyclopropyl, cyclohexyl); a C$_{6-14}$ aryl group (preferably phenyl, biphenylyl) optionally substituted by a C$_{1-6}$ alkyl group; a C$_{7-13}$ aralkyl group (preferably benzyl, phenethyl, phenylpropyl, naphthylmethyl, benzhydryl) and the like.

As the "heterocyclic group" represented by R$^{15}$, R$^{16}$, R$^{17}$ and R$^{18}$, those exemplified as the substituent of R$^1$ can be mentioned.

The heterocyclic group is preferably thiazolyl, oxazolyl, isothiazolyl, isoxazolyl, pyrazolyl, pyridyl, pyrazinyl, benzoxazolyl, benzothiazolyl, benzothiadiazolyl, quinolyl, isoquinolyl, pyrrolidinyl, piperidinyl, piperazinyl and the like.

As the ring formed by the bonding of R$^{15}$ and R$^{16}$, those exemplified as the ring of the "optionally substituted ring" formed by the bonding of R$^9$ and R$^{10}$ to be mentioned below can be mentioned.

As the "nitrogen-containing heterocycle" formed by R$^{17}$ and R$^{18}$ together with the adjacent nitrogen atom, for example, a 5 to 7-membered nitrogen-containing heterocycle containing, as a ring-constituting atom besides carbon atom, at least one nitrogen atom, and optionally further containing 1 or 2 hetero atoms selected from oxygen atom, sulfur atom and nitrogen atom can be mentioned. As preferable examples of the nitrogen-containing heterocycle, pyrrolidine, imidazolidine, pyrazolidine, piperidine, piperazine, morpholine, thiomorpholine and the like can be mentioned.

The acyl group may have 1 to 3 substituents at substitutable position(s), an as such substituent, for example, a C$_{1-6}$ alkyl group (e.g., methyl, ethyl) optionally substituted by 1 to 3 halogen atoms (e.g., fluorine, chlorine, bromine, iodine), a C$_{1-6}$ alkoxy group (e.g., methoxy, ethoxy) optionally substituted by 1 to 3 halogen atoms (e.g., fluorine, chlorine, bromine, iodine), a halogen atom (e.g., fluorine, chlorine, bromine, iodine), a nitro group, a hydroxy group, an amino group optionally mono- or di-substituted by a C$_{1-6}$ alkyl group (e.g., methyl, ethyl) and the like can be mentioned.

As preferable examples of the acyl group, formyl, carboxyl, carbamoyl, thiocarbamoyl, a C$_{1-10}$ alkyl-carbonyl (e.g., acetyl, propionyl, butyryl, isobutyryl, valeryl, isovaleryl, pivaloyl, hexanoyl, heptanoyl, octanoyl), a C$_{2-10}$ alkenyl-carbonyl (e.g., crotonyl), a C$_{3-10}$ cycloalkyl-carbonyl (e.g., cyclobutanecarbonyl, cyclopentanecarbonyl, cyclohexanecarbonyl, cycloheptanecarbonyl), a C$_{3-10}$ cycloalkenyl-carbonyl (e.g., 2-cyclohexenecarbonyl), a C$_{6-14}$ aryl-carbonyl (e.g., benzoyl, 1-naphthoyl, 2-naphthoyl), a C$_{7-13}$ aralkyl-carbonyl (e.g., benzylcarbonyl, phenethylcarbonyl), an aromatic heterocyclic carbonyl (e.g., nicotinoyl, isonicotinoyl), a non-aromatic heterocyclic carbonyl (e.g., pyrrolidinylcarbonyl, piperidinocarbonyl), a C$_{1-6}$ alkoxy-carbonyl (e.g., methoxycarbonyl, ethoxycarbonyl, propoxycarbonyl, butoxycarbonyl, tert-butoxycarbonyl), a C$_{6-14}$ aryloxy-carbonyl (e.g., phenyloxycarbonyl, naphthyloxycarbonyl), a C$_{7-13}$ aralkyloxy-carbonyl (e.g., benzyloxycarbonyl, phenethyloxycarbonyl), a mono- or di-(C$_{1-6}$ alkyl optionally having 1 to 3 substituents selected from a halogen atom and a C$_{1-6}$ alkoxy-carbonyl)-carbamoyl (e.g., methylcarbamoyl, ethylcarbamoyl, dimethylcarbamoyl, diethylcarbamoyl, ethylmethylcarbamoyl, propylcarbamoyl, trifluoroethylcarbamoyl), a mono- or di-(C$_{1-6}$ alkyl optionally substituted by 1 to 3 halogens)-thiocarbamoyl (e.g., methylthiocarbamoyl, ethylthiocarbamoyl), a C$_{6-14}$ aryl-carbamoyl (e.g., phenylcarbamoyl), a C$_{3-10}$ cycloalkyl-carbamoyl (e.g., cyclopropylcarbamoyl), a C$_{7-13}$ aralkyl-carbamoyl (e.g., benzylcarbamoyl), a C$_{1-6}$ alkoxy-carbamoyl (e.g., methoxycarbamoyl), a C$_{1-10}$ alkylsulfinyl group (e.g., methylsulfinyl, ethylsulfinyl), a C$_{1-10}$ alkylsulfonyl group (e.g., methylsulfonyl, ethylsulfonyl), a C$_{6-14}$ arylsulfonyl (e.g., phenylsulfonyl), a (mono- or di-C$_{1-10}$ alkyl) phosphono group optionally forming a ring (e.g., dimethylphosphono; diethylphosphono; diisopropylphosphono; dibutylphosphono; 2-oxide-1,3,2-dioxaphosphinanyl), a mono- or di-(C$_{1-6}$ alkyl optionally substituted by 1 to 3 halogens)-sulfamoyl (e.g., methylsulfamoyl, ethylsulfamoyl) and the like can be mentioned.

As the "optionally substituted amino group", for example, an amino group optionally mono- or di-substituted by a C$_{1-10}$ alkyl group, a C$_{2-10}$ alkenyl group, a C$_{3-10}$ cycloalkyl group, a C$_{3-10}$ cycloalkenyl group, a C$_{6-14}$ aryl group or a C$_{1-13}$ acyl group and the like can be mentioned. As these groups, those exemplified as the substituents of the aforementioned R$^1$ can be mentioned. In addition, the C$_{1-13}$ acyl group is preferably a C$_{1-6}$ alkyl-carbonyl group, a C$_{7-13}$ arylcarbonyl group and the like.

As preferable examples of the substituted amino group, methylamino, dimethylamino, ethylamino, diethylamino, propylamino, dibutylamino, diallylamino, cyclohexylamino, acetylamino, propionylamino, benzoylamino, phenylamino, N-methyl-N-phenylamino and the like can be mentioned.

As the "optionally substituted hydroxy group", for example, a hydroxy group optionally substituted by an optionally substituted $C_{1-10}$ alkyl group, an optionally substituted $C_{2-10}$ alkenyl group, an optionally substituted $C_{6-14}$ aryl group, an optionally substituted $C_{7-13}$ aralkyl group or an optionally substituted $C_{1-13}$ acyl group can be mentioned. As these alkyl group, alkenyl group, aryl group and acyl group, those exemplified as the substituents for the aforementioned $R^1$ can be mentioned. As the "$C_{7-13}$ aralkyl group", that exemplified as the aforementioned hydrocarbon groups for $R^{15}$ can be mentioned.

As the aforementioned substituents which may be possessed by the alkyl group, alkenyl group, aryl group, acyl group and aralkyl group, for example, a halogen atom (e.g., fluorine, chlorine, bromine, iodine), a $C_{1-6}$ alkoxy group optionally substituted by 1 to 3 halogen atoms (e.g., fluorine, chlorine, bromine, iodine), a hydroxy group, a nitro group, an amino group and the like can be mentioned. The number of the substituents is, for example, 1 or 2.

As the substituted hydroxy group, for example, an alkoxy group, an alkenyloxy group, an aryloxy group, an acyloxy group and an aralkyloxy group, each of which is optionally substituted, and the like can be mentioned.

As preferable examples of the alkoxy group, $C_{1-10}$ alkoxy groups, such as methoxy, ethoxy, propoxy, isopropoxy, butoxy, isobutoxy, sec-butoxy, tert-butoxy, pentyloxy, isopentyloxy, neopentyloxy, hexyloxy, heptyloxy, nonyloxy, cyclobutoxy, cyclopentyloxy, cyclohexyloxy and the like can be mentioned.

As preferable examples of the alkenyloxy group, $C_{2-10}$ alkenyloxy groups, such as allyloxy, crotyloxy, 2-pentenyloxy, 3-hexenyloxy, 2-cyclopentenylmethoxy, 2-cyclohexenylmethoxy and the like can be mentioned.

As preferable examples of the aryloxy group, a $C_{6-14}$ aryloxy group, such as phenoxy, naphthyloxy and the like can be mentioned.

As preferable examples of the acyloxy group, a $C_{2-13}$ acyloxy group, more preferably a $C_{1-6}$ alkyl-carbonyloxy group (e.g., acetyloxy, propionyloxy, butyryloxy, isobutyryloxy, pivaloyloxy), a $C_{1-6}$ alkylsulfonyloxy group (e.g., methylsulfonyloxy) and the like can be mentioned.

As preferable examples of the aralkyloxy group, a $C_{7-10}$ aralkyloxy group, such as a phenyl-$C_{1-4}$ alkyloxy (e.g., benzyloxy, phenethyloxy) and the like can be mentioned.

The above-mentioned alkoxy group, alkenyloxy group, aryloxy group, acyloxy group and aralkyloxy group may have 1 or 2 substituents at substitutable position(s). As such substituent, for example, a halogen atom (e.g., fluorine, chlorine, bromine, iodine), a $C_{1-6}$ alkoxy group optionally substituted by 1 to 3 halogen atoms (e.g., fluorine, chlorine, bromine, iodine), a hydroxy group, a nitro group, an amino group and the like can be mentioned.

As the optionally substituted thiol group, for example, a thiol group optionally substituted by a $C_{1-10}$ alkyl group, a $C_{3-10}$ cycloalkyl group, a $C_{6-14}$ aryl group, a $C_{2-13}$ acyl group, a $C_{7-13}$ aralkyl group, a heteroaryl group or the like can be mentioned. As the alkyl group, cycloalkyl group, aryl group and acyl group, those exemplified as the substituents for the aforementioned $R^1$ can be mentioned. As the aralkyl group, those exemplified as the hydrocarbon groups for the aforementioned $R^{15}$ can be mentioned. As preferable examples of the heteroaryl group, pyridyl (e.g., 2- or 3-pyridyl), imidazolyl (e.g., 2-imidazolyl), triazolyl (e.g., 1,2,4-triazol-5-yl) and the like can be mentioned.

As the substituted thiol group, for example, an alkylthio group, a cycloalkylthio group, an arylthio group, an acylthio group, an aralkylthio group, a heteroarylthio group and the like can be mentioned.

As preferable examples of the alkylthio group, a $C_{1-10}$ alkylthio group, such as methylthio, ethylthio, propylthio, isopropylthio, butylthio, isobutylthio, sec-butylthio, tert-butylthio, pentylthio, isopentylthio, neopentylthio, hexylthio, heptylthio, nonylthio and the like can be mentioned.

As preferable examples of the cycloalkylthio group, a $C_{3-10}$ cycloalkylthio group, such as cyclobutylthio, cyclopentylthio, cyclohexylthio and the like can be mentioned.

As preferable examples of the arylthio group, a $C_{6-14}$ arylthio group, such as phenylthio, naphthylthio and the like can be mentioned.

As preferable examples of the acylthio group, a $C_{2-13}$ acylthio group, more preferably a $C_{1-6}$ alkyl-carbonylthio group (e.g., acetylthio, propionylthio, butyrylthio, isobutyrylthio, pivaloylthio), a $C_{1-6}$ alkylsulfonylthio group (e.g., methylsulfonylthio) and the like can be mentioned.

As preferable examples of the aralkylthio group, a $C_{7-10}$ aralkylthio group, such as a phenyl-$C_{1-4}$ alkylthio (e.g., benzylthio, phenethylthio) and the like can be mentioned.

As preferable examples of the heteroarylthio group, pyridylthio (e.g., 2- or 3-pyridylthio), imidazolylthio (e.g., 2-imidazolylthio), triazolylthio (e.g., 1,2,4-triazole-5-ylthio) and the like can be mentioned.

The substituent for $R^1$ is preferably 1) a $C_{1-6}$ alkyl group and a $C_{2-6}$ alkenyl group, each optionally having 1 to 3 substituents selected from a $C_{1-6}$ alkoxy group optionally substituted by 1 to 3 halogen atoms (e.g., fluorine, chlorine, bromine, iodine), a halogen atom (e.g., fluorine, chlorine, bromine, iodine), a nitro group, a hydroxy group, an amino group, a carboxyl group and a $C_{1-6}$ alkoxy-carbonyl group;

2) a $C_{3-7}$ cycloalkyl group optionally having 1 to 3 substituents selected from a $C_{1-6}$ alkyl group optionally substituted by 1 to 3 halogen atoms (e.g., fluorine, chlorine, bromine, iodine), a $C_{1-6}$ alkoxy group optionally substituted by 1 to 3 halogen atoms (e.g., fluorine, chlorine, bromine, iodine), a halogen atom (e.g., fluorine, chlorine, bromine, iodine), a nitro group, a hydroxy group and an amino group;

3) a $C_{6-14}$ aryl group (preferably, phenyl, naphthyl and the like) optionally having 1 to 3 substituents selected from a $C_{1-6}$ alkyl group optionally substituted by 1 to 3 substituents selected from a halogen atom (e.g., fluorine, chlorine, bromine, iodine), a hydroxy group, a carboxyl group, a carbamoyl group and a $C_{1-6}$ alkoxy-carbonyl group;

a $C_{1-6}$ alkoxy group optionally substituted by 1 to 3 substituents selected from a halogen atom (e.g., fluorine, chlorine, bromine, iodine), a carboxyl group, a carbamoyl group and a $C_{1-6}$ alkoxy-carbonyl group;

a halogen atom (e.g., fluorine, chlorine, bromine, iodine); a hydroxy group; a $C_{1-6}$ alkylsulfonyloxy group; n amino group optionally substituted by a $C_{1-6}$ alkylsulfonyl group; a carboxyl group; a carbamoyl group optionally substituted by a $C_{1-6}$ alkylsulfonyl group; a $C_{1-6}$ alkoxy-carbonyl group; a cyano group; an aromatic heterocyclic group (preferably tetrazolyl); a non-aromatic heterocyclic group (preferably oxodihydrooxadiazolyl, oxodihydrothiadiazolyl, thioxodihydrooxadiazolyl, thioxodihydrothiadiazolyl, oxideoxathiadiazolyl); and an amidino group optionally substituted by a hydroxy group;

4) a heterocyclic group (preferably an aromatic heterocyclic group such as furyl, thienyl, pyridyl, pyrazinyl and the like; a non-aromatic heterocyclic group such as piperidino, morpholino and the like) optionally having 1 to 3 substituents selected from a $C_{1-6}$ alkyl group optionally substituted by 1 to 3 substituents selected from a halogen atom (e.g., fluorine, chlorine, bromine, iodine), a carboxyl group, a carbamoyl group and a $C_{1-6}$ alkoxy-carbonyl group;

a $C_{1-6}$ alkoxy group optionally substituted by 1 to 3 substituents selected from a halogen atom (e.g., fluorine, chlorine, bromine, iodine), a carboxyl group, a carbamoyl group and a $C_{1-6}$ alkoxy-carbonyl group;

a halogen atom (e.g., fluorine, chlorine, bromine, iodine); a hydroxy group; a $C_{1-6}$ alkylsulfonyloxy group; an amino group optionally substituted by a $C_{1-6}$ alkylsulfonyl group; a carboxyl group; a carbamoyl group optionally substituted by a $C_{1-6}$ alkylsulfonyl group; a $C_{1-6}$ alkoxy-carbonyl group; a cyano group; an aromatic heterocyclic group (preferably tetrazolyl); a non-aromatic heterocyclic group (preferably oxodihydrooxadiazolyl, oxodihydrothiadiazolyl, thioxodihydrooxadiazolyl, thioxodihydrothiadiazolyl, oxideoxathiadiazolyl); an amidino group optionally substituted by a hydroxy group; and the like. The number of the substituents for $R^1$ is preferably 1 to 3, more preferably 1 or 2.

$R^1$ is preferably oxazolyl, thiazolyl, pyrazolyl, imidazolyl or triazolyl, each optionally having 1 to 3 substituents selected from 1) a $C_{1-6}$ alkyl group or a $C_{2-6}$ alkenyl group, each optionally having 1 to 3 substituents selected from a $C_{1-6}$ alkoxy group optionally substituted by 1 to 3 halogen atoms (e.g., fluorine, chlorine, bromine, iodine), a halogen atom (e.g., fluorine, chlorine, bromine, iodine) a nitro group, a hydroxy group, an amino group, carboxyl group and a $C_{1-6}$ alkoxy-carbonyl group;

2) a $C_{3-7}$ cycloalkyl group optionally having 1 to 3 substituents selected from a $C_{1-6}$ alkyl group optionally substituted by 1 to 3 halogen atoms (e.g., fluorine, chlorine, bromine, iodine), a $C_{1-6}$ alkoxy group optionally substituted by 1 to 3 halogen atoms (e.g., fluorine, chlorine, bromine, iodine), a halogen atom (e.g., fluorine, chlorine, bromine, iodine), a nitro group, a hydroxy group and an amino group;

3) a $C_{6-14}$ aryl group (preferably phenyl, naphthyl and the like) optionally having 1 to 3 substituents selected from a $C_{1-6}$ alkyl group optionally substituted by 1 to 3 substituents selected from a halogen atom (e.g., fluorine, chlorine, bromine, iodine), a hydroxy group, a carboxyl group, a carbamoyl group and a $C_{1-6}$ alkoxy-carbonyl group;

a $C_{1-6}$ alkoxy group optionally substituted by 1 to 3 substituents selected from a halogen atom (e.g., fluorine, chlorine, bromine, iodine), a carboxyl group, a carbamoyl group and a $C_{1-6}$ alkoxy-carbonyl group;

a halogen atom (e.g., fluorine, chlorine, bromine, iodine); a hydroxy group; a $C_{1-6}$ alkylsulfonyloxy group; an amino group optionally substituted by a $C_{1-6}$ alkylsulfonyl group; a carboxyl group; a carbamoyl group optionally substituted by a $C_{1-6}$ alkylsulfonyl group; a $C_{1-6}$ alkoxy-carbonyl group; a cyano group; an aromatic heterocyclic group (preferably tetrazolyl); a non-aromatic heterocyclic group (preferably oxodihydrooxadiazolyl, oxodihydrothiadiazolyl, thioxodihydrooxadiazolyl, thioxodihydrothiadiazolyl, oxideoxathiadiazolyl); and an amidino group optionally substituted by a hydroxy group;

4) a heterocyclic group (preferably an aromatic heterocyclic group such as furyl, thienyl, pyridyl, pyrazinyl and the like; a non-aromatic heterocyclic group such as piperidino, morpholino and the like) optionally having 1 to 3 substituents selected from a $C_{1-6}$ alkyl group optionally substituted by 1 to 3 substituents selected from a halogen atom (e.g., fluorine, chlorine, bromine, iodine), a carboxyl group, a carbamoyl group and a $C_{1-6}$ alkoxy-carbonyl group;

a $C_{1-6}$ alkoxy group optionally substituted by 1 to 3 substituents selected from halogen atoms (e.g., fluorine, chlorine, bromine, iodine), a carboxyl group, a carbamoyl group and a $C_{1-6}$ alkoxy-carbonyl group;

a halogen atom (e.g., fluorine, chlorine, bromine, iodine); a hydroxy group; a $C_{1-6}$ alkylsulfonyloxy group; an amino group optionally substituted by a $C_{1-6}$ alkylsulfonyl group; a carboxyl group; a carbamoyl group optionally substituted by a $C_{1-6}$ alkylsulfonyl group; a $C_{1-6}$ alkoxy-carbonyl group; a cyano group; an aromatic heterocyclic group (preferably tetrazolyl); a non-aromatic heterocyclic group (preferably oxodihydrooxadiazolyl, oxodihydrothiadiazolyl, thioxodihydrooxadiazolyl, thioxodihydrothiadiazolyl, oxideoxathiadiazolyl); and an amidino group optionally substituted by a hydroxy group; and the like.

In the formula (I), X, Y and V are the same or different and each is a bond, an oxygen atom, a sulfur atom, —CO—, —CS—, —SO—, —SO$_2$—, —CR$^3$(OR$^4$)—, —NR$^5$—, —CONR$^6$—, —NR$^6$CO—, —CSNR$^6$—, —NR$^6$CS— or —CONR$^6$NR$^7$— (R$^3$ is a hydrogen atom or an optionally substituted hydrocarbon group, R$^4$ is a hydrogen atom or a hydroxyl-protecting group, R$^5$ is a hydrogen atom, an optionally substituted hydrocarbon group or an amino-protecting group, R$^6$ and R$^7$ are the same or different and each is a hydrogen atom or an optionally substituted hydrocarbon group).

As the "hydrocarbon group" of the "optionally substituted hydrocarbon group" represented by R$^3$, R$^5$, R$^6$ and R$^7$, those exemplified for the aforementioned R$^{15}$ can be mentioned. Of these, a $C_{1-4}$ alkyl group, such as methyl, ethyl, propyl, isopropyl, butyl, isobutyl, sec-butyl, tert-butyl and the like are preferable. The hydrocarbon group may have 1 to 3 substituents at substitutable position(s) and as such substituent, for example, a halogen atom (e.g., fluorine, chlorine, bromine, iodine), a $C_{1-4}$ alkoxy group (e.g., methoxy, ethoxy, propoxy, isopropoxy, butoxy, isobutoxy, sec-butoxy, tert-butoxy), a hydroxy group, a nitro group, an amino group, a $C_{1-4}$ acyl group (e.g., formyl; a $C_{1-3}$ alkyl-carbonyl group such as acetyl, propionyl and the like) and the like can be mentioned.

R$^3$, R$^5$, R$^6$ and R$^7$ are each preferably a hydrogen atom or a $C_{1-4}$ alkyl group.

As the hydroxyl-protecting group represented by R$^4$, for example, a $C_{1-6}$ alkyl group (e.g., methyl, ethyl, propyl, isopropyl, butyl, tert-butyl), a phenyl group, a trityl group, a $C_{7-10}$ aralkyl group (e.g., benzyl), a formyl group, a $C_{1-6}$ alkyl-carbonyl group (e.g., acetyl, propionyl), a benzoyl group, a $C_{7-10}$ aralkyl-carbonyl group (e.g., benzylcarbonyl), a 2-tetrahydropyranyl group, a 2-tetrahydrofuranyl group, a silyl group (e.g., trimethylsilyl, triethylsilyl, dimethylphenylsilyl, tert-butyldimethylsilyl, tert-butyldiethylsilyl, tert-butyldiphenylsilyl), a $C_{2-6}$ alkenyl group (e.g., 1-allyl) and the like can be mentioned. These groups are optionally substituted by 1 to 3 halogen atoms (e.g., fluorine, chlorine, bromine, iodine), a $C_{1-6}$ alkyl group (e.g., methyl, ethyl, propyl), a $C_{1-6}$ alkoxy group (e.g., methoxy, ethoxy, propoxy), or a nitro group and the like.

As the amino-protecting group represented by R$^5$, for example, a formyl group, a $C_{1-6}$ alkyl-carbonyl group (e.g., acetyl, propionyl), a $C_{1-6}$ alkoxy-carbonyl group (e.g., methoxycarbonyl, ethoxycarbonyl, tert-butoxycarbonyl), a benzoyl group, a $C_{7-10}$ aralkyl-carbonyl group (e.g., benzylcarbonyl), a $C_{7-14}$ aralkyloxy-carbonyl group (e.g., benzyloxycarbonyl, 9-fluorenylmethoxycarbonyl), a trityl group, a phthaloyl group, a N,N-dimethylaminomethylene group, a silyl group (e.g., trimethylsilyl, triethylsilyl, dimethylphenylsilyl, tert-butyldimethylsilyl, tert-butyldiethylsilyl), a $C_{2-6}$ alkenyl group (e.g., 1-allyl) and the like can be mentioned. These groups are optionally substituted by 1 to 3 halogen atoms (e.g., fluorine, chlorine, bromine, iodine), a $C_{1-6}$ alkoxy group (e.g., methoxy, ethoxy, propoxy), a nitro group and the like.

X is preferably a bond or —$NR^5$— ($R^5$ is as defined above), more preferably a bond.

Y is preferably an oxygen atom or —$NR^5$— ($R^5$ is as defined above), more preferably an oxygen atom.

V is preferably a bond, an oxygen atom, —SO—, —$SO_2$—, —$CR^3(OR^4)$—, —$NR^5$—, —$CSNR^6$— or —$CONR^6NR^7$— ($R^3$, $R^4$, $R^5R^7$ are as defined above). Here, $R^3$ is preferably a hydrogen atom, $R^4$ is preferably a hydrogen atom or a hydroxyl-protecting group, $R^5$ is preferably a hydrogen atom, $R^6$ and $R^7$ are preferably hydrogen atoms. V is more preferably a bond or an oxygen atom. Of these, a bond is preferable.

In the formula (I), as the "divalent hydrocarbon group having 1 to 20 carbon atoms" represented by Q, for example, a "divalent acyclic hydrocarbon group", a "divalent cyclic hydrocarbon group" and a divalent group obtained by combining one or more kinds of "divalent acyclic hydrocarbon group" and one or more kinds of "divalent cyclic hydrocarbon group" can be mentioned.

Here, as the "divalent acyclic hydrocarbon group", for example, a $C_{1-20}$ alkylene, a $C_{2-20}$ alkenylene, a $C_{2-20}$ alkynylene and the like can be mentioned.

As the "divalent cyclic hydrocarbon group", a divalent group obtained by removing any two hydrogen atoms from a $C_{5-20}$ cycloalkane, a $C_{5-20}$ cycloalkene or a $C_{6-18}$ aromatic hydrocarbon (e.g., benzene, naphthalene, indene, anthracene) and the like can be mentioned. As specific examples, 1,2-cyclopentylene, 1,3-cyclopentylene, 1,2-cyclohexylene, 1,3-cyclohexylene, 1,4-cyclohexylene, 1,2-cycloheptylene, 1,3-cycloheptylene, 1,4-cycloheptylene, 3-cyclohexen-1,4-ylene, 3-cyclohexen-1,2-ylene, 2,5-cyclohexadien-1,4-ylene, 1,2-phenylene, 1,3-phenylene, 1,4-phenylene, 1,4-naphthylene, 1,6-naphthylene, 2,6-naphthylene, 2,7-naphthylene, 1,5-indenylene, 2,5-indenylene and the like can be mentioned.

Q is preferably a divalent hydrocarbon group having 1 to 6 carbon atoms and (1) a $C_{1-6}$ alkylene (e.g., —$CH_2$—, —$(CH_2)_2$—, —$(CH_2)_3$—, —$(CH_2)_4$—, —$(CH_2)_5$—, —$(CH_2)_6$—, —CH($CH_3$)—, —C($CH_3$)$_2$—$(CH(CH_3))_2$—, —$(CH_2)_2C(CH_3)_2$—, —$(CH_2)_3C(CH_3)_2$—);

(2) a $C_{2-6}$ alkenylene (e.g., —CH=CH—, —$CH_2$—CH=CH—, —CH(CH=$CH_2$)—, —C($CH_3$)$_2$—CH=CH—, —$CH_2$—CH=CH—$CH_2$—, —$CH_2$—$CH_2$CH=CH—, —CH=CH—CH=CH—, —CH=CH—$CH_2$—$CH_2$—$CH_2$—); and (3) a $C_{2-6}$ alkynylene (e.g., —C≡C—, —$CH_2$—C≡C—, —$CH_2$—C≡C—$CH_2$—$CH_2$—) and the like are particularly preferable.

Q is more preferably a $C_{1-6}$ alkylene or a $C_{2-6}$ alkenylene, and —$CH_2$—, —$(CH_2)_2$—, —$(CH_2)_3$—, —$(CH_2)_4$—, —CH=CH— and the like are particularly preferable. Q is particularly preferably —$CH_2$—, —$(CH_2)_2$— and the like.

In the formula (I), as the "aromatic ring" of the "aromatic ring optionally further having 1 to 3 substituents" represented by ring A, for example, benzene ring, condensed aromatic hydrocarbon ring, 5- or 6-membered aromatic heterocycle, condensed aromatic heterocycle and the like can be mentioned.

Here, as the "condensed aromatic hydrocarbon ring", for example, a $C_{9-14}$ condensed aromatic hydrocarbon ring and the like can be mentioned. Concretely, naphthalene, indene, fluorene, anthracene and the like can be mentioned.

As the "5- or 6-membered aromatic heterocycle", for example, a 5- or 6-membered aromatic heterocycle containing, besides carbon atoms, 1 to 3 hetero atoms selected from a nitrogen atom, a sulfur atom and an oxygen atom and the like can be mentioned. Concretely, thiophene, furan, pyrrole, imidazole, pyrazole, thiazole, isothiazole, oxazole, isoxazole, pyridine, pyrazine, pyrimidine, pyridazine, 1,2,4-oxadiazole, 1,3,4-oxadiazole, 1,2,4-thiadiazole, 1,3,4-thiadiazole, furazan and the like can be mentioned.

As the "condensed aromatic heterocycle", for example, a 9- to 14-membered (preferably 9- or 10-membered) condensed aromatic heterocycle containing, besides carbon atoms, 1 to 4 hetero atoms selected from a nitrogen atom, a sulfur atom and an oxygen atom and the like can be mentioned. Concretely, benzofuran, benzothiophene, benzimidazole, benzoxazole, benzothiazole, benzisothiazole, naphtho[2,3-b]thiophene, isoquinoline, quinoline, indole, quinoxaline, phenanthridine, phenothiazine, phenoxazine, phthalazine, naphthyridine, quinazoline, cinnoline, carbazole, β-carboline, acridine, phenazine, phthalimide and the like can be mentioned.

The "aromatic ring" is preferably a benzene ring, a 5- or 6-membered aromatic heterocycle (preferably pyridine, oxazole, isoxazole, thiazole, oxadiazole and the like), a 9- or 10-membered condensed aromatic heterocycle (preferably benzofuran and the like) and the like; more preferably a benzene ring.

As the "substituent" of the "aromatic ring optionally further having 1 to 3 substituents" represented by ring A, an optionally substituted aliphatic hydrocarbon group, an optionally substituted aromatic hydrocarbon group, an optionally substituted hydroxy group, a halogen atom, an optionally substituted acyl group and the like can be mentioned. As these substituents, those exemplified as the substituent for $R^1$ are used. The substituents for ring A are preferably a $C_{1-6}$ alkyl group (preferably methyl, ethyl), a $C_{6-14}$ aryl group (preferably phenyl), a hydroxy group, a $C_{1-6}$ alkoxy group (preferably methoxy, ethoxy), a $C_{1-6}$ alkoxy-$C_{1-6}$ alkoxy group (preferably methoxymethoxy), a $C_{7-10}$ aralkyloxy group (preferably benzyloxy), a halogen atom, a carboxyl group, a $C_{1-6}$ alkoxy-carbonyl group (preferably methoxycarbonyl).

The ring A is preferably a benzene ring or a 5- or 6-membered aromatic heterocycle (preferably pyridine or isoxazole; more preferably pyridine), each optionally having 1 or 2 substituents selected from a $C_{1-6}$ alkyl group (preferably methyl, ethyl), a $C_{6-14}$ aryl group (preferably phenyl), a hydroxy group, a $C_{1-6}$ alkoxy group (preferably methoxy, ethoxy), a $C_{1-6}$ alkoxy-$C_{1-6}$ alkoxy group (preferably methoxymethoxy), a $C_{7-10}$ aralkyloxy group (preferably benzyloxy), a halogen atom, a carboxyl group and a $C_{1-6}$ alkoxy-carbonyl group (preferably methoxycarbonyl).

In the formula (I), Z is —$(CH_2)_n$-$Z^1$- or -$Z^1$-$(CH_2)_n$— (n is an integer of 0 to 8, $Z^1$ is a bond, an oxygen atom, a sulfur atom, —CO—, —CS—, —SO—, —$SO_2$—, —$NR^8$—, —$CONR^8$—, —$NR^8CO$—, —$CSNR^8$— or —$NR^8CS$— ($R^8$ is a hydrogen atom or an optionally substituted hydrocarbon group)).

Here, as the "optionally substituted hydrocarbon group" represented by $R^8$, those exemplified for the aforementioned $R^3$ can be mentioned, which is preferably a $C_{1-4}$ alkyl group (e.g., methyl, ethyl, propyl).

$R^8$ is preferably a hydrogen atom or a $C_{1-4}$ alkyl group (e.g., methyl, ethyl, propyl).

n is preferably an integer of 0 to 3, more preferably an integer of 1 to 3.

$Z^1$ is preferably a bond, an oxygen atom, a sulfur atom, —$NR^8$—, —$CONR^8$— or —$NR^8CO$— ($R^8$ is as defined above). Here, $R^8$ is preferably a hydrogen atom or a $C_{1-4}$ alkyl group. $Z^1$ is more preferably an oxygen atom.

Z is preferably —$(CH_2)_n$-$Z^1$-. Here, n is preferably 1, $Z^1$ is preferably an oxygen atom.

In the formula (I), as the "nitrogen-containing heterocycle" represented by ring B, for example, a 5- to 7-membered heterocycle containing, as a ring-constituting atom besides carbon atoms, at least one nitrogen atom, and optionally further containing 1 to 3 hetero atoms selected from an oxygen atom, a sulfur atom and a nitrogen atom, and the like can be mentioned.

As preferable examples of the "nitrogen-containing heterocycle", a nitrogen-containing non-aromatic heterocycle such as pyrrolidine, imidazolidine, pyrazolidine, 1,3-oxazolidine, 1,3-thiazolidine, isoxazolidine, isothiazolidine, piperidine, morpholine, thiomorpholine, piperazine and the like; and a nitrogen-containing aromatic heterocycle such as pyrrole, imidazole, pyrazole, triazole, tetrazole, oxazole, thiazole, isoxazole, isothiazole, pyridine, pyrimidine, pyridazine, pyrazine, triazine and the like can be mentioned.

The "nitrogen-containing heterocycle" represented by ring B is preferably a nitrogen-containing 5-membered aromatic heterocycle, which is more preferably a pyrazole ring, an oxazole ring, a thiazole ring and the like.

The ring B optionally has 1 to 3, preferably 1 or 2, substituent(s) at substitutable position(s). As such substituents, for example, "halogen atom", "nitro group", "optionally substituted heterocyclic group", "optionally substituted acyl group", "optionally substituted amino group", "optionally substituted hydroxy group", "optionally substituted thiol group", "optionally substituted hydrocarbon group" and the like can be mentioned. As these "halogen atom", "optionally substituted heterocyclic group", "optionally substituted acyl group", "optionally substituted amino group", "optionally substituted hydroxy group" and "optionally substituted thiol group", those exemplified as the substituent for $R^1$ can be mentioned. In addition, as the "hydrocarbon group" of the "optionally substituted hydrocarbon group", those exemplified for the aforementioned $R^{15}$ can be mentioned. The "hydrocarbon group" may have 1 to 3 substituents at substitutable positions. As such substituents, for example, a halogen atom (e.g., fluorine, chlorine, bromine, iodine), a hydroxy group, an aromatic heterocyclic group (e.g., pyridyl, oxazolyl, thiazolyl) and the like can be mentioned.

The "substituent" for ring B is preferably a hydrocarbon group, more preferably a $C_{1-10}$ alkyl group (preferably methyl, ethyl); a $C_{7-13}$ aralkyl group (preferably benzyl); a $C_{6-14}$ aryl group (preferably phenyl) optionally substituted by a $C_{1-6}$ alkyl group; and the like.

The ring B is preferably a 5-membered aromatic heterocycle (preferably a pyrazole ring, an oxazole ring or a thiazole ring) optionally having 1 or 2 substituent(s) selected from (1) a $C_{1-10}$ alkyl group (preferably methyl, ethyl), (2) a $C_{7-13}$ aralkyl group (preferably benzyl) and (3) a $C_{6-14}$ aryl group (preferably phenyl) optionally substituted by a $C_{1-6}$ alkyl group.

In the formula (I), as the "divalent hydrocarbon group having 1 to 20 carbon atoms" represented by W, those exemplified for the aforementioned Q can be mentioned. W is preferably a bond, $C_{1-6}$ alkylene or $C_{2-6}$ alkenylene, and particularly, a bond, —$CH_2$—, —$(CH_2)_2$—, —$CH=CH$— and the like are preferable.

In the formula (I), $R^2$ is a hydrogen atom, a cyano group, —$PO(OR^9)(OR^{10})$ ($R^9$ and $R^{10}$ are the same or different and each is a hydrogen atom or an optionally substituted hydrocarbon group, or $R^9$ and $R^{10}$ are optionally bonded to form an optionally substituted ring), —$COR^{11}$ [$R^{11}$ is a hydrogen atom, an optionally substituted hydrocarbon group, an optionally substituted heterocyclic group, —$OR^{12}$ ($R^{12}$ is a hydrogen atom or an optionally substituted hydrocarbon group) or —$NR^{13}R^{14}$ ($R^{13}$ and $R^{14}$ are the same or different and each is a hydrogen atom, an optionally substituted hydrocarbon group, an optionally substituted heterocyclic group, an optionally substituted acyl group or an optionally substituted hydroxy group, or $R^{13}$ and $R^{14}$ are optionally bonded to form an optionally substituted ring)], an optionally substituted hydrocarbon group, or an optionally substituted heterocyclic group.

As the "optionally substituted hydrocarbon group" represented by $R^9$, $R^{10}$, $R^{11}$, $R^{12}$, $R^{13}$ or $R^{14}$, those exemplified for the aforementioned $R^3$ can be mentioned.

The "optionally substituted hydrocarbon group" represented by $R^9$, $R^{10}$, $R^{11}$, $R^{12}$, $R^{13}$ or $R^{14}$ is preferably a $C_{1-4}$ alkyl group and the like. Here, as the $C_{1-4}$ alkyl group, for example, methyl, ethyl, propyl, isopropyl, butyl, isobutyl, sec-butyl, tert-butyl and the like can be mentioned, with preference given to methyl and ethyl.

As the "optionally substituted ring" formed by $R^9$ and $R^{10}$ bonded to each other, together with the adjacent oxygen atom and phosphorus atom", for example, a ring represented by the formula:

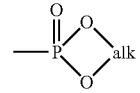

wherein alk is an optionally substituted $C_{1-10}$ alkylene group, can be mentioned.

Here, as the "$C_{1-10}$ alkylene group" of the "optionally substituted $C_{1-10}$ alkylene group" represented by alk, for example, —$CH_2$—, —$(CH_2)_2$—, —$(CH_2)_3$—, —$(CH_2)_4$—, —$(CH_2)_5$—, —$(CH_2)_6$—, —$CH(CH_3)$—, —$C(CH_3)_2$—, —$(CH(CH_3))_2$—, —$(CH_2)_2C(CH_3)_2$—, —$(CH_2)_3C(CH_3)_2$—, —$CH(CH_3)$—$CH_2$—, —$CH_2$—$CH(CH_3)$—$CH_2$—, —$CH_2$—$C(CH_3)_2$—$CH_2$—, —$CH_2$—$CH(CH_2CH_3)$—$CH_2$—, —$CH(CH_3)$—$CH_2$—$CH(CH_3)$— and the like can be mentioned.

The "$C_{1-10}$ alkylene group" may have 1 to 3, preferably 1 or 2 substituents at substitutable position(s). As such substituent, for example, a hydroxy group, a halogen atom (e.g., fluorine, chlorine, bromine, iodine) and the like can be mentioned.

$R^9$ and $R^{10}$ are the same or different and each is preferably a hydrogen atom or a $C_{1-4}$ alkyl group.

As the "optionally substituted heterocyclic group" represented by $R^{11}$, those exemplified as the substituents for $R^1$ can be mentioned.

$R^{11}$ is preferably a hydrogen atom or a $C_{1-4}$ alkyl group.

$R^{12}$ is preferably a hydrogen atom or a $C_{1-4}$ alkyl group optionally substituted by a $C_{1-6}$ alkyl-carbonyloxy group.

As the "optionally substituted heterocyclic group", "optionally substituted acyl group" and "optionally substituted hydroxy group" represented by $R^{13}$ or $R^{14}$, those exemplified as the substituent for $R^1$ can be mentioned.

As the ring formed by $R^{13}$ and $R^{14}$ bonded to each other, together with the adjacent nitrogen atom, for example, a 5- to 7-membered nitrogen-containing heterocycle can be mentioned. As preferable examples of the 5- to 7-membered nitrogen-containing heterocycle, pyrrolidine, piperidine, hexamethylenimine, morpholine, thiomorpholine, piperazine and the like can be mentioned.

The "ring formed by $R^{13}$ and $R^{14}$ bonded to each other, together with the adjacent nitrogen atom" may be a ring optionally having 1 to 3 substituents at substitutable positions (optionally substituted ring). As such substituent, for example, a halogen atom (e.g., fluorine, chlorine, bromine, iodine), a $C_{1-6}$ alkyl group optionally substituted by 1 to 3 halogen atoms (e.g., fluorine, chlorine, bromine, iodine), a $C_{1-6}$ alkoxy group optionally substituted by 1 to 3 halogen atoms (e.g., fluorine, chlorine, bromine, iodine), a nitro group, a hydroxy group, an amino group and the like can be mentioned.

$R^{13}$ and $R^{14}$ are the same or different and each is preferably a hydrogen atom, a $C_{1-4}$ alkyl group or a $C_{1-6}$ alkoxy group. In addition, $R^{13}$ and $R^{14}$ may be preferably bonded to form a 5- to 7-membered nitrogen-containing heterocycle (preferably morpholine).

As the "optionally substituted hydrocarbon group" represented by $R^2$, the "optionally substituted aliphatic hydrocarbon group" exemplified as the substituent for $R^1$ and the like can be mentioned. The "optionally substituted hydrocarbon group" is preferably a $C_{1-6}$ alkyl group or a $C_{2-6}$ alkenyl group, each optionally substituted by 1 to 3 substituents selected from a cyano group, a nitro group, a hydroxy group, a $C_{1-6}$ alkoxy group and the like, and the like.

As the "optionally substituted hydrocarbon group", a $C_{1-6}$ alkyl group substituted by a divalent 5-membered non-aromatic heterocyclic group (e.g., dioxothiazolidinylidene, dioxooxazolidinylidene) optionally substituted by a $C_{1-6}$ alkyl group, and the like are also preferable.

Furthermore, as the "optionally substituted hydrocarbon group", a $C_{1-6}$ alkyl group or a $C_{2-6}$ alkenyl group, each optionally substituted by a substituent represented by the formula: —PO(OR$^{9a}$)(OR$^{10a}$) (R$^{9a}$ and R$^{10a}$ are the same or different and each is a hydrogen atom or an optionally substituted hydrocarbon group, or R$^{9a}$ and R$^{10a}$ are optionally bonded to form an optionally substituted ring) and the like are also preferable. Here, as the "optionally substituted hydrocarbon group" represented by R$^{9a}$ and R$^{10a}$, and the "optionally substituted ring" formed by R$^{9a}$ and R$^{10a}$ bonded to each other, those similar to the case of the aforementioned $R^9$ and $R^{10}$ can be mentioned. R$^{9a}$ and R$^{10a}$ are preferably a hydrogen atom or a $C_{1-6}$ alkyl group.

Moreover, as the "optionally substituted hydrocarbon group", a $C_{6-14}$ aryl group (preferably phenyl) optionally substituted by a $C_{1-6}$ alkyl group and the like are also preferable.

As the "optionally substituted heterocyclic group" represented by $R^2$, those exemplified as the substituent for $R^1$ can be mentioned. Particularly, a 5- to 7-membered monocyclic heterocyclic group (preferably oxazolyl, oxazolinyl, oxazolidinyl, dioxooxazolidinyl, thiazolyl, thiazolinyl, thiazolidinyl, dioxothiazolidinyl, imidazolyl, oxadiazolyl, thiadiazolyl, triazolyl, pyridyl, pyrazolyl, pyrazinyl) optionally substituted by 1 or 2 substituents selected from (1) a $C_{1-6}$ alkyl group optionally substituted by 1 or 2 substituents selected from a hydroxy group and a $C_{6-14}$ aryl-carbonyloxy group (e.g., benzoyloxy), (2) a carboxyl group, (3) a $C_{1-6}$ alkoxy-carbonyl group and (4) a non-aromatic heterocyclic group (preferably morpholino, piperidino, piperazinyl) and the like are preferable.

The "optionally substituted heterocyclic group" represented by $R^2$ is more preferably a 5- to 7-membered monocyclic heterocyclic group (preferably oxazolyl, thiazolyl, oxadiazolyl, thiadiazolyl, triazolyl, pyridyl, pyrazolyl, pyrazinyl) optionally substituted by a $C_{1-6}$ alkyl group.

$R^2$ is preferably —PO(OR$^9$)(OR$^{10}$) (R$^9$ and R$^{10}$ are as defined above) or an optionally substituted heterocyclic group. Particularly, an optionally substituted heterocyclic group is preferable.

In the formula (I), as preferable combinations of W, V and $R^2$, the following combinations can be mentioned.

(a) W is a bond; V is a bond; $R^2$ is a cyano group, —COR$^{11}$ (R$^{11}$ is as defined above) or an optionally substituted hydrocarbon group.

(b) W is a $C_{2-6}$ alkenylene; V is a bond; $R^2$ is a cyano group or —COR$^{11}$ (R$^{11}$ is as defined above).

(c) W is a $C_{1-6}$ alkylene or a $C_{2-6}$ alkenylene; V is an oxygen atom, —SO—, —SO$_2$—, —CR$^3$ (OR$^4$)—, —NR$^5$—, —CSNR$^6$— or —CONR$^6$NR$^7$— (R$^3$, R$^4$, R$^5$, R$^6$ and R$^7$ are as defined above); $R^2$ is a hydrogen atom.

(d) W is a $C_{1-6}$ alkylene or a $C_{2-6}$ alkenylene; V is a bond; $R^2$ is —PO(OR$^9$)(OR$^{10}$) (R$^9$ and R$^{10}$ are as defined above) or an optionally substituted heterocyclic group.

In the formula (I),

1) —W—V—R$^2$ is not "-Wa-(C=O)—R$^a$ [Wa is a saturated divalent hydrocarbon group having 1 to 20 carbon atoms, R$^a$ is —OR$^b$ (R$^b$ is a hydrogen atom or an optionally substituted hydrocarbon group) or —NR$^c$R$^d$ (R$^c$ and R$^d$ are the same or different and each is a hydrogen atom, an optionally substituted hydrocarbon group, an optionally substituted heterocyclic group or an acyl group, and R$^c$ and R$^d$ are optionally bonded to form an optionally substituted ring, together with the adjacent nitrogen atom)]", 2) ring A and ring B do not have a substituent represented by the formula: -Wa-(C=O)—R$^a$ (Wa and R$^a$ are as defined above), 3) ring B does not have, on a ring-constituting N atom, a substituent represented by the formula:

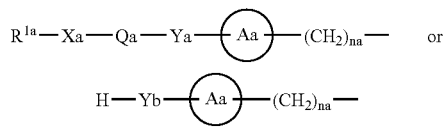

wherein R$^{1a}$ is an optionally substituted hydrocarbon group or an optionally substituted heterocyclic group; Xa and Ya are the same or different and each is a bond, an oxygen atom, a sulfur atom, —CO—, —CS—, —SO—, —SO$_2$—, —CR$^{3a}$(OR$^{4a}$)—, —NR$^{5a}$—, —CONR$^{6a}$— or —NR$^{6a}$CO— (R$^{3a}$ is a hydrogen atom or an optionally substituted hydrocarbon group, R$^{4a}$ is a hydrogen atom or a hydroxyl-protecting group, R$^{5a}$ is a hydrogen atom, an optionally substituted hydrocarbon group or an amino-protecting group, R$^{6a}$ is a hydrogen atom or an optionally substituted hydrocarbon group);

Qa is a divalent hydrocarbon group having 1 to 20 carbon atoms;

ring Aa is an aromatic ring optionally further having 1 to 3 substituents;

na is an integer of 1 to 8;

Yb is an oxygen atom, a sulfur atom or —NR$^{6a}$— (R$^{6a}$ is as defined above)], 4) —X-Q-Y— is not —(CH$_2$)na- (na is an integer of 1 to 8), 5) when the nitrogen-containing heterocycle represented by ring B is a pyridine ring, ring B does not have a further substituent, W is a divalent hydrocarbon group having 1 to 20 carbon atoms, V is a bond, and R$^2$ is —PO(OR$^9$)(OR$^{10}$) or an optionally substituted heterocyclic group, and 6) when R$^1$ has a substituent represented by the formula: -Wa-(C=O)—R$^a$ (Wa and R$^a$ are as defined above), W is a divalent hydrocarbon group having 1 to 20 carbon atoms, V is a bond, and R$^2$ is —PO(OR$^9$)(OR$^{10}$) or an optionally substituted heterocyclic group.

As preferable examples of a compound represented by the formula (I) (hereinafter to be sometimes to be abbreviated as Compound (I)), the following compounds can be mentioned.

[Compound A]

A compound wherein

R$^1$ is oxazolyl, thiazolyl, pyrazolyl, imidazolyl or triazolyl, each optionally having 1 to 3 substituents selected from 1) a C$_{1-6}$ alkyl group optionally having 1 to 3 substituents selected from a C$_{1-6}$ alkoxy group optionally substituted by 1 to 3 halogen atoms, a halogen atom, a nitro group, a hydroxy group and an amino group;

2) a C$_{3-7}$ cycloalkyl group optionally having 1 to 3 substituents selected from a C$_{1-6}$ alkyl group optionally substituted by 1 to 3 halogen atoms, a C$_{1-6}$ alkoxy group optionally substituted by 1 to 3 halogen atoms, a halogen atom, a nitro group, a hydroxy group and an amino group;

3) a C$_{6-14}$ aryl group optionally having 1 to 3 substituents selected from a C$_{1-6}$ alkyl group optionally substituted by 1 to 3 substituents selected from a halogen atom, a carboxyl group, a carbamoyl group and a C$_{1-6}$ alkoxy-carbonyl group;

a C$_{1-6}$ alkoxy group optionally substituted by 1 to 3 substituents selected from a halogen atom, a carboxyl group, a carbamoyl group and a C$_{1-6}$ alkoxy-carbonyl group;

a halogen atom; a hydroxy group; a C$_{1-6}$ alkylsulfonyloxy group; an amino group; a carboxyl group; a carbamoyl group; and a C$_{1-6}$ alkoxy-carbonyl group;

4) a heterocyclic group (preferably an aromatic heterocyclic group such as furyl, thienyl, pyridyl, pyrazinyl and the like; and a non-aromatic heterocyclic group such as piperidino, morpholino and the like) optionally having 1 to 3 substituents selected from a C$_{1-6}$ alkyl group optionally substituted by 1 to 3 substituents selected from a halogen atom, a carboxyl group, a carbamoyl group and a C$_{1-6}$ alkoxy-carbonyl group;

a C$_{1-6}$ alkoxy group optionally substituted by 1 to 3 substituents selected from a halogen atom, a carboxyl group, a carbamoyl group and a C$_{1-6}$ alkoxy-carbonyl group;

a halogen atom; a hydroxy group; a C$_{1-6}$ alkylsulfonyloxy group; an amino group; a carboxyl group; a carbamoyl group; and a C$_{1-6}$ alkoxy-carbonyl group;

and the like

X is a bond;

Q is a C$_{1-6}$ alkylene or a C$_{2-6}$ alkenylene;

Y is an oxygen atom;

ring A is a benzene ring or 5- or 6-membered aromatic heterocycle (preferably pyridine), each optionally having 1 or 2 substituents selected from a C$_{1-6}$ alkyl group, a C$_{6-14}$ aryl group, a hydroxy group, a C$_{1-6}$ alkoxy group, a C$_{1-6}$ alkoxy-C$_{1-6}$ alkoxy group, a C$_{7-10}$ aralkyloxy group, a halogen atom, a carboxyl group and a C$_{1-6}$ alkoxy-carbonyl group;

Z is —(CH$_2$)$_n$-Z$^1$- or -Z$^1$-(CH$_2$)$_n$—, n is an integer of 1 to 3, Z$^1$ is an oxygen atom;

ring B is a 5-membered aromatic heterocycle (preferably a pyrazole ring, an oxazole ring or a thiazole ring) optionally having 1 or 2 substituent(s) selected from a C$_{1-10}$ alkyl group, a C$_{7-13}$ aralkyl group and a C$_{6-14}$ aryl group;

W is a bond;

V is a bond; and

R$^2$ is a cyano group; —COR$^{11}$ (R$^{11}$ is a hydrogen atom or a C$_{1-4}$ alkyl group); or a C$_{1-6}$ alkyl group or a C$_{2-6}$ alkenyl group optionally substituted by 1 to 3 substituents selected from a cyano group, a nitro group, a hydroxy group, a C$_{1-6}$ alkoxy group, —PO(OR$^{9a}$)(OR$^{10a}$) (R$^{9a}$ and R$^{10a}$ are the same or different and each is a hydrogen atom or a C$_{1-6}$ alkyl group) and the like.

[Compound B]

A compound wherein

R$^1$ is oxazolyl, thiazolyl, pyrazolyl, imidazolyl or triazolyl, each optionally having 1 to 3 substituents selected from 1) a C$_{1-6}$ alkyl group optionally having 1 to 3 substituents selected from a C$_{1-6}$ alkoxy group optionally substituted by 1 to 3 halogen atoms, a halogen atom, a nitro group, a hydroxy group and an amino group;

2) a C$_{3-7}$ cycloalkyl group optionally having 1 to 3 substituents selected from a C$_{1-6}$ alkyl group optionally substituted by 1 to 3 halogen atoms, a C$_{1-6}$ alkoxy group optionally substituted by 1 to 3 halogen atoms, a halogen atom, a nitro group, a hydroxy group and an amino group;

3) a C$_{6-14}$ aryl group optionally having 1 to 3 substituents selected from a C$_{1-6}$ alkyl group optionally substituted by 1 to 3 substituents selected from a halogen atom, a carboxyl group, a carbamoyl group and a C$_{1-6}$ alkoxy-carbonyl group;

a C$_{1-6}$ alkoxy group optionally substituted by 1 to 3 substituents selected from a halogen atom, a carboxyl group, a carbamoyl group and a C$_{1-6}$ alkoxy-carbonyl group;

a halogen atom; a hydroxy group; a C$_{1-6}$ alkylsulfonyloxy group; an amino group; a carboxyl group; a carbamoyl group; and a C$_{1-6}$ alkoxy-carbonyl group;

4) a heterocyclic group (preferably an aromatic heterocyclic group such as furyl, thienyl, pyridyl, pyrazinyl and the like; and a non-aromatic heterocyclic group such as piperidino, morpholino and the like) optionally having 1 to 3 substituents selected from a C$_{1-6}$ alkyl group optionally substituted by 1 to 3 substituents selected from a halogen atom, a carboxyl group, a carbamoyl group and a C$_{1-6}$ alkoxy-carbonyl group;

a C$_{1-6}$ alkoxy group optionally substituted by 1 to 3 substituents selected from a halogen atom, a carboxyl group, a carbamoyl group and a C$_{1-6}$ alkoxy-carbonyl group;

a halogen atom; a hydroxy group; a C$_{1-6}$ alkylsulfonyloxy group; an amino group; a carboxyl group; a carbamoyl group; and a C$_{1-6}$ alkoxy-carbonyl group;

and the like

X is a bond;

Q is a C$_{1-6}$ alkylene or a C$_{2-6}$ alkenylene;

Y is an oxygen atom;

ring A is a benzene ring or a 5- or 6-membered aromatic heterocycle (preferably pyridine), each optionally having 1 or 2 substituents selected from a C$_{1-6}$ alkyl group, a C$_{6-14}$ aryl group, a hydroxy group, a C$_{1-6}$ alkoxy group, a C$_{1-6}$ alkoxy-$C_{1-6}$ alkoxy group, a $C_{7-10}$ aralkyloxy group, a halogen atom, a carboxyl group and a $C_{1-6}$ alkoxy-carbonyl group;

Z is —$(CH_2)$-$Z^1$- or -$Z^1$-$(CH_2)_n$—, n is an integer of 1 to 3, $Z^1$ is an oxygen atom;

ring B is a 5-membered aromatic heterocycle (preferably a pyrazole ring, an oxazole ring or a thiazole ring) optionally having 1 or 2 substituent(s) selected from a $C_{1-10}$ alkyl group, a $C_{7-13}$ aralkyl group and a $C_{6-14}$ aryl group;

W is a $C_{2-6}$ alkenylene;

V is a bond; and $R^2$ is a cyano group or —$COR^{11}$ ($R^{11}$ is a hydrogen atom or a $C_{1-4}$ alkyl group).

[Compound C]

A compound wherein $R^1$ is oxazolyl, thiazolyl, pyrazolyl, imidazolyl or triazolyl, each optionally having 1 to 3 substituents selected from 1) a $C_{1-6}$ alkyl group optionally having 1 to 3 substituents selected from a $C_{1-6}$ alkoxy group optionally substituted by 1 to 3 halogen atoms, a halogen atom, a nitro group, a hydroxy group and an amino group;

2) a $C_{3-7}$ cycloalkyl group optionally having 1 to 3 substituents selected from a $C_{1-6}$ alkyl group optionally substituted by 1 to 3 halogen atoms, a $C_{1-6}$ alkoxy group optionally substituted by 1 to 3 halogen atoms, a halogen atom, a nitro group, a hydroxy group and an amino group;

3) a $C_{6-14}$ aryl group optionally having 1 to 3 substituents selected from a $C_{1-6}$ alkyl group optionally substituted by 1 to 3 substituents selected from a halogen atom, a carboxyl group, a carbamoyl group and a $C_{1-6}$ alkoxy-carbonyl group;

a $C_{1-6}$ alkoxy group optionally substituted by 1 to 3 substituents selected from a halogen atom, a carboxyl group, a carbamoyl group and a $C_{1-6}$ alkoxy-carbonyl group;

a halogen atom; a hydroxy group; a $C_{1-6}$ alkylsulfonyloxy group; an amino group; a carboxyl group; a carbamoyl group; and a $C_{1-6}$ alkoxy-carbonyl group;

4) a heterocyclic group (preferably an aromatic heterocyclic group such as furyl, thienyl, pyridyl, pyrazinyl and the like; and a non-aromatic heterocyclic group such as piperidino, morpholino and the like) optionally having 1 to 3 substituents selected from a $C_{1-6}$ alkyl group optionally substituted by 1 to 3 substituents selected from a halogen atom, a carboxyl group, a carbamoyl group and a $C_{1-6}$ alkoxy-carbonyl group;

a $C_{1-6}$ alkoxy group optionally substituted by 1 to 3 substituents selected from a halogen atom, a carboxyl group, a carbamoyl group and a $C_{1-6}$ alkoxy-carbonyl group;

a halogen atom; a hydroxy group; a $C_{1-6}$ alkylsulfonyloxy group; an amino group; a carboxyl group; a carbamoyl group; and a $C_{1-6}$ alkoxy-carbonyl group;

and the like;

X is a bond;

Q is a $C_{1-6}$ alkylene or a $C_{2-6}$ alkenylene;

Y is an oxygen atom;

ring A is a benzene ring or a 5- or 6-membered aromatic heterocycle (preferably pyridine), each optionally having 1 or 2 substituents selected from a $C_{1-6}$ alkyl group, a $C_{6-14}$ aryl group, a hydroxy group, a $C_{1-6}$ alkoxy group, a $C_{1-6}$ alkoxy-$C_{1-6}$ alkoxy group, a $C_{7-10}$ aralkyloxy group, a halogen atom, a carboxyl group and a $C_{1-6}$ alkoxy-carbonyl group;

Z is —$(CH_2)$-$Z^1$- or -$Z^1$-$(CH_2)_n$—, n is an integer of 1 to 3, $Z^1$ is an oxygen atom;

ring B is a 5-membered aromatic heterocycle (preferably a pyrazole ring, an oxazole ring or a thiazole ring) optionally having 1 or 2 substituent(s) selected from a $C_{1-10}$ alkyl group, a $C_{7-13}$ aralkyl group and a $C_{6-14}$ aryl group;

W is a $C_{1-6}$ alkylene or a $C_{2-6}$ alkenylene;

V is an oxygen atom, —SO—, —$SO_2$—, —$CR^3(OR^4)$—, —$NR^5$—, —$CSNR^6$— or —$CONR^6NR^7$— ($R^3$, $R^5$, $R^6$ and $R^7$ are each a hydrogen atom, $R^4$ is a hydrogen atom or a hydroxyl-protecting group); and $R^2$ is a hydrogen atom.

[Compound D]

A compound wherein $R^1$ is oxazolyl, thiazolyl, pyrazolyl, imidazolyl or triazolyl, each optionally having 1 to 3 substituents selected from 1) a $C_{1-6}$ alkyl group optionally having 1 to 3 substituents selected from a $C_{1-6}$ alkoxy group optionally substituted by 1 to 3 halogen atoms, a halogen atom, a nitro group, a hydroxy group and an amino group;

2) a $C_{3-7}$ cycloalkyl group optionally having 1 to 3 substituents selected from a $C_{1-6}$ alkyl group optionally substituted by 1 to 3 halogen atoms, a $C_{1-6}$ alkoxy group optionally substituted by 1 to 3 halogen atoms, a halogen atom, a nitro group, a hydroxy group and an amino group;

3) a $C_{6-14}$ aryl group optionally having 1 to 3 substituents selected from a $C_{1-6}$ alkyl group optionally substituted by 1 to 3 substituents selected from a halogen atom, a carboxyl group, a carbamoyl group and a $C_{1-6}$ alkoxy-carbonyl group;

a $C_{1-6}$ alkoxy group optionally substituted by 1 to 3 substituents selected from a halogen atom, a carboxyl group, a carbamoyl group and a $C_{1-6}$ alkoxy-carbonyl group;

a halogen atom; a hydroxy group; a $C_{1-6}$ alkylsulfonyloxy group; an amino group; a carboxyl group; a carbamoyl group; and a $C_{1-6}$ alkoxy-carbonyl group;

4) a heterocyclic group (preferably an aromatic heterocyclic group such as furyl, thienyl, pyridyl, pyrazinyl and the like; and a non-aromatic heterocyclic group such as piperidino, morpholino and the like) optionally having 1 to 3 substituents selected from a $C_{1-6}$ alkyl group optionally substituted by 1 to 3 substituents selected from a halogen atom, a carboxyl group, a carbamoyl group and a $C_{1-6}$ alkoxy-carbonyl group;

a $C_{1-6}$ alkoxy group optionally substituted by 1 to 3 substituents selected from a halogen atom, a carboxyl group, a carbamoyl group and a $C_{1-6}$ alkoxy-carbonyl group;

a halogen atom; a hydroxy group; a $C_{1-6}$ alkylsulfonyloxy group; an amino group; a carboxyl group; a carbamoyl group; and a $C_{1-6}$ alkoxy-carbonyl group;

and the like;

X is a bond;

Q is a $C_{1-6}$ alkylene or a $C_{2-6}$ alkenylene;

Y is an oxygen atom;

ring A is a benzene ring or 5- or 6-membered aromatic heterocycle (preferably pyridine), each optionally having 1 or 2 substituents selected from a $C_{1-6}$ alkyl group, a $C_{6-14}$ aryl group, a hydroxy group, a $C_{1-6}$ alkoxy group, a $C_{1-6}$ alkoxy-$C_{1-6}$ alkoxy group, a $C_{7-10}$ aralkyloxy group, a halogen atom, a carboxyl group and a $C_{1-6}$ alkoxy-carbonyl group;

Z is —$(CH_2)_n$-$Z^1$- or -$Z^1$-$(CH_2)_n$—, n is an integer of 1 to 3, $Z^1$ is an oxygen atom;

ring B is a 5-membered aromatic heterocycle (preferably a pyrazole ring, an oxazole ring or a thiazole ring) optionally having 1 or 2 substituent(s) selected from a $C_{1-10}$ alkyl group, a $C_{7-13}$ aralkyl group and a $C_{6-14}$ aryl group;

W is a $C_{1-6}$ alkylene or a $C_{2-6}$ alkenylene;

V is a bond; and $R^2$ is —PO(OR$^9$)(OR$^{10}$) (R$^9$ and R$^{10}$ are each a hydrogen atom or a C$_{1-4}$ alkyl group); or a 5- to 7-membered monocyclic heterocyclic group (preferably oxazolyl, oxazolinyl, oxazolidinyl, dioxooxazolidinyl, thiazolyl, thiazolinyl, thiazolidinyl, dioxothiazolidinyl, imidazolyl, oxadiazolyl, thiadiazolyl, triazolyl, pyridyl) optionally substituted by 1 or 2 substituents selected from a C$_{1-6}$ alkyl group, a carboxyl group and a C$_{1-6}$ alkoxy-carbonyl group.

[Compound E]

A compound wherein

R$^1$ is oxazolyl, thiazolyl, pyrazolyl, imidazolyl or triazolyl, each optionally having 1 to 3 substituents elected from 1) a C$_{1-6}$ alkyl group or a C$_{2-6}$ alkenyl group, each optionally having 1 to 3 substituents selected from a C$_{1-6}$ alkoxy group optionally substituted by 1 to 3 halogen atoms, a halogen atom, a nitro group, a hydroxy group, an amino group, a carboxyl group, and a C$_{1-6}$ alkoxy-carbonyl group;

2) a C$_{3-7}$ cycloalkyl group optionally having 1 to 3 substituents selected from a C$_{1-6}$ alkyl group optionally substituted by 1 to 3 halogen atoms, a C$_{1-6}$ alkoxy group optionally substituted by 1 to 3 halogen atoms, a halogen atom, a nitro group, a hydroxy group and an amino group;

3) a C$_{6-14}$ aryl group optionally having 1 to 3 substituents selected from a C$_{1-6}$ alkyl group optionally substituted by 1 to 3 substituents selected from a halogen atom, a hydroxy group, a carboxyl group, a carbamoyl group and a C$_{1-6}$ alkoxy-carbonyl group;

a C$_{1-6}$ alkoxy group optionally substituted by 1 to 3 substituents selected from a halogen atom, a carboxyl group, a carbamoyl group and a C$_{1-6}$ alkoxy-carbonyl group;

a halogen atom; a hydroxy group; a C$_{1-6}$ alkylsulfonyloxy group; an amino group optionally substituted by a C$_{1-6}$ alkylsulfonyl group; a carboxyl group; a carbamoyl group optionally substituted by a C$_{1-6}$ alkylsulfonyl group; a C$_{1-6}$ alkoxy-carbonyl group; a cyano group; an aromatic heterocyclic group (preferably tetrazolyl); a non-aromatic heterocyclic group (preferably oxodihydrooxadiazolyl, oxodihydrothiadiazolyl, thioxodihydrooxadiazolyl, thioxodihydrothiadiazolyl, oxideoxathiadiazolyl); an amidino group optionally substituted by a hydroxy group;

4) a heterocyclic group (preferably an aromatic heterocyclic group such as furyl, thienyl, pyridyl, pyrazinyl and the like; a non-aromatic heterocyclic group such as piperidino, morpholino and the like) optionally having 1 to 3 substituents selected from a C$_{1-6}$ alkyl group optionally substituted by 1 to 3 substituents selected from a halogen atom, a carboxyl group, a carbamoyl group and a C$_{1-6}$ alkoxy-carbonyl group;

a C$_{1-6}$ alkoxy group optionally substituted by 1 to 3 substituents selected from a halogen atom, a carboxyl group, a carbamoyl group and a C$_{1-6}$ alkoxy-carbonyl group;

a halogen atom; a hydroxy group; a C$_{1-6}$ alkylsulfonyloxy group; an amino group optionally substituted by a C$_{1-6}$ alkylsulfonyl group; a carboxyl group; a carbamoyl group optionally substituted by a C$_{1-6}$ alkylsulfonyl group; a C$_{1-6}$ alkoxy-carbonyl group; a cyano group; an aromatic heterocyclic group (preferably tetrazolyl); a non-aromatic heterocyclic group (preferably oxodihydrooxadiazolyl, oxodihydrothiadiazolyl, thioxodihydrooxadiazolyl, thioxodihydrothiadiazolyl, oxideoxathiadiazolyl); an amidino group optionally substituted by a hydroxy group; and the like;

X is a bond;

Q is a C$_{1-6}$ alkylene or a C$_{2-6}$ alkenylene;

Y is an oxygen atom;

ring A is a benzene ring or a 5- or 6-membered aromatic heterocycle (preferably pyridine or isoxazole), each optionally having 1 or 2 substituents selected from a C$_{1-6}$ alkyl group, a C$_{6-14}$ aryl group, a hydroxy group, a C$_{1-6}$ alkoxy group, a C$_{1-6}$ alkoxy-C$_{1-6}$ alkoxy group, a C$_{7-10}$ aralkyloxy group, a halogen atom, a carboxyl group and a C$_{1-6}$ alkoxy-carbonyl group;

Z is —(CH$_2$)$_n$-Z$^1$- or -Z$^1$-(CH$_2$)$_n$—, and n is an integer of 1 to 3, Z$^1$ is an oxygen atom;

ring B is a 5-membered aromatic heterocycle (preferably a pyrazole ring, an oxazole ring or a thiazole ring) optionally having 1 or 2 substituent(s) selected from (1) a C$_{1-10}$ alkyl group, (2) a C$_{7-13}$ aralkyl group, and (3) a C$_{6-14}$ aryl group optionally substituted by a C$_{1-6}$ alkyl group;

W is a C$_{1-6}$ alkylene or a C$_{2-6}$ alkenylene;

V is a bond; and

R$^2$ is (1) —PO(OR$^9$)(OR$^{10}$) (R$^9$ and R$^{10}$ are each a hydrogen atom or a C$_{1-4}$ alkyl group); or (2) a 5- to 7-membered monocyclic heterocyclic group (preferably oxazolyl, oxazolinyl, oxazolidinyl, dioxooxazolidinyl, thiazolyl, thiazolinyl, thiazolidinyl, dioxothiazolidinyl, imidazolyl, oxadiazolyl, thiadiazolyl, triazolyl, pyridyl, pyrazolyl, pyrazinyl) optionally substituted by 1 or 2 substituents selected from 1) a C$_{1-6}$ alkyl group optionally substituted by 1 or 2 substituents selected from a hydroxy group and a C$_{6-14}$ aryl-carbonyloxy group, 2) a carboxyl group, 3) a C$_{1-6}$ alkoxy-carbonyl group and 4) a non-aromatic heterocyclic group (preferably morpholino, piperidino, piperazinyl).

[Compound F]

A compound wherein

R$^1$ is oxazolyl, thiazolyl or triazolyl, each optionally having 1 to 3 substituents selected from 1) a C$_{1-6}$ alkyl group or a C$_{2-6}$ alkenyl group, each optionally having 1 to 3 substituents selected from a carboxyl group and a C$_{1-6}$ alkoxy-carbonyl group;

2) a C$_{6-14}$ aryl group optionally having 1 to 3 substituents selected from a C$_{1-6}$ alkyl group optionally substituted by 1 to 3 substituents selected from a carboxyl group and a C$_{1-6}$ alkoxy-carbonyl group;

a C$_{1-6}$ alkoxy group optionally substituted by 1 to 3 substituents selected from a carboxyl group and a C$_{1-6}$ alkoxy-carbonyl group;

a carboxyl group; a C$_{1-6}$ alkoxy-carbonyl group; a cyano group; an aromatic heterocyclic group (preferably tetrazolyl); a non-aromatic heterocyclic group (preferably oxodihydrooxadiazolyl, oxodihydrothiadiazolyl, thioxodihydrooxadiazolyl, thioxodihydrothiadiazolyl, oxideoxathiadiazolyl);

3) a heterocyclic group (preferably an aromatic heterocyclic group such as furyl, thienyl, pyridyl, pyrazinyl and the like; a non-aromatic heterocyclic group such as piperidino, morpholino and the like) optionally having 1 to 3 substituents selected from a C$_{1-6}$ alkyl group optionally substituted by 1 to 3 substituents selected from a carboxyl group and a C$_{1-6}$ alkoxy-carbonyl group;

a C$_{1-6}$ alkoxy group optionally substituted by 1 to 3 substituents selected from a carboxyl group and a C$_{1-6}$ alkoxy-carbonyl group;

a carboxyl group; a C$_{1-6}$ alkoxy-carbonyl group; cyano group; an aromatic heterocyclic group (preferably tetrazolyl); a non-aromatic heterocyclic group (preferably oxodihydrooxadiazolyl, oxodihydrothiadiazolyl, thioxodihydrooxadiazolyl, thioxodihydrothiadiazolyl, oxideoxathiadiazolyl);

and the like;

X is a bond;

Q is a $C_{1-6}$ alkylene;

Y is an oxygen atom;

ring A is a benzene ring optionally having 1 or 2 substituent(s) selected from a $C_{1-6}$ alkyl group, a $C_{6-14}$ aryl group, a hydroxy group, a $C_{1-6}$ alkoxy group, a $C_{1-6}$ alkoxy-$C_{1-6}$ alkoxy group, a $C_{7-10}$ aralkyloxy group, a halogen atom, a carboxyl group and a $C_{1-6}$ alkoxy-carbonyl group;

Z is —$(CH_2)_n$-$Z^1$-, and n is an integer of 1 to 3, $Z^1$ is an oxygen atom;

ring B is a pyrazole ring optionally having 1 or 2 substituent(s) selected from (1) a $C_{1-10}$ alkyl group, (2) a $C_{7-13}$ aralkyl group, and (3) a $C_{6-14}$ aryl group optionally substituted by a $C_{1-6}$ alkyl group;

W is a $C_{1-6}$ alkylene or a $C_{2-6}$ alkenylene;

V is a bond; and $R^2$ is (1) —$PO(OR^9)(OR^{10})$ ($R^9$ and $R^{10}$ are each a hydrogen atom or a $C_{1-4}$ alkyl group); or (2) a 5- to 7-membered monocyclic heterocyclic group (preferably oxazolyl, oxazolinyl, oxazolidinyl, dioxooxazolidinyl, thiazolyl, thiazolinyl, thiazolidinyl, dioxothiazolidinyl, imidazolyl, oxadiazolyl, thiadiazolyl, triazolyl, pyridyl, pyrazolyl, pyrazinyl) optionally substituted by 1 or 2 substituents selected from 1) a $C_{1-6}$ alkyl group optionally substituted by 1 or 2 substituents selected from a hydroxyl group and a $C_{6-14}$-aryl-carbonyloxy group, 2) a carboxyl group, 3) a $C_{1-6}$ alkoxy-carbonyl group and 4) a non-aromatic heterocyclic group (preferably morpholino, piperidino, piperazinyl).

The salt of Compound (I) is preferably a pharmacologically acceptable salt, and is exemplified by salts with inorganic bases, salts with organic bases, salts with inorganic acids, salts with organic acids, and salts with basic or acidic amino acids, and the like.

Preferable examples of the salts with inorganic bases include alkali metal salts such as sodium salts, potassium salts and lithium salts; alkaline earth metal salts such as calcium salts and magnesium salts; aluminum salts and ammonium salts; and the like.

Preferable examples of the salts with organic bases include salts with trimethylamine, triethylamine, pyridine, picoline, ethanolamine, diethanolamine, triethanolamine, dicyclohexylamine, N,N-dibenzylethylenediamine and the like.

Preferable examples of the salts with inorganic acids include salts with hydrochloric acid, hydrobromic acid, nitric acid, sulfuric acid, phosphoric acid and the like.

Preferable examples of the salts with organic acids include salts with formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid and the like.

Preferable examples of the salts with basic amino acids include salts with arginine, lysine, ornithine and the like.

Preferable examples of the salts with acidic amino acids include salts with aspartic acid, glutamic acid and the like.

A prodrug of Compound (I) refers to a compound capable of being converted to Compound (I) by reactions of an enzyme, gastric juice and the like, under physiological conditions in vivo, i.e., a compound capable of being converted to Compound (I) upon enzymatic oxidation, reduction, hydrolysis and the like, or a compound capable of being converted to Compound (I) upon hydrolysis and the like by gastric juice and the like. Examples of the prodrugs of Compound (I) include compounds derived by acylation, alkylation or phosphorylation of the amino group of Compound (I) (e.g., compounds derived by eicosanoylation, alanylation, pentylaminocarbonylation, (5-methyl-2-oxo-1,3-dioxolen-4-yl)methoxycarbonylation, tetrahydrofuranylation, tetrahydropyranylation, pyrrolidylmethylation, pivaloyloxymethylation or tert-butylation of the amino group of Compound (I)); compounds derived by acylation, alkylation, phosphorylation or boration of the hydroxyl group of Compound (I) (e.g.; compounds derived by acetylation, palmitoylation, propanoylation, pivaloylation, succinylation, fumarylation, alanylation, dimethylaminomethylcarbonylation or tetrahydropyranylation of the hydroxyl group of Compound (I)); compounds derived by esterification or amidation of the carboxyl group of Compound (I) (e.g., compounds derived by ethyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl)methyl esterification, cyclohexyloxycarbonylethyl esterification or methylamidation of the carboxyl group of Compound (I)); etc.

The prodrug of Compound (I) may be one capable of being converted to Compound (I) under physiological conditions, as described in "Iyakuhin No Kaihatsu (Development of Drugs)", vol. 7, Molecular Designing, published by Hirokawa Shoten, 1990, pages 163-198.

In addition, Compound (I) may be labeled with an isotope (e.g., $^3H$, $^{14}C$, $^{35}S$, $^{125}I$).

Furthermore, Compound (I) may be anhydrides or hydrates.

Compound (I), a salt thereof or a prodrug thereof (hereinafter also simply referred to as "compound of the present invention") have low toxicity and can be used as an agent for the prophylaxis or treatment of various diseases mentioned below in mammals (e.g., humans, mice, rats, rabbits, dogs, cats, bovines, horses, swine, monkeys), as such or in the form of pharmaceutical compositions prepared by admixing with a pharmacologically acceptable carrier and the like.

Here, the pharmacologically acceptable carriers are exemplified by various organic or inorganic carrier substances in common use as materials for pharmaceutical preparations, and they are formulated as excipients, lubricants, binders, and disintegrants for solid preparations; solvents, solubilizers, suspending agents, isotonizing agents, buffers, soothing agents for liquid preparations; etc. In addition, other additives for pharmaceutical preparations, such as antiseptics, antioxidants, coloring agents, and sweetening agents, may be also used as necessary.

Preferable examples of the excipients include lactose, saccharose, D-mannitol, D-sorbitol, starch, gelatinized starch, dextrin, crystalline cellulose, low-substituted hydroxypropylcellulose, carboxymethylcellulose sodium, gum arabic, dextrin, pullulan, light silicic anhydride, synthetic aluminum silicate, magnesium metasilicate aluminate and the like.

Preferable examples of the lubricants include magnesium stearate, calcium stearate, talc, colloidal silica and the like.

Preferable examples of the binders include gelatinized starch, sucrose, gelatin, gum arabic, methylcellulose, carboxymethylcellulose, carboxymethylcellulose sodium, crystalline cellulose, saccharose, D-mannitol, trehalose, dextrin, pullulan, hydroxypropylcellulose, hydroxypropylmethylcellulose, polyvinylpyrrolidone and the like.

Preferable examples of the disintegrants include lactose, saccharose, starch, carboxymethylcellulose, carboxymethylcellulose calcium, croscarmellose sodium, carboxymethyl starch sodium, light silicic anhydride, low-substituted hydroxypropylcellulose and the like.

Preferable examples of the solvents include water for injection, physiological saline, Ringer's solution, alcohol, propylene glycol, polyethylene glycol, sesame oil, corn oil, olive oil, cottonseed oil and the like.

Preferable examples of the solubilizers include polyethylene glycol, propylene glycol, D-mannitol, trehalose, benzyl benzoate, ethanol, trisaminomethane, cholesterol, triethanolamine, sodium carbonate, sodium citrate, sodium salicylate, sodium acetate and the like.

Preferable examples of the suspending agents include surfactants such as stearyltriethanolamine, sodium lauryl sulfate, laurylaminopropionic acid, lecithin, benzalkonium chloride, benzethonium chloride, monostearic glycerol etc.; hydrophilic polymers such as polyvinyl alcohol, polyvinylpyrrolidone, carboxymethylcellulose sodium, methylcellulose, hydroxymethylcellulose, hydroxyethylcellulose, hydroxypropylcellulose etc.; polysorbates, polyoxyethylene-hardened castor oil and the like.

Preferable examples of the isotonizing agents include sodium chloride, glycerol, D-mannitol, D-sorbitol, glucose and the like.

Preferable examples of the buffers include buffer solutions of phosphates, acetates, carbonates, citrates and the like.

Preferable examples of the soothing agents include benzyl alcohol and the like.

Preferable examples of the antiseptics include p-oxybenzoic acid esters, chlorobutanol, benzyl alcohol, phenethyl alcohol, dehydroacetic acid, sorbic acid and the like.

Preferable examples of the antioxidants include sulfites, ascorbates and the like.

Preferable examples of the coloring agents include food colors such as water-soluble tar colors for food (e.g., Food Color Red Nos. 2 and 3, Food Color Yellow Nos. 4 and 5, Food Color Blue Nos. 1 and 2 etc.), water-insoluble lake colors (e.g., aluminum salts of the aforementioned water-soluble tar colors for food etc.), and natural colors (e.g., β-carotene, chlorophyll, red oxide etc.).

Preferable examples of the sweetening agents include saccharin sodium, dipotassium glycyrrhetinate, aspartame, stevia and the like.

Examples of the dosage forms of the pharmaceutical composition include oral preparations such as tablets (including sublingual tablets and orally disintegrating tablets), capsules (including soft capsules and microcapsules), granules, powders, troches, syrups, emulsions, suspensions etc.; and parenteral preparations such as injections (e.g., subcutaneous injections, intravenous injections, intramuscular injections, intraperitoneal injections etc.), external preparations (e.g., preparations for nasal administration, dermal preparations, ointments etc.), suppositories (e.g., rectal suppositories, vaginal suppositories etc.), pellets, drip infusions, eye drops, pulmonary preparations (inhalants) and the like. These preparations can each be orally or parenterally administered safely. Moreover, these preparations may be release control preparations such as rapid-release preparations or sustained-release preparations (e.g., sustained-release microcapsules and the like) and the like.

The pharmaceutical composition can be prepared by conventional methods in the fields of pharmaceutical manufacturing techniques, such as the methods described in the Japanese Pharmacopoeia. Specific production methods for such preparations are hereinafter described in detail.

An oral preparation, for instance, is produced by adding to the active ingredient, an excipient (e.g., lactose, saccharose, starch, D-mannitol etc.), a disintegrant (e.g., carboxymethylcellulose calcium etc.), a binder (e.g., gelatinized starch, gum arabic, carboxymethylcellulose, hydroxypropylcellulose, polyvinylpyrrolidone etc.) or a lubricant (e.g., talc, magnesium stearate, polyethyleneglycol 6000 etc.), compression molding the obtained mixture, and, if necessary, coating by a method known per se using a coating base for the purpose of taste masking, enteric coating or sustained release.

Examples of the coating base include a sugar coating base, a water-soluble film coating base, an enteric film coating base, a sustained-release film coating base and the like.

As the sugar coating base, saccharose is employed. Further, one or more kinds selected from talc, precipitated calcium carbonate, gelatin, gum arabic, pullulan, carnauba wax and the like may be used in combination.

Examples of the water-soluble film coating base include cellulose polymers such as hydroxypropylcellulose, hydroxypropylmethylcellulose, hydroxyethylcellulose, methylhydroxyethylcellulose; synthetic polymers such as polyvinylacetal diethylaminoacetate, aminoalkyl methacrylate copolymer E [Eudragit E (tradename), Rhom Pharma] and polyvinylpyrrolidone; and polysaccharides such as pullulan.

Examples of the enteric film coating base include cellulose polymers such as hydroxypropylmethylcellulose phthalate, hydroxypropylmethylcellulose acetate succinate, carboxymethylethylcellulose, cellulose acetate phthalate; acrylic acid polymers such as methacrylic acid copolymer L [Eudragit L (tradename), Rhom Pharma], methacrylic acid copolymer LD [Eudragit L-30D55 (tradename), Rhom Pharma], methacrylic acid copolymer S [Eudragit S (tradename), Rhom Pharma]; natural products such as shellac and the like.

Examples of the sustained-release film coating base include cellulose polymers such as ethylcellulose; acrylic acid polymers such as aminoalkyl methacrylate copolymer RS [Eudragit RS (tradename), Rhom Pharma] and an ethyl acrylate-methyl methacrylate copolymer suspension [Eudragit NE (tradename), Rhom Pharma].

Two or more of the above coating bases may be used in admixture in an appropriate ratio. For coating, a shading agent such as titanium oxide or red ferric oxide may be used.

Injections are produced by dissolving, suspending or emulsifying the active ingredient in an aqueous solvent (e.g. distilled water, physiological saline, Ringer's solution etc.) or an oleaginous solvent (e.g. vegetable oils such as olive oil, sesame oil, cotton seed oil, corn oil etc.; propylene glycol etc.), together with a dispersant (e.g. polysorbate 80, polyoxyethylene-hardened castor oil 60 etc.), polyethylene glycol, carboxymethylcellulose, sodium alginate etc.), a preservative (e.g. methylparaben, propylparaben, benzyl alcohol, chlorobutanol, phenol etc.), an isotonizing agent (e.g. sodium chloride, glycerol, D-mannitol, D-sorbitol, glucose etc.) and the like. If desirable, additives such as a solubilizer (e.g. sodium salicylate, sodium acetate etc.), a stabilizer (e.g. human serum albumin etc.), a soothing agent (e.g. benzyl alcohol etc.) and the like, may be used.

The compound of the present invention has an adipose tissue weight decreasing action, a hypoglycemic action, a hypolipidemic action, a hypoinsulinemic action, an insulin resistance improving action, an insulin sensitizing action, and a retinoid-related receptor function regulating action.

The function regulating action here means both an agonist activity and an antagonist activity.

In addition, the term "retinoid-related receptor" used here is classified as a nuclear receptor, and is a DNA-binding transcription factor whose ligand is a signal molecule such as oil-soluble vitamins etc., and may be any of a monomer receptor, a homodimer receptor and a heterodimer receptor.

Here, examples of the monomer receptor include retinoid O receptor (hereinafter also abbreviated as ROR) α (GenBank Accession No. L14611), RORβ (GenBank Accession No. L14160), RORγ (GenBank Accession No. U16997); Rev-erb α (GenBank Accession No. M24898), Rev-erbβ (GenBank Accession No. L31785); ERRα (GenBank Accession No. X51416), ERRβ (GenBank Accession No. X51417); Ftz-FIα (GenBank Accession No. S65876), Ftz-FIβ (GenBank Accession No. M81385); TIx (GenBank Accession No. S77482); GCNF (GenBank Accession No. U14666) and the like.

Examples of the homodimer receptor include homodimers formed by retinoid X receptor (hereinafter also abbreviated as RXR) α (GenBank Accession No. X52773), RXRβ (GenBank Accession No. M84820), RXRγ (GenBank Accession No. U38480); COUPα (GenBank Accession No. X12795), COUPβ (GenBank Accession No. M64497), COUPγ (GenBank Accession No. X12794); TR2α (GenBank Accession No. M29960), TR2β (GenBank Accession No. L27586); or HNF4α (GenBank Accession No. X76930), HNF4γ (GenBank Accession No. Z49826) and the like.

Examples of the heterodimer receptor include heterodimers which are formed by the above-mentioned retinoid X receptor (RXRα, RXRβ or RXRγ) and one receptor selected from retinoid A receptor (hereinafter also abbreviated as RAR) α (GenBank Accession No. X06614), RARβ (GenBank Accession No. Y00291), RARγ (GenBank Accession No. M24857); thyroid hormone receptor (hereinafter also abbreviated as TR) α (GenBank Accession No. M24748), TRβ (GenBank Accession No. M26747); vitamin D receptor (VDR) (GenBank Accession No. J03258); peroxisome proliferator-activated receptor (hereinafter also abbreviated as PPAR) α (GenBank Accession No. L02932), PPARβ (PPAR δ) (GenBank Accession No. U10375), PPARγ (GenBank Accession No. L40904); LXRα (GenBank Accession No. U22662), LXRβ (GenBank Accession No. U14534); FXR (GenBank Accession No. U18374); MB67 (GenBank Accession No. L29263); ONR (GenBank Accession No. X75163); and NURα (GenBank Accession No. L13740), NURβ (GenBank Accession No. X75918) and NURγ (GenBank Accession No. U12767).

The compound of the present invention has an excellent ligand activity, in particular to retinoid X receptors (RXRα, RXRβ, RXRγ) and to peroxisome proliferator-activated receptors (PPARα, PPARβ PPARδ), PPARγ), among the above-mentioned retinoid-related receptors, and is useful as an agonist, a partial agonist, an antagonist or a partial antagonist.

Further, the compound of the present invention has an excellent ligand activity to peroxisome proliferator-activated receptors in heterodimer receptors formed from a retinoid X receptor and a peroxisome proliferator-activated receptor (e.g., heterodimer receptors formed from RXRα and PPARδ, heterodimer receptors formed from RXRα and PPARγ etc.).

Accordingly, the retinoid-related receptor ligand of the present invention can be used preferably as a peroxisome proliferator-activated receptor ligand or a retinoid X receptor ligand.

Moreover, since the compound of the present invention has a superior antagonist activity against peroxisome proliferator-activated receptor γ (PPARγ), it is free of a body weight increasing action. Furthermore, the compound of the present invention suppresses differentiation of a preadipocyte to an adipocyte and decreases adipose tissue weight, based on its PPARγ antagonistic activity. Due to the suppression, the compound of the present invention can improve insulin resistance and lowers the blood glucose level.

The compound of the present invention can be used as, for example, an agent for the prophylaxis or treatment of diabetes mellitus (e.g., type 1 diabetes mellitus, type 2 diabetes mellitus, gestational diabetes mellitus, etc.); an agent for the prophylaxis or treatment of hyperlipidemia (e.g., hypertriglyceridemia, hypercholesterolemia, hypo-high-density-lipoproteinemia, postprandial hyperlipemia etc.); an agent for improving insulin resistance; an insulin sensitizer; an agent for the prophylaxis or treatment of impaired glucose tolerance (IGT); an agent for the prophylaxis or treatment of obesity; an agent for the prophylaxis or treatment of hypertension; and an agent for preventing progress from impaired glucose tolerance to diabetes mellitus.

Regarding diagnostic criteria of diabetes mellitus, new diagnostic criteria were reported by the Japan Diabetes Society in 1999.

According to this report, diabetes mellitus is a condition wherein the fasting blood glucose level (glucose concentration in venous plasma) is not less than 126 mg/dl, the 2-hour value (glucose concentration in venous plasma) of the 75 g oral glucose tolerance test (75 g OGTT) is not less than 200 mg/dl, or the non-fasting blood glucose level (glucose concentration in venous plasma) is not less than 200 mg/dl. In addition, a condition that does not fall within the scope of the above definition of diabetes mellitus, and which is not a "condition wherein the fasting blood glucose level (glucose concentration in venous plasma) is less than 110 mg/dl or the 2-hour value (glucose concentration in venous plasma) of the 75 g oral glucose tolerance test (75 g OGTT) is less than 140 mg/dl" (normal type), is called the "borderline type".

As regards the diagnostic criteria for diabetes mellitus, moreover, new diagnostic criteria were reported by ADA (American Diabetic Association) in 1997 and by WHO in 1998.

According to these reports, diabetes mellitus is a condition where the fasting blood glucose level (glucose concentration in venous plasma) is not less than 126 mg/dl, and the 2-hour value (glucose concentration in venous plasma) of the 75 g oral glucose tolerance test is not less than 200 mg/dl.

In addition, according to the above reports, impaired glucose tolerance is a condition where the fasting blood glucose level (glucose concentration in venous plasma) is less than 126 mg/dl, and the 2-hour value (glucose concentration in venous plasma) of the 75 g oral glucose tolerance test is not less than 140 mg/dl and less than 200 mg/dl. Furthermore, according to the DA report, a condition where the fasting blood glucose level (glucose concentration in venous plasma) is not less than 110 mg/dl and less than 126 mg/dl, is called IFG (impaired fasting glucose). On the other hand, according to the WHO report, a condition of IFG (impaired fasting glucose) as such, where the 2-hour value (glucose concentration in venous plasma) of the 75 g oral glucose tolerance test is less than 140 mg/dl, is called IFG (impaired fasting glycemia).

The compound of the present invention can also be used as an agent for the prophylaxis or treatment of diabetes mellitus, borderline type, impaired glucose tolerance, IFG (impaired fasting glucose) and IFG (impaired fasting glycemia) as defined by the foregoing new diagnostic criteria. Furthermore, the compound of the present invention can be also used to prevent the progression of the borderline type, impaired glucose tolerance, IFG (impaired fasting glucose) or IFG (impaired fasting glycemia) to diabetes mellitus.

The compound of the present invention can be also used as an agent for the prophylaxis or treatment of diabetic complications (e.g., neuropathy, nephropathy, retinopathy, cataract, macroangiopathy, osteopenia, diabetic hyperosmolar coma, infectious diseases (e.g., respiratory infection, urinary tract infection, gastrointestinal tract infection, dermal soft tissue infection, lower limb infection etc.), diabetic gangrene, xerostomia, decreased sense of hearing, cerebrovascular disease, peripheral circulatory disturbance etc.), osteoporosis, cachexia (e.g., carcinomatous cachexia, tuberculous cachexia, diabetic cachexia, hemopathic cachexia, endocrinopathic cachexia, infectious cachexia, cachexia induced by acquired immunodeficiency syndrome), fatty liver, hypertension, polycystic ovary syndrome, renal diseases (e.g., diabetic nephropathy, glomerular nephritis, glomerulosclerosis, nephrotic syndrome, hypertensive nephrosclerosis, terminal renal disorder etc.), muscular dystrophy, myocardiac infarction, angina pectoris, cerebrovascular disease (e.g., cerebral infarction, cerebral apoplexy), insulin resistant syndrome, syndrome X, hyperinsulinemia, hyperinsulinemia-induced sensory disorder, tumor (e.g., leukemia, breast cancer, prostate cancer, skin cancer etc.), irritable bowel syndrome, acute or chronic diarrhea, inflammatory diseases (e.g., Alzheimer's disease, chronic rheumatoid arthritis, spondylitis deformans, osteoarthritis, lumbago, gout, postoperative or traumatic inflammation, swelling, neuralgia, pharyngolaryngitis, cystitis, hepatitis (including non-alcoholic steatohepatitis), pneumonia, pancreatitis, inflammatory colitis, ulcerative colitis), visceral obesity syndrome and the like.

The compound of the present invention possesses a total cholesterol lowering action and enhances a plasma anti-arteriosclerosis index [(HDL cholesterol/total cholesterol)× 100], and therefore, can be used as an agent for the prophylaxis or treatment of arteriosclerosis (e.g., atherosclerosis etc.) and the like.

Also, the compound of the present invention can be used for ameliorating bellyache, nausea, vomiting, or dysphoria in epigastrium, each of which is accompanied by gastrointestinal ulcer, acute or chronic gastritis, biliary dyskinesia, cholecystitis and the like.

Furthermore, the compound of the present invention can control (enhance or inhibit) appetite, and therefore, can be used as a therapeutic agent of leanness and cibophobia (the weight increase in administration subjects suffering from leanness or cibophobia) or a therapeutic agent of obesity.

The compound of the present invention has a TNF-α suppressive effect (effects of reduction of TNF-α production amount and TNF-α activity in tissues of living organisms) and can be also used as an agent for the prophylaxis or treatment of TNF-α mediated inflammatory diseases. Examples of such inflammatory diseases include diabetic complications (e.g., retinopathy, nephropathy, neuropathy, macroangiopathy etc.), rheumatoid arthritis, spondylitis deformans, osteoarthritis, lumbago, gout, postoperative or traumatic inflammation, swelling, neuralgia, pharyngolaryngitis, cystitis, hepatitis, pneumonia, gastric mucosal injury (including aspirin-induced gastric mucosal injury) and the like.

The compound of the present invention has an apoptosis inhibitory activity, and can be used as an agent for the prophylaxis or treatment of diseases mediated by promotion of apoptosis. Examples of the diseases mediated by promotion of apoptosis include viral diseases (e.g., AIDS, fulminant hepatitis etc.), neurodegenerative diseases (e.g., Alzheimer's disease, Parkinson's disease, amyotropic lateral sclerosis, retinitis pigmentosa, cerebellar degeneration etc.), myelodysplasia (e.g., aplastic anemia etc.), ischemic diseases (e.g., myocardial infarction, cerebral apoplexy etc.), hepatic diseases (e.g., alcoholic hepatitis, hepatitis B, hepatitis C etc.), joint-diseases (e.g., osteoarthritis etc.), atherosclerosis and the like.

The compound of the present invention can be used for reducing visceral fats, inhibiting accumulation of visceral fats, ameliorating glycometabolism, ameliorating lipid metabolism, ameliorating insulin resistance, inhibiting production of oxidized LDL, ameliorating lipoprotein metabolism, ameliorating coronary artery metabolism, preventing or treating cardiovascular complications, preventing or treating heart failure complications, lowering blood remnant, preventing or treating anovulation, preventing or treating hirsutism, preventing or treating hyperandrogenism and the like.

The compound of the present invention can be used for secondary prevention and for inhibition of progress of the various diseases described above (e.g., cardiovascular events such as myocardial infarction etc.).

Although the dose of the compound of the present invention varies depending on the administration subject, the administration route, the target disease, the clinical condition etc., it is desirable that the compound of the present invention be administered at a usual dosage per administration of about 0.005 to 50 mg/kg body weight, preferably 0.01 to 5 mg/kg body weight, more preferably 0.025 to 2 mg/kg body weight, 1 to 3 times a day, for oral administration to an adult diabetic patient, for instance.

The compound of the present invention can be used in combination with a drug such as a therapeutic agent for diabetes mellitus, a therapeutic agent for diabetic complications, a therapeutic agent for hyperlipidemia, a hypotensive agent, an antiobesity agent, a diuretic agent, a chemotherapeutic agent, an immunotherapeutic agent, an antithrombotic agent, a pharmaceutical agent for ameliorating cachexia etc. (hereinafter, abbreviated as a concomitant drug). On such occasions, the timing of administration of the compound of the present invention and that of the concomitant drug is not limited. They may be administered simultaneously or in a staggered manner to the administration subject. Moreover, the compound of the present invention and the concomitant drug may be administered as two kinds of preparations containing each active ingredient, or as a single preparation containing both active ingredients.

The concomitant drug may be a compound having a low molecular weight, or may be a protein, a polypeptide or an antibody, each of which has a high molecular weight, or may be a vaccine and the like. The dose of the concomitant drug can be appropriately selected based on a clinically employed dose. The proportion of the compound of the present invention and the concomitant drug can be appropriately determined according to the administration subject, the administration route, the target disease, the clinical condition, the combination, and other factors. In cases where the administration subject is a human, for instance, the concomitant drug may be used in an amount of 0.01 to 100 parts by weight per part by weight of the compound of the present invention.

Examples of the therapeutic agent for diabetes mellitus include insulin preparations (e.g., animal insulin preparations extracted from the bovine or swine pancreas; human insulin preparations synthesized by a genetic engineering technique using *Escherichia coli* or a yeast; zinc insulin; protamine zinc insulin; fragment of insulin or derivatives thereof (e.g., INS-1 etc.)), insulin sensitizers (e.g., pioglitazone or its hydrochloride, troglitazone, rosiglitazone or its maleate, GI-262570, Reglixane (JTT-501), Netoglitazone (MCC-555), YM-440, KRP-297, CS-011, FK-614, compounds described in WO99/58510 (e.g., (E)-4-[4-(5-methyl-2-phenyl-4-oxazolylmethoxy)benzyloxyimino]-4-phenyl-butyric acid), Ragaglitazar (NN-622), Tesaglitazar (AZ-242), BMS-298585, ONO-5816, LM-4156, BM-13-1258, MBX-102, GW-1536), α-glucosidase inhibitors (e.g., voglibose, acarbose, miglitol, emiglitate), biguanides (e.g., phenformin, metformin, buformin), insulin secretagogues [sulfonylureas (e.g., tolbutamide, glibenclamide, gliclazide, chlorpropamide, tolazamide, acetohexamide, glyclopyramide, glimepiride, glipizide, glybuzole), repaglinide, nateglinide, mitiglinide or its calcium salt hydrate, GLP-1 etc.], dipeptidylpeptidase IV inhibitors (e.g., NVP-DPP-278, PT-100, NVP-DPP-728, LAF237), β3 agonists (e.g., CL-316243, SR-58611-A, UL-TG-307, SB-226552, AJ-9677, BMS-196085, AZ-40140), amylin agonists (e.g., pramlintide), phosphotyrosine phosphatase inhibitors (e.g., vanadic acid), gluconeogenesis inhibitors (e.g., glycogen phosphorylase inhibitors, glucose-6-phosphatase inhibitors, glucagon antagonists), SGLUT (sodium-glucose cotransporter) inhibitors (e.g., T-1095 etc.) and the like.

Examples of the therapeutic agent for diabetic complications include aldose reductase inhibitors (e.g., tolrestat, epalrestat, zenarestat, zopolrestat, minalrestat, fidarestat (SNK-860), CT-112), neurotrophic factors (e.g., NGF, NT-3, BDNF), neurotrophic factor production-secretion promoters [e.g., neurotrophin production-secretion promoters described in WO01/14372 (e.g., 4-(4-chlorophenyl)-2-(2-methyl-1-imidazolyl)-5-(3-(2-methylphenoxy)propyl)oxazole)], PKC inhibitors (e.g., LY-333531), AGE inhibitors (e.g., ALT946, pimagedine, pyratoxathine, N-phenacylthiazolium bromide (ALT766), EXO-226), active oxygen scavengers (e.g. thioctic acid), and cerebral vasodilators (e.g., tiapuride, mexiletine).

Examples of the therapeutic agent for hyperlipidemia include HMG-CoA reductase inhibitors (e.g., pravastatin, simvastatin, lovastatin, atorvastatin, fluvastatin, lipantil, cerivastatin, itavastatin, ZD-4522 or a salt thereof (e.g., sodium salt)), fibrate compounds (e.g., bezafibrate, beclobrate, binifibrate, ciprofibrate, clinofibrate, clofibrate, clofibric acid, etofibrate, fenofibrate, gemfibrozil, nicofibrate, pirifibrate, ronifibrate, simfibrate, theofibrate), squalene synthase inhibitors (e.g., compounds described in WO97/10224 such as 1-[[(3R,5S)-1-(3-acetoxy-2,2-dimethylpropyl)-7-chloro-5-(2,3-dimethoxyphenyl)-2-oxo-1,2,3,5-tetrahydro-4,1-benzoxazepin-3-yl]acetyl]piperidine-4-acetic acid), ACAT inhibitors (e.g., Avasimibe, Eflucimibe, anion exchange resins (e.g., colestyramine), probucol, nicotinic acid pharmaceutical agents (e.g., nicomol, niceritrol), ethyl eicosapentanoate, phytosterols (e.g., soysterol, γ-oryzanol) and the like.

Examples of the hypotensive agent include angiotensin converting enzyme inhibitors (e.g., captopril, enalapril, delapril), angiotensin II antagonists (e.g., candesartan cilexetil, losartan, eprosartan, valsartan, termisartan, irbesartan, tasosartan etc.), calcium antagonists (e.g., manidipine, nifedipine, nicardipine, amlodipine, efonidipine), potassium channel openers (e.g., levchromakalim, L-27152, AL 0671, NIP-121), clonidine and the like.

Examples of the antiobesity agent include antiobesity drugs acting on the central nervous system (e.g. dexfenfluramine, fenfluramine, phentermine, sibutramine, anfepramon, dexamphetamine, mazindol, phenylpropanolamine, clobenzorex), pancreatic lipase inhibitors (e.g. orlistat), β3 agonists (e.g. CL-316243, SR-58611-A, UL-TG-307, SB-226552, AJ-9677, BMS-196085, AZ-40140), anorectic peptides (e.g. leptin, CNTF (Ciliary Neurotrophic Factor) etc.) and cholecystokinin agonists (e.g. lintitript, FPL-15849).

Examples of the diuretic agent include xanthine derivatives (e.g., theobromine and sodium salicylate, theobromine and calcium salicylate), thiazide preparations (e.g., ethiazide, cyclopenthiazide, trichlormethiazide, hydrochlorothiazide, hydroflumethiazide, benzylhydrochlorothiazide, penflutizide, polythiazide, methyclothiazide), antialdosterone preparations (e.g., spironolactone, triamterene), carbonate dehydratase inhibitors (e.g., acetazolamide), chlorobenzene-sulfonamide preparations (e.g., chlorthalidone, mefruside, indapamide), azosemide, isosorbide, ethacrynic acid, piretanide, bumetanide, furosemide and the like.

Examples of the chemotherapeutic agent include alkylating agents (e.g., cyclophosphamide, ifosfamide), metabolic antagonists (e.g., methotrexate, 5-fluorouracil and a derivative thereof), antitumor antibiotics (e.g., mitomycin, adriamycin), plant-derived antitumor agents (e.g., vincristine, vindesine, Taxol), cisplatin, carboplatin, etoposide and the like. Of these, 5-fluorouracil derivatives such as Furtulon and Neo-Furtulon are preferable.

Examples of the immunotherapeutic agent include microorganism- or bacterium-derived components (e.g., muramyl dipeptide derivatives, Picibanil), immunopotentiator polysaccharides (e.g., lentinan, schizophyllan, krestin), genetically engineered cytokines (e.g., interferons, interleukins (IL)), colony stimulating agents (e.g., granulocyte colony stimulating factor, erythropoietin) and the like. Of these, interleukins such as IL-1, IL-2, IL-12 and the like are referable.

Examples of the antithrombotic agent include heparins (e.g., heparin sodium, heparin calcium, sodium dalteparin), warfarins (e.g., warfarin potassium), antithrombin agents (e.g., aragatroban), thrombolytic agents (e.g., urokinase, tisokinase, alteplase, nateplase, monteplase, pamiteplase), platelet coagulation suppressants (e.g., ticlopidine hydrochloride, cilostazol, ethyl eicosapentanoate, beraprost sodium, sarpogrelate hydrochloride) and the like.

Examples of the pharmaceutical agent for ameliorating cachexia include cyclooxygenase inhibitors (e.g., indomethacin) (*Cancer Research*, vol. 49, pp. 5935-5939, 1989), progesterone derivatives (e.g., megestrol acetate) (*Journal of Clinical Oncology*, vol. 12, pp. 213-225, 1994), glucocorticoids (e.g. dexamethasone), metoclopramide pharmaceuticals, tetrahydrocannabinol pharmaceuticals (the above references are applied to both), fat metabolism ameliorating agents (e.g., eicosapentanoic acid) (*British Journal of Cancer*, vol. 68, pp. 314-318, 1993), growth hormones, IGF-1, and antibodies to the cachexia-inducing factor TNF-α, LIF, IL-6 or oncostatin M.

As the concomitant drug, moreover, neuranagenesis promoters (e.g., Y-128, VX-853, prosaptide), antidepressants (e.g., desipramine, amitriptyline, imipramine), antiepileptics (e.g., lamotrigine), antiarrhythmic drug (e.g., mexiletine), acetylcholine receptor ligands (e.g., ABT-594), endothelin receptor antagonists (e.g., ABT-627), monoamine uptake inhibitor (e.g., tramadol), anesthetic analgesics (e.g., morphine) GABA receptor agonists (e.g., gabapentin), $α^2$ receptor agonists (e.g., clonidine), topical analgesics (e.g., capsaicin), protein kinase C inhibitors (e.g., LY-33531), antianxiety drugs (e.g., benzodiazepine), phosphodiesterase inhibitors (e.g., sildenafil (citrate)), dopamine agonists (e.g., apomorphine), therapeutic agents for osteoporosis (e.g., alfacalcidol, calcitriol, elcatonin, calcitonin salmon, estriol, ipriflavone, pamidronate disodium, alendronate sodium hydrate, incadronate disodium), antidementia agents (e.g., tacrine, donepezil, rivastigmine, galanthamine), therapeutic agents for incontinentia or pollakiuria (e.g., flavoxate hydrochloride, oxybutynin hydrochloride, propiverine hydrochloride) midazolam, ketoconazole and the like can be mentioned.

The above concomitant drugs can be used as a mixture of two or more species in an appropriate ratio.

When the compound of the present invention is used in combination with a concomitant drug, the amount of each agent can be reduced within a safe range by taking their adverse effects into consideration. Particularly, the dose of an insulin sensitizer, an insulin secretagogue and a biguanide can be reduced as compared with the normal dose. Accordingly, an adverse effect which may be caused by these agents can be safely prevented. In addition, the dose of a therapeutic agent for diabetic complications, a therapeutic agent for hyperlipidemia and a hypotensive agent can be reduced, whereby an adverse effect which may be caused by these agents can be effectively prevented.

In the following, the production method of the compound of the present invention is explained.

Compound (I) can be produced by a method known per se, such as the following Method A to Method Q or a method analogous thereto. In each of the following production methods, the starting compound may be used in the form of a salt, and as such salt, those exemplified as the salt of Compound (I) can be used.

Compound (I-1) of the formula (I) wherein Z is $-(CH_2)_n-Z^{1a}-$ ($Z^{1a}$ is an oxygen atom, a sulfur atom or $-NR^8-$ ($R^8$ is as defined above) and n is as defined above) can be produced by, for example, the following Method A.

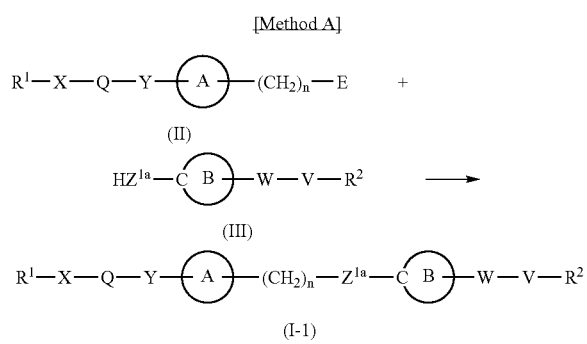

wherein E is a leaving group, and other symbols are as defined above.

As used herein, as the leaving group for E, for example, a hydroxy group, a halogen atom and $-OSO_2R^{19}$ wherein $R^{19}$ is a $C_{1-4}$ alkyl group or a $C_{6-10}$ aryl group which may be substituted by a $C_{1-4}$ alkyl group can be mentioned.

The $C_{1-4}$ alkyl group in the "$C_{1-4}$ alkyl group" and the "$C_{6-10}$ aryl group which may be substituted by a $C_{1-4}$ alkyl group" for $R^{19}$ is exemplified by methyl, ethyl, propyl, isopropyl, butyl, isobutyl, sec-butyl, and tert-butyl, with preference given to methyl.

The $C_{6-10}$ aryl group in the "$C_{6-10}$ aryl group which may be substituted by a $C_{1-4}$ alkyl group" for $R^{19}$ is exemplified by phenyl and naphthyl, with preference given to phenyl.

$R^{19}$ is particularly preferably methyl, tolyl and the like.

In this method, Compound (I-1) is produced by a reaction of Compound (II) with Compound (III).

When E is a hydroxy group, this reaction is carried out by a method known per se, e.g., the method described in *Synthesis*, page 1 (1981), or a method analogous thereto. Namely, this reaction is normally carried out in the presence of an organic phosphorus compound and an electrophilic agent in a solvent which does not interfere with the reaction.

Examples of the organic phosphorus compound include triphenylphosphine, tributylphosphine and the like.

Examples of the electrophilic agent include diethyl azodicarboxylate, diisopropyl azodicarboxylate, azodicarbonylpiperazine and the like.

The amount of the organic phosphorus compound and electrophilic agent used is preferably about 1 to about 5 molar equivalents relative to Compound (III).

Examples of the solvent which does not interfere with the reaction include ethers such as diethyl ether, tetrahydrofuran, dioxane and the like; halogenated hydrocarbons such as chloroform, dichloromethane and the like; aromatic hydrocarbons such as benzene, toluene, xylene and the like; amides such as N,N-dimethylformamide and the like; and sulfoxides such as dimethyl sulfoxide and the like. These solvents may be used in a mixture of two more kinds thereof at appropriate ratios.

The reaction temperature is normally about −50 to about 150° C., preferably about −10 to about 100° C.

The reaction time is normally about 0.5 to about 20 hours.

When E is a halogen atom or $-OSO_2R^{19}$, this reaction is carried out by a conventional method in the presence of a base in a solvent which does not interfere with the reaction.

Examples of the base include alkali metal salts such as potassium hydroxide, sodium hydroxide, sodium hydrogen carbonate, potassium carbonate and the like; amines such as pyridine, triethylamine, N,N-dimethylaniline, 1,8-diazobicyclo[5.4.0]undec-7-ene and the like; metal hydrides such as potassium hydride, sodium hydride and the like; and alkali metal alkoxides such as sodium methoxide, sodium ethoxide, potassium tert-butoxide and the like.

The amount of these bases used is preferably about 1 to about 5 molar equivalents relative to Compound (III).

Examples of the solvent which does not interfere with the reaction include aromatic hydrocarbons such as benzene, toluene, xylene and the like; ethers such as tetrahydrofuran, dioxane, diethyl ether and the like; ketones such as acetone, 2-butanone and the like; halogenated hydrocarbons such as chloroform, dichloromethane and the like; amides such as N,N-dimethylformamide and the like; and sulfoxides such as dimethyl sulfoxide and the like. These solvents may be used in a mixture of two more kinds thereof at appropriate ratios.

The reaction temperature is normally about −50 to about 150° C., preferably about −10 to about 100° C.

The reaction time is normally about 0.5 to about 20 hours.

Compound (I-1) thus obtained may be isolated and purified by known means of separation and purification such as concentration, concentration under reduced pressure, solvent extraction, crystallization, recrystallization, phase transfer, chromatography and the like.

Compound (II) and Compound (III), which are used as the starting compounds in Method A above can be produced any methods known per se.

For example, Compound (II) wherein E is a hydroxy group can be produced by methods described in EP-A 710659, EP-A 629624 (JP-A 7(1995)-53555), WO 98/03505 and the like or methods analogous thereto.

In addition, Compound (III) can be produced by the methods described in *Tetrahedron*, vol. 43, p. 607 (1987) or methods analogous.

Compound (I-2) of the formula (I) wherein Z is -$Z^{1a}$-$(CH_2)_n$— (wherein the symbols are as defined above) can be produced by, for example, the following Method B.

[Method B]

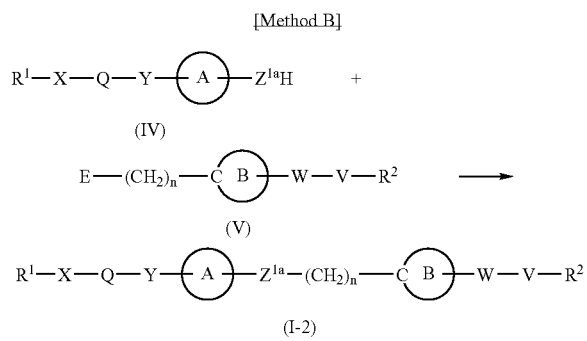

wherein the symbols are as defined above.

In this method, Compound (IV) is reacted with Compound (V) to produce Compound (I-2). This reaction is carried out in the same manner as the reaction of Compound (II) with Compound (III) in the aforementioned Method A.

The Compound (I-2) thus obtained can be isolated and purified by known means of separation and purification such as concentration, concentration under reduced pressure, solvent extraction, crystallization, recrystallization, phase transfer, chromatography and the like.

Compound (VI) and Compound (V), which are to be used as starting compounds in the above-mentioned Method B can be produced by methods known per se.

The Compound (V-1), which is Compound (V) wherein E is a hydroxy group and n is 1 can be produced by the following Method C or methods analogous thereto.

[Method C]

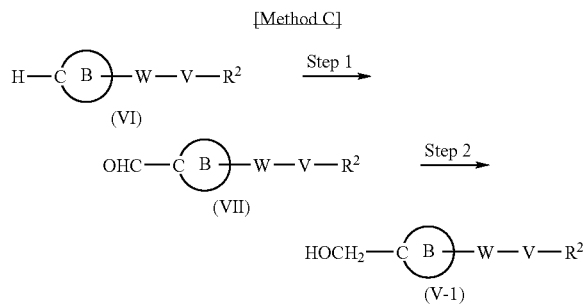

wherein the symbols are as defined above.

In this Method, Compound (VI) is lithiated and then formylated to give Compound (VII), which Compound (VII) is subjected to reduction reaction to give Compound (V-1).

(Step 1)

In this Step, Compound (VI) is lithiated and then formylated to give Compound (VII). This reaction is generally carried out using a lithiating agent and a formylating agent in a solvent that does not influence the reaction.

As the lithiating agent, for example, n-butyllithium, sec-butyllithium, tert-butyllithium, lithiumdiisopropylaluminum and the like can be mentioned.

As the formylating agent, for example, N,N-dimethylformamide and the like can be mentioned.

As examples of the solvent which does not influence the reaction, for example, ethers such as tetrahydrofuran, dioxane, diethyl ether and the like and the like can be mentioned. These solvents may be used in a mixture of two more kinds thereof at appropriate ratios.

The amount of the lithiating agent to be used is preferably about 1 to about 5 molar equivalents relative to Compound (VI).

The amount of the formylating agent to be used is preferably about 1 to about 5 molar equivalents relative to Compound (VI).

The reaction temperature is generally about −100 to about 150° C., preferably about −80 to about 40° C.

The reaction time is generally about 0.5 to about 20 hrs.

The thus-obtained Compound (VII) can be isolated and purified by known separation and purification means, such as concentration, concentration under reduced pressure, solvent extraction, crystallization, recrystallization, phase transfer, chromatography and the like.

A reaction mixture containing Compound (VII) may be used as it is as a starting material of the next Step 2 without isolating Compound (VII).

(Step 2)

In this Step, Compound (VII) is subjected to reduction reaction to give Compound (V-1). This reaction is carried out according to a conventional method in the presence of a reducing agent, in a solvent which does not interfere with the reaction.

As the reducing agent, for example, sodium borohydride, lithium borohydride, aluminum lithium hydride, diisobutyl aluminum hydride and the like can be mentioned.

The amount of the reducing agent to be used is preferably about 0.5 to about 10 molar equivalents relative to Compound (VII).

As examples of the solvent which does not interfere with the reaction, for example, aromatic hydrocarbons such as benzene, toluene, xylene and the like; halogenated hydrocarbons such as chloroform, dichloromethane and the like; ethers such as tetrahydrofuran, dioxane, diethyl ether and the like; water; alcohols such as methanol, ethanol, isopropanol and the like and the like can be mentioned. These solvents may be used in a mixture of two more kinds thereof at appropriate ratios.

The reaction temperature is generally about −50° C. to about 150° C., preferably about −10° C. to about 100° C.

The reaction time is generally about 0.5 to about 20 hr.

The thus-obtained Compound (V-1) can be isolated and purified by known separation and purification means, such as concentration, concentration under reduced pressure, solvent extraction, crystallization, recrystallization, phase transfer, chromatography and the like.

Compound (I-4) of the formula (I) wherein W is —W'$CH_2$— (W' is a bond or a divalent hydrocarbon group having 1 to 19 carbon atoms), can be produced by, for example, the following Method D.

As the "divalent hydrocarbon group having 1 to 19 carbon atoms" here, which is represented by W', a "divalent hydrocarbon group having 1 to 20 carbon atoms" exemplified for the aforementioned W, wherein the number of carbons is 1 to 19, can be mentioned.

[Method D]

R¹—X—Q—Y—(A)—Z—C(B)—W'CH₂—E  +

(I-3)

H—V—R² ⟶

(VIII)

R¹—X—Q—Y—(A)—Z—C(B)—W'CH₂—V—R²

(I-4)

wherein the symbols are as defined above.

In this Method, Compound (I-3) and Compound (VIII) are reacted to give Compound (I-4). This reaction is carried out in the same manner as the reaction of Compound (II) with Compound (III) in the aforementioned Method A.

The thus-obtained Compound (I-4) can be isolated and purified by known separation and purification means, such as concentration, concentration under reduced pressure, solvent extraction, crystallization, recrystallization, phase transfer, chromatography and the like.

Compound (I-3), which is used as a starting compound in the above-mentioned Method D can be produced by, for example, the aforementioned Method A or Method H to be mentioned later.

In addition, Compound (VIII), which is used as a starting compound in Method D can be produced by a method known per se. As preferable examples of Compound (VIII), azole compounds (e.g., imidazole, pyrazole, 1,2,3-triazole, 1,2,4-triazole, pyrrole); optionally substituted hydrocarbon compound or optionally substituted heterocyclic compound (e.g., phenol, thiophenol), each having a hydroxyl group or a thiol group; hydrogen cyanide and the like can be mentioned.

Compound (I-6) of the formula (I), wherein W is —W'''—CH═CH— (W''' is a bond or a divalent hydrocarbon group having 1 to 18 carbon atoms), V is a bond, and R² is R²' [R²' is a cyano group, —PO(OR⁹)(OR¹⁰) (R⁹ and R¹⁰ are as defined above), —COR¹¹ (R¹¹ is as defined above) an optionally substituted hydrocarbon group or an optionally substituted heterocyclic group; and Compound (I-7) of the formula (I), wherein W is —W'''—CH₂CH₂— (W''' is as defined above), V is a bond, and R² is R²' (R²' is as defined above) are also produced by the following Method E.

As the "divalent hydrocarbon group having 1 to 18 carbon atoms" which is represented by W''' here, a "divalent hydrocarbon group having 1 to 20 carbon atoms" exemplified for the aforementioned W, wherein the number of carbons is 1 to 18, can be mentioned.

In addition, as the "optionally substituted hydrocarbon group" and "optionally substituted heterocyclic group" represented by R²', those exemplified for the aforementioned R² can be mentioned.

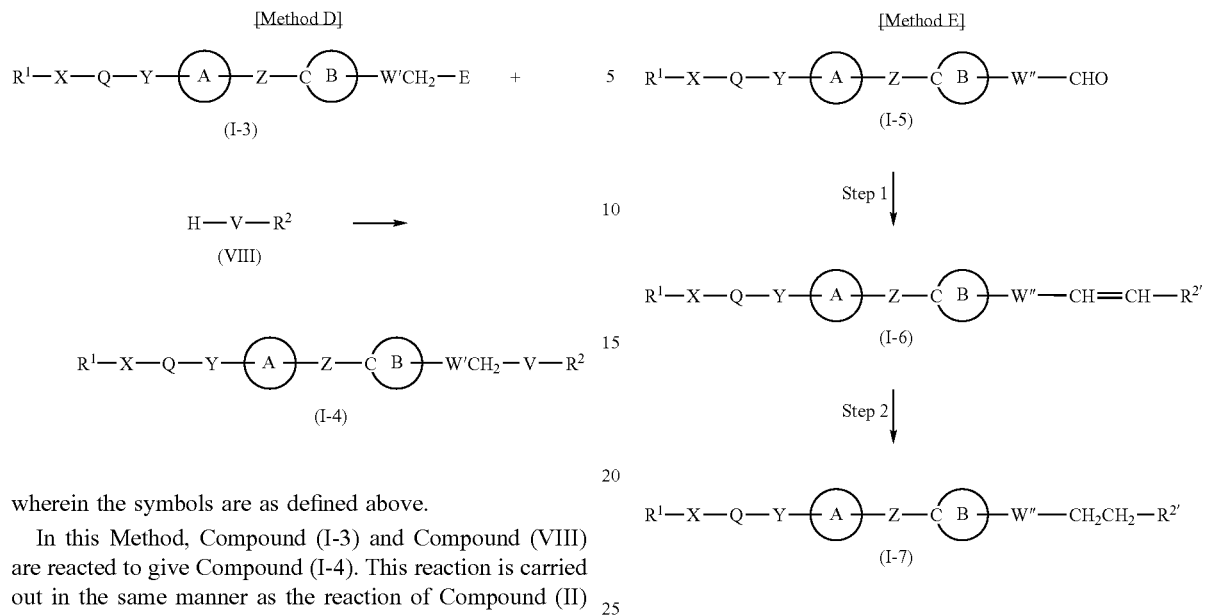

[Method E]

R¹—X—Q—Y—(A)—Z—C(B)—W''—CHO (I-5)

Step 1 ↓

R¹—X—Q—Y—(A)—Z—C(B)—W''—CH═CH—R²'

(I-6)

Step 2 ↓

R¹—X—Q—Y—(A)—Z—C(B)—W''—CH₂CH₂—R²'

(I-7)

wherein the symbols are as defined above.

In this Method, Compound (I-5) is reacted with an organic phosphorus reagent to give Compound (I-6), which Compound (I-6) is subjected to reduction reaction to give Compound (I-7).

(Step 1)

In this Step, Compound (I-5) is reacted with an organic phosphorus reagent to give Compound (I-6).

Here, as the organic phosphorus reagent, for example, a phosphonium salt, a phosphonate compound and the like can be mentioned.

As the phosphonium salt, for example, a compound represented by the formula: R²'—CH₂P(C₆H₅)₃Ea (R²' is as defined above and Ea is a halogen atom) can be mentioned.

Here, as the halogen atom represented by Ea, for example, chlorine, bromine and iodine can be mentioned. The phosphonium salt can be produced by a method known per se.

As the phosphonate compound, for example, a compound represented by the formula: R²'—CH₂PO(OR²⁰)(OR²¹) (R²' is as defined above, R²⁰ and R²¹ are the same or different and each is a hydrogen atom or an optionally substituted hydrocarbon group, and R²⁰ and R²¹ are optionally bonded to form an optionally substituted ring) can be mentioned.

Here, as the "optionally substituted hydrocarbon group" represented by R²⁰ and R²¹ and the "optionally substituted ring" formed by R²⁰ and R²¹ bonded to each other, those similar to the aforementioned R⁹ and R¹⁰ can be mentioned. R²⁰ and R²¹ are preferably a $C_{1-4}$ alkyl such as methyl, ethyl and the like. The phosphonate compound can be produced by a method known per se.

The reaction between Compound (I-5) and an organic phosphorus reagent is carried out according to conventional methods in the presence of a base in a solvent which does not interfere with the reaction.

The amount of the organic phosphorus reagent to be used is generally about 1 to about 5 molar equivalents, preferably about 1 to about 3 molar equivalents, relative to Compound (I-5).

As the base, for example, alkali metal salts such as sodium hydroxide, potassium hydroxide, potassium carbonate, sodium carbonate, sodium hydrogen carbonate and the like; amines such as pyridine, triethylamine, N,N-dimethylaniline and the like; metal hydrides such as sodium hydride, potassium hydride and the like; alkali metal alkoxides such as sodium ethoxide, sodium methoxide, potassium tert-butoxide and the like, and the like can be mentioned.

The amount of these bases to be used is preferably about 1 to about 5 molar equivalents relative to Compound (I-5).

As examples of the solvent which does not interfere with the reaction, for example, aromatic hydrocarbons such as benzene, toluene, xylene and the like; ethers such as dioxane, tetrahydrofuran, dimethoxyethane and the like; alcohols such as methanol, ethanol, propanol and the like; amides such as N,N-dimethylformamide and the like; sulfoxides such as dimethyl sulfoxide and the like; halogenated hydrocarbons such as chloroform, dichloromethane, 1,2-dichloroethane, 1,1,2,2-tetrachloroethane and the like, and the like can be mentioned. These solvents may be used in a mixture of two more kinds thereof at appropriate ratios.

The reaction temperature is generally about −50° C. to about 150° C., preferably about −10° C. to about 100° C.

The reaction time is, for example, about 0.5 to about 30 hrs.

The thus-obtained Compound (I-6) can be isolated and purified by known separation and purification means, such as concentration, concentration under reduced pressure, solvent extraction, crystallization, recrystallization, phase transfer, chromatography and the like.

In addition, a reaction mixture containing Compound (I-6) may be used as it is as a starting material of the next Step 2 without isolating Compound (I-6).

(Step 2)

In this Step, Compound (I-6) is subjected to reduction reaction to give Compound (I-7).

This reaction is carried out according to conventional methods under a hydrogen atmosphere, or in the presence of a hydrogen source such as formic acid and the like and a metal catalyst, in a solvent which does not interfere with the reaction. As the metal catalyst, for example, transitional metal catalysts such as palladium-carbon, palladium black, platinum oxide, Raney-nickel, Wilkinson's catalyst and the like, and the like can be mentioned.

The amount of the metal catalyst to be used is preferably about 0.01 to about 10 molar equivalents relative to Compound (I-6).

As examples of the solvent which does not interfere with the reaction, for example, aromatic hydrocarbons such as benzene, toluene, xylene and the like; ethers such as tetrahydrofuran, dioxane, diethyl ether and the like; halogenated hydrocarbons such as chloroform, dichloromethane and the like; amides such as N,N-dimethylformamide and the like; alcohols such as methanol, ethanol, isopropanol and the like, and the like can be mentioned. These solvents may be used in a mixture of two more kinds thereof at appropriate ratios.

The reaction temperature is generally about −50° C. to about 150° C., preferably about −10° C. to about 100° C.

The reaction time is generally about 0.5 to about 20 hrs.

The thus-obtained Compound (I-7) can be isolated and purified by known separation and purification means, such as concentration, concentration under reduced pressure, solvent extraction, crystallization, recrystallization, phase transfer, chromatography and the like.

The Compound (I-5) to be used as a starting compound in the above-mentioned Method E can be produced by, for example, the aforementioned Method A or Method G to be mentioned later, or methods analogous thereto.

Compound (I-11) of the formula (I), wherein V is a bond and $R^2$ is COOH; Compound (I-12) of the formula (I), wherein V is a bond and $R^2$ is $CONR^{13}R^{14}$ ($R^{13}$ and $R^{14}$ are as defined above); and Compound (I-12') of the formula (I), wherein $VR^2$ is $CSNR^{13}R^{14}$ ($R^{13}$ and $R^{14}$ are as defined above) are also produced by the following Method F.

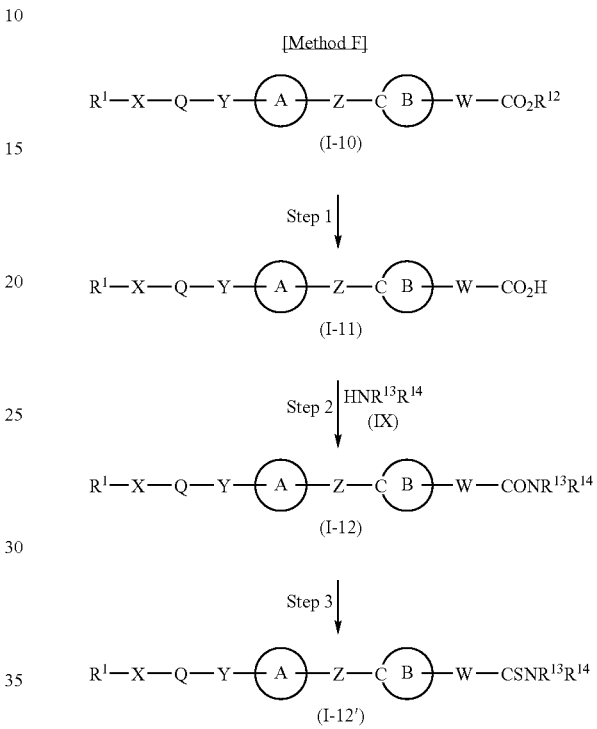

wherein the symbols are as defined above.

In this Method, Compound (I-12') is produced by subjecting Compound (I-10) to a hydrolysis reaction to give Compound (I-11), which is then reacted with Compound (IX) to give Compound (I-12), which is then subjected to thioamidation reaction.

(Step 1)

In this Step, Compound (I-11) is produced by subjecting Compound (I-10) to a hydrolysis reaction.

This reaction is carried out according to a conventional method in an aqueous solvent in the presence of an acid or a bate.

As the acid, for example, inorganic acids such as hydrochloric acid, sulfuric acid, hydrobromic acid and the like; organic acids such as acetic acid and the like; and the like can be mentioned.

As the base, alkali metal carbonates such as potassium carbonate, sodium carbonate and the like; alkali metal alkoxides such as sodium methoxide and the like; and alkali metal hydroxides such as potassium hydroxide, sodium hydroxide, lithium hydroxide and the like, and the like can be mentioned.

The amount of the acid or base used is normally in excess to Compound (I-10). Preferably, the amount of the acid used is about 2 to about 50 equivalents relative to Compound (I-10), and the amount of the base used is about 1.2 to about 5 equivalents relative to Compound (I-10).

Examples of the aqueous solvents include solvent mixtures of water and one or more solvents selected from alcohols such as methanol, ethanol and the like; ethers such as tetrahydrofuran, dioxane, diethyl ether and the like; sulfoxides such as dimethyl sulfoxide, ketones such as acetone and the like, and the like.

The reaction temperature is normally about −20 to about 150° C., preferably about −10 to about 100° C.

The reaction time is normally about 0.1 to about 20 hours.

Compound (I-11) thus obtained may be isolated and purified by known means of separation and purification such as concentration, concentration under reduced pressure, solvent extraction, crystallization, recrystallization, phase transfer, chromatography and the like.

In addition, a reaction mixture containing Compound (I-11) may be used as it is as a starting material of the next Step 2 without isolating Compound (I-11).

(Step 2)

In this Step, Compound (I-11) is reacted with Compound (IX) to give Compound (I-12).

This reaction is carried out according to a method known per se, such as a method comprising, for example, direct condensation of Compound (I-11) with Compound (IX) using a condensation agent, or suitable reaction of a reactive derivative of Compound (I-11) with Compound (IX) and the like.

Here, the reactive derivative of Compound (I-11) is exemplified by acid anhydrides, acid halides (e.g., acid chlorides, acid bromides), imidazolides, or mixed acid anhydrides (e.g., anhydrides with methyl carbonate, ethyl carbonate, or isobutyl carbonate etc.) and the like.

When a condensation agent is used, for example, the reaction is carried out in the presence of a condensation agent in a solvent which does not interfere with the reaction.

As the condensation agent, for example, carbodiimide condensation reagents such as dicyclohexylcarbodiimide, diisopropylcarbodiimide, 1-ethyl-3-dimethylaminopropylcarbodiimide, hydrochloride thereof and the like; phosphoric acid condensation reagents such as diethyl cyanophosphate, diphenylphosphoryl azide and the like; carbonyldiimidazole, 2-chloro-1,3-dimethylimidazolium tetrafluoroborate and the like can be mentioned.

As examples of the solvent which does not interfere with the reaction, for example, amides such as N,N-dimethylformamide, N,N-dimethylacetamide and the like; halogenated hydrocarbons such as chloroform, dichloromethane and the like; aromatic hydrocarbons such as benzene, toluene and the like; ethers such as tetrahydrofuran, dioxane, diethyl ether and the like; ethyl acetate; water and the like can be mentioned. These solvents may be used in a mixture at appropriate ratios.

The amount of Compound (IX) to be used is generally 0.1-10 molar equivalents, preferably 0.3-3 molar equivalents, relative to Compound (I-11).

The amount of the condensation agent to be used is generally 0.1-10 molar equivalents, preferably 0.3-3 molar equivalents, relative to Compound (I-11).

When the aforementioned carbodiimide condensation reagent is used as a condensation agent, the reaction efficiency can be improved by using a suitable condensation promoter (e.g., 1-hydroxy-7-azabenzotriazole, 1-hydroxybenzotriazole, N-hydroxysuccinimide, N-hydroxyphthalimide) as necessary. When the aforementioned phosphoric acid condensation reagent is used as the condensation agent, the reaction efficiency can be generally improved by adding an organic amine base such as triethylamine and the like.

The amount of the above-mentioned condensation promoter and organic amine base to be used is generally 0.1-10 molar equivalents, preferably 0.3-3 molar equivalents, relative to Compound (I-11).

The reaction temperature is generally −30° C. to 100° C.

The reaction time is generally 0.5-60 hr.

When, for example, an acid halide is used as a reactive derivative of Compound (I-11), the reaction is carried out in the presence of a base in a solvent which does not interfere with the reaction.

As the base, amines such as triethylamine, N-methylmorpholine, N,N-dimethylaniline and the like; alkali metal salts such as sodium hydrogencarbonate, sodium carbonate, potassium carbonate and the like, and the like can be mentioned.

As examples of the solvent which does not interfere with the reaction, for example, halogenated hydrocarbons such as chloroform, dichloromethane and the like; aromatic hydrocarbons such as benzene, toluene and the like; ethers such as tetrahydrofuran, dioxane, diethyl ether and the like; esters such as ethyl acetate and the like; water and the like can be mentioned. These solvents may be used in a mixture of two more kinds thereof at appropriate ratios.

The amount of Compound (IX) to be used is 0.1-10 molar equivalents, preferably 0.3-3 molar equivalents, relative to Compound (I-11).

The reaction temperature is generally carried out at −30° C. to 100° C.

The reaction time is generally 0.5-20 hrs.

When a mixed acid anhydride is used as a reactive derivative of Compound (I-11), Compound (I-11) is reacted with chlorocarbonate in the presence of a base and then reacted with Compound (IX).

As the chlorocarbonate, for example, methyl chlorocarbonate, ethyl chlorocarbonate, isobutyl chlorocarbonate and the like can be mentioned.

As the base, amines such as triethylamine, N-methylmorpholine, N,N-dimethylaniline and the like; alkali metal salts such as sodium hydrogencarbonate, sodium carbonate, potassium carbonate and the like, and the like can be mentioned.

The amount of Compound (IX) to be used is generally 0.1-10 molar equivalents, preferably 0.3-3 molar equivalents, relative to Compound (I-11).

The reaction temperature is generally −30° C. to 100° C.

The reaction time is generally 0.5-20 hrs.

The thus-obtained Compound (I-12) can be isolated and purified by known separation and purification means, such as concentration, concentration under reduced pressure, solvent extraction, crystallization, recrystallization, phase transfer, chromatography and the like.

In addition, a reaction mixture containing Compound (I-12) may be used as it is as a starting material of the next Step 3 without isolating Compound (I-12).

(Step 3)

In this Step, Compound (I-12) is subjected to thioamidation reaction to give Compound (I-12').

This reaction can be carried out by a method known per se, such as a method described in Journal of American Chemical Society, vol. 108, p. 212 (1986) and the like, or a method analogous thereto.

The thus-obtained Compound (I-12') can be isolated and purified by known separation and purification means, such as concentration, concentration under reduced pressure, solvent extraction, crystallization, recrystallization, phase transfer, chromatography and the like.

Compound (I-10) to be used as a starting compound in the above-mentioned Method F can be produced by, for example, the aforementioned Method A or a method analogous thereto.

Compound (IX) to be used for the above-mentioned Method F can be produced by a method known per se.

Compound (I-13) of the formula (I), wherein V is —CH(OH)— and $R^2$ is a hydrogen atom; and Compound (I-14) of the formula (I), wherein V is a bond and $R^2$ is CHO are also produced by the following Method G.

[Method G]

$$R^1-X-Q-Y-(A)-Z-C(B)-W-CO_2R^{12}$$
(I-10)

Step 1 ↓

$$R^1-X-Q-Y-(A)-Z-C(B)-W-CH_2OH$$
(I-13)

Step 2 ↓

$$R^1-X-Q-Y-(A)-Z-C(B)-W-CHO$$
(I-14)

wherein the symbols are as defined above.

In this Method, Compound (I-10) is subjected to reduction reaction to give Compound (I-13), which Compound (I-13) is subjected to oxidization reaction to give Compound (I-14).

(Step 1)

In this Step, Compound (I-10) is subjected to reduction reaction to give Compound (I-13).

This reaction is carried out in the same manner as in, for example, the aforementioned step 2 of Method C.

The thus-obtained Compound (I-13) can be isolated and purified by known separation and purification means, such as concentration, concentration under reduced pressure, solvent extraction, crystallization, recrystallization, phase transfer, chromatography and the like.

In addition, a reaction mixture containing Compound (I-13) may be used as it is as a starting material of the next Step 2 without isolating Compound (I-13).

(Step 2)

In this Step, Compound (I-13) is subjected to oxidization reaction to give Compound (I-14).

This reaction is carried out according to conventional methods in the presence of an oxidant in a solvent which does not interfere with the reaction.

As the oxidant, for example, metal oxidants such as manganese dioxide, pyridinium chlorochromate, pyridinium dichromate, ruthenium oxide and the like, and the like can be mentioned.

The amount of the oxidant to be used is preferably about 1 to about 10 molar equivalents relative to Compound (I-13).

As examples of the solvent which does not interfere with the reaction, for example, aromatic hydrocarbons such as benzene, toluene, xylene and the like; ethers such as tetrahydrofuran, dioxane, diethyl ether and the like; halogenated hydrocarbons such as chloroform, dichloromethane and the like; and the like can be mentioned. These solvents may be used in a mixture of two more kinds thereof at appropriate ratios.

The reaction temperature is generally about −50° C. to about 150° C., preferably about −10° C. to about 100° C.

The reaction time is generally about 0.5 to about 20 hrs.

Compound (I-14) can be also produced by reacting Compound (I-13) with a reaction reagent such as sulfur trioxide-pyridine complex, oxalyl chloride and the like and an organic base such as triethylamine, N-methylmorpholine and the like in a mixed solvent of halogenated hydrocarbons such as chloroform, dichloromethane and the like and dimethyl sulfoxide, or in dimethyl sulfoxide.

The amount of the reaction reagent to be used is preferably about 1 to about 10 molar equivalents relative to Compound (I-13).

The amount of the organic base to be used is preferably about 1 to about 10 molar equivalents relative to Compound (I-13).

The reaction temperature is generally about −50 to about 150° C., preferably about −10 to about 100° C.

The reaction time is generally about 0.5 to about 20 hr.

The thus-obtained Compound (I-14) can be isolated and purified by known separation and purification means, such as concentration, concentration under reduced pressure, solvent extraction, crystallization, recrystallization, phase transfer, chromatography and the like.

Of Compounds (I-3) used as starting compounds in the aforementioned Method D, Compound (I-3a) wherein E is Eb (Eb is a halogen atom or $-OSO_2R^{19}$ ($R^{19}$ is as defined above)) is also produced by the following Method H.

[Method H]

$$R^1-X-Q-Y-(A)-Z-C(B)-W'CH_2-OH$$
(I-13a)

↓

$$R^1-X-Q-Y-(A)-Z-C(B)-W'CH_2-Eb$$
(I-3a)

wherein the symbols are as defined above.

In this Method, Compound (I-13a) is reacted with a halogenation agent or a sulfonylation agent to give Compound (I-3a).

As the halogenation agent, for example, hydrochloric acid, thionyl chloride, phosphorus tribromide and the like can be mentioned. In this case, Compound (I-3a) wherein Eb is a halogen atom (e.g., chlorine, bromine) can be obtained.

As the sulfonylation agent, for example, a compound represented by the formula: $Ea-OSO_2R^{19}$ (the symbols are as defined above) can be mentioned. As preferable examples of the sulfonylation agent, methanesulfonyl chloride, benzenesulfonyl chloride, p-toluenesulfonyl chloride and the like can be mentioned. In this case, Compound (I-3a) wherein Eb is methanesulfonyloxy, benzenesulfonyloxy, p-toluenesulfonyloxy and the like can be mentioned.

The reaction using the above-mentioned halogenation agent is generally carried out in a solvent which does not interfere with the reaction. As such solvent, for example, aromatic hydrocarbons such as benzene, toluene, xylene and the like; halogenated hydrocarbons such as dichloromethane, chloroform and the like; ethers such as tetrahydrofuran, dioxane, diethyl ether and the like; and the like can be mentioned. These solvents may be used in a mixture of two more kinds thereof at appropriate ratios. In addition, excess halogenation agent may be used as a solvent.

The amount of the halogenation agent to be used is generally about 1 to about 10 molar equivalents relative to Compound (I-13a).

The reaction temperature is generally about −20° C. to about 100° C.

The reaction time is generally about 0.5 to about 24 hrs.

The reaction using the above-mentioned sulfonylation agent is carried out in the presence of a base in a solvent which does not interfere with the reaction. As such solvent, for example, aromatic hydrocarbons such as benzene, toluene, xylene and the like; halogenated hydrocarbons such as dichloromethane, chloroform and the like; ethers such as tetrahydrofuran, dioxane, diethyl ether and the like; esters such as ethyl acetate and the like; and the like can be mentioned. These solvents may be used in a mixture of two more kinds thereof at appropriate ratios.

As the base, amines such as triethylamine, N-methylmorpholine and the like; alkali metal salts such as sodium hydrogencarbonate, sodium carbonate, potassium carbonate and the like, and the like can be mentioned.

The amount of the base to be used is generally about 1 to about 10 molar equivalents relative to Compound (I-13a).

The amount of the sulfonylation agent to be used is generally about 1 to about 10 molar equivalents relative to Compound (I-13a).

The reaction temperature is generally about −20° C. to about 100° C.

The reaction time is generally about 0.5 to about 24 hrs.

The thus-obtained Compound (I-3a) can be isolated and purified by known separation and purification means, such as concentration, concentration under reduced pressure, solvent extraction, crystallization, recrystallization, phase transfer, chromatography and the like.

Compound (I-13a) to be used as a starting compound in the above-mentioned Method H can be produced by, for example, the aforementioned Method G.

Compound (I-16) of the formula (I), wherein V is a bond and $R^2$ is a cyano group, can be also produced by, for example, the following Method I.

[Method I]

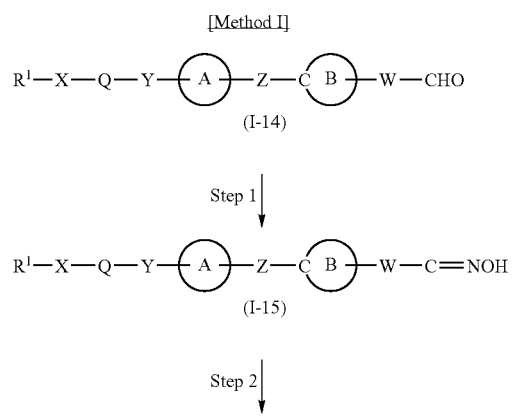

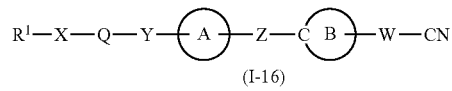

wherein the symbols are as defined above.

In this Method, Compound (I-14) is reacted with an oximation agent to give Compound (I-15), which Compound (I-15) is reacted with a dehydrating agent to give Compound (I-16).

(Step 1)

In this Step, Compound (I-14) is reacted with an oximation agent to give Compound (I-15). This reaction is carried out according to conventional methods in a solvent which does not interfere with the reaction.

As the oximation agent, for example, hydroxylamine and a salt thereof can be mentioned. Here, as the salt, for example, hydrochloride, oxalate and the like can be mentioned.

As examples of the solvent which does not interfere with the reaction, for example, aromatic hydrocarbons such as benzene, toluene, xylene and the like; ethers such as tetrahydrofuran, dioxane, diethyl ether and the like; halogenated hydrocarbons such as chloroform, dichloromethane and the like; alcohols such as ethanol, methanol and the like; amides such as N,N-dimethylformamide and the like; sulfoxides such as dimethyl sulfoxide and the like; aliphatic carboxylic acids such as acetic acid and the like; water and the like can be mentioned. These solvents may be used in a mixture of two more kinds thereof at appropriate ratios.

The reaction temperature is generally about −50° C. to about 150° C., preferably about −10° C. to about 100° C.

The reaction time is generally about 0.5 to about 20 hrs.

When a hydroxylamine salt is used as an oximation agent, this reaction may be carried out in the presence of a neutralizing agent. As the neutralizing agent, for example, bases such as pyridine, triethylamine, sodium carbonate, sodium acetate and the like can be mentioned.

The thus-obtained Compound (I-15) can be isolated and purified by known separation and purification means, such as concentration, concentration under reduced pressure, solvent extraction, crystallization, recrystallization, phase transfer, chromatography and the like.

In addition, a reaction mixture containing Compound (I-15) may be used as it is as a starting material of the next Step 2 without isolating Compound (I-15).

(Step 2)

In this Step, Compound (I-15) is subjected to dehydration reaction to give Compound (I-16). This reaction is carried out according to conventional methods using a dehydrating agent, in a solvent which does not interfere with the reaction.

As the dehydrating agent, for example, acetic anhydride, thionyl chloride, phosphorus pentaoxide, phosphorus pentachloride, N,N'-dicyclohexylcarbodiimide and the like can be mentioned.

As examples of the solvent which does not interfere with the reaction, for example, aromatic hydrocarbons such as benzene, toluene, xylene and the like; ethers such as tetrahydrofuran, dioxane, diethyl ether and the like; halogenated hydrocarbons such as chloroform, dichloromethane and the like; amides such as N,N-dimethylformamide and the like; sulfoxides such as dimethyl sulfoxide and the like; amines such as pyridine and the like; water and the like can be mentioned. These solvents may be used in a mixture of two more kinds thereof at appropriate ratios. When acetic anhydride, thionyl chloride and the like are used as a dehydrating agent, these may be used as a solvent.

The reaction temperature is generally about −50° C. to about 150° C., preferably about −10° C. to about 150° C.

The reaction time is generally about 0.5 to about 20 hrs.

The thus-obtained Compound (I-16) can be isolated and purified by known separation and purification means, such as concentration, concentration under reduced pressure, solvent extraction, crystallization, recrystallization, phase transfer, chromatography and the like.

Compound (I-17) of the formula (I), wherein V is —CH(OH)— and $R^2$ is $R^{2''}$ ($R^{2''}$ is an optionally substituted hydrocarbon group or an optionally substituted heterocyclic group); and Compound (I-18) of the formula (I), wherein V is —CO— and $R^2$ is $R^{2''}$ ($R^{2''}$ is as defined above) are also produced by, for example, the following Method J.

As the "optionally substituted hydrocarbon group" and "optionally substituted heterocyclic group" represented by $R^{2''}$, those exemplified for the aforementioned $R^2$ can be mentioned.

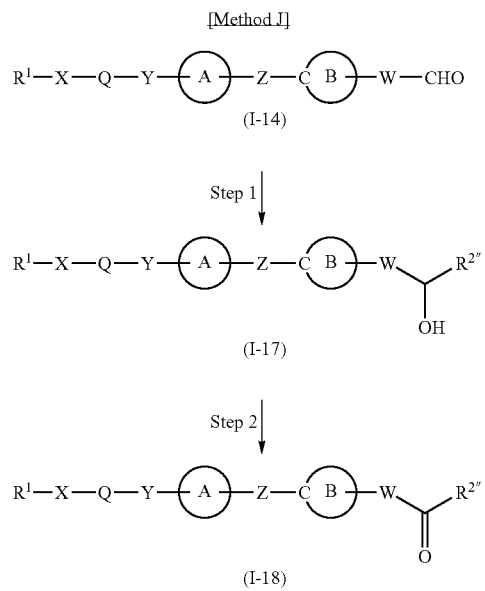

wherein the symbols are as defined above.

In this Method, Compound (I-14) is reacted with an organometallic reagent to give Compound (I-17), which Compound (I-17) is subjected to oxidization reaction to give Compound (I-18).

(Step 1)

In this Step, Compound (I-14) is reacted with an organometallic reagent to give Compound (I-17).

As the organometallic reagent, a Grignard reagent represented by the formula: $EaMgR^{2''}$ (the symbols are as defined above), an organic lithium reagent represented by the formula: $LiR^{2''}$ (the symbol is as defined above) and the like can be mentioned. The organometallic reagent can be produced by a method known per se.

This reaction is carried out according to conventional methods in a solvent which does not interfere with the reaction.

As examples of the solvent which does not interfere with the reaction, for example, aromatic hydrocarbons such as benzene, toluene, xylene and the like; ethers such as tetrahydrofuran, dioxane, diethyl ether and the like; and the like can be mentioned. These solvents may be used in a mixture of two more kinds thereof at appropriate ratios. The amount of the organometallic reagent to be used is generally about 1 to about 10 molar equivalents, relative to Compound (I-14).

The reaction temperature is generally about −100° C. to about 150° C., preferably about −80° C. to about 100° C.

The reaction time is generally about 0.5 to about 20 hrs.

The thus-obtained Compound (I-17) can be isolated and purified by known separation and purification means, such as concentration, concentration under reduced pressure, solvent extraction, crystallization, recrystallization, phase transfer, chromatography and the like.

In addition, a reaction mixture containing Compound (I-17) may be used as it is as a starting material of the next Step 2 without isolating Compound (I-17).

(Step 2)

In this Step, Compound (I-17) is subjected to oxidization reaction to give Compound (I-18). This reaction is carried out in the same manner as in, for example, Step 2 of the aforementioned Method G.

The thus-obtained Compound (I-18) can be isolated and purified by known separation and purification means, such as concentration, concentration under reduced pressure, solvent extraction, crystallization, recrystallization, phase transfer, chromatography and the like.

Compound (I-19) of the formula (I), wherein V is —$CONR^6NR^7$— and $R^2$ is $COR^{11'}$ ($R^{11'}$ is an optionally substituted hydrocarbon group or an optionally substituted heterocyclic group) is also produced by, for example, the following Method K.

Here, as the "optionally substituted hydrocarbon group" and "optionally substituted heterocyclic group" represented by $R^{11'}$, those exemplified for the aforementioned $R^{11}$ can be mentioned.

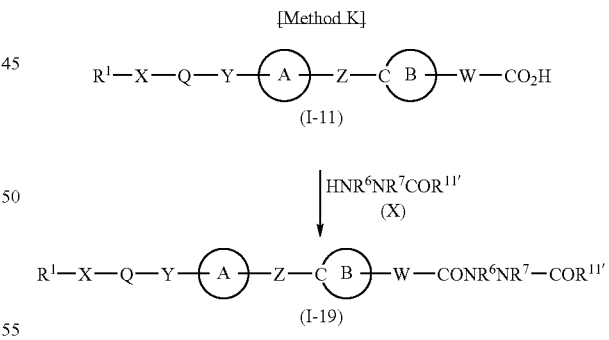

wherein the symbols are as defined above.

In this Method, Compound (I-11) is reacted with Compound (X) to give Compound (I-19). This reaction is carried out in the same manner as in Step 2 of the aforementioned Method F.

The thus-obtained Compound (I-19) can be isolated and purified by known separation and purification means, such as concentration, concentration under reduced pressure, solvent extraction, crystallization, recrystallization, phase transfer, chromatography and the like.

The above-mentioned Compound (X) to be used as a starting compound in Method K can be produced by a method known per se.

Compound (I-20) of the formula (I), wherein W is W' (W' is as defined above), V is a bond, and $R^2$ is CH=C(OH)PO(OR$^9$)(OR$^{10a}$) [the symbols are as defined above] can be produced by, for example, the following Method L.

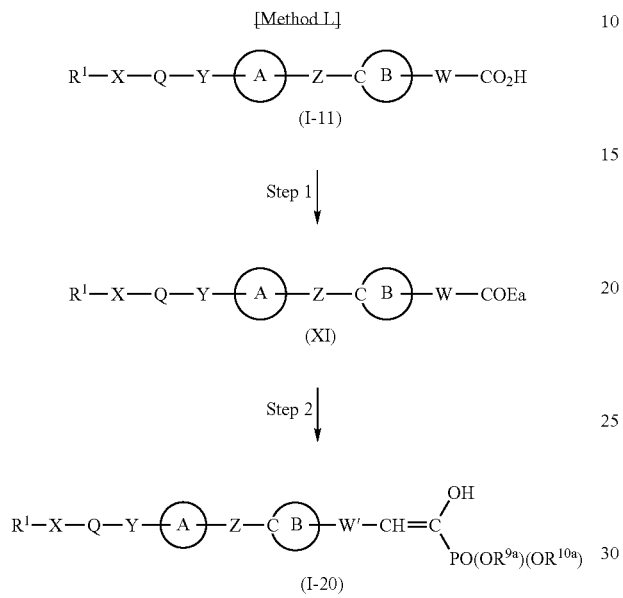

wherein the symbols are as defined above.

In this Method, Compound (I-11) is reacted with a halogenation agent to give Compound (XI), which Compound (XI) is reacted with an organic phosphorus reagent to give Compound (I-20).

(Step 1)

In this Step, Compound (I-11) is reacted with a halogenation agent to give Compound (XI).

This reaction is carried out according to conventional methods in a solvent which does not interfere with the reaction.

As the halogenation agent, for example, thionyl chloride, phosphorus trichloride, phosphorus pentachloride, oxalyl chloride and the like can be mentioned.

As examples of the solvent which does not interfere with the reaction for example, halogenated hydrocarbons such as chloroform, dichloromethane and the like; aromatic hydrocarbons such as benzene, toluene and the like; ethers such as tetrahydrofuran, dioxane, diethyl ether and the like, and the like can be mentioned. These solvents may be used in a mixture of two more kinds thereof at appropriate ratios. In addition, the above-mentioned halogenation agent may be used as a solvent.

The amount of the halogenation agent to be used is generally 0.1-10 molar equivalents, preferably 0.3-3 molar equivalents, relative to Compound (I-11).

The reaction temperature is generally −30° C. to 100° C.

The reaction time is generally 0.5 to 20 hrs.

The thus-obtained Compound (XI) can be isolated and purified by known separation and purification means, such as concentration, concentration under reduced pressure, solvent extraction, crystallization, recrystallization, phase transfer, chromatography and the like.

In addition, a reaction mixture containing Compound (XI) may be used as it is as a starting material of the next Step 2 without isolating Compound (XI).

(Step 2)

In this Step, Compound (XI) is reacted with an organic phosphorus reagent to give Compound (I-20).

This reaction can be carried out by a method known per se, such as a method described in Journal of American Chemical Society, vol. 78, p. 4450 (1956) and the like, or a method analogous thereto.

As the organic phosphorus reagent, for example, tri $C_{1-4}$ alkyl phosphite and the like can be mentioned. The $C_{1-4}$ alkyl is preferably methyl, ethyl and the like.

The thus-obtained Compound (I-20) can be isolated and purified by known separation and purification means, such as concentration, concentration under reduced pressure, solvent extraction, crystallization, recrystallization, phase transfer, chromatography and the like.

Compound (I-21) of the formula (I), wherein W is W' (W' is as defined above), V is a bond, and $R^2$ is $T_1$ ($T_1$ is optionally substituted 2-oxazolinyl) can be produced by, for example, the following Method M. Here, as the substituent for $T_1$, those exemplified as the substituents of the "optionally substituted heterocyclic group", which is the substituent of the aforementioned $R^1$, can be mentioned.

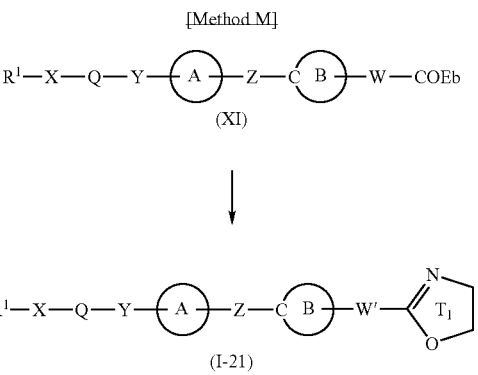

wherein the symbols are as defined above.

In this Method, Compound (I-21) is produced from Compound (XI).

This Method is performed by a method known per se, such as a method described in Synthesis, vol. 11, p. 873 (1989) and the like, or a method analogous thereto.

The thus-obtained Compound (I-21) can be isolated and purified by known separation and purification means, such as concentration, concentration under reduced pressure, solvent extraction, crystallization, recrystallization, phase transfer, chromatography and the like.

Compound (I-22) of the formula (I), wherein V is a bond and $R^2$ is $T_2$ ($T_2$ is an optionally substituted oxadiazolyl, thiadiazolinyl or triazolyl) can be produced by, for example, the following Method N.

Here, As the substituent for $T_2$, those exemplified as the substituent of the "optionally substituted heterocyclic group", which is a substituent for the aforementioned $R^1$ can be mentioned.

[Method N]

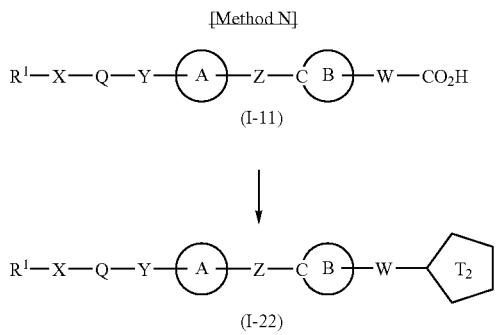

wherein the symbols are as defined above.

In this Method, Compound (I-22) is produced from Compound (I-11).

This Method can be performed by a method known per se, such as a method described in WO01/17994 and the like, or a method analogous thereto.

The thus-obtained Compound (I-22) can be isolated and purified by known separation and purification means, such as concentration, concentration under reduced pressure, solvent extraction, crystallization, recrystallization, phase transfer, chromatography and the like.

Compound (I-23) of the formula (I), wherein V is a bond and $R^2$ is $T_3$ ($T_3$ is an optionally substituted 5-oxazolyl), can be produced by, for example, the following Method O. Here, As the substituent of $T_3$, those exemplified as the substituent of the "optionally substituted heterocyclic group", which is a substituent for the aforementioned $R^1$ can be mentioned.

[Method O]

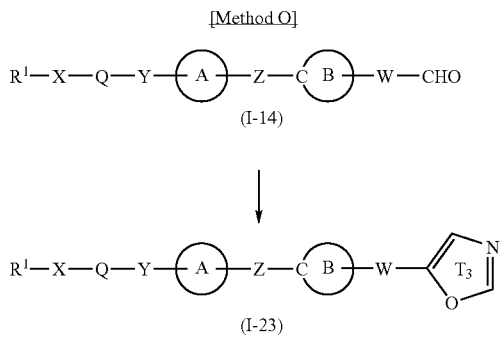

wherein the symbols are as defined above.

In this Method, Compound (I-23) is produced from Compound (I-14).

This Method can be performed by a method known per se, such as a method described in Tetrahedron Letters, p. 2369 (1972) and the like, or a method analogous thereto.

The thus-obtained Compound (I-23) can be isolated and purified by known separation and purification means, such as concentration, concentration under reduced pressure, solvent extraction, crystallization, recrystallization, phase transfer, chromatography and the like.

Compound (I-24) of the formula (I), wherein Z is $-(CH_2)_n-CONR^8-$ (the symbols are as defined above) is produced by, for example, the following Method P.

[Method P]

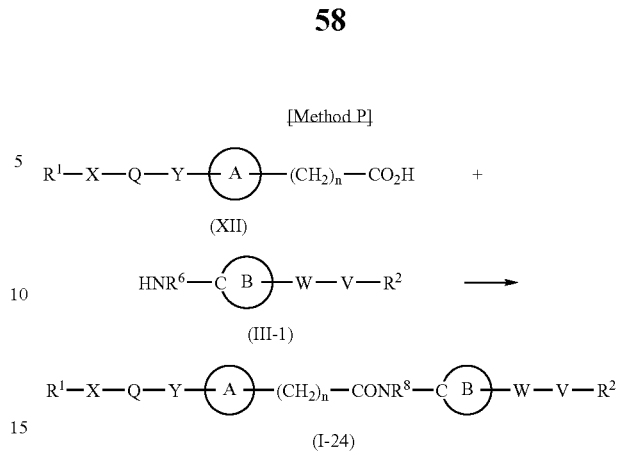

wherein the symbols are as defined above.

In this Method, Compound (XII) is reacted with Compound (III-1) to give Compound (I-24). This reaction is carried out in the same manner as in the aforementioned step 2 of Method F.

The thus-obtained Compound (I-24) can be isolated and purified by known separation and purification means, such as concentration, concentration under reduced pressure, solvent extraction, crystallization, recrystallization, phase transfer, chromatography and the like.

The above-mentioned Compound (XII) and (III-1), which are used as starting compounds in Method P can be produced by a method known per se. For example, Compound (XII) can be produced by a method described in WO99/58510 and the like, or a method analogous thereto. In addition, Compound (III-1) can be produced by a method described in Journal of Heterocyclic Chemistry, vol. 27, p. 1805 (1990) and the like, or a method analogous thereto.

Compound (I-25) of the formula (I), wherein V is a bond and $R^2$ is methyl substituted by $T_4$ ($T_4$ is an optionally substituted dioxooxazolidinylidene, an optionally substituted dioxothiazolidinylidene or an optionally substituted diokiimidazolidinylidene); and Compound (I-26) wherein V is a bond and $R^2$ is methyl substituted by $T_5$ ($T_5$ is an optionally substituted dioxooxazolidinyl, an optionally substituted dioxothiazolidinyl or an optionally substituted diokiimidazolidinyl) can be produced by, for example, the following Method Q. Here, as the substituent of $T_4$ and $T_5$, a $C_{1-6}$ alkyl group and the like can be mentioned.

[Method Q]

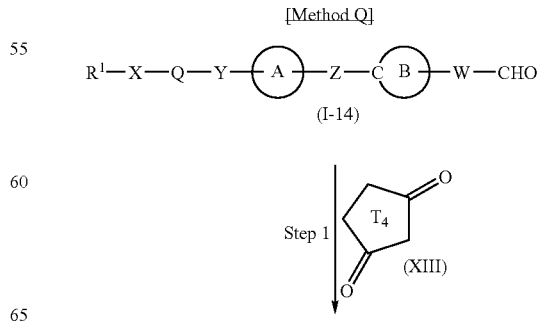

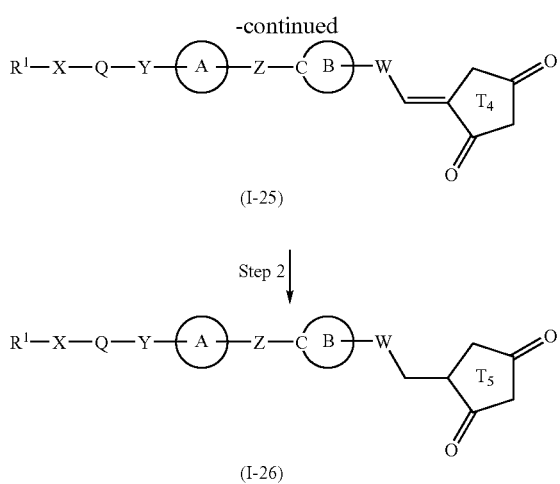

wherein the symbols are as defined above.

In this Method, Compound (I-14) is reacted with Compound (XIII) to give Compound (I-25), which Compound (I-25) is subjected to reduction reaction to give Compound (I-26).

(Step 1)

In this Step, Compound (I-14) is reacted with Compound (XIII) to give Compound (I-25).

This Method can be performed by a method known per se, such as a method described in Chemical & Pharmaceutical Bulletin, vol. 39, p. 1440 (1991) and the like, or a method analogous thereto.

The thus-obtained Compound (I-25) can be isolated and purified by known separation and purification means, such as concentration, concentration under reduced pressure, solvent extraction, crystallization, recrystallization, phase transfer, chromatography and the like.

In addition, a reaction mixture containing Compound (I-25) may be used as it is as a starting material of the next Step 2 without isolating Compound (I-25).

(Step 2)

In this Step, Compound (I-25) is subjected to reduction reaction to give Compound (I-26). This reaction is carried out in the same manner as in the aforementioned Step 2 of Method E.

The thus-obtained Compound (I-26) can be isolated and purified by known separation and purification means, such as concentration, concentration under reduced pressure, solvent extraction, crystallization, recrystallization, phase transfer, chromatography and the like.

The above-mentioned Compound (XIII) to be used as a starting compound in Method Q can be produced by a method known per se.

A compound of the formula (I), wherein W is a divalent hydrocarbon group having 1 to 20 carbon atoms, V is a bond, and $R^2$ is an optionally substituted dioxooxazolidinyl, dioxothiazolidinyl or diokiimidazolidinyl can be also produced in the same manner as in the aforementioned Method Q.

When the starting compound has an amino group, a carboxyl group, a hydroxy group, or a carbonyl group as a substituent in the respective reactions described above, a protective group in common use in peptide chemistry and other fields may be introduced therein. The desired compound can be obtained by removing the protective group after the reaction, if necessary.

Examples of the amino-protecting group include those exemplified as the above-mentioned $R^5$.

Examples of the carboxyl-protecting group include a $C_{1-6}$ alkyl group (e.g., methyl, ethyl, propyl, isopropyl, butyl, tert-butyl), a $C_{7-11}$ aralkyl group (e.g., benzyl), a phenyl group, a trityl group, a silyl group (e.g., trimethylsilyl, triethylsilyl, dimethylphenylsilyl, tert-butyldimethylsilyl, tert-butyldiethylsilyl, tert-butyldiphenylsilyl), a $C_{2-6}$ alkenyl group (e.g., 1-allyl) and the like. These groups may be substituted by 1 to 3 halogen atoms (e.g., fluorine, chlorine, bromine, iodine), a $C_{1-6}$ alkoxy group (e.g., methoxy, ethoxy, propoxy), a nitro group and the like.

Examples of the hydroxyl-protecting group include those exemplified as the above-mentioned $R^4$.

Examples of the carbonyl-protecting group include a cyclic acetal (e.g., 1,3-dioxane) and a non-cyclic acetal (e.g., di-$C_{1-6}$ alkylacetal).

In addition, these protecting groups can be removed by a method known per se, e.g., the method described in *Protective Groups in Organic Synthesis*, published by John Wiley and Sons (1980). For example, methods employing an acid, a base, ultraviolet rays, hydrazine, phenylhydrazine, sodium N-methyldithiocarbamate, tetrabutylammonium fluoride, palladium acetate, a trialkylsilyl halide (e.g., trimethylsilyl iodide, trimethylsilyl bromide etc.) or the like, the reduction method, and the like may be used.

When Compound (I) contains an optical isomer, a stereomer, a position isomer or a rotation isomer, these isomers are also encompassed as Compound (I) and can be each obtained as a single substance by means of a method known per se of synthesis or separation. For example, when an optical isomer is present in Compound (I), the optical isomer separated from said compound is also included in Compound (I).

Optical isomers can be produced by a method known per se. Specifically, optical isomers are obtained by using an optically active synthesis intermediate, or optically resolving a racemate of the final product by a conventional method.

Examples of the method of optical resolution include methods known per se, such as the fractional recrystallization methods, the chiral column methods and the diastereomer methods.

1) Fractional Recrystallization Method

A method wherein a salt is formed between a racemate and an optically active compound [e.g., (+)-mandelic acid, (−)-mandelic acid, (+)-tartaric acid, (−)-tartaric acid, (+)-1-phenethylamine, (−)-1-phenethylamine, cinchonine, (−)-cinchonidine, brucine etc], which salt is separated by fractional recrystallization etc., and, if desired, subjected to a neutralization process, to yield a free optical isomer.

2) Chiral Column Method

A method wherein a racemate or a salt thereof is applied to a column for optical isomer separation (chiral column). In the case of liquid chromatography, for example, optical isomers are separated by adding a mixture of the optical isomers to a chiral column such as ENANTIO-OVM (produced by Tosoh Corporation) or CHIRAL series produced by DAICEL CHEMICAL IND., and developing it in water, various buffers (e.g., phosphate buffer), an organic solvent (e.g., ethanol, methanol, isopropanol, acetonitrile, trifluoroacetic acid, diethylamine etc.), or a solvent mixture thereof. In the case of gas chromatography, for example, a chiral column such as CP-Chirasil-DeX CB (produced by GL Science) is used to separate optical isomers.

3) Diastereomer Method

A method wherein a racemate mixture and an optically active reagent are chemically reacted to yield a diastereomer mixture, which is then subjected to ordinary means of separation (e.g., fractional recrystallization, chromatography etc.) to obtain single substances, which are subjected to a chemical reaction such as a hydrolysis reaction to cut off the optically active reagent moiety, whereby the desired optical isomer is obtained. For example, when Compound (I) has hydroxy or primary or secondary amino in the molecule thereof, said compound, an optically active organic acid (e.g., MTPA [α-methoxy-α-(trifluoromethyl) phenylacetic acid], (−)-menthoxyacetic acid) and the like may be subjected to a condensing reaction to yield a diastereomer of an ester or amide, respectively. On the other hand, when Compound (I) has a carboxyl group, said compound and an optically active amine or an alcohol reagent may be subjected to a condensing reaction to yield a diastereomer of an amide or ester, respectively. The diastereomer thus separated is converted to an optical isomer of the original compound by subjecting it to an acid hydrolysis or a basic hydrolysis reaction.

The present invention is hereinafter described in more detail by means of, but is not limited to, the following Test Examples, Reference Examples, Examples and Formulation Examples.

In addition, % in the Reference Examples and Examples below means percent by weight, unless specified otherwise. Room temperature means the temperature of 1 to 30° C.

In the Test Examples, compound A refers to 5-{4-[2-(5-methyl-2-phenyl-1,3-oxazol-4-yl)ethoxy]benzyl}-1,3-thiazolidine-2,4-dione, [$^3$H]-compound A refers to a $^3$H-labeled compound A, respectively. The compound A is a compound that bounds to PPARγ to activate PPARγ.

The sequence numbers in the sequence listing in the present specification show the following respective sequences.

[SEQ ID NO:1]
Shows the base sequence of the primer XRA-U used in Reference Example 1a.
[SEQ ID NO:2]
Shows the base sequence of the primer XRA-L used in Reference Example 1a.
[SEQ ID NO:3]
Shows the base sequence of the PPRE-U used in Reference Example 2a.
[SEQ ID NO:4]
Shows the base sequence of the PPRE-L used in Reference Example 2a.
[SEQ ID NO:5]
Shows the base sequence of the primer TK-U used in Reference Example 2a.
[SEQ ID NO:6]
Shows the base sequence of the primer TK-L used in Reference Example 2a.
[SEQ ID NO:7]
Shows the base sequence of the primer PAG-U used in Reference Example 3a.
[SEQ ID NO:8]
Shows the base sequence of the primer PAG-L used in Reference Example 3a.

EXAMPLES

Test Example 1

Measurement of Human PPARγ1 Binding Activity

A cell extract containing 1.5 μg/ml of full length hPPARγ1 prepared in Reference Example 7a, 20 nM [$^3$H]-compound A (16 Ci/mmol)(Amersham Pharmacia Biotech) and a test compound were reacted in TEGM buffer at 4° C. for 16 hrs. To the reaction mixture was added activated carbon (Sigma) coated with 140 μl of dextran (Amersham Pharmacia Biotech) and gelatin (Sigma), and the mixture was left standing at 4° C. for 10 min and centrifuged at 910×g for 10 min. After centrifugation, the radioactivity of 30 μl of supernatant was measured with Topcount (Packard). In addition, a test similar to the above was conducted for the non-use of the aforementioned test compound and for the use of 100 μM of compound A instead of the aforementioned test compound, and the radioactivity was determined.

The human PPARγ1 binding activity of the test compound was evaluated using percentages wherein the measured value of the radioactivity when 20 nM [$^3$H]-compound A alone was added was 100%, and the measured value of the radioactivity when 20 nM [$^3$H]-compound A and 100 μM of compound A were simultaneously added was 0%. Moreover, the $IC_{50}$ value of the test compound was calculated based on the analysis of the compound concentration and the percentage using PRISM3.0 (Graph Pad, Inc.). The results are shown in Table 1.

TABLE 1

| Test compound (Example No.) | $IC_{50}$ (nM) |
|---|---|
| 42 | 1100 |
| 72 | 770 |
| 75 | 660 |
| 76 | 190 |
| 77 | 79 |
| 100 | 210 |
| 116 (E form) | 39 |
| 150 (E form) | 50 |
| 145 | 80 |
| 146 | 68 |
| 156 | 7300 |
| 191 | 810 |
| 203 | 4.8 |
| 211 | 27 |
| 224 | 3.6 |
| 239 | 61 |
| 241 | 69 |
| 249 | 33 |
| 252 | 23 |
| 282 | 120 |
| 284 | 75 |
| 307 | 7.4 |
| 315 | 500 |
| 336 | 7.7 |
| 337 | 66 |
| 344 | 46 |
| 357 | 150 |
| 361 | 38 |
| 369 | 83 |
| 370 | 32 |

As shown above, the compound of the present invention has superior PPARγ binding activity.

Test Example 2

Evaluation of Compound Based on Human PPARγ1 Antagonist Assay

PPARγ:RXRα:4ERPP/CHO-K1 cells (obtained in Reference Example 5a) cultured in Ham's F-12 medium (GIBCO, Inc.) supplemented with 10% fetal bovine serum (TRACE SCIENTIFIC, Ltd.) were seeded in a well of a 96 well white plate at $2 \times 10^4$ cells/well and cultured under 37° C. 5% $CO_2$ conditions for 24 hrs. After removal of the medium, Ham's F-12 medium (GIBCO) containing 60 μl of 0.1% BSA (not containing fatty acid) (Wako Pure Chemical Industries, Ltd.), 20 μl of $10^{-5}$M or $10^{-6}$ M test compound and 20 μl of compound A having a final concentration of 10 nM as a stimulant were added, and the cells were cultured under 37° C. 5% $CO_2$ conditions for 24 hrs. After removal of the medium, 40 μl of Pickagene LT7.5 (Wako Pure Chemical Industries, Ltd.) 2-fold diluted with HBSS (HANKS' BALANCED SALT SOLUTION) (BIO WHITTAKER Inc.) was added. After stirring, luciferase activity was measured using 1420 ARVO Multilabel Counter (Wallac, Inc.). In addition, a test similar to the above was conducted for the non-use of the aforementioned test compound alone and for the non-use of the aforementioned test compound and compound A to determine the luciferase activity.

The human PPARγ1 antagonistic activity of the test compound was evaluated using percentages (% inhibition) wherein the luciferase activity when 10 nM compound A alone was added was 0%, and the luciferase activity when the test compound and compound A were not added was 100%. The concentration of the test compound was $10^{-5}$ M for the compounds of Example 42 and 315 and $10^{-6}$ M for other test compounds. The results are shown in Table 2.

TABLE 2

| Test compound (Example No.) | Inhibitory rate (%) |
| --- | --- |
| 42 | 50 |
| 72 | 62 |
| 75 | 70 |
| 76 | 63 |
| 77 | 51 |
| 100 | 74 |
| 116 (E form) | 97 |
| 150 (E form) | 82 |
| 145 | 96 |
| 146 | 111 |
| 156 | 66 |
| 191 | 79 |
| 203 | 111 |
| 211 | 110 |
| 224 | 112 |
| 239 | 116 |
| 241 | 113 |
| 249 | 108 |
| 252 | 111 |
| 282 | 69 |
| 284 | 107 |
| 307 | 108 |
| 315 | 112 |
| 336 | 102 |
| 337 | 110 |
| 344 | 103 |
| 357 | 103 |
| 359 | 111 |
| 361 | 110 |
| 369 | 108 |
| 370 | 111 |
| 371 | 114 |
| 373 | 112 |

As shown above, the compound of the present invention has superior PPARγ-RXRα heterodimer antagonistic activity.

Reference Example 1a

Cloning of Human RXRα Gene

A human RXRα gene was cloned using a kidney cDNA (produced by Toyobo Co., Ltd., trade name: QUICK-Clone cDNA) as a template by means of a PCR method employing a primer set shown below which was prepared with reference to the base sequence of RXRα gene reported by Mangelsdorf, D. J. et al (*Nature*, 1990, Vol. 345 (6272), page 224-229).

XRA-U:
(SEQ ID NO: 1)
5'-TTA GAA TTC GAC ATG GAC ACC AAA CAT TTC CTG-3'

XRA-L:
(SEQ ID NO: 2)
5'-CCC CTC GAG CTA AGT CAT TTG GTG CGG CGC CTC-3'

The PCR reaction was performed by Hot Start method using AmpliWax PCR Gem 100 (produced by TAKARA SHUZO CO., LTD.). First, 2 μl of 10×LA PCR Buffer, 3 μl of 2.5 mM dNTP solution, 2.5 μl each of 12.5 μM primer solutions and 10 μl of sterilized distilled water were mixed to obtain a bottom layer solution mixture. 1 μl of 1 ng/ml of human kidney cDNA as a template, 3 μl of 10×LA PCR Buffer, 1 μl of 2.5 mM dNTP solution, 0.5 μl of TaKaRa LA Taq DNA polymerase (produced by TAKARA SHUZO CO., LTD.) and 24.5 μl of sterilized distilled water were mixed to obtain a top layer solution mixture.

To the bottom layer solution mixture described above, added was one unit of AmpliWax PCR Gem 100 (produced by TAKARA SHUZO CO., LTD.), which was treated at 70° C. for 5 minutes and then in ice for 5 minutes. Then, the top layer solution mixture was added to the mixture to prepare the reaction mixture of PCR. A tube containing the reaction mixture was set on a thermal cycler (produced by Perkin Elmer, USA) and treated at 95° C. for 2 minutes. After repeating the cycle of 95° C. for 15 seconds and 68° C. for 2 minutes a further 35 times, the tube was treated at 72° C. for 8 minutes.

The PCR product thus obtained was subjected to electrophoresis on agarose gel (1%), and 1.4 kb DNA fragment containing RXRα gene was recovered from the gel, and then inserted into pT7 Blue-T vector (produced by TAKARA SHUZO CO., LTD.) to obtain plasmid PTBT-hRXRα.

Reference Example 2a

Construction of Reporter Plasmids

A DNA fragment containing PPAR-responding element (PPRE) of an acyl CoA oxidase was prepared using the following 5'-terminal phosphorylated synthetic DNA.

```
PPRE-U:
                                        (SEQ ID NO: 3)
5'-pTCGACAGGGGACCAGGACAAAGGTCACGTTCGGGAG-3'

PPRE-L:
                                        (SEQ ID NO: 4)
5'-pTCGACTCCCGAACGTGACCTTTGTCCTGGTCCCCTG-3'
```

First, PPRE-U and PPRE-L were annealed and inserted to Sal I site of plasmid pBlue Script SK+. By determining the base sequence of the inserted fragment, plasmid pBSS-PPRE4, in which 4 PPREs were ligated in tandem, was selected.

An HSV thymidine kinase minimum promoter (TK promoter) region was cloned using pRL-TK vector (produced by Promega, USA) as a template by means of a PCR method employing a primer set shown below which was prepared with reference to the base sequence of the promoter region of thymidine kinase reported by Luckow, et al (*Nucleic Acids Res.*, 1987, Vol. 15(13), p. 5490)

```
                                        (SEQ ID NO: 5)
TK-U: 5'-CCCAGATCTCCCCAGCGTCTTGTCATTG-3'

(SEQ ID NO: 6)
TK-L: 5'-TCACCATGGTCAAGCTTTTAAGCGGGTC-3'
```

The PCR reaction was performed by Hot Start method using AmpliWax PCR Gem 100 (TAKARA SHUZO CO., LTD.). First, 2 µl of 10×LA PCR Buffer, 3 µl of 2.5 mM dNTP solution, 2.5 µl each of 12.5 µM primer solutions and 10 µl of sterilized distilled water were mixed to obtain a bottom layer solution mixture. 1 µl of PRL-TK vector [produced by Promega, USA] as a template, 3 µl of 10×LA PCR Buffer, 1 µl of 2.5 mM dNTP solution, 0.5 µl of TaKaRa LA Taq DNA polymerase (produced by TAKARA SHUZO CO. LTD.) and 24.5 µl of sterilized distilled water were mixed to obtain a top layer solution mixture.

To the bottom layer solution mixture described above, added was one unit of AmpliWax PCR Gem 100 (produced by TAKARA SHUZO CO., LTD.), which was treated at 70° C. for 5 minutes and then in ice for 5 minutes. Then, the top layer solution mixture was added to the mixture to prepare the reaction mixture of PCR. A tube containing the reaction mixture was set on a thermal cycler (produced by Perkin Elmer, USA) and treated at 95° C. for 2 minutes. After repeating the cycle of 95° C. for 15 seconds and 68° C. for 2 minutes a further 35 times, the tube was treated at 72° C. for 8 minutes.

The PCR product thus obtained was subjected to electrophoresis on agarose gel (1%), and 140 b DNA fragment containing TK promoter was recovered from the gel, and then inserted into pT7 Blue-T vector (produced by TAKARA SHUZO CO., LTD.). By digesting the plasmid thus obtained with the restriction enzymes Bgl II and NcoI, a fragment containing TK promoter was obtained, which was ligated to the Bgl II-NcoI fragment of plasmid pGL3-Basic vector (produced by Promega, USA) to obtain plasmid pGL3-TK.

A 4.9 kb NheI-XhoI fragment of plasmid pGL3-TK thus obtained was ligated to a 200 b NheI-XhoI fragment of plasmid pBSS-PPRE4 to obtain plasmid pGL3-4ERPP-TK.

This plasmid pGL3-4ERPP-TK thus obtained was digested with BamHI (produced by TAKARA SHUZO CO., LTD.) and then treated with T4 DNA polymerase (produced by TAKARA SHUZO CO., LTD.) to form a blunt terminal, whereby obtaining a DNA fragment.

On the other hand, pGFP-C1 (produced by Toyobo Co., Ltd.) was digested with Bsu36I (NEB) and then treated with T4 DNA polymerase (produced by TAKARA SHUZO CO., LTD.) to form a blunt terminal whereby obtaining a 1.6 kb of a DNA fragment.

The both DNA fragments were ligated to construct a reporter plasmid pGL3-4ERPP-TK neo.

Reference Example 3a

Cloning of Human PPARγ Gene

A human PPARγ gene was cloned using a heart cDNA (produced by Toyobo Co., Ltd., trade name: QUICK-Clone cDNA) as a template by means of a PCR method employing a primer set shown below which was prepared with reference to the base sequence of PPARγ gene reported by Greene et al (*Gene Expr.*, 1995, Vol. 4 (4-5), pages 281-299).

```
PAG-U:
                                        (SEQ ID NO: 7)
5'-GTG GGT ACC GAA ATG ACC ATG GTT GAC ACA GAG-3'

PAG-L:
                                        (SEQ ID NO: 8)
5'-GGG GTC GAC CAG GAC TCT CTG CTA GTA CAA GTC-3'
```

The PCR reaction was performed by Hot Start method using AmpliWax PCR Gem 100 (TAKARA SHUZO CO., LTD.). First, 2 µl of 10×LA PCR Buffer, 3 µl of 2.5 mM dNTP solution, 2.5 µl each of 12.5 µM primer solutions and 10 µl of sterilized distilled water were mixed to obtain a bottom layer solution mixture. 1 µl of human heart cDNA (1 ng/ml) as a template, 3 µl of 10×LA PCR Buffer, 1 µl of 2.5 mM dNTP solution, 0.5 µl of TaKaRa LA Taq DNA polymerase (produced by TAKARA SHUZO CO., LTD.) and 24.5 µl of sterilized distilled water were mixed to obtain a top layer solution mixture.

To the bottom layer solution mixture described above, added was one unit of AmpliWax PCR Gem 100 (produced by TAKARA SHUZO CO., LTD.), which was treated at 70° C. for 5 minutes and then in ice for 5 minutes. Then, the top layer solution mixture was added to the mixture to prepare the reaction mixture of PCR. A tube containing the reaction mixture was set on a thermal cycler (produced by Perkin Elmer, USA) and treated at 95° C. for 2 minutes. After repeating the cycle of 95° C. for 15 seconds and 68° C. for 2 minutes a further 35 times, the tube was treated at 72° C. for 8 minutes.

The PCR product thus obtained was subjected to electrophoresis on agarose gel (1%), and 1.4 kb DNA fragment containing PPARγ gene was recovered from the gel, and then inserted into pT7 Blue-T vector (produced by TAKARA SHUZO CO., LTD.) to obtain plasmid pTBT-hPPARγ.

Reference Example 4a

Construction of Plasmids for Expressing Human PPARγ, RXRα

A 7.8 kb FspI-NotI fragment of plasmid pVgRXR (produced by Invitrogen, USA) was ligated to a 0.9 kb FspI-NotI fragment containing RXRα gene of plasmid pTBT-hRXRα obtained in Reference Example 1a to prepare plasmid pVgRXR2. Then, pVgRXR2 was digested with BstXI and then treated with T4 DNA polymerase (produced by TAKARA SHUZO CO., LTD.) to obtain a blunt terminal. Then digestion at KpnI gave a 6.5 kb DNA fragment.

On the other hand, plasmid pTBT-hPPARγ obtained in Reference Example 3a was digested with Sal I and then treated with T4DNA polymerase (produced by TAKARA SHUZO CO., LTD.) to obtain a blunt terminal. Then digestion at KpnI gave a 1.4 kb DNA fragment containing human PPARγ gene. The both DNA fragments were ligated to construct plasmid pVgRXR2-hPPARγ.

Reference Example 5a

Introduction of Human PPARγ- and RXRα-Expression Plasmid and Reporter Plasmid into CHO-K1 Cell and Establishment of Expressing Cell After a CHO-K1 cell cultured in a cell culture flask (150 cm$^2$) (produced by Corning Costar Corporation, USA) containing Ham's F-12 medium (produced by Life Technologies, Inc., USA) supplemented with 10% fetal bovine serum (produced by Life Technologies, Inc., USA) was detached by treating with 0.5 g/L trypsin-0.2 g/L EDTA (ethylenediaminetetraacetic acid) (produced by Life Technologies, Inc., USA), the cell was washed with PBS (phosphate-buffered saline) (produced by Life Technologies, Inc., USA), centrifuged (1000 rpm, 5 minutes), and then suspended in PBS. Subsequently, the DNA was introduced into the cells under the conditions shown below using GENE PULSER (produced by Bio-Rad Laboratories, USA).

Namely, to a cuvette having a 0.4 cm gap, added were 8×10$^6$ cells and 10 μg of plasmid pVgRXR2-hPPARγ obtained in Reference Example 4a and 10 μg of reporter plasmid pGL3-4ERPP-TK neo obtained in Reference Example 2a, which was subjected to electroporation at the voltage of 0.25 kV under the capacitance of 960 μF. Subsequently, the cell was transferred into a Ham's F-12 medium containing 10% fetal bovine serum and cultured for 24 hours and then the cells were detached again and centrifuged, and then suspended in HAM F12 medium containing 10% fetal bovine serum supplemented with 500 μg/ml of GENETICIN (produced by Life Technologies, Inc., USA) and 250 μg/ml of ZEOCIN (produced by Invitrogen, USA). The obtained suspension was diluted to the density of 10$^4$ cells/ml and inoculated to a 96-well plate (produced by Corning Costar Corporation, USA), which was cultured in a CO$_2$ gas incubator at 37° C., whereby obtaining a GENETICIN- and ZEOCIN-resistant transformant. Subsequently, after the transformant cell line thus obtained was cultured in a 24-well plate (produced by Corning Costar Corporation, USA), selected was a cell line in which the luciferase was expressed and induced, i.e., PPARγ:RXRα:4ERPP/CHO-K1 cell by the addition of 10 μM pioglitazone hydrochloride.

Reference Example 6a

Preparation of Plasmid for Human PPARγ Expression

A 5.6 Kb KpnI-SalI fragment of plasmid pMCMVneo and a 1.4 kb KpnI-SalI fragment containing hPPARγ gene of plasmid pTBT-hPPARγ described in Reference Example 3a were ligated to give plasmid pMCMVneo-hPPARγ.

Reference Example 7a

Preparation of Human PPARγ1 Protein Using COS-1 Cells

COS-1 cells were seeded in a 150 cm$^2$ tissue culture flask (Corning Inc.) at 5×10$^6$ cells, and cultured under 37° C. 5% CO$_2$ conditions for 24 hrs. Transfection was performed using lipofectamine (GIBCO BRL). To be specific, 125 μl of lipofectamine, 100 μl of PLUS Reagent and 15 μg of hPPARγ expression plasmid (plasmid pMCMVneo-hPPARγ obtained in Reference Example 6a) were mixed with opti-MEM (GIBCO BRL) to give a transfection mixture. The transfection mixture (25 ml) was added to COS-1 cells and the cells were cultured under 37° C. 5% CO$_2$ conditions for 3 hrs. Then 25 ml of DMEM medium (Nikken Biomedical Laboratory) containing 10% FCS treated with activated carbon (Sigma) was added to the cells and the cells were cultured under 37° C. 5% CO$_2$ conditions. After 24 hrs., the medium was substituted with 50 ml of DMEM medium (Nikken Biomedical Laboratory) containing 5% FCS treated with activated carbon, and the cells were cultured under 37° C., 5% CO$_2$ conditions. After 48 hrs, the transfected cells were recovered and washed with TEG buffer (10 mM Tris-HCl (pH 7.2), 50 mM EDTA, 10% glycerol). The cells were suspended in 1 ml TEGM buffer (10 mM Tris-HCl (pH 7.2), 1 mM EDTA, 10% glycerol, 7 μl/100 ml β-mercaptoethanol, 10 mM Na molybdate, 1 mM dithiothreitol, 2 tablets/100 ml Protease inhibitor Cocktail tablets (Boehringer Mannheim)) and, for cell lysis, frozen with liquid nitrogen and thawed on ice. To remove the debris of the cells, the extract was centrifuged at 228,000×g, 4° C. for 20 min. and the supernatant was preserved at −80° C. until use.

Reference Example 1

A mixture of 4-chloromethyl-2-(2-furyl)-1,3-oxazole (10.0 g), vanillin (8.29 g), potassium carbonate (7.53 g) and N,N-dimethylformamide (100 mL) was stirred at 80° C. for 15 hrs. Water was poured into the reaction mixture, and the precipitated crystals were collected by filtration to give 4-{[2-(2-furyl)-1,3-oxazol-4-yl]methoxy}-3-methoxybenzaldehyde as brown crystals (14.90 g, yield 91%). Recrystallization from hexane-ethyl acetate gave pale-yellow prism crystals. melting point: 138-139° C.

Reference Example 2

To a solution of 4-{[2-(2-furyl)-1,3-oxazol-4-yl]methoxy}-3-methoxybenzaldehyde (9.70 g) in tetrahydrofuran (100 mL)-ethanol (50 mL) was gradually added sodium borohydride (1.23 g) at room temperature. After stirring at room temperature for 30 min., water was added to the reaction mixture and the precipitated crystals were collected by filtration to give (4-{[2-(2-furyl)-1,3-oxazol-4-yl]methoxy}-3-methoxyphenyl)methanol as pale-brown crystals (8.40 g, yield 86%). Recrystallization from ethyl acetate-hexane gave colorless prism crystals. melting point: 117-118° C.

Reference Example 3

A mixture of 4-chloromethyl-2-(2-furyl)-5-methyl-1,3-oxazole (22.3 g), 3-hydroxybenzyl alcohol (10.0 g), potassium carbonate (11.14 g) and N,N-dimethylformamide (200 mL) was stirred at 90° C. for 4 hrs. Water was poured into the reaction mixture, and the mixture was extracted with ethyl acetate. The ethyl acetate layer was washed with saturated brine, dried over anhydrous magnesium sulfate and concentrated. The residue was subjected to silica gel column chromatography, and eluted with ethyl acetate-hexane (1:1, v/v) to give (3-{[2-(2-furyl)-5-methyl-1,3-oxazol-4-yl]methoxy}phenyl)methanol as colorless crystals (12.75 g, yield 55%). Recrystallization from ethyl acetate-hexane gave colorless prism crystals. melting point: 100-101° C.

Reference Example 4

To a mixture of (3-{[2-(2-furyl)-5-methyl-1,3-oxazol-4-yl]methoxy}phenyl)methanol (8.0 g) and toluene (100 mL) was added thionyl chloride (4.00 g), and the mixture was heated under reflux for 2 hrs. The reaction mixture was concentrated and ethyl acetate was added to the residue. The organic layer was washed successively with saturated aqueous sodium hydrogen carbonate and saturated brine, dried over anhydrous magnesium sulfate and concentrated. The residue was subjected to silica gel column chromatography, and eluted with ethyl acetate-hexane (1:4, v/v) to give {4-[(3-chloromethylphenoxy)methyl]-2-(2-furyl)-5-methyl-1,3-oxazole as a colorless oil (8.40 g, yield 99%).
NMR (CDCl$_3$) δ: 2.43 (3H, s), 4.56 (2H, s), 5.00 (2H, s), 6.51-6.54 (1H, m), 6.90-7.03 (4H, m), 7.19-7.32 (1H, m), 7.53-7.54 (1H, m).

Reference Example 5

A mixture of 4-chloromethyl-2-(2-furyl)-5-methyl-1,3-oxazole (30.0 g), 3-ethoxy-4-hydroxybenzaldehyde (22.9 g), potassium carbonate (21.01 g) and N,N-dimethylformamide (300 mL) was stirred at 90° C. for 2 hrs. Water was poured into the reaction mixture, and the precipitated crystals were collected by filtration to give 3-ethoxy-4-[[2-(2-furyl)-5-methyl-1,3-oxazol-4-yl]methoxy]benzaldehyde as brown crystals (31.20 g, yield 69%). Recrystallization from ethyl acetate-hexane gave pale-yellow needle. melting point: 159-160° C.

Reference Example 6

To a solution of 3-ethoxy-4-[[2-(2-furyl)-5-methyl-1,3-oxazol-4-yl]methoxy]benzaldehyde (20.00 g) in tetrahydrofuran (250 mL)-ethanol (100 mL) was gradually added sodium borohydride (2.31 g) at 0° C. After stirring at room temperature for 1 hr, water was added to the reaction mixture and the precipitated crystals were collected by filtration to give (3-ethoxy-4-{[2-(2-furyl)-5-methyl-1,3-oxazol-4-yl]methoxy}phenyl)methanol as pale-yellow crystals (18.80 g, yield 93%). Recrystallization from ethyl acetate-hexane gave colorless prism crystals. melting point: 141-142° C.

Reference Example 7

To a mixture of (3-ethoxy-4-{[2-(2-furyl)-5-methyl-1,3-oxazol-4-yl]methoxy}phenyl)methanol (10.0 g) and toluene (100 mL) was added thionyl chloride (4.34 g), and the mixture was heated under reflux for 2 hrs. The reaction mixture was concentrated and ethyl acetate was added to the residue. The organic layer was washed successively with saturated aqueous sodium hydrogen carbonate and saturated brine, dried over anhydrous magnesium sulfate and concentrated to give 4-[(4-chloromethyl-3-ethoxyphenoxy)methyl]-2-(2-furyl)-5-methyl-1,3-oxazole as colorless crystals (9.70 g, yield 92%). Recrystallization from ethyl acetate-hexane gave colorless prism crystals. melting point: 145-146° C.

Reference Example 8

A mixture of 4-chloromethyl-2-(2-furyl)-5-methyl-1,3-oxazole (20.0 g), 3-hydroxy-4-methoxybenzaldehyde (13.97 g), potassium carbonate (13.96 g) and N,N-dimethylformamide (200 mL) was stirred at 90° C. for 3 hrs. Water was poured into the reaction mixture, and the precipitated crystals were collected by filtration to give 3-{[2-(2-furyl)-5-methyl-1,3-oxazol-4-yl]methoxy}-4-methoxybenzaldehyde as colorless crystals (19.4 g, yield 67%). Recrystallization from ethyl acetate-hexane gave colorless prism crystals. melting point: 125-126° C.

Reference Example 9

To a solution of 3-{[2-(2-furyl)-5-methyl-1,3-oxazol-4-yl]methoxy}-4-methoxybenzaldehyde (14.0 g) in tetrahydrofuran (100 mL)-ethanol (30 mL) was gradually added sodium borohydride (1.69 g) at 0° C. After stirring at room temperature for 2 hrs., water was added to the reaction mixture and the precipitated crystals were collected by filtration to give (3-{[2-(2-furyl)-5-methyl-1,3-oxazol-4-yl]methoxy}-4-methoxyphenyl)methanol as pale-yellow crystals (12.87 g, yield 91%). Recrystallization from ethyl acetate-hexane gave pale-yellow prism crystals. melting point: 145-146° C.

Reference Example 10

To a mixture of (3-{[2-(2-furyl)-5-methyl-1,3-oxazol-4-yl]methoxy}-4-methoxyphenyl)methanol (7.0 g) and toluene (150 mL) was added thionyl chloride (3.16 g), and the mixture was heated under reflux for 1 hr. The reaction mixture was concentrated and ethyl acetate was added to the residue. The organic layer was washed successively with saturated aqueous sodium hydrogen carbonate and saturated brine, dried over anhydrous magnesium sulfate and concentrated to give 4-(5-chloromethyl-2-methoxyphenoxy)methyl-2-(2-furyl)-5-methyl-1,3-oxazole as pale-brown crystals (7.30 g, yield 99%). Recrystallization from ethyl acetate-hexane gave colorless prism crystals. melting point: 115-116° C.

Reference Example 11

A mixture of 4-chloromethyl-2-(2-furyl)-5-methyl-1,3-oxazole (8.0 g), ethyl 3-chloro-4-hydroxybenzoate (7.38 g), potassium carbonate (5.09 g) and N,N-dimethylformamide (200 mL) was stirred at 90° C. for 2 hrs. Water was poured into the reaction mixture, and the precipitated crystals were collected by filtration and dried to give ethyl 3-chloro-4-{[2-(2-furyl)-5-methyl-1,3-oxazol-4-yl]methoxy}benzoate as brown crystals (9.90 g, yield 74%). Recrystallization from ethyl acetate-hexane gave colorless prism crystals. melting point: 145-146° C.

Reference Example 12

To a solution of ethyl 3-chloro-4-{[2-(2-furyl)-5-methyl-1,3-oxazol-4-yl]methoxy}benzoate (9.50 g) in tetrahydrofuran (200 mL) was added lithium aluminum hydride (1.00 g) at 0° C. and the mixture was stirred at room temperature for 1 hr. Sodium sulfate decahydrate (8.47 g) was added to the reaction mixture, and the mixture was stirred at room temperature for 30 min. The reaction mixture was diluted with ethyl acetate and the precipitate was filtered off. The filtrate was concentrated to give (3-chloro-4-{[2-(2-furyl)-5-methyl-1,3-oxazol-4-yl]methoxy}phenyl)methanol as colorless crystals (7.68 g, yield 91%). Recrystallization from ethyl acetate-hexane gave colorless prism crystals. melting point: 143-144° C.

Reference Example 13

(3-Chloro-4-{[2-(2-furyl)-5-methyl-1,3-oxazol-4-yl] methoxy}phenyl)methanol (4.0 g) was added to thionyl chloride (10 mL) at 0° C., and the mixture was stirred for 2 hrs. The reaction mixture was concentrated, saturated aqueous sodium hydrogen carbonate was added to the residue and the mixture was extracted with ethyl acetate. The organic layer was washed successively with saturated aqueous sodium hydrogen carbonate and saturated brine, dried over anhydrous magnesium sulfate and concentrated to give 4-(2-chloro-4-chloromethylphenoxy)methyl-2-(2-furyl)-5-methyl-1,3-oxazole as colorless crystals (3.96 g, yield 94%). Recrystallization from ethyl acetate-hexane gave colorless needle crystals. melting point: 103-104° C.

Reference Example 14

To a mixture of 4-benzyloxy-3-hydroxybenzaldehyde (27.30 g) and N,N-dimethylformamide (300 mL) was added sodium hydride (60% in oil, 5.28 g) at 0° C., and the mixture was stirred at room temperature for 1 hr. Chloromethylmethyl ether (16.10 g) was added to the reaction mixture and the mixture was further stirred at room temperature for 15 hrs. The reaction mixture was poured into water and the mixture was extracted with ethyl acetate. The organic layer was washed with saturated brine, dried over anhydrous magnesium sulfate and concentrated. The residue was subjected to silica gel column chromatography to give 4-benzyloxy-3-methoxymethoxybenzaldehyde as a colorless oil (32.60 g, yield 100%) from a fraction eluted with ethyl acetate-hexane (1:3, v/v).
NMR (CDCl$_3$) δ: 3.53 (3H, s), 5.24 (2H, s), 5.28 (2H, s), 7.02 (1H, d, J=8.0 Hz), 7.32-7.42 (5H, m), 7.48 (1H, dd, J=8.0, 2.0 Hz), 7.66 (1H, d, J=2.0 Hz), 9.83 (1H, s).

Reference Example 15

A mixture of 4-chloromethyl-2-(2-furyl)-5-methyl-1,3-oxazole (13.12 g), 4-hydroxy-3-methoxymethoxybenzaldehyde (11.0 g), potassium carbonate (8.35 g) and N,N-dimethylformamide (200 mL) was stirred at 90° C. for 3 hrs. Water was poured into the reaction mixture, and the precipitated crystals were collected by filtration and dried to give 4-{[2-(2-furyl)-5-methyl-1,3-oxazol-4-yl]methoxy}-3-(methoxymethoxy)benzaldehyde as pale-brown crystals (16.11 g, yield 78%). Recrystallization from ethyl acetate-hexane gave colorless prism crystals. melting point: 102-103° C.

Reference Example 16

To a solution of 4-{[2-(2-furyl)-5-methyl-1,3-oxazol-4-yl]methoxy}-3-(methoxymethoxy)benzaldehyde (15.50 g) in tetrahydrofuran (100 mL)-ethanol (50 mL) was gradually added sodium borohydride (1.71 g) at 0° C. After stirring at room temperature for 2 hrs, water was added to the reaction mixture, and the mixture was extracted with ethyl acetate. The organic layer was washed with saturated brine, dried over anhydrous magnesium sulfate and concentrated to give (4-{[2-(2-furyl)-5-methyl-1,3-oxazol-4-yl]methoxy}-3-(methoxymethoxy)phenyl)methanol as colorless crystals (14.11 g, yield 91%). Recrystallization from ethyl acetate-hexane gave colorless prism crystals. melting point: 92-93° C.

Reference Example 17

A mixture of 4-chloromethyl-2-(2-furyl)-5-methyl-1,3-oxazole (3.28 g), 3-hydroxy-2-methoxybenzaldehyde (2.10 g), potassium carbonate (1.91 g) and N,N-dimethylformamide (50 mL) was stirred at 90° C. for 2 hrs. Water was poured into the reaction mixture, and the mixture was extracted with ethyl acetate. The ethyl acetate layer was washed with saturated brine, dried over anhydrous magnesium sulfate and concentrated. The residue was subjected to silica gel column chromatography, and eluted with ethyl acetate-hexane (1:2, v/v) to give 4-{[2-(2-furyl)-5-methyl-1,3-oxazol-4-yl]methoxy}-2-methoxybenzaldehyde as colorless crystals (3.35 g, yield 78%). Recrystallization from ethyl acetate-hexane gave colorless prism crystals. melting point: 111-112° C.

Reference Example 18

To a solution of 4-{[2-(2-furyl)-5-methyl-1,3-oxazol-4-yl]methoxy}-2-methoxybenzaldehyde (3.00 g) in tetrahydrofuran (30 mL)-ethanol (10 mL) was gradually added sodium borohydride (0.36 g) at 0° C. After stirring at room temperature for 1 hr., water was added to the reaction mixture and the precipitated crystals were collected by filtration to give (4-{[2-(2-furyl)-5-methyl-1,3-oxazol-4-yl]methoxy}-2-methoxyphenyl)methanol as colorless crystals (2.91 g, yield 96%). Recrystallization from ethyl acetate-hexane gave colorless prism crystals. melting point: 117-118° C.

Reference Example 19

A mixture of 4-chloromethyl-2-(2-furyl)-5-methyl-1,3-oxazole (4.62 g), 3-bromo-4-hydroxybenzaldehyde (4.28 g), potassium carbonate (2.94 g) and N,N-dimethylformamide (50 mL) was stirred at 90° C. for 4 hrs. Water was poured into the reaction mixture, and the precipitated crystals were collected by filtration to give 3-bromo-4-{[2-(2-furyl)-5-methyl-1,3-oxazol-4-yl]methoxy}benzaldehyde as pale-brown crystals (5.20 g, yield 67%). Recrystallization from ethyl acetate-hexane gave colorless prism crystals. melting point: 146-147° C.

Reference Example 20

To a solution of 3-bromo-4-{[2-(2-furyl)-5-methyl-1,3-oxazol-4-yl]methoxy}benzaldehyde (4.93 g) in tetrahydrofuran (100 mL)-ethanol (50 mL) was gradually added sodium borohydride (0.51 g) at 0° C. After stirring at room temperature for 2 hrs, water was added to the reaction mixture and the precipitated crystals were collected by filtration to give (3-bromo-4-{[2-(2-furyl)-5-methyl-1,3-oxazol-4-yl]methoxy}phenyl)methanol as colorless crystals (4.40 g, yield 89%). Recrystallization from ethyl acetate-hexane gave colorless prism crystals. melting point: 141-142° C.

Reference Example 21

(3-bromo-4-{[2-(2-furyl)-5-methyl-1,3-oxazol-4-yl]methoxy}phenyl)methanol (4.20 g) was added to thionyl chloride (5 mL) at 0° C., and the mixture was stirred for 2 hrs. The reaction mixture was concentrated, saturated aqueous sodium hydrogen carbonate was added to the residue and the mixture was extracted with ethyl acetate. The organic layer was washed successively with saturated aqueous sodium hydrogen carbonate and saturated brine, dried over anhydrous magnesium sulfate and concentrated to give 4-{[2-bromo-4-(chloromethyl)phenoxy]methyl}-2-(2-furyl)-5-methyloxazole as pale-yellow crystals (3.82 g, yield 87%). Recrystallization from ethyl acetate-hexane gave pale-yellow needle crystals. melting point: 125-126° C.

Reference Example 22

A mixture of 4-chloromethyl-5-methyl-2-phenyl-1,3-oxazole (46.10 g), (2,4-dihydroxyphenyl)(phenyl)methanone (50.14 g), potassium carbonate (48.51 g) and acetone (700 mL) was heated under reflux for 20 hrs. The reaction mixture was concentrated, water was poured into the residue, and the mixture was extracted with ethyl acetate. The ethyl acetate layer was washed with saturated brine, dried over anhydrous magnesium sulfate and concentrated to give 4-(4-benzoyl-3-hydroxyphenoxymethyl)-5-methyl-2-phenyl-1,3-oxazole as colorless crystals (49.6 g, yield 55%). Recrystallization from ethyl acetate-hexane gave colorless prism crystals. melting point: 115-116° C.

Reference Example 23

A mixture of 4-(4-benzoyl-3-hydroxyphenoxymethyl)-5-methyl-2-phenyl-1,3-oxazole (54.93 g), methyl bromoacetate (32.88 g), potassium carbonate (19.76 g) and N,N-dimethylformamide (200 mL) was stirred at 90° C. for 15 hrs. Water was poured into the reaction mixture, and the mixture was extracted with ethyl acetate. The ethyl acetate layer was washed with saturated brine, dried over anhydrous magnesium sulfate and concentrated. A mixture of the obtained residue, 1,8-diazabicyclo[5.4.0]-7-undecene (21.77 g), and toluene (750 mL) was heated under reflux for 20 hrs with azeotropic removal of water. The reaction mixture was concentrated, and the residue was subjected to silica gel column chromatography and eluted with ethyl acetate-hexane (1:8, v/v) to give methyl 6-[(5-methyl-2-phenyl-1,3-oxazol-4-yl)methoxy]-3-phenyl-1-benzofuran-2-carboxylate as colorless crystals (34.36 g, yield 55%). Recrystallization from ethyl acetate-hexane gave colorless prism crystals. melting point: 139-140° C.

Reference Example 24

To a mixture of methyl 6-[(5-methyl-2-phenyl-1,3-oxazol-4-yl)methoxy]-3-phenyl-1-benzofuran-2-carboxylate (32.70 g) and tetrahydrofuran (500 mL) was added dropwise diisobutylaluminum hydride (0.95M hexane solution, 235 mL) at 0° C. The reaction mixture was stirred at 0° C. for 2 hrs, sodium sulfate decahydrate (71.85 g) was added, and the mixture was stirred at room temperature for 30 min. The reaction mixture was diluted with ethyl acetate and the precipitate was filtered off. The filtrate was concentrated to give {6-[(5-methyl-2-phenyl-1,3-oxazol-4-yl)methoxy]-3-phenyl-1-benzofuran-2-yl}methanol as colorless crystals (27.80 g, yield 91%). Recrystallization from ethyl acetate-hexane gave colorless prism crystals. melting point: 152-153° C.

Reference Example 25

{6-[(5-Methyl-2-phenyl-1,3-oxazol-4-yl)methoxy]-3-phenyl-1-benzofuran-2-yl}methanol (1.50 g) was added to thionyl chloride (5 mL) at 0° C., and the mixture was stirred for 1 hr. After concentration of the reaction mixture, saturated aqueous sodium hydrogen carbonate was added to the residue and the mixture was extracted with ethyl acetate. The organic layer was washed successively with saturated aqueous sodium hydrogen carbonate and saturated brine, dried over anhydrous magnesium sulfate and concentrated to give 4-{[(2-chloromethyl-3-phenyl-1-benzofuran-6-yl)oxy]methyl}-5-methyl-2-phenyl-1,3-oxazole as colorless crystals (1.43 g, yield 92%). Recrystallization from ethyl acetate-hexane gave colorless prism crystals. melting point: 129-130° C.

Reference Example 26

3-Benzyloxy-1-phenyl-1H-pyrazole-4-carbaldehyde (0.30 g), 5% palladium on carbon (0.50 g) and tetrahydrofuran (10 mL) were subjected to catalytic reduction under a hydrogen atmosphere and atmospheric pressure. The catalyst was filtered off and the filtrate was concentrated to give 3-hydroxy-1-phenyl-1H-pyrazole-4-carbaldehyde as colorless crystals (0.16 g, yield 76%). Recrystallization from ethyl acetate-hexane gave colorless prism crystals. melting point: 196-197° C.

Reference Example 27

A mixture of 4-methoxymethoxymethyl-2-phenyl-1,3-oxazole-5-carbaldehyde (4.50 g), 1N hydrochloric acid (50 mL) and tetrahydrofuran (100 mL) was heated under reflux for 15 hrs. Water was added to the reaction mixture, and the mixture was extracted with ethyl acetate. The ethyl acetate layer was washed with saturated brine, dried over anhydrous magnesium sulfate and concentrated. The residue was subjected to silica gel column chromatography, and eluted with ethyl acetate-hexane (1:1, v/v) to give 4-hydroxymethyl-2-phenyl-1,3-oxazole-5-carbaldehyde as pale-yellow crystals (2.6 g, yield 70%). Recrystallization from ethyl acetate-hexane gave pale-yellow prism crystals. melting point: 134-135° C.

Reference Example 28

To a solution of 4-hydroxymethyl-2-phenyloxazole-5-carbaldehyde (0.25 g) in tetrahydrofuran (5 mL)-ethanol (3 mL) was gradually added sodium borohydride (0.04 g) at 0° C. After stirring at room temperature for 1 hr, water was added to the reaction mixture, and the mixture was extracted with ethyl acetate. The ethyl acetate layer was washed with saturated brine, dried over anhydrous magnesium sulfate and concentrated to give (4-methoxymethoxymethyl-2-phenyl-1,3-oxazol-5-yl)methanol as colorless crystals (0.19 g, yield 76%). Recrystallization from ethyl acetate-hexane gave colorless prism crystals. melting point: 70-71° C.

Reference Example 29

To a mixture of (4-methoxymethoxymethyl-2-phenyl-5-oxazolyl)methanol (5.0 g), imidazole (2.87 g) and N,N-dimethylformamide (80 mL) was added tert-butyldiphenylmethylsilyl chloride (7.17 g) at 0° C., and the mixture was stirred at room temperature for 15 hrs. Water was added to the reaction mixture, and the mixture was extracted with ethyl acetate. The ethyl acetate layer was washed with saturated brine, dried over anhydrous magnesium sulfate and concentrated. The residue was subjected to silica gel column chromatography, and eluted with ethyl acetate-hexane (1:4, v/v) to give 5-tert-butyldiphenylsiloxymethyl-4-methoxymethoxymethyl-2-phenyl-1,3-oxazole as a colorless oil (7.42 g, yield 76%).

NMR (CDCl$_3$) δ: 1.06 (9H, s), 3.34 (3H, s), 4.37 (2H, s), 4.65 (2H, s), 4.80 (2H, s), 7.35-7.48 (9H, m), 7.69-7.75 (4H, m), 7.98-8.03 (2H, m).

Reference Example 30

To a mixture of 3-benzyloxy-1-phenyl-1H-pyrazole-4-carbaldehyde (1.00 g), tetraethyl methylenediphosphonate (1.15 g) and N,N-dimethylformamide (30 mL) was added sodium hydride (60% in oil, 0.17 g) at 0° C. The mixture was stirred at room temperature for 15 hrs. Water was poured into the reaction mixture, and the mixture was extracted with ethyl acetate. The organic layer was washed with saturated brine, dried over anhydrous magnesium sulfate and concentrated. The residue was subjected to silica gel column chromatography, and eluted with ethyl acetate-hexane (3:1, v/v) to give diethyl (E)-2-(3-benzyloxy-1-phenyl-1H-pyrazol-4-yl)ethenylphosphonate as colorless crystals (1.08 g, yield 73%). Recrystallization from ethyl acetate-hexane gave colorless prism crystals. melting point: 89-90° C.

Reference Example 31

Diethyl (E)-2-(3-benzyloxy-1-phenyl-1H-pyrazol-4-yl)ethenylphosphonate (0.89 g), 5% palladium on carbon (1.0 g) and tetrahydrofuran (50 mL) were subjected to catalytic reduction under a hydrogen atmosphere and atmospheric pressure. The catalyst was filtered off and the filtrate was concentrated to give diethyl 2-(3-hydroxy-1-phenyl-1H-pyrazol-4-yl)ethylphosphonate as colorless crystals (0.54 g, yield 76%). Recrystallization from ethyl acetate-hexane gave colorless prism crystals. melting point: 121-122° C.

Reference Example 32

A mixture of 3-benzyloxy-1-phenyl-1H-pyrazole-4-carbaldehyde (2.50 g), 1,3-thiazolidine-2,4-dione (1.05 g), piperidine (0.15 g) and ethanol (80 mL) was heated under reflux for 1 hr. The reaction mixture was concentrated, and the obtained crystals were washed with ethanol to give (5Z)-5-[(3-benzyloxy-1-phenyl-1H-pyrazol-4-yl)methylene]-1,3-thiazolidine-2,4-dione as yellow crystals (2.97 g, yield 87%). Recrystallization from tetrahydrofuran-hexane gave yellow prism crystals. melting point: >300° C.

Reference Example 33

To a mixture of (5Z)-5-[(3-benzyloxy-1-phenyl-1H-pyrazol-4-yl)methylene]-1,3-thiazolidine-2,4-dione (1.30 g) and N,N-dimethylformamide (5 mL) was added sodium hydride (60% in oil, 0.15 g) at 0° C. After stirring the reaction mixture at 0° C. for 30 min, methyl iodide (0.58 g) was added to the reaction mixture, and the mixture was further stirred at room temperature for 4 hrs. The reaction mixture was poured into water, and the precipitated crystals were collected by filtration to give (5Z)-5-[(3-benzyloxy-1-phenyl-1H-pyrazol-4-yl)methylene]-3-methyl-1,3-thiazolidine-2,4-dione as yellow crystals (1.30 g, yield 98%). Recrystallization from tetrahydrofuran-hexane gave yellow prism crystals. melting point: 226-227° C.

Reference Example 34

(5Z)-5-[(3-Benzyloxy-1-phenyl-1H-pyrazol-4-yl)methylene]-3-methyl-1,3-thiazolidine-2,4-dione (1.0 g), 5% palladium on carbon (1.0 g) and tetrahydrofuran (150 mL) were subjected to catalytic reduction under a hydrogen atmosphere and 4.8 kgf/cm$^2$ pressure. The catalyst was filtered off and the filtrate was concentrated. The residue was subjected to silica gel column chromatography, and eluted with ethyl acetate-hexane (1:6, v/v) to give 5-[(3-benzyloxy-1-phenyl-1H-pyrazol-4-yl)methyl]-3-methyl-1,3-thiazolidine-2,4-dione as colorless crystals (0.56 g, yield 55%). Recrystallization from ethyl acetate-hexane gave colorless prism crystals. melting point: 115-116° C.

Reference Example 35

A mixture of 4-chloromethyl-1,3-oxazole hydrochloride (5.16 g), potassium carbonate (4.19 g), water (60 mL) and ethyl acetate (60 mL) was stirred for 15 min. The reaction mixture was extracted with ethyl acetate. The organic layer was washed with saturated brine, dried over anhydrous magnesium sulfate and concentrated. A mixture of the obtained residue, triphenylphosphine (7.95 g) and acetonitrile (200 mL) was heated under reflux for 15 hrs. After cooling the reaction mixture, the precipitated crystals were washed with diethyl ether to give [(1,3-oxazol-4-yl)methyl]triphenylphosphonium chloride as colorless crystals (8.11 g, yield 68%). melting point: 268-270° C.

Reference Example 36

A mixture of 2-chloromethylpyridine hydrochloride (8.0 g), potassium carbonate (6.74 g), water (100 mL) and ethyl acetate (100 mL) was stirred for 15 min. The reaction mixture was extracted with ethyl acetate. The organic layer was washed with saturated brine, dried over anhydrous magnesium sulfate and concentrated. A mixture of the obtained residue, triphenylphosphine (12.8 g) and acetonitrile (300 mL) was heated under reflux for 15 hrs. After cooling the reaction mixture, the precipitated crystals were washed with diethyl ether to give [(2-pyridyl)methyl]triphenylphosphonium chloride as orange crystals (13.68 g, yield 72%). Recrystallization from acetonitrile-diethyl ether gave orange prism crystals. melting point: 280-281° C.

Reference Example 37

4-Benzyloxy-3-methoxymethoxybenzaldehyde (32.60 g) 5% palladium on carbon (30.0 g) and tetrahydrofuran (500 mL) were subjected to catalytic reduction under a hydrogen atmosphere and atmospheric pressure. The catalyst was filtered off and the filtrate was concentrated. The residue was subjected to silica gel column chromatography, and eluted with ethyl acetate-hexane (1:3, v/v) to give 4-hydroxy-3-methoxymethoxybenzaldehyde as a colorless oil (11.08 g, yield 51%).

NMR (CDCl$_3$) δ: 3.54 (3H, s), 5.29 (2H, s), 6.50 (1H, brs), 7.07 (1H, d, J=8.0 Hz), 7.51 (1H, dd, J=8.0, 1.8 Hz), 7.64 (1H, d, J=1.8 Hz), 9.83 (1H, s).

Reference Example 38

To a mixture of 3-hydroxybenzaldehyde (25.31 g), triethylamine (23.07 g) and ethyl acetate (500 mL) was added methanesulfonyl chloride (26.12 g) at 0° C. The mixture was stirred at room temperature for 15 hrs. The reaction mixture was washed successively with water, 1N hydrochloric acid, saturated aqueous sodium hydrogen carbonate and saturated brine, dried over anhydrous magnesium sulfate and concentrated to give 3-formylphenyl methanesulfonate as a pale-yellow oil (41.40 g, yield 100%).

NMR (CDCl$_3$) δ: 3.22 (3H, s), 7.53-7.67 (2H, m), 7.78-7.89 (2H, m), 10.03 (1H, s).

Reference Example 39

To a mixture of 4-[(4-chloromethyl-2-methoxyphenoxy)methyl]-2-(2-furyl)-5-methyl-1,3-oxazole (2.53 g), ethyl (4-ethoxycarbonyl-3-hydroxy-1H-pyrazol-1-yl) acetate (1.40 g) and N,N-dimethylformamide (30 mL) was added sodium hydride (60% in oil, 0.26 g) at room temperature. The reaction mixture was stirred at 90° C. for 2 hrs. Water was poured into the reaction mixture, and the mixture was extracted with ethyl acetate. The organic layer was washed with saturated brine, dried over anhydrous magnesium sulfate and concentrated. The residue was subjected to silica gel column chromatography to give ethyl {4-ethoxycarbonyl-3-[(4-{[2-(2-furyl)-5-methyl-1,3-oxazol-4-yl]methoxy}-3-methoxybenzyl)oxy]-1H-pyrazol-1-yl} acetate as colorless crystals (1.60 g, yield 51%) from a fraction eluted with ethyl acetate-hexane (3:1, v/v). Recrystallization from ethyl acetate-hexane gave colorless prism crystals. melting point: 116-118° C.

Reference Example 40

To a mixture of 5-[(3-benzyloxy-1-phenyl-1H-pyrazol-4-yl)methyl]-3-methyl-1,3-thiazolidine-2,4-dione (0.30 g) and acetonitrile (10 mL) was added iodotrimethylsilane (0.46 g) at room temperature. After stirring the reaction mixture at room temperature for 15 hrs, water was added to the reaction mixture, and the mixture was extracted with ethyl acetate. The organic layer was washed with saturated brine, dried over anhydrous magnesium sulfate and concentrated. The residue was subjected to silica gel column chromatography, and eluted with ethyl acetate-hexane (2:3, v/v) to give 5-[(3-hydroxy-1-phenyl-1H-pyrazol-4-yl)methyl]-3-methyl-1,3-thiazolidine-2,4-dione as colorless crystals (0.15 g, yield 65%). Recrystallization from ethyl acetate-hexane gave colorless prism crystals. melting point: 233-234° C.

Reference Example 41

A mixture of 3-benzyloxy-1-phenyl-1H-pyrazole-4-carbaldehyde (1.70 g), [(1,3-thiazol-4-yl)methyl]triphenylphosphonium chloride (3.64 g), potassium carbonate (1.27 g) and N,N-dimethylformamide (100 mL) was stirred at room temperature for 15 hrs. Water was poured into the reaction mixture, and the mixture was extracted with ethyl acetate. The organic layer was washed with saturated brine, dried over anhydrous magnesium sulfate and concentrated. The residue was subjected to silica gel column chromatography, and eluted with ethyl acetate-hexane (1:3, v/v) to give 4-{(Z)-2-[3-(benzyloxy)-1-phenyl-1H-pyrazol-4-yl]ethenyl}-1,3-thiazole as a colorless oil (0.82 g, yield 37%).

NMR (CDCl$_3$) δ: 5.40 (2H, s), 6.41 (1H, d, J=12.8 Hz), 6.49 (1H, d, J=12.8 Hz), 7.17-7.53 (9H, m), 7.63-7.68 (2H, m), 8.90 (1H, d, J=2.2 Hz), 8.97 (1H, s).

In addition, 4-{(E)-2-[3-(benzyloxy)-1-phenyl-1H-pyrazol-4-yl]ethenyl}-1,3-thiazole was obtained as colorless crystals (1.09 g, yield 50%) from a fraction successively obtained by elution. Recrystallization from ethyl acetate-hexane gave colorless needle crystals. melting point: 101-102° C.

Reference Example 42

4-[(E)-2-(3-Benzyloxy-1-phenyl-1H-pyrazol-4-yl)ethenyl]-1,3-thiazole (0.81 g), 5% palladium on carbon (0.80 g) and tetrahydrofuran (80 mL) were subjected to catalytic reduction under a hydrogen atmosphere and atmospheric pressure. The catalyst was filtered off and the filtrate was concentrated. The residue was subjected to silica gel column chromatography, and eluted with ethyl acetate-hexane (1:3, v/v) to give 4-[2-(3-benzyloxy-1-phenyl-1H-pyrazol-4-yl)ethyl]-1,3-thiazole as a colorless oil (0.58 g, yield 70%).

NMR (CDCl$_3$) δ: 2.89 (2H, t, J=7.5 Hz), 3.13 (2H, t, J=7.5 Hz), 5.36 (2H, s), 6.90-6.91 (1H, m), 7.13-7.18 (1H, m), 7.30-7.56 (10H, m), 8.74-8.75 (1H, m).

Reference Example 43

To a mixture of 4-[2-(3-benzyloxy-1-phenyl-1H-pyrazol-4-yl)ethyl]-1,3-thiazole (1.24 g) and acetonitrile (50 mL) was added iodotrimethylsilane (2.04 g) at room temperature. After stirring the reaction mixture at room temperature for 15 hrs., water was added to the reaction mixture, and the mixture was extracted with ethyl acetate. The organic layer was washed with saturated brine, dried over anhydrous magnesium sulfate and concentrated. The residue was subjected to silica gel column chromatography, and eluted with ethyl acetate-hexane (1:2, v/v) to give 1-phenyl-4-[2-(1,3-thiazol-4-yl)ethyl]-1H-pyrazol-3-ol as colorless crystals (0.48 g, yield 52%). Recrystallization from ethyl acetate-hexane gave colorless prism crystals. melting point: 152-153° C.

Reference Example 44

A mixture of 3-hydroxy-1-phenyl-1H-pyrazole-5-carbaldehyde (2.0 g), [(2-pyridyl)methyl]triphenylphosphonium chloride (4.21 g), potassium carbonate (1.49 g) and N,N-dimethylformamide (150 mL) was stirred at room temperature for 15 hrs. Water was poured into the reaction mixture, and the mixture was extracted with ethyl acetate. The organic layer was washed with saturated brine, dried over anhydrous magnesium sulfate and concentrated. The residue was subjected to silica gel column chromatography, and eluted with ethyl acetate-hexane (1:4, v/v) to give 2-[(E)-2-(3-benzyloxy-1-phenyl-1H-pyrazol-5-yl)ethenyl]pyridine as a colorless oil (2.52 g, yield 74%).

NMR (CDCl$_3$) δ: 5.31 (2H, s), 6.19 (1H, s), 7.07 (1H, d, =16.2 Hz), 7.11-7.18 (1H, m), 7.26-7.52 (12H, m), 7.59-7.67 (1H, m), 8.54-8.56 (1H, m).

Reference Example 45

2-[(E)-2-(3-Benzyloxy-1-phenyl-1H-pyrazol-5-yl)ethenyl]pyridine (2.52 g), 5% palladium on carbon (3.0 g) and tetrahydrofuran (200 mL) were subjected to catalytic reduction under a hydrogen atmosphere and atmospheric pressure. The catalyst was filtered off and the filtrate was concentrated to give 1-phenyl-5-[(E)-2-pyridin-2-ylethenyl]-1H-pyrazol-3-ol as colorless crystals (1.50 g, yield 80%). Recrystallization from ethyl acetate-hexane gave colorless prism crystals. melting point: 167-168° C.

Reference Example 46

To a mixture of 3-hydroxy-1-phenyl-1H-pyrazole-5-carbaldehyde (0.62 g), tetraethyl methylenediphosphonate (0.68 g) and N,N-dimethylformamide (30 mL) was added sodium hydride (60% in oil, 0.10 g) at room temperature. The mixture was stirred at room temperature for 2 hrs. The reaction mixture was poured into water and the mixture was extracted with ethyl acetate. The organic layer was washed with saturated brine, dried over anhydrous magnesium sulfate and concentrated. The residue was subjected to silica gel column chromatography to give diethyl (E)-2-(3-benzyloxy-1-phenyl-1H-pyrazol-5-yl)ethenylphosphonate as a colorless oil (0.83 g, yield 91%) from a fraction eluted with ethyl acetate-hexane (1:1, v/v).

NMR (CDCl$_3$) δ: 1.32 (6H, t, J=7.2 Hz), 4.08 (2H, q, J=7.2 Hz), 4.10 (2H, q, J=7.2 Hz), 5.29 (2H, s), 6.09-6.22 (2H, m), 7.23 (1H, dd, J=22.2, 17.4 Hz), 7.30-7.51 (10H, m).

Reference Example 47

Diethyl (E)-2-(3-benzyloxy-1-phenyl-1H-pyrazol-5-yl)ethenylphosphonate (0.82 g), 5% palladium on carbon (0.50 g) and tetrahydrofuran (50 mL) were subjected to catalytic reduction under a hydrogen atmosphere and atmospheric pressure. The catalyst was filtered off and the filtrate was concentrated to give diethyl (E)-2-(3-hydroxy-1-phenyl-1H-pyrazol-5-yl)ethylphosphonate as a colorless oil (0.63 g, yield 97%).

NMR (CDCl$_3$) δ: 1.26 (6H, t, J=7.2 Hz), 1.85-2.03 (2H, m), 2.80-2.93 (2H, m), 4.01 (2H, q, J=7.2 Hz), 4.05 (2H, q, J=7.2 Hz), 5.61 (1H, s), 7.34-7.51 (5H, m).

Reference Example 48

A mixture of 4-chloromethyl-2-(2-furyl)-5-methyl-1,3-oxazole (7.13 g), potassium carbonate (3.84 g), methyl 5-formyl-2-hydroxybenzoate (5.0 g) and N,N-dimethylformamide (100 mL) was stirred at 90° C. for 15 hrs. Water was poured into the reaction mixture, and the precipitated crystals were collected by filtration to give methyl 5-formyl-2-{[2-(2-furyl)-5-methyl-1,3-oxazol-4-yl]methoxy}benzoate as pale-brown crystals (8.67 g, 91%). Recrystallization from ethyl acetate-hexane gave colorless prism crystals. melting point: 121-122° C.

Reference Example 49

To a solution of methyl 5-formyl-2-{[2-(2-furyl)-5-methyl-1,3-oxazol-4-yl]methoxy}benzoate (8.18 g) in tetrahydrofuran (50 mL)-ethanol (50 mL) was gradually added sodium borohydride (0.91 g) at room temperature. After stirring for 2 hrs, water was added to the reaction mixture, and the mixture was extracted with ethyl acetate. The ethyl acetate layer was washed with saturated brine, dried over anhydrous magnesium sulfate and concentrated. The residue was subjected to silica gel column chromatography to give methyl 2-{[2-(2-furyl)-5-methyl-1,3-oxazol-4-yl]methoxy}-5-hydroxymethylbenzoate as pale-yellow crystals (6.53 g, yield 79%) from a fraction eluted with ethyl acetate-hexane (2:1, v/v). Recrystallization from ethyl acetate-hexane gave pale-yellow prism crystals. melting point: 131-132° C.

Reference Example 50

To a mixture of methyl 2-{[2-(2-furyl)-5-methyl-1,3-oxazol-4-yl]methoxy}-5-hydroxymethylbenzoate (2.50 g) and toluene (100 mL) was added thionyl chloride (0.95 g), and the mixture was heated under reflux for 1 hr. After concentration of the reaction mixture, ethyl acetate was added to the residue, and the mixture was washed successively with saturated aqueous sodium hydrogen carbonate and saturated brine. The organic layer was dried over anhydrous magnesium sulfate and concentrated to give methyl 5-chloromethyl-2-{[2-(2-furyl)-5-methyl-1,3-oxazol-4-yl]methoxy}benzoate as colorless crystals (2.23 g, yield 84%). Recrystallization from ethyl acetate-hexane gave colorless prism crystals. melting point: 107-108° C.

Reference Example 51

After stirring a mixture of (4-trifluoromethylphenyl)hydrazine (13.37 g), diethyl ethoxymethylenemalonate (15 mL), sodium ethoxide (20% ethanol solution, 75 mL) and ethanol (1 L) under a nitrogen atmosphere at room temperature for 3 hrs, the mixture was acidified by adding dilute hydrochloric acid. After concentration of the reaction mixture, the residue was dissolved in ethyl acetate. The obtained ethyl acetate solution was washed with saturated brine, dried over anhydrous magnesium sulfate and concentrated. The residue was subjected to silica gel column chromatography to give ethyl 3-hydroxy-1-(4-trifluoromethyl)phenyl-1H-pyrazole-4-carboxylate (13.11 g, yield 60%) as colorless crystals from a fraction eluted with ethyl acetate-hexane (1:4, v/v). The crystals were recrystallized from ethyl acetate-hexane. melting point: 190-191° C.

Reference Example 52

A mixture of ethylhydrazine oxalate (5.0 g), sodium hydrogen carbonate (5.60 g), water (10 mL) and ethanol (50 mL) was stirred at room temperature for 15 min. Benzaldehyde (3.53 g) was added to the reaction mixture, and the mixture was further stirred at room temperature for 1 hr. To the reaction mixture was added diethyl ethoxymethylenemalonate (7.91 g), and the mixture was heated under reflux for 2 hrs. The reaction mixture was cooled to room temperature, concentrated hydrochloric acid (3 mL) was added and the mixture was further heated under reflux for 15 hrs. Water was added to the reaction mixture, and the mixture was extracted with ethyl acetate. The organic layer was washed with saturated brine, dried over anhydrous magnesium sulfate and concentrated to give ethyl 1-ethyl-3-hydroxy-1H-pyrazole-4-carboxylate as pale-yellow crystals (1.72 g, yield 28%). The crystals were recrystallized from ethyl acetate-hexane. melting point: 109-110° C.

Reference Example 53

A mixture of ethyl hydrazinoacetate hydrochloride (15.5 g), sodium hydrogen carbonate (8.40 g), water (15 mL) and ethanol (100 mL) was stirred at room temperature for 30 min. Benzaldehyde (10.61 g) was added to the reaction mixture, and after stirring for 1 hr, diethyl ethoxymethylenemalonate (21.6 g) was added. The mixture was heated under reflux for 15 hrs. Water was poured into the reaction mixture, and the mixture was extracted with ethyl acetate. The organic layer was washed with saturated brine, dried over anhydrous magnesium sulfate and concentrated. The residue was subjected to silica gel column chromatography, and eluted with ethyl acetate-hexane (1:3, v/v) to give diethyl [(2-benzylidene-1-(ethoxycarbonylmethyl)hydrazino]methylene}malonate as colorless crystals (8.75 g, yield 23%). The crystals were recrystallized from ethyl acetate-hexane. melting point: 105-106° C.

Reference Example 54

A mixture of diethyl [(2-benzylidene-1-(ethoxycarbonylmethyl)hydrazino)methylene]malonate (8.60 g), concentrated hydrochloric acid (10 mL) and ethanol (100 mL) was heated under reflux for 15 hrs. After concentration of the reaction mixture, water was added to the residue, and the mixture was extracted with ethyl acetate. The organic layer was washed with saturated brine, dried over anhydrous magnesium sulfate and concentrated to give ethyl (4-ethoxycarbonyl-3-hydroxy-1H-pyrazol-1-yl) acetate as pale-yellow crystals (1.71 g, yield 31%). Recrystallization from ethyl acetate-hexane gave colorless prism crystals. melting point: 121-122° C.

Reference Example 55

A mixture of piperidine-1-carbothioamide (1.0 g), 1,3-dichloro-2-propanone (0.91 g) and ethanol (30 mL) was heated under reflux for 1 hr. After concentration of the reaction mixture, saturated aqueous sodium hydrogen carbonate was added to the residue and the mixture was extracted with ethyl acetate. The ethyl acetate layer was washed with saturated brine, dried over anhydrous magnesium sulfate and concentrated. The residue was subjected to silica gel column chromatography to give 1-(4-chloromethyl-1,3-thiazol-2-yl)piperidine as a colorless oil (1.00 g, yield 67%) from a fraction eluted with ethyl acetate-hexane (1:4, v/v).

NMR(CDCl$_3$) δ: 1.64-1.69 (6H, m), 3.42-3.47 (4H, m), 4.47 (2H, d, J=0.8 Hz), 6.49 (1H, t, J=0.8 Hz).

Reference Example 56

A mixture of 1-(4-chloromethyl-1,3-thiazol-2-yl)piperidine (1.00 g), potassium carbonate (0.64 g), vanillin (0.70 g) and N,N-dimethylformamide (30 mL) was stirred at 80° C. for 2 hrs. Water was poured into the reaction mixture, and the mixture was extracted with ethyl acetate. The ethyl acetate layer was washed with saturated brine, dried over anhydrous magnesium sulfate and concentrated. The residue was subjected to silica gel column chromatography to give 3-methoxy-4-[(2-piperidin-1-yl-1,3-thiazol-4-yl)methoxy]benzaldehyde as colorless crystals (1.34 g, 88%) from a fraction eluted with ethyl acetate-hexane (1:1, v/v). Recrystallization from ethyl acetate-hexane gave colorless prism crystals. melting point: 129-130° C.

Reference Example 57

To a solution of 3-methoxy-4-[(2-piperidin-1-yl-1,3-thiazol-4-yl)methoxy]benzaldehyde (1.20 g) in tetrahydrofuran (10 mL)-ethanol (10 mL) was gradually added sodium borohydride (0.14 g) at room temperature. After stirring the reaction mixture for 2 hrs, water was added, and the mixture was extracted with ethyl acetate. The ethyl acetate layer was washed with saturated brine, dried over anhydrous magnesium sulfate and concentrated to give {3-methoxy-4-[(2-piperidin-1-yl-1,3-thiazol-4-yl)methoxy]phenyl}methanol as a colorless oil (1.18 g, yield 98%).

NMR(CDCl$_3$) δ: 1.65-1.71 (7H, m), 3.42-3.45 (4H, m), 3.90 (3H, s), 4.62 (2H, d, J=5.8 Hz), 5.07 (2H, d, J=1.0 Hz), 6.80-6.95 (3H, m).

Reference Example 58

A mixture of morpholine-1-carbothioamide (1.50 g), 1,3-dichloro-2-propanone (1.37 g) and ethanol (30 mL) was heated under reflux for 1 hr. After concentration of the reaction mixture, saturated aqueous sodium hydrogen carbonate was added to the residue and the mixture was extracted with ethyl acetate. The ethyl acetate layer was washed with saturated brine, dried over anhydrous magnesium sulfate and concentrated. The residue was subjected to silica gel column chromatography to give 4-(4-chloromethyl-1,3-thiazol-2-yl)morpholine as colorless crystals (1.35 g, yield 60%) from a fraction eluted with ethyl acetate-hexane (2:3, v/v). melting point: 87-88° C.

Reference Example 59

A mixture of 4-(4-chloromethyl-1,3-thiazol-2-yl)morpholine (1.00 g), potassium carbonate (0.64 g), vanillin (0.70 g) and N,N-dimethylformamide (30 mL) was stirred at 90° C. for 2 hrs. Water was poured into the reaction mixture, and the precipitated crystals were collected by filtration to give 3-methoxy-4-[(2-morpholin-4-yl-1,3-thiazol-4-yl)methoxy]benzaldehyde as colorless crystals (1.33 g, 86%). Recrystallization from ethyl acetate-hexane gave colorless prism crystals. melting point: 122-123° C.

Reference Example 60

To a solution of 3-methoxy-4-[(2-morpholin-4-yl-1,3-thiazol-4-yl)methoxy]benzaldehyde (1.20 g) in tetrahydrofuran (10 mL)-ethanol (10 mL) was gradually added sodium borohydride (0.14 g) at room temperature. After stirring the reaction mixture for 2 hrs, water was added, and the mixture was extracted with ethyl acetate. The ethyl acetate layer was washed with saturated brine, dried over anhydrous magnesium sulfate and concentrated to give {3-methoxy-4-[(2-morpholin-4-yl-1,3-thiazol-4-yl)methoxy]phenyl}methanol as colorless crystals (1.03 g, yield 85%). melting point: 94-95° C.

Reference Example 61

A mixture of piperidine-1-carbothioamide (3.00 g), 3-chloro-2-butanone (4.43 g) and 2-propanol (30 mL) was heated under reflux for 15 hrs. After concentration of the reaction mixture, saturated aqueous sodium hydrogen carbonate was added to the residue and the mixture was extracted with ethyl acetate. The organic layer was washed with saturated brine, dried over anhydrous magnesium sulfate and concentrated. The residue was subjected to silica gel column chromatography to give 1-(4,5-dimethyl-1,3-thiazol-2-yl)piperidine as a colorless oil (4.05 g, yield 99%) from a fraction eluted with ethyl acetate-hexane (1:6, v/v).

NMR(CDCl$_3$) δ: 1.62-1.72 (6H, m), 2.12-2.14 (3H, m), 2.18-2.19 (3H, m), 3.33-3.36 (4H, m).

Reference Example 62

To a solution of 1-(4,5-dimethyl-1,3-thiazol-2-yl)piperidine (4.00 g) in acetonitrile (100 mL) was added N-chlorosuccinimide (2.72 g) at room temperature, and the mixture was stirred at the same temperature for 15 hrs. After concentration of the reaction mixture, saturated aqueous sodium hydrogen carbonate was added to the residue and the mixture was extracted with ethyl acetate. The organic layer was washed with saturated brine, dried over anhydrous magnesium sulfate and concentrated. The residue was subjected to silica gel column chromatography to give 1-(4-chloromethyl-5-methyl-1,3-thiazol-2-yl]piperidine as colorless crystals (0.67 g, yield 14%) from a fraction eluted with ethyl acetate-hexane (1:8, v/v). Recrystallization from ethyl acetate-hexane gave colorless needle crystals. melting point: 79-80° C.

Reference Example 63

A mixture of 1-(4-chloromethyl-5-methyl-1,3-thiazol-2-yl)piperidine (0.57 g), potassium carbonate (0.35 g), vanillin (0.38 g) and N,N-dimethylformamide (20 mL) was stirred at 80° C. for 2 hrs. Water was poured into the reaction mixture, and the mixture was extracted with ethyl acetate. The organic layer was washed with saturated brine, dried over anhydrous magnesium sulfate and concentrated. The residue was subjected to silica gel column chromatography to give 3-methoxy-4-[(5-methyl-2-piperidin-1-yl-1,3-thiazol-4-yl)methoxy]benzaldehyde as colorless crystals (0.61 g, yield 70%) from a fraction eluted with ethyl acetate-hexane (1:1, v/v). Recrystallization from ethyl acetate-hexane gave colorless prism crystals. melting point: 80-81° C.

Reference Example 64

To a solution of 3-methoxy-4-[(5-methyl-2-piperidin-1-yl-1,3-thiazol-4-yl)methoxy]benzaldehyde (0.50 g) in tetrahydrofuran (5 mL)-ethanol (5 mL) was gradually added sodium borohydride (0.05 g) at room temperature. After stirring for 1 hr, water was added to the reaction mixture and the precipitated crystals were collected by filtration to give {3-methoxy-4-[(5-methyl-2-piperidin-1-yl-1,3-thiazol-4-yl)methoxy]phenyl}methanol as colorless crystals (0.44 g, yield 90%). melting point: 92-93° C.

Reference Example 65

To a mixture of ethyl 3-hydroxy-1H-pyrazole-4-carboxylate (1.06 g), 3-chloromethylpyridine hydrochloride (2.79 g) and N,N-dimethylformamide (50 mL) was added sodium hydride (60% in oil, 1.36 g) at 0° C. The mixture was stirred at room temperature for 15 hrs. Saturated aqueous sodium hydrogen carbonate was poured into the reaction mixture, and the mixture was extracted with ethyl acetate. The organic layer was washed with saturated brine, dried over anhydrous magnesium sulfate and concentrated. The residue was subjected to silica gel column chromatography, from a fraction eluted with ethyl acetate-methanol (10:1, v/v), ethyl 3-(pyridin-3-ylmethoxy)-1-(pyridin-3-ylmethyl)-1H-pyrazole-4-carboxylate as colorless crystals (1.23 g, yield 53%). Recrystallization from ethyl acetate-hexane gave colorless needle crystals. melting point: 120-121° C.

Reference Example 66

Ethyl 3-(pyridin-3-ylmethoxy)-1-(pyridin-3-ylmethyl)-1H-pyrazole-4-carboxylate (1.14 g), 5% palladium on carbon (1.0 g) and tetrahydrofuran (100 mL) were stirred under a hydrogen atmosphere to perform catalytic reduction. After removing palladium on carbon by filtration, the filtrate was concentrated to give ethyl 3-hydroxy-1-(pyridin-3-ylmethyl)-1H-pyrazole-4-carboxylate as colorless crystals (0.62 g, yield 74%). The crystals were recrystallized from ethyl acetate-hexane. melting point: 148-149° C.

Reference Example 67

A mixture of methyl 2-formylbenzoate (7.40 g), 2,3-butanedione-2-oxime (4.56 g) and 4N hydrogenchloride-ethyl acetate solution (100 mL) was stirred at room temperature for 2 days. After concentration of the reaction mixture, diethyl ether was added to the residue, and the residue was decanted and washed. To this residue was added tetrahydrofuran (100 mL), and thionyl chloride (8.05 g) was further added. The mixture was heated under reflux for 2 hrs. The reaction mixture was concentrated and ethyl acetate was added to the residue. The ethyl acetate layer was washed successively with saturated aqueous sodium hydrogen carbonate solution and saturated brine, dried over anhydrous magnesium sulfate and concentrated. The residue was subjected to silica gel column chromatography to give colorless oil from a fraction eluted with ethyl acetate-hexane (1:4, v/v). A mixture of the obtained oily substance, potassium carbonate (0.90 g), vanillin (0.99 g) and N,N-dimethylformamide (50 mL) was stirred at 90° C. for 2 hrs. Water was poured into the reaction mixture, and the mixture was extracted with ethyl acetate. The organic layer was washed with saturated brine, dried over anhydrous magnesium sulfate and concentrated. To the residue were added potassium carbonate (0.90 g) and methanol (50 mL), and the mixture was heated under reflux for 5 hrs. The reaction mixture was concentrated, obtained water was added to the residue, and the mixture was extracted with ethyl acetate. The organic layer was washed with saturated brine, dried over anhydrous magnesium sulfate and concentrated to give methyl 2-{4-[(4-formyl-2-methoxyphenoxy)methyl]-5-methyl-1,3-oxazol-2-yl}benzoate as pale-yellow crystals (1.40 g, yield 8%). Recrystallization from ethyl acetate-hexane gave colorless prism crystals. melting point: 129-130° C.

Reference Example 68

To a mixture of methyl 3-{4-[(4-hydroxymethyl-2-methoxyphenoxy)methyl]-5-methyl-1,3-oxazol-2-yl}benzoate (1.50 g) and toluene (100 mL) was added thionyl chloride (0.51 g), and the mixture was heated under reflux for 1 hr. The reaction mixture was concentrated and ethyl acetate was added to the residue. The organic layer was washed successively with saturated aqueous sodium hydrogen carbonate and saturated brine, dried over anhydrous magnesium sulfate and concentrated to give methyl 3-{4-[(4-chloromethyl-2-methoxyphenoxy)methyl]-5-methyl-1,3-oxazol-2-yl}benzoate as colorless crystals (1.20 g, yield 76%). Recrystallization from ethyl acetate-hexane gave colorless prism crystals. melting point: 125-126° C.

Reference Example 69

To a solution of methyl 2-{4-[(4-formyl-2-methoxyphenoxy)methyl]-5-methyl-1,3-oxazol-2-yl}benzoate (1.30 g) in tetrahydrofuran (20 mL)-ethanol (10 mL) was gradually added sodium borohydride (0.13 g) at room temperature. After stirring for 2 hrs, water was added to the reaction mixture and the precipitated crystals were collected by filtration to give methyl 2-{4-[(4-hydroxymethyl-2-methoxyphenoxy)methyl]-5-methyl-1,3-oxazol-2-yl}benzoate as colorless crystals (1.20 g, yield 92%). Recrystallization from ethyl acetate-hexane gave colorless prism crystals. melting point: 100-101° C.

Reference Example 70

A mixture of methyl 3-formylbenzoate (11.10 g), 2,3-butanedione-2-oxime (6.84 g) and 4N hydrogenchloride-ethyl acetate solution (100 mL) was stirred at room temperature for 4 days. The reaction mixture was concentrated, and the obtained crystals were washed with diethyl ether. Tetrahydrofuran (150 mL) was added to the crystals and thionyl chloride (12.06 g) was further added. The mixture was heated under reflux for 3 hrs. After concentration of the reaction mixture, saturated aqueous sodium hydrogen carbonate was added to the residue, and the mixture was extracted with ethyl acetate. The ethyl acetate layer was washed with saturated brine, dried over anhydrous magnesium sulfate and concentrated. The residue was subjected to silica gel column chromatography to give methyl 3-(4-chloromethyl-5-methyl-1,3-oxazol-2-yl)benzoate as colorless crystals (9.88 g, 55%) from a fraction eluted with ethyl acetate-hexane (1:4, v/v). Recrystallization from ethyl acetate-hexane gave colorless prism crystals. melting point: 119-120° C.

Reference Example 71

A mixture of methyl 3-(4-chloromethyl-5-methyl-1,3-oxazol-2-yl)benzoate (3.0 g), potassium carbonate (1.42 g), vanillin (1.57 g) and N,N-dimethylformamide (50 mL) was stirred at 90° C. for 2 hrs. Water was poured into the reaction mixture, and the precipitated crystals were collected by filtration to give methyl 3-{4-[(4-formyl-2-methoxyphenoxy)methyl]-5-methyl-1,3-oxazol-2-yl}benzoate as colorless crystals (3.76 g, 87%). Recrystallization from ethyl acetate-hexane gave colorless prism crystals. melting point: 168-169° C.

Reference Example 72

To a solution of methyl 3-{4-[(4-formyl-2-methoxyphenoxy)methyl]-5-methyl-1,3-oxazol-2-yl}benzoate (3.60 g) in tetrahydrofuran (100 mL)-ethanol (10 mL) was gradually added sodium borohydride (0.36 g) at room temperature. After stirring for 1 hr, water was added to the reaction mixture, and the mixture was extracted with ethyl acetate. The ethyl acetate layer was washed with saturated brine, dried over anhydrous magnesium sulfate and concentrated to give methyl 3-{4-[(4-hydroxymethyl-2-methoxyphenoxy)methyl]-5-methyl-1,3-oxazol-2-yl}benzoate as colorless crystals (3.60 g, yield 100%). Recrystallization from ethyl acetate-hexane gave colorless prism crystals. melting point: 141-142° C.

Reference Example 73

A mixture of methyl 4-formylbenzoate (1.63 g), 2,3-butanedione-2-oxime (1.0 g) and 4N hydrogenchloride-ethyl acetate solution (10 mL) was stirred at room temperature for 4 days. After concentration of the reaction mixture, the obtained crystals were washed with diethyl ether. Tetrahydrofuran (30 mL) was added to the crystals, and thionyl chloride (1.90 g) was further added. The mixture was heated under reflux for 3 hrs. After concentration of the reaction mixture, saturated aqueous sodium hydrogen carbonate was added to the residue, and the mixture was extracted with ethyl acetate. The ethyl acetate layer was washed with saturated brine, dried over anhydrous magnesium sulfate and concentrated. The residue was subjected to silica gel column chromatography to give methyl 4-(4-chloromethyl-5-methyl-1,3-oxazol-2-yl)benzoate as colorless crystals (1.10 g, 42%) from a fraction eluted with ethyl acetate-hexane (1:3, v/v). Recrystallization from ethyl acetate-hexane gave colorless prism crystals. melting point: 130-131° C.

Reference Example 74

A mixture of methyl 4-(4-chloromethyl-5-methyl-1,3-oxazol-2-yl)benzoate (0.80 g), potassium carbonate (0.40 g), vanillin (0.44 g) and N,N-dimethylformamide (30 mL) was stirred at 90° C. for 2 hrs. Water was poured into the reaction mixture, and the precipitated crystals were collected by filtration to give methyl 4-{4-[(4-formyl-2-methoxyphenoxy)methyl]-5-methyl-1,3-oxazol-2-yl}benzoate as colorless crystals (1.02 g, 92%). Recrystallization from tetrahydrofuran-hexane gave colorless prism crystals. melting point: 185-186° C.

Reference Example 75

To a solution of methyl 4-{4-[(4-formyl-2-methoxyphenoxy)methyl]-5-methyl-1,3-oxazol-2-yl}benzoate (0.92 g) in tetrahydrofuran (20 mL)-ethanol (10 mL) was gradually added sodium borohydride (0.09 g) at room temperature. After stirring the reaction mixture for 1 hr, water was added, and the precipitated crystals were collected by filtration to give methyl 4-{4-[(4-hydroxymethyl-2-methoxyphenoxy)methyl]-5-methyl-1,3-oxazol-2-yl}benzoate as colorless crystals (0.83 g, yield 90%). Recrystallization from ethyl acetate-hexane gave colorless prism crystals. melting point: 170-171° C.

Reference Example 76

A mixture of 4-chloromethyl-5-methyl-2-phenyl-1,3-thiazole (1.0 g), potassium carbonate (0.57 g), vanillin (0.62 g) and N,N-dimethylformamide (30 mL) was stirred at 90° C. for 2 hrs. Water was poured into the reaction mixture, and the precipitated crystals were collected by filtration to give 3-methoxy-4-[(5-methyl-2-phenyl-1,3-thiazol-4-yl)methoxy]benzaldehyde as colorless crystals (1.28 g, 92%). Recrystallization from ethyl acetate-hexane gave colorless prism crystals. melting point: 133-134° C.

Reference Example 77

To a solution of 3-methoxy-4-[(5-methyl-2-phenyl-1,3-thiazol-4-yl)methoxy]benzaldehyde (1.15 g) in tetrahydrofuran (10 mL)-ethanol (10 mL) was gradually added sodium borohydride (0.13 g) at room temperature. After stirring the reaction mixture for 2 hrs, water was added, and the precipitated crystals were collected by filtration to give {3-methoxy-4-[(5-methyl-2-phenyl-1,3-thiazol-4-yl)methoxy]phenyl}methanol as colorless crystals (1.05 g, yield 91%). Recrystallization from ethyl acetate-hexane gave colorless prism crystals. melting point: 134-135° C.

Reference Example 78

(4-([2-(2-Furyl)-1,3-oxazol-4-yl]methoxy)-3-methoxyphenyl)methanol (5.0 g) was added to thionyl chloride (5 mL) at 0° C., and the mixture was stirred at room temperature for 30 min. The reaction mixture was concentrated and ethyl acetate was added to the residue. The ethyl acetate layer was washed successively with saturated aqueous sodium hydrogen carbonate, saturated brine, dried over anhydrous magnesium sulfate and concentrated to give 4-[(4-chloromethyl-2-methoxyphenoxy)methyl]-2-(2-furyl)-1,3-oxazole as pale-brown crystals (3.95 g, yield 74%). Recrystallization from ethyl acetate-hexane gave colorless prism crystals. melting point: 123-124° C.

Reference Example 79

A mixture of 5-chloromethyl-4-methyl-2-phenyl-1,3-thiazole (2.30 g), vanillin (1.49 g), potassium carbonate (1.35 g) and N,N-dimethylformamide (50 mL) was stirred at 90° C. for 3 hrs. Water was poured into the reaction mixture, and the mixture was extracted with ethyl acetate. The organic layer was washed with saturated brine, dried over anhydrous magnesium sulfate and concentrated to give 3-methoxy-4-[(4-methyl-2-phenyl-1,3-thiazol-5-yl)methoxy]benzaldehyde as pale-yellow crystals (3.02 g, yield 91%). Recrystallization from ethyl acetate-hexane gave colorless prism crystals. melting point: 118-119° C.

Reference Example 80

To a solution of 3-methoxy-4-[(4-methyl-2-phenyl-1,3-thiazol-5-yl)methoxy]benzaldehyde (2.80 g) in tetrahydrofuran (50 mL)-ethanol (10 mL) was gradually added sodium borohydride (0.31 g) at room temperature. After stirring the reaction mixture at room temperature for 2 hrs, water was added, and the precipitated crystals were collected by filtration to give {3-methoxy-4-[(4-methyl-2-phenyl-1,3-thiazol-5-yl)methoxy]phenyl}methanol as colorless crystals (2.57 g, yield 92%). Recrystallization from ethyl acetate-hexane gave colorless prism crystals. melting point: 152-153° C.

Reference Example 81

To a mixture of (3-methyl-1-pyridin-2-yl-1H-pyrazol-4-yl)methanol (1.07 g), vanillin (0.85 g), tributylphosphine (1.70 g) and tetrahydrofuran (100 mL) as added 1,1'-(azodicarbonyl)dipiperidine (2.12 g) at room temperature, and the mixture was stirred for 15 hrs. The precipitated crystals were removed by filtration. The filtrate was concentrated and the residue was subjected to silica gel column chromatography to give 3-methoxy-4-[(3-methyl-1-pyridin-2-yl-1H-pyrazol-4-yl)methoxy]benzaldehyde as colorless crystals (1.40 g, yield 77%) from a fraction eluted with ethyl acetate-hexane (1:1, v/v). Recrystallization from ethyl acetate-hexane gave colorless prism crystals. melting point: 141-142° C.

Reference Example 82

To a solution of 3-methoxy-4-[(3-methyl-1-pyridin-2-yl-1H-pyrazol-4-yl)methoxy]benzaldehyde (1.30 g) in tetrahydrofuran (30 mL)-ethanol (10 mL) was gradually added sodium borohydride (0.15 g) at room temperature. After stirring at room temperature for 1 hr, water was added to the reaction mixture, and the mixture was extracted with ethyl acetate. The organic layer was washed with water, dried over anhydrous magnesium sulfate and concentrated. The residue was subjected to silica gel column chromatography to give {3-methoxy-4-[(3-methyl-1-pyridin-2-yl-1H-pyrazol-4-yl)methoxy]phenyl}methanol as colorless crystals (0.90 g, yield 69%) from a fraction eluted with ethyl acetate-hexane (3:2, v/v). Recrystallization from ethyl acetate-hexane gave colorless prism crystals. melting point: 135-136° C.

Reference Example 83

To a solution of 1-methyl-4-phenyl-1H-imidazole-2-carbaldehyde (7.24 g) in tetrahydrofuran (50 mL)-ethanol (10 mL) was gradually added sodium borohydride (1.47 g) at room temperature and the mixture was stirred at room temperature for 30 min. Water was added to the reaction mixture and the precipitated crystals were collected by filtration to give (1-methyl-4-phenyl-1H-imidazol-2-yl)methanol as colorless crystals (5.71 g, yield 78%). Recrystallization from ethyl acetate-hexane gave colorless prism crystals. melting point: 191-192° C.

Reference Example 84

A mixture of (1-methyl-4-phenyl-1H-imidazol-2-yl)methanol (1.36 g), thionyl chloride (940 mg) and toluene (100 mL) was heated under reflux for 2 hrs. The reaction mixture was concentrated and ethyl acetate was added to the residue. The ethyl acetate layer was washed successively with saturated aqueous sodium hydrogen carbonate and saturated brine, dried over magnesium sulfate and concentrated. A mixture of the obtained residue, potassium carbonate (1.00 g), vanillin (1.10 g) and N,N-dimethylformamide (10 mL) was stirred at 90° C. for 2 hrs. Water was poured into the reaction mixture, and the mixture was extracted with ethyl acetate. The organic layer was washed with saturated brine, dried over anhydrous magnesium sulfate and concentrated. The residue was subjected to silica gel column chromatography to give 3-methoxy-4-[(1-methyl-4-phenyl-1H-imidazol-2-yl)methoxy]benzaldehyde as colorless crystals (1.05 g, yield 45%) from a fraction eluted with ethyl acetate-hexane (1:1, v/v). Recrystallization from ethyl acetate-hexane gave colorless prism crystals. melting point: 128-129° C.

Reference Example 85

To a solution of 3-methoxy-4-[(1-methyl-4-phenyl-1H-imidazol-2-yl)methoxy]benzaldehyde (1.37 g) in tetrahydrofuran (50 mL)-ethanol (10 mL) was gradually added sodium borohydride (0.16 g) at room temperature, and the mixture was stirred at room temperature for 1 hr. Water was added to the reaction mixture and the precipitated crystals were collected by filtration to give {3-methoxy-4-[(1-methyl-4-phenyl-1H-imidazol-2-yl)methoxy]phenyl}methanol as colorless crystals (1.15 g, yield 85%). Recrystallization from ethyl acetate-hexane gave colorless needle crystals. melting point: 126-127° C.

Reference Example 86

A mixture of pyridine-3-carbaldehyde (26.26 g), 2,3-butanedione-2-oxime (24.77 g) and 4N hydrogenchloride-ethyl acetate solution (300 mL) was stirred at room temperature for 3 days. The reaction mixture was concentrated, and the obtained crystals were washed with diethyl ether. To the crystals was added tetrahydrofuran (250 mL), and a solution of thionyl chloride (43.78 g) in tetrahydrofuran (50 mL) was further added. The mixture was heated under reflux for 3 hrs. The reaction mixture was concentrated and ethyl acetate was added to the residue. The ethyl acetate layer was washed successively with saturated aqueous sodium hydrogen carbonate solution and saturated brine, dried over anhydrous magnesium sulfate and concentrated. The residue was subjected to silica gel column chromatography to give 3-(4-chloromethyl-5-methyl-1,3-oxazol-2-yl)pyridine as colorless crystals (9.48 g, 19%) from a fraction eluted with ethyl acetate-hexane (1:1, v/v). Recrystallization from ethyl acetate-hexane gave colorless prism crystals. melting point: 87-88° C.

Reference Example 87

A mixture of 3-(4-chloromethyl-5-methyl-1,3-oxazol-2-yl)pyridine (3.00 g), potassium carbonate (1.89 g), vanillin (2.08 g) and N,N-dimethylformamide (50 mL) was stirred at 90° C. for 2 hrs. Water was poured into the reaction mixture, and the mixture was extracted with ethyl acetate. The ethyl acetate layer was washed with saturated brine, dried over anhydrous magnesium sulfate and concentrated. The residue was subjected to silica gel column chromatography to give 3-methoxy-4-[(5-methyl-2-pyridin-3-yl-1,3-oxazol-4-yl)methoxy]benzaldehyde as colorless crystals (3.61 g, 81%) from a fraction eluted with ethyl acetate-hexane (3:1, v/v). Recrystallization from ethyl acetate-hexane gave colorless prism crystals. melting point: 164-165° C.

Reference Example 88

To a solution of 3-methoxy-4-[(5-methyl-2-pyridin-3-yl-1,3-oxazol-4-yl)methoxy]benzaldehyde (3.26 g) in tetrahydrofuran (50 mL)-ethanol (10 mL) was gradually added sodium borohydride (0.38 g) at room temperature. After stirring the reaction mixture at room temperature for 30 min, water was added, and the precipitated crystals were collected by filtration to give {3-methoxy-4-[(5-methyl-2-pyridin-3-yl-1,3-oxazol-4-yl)methoxy]phenyl}methanol as colorless crystals (3.00 g, yield 91%). Recrystallization from ethyl acetate-hexane gave colorless prism crystals. melting point: 117-118° C.

Reference Example 89

A mixture of 3-formylphenyl methanesulfonate (41.40 g), 2,3-butanedione-2-oxime (20.91 g) and 4N hydrogenchloride-ethyl acetate solution (250 mL) was stirred at room temperature for 5 days. After concentration of the reaction mixture, the residue was decanted and washed with diethyl ether. To the obtained residue was added tetrahydrofuran (300 mL), and thionyl chloride (37.00 g) was further added. The mixture was heated under reflux for 3 hrs. The reaction mixture was concentrated and ethyl acetate was added to the residue. The ethyl acetate layer was washed successively with saturated aqueous sodium hydrogen carbonate solution and saturated brine, dried over anhydrous magnesium sulfate and concentrated. The residue was subjected to silica gel column chromatography. 3-(4-Chloromethyl-5-methyl-1,3-oxazol-2-yl)phenyl methanesulfonate from the eluted portion of ethyl acetate-hexane (1:3 to 1:1, v/v) was obtained as colorless crystals (34.29 g, 55%). Recrystallization from ethyl acetate-hexane gave colorless prism crystals. melting point: 102-103° C.

Reference Example 90

A mixture of 3-(4-chloromethyl-5-methyl-1,3-oxazol-2-yl)phenyl methanesulfonate (8.35 g), potassium carbonate (3.65 g), vanillin (4.02 g) and N,N-dimethylformamide (100 mL) was stirred at 90° C. for 2 hrs. Water was poured into the reaction mixture, and the mixture was extracted with ethyl acetate. The ethyl acetate layer was washed with saturated brine, dried over anhydrous magnesium sulfate and concentrated to give 3-{4-[(4-formyl-2-methoxyphenoxy)methyl]-5-methyl-1,3-oxazol-2-yl}phenyl methanesulfonate as colorless crystals (7.95 g, 72%). Recrystallization from ethyl acetate-hexane gave colorless prism crystals. melting point: 136-137° C.

Reference Example 91

To a solution of 3-{4-[(4-formyl-2-methoxyphenoxy)methyl]-5-methyl-1,3-oxazol-2-yl}phenyl methanesulfonate (3.0 g) in tetrahydrofuran (50 mL)-ethanol (10 mL) was gradually added sodium borohydride (0.38 g) at room temperature. After stirring the reaction mixture at room temperature for 1 hr, water was added, and the mixture was extracted with ethyl acetate. The ethyl acetate layer was washed with saturated brine, dried over anhydrous magnesium sulfate and concentrated to give 3-{4-[(4-hydroxymethyl-2-methoxyphenoxy)methyl]-5-methyl-1,3-oxazol-2-yl}phenyl methanesulfonate as colorless crystals. Recrystallization from ethyl acetate-hexane gave colorless prism crystals. (2.62 g, yield 87%). melting point: 140-141° C.

Reference Example 92

To a mixture of 3-{4-[(4-hydroxymethyl-2-methoxyphenoxy)methyl]-5-methyl-1,3-oxazol-2-yl}phenyl (1.0 g) and toluene (50 mL) was added thionyl chloride (0.31 g), and the mixture was heated under reflux for 1 hr. The reaction mixture was concentrated and ethyl acetate was added to the residue. The organic layer was washed successively with saturated aqueous sodium hydrogen carbonate and saturated brine, dried over anhydrous magnesium sulfate and concentrated to give 3-{4-[(4-chloromethyl-2-methoxyphenoxy)methyl]-5-methyl-1,3-oxazol-2-yl}phenyl methanesulfonate as colorless crystals (0.94 g, yield 90%). Recrystallization from ethyl acetate-hexane gave colorless prism crystals. melting point: 112-114° C.

Reference Example 93

A mixture of methyl 3-(4-chloromethyl-5-methyl-1,3-oxazol-2-yl)benzoate (2.0 g), 4-hydroxybenzaldehyde (0.87 g), potassium carbonate (0.98 g) and N,N-dimethylformamide (50 mL) was stirred at 90° C. for 2 hrs. Water was poured into the reaction mixture, and the mixture was extracted with ethyl acetate. The ethyl acetate layer was washed with saturated brine, dried over anhydrous magnesium sulfate and concentrated to give methyl 3-{4-[(4-formylphenoxy)methyl]-5-methyl-1,3-oxazol-2-yl}benzoate as colorless crystals (2.33 g, yield 94%). Recrystallization from ethyl acetate-hexane gave colorless prism crystals. melting point: 103-104° C.

Reference Example 94

To a solution of methyl 3-{4-[(4-formylphenoxy)methyl]-5-methyl-1,3-oxazol-2-yl}benzoate (2.12 g) in tetrahydrofuran (30 mL)-ethanol (5 mL) was gradually added sodium borohydride (0.23 g) at room temperature. After stirring the reaction mixture at room temperature for 1 hr, water was added, and the mixture was extracted with ethyl acetate. The organic layer was washed with saturated brine, dried over anhydrous magnesium sulfate and concentrated to give methyl 3-(4-{[4-(hydroxymethyl)phenoxy]methyl}-5-methyl-1,3-oxazol-2-yl)benzoate as colorless crystals (1.93 g, yield 91%). Recrystallization from ethyl acetate-hexane gave colorless prism crystals. melting point: 105-106° C.

Reference Example 95

A mixture of morpholine-4-carbothioamide (15.40 g) 3-chloro-2-butanone (22.38 g) and 2-propanol (150 mL) was heated under reflux for 20 hrs. The reaction mixture was concentrated and ethyl acetate was added to the residue. The ethyl acetate layer was washed successively with saturated aqueous sodium hydrogen carbonate and saturated brine, dried over anhydrous magnesium sulfate and concentrated to give 4-(4,5-dimethyl-1,3-thiazol-2-yl)morpholine as colorless crystals (17.50 g, yield 84%). Recrystallization from ethyl acetate-hexane gave colorless prism crystals. melting point: 122-123° C.

Reference Example 96

To a solution of 4-(4,5-dimethyl-1,3-thiazol-2-yl)morpholine (5.0 g) in acetonitrile (100 mL) was added N-chlorosuccinimide (3.36 g) at room temperature, and the mixture was stirred at the same temperature for 1 hr. The reaction mixture was concentrated and ethyl acetate was added to the residue. The ethyl acetate layer was washed successively with saturated aqueous sodium hydrogen carbonate and saturated brine, dried over anhydrous magnesium sulfate and concentrated. The residue was subjected to silica gel column chromatography to give 4-(4-chloromethyl-5-methyl-1,3-thiazol-2-yl)morpholine as colorless crystals (2.06 g, 35%) from a fraction eluted with ethyl acetate-hexane (1:3, v/v). Recrystallization from ethyl acetate-hexane gave colorless prism crystals. melting point: 110-111° C.

Reference Example 97

A mixture of 4-(4-chloromethyl-5-methyl-1,3-thiazol-2-yl)morpholine (5.0 g), vanillin (3.27 g), potassium carbonate (2.97 g) and N,N-dimethylformamide (100 mL) was stirred at 90° C. for 3 hrs. Water was poured into the reaction mixture, and the precipitated crystals were collected by filtration to give 3-methoxy-4-[(5-methyl-2-morpholin-4-yl-1,3-thiazol-4-yl)methoxy]benzaldehyde as crystals (7.25 g, yield 96%). Recrystallization from hexane-ethyl acetate gave colorless prism crystals. melting point: 127-128° C.

Reference Example 98

To a solution of 3-methoxy-4-[(5-methyl-2-morpholin-4-yl-1,3-thiazol-4-yl)methoxy]benzaldehyde (7.00 g) in tetrahydrofuran (100 mL)-ethanol (30 mL) was gradually added sodium borohydride (0.76 g) at room temperature. After stirring the reaction mixture at room temperature for 2 hrs, water was added, and the mixture was extracted with ethyl acetate. The organic layer was washed with water, dried over anhydrous magnesium sulfate and concentrated to give {3-methoxy-4-[(5-methyl-2-morpholin-4-yl-1,3-thiazol-4-yl)methoxy]phenyl}methanol as colorless crystals (6.29 g, yield 89%). Recrystallization from ethyl acetate-hexane gave colorless prism crystals. melting point: 121-122° C.

Reference Example 99

A mixture of ethyl 5-formyl-2-furancarboxylate (5.33 g), 2,3-butanedione-2-oxime (3.21 g) and 4N hydrogenchloride-ethyl acetate solution (100 mL) was stirred at room temperature for 3 days. After concentration of the reaction mixture, diethyl ether was added to the residue and the precipitated crystals were collected by filtration. A mixture of the obtained crystal, tetrahydrofuran (100 mL) and thionyl chloride (5.66 g) was heated under reflux for 3 hrs. The reaction mixture was concentrated and ethyl acetate was added to the residue. The ethyl acetate layer was washed successively with saturated aqueous sodium hydrogen carbonate solution and saturated brine, dried over anhydrous magnesium sulfate and concentrated. The residue was subjected to silica gel column chromatography to give ethyl 5-(4-chloromethyl-5-methyl-1,3-oxazol-2-yl)-2-furancarboxylate as colorless crystals (2.60 g, yield 30%) from a fraction eluted with ethyl acetate-hexane (1:4, v/v). Recrystallization from ethyl acetate-hexane gave colorless prism crystals. melting point: 117-118° C.

Reference Example 100

A mixture of ethyl 5-(4-chloromethyl-5-methyl-1,3-oxazol-2-yl)-2-furancarboxylate (2.38 g), vanillin (1.34 g), potassium carbonate (1.22 g) and N,N-dimethylformamide (50 mL) was stirred at 90° C. for 2 hrs. Water was poured into the reaction mixture, and the precipitated crystals were collected by filtration to give ethyl 5-{4-[2-(4-formyl-2-methoxyphenoxy)methyl]-5-methyl-1,3-oxazol-2-yl}-2-furancarboxylate as crystals (3.16 g, yield 93%). Recrystallization from hexane-ethyl acetate gave colorless prism crystals. melting point: 163-164° C.

Reference Example 101

To a solution of ethyl 5-{4-[2-(4-formyl-2-methoxyphenoxy)methyl]-5-methyl-1,3-oxazol-2-yl}-2-furancarboxylate (3.00 g) in tetrahydrofuran (50 mL)-ethanol (10 mL) was gradually added sodium borohydride (300 mg) at 0° C. After stirring the reaction mixture at room temperature for 1 hr, water was added, and the mixture was extracted with ethyl acetate. The organic layer was washed with water, dried over anhydrous magnesium sulfate and concentrated to give ethyl 5-{4-[(4-hydroxymethyl-2-methoxyphenoxy)methyl]-5-methyl-1,3-oxazol-2-yl}-2-furancarboxylate as colorless crystals (2.85 g, yield 94%). Recrystallization from ethyl acetate-hexane gave colorless prism crystals. melting point: 105-106° C.

Reference Example 102

To a mixture of ethyl 5-{4-[(4-hydroxymethyl-2-methoxyphenoxy)methyl]-5-methyl-1,3-oxazol-2-yl}-2-furancarboxylate (2.70 g) and toluene (100 mL) was added thionyl chloride (0.92 g), and the mixture was heated under reflux for 1 hr. The reaction mixture was concentrated and ethyl acetate was added to the residue. The organic layer was washed successively with saturated aqueous sodium hydrogen carbonate and saturated brine, dried over anhydrous magnesium sulfate and concentrated to give ethyl 5-(4-{[(4-chloromethyl-2-methoxyphenoxy)methyl]-5-methyl-1,3-oxazol-2-yl}-2-furancarboxylate (2.50 g, yield 88%) as colorless crystals. Recrystallization from ethyl acetate-hexane gave colorless prism crystals. melting point: 132-133° C.

Reference Example 103

A mixture of ethyl 3-formylphenylacetate (1.52 g), 2,3-butanedione-2-oxime (0.80 g) and 4N hydrogenchloride-ethyl acetate solution (30 mL) was stirred at room temperature for 2 days. After concentration of the reaction mixture, diethyl ether was added to the residue and the precipitated crystals were collected by filtration. A mixture of the obtained crystal, tetrahydrofuran (50 mL) and thionyl chloride (1.42 g) was heated under reflux for 1 hr. After concentration of the reaction mixture, saturated aqueous sodium hydrogen carbonate was added to the residue, and the mixture was extracted with ethyl acetate. The ethyl acetate layer was washed successively with saturated aqueous sodium hydrogen carbonate solution and saturated brine, dried over anhydrous magnesium sulfate and concentrated. The residue was subjected to silica gel column chromatography to give ethyl [4-(4-chloromethyl-5-methyl-1,3-oxazol-2-yl)phenyl]acetate as colorless crystals (0.85 g, yield 37%) from a fraction eluted with ethyl acetate-hexane (1:6, v/v). Recrystallization from ethyl acetate-hexane gave colorless prism crystals. melting point: 87-88° C.

Reference Example 104

A mixture of ethyl [4-(4-chloromethyl-5-methyl-1,3-oxazol-2-yl)phenyl] acetate (0.76 g), vanillin (0.38 g), potassium carbonate (0.35 g) and N,N-dimethylformamide (30 mL) was stirred at 80° C. for 3 hrs. Water was poured into the reaction mixture, and the precipitated crystals were collected by filtration to give ethyl (4-{4-[(4-formyl-2-methoxyphenoxy)methyl]-5-methyl-1,3-oxazol-2-yl}phenyl)acetate as crystals (0.98 g, yield 96%). Recrystallization from hexane-ethyl acetate gave colorless prism crystals. melting point: 151-152° C.

Reference Example 105

To a solution of ethyl 4-{4-[(4-formyl-2-methoxyphenoxy)methyl]-5-methyl-1,3-oxazol-2-yl}phenyl)acetate (0.88 g) in tetrahydrofuran (20 mL)-ethanol (2 mL) was gradually added sodium borohydride (0.040 g) at 0° C. After stirring the reaction mixture at room temperature for 1 hr., water was added, and the mixture was extracted with ethyl acetate. The organic layer was washed with water, dried over anhydrous magnesium sulfate and concentrated to give ethyl (4-{4-[(4-hydroxymethyl-2-methoxyphenoxy)methyl]-5-methyl-1,3-oxazol-2-yl}phenyl)acetate as colorless crystals (0.82 g, yield 95%). Recrystallization from ethyl acetate-hexane gave colorless prism crystals. melting point: 97-98° C.

Reference Example 106

To a mixture of ethyl (4-{4-[(4-hydroxymethyl-2-methoxyphenoxy)methyl]-5-methyl-1,3-oxazol-2-yl}phenyl)acetate (0.68 g) and toluene (50 mL) was added thionyl chloride (0.23 g), and the mixture was heated under reflux for 1 hr. After concentration of the reaction mixture, saturated aqueous sodium hydrogen carbonate was added to the residue and the mixture was extracted with ethyl acetate. The organic layer was washed with saturated brine, dried over anhydrous magnesium sulfate and concentrated to give ethyl (4-{4-[(4-chloromethyl-2-methoxyphenoxy)methyl]-5-methyl-1,3-oxazol-2-yl}phenyl)acetate as colorless crystals (0.58 g, yield 79%). Recrystallization from ethyl acetate-hexane gave colorless prism crystals. melting point: 121-122° C.

Reference Example 107

A mixture of methyl 3-formylphenylacetate (16.20 g), 2,3-butanedione-2-oxime (8.52 g) and 4N hydrogenchloride-ethyl acetate solution (300 mL) was stirred at room temperature for 2 days. After concentration of the reaction mixture, diethyl ether was added to the residue and the precipitated crystals were collected by filtration. A mixture of the obtained crystal, tetrahydrofuran (300 mL) and thionyl chloride (14.99 g) was heated under reflux for 1 hr. After concentration of the reaction mixture, saturated aqueous sodium hydrogen carbonate was added to the residue, and the mixture was extracted with ethyl acetate. The ethyl acetate layer was washed successively with saturated aqueous sodium hydrogen carbonate solution and saturated brine, dried over anhydrous magnesium sulfate and concentrated. The residue was subjected to silica gel column chromatography to give ethyl [3-(4-chloromethyl-5-methyl-1,3-oxazol-2-yl)phenyl]acetate as colorless crystals (11.77 g, yield 48%) from a fraction eluted with ethyl acetate-hexane (1:6, v/v). Recrystallization from ethyl acetate-hexane gave colorless prism crystals. melting point: 64-65° C.

Reference Example 108

A mixture of ethyl ([3-(4-chloromethyl-5-methyl-1,3-oxazol-2-yl)phenyl]acetate (11.37 g), vanillin (5.61 g), potassium carbonate (5.10 g) and N,N-dimethylformamide (100 mL) was stirred at 80° C. for 3 hrs. Water was poured into the reaction mixture, and the precipitated crystals were collected by filtration to give ethyl (3-{4-[(4-formyl-2-methoxyphenoxy)methyl]-5-methyl-1,3-oxazol-2-yl}phenyl)acetate as crystals (14.11 g, yield 93%). Recrystallization from hexane-ethyl acetate gave colorless prism crystals. melting point: 113-114° C.

Reference Example 109

To a solution of ethyl (3-{4-[(4-formyl-2-methoxyphenoxy)methyl]-5-methyl-1,3-oxazol-2-yl}phenyl)acetate (13.91 g) in tetrahydrofuran (200 mL)-ethanol (20 mL) was gradually added sodium borohydride (640 mg) at 0° C. After stirring at room temperature for 2 hrs, water was added to the reaction mixture, and the mixture was extracted with ethyl acetate. The organic layer was washed with water, dried over anhydrous magnesium sulfate and concentrated to give ethyl (3-{4-[(4-hydroxymethyl-2-methoxyphenoxy)methyl]-5-methyl-1,3-oxazol-2-yl}phenyl)acetate as colorless crystals (13.20 g, yield 94%). Recrystallization from ethyl acetate-hexane gave colorless prism crystals. melting point: 96-98° C.

Reference Example 110

To a mixture of ethyl (3-{4-[(4-hydroxymethyl-2-methoxyphenoxy)methyl]-5-methyl-1,3-oxazol-2-yl}phenyl)acetate (7.50 g) and toluene (300 mL) was added thionyl chloride (2.38 g), and the mixture was heated under reflux for 1 hr. After concentration of the reaction mixture, saturated aqueous sodium hydrogen carbonate was added to the residue and the mixture was extracted with ethyl acetate. The organic layer was washed with saturated brine, dried over anhydrous magnesium sulfate and concentrated to give ethyl (3-{4-[(4-chloromethyl-2-methoxyphenoxy)methyl]-5-methyl-1,3-oxazol-2-yl}phenyl)acetate as colorless crystals (7.32 g, yield 94%). Recrystallization from ethyl acetate-hexane gave colorless prism crystals. melting point: 95-96° C.

Reference Example 111

To a mixture of methyl 5-formyl-2-hydroxybenzoate (21.76 g), triethylamine (13.46 g), ethyl acetate (300 mL)

was added dropwise methanesulfonyl chloride (15.24 g) at 0° C., and the mixture was stirred at room temperature for 3 hr. The reaction mixture was washed successively with water, saturated aqueous sodium hydrogen carbonate, 1N hydrochloric acid and saturated brine, dried over anhydrous magnesium sulfate and concentrated to give methyl 5-formyl-2-methanesulfonyloxybenzoate as a colorless oil (31.20 g, yield 100%).

NMR(CDCl$_3$) δ: 3.36 (3H, s), 3.98 (3H, s), 7.63 (1H, d, J=8.4 Hz), 8.08-8.14 (1H, m), 8.51 (1H, d, J=1.8 Hz), 10.05 (1H, s).

Reference Example 112

A mixture of methyl 5-formyl-2-methanesulfonyloxybenzoate (31.20 g), 2,3-butanedione-2-oxime (12.23 g) and 4N hydrogenchloride-ethyl acetate solution (300 mL) was stirred at room temperature for 2 days. After concentration of the reaction mixture, diethyl ether was added to the residue and the precipitated crystals were collected by filtration. A mixture of the obtained crystal, tetrahydrofuran (300 mL) and thionyl chloride (21.65 g) was heated under reflux for 1 hr. After concentration of the reaction mixture, saturated aqueous sodium hydrogen carbonate was added to the residue, and the mixture was extracted with ethyl acetate. The ethyl acetate layer was washed successively with saturated aqueous sodium hydrogen carbonate solution and saturated brine, dried over anhydrous magnesium sulfate and concentrated. The residue was subjected to silica gel column chromatography to give methyl 5-(4-chloromethyl-5-methyl-1,3-oxazol-2-yl)-2-methanesulfonyloxybenzoate as colorless crystals (22.0 g, yield 51%) from a fraction eluted with ethyl acetate-hexane (1:1, v/v). Recrystallization from ethyl acetate-hexane gave colorless prism crystals. melting point: 160-161° C.

Reference Example 113

A mixture of methyl 5-(4-chloromethyl-5-methyl-1,3-oxazol-2-yl)-2-methanesulfonyloxybenzoate (0.30 g), vanillin (0.13 g), potassium carbonate (0.11 g) and N,N-dimethylformamide (5 mL) was stirred at room temperature for 4 hr. The reaction mixture was acidified by adding 1N hydrochloric acid, and the mixture was extracted with ethyl acetate. The ethyl acetate layer was washed with saturated brine, dried over anhydrous magnesium sulfate and concentrated. The residue was subjected to silica gel column chromatography and eluted with ethyl acetate-hexane (2:3 to 3:2, v/v) to give methyl (5-{4-[(4-formyl-2-methoxyphenoxy)methyl]-5-methyl-1,3-oxazol-2-yl}-2-methanesulfonyloxybenzoate as pale-yellow crystals (0.12 g, yield 30%). Recrystallization from ethyl acetate-hexane gave pale-yellow prism crystals. melting point: 150-151° C.

Reference Example 114

To a solution of methyl (5-{4-[(4-formyl-2-methoxyphenoxy)methyl]-5-methyl-1,3-oxazol-2-yl}-2-methanesulfonyloxybenzoate (5.70 g) in tetrahydrofuran (100 mL)-ethanol (10 mL) was gradually added sodium borohydride (0.23 g) at 0° C. After stirring the reaction mixture at room temperature for 2 hrs, dilute hydrochloric acid was added to acidify the solution, and the mixture was extracted with ethyl acetate. The organic layer was washed with saturated brine, dried over anhydrous magnesium sulfate and concentrated. The residue was subjected to silica gel column chromatography, and eluted with ethyl acetate-hexane (5:1, v/v) to give methyl 5-{4-[(4-hydroxymethyl-2-methoxyphenoxy)methyl]-5-methyl-1,3-oxazol-2-yl}-2-methanesulfonyloxybenzoate as colorless crystals (4.02 g, yield 70%). Recrystallization from ethyl acetate-hexane gave colorless prism crystals. melting point: 126-127° C.

Reference Example 115

To a mixture of methyl 5-{4-[(4-hydroxymethyl-2-methoxyphenoxy)methyl]-5-methyl-1,3-oxazol-2-yl}-2-methanesulfonyloxybenzoate (0.20 g) and toluene (10 mL) was added thionyl chloride (0.055 g), and the mixture was heated under reflux for 1 hr. After concentration of the reaction mixture, ethyl acetate was added to the residue. The ethyl acetate layer was washed successively with saturated aqueous sodium hydrogen carbonate and saturated brine, dried over anhydrous magnesium sulfate and concentrated to give methyl 5-{4-[(4-chloromethyl-2-methoxyphenoxy)methyl]-5-methyl-1,3-oxazol-2-yl}-2-methanesulfonyloxybenzoate (0.14 g, yield 67%) as colorless crystals. Recrystallization from ethyl acetate-hexane gave colorless prism crystals. melting point: 146-147° C.

Reference Example 116

A mixture of propionamide (25.34 g) and 1,3-dichloro-2-propanone (22.09 g) was stirred at 130° C. for 2 hrs. The reaction mixture was basified by adding aqueous potassium carbonate solution, and the mixture was extracted with ethyl acetate. The organic layer was washed with saturated brine, dried over anhydrous magnesium sulfate and concentrated. The residue was subjected to silica gel column chromatography to give a mixture of 4-chloromethyl-2-ethyl-1,3-oxazole from a fraction eluted with ethyl acetate-hexane (1:4, v/v), which was then purified by distillation under reduced pressure to give 4-chloromethyl-2-ethyl-1,3-oxazole as a colorless oil (2.90 g, yield 11%). boiling point 52-54° C. (2.6 mmHg).

NMR (CDCl$_3$) δ: 1.34 (3H, t, J=7.6 Hz), 2.80 (2H, q, J=7.6 Hz), 4.49 (2H, d, J=0.8 Hz), 7.54-7.55 (1H, m).

Reference Example 117

A mixture of 4-chloromethyl-2-ethyl-1,3-oxazole (2.90 g), triphenylphosphine (5.22 g) and acetonitrile (100 mL) was heated under reflux for 15 hrs. After concentration of the reaction mixture, the precipitated crystals were washed with diethyl ether to give [(2-ethyl-1,3-oxazol-4-yl)methyl]triphenylphosphonium chloride as colorless crystals (6.57 g, yield 81%). Recrystallization from acetonitrile-diethyl ether gave colorless prism crystals. melting point: 223-224° C.

Reference Example 118

A mixture of 4-(4-chloromethyl-5-methyl-1,3-thiazol-2-yl)morpholine (1.00 g), triphenylphosphine (1.13 g) and acetonitrile (50 mL) was heated under reflux for 15 hrs. After concentration of the reaction mixture, the precipitated crystals were washed with acetonitrile and diethyl ether to give (5-methyl-2-morpholin-4-yl-1,3-thiazol-4-yl)triphenylphosphonium chloride as pale-yellow crystals (1.93 g, yield 91%). Recrystallization from acetonitrile-diethyl ether gave colorless prism crystals. melting point: 242-243° C.

Reference Example 119

A mixture of 2-methylpropanethioamide (5.20 g), 1,3-dichloro-2-propanone (7.03 g) and ethanol (100 mL) was heated under reflux for 2 hrs. The reaction mixture was concentrated and ethyl acetate was added to the residue. The ethyl acetate layer was washed successively with saturated aqueous sodium hydrogen carbonate and saturated brine, dried over anhydrous magnesium sulfate and concentrated. The residue was subjected to silica gel column chromatography to give 4-chloromethyl-2-isopropyl-1,3-thiazole as a colorless oil (6.33 g, yield 72%) from a fraction eluted with ethyl acetate-hexane (1:20, v/v).

NMR (CDCl$_3$) δ: 1.40 (6H, t, J=7.0 Hz), 3.22-3.44 (1H, m), 4.68 (2H, s), 7.17 (1H, s).

Reference Example 120

A mixture of 4-chloromethyl-2-isopropyl-1,3-thiazole (6.30 g), triphenylphosphine (9.42 g) and acetonitrile (200 mL) was heated under reflux for 15 hrs. After concentration of the reaction mixture, the precipitated crystals were washed with diethyl ether to give [(2-isopropyl-1,3-thiazol-4-yl)methyl]triphenylphosphonium chloride as colorless crystals (13.21 g, yield 84%). Recrystallization from acetonitrile-diethyl ether gave colorless prism crystals. melting point: 246-247° C.

Reference Example 121

A mixture of ethyl 4-oxobutenate (25.31 g), 2,3-butanedione-2-oxime (20.02 g) and 4N hydrogenchloride-ethyl acetate solution (300 mL) was stirred at room temperature for 4 days. After concentration of the reaction mixture, diethyl ether was added to the residue, and the residue was decanted and washed. Tetrahydrofuran (300 mL) was added to the residue, and thionyl chloride (35.33 g) was further added. The mixture was heated under reflux for 2 hrs. After concentration of the reaction mixture, ethyl acetate was added to the residue. The ethyl acetate layer was washed successively with saturated aqueous sodium hydrogen carbonate solution and saturated brine, dried over anhydrous magnesium sulfate and concentrated. The residue was subjected to silica gel column chromatography to give from a fraction eluted with ethyl acetate-hexane (1:8, v/v), ethyl (2E)-3-(4-chloromethyl-5-methyl-1,3-oxazol-2-yl)-2-propenoate as colorless crystals (24.98 g, yield 55%). Recrystallization from hexane gave prism crystals. melting point: 53-54° C.

Reference Example 122

A mixture of ethyl (2E)-3-(4-chloromethyl-5-ethyl-1,3-oxazol-2-yl)-2-propenoate (11.62 g), vanillin (7.70 g), potassium carbonate (6.99 g) and N,N-dimethylformamide (200 mL) was stirred at room temperature for 15 hr. Water was poured into the reaction mixture, and the mixture was extracted with ethyl acetate. The organic layer was washed with saturated brine, dried over anhydrous magnesium sulfate and concentrated to give crystals of ethyl (2E)-3-{4[(4-formyl-2-methoxyphenoxy)methyl]-5-methyl-1,3-oxazol-2-yl}-2-propenoate (12.15 g, yield 70%). Recrystallization from hexane-ethyl acetate gave colorless prism crystals. melting point: 117-118° C.

Reference Example 123

To a solution of ethyl (2E)-3-{4[(4-formyl-2-methoxyphenoxy)methyl]-5-methyl-1,3-oxazol-2-yl}-2-propenoate (11.94 g) in tetrahydrofuran (200 mL)-ethanol (20 mL) was gradually added sodium borohydride (650 mg) at 0° C. After stirring the reaction mixture for 1 hr, water was added, and the mixture was extracted with ethyl acetate. The organic layer was washed with water, dried over anhydrous magnesium sulfate and concentrated to give crystals of ethyl (2E)-3-{4[(4-hydroxymethyl-2-methoxyphenoxy)methyl]-5-methyl-1,3-oxazol-2-yl}-2-propenoate (11.0 g, yield 92%). Recrystallization from ethyl acetate-hexane gave colorless prism crystals. melting point: 96-97° C.

Reference Example 124

To mixture of ethyl (2E)-3-{4[(4-hydroxymethyl-2-methoxyphenoxy)methyl]-5-methyl-1,3-oxazol-2-yl}-2-propenoate (5.0 g) and toluene (100 mL) was added thionyl chloride (1.88 g), and the mixture was heated under reflux for 1 hr. After concentration of the reaction mixture, ethyl acetate was added to the residue. The ethyl acetate layer was washed successively with saturated aqueous sodium hydrogen carbonate and saturated brine, dried over anhydrous magnesium sulfate and concentrated to give ethyl(2E)-3-{4[(4-chloromethyl-2-methoxyphenoxy)methyl]-5-methyl-1,3-oxazol-2-yl}-2-propenoate (4.69 g, yield 89%) as colorless crystals. Recrystallization from ethyl acetate-hexane gave colorless prism crystals. melting point: 107-108° C.

Reference Example 125

Ethyl (2E)-3-{4[(4-hydroxymethyl-2-methoxyphenoxy)methyl]-5-methyl-1,3-oxazol-2-yl}-2-propenoate (4.0 g), 5% palladium on carbon (2.0 g) and tetrahydrofuran (200 mL) were subjected to catalytic reduction with stirring under a hydrogen atmosphere at room temperature. After removing palladium on carbon by filtration, the filtrate was concentrated to give ethyl 3-{4[(4-hydroxymethyl-2-methoxyphenoxy)methyl]-5-methyl-1,3-oxazol-2-yl}-2-propionate as a colorless oil. (4.01 g, yield 100%).

NMR(CDCl$_3$) δ: 1.26 (3H, t, J=7.2 Hz), 2.29 (3H, s), 2.74-2.83 (2H, m), 2.99-3.06 (2H, m), 3.86 (3H, s), 4.16 (2H, q, J=7.2 Hz), 4.63 (2H, s), 4.91 (2H, s), 6.82-6.99 (3H, m).

Reference Example 126

To a mixture of ethyl 3-{4[(4-hydroxymethyl-2-methoxyphenoxy)methyl]-5-methyl-1,3-oxazol-2-yl}-2-propionate (4.0 g) and toluene (100 mL) was added thionyl chloride (1.49 g), and the mixture was heated under reflux for 1 hr. The reaction mixture was concentrated and ethyl acetate was added to the residue. The ethyl acetate layer was washed successively with saturated aqueous sodium hydrogen carbonate and saturated brine, dried over anhydrous magnesium sulfate and concentrated to give ethyl 3-{4[(4-chloromethyl-2-methoxyphenoxy)methyl]-5-methyl-1,3-oxazol-2-yl}-2-propionate (3.23 g, yield 77%) as pale-yellow crystals. Recrystallization from ethyl acetate-hexane gave colorless prism crystals. melting point: 89-91° C.

Reference Example 127

A mixture of ethyl 3-hydroxy-1-phenyl-1H-pyrazole-4-carboxylate (7.76 g), benzyl bromide (3.97 mL), potassium carbonate (6.91 g) and N,N-dimethylformamide (75 mL) was stirred overnight at 50° C. The reaction mixture was poured into water and the mixture was extracted with ethyl acetate. The ethyl acetate layer was washed successively with dilute hydrochloric acid and saturated brine, dried over anhydrous magnesium sulfate and concentrated. The residue was subjected to silica gel column chromatography to give ethyl 3-benzyloxy-1-phenyl-1H-pyrazole-4-carboxylate (8.29 g, yield 77%) as colorless crystals from a fraction eluted with ethyl acetate-hexane (1:1, v/v). The crystals were recrystallized from ethyl acetate-hexane. melting point: 113-114° C.

Reference Example 128

To a solution of ethyl 3-benzyloxy-1-phenyl-1H-pyrazole-4-carboxylate (8.06 g) in tetrahydrofuran (100 mL) was added lithium aluminum hydride (0.95 g) at 0° C. and the mixture was stirred at room temperature for 1 hr. To the reaction mixture was added sodium sulfate decahydrate (8.06 g) and the mixture was stirred at room temperature for 1 hr. After removing the precipitate by filtration, the filtrate was concentrated. The residue was subjected to silica gel column chromatography to give (3-benzyloxy-1-phenyl-1H-pyrazol-4-yl)methanol (5.91 g, yield 84%) as colorless crystals from a fraction eluted with ethyl acetate. The crystals were recrystallized from ethyl acetate-hexane. melting point: 93-94° C.

Reference Example 129

A mixture of (3-benzyloxy-1-phenyl-1H-pyrazol-4-yl)methanol (5.61 g), activated manganese dioxide (15.00 g) and tetrahydrofuran (75 mL) was stirred overnight at room temperature. Manganese dioxide was removed by filtration, and the filtrate was concentrated. The residue was subjected to silica gel column chromatography to give 3-benzyloxy-1-phenyl-1H-pyrazole-4-carbaldehyde (5.03 g, yield 90%) as colorless crystals from a fraction eluted with ethyl acetate-hexane (2:1, v/v). The crystals were recrystallized from tetrahydrofuran-hexane. melting point: 153-154° C.

Reference Example 130

A mixture of 3-benzyloxy-1-phenyl-1H-pyrazole-5-carboxylic acid (33.00 g), methyl iodide (8.5 mL), potassium carbonate (18.88 g) and N,N-dimethylformamide (300 mL) was stirred overnight at room temperature. The reaction mixture was poured into dilute hydrochloric acid, and the mixture was extracted with ethyl acetate. The ethyl acetate layer was washed with saturated brine, dried over anhydrous magnesium sulfate and concentrated. The residue was subjected to silica gel column chromatography to give methyl 3-benzyloxy-1-phenyl-1H-pyrazole-5-carboxylate (33.48 g, yield 97%) as colorless crystals from a fraction eluted with ethyl acetate-hexane (1:4, v/v). The crystals were recrystallized from ethyl acetate-hexane. melting point: 53-54° C.

Reference Example 131

To a mixture of methyl 3-benzyloxy-1-phenyl-1H-pyrazole-5-carboxylate (14.53 g) and tetrahydrofuran (300 mL) was gradually added lithium aluminum hydride (1.79 g) at 0° C. and the mixture was stirred at room temperature for 1 hr. To the reaction mixture was gradually added sodium sulfate decahydrate (15.20 g) at 0° C., and the mixture was stirred at room temperature for 30 min. The insoluble material was removed by filtration, and the mother liquid was concentrated. The residue was subjected to silica gel column chromatography to give (3-benzyloxy-1-phenyl-1H-pyrazol-5-yl)methanol (11.65 g, yield 88%) as colorless crystals from a fraction eluted with ethyl acetate-hexane (1:2, v/v). The crystals were recrystallized from ethyl acetate-hexane. melting point: 87-88° C.

Reference Example 132

A mixture of (3-benzyloxy-1-phenyl-1H-pyrazol-5-yl)methanol (11.20 g), activated manganese dioxide (30.00 g) and tetrahydrofuran (300 mL) was stirred overnight at room temperature. The insoluble material was removed by filtration, and the mother liquid was concentrated. The residue was subjected to silica gel column chromatography to give 3-benzyloxy-1-phenyl-1H-pyrazole-5-carbaldehyde (10.10 g, yield 91%) as a pale-yellow oil from a fraction eluted with ethyl acetate-hexane (1:2, v/v).
NMR(CDCl$_3$) δ: 5.31 (2H, s), 6.51 (1H, s), 7.32-7.52 (10H, m), 9.78 (1H, s).

Reference Example 133

A mixture of methyl 3-benzyloxy-1-phenyl-1H-pyrazole-5-carboxylate (15.00 g), 5% palladium on carbon (10.92 g) and tetrahydrofuran (200 mL) was stirred under a hydrogen atmosphere at room temperature for 1 hr. After removing palladium on carbon by filtration, the mother liquid was concentrated. The residue was subjected to silica gel column chromatography to give methyl 3-hydroxy-1-phenyl-1H-pyrazole-5-carboxylate (10.30 g, yield 97%) as colorless crystals from a fraction eluted with ethyl acetate-hexane (1:2, v/v). The crystals were recrystallized from tetrahydrofuran-isopropyl ether. melting point: 227-228° C.
NMR(CDCl$_3$) δ: 3.77 (3H, s), 6.32 (1H, s), 7.35-7.54 (5H, m), 10.77 (1H, br s).

Reference Example 134

A mixture of methyl 3-hydroxy-1-phenyl-1H-pyrazole-5-carboxylate (5.60 g), 4-(4-chloromethyl-2-methoxyphenoxymethyl)-2-(2-furyl)-5-methyloxazole (9.45 g), potassium carbonate (3.55 g) and N,N-dimethylformamide (200 mL) was stirred at 90° C. for 15 hrs. The reaction mixture was poured into water and the mixture was extracted with ethyl acetate. The ethyl acetate layer was washed with saturated brine, dried over anhydrous magnesium sulfate and concentrated. The obtained colorless crystals were collected by filtration to give methyl 3-(4-{[2-(2-furyl)-5-methyl-1,3-oxazol-4-ylmethoxy]-3-methoxybenzyl}oxy)-1-phenyl-1H-pyrazole-5-carboxylate (12.40 g, yield 94%). The crystals were recrystallized from ethyl acetate-hexane. melting point: 146-147° C.

Reference Example 135

To a solution of methyl 3-(4-{[2-(2-furyl)-5-methyl-1,3-oxazol-4-ylmethoxy]-3-methoxybenzyl}oxy)-1-phenyl-1H-pyrazole-5-carboxylate (12.10 g) in tetrahydrofuran (300 mL) was added lithium aluminum hydride (890 mg) at 0° C. and the mixture was stirred at room temperature for 1 hr. Sodium sulfate decahydrate (7.57 g) was added to the reaction mixture and the mixture was stirred at room temperature for 1 hr. After removing the precipitate by filtration, the filtrate was concentrated. The obtained colorless crystals were collected by filtration to give [3-(4-{[2-(2-furyl)-5- methyl-1,3-oxazol-4-ylmethoxy]-3-methoxybenzyl}oxy)-1-phenyl-1H-pyrazol-5-yl]methanol (11.19 g, yield 98%). The crystals were recrystallized from ethyl acetate-hexane. melting point: 106-107° C.

Reference Example 136

A mixture of {3-(4-{[2-(2-furyl)-5-methyl-1,3-oxazol-4-ylmethoxy]-3-methoxybenzyl}oxy)-1-phenyl-1H-pyrazol-5-yl}methanol (9.50 g), activated manganese dioxide (30.00 g) and tetrahydrofuran (300 mL) was stirred at room temperature for 15 hr. Manganese dioxide was removed by filtration, and the filtrate was concentrated. The residue was subjected to silica gel column chromatography to give 3-(4-{[2-(2-furyl)-5-methyl-1,3-oxazol-4-ylmethoxy]-3-methoxybenzyl}oxy)-1-phenyl-1H-pyrazole-5-carbaldehyde as colorless crystals (7.27 g, yield 77%) from a fraction eluted with ethyl acetate-hexane (1:1, v/v). The crystals were recrystallized from ethyl acetate-hexane. melting point: 103-104° C.

Reference Example 137

To a mixture of potassium tert-butoxide (1.46 g) and dimethoxyethane (50 mL) was added a solution of p-toluenesulfonylmethylisocyanide (1.33 g) in dimethoxyethane (50 mL) at −78° C. and, after stirring for 5 min, a solution of 3-(4-{[2-(2-furyl)-5-methyl-1,3-oxazol-4-ylmethoxy]-3-methoxybenzyl}oxy)-1-phenyl-1H-pyrazole-5-carbaldehyde (3.00 g) in dimethoxyethane (50 mL) was added. After stirring the obtained mixture at the same temperature for 1 hr, the mixture was stirred for 1 hr while warming to room temperature. To the obtained mixture was added methanol (50 mL), and the mixture was refluxed for 2 hrs. After cooling, the reaction mixture was poured into saturated aqueous ammonium chloride solution, and the mixture was extracted with ethyl acetate. The ethyl acetate layer was washed with saturated brine, dried over anhydrous magnesium sulfate and concentrated. The residue was subjected to silica gel column chromatography to give [3-(4-{[2-(2-furyl)-5-methyl-1,3-oxazol-4-ylmethoxy]-3-methoxybenzyl}oxy)-1-phenyl-1H-pyrazol-5-yl]acetonitrile as colorless crystals (0.045 g, yield 15%) from a fraction eluted with ethyl acetate-hexane (1:1, v/v). The crystals were recrystallized from ethyl acetate-hexane. melting point: 141-142° C.

Reference Example 138

A mixture of 5-{2-[4-(5-methyl-2-phenyl-1,3-oxazol-4-yl)methoxyphenyl]ethyl}-4-methoxymethoxymethyl-2-phenyloxazole (3.80 g), 10% sulfuric acid (10 mL) and tetrahydrofuran (100 mL) was refluxed for 2 hrs and concentrated. Ethyl acetate was poured into the residue, and the mixture was washed with saturated brine, dried over anhydrous magnesium sulfate and concentrated. The residue was subjected to silica gel column chromatography to give (5-{2-[4-(5-methyl-2-phenyl-1,3-oxazol-4-yl)methoxyphenyl]ethyl}-2-phenyl-1,3-oxazol-4-yl)methanol as colorless crystals (2.03 g, yield 59%) from a fraction eluted with ethyl acetate-hexane (1:2, v/v). The crystals were recrystallized from ethyl acetate-hexane. melting point: 142-143° C.

Reference Example 139

A mixture of (5-{2-[4-(5-methyl-2-phenyl-1,3-oxazol-4-yl)methoxyphenyl]ethyl}-2-phenyl-1,3-oxazol-4-yl)methanol (1.00 g) and thionyl chloride (2 mL) was stirred at 0° C. for 1 hr. After concentration of the reaction mixture, ethyl acetate was poured into the residue. The ethyl acetate layer was washed successively with saturated aqueous sodium hydrogen carbonate and saturated brine, dried over anhydrous magnesium sulfate and concentrated. A mixture of the obtained residue, sodium cyanide (0.21 g) and dimethyl sulfoxide (20 mL) was stirred at room temperature for 15 hrs. The reaction mixture was poured into water and the mixture was extracted with ethyl acetate. The organic layer was washed successively with dilute hydrochloric acid and saturated brine, dried over anhydrous magnesium sulfate and concentrated. The residue was subjected to silica gel column chromatography to give (5-{2-[4-(5-methyl-2-phenyl-1,3-oxazol-4-yl)methoxyphenyl]ethyl}-2-phenyl-1,3-oxazol-4-yl)acetonitrile (0.56 g, yield 56%) as colorless crystals from a fraction eluted with ethyl acetate-hexane (1:2, v/v). The crystals were recrystallized from ethyl acetate-hexane. melting point: 97-98° C.

Reference Example 140

A mixture of (5-{2-[4-(5-methyl-2-phenyl-1,3-oxazol-4-yl)methoxyphenyl]ethyl}-2-phenyl-1,3-oxazol-4-yl)methanol (0.78 g) and thionyl chloride (2 mL) was stirred at 0° C. for 30 min. After concentration of the reaction mixture, ethyl acetate was poured into the residue. The ethyl acetate layer was washed successively with saturated aqueous sodium hydrogen carbonate and saturated brine, dried over anhydrous magnesium sulfate and concentrated. To a solution of the obtained residue in tetrahydrofuran (10 mL) was added a mixture of diethyl malonate (1.36 g), sodium hydride (60% in oil, 0.33 g) and tetrahydrofuran (30 mL) at 0° C. After stirring at room temperature for 15 hr, the mixture was refluxed for 1 hr. The reaction mixture was poured into water and the mixture was extracted with ethyl acetate. The organic layer was washed successively with dilute hydrochloric acid and saturated brine, dried over anhydrous magnesium sulfate and concentrated. The residue was subjected to silica gel column chromatography to give ethyl 2-ethoxycarbonyl-3-(5-{2-[4-(5-methyl-2-phenyl-1,3-oxazol-4-yl)methoxyphenyl]ethyl}-2-phenyl-1,3-oxazol-4-yl)propionate (0.55 g, yield 53%) as a colorless oil from a fraction eluted with ethyl acetate-hexane (1:6, v/v).

NMR(CDCl$_3$) δ: 1.23 (6H, t, J=7.0 Hz), 2.43 (3H, s), 2.86-2.99 (6H, m), 3.82 (1H, t, J=7.6 Hz), 4.18 (4H, q, J=7.0 Hz), 4.97 (2H, S), 6.92-6.97 (2H, m), 7.11-7.15 (2H, m), 7.40-7.45 (6H, m), 7.93-8.05 (4H, m).

Reference Example 141

A mixture of 4-methoxymethoxymethyl-2-phenyl-1,3-oxazole-5-carbaldehyde (3.00 g), 4-benzyloxybenzyltriphenylphosphonium chloride (6.58 g), potassium carbonate (1.84 g) and N,N-dimethylformamide (50 mL) was stirred at room temperature for 15 hrs. The reaction mixture was poured into water and the mixture was extracted with ethyl acetate. The organic layer was washed successively with dilute hydrochloric acid and saturated brine, dried over anhydrous magnesium sulfate and concentrated. The residue was subjected to silica gel column chromatography to give a colorless oil from a fraction eluted with ethyl acetate-hexane (1:4, v/v). A mixture of the obtained colorless oil, 5% palladium on carbon (5.00 g) and tetrahydrofuran (200 mL) was stirred under a hydrogen atmosphere at room temperature for 3 hrs. After removing palladium on carbon by filtration, the filtrate was concentrated. The obtained crystals were collected by filtration to give 5-[2-(4-hydroxyphenyl) ethyl]-4-methoxymethoxymethyl-2-phenyl-1,3-oxazole (3.24 g, yield 79%). The crystals were recrystallized from ethyl acetate-hexane. melting point: 102-103° C.

Reference Example 142

A mixture of 5-[2-(4-hydroxyphenyl)ethyl]-4-methoxymethoxymethyl-2-phenyl-1,3-oxazole (3.12 g), 4-chloromethyl-5-methyl-2-phenyl-1,3-oxazole (2.28 g), potassium carbonate (1.27 g) and N,N-dimethylformamide (50 mL) was stirred at 90° C. for 15 hrs. The reaction mixture was poured into water and the mixture was extracted with ethyl acetate. The organic layer was washed successively with dilute hydrochloric acid and saturated brine, dried over anhydrous magnesium sulfate and concentrated. The residue was subjected to silica gel column chromatography to give 5-{2-[4-(5-methyl-2-phenyl-1,3-oxazol-4-yl)methoxyphenyl]ethyl}-4-methoxymethoxymethyl-2-phenyl-1,3-oxazole as colorless crystals (4.70 g, yield 85%) from a fraction eluted with ethyl acetate-hexane (1:3, v/v). The crystals were recrystallized from ethyl acetate-hexane. melting point: 124-125° C.

Reference Example 143

A solution (70 mL) of ethyl 3-amino-1-phenyl-1H-pyrazole-4-carboxylate (17.2 g) in tetrahydrofuran was added dropwise to a mixture of lithium aluminum hydride (3.39 g) and tetrahydrofuran (130 mL) on an ice bath. The reaction mixture was heated under reflux for 2 hrs. To this reaction mixture was added sodium sulfate decahydrate by small portions with stirring until foams disappeared on an ice bath, and tetrahydrofuran (50 mL) was further added. After further stirring for 2 hrs., the reaction mixture was filtered, and the filtrate was concentrated. Recrystallization of the residue from tetrahydrofuran-hexane gave (3-amino-1-phenyl-1H-pyrazol-4-yl)methanol as pale-yellow crystals (10.02 g, yield 82%). The crystals were recrystallized from ethyl acetate-hexane. melting point: 127-128° C.

Reference Example 144

A mixture of (3-amino-1-phenyl-1H-pyrazol-4-yl)methanol (12.29 g), activated manganese dioxide (35 g) and tetrahydrofuran (200 mL) was stirred at room temperature for 16 hrs. The reaction mixture was filtered, and the filtrate was concentrated. Recrystallization of the residue from tetrahydrofuran-hexane gave 3-amino-1-phenyl-1H-pyrazole-4-carbaldehyde as pale-yellow crystals (10.02 g, yield 82%). melting point: 129-130° C.

Reference Example 145

A mixture of (4-hydroxy-3-methoxyphenyl)acetic acid (15.00 g), conc. sulfuric acid (5 mL) and anhydrous ethanol (100 mL) was heated under reflux for 17 hrs. The reaction mixture was concentrated under reduced pressure, and the residue was dissolved in ethyl acetate. The ethyl acetate solution was washed successively with distilled water and saturated brine, dried over anhydrous magnesium sulfate and concentrated. The residue was subjected to silica gel column chromatography, and eluted with ethyl acetate-hexane (1:9 to 7:3, v/v) to give ethyl (4-hydroxy-3-methoxyphenyl)acetate as a colorless oil (14.55 g, yield 90%).
NMR(CDCl$_3$) δ: 1.26 (3H, t, J=7.2 Hz), 3.54 (2H, s), 3.89 (3H, s), 4.15 (2H, q, J=7.2 Hz), 5.57 (1H, s), 6.74-6.89 (3H, m).

Reference Example 146

To a mixture of ethyl (4-hydroxy-3-methoxyphenyl)acetate (7.00 g), potassium carbonate (5.43 g) and N,N-dimethylformamide (100 mL) was added 4-chloromethyl-2-(2-furyl)-5-methyl-1,3-oxazole (7.77 g) with stirring, and the mixture was stirred overnight at 80° C. Water was poured into the reaction mixture, and the mixture was extracted with ethyl acetate. The ethyl acetate layer was washed successively with distilled water and saturated brine, dried over anhydrous magnesium sulfate and concentrated. The residue was subjected to silica gel column chromatography to give ethyl(4-{[2-(2-furyl)-5-methyl-1,3-oxazol-4-yl]methoxy}-3-methoxyphenyl)acetate from a fraction eluted with ethyl acetate-hexane (1:4, v/v). Recrystallization from ethyl acetate-hexane gave white crystal (8.22 g, yield 56%) melting point: 106-107° C.

Reference Example 147

Ethyl (4-{[2-(2-furyl)-5-methyl-1,3-oxazol-4-yl]methoxy}-3-methoxyphenyl)acetate (6.19 g) was dissolved in 0.25N potassium hydroxide mixed solution (potassium hydroxide 7.01 g/methanol 125 mL/tetrahydrofuran 354 mL/distilled water 21 mL), and the mixture was stirred overnight at room temperature. The reaction mixture was acidified by adding hydrochloric acid, and the mixture was extracted with ethyl acetate. The extract was washed successively with distilled water and saturated brine, dried over anhydrous magnesium sulfate and concentrated. The residue was recrystallized from ethanol-diisopropyl ether to give (4-{[2-(2-furyl)-5-methyl-1,3-oxazol-4-yl]methoxy}-3-methoxyphenyl)acetic acid as a white solid (5.43 g, yield 95%). melting point: 162-164° C.

Reference Example 148

To a mixture of ethyl 4-hydroxy-3-methoxybenzoate (15.00 g), potassium carbonate (11.63 g) and N,N-dimethylformamide (2.00 mL) was added 4-chloromethyl-5-methyl-2-phenyl-1,3-oxazole (17.45 g) with stirring, and the mixture was stirred overnight at 80° C. Water was poured into the reaction mixture and extracted with ethyl acetate. The ethyl acetate layer was washed successively with distilled water and saturated brine, dried over anhydrous magnesium sulfate and concentrated. The residue was subjected to silica gel column chromatography to give ethyl 3-methoxy-4-[(5-methyl-2-phenyl-1,3-oxazol-4-yl)methoxy]benzoate from a fraction eluted with ethyl acetate-hexane (1:4, v/v). Recrystallization from ethyl acetate-hexane gave a pale-brown solid (25.45 g, yield 91%). melting point: 103-104° C.

Reference Example 149

A mixture of ethyl 3-methoxy-4-[(5-methyl-2-phenyl-1,3-oxazol-4-yl)methoxy]benzoate (10.00 g), 2N aqueous sodium hydroxide solution (40 mL), tetrahydrofuran (100 mL) and ethanol (40 mL) was stirred overnight at room temperature. The reaction mixture was acidified by adding hydrochloric acid and concentrated. The residue was extracted with a mixed solvent of ethyl acetate/tetrahydrofuran (1:1, v/v). The organic layer was washed successively with distilled water and saturated brine, dried over anhydrous magnesium sulfate and concentrated. The residue was recrystallized from ethanol-diisopropyl ether to give 3-methoxy-4-[(5-methyl-2-phenyl-1,3-oxazol-4-yl)methoxy]benzoic acid as a white solid (3.93 g, yield 44%). melting point: 219-220° C.

Reference Example 150

To a mixture of ethyl 4-hydroxy-3-methoxybenzoate ethyl (6.00 g), potassium carbonate (4.65 g) and N,N-dimethylformamide (200 mL) was added 4-chloromethyl-2-(2-furyl)-5-methyl-1,3-oxazole (6.66 g) with stirring and the mixture was stirred overnight at 80° C. Water was poured into the reaction mixture, and the mixture was extracted with ethyl acetate. The ethyl acetate layer was washed successively with distilled water and saturated brine, dried over anhydrous magnesium sulfate and concentrated. The residue was subjected to silica gel column chromatography to give ethyl 4-{[2-(2-furyl)-5-methyl-1,3-oxazol-4-yl]methoxy}-3-methoxybenzoate from a fraction eluted with ethyl acetate-hexane (1:4, v/v). Recrystallization from ethyl acetate-hexane gave white solid (8.45 g, yield 77%). melting point: 133-134° C.

Reference Example 151

Ethyl 4-{[2-(2-furyl)-5-methyl-1,3-oxazol-4-yl]methoxy}-3-methoxybenzoate (6.00 g) was dissolved in a 0.25N potassium hydroxide mixed solution (potassium hydroxide 7.01 g/ethanol 125 mL/tetrahydrofuran 354 mL/distilled water 21 mL) and the mixture was stirred overnight at room temperature. The reaction mixture was acidified by adding hydrochloric acid and concentrated. The residue was extracted with an ethyl acetate/tetrahydrofuran (1:1, v/v) mixed solvent. The organic layer was washed successively with distilled water and saturated brine, dried over anhydrous magnesium sulfate and concentrated. The residue was recrystallized from ethanol diisopropyl ether to give 4-{([2-(2-furyl)-5-methyl-1,3-oxazol-4-yl]methoxy}-3-methoxybenzoic acid as a white solid (6.05 g, yield 92%). melting point: 198-199° C.

Reference Example 152

To a mixture of ethyl (4-hydroxy-3-methoxyphenyl)acetate (7.00 g), potassium carbonate (5.43 g) and N,N-dimethylformamide (100 mL) was added 4-chloromethyl-5-methyl-2-phenyl-1,3-oxazole (8.16 g) with stirring, and the mixture was stirred overnight at 80° C. Water was poured into the reaction mixture, and the mixture was extracted with ethyl acetate. The ethyl acetate layer was washed successively with distilled water and saturated brine, dried over anhydrous magnesium sulfate and concentrated. Recrystallization of the residue from ethyl acetate-hexane gave ethyl {3-methoxy-4-[(5-methyl-2-phenyl-1,3-oxazol-4-yl)methoxy]phenyl}acetate as white crystals (11.38 g, yield 76%). melting point: 86-87° C.

Reference Example 153

A mixture of ethyl {3-methoxy-4-[(5-methyl-2-phenyl-1,3-oxazol-4-yl)methoxy]phenyl}acetate (10.00 g), 2N aqueous sodium hydroxide solution (40 mL), tetrahydrofuran (100 mL) and ethanol (20 mL) was stirred overnight at room temperature. The reaction mixture was acidified by adding hydrochloric acid and concentrated. The residue was extracted with an ethyl acetate/tetrahydrofuran (1:1, v/v) mixed solvent. The organic layer was washed successively with distilled water and saturated brine, dried over anhydrous magnesium sulfate and concentrated. The residue was recrystallized from methanol-diethyl ether to give {3-methoxy-4-[(5-methyl-2-phenyl-1,3-oxazol-4-yl)methoxy]phenyl}acetic acid as a white solid (7.92 g, yield 85%). melting point: 176-177° C.

Reference Example 154

To a mixture of methyl 4-hydroxybenzoate (4.84 g), potassium carbonate (4.80 g), and N,N-dimethylformamide (50 mL) was added 4-(chloromethyl)-5-methyl-2-phenyl-1,3-oxazole (6.00 g) with stirring, and the mixture was stirred at 80° C. for 3 hrs. Water was poured into the reaction mixture, and the mixture was extracted with ethyl acetate. The ethyl acetate layer was washed successively with distilled water and saturated brine, dried over anhydrous magnesium sulfate and concentrated. The residue was subjected to silica gel column chromatography to give methyl 4-[(5-methyl-2-phenyl-1,3-oxazol-4-yl)methoxy]benzoate (8.09 g, yield 87%) from a fraction eluted with ethyl acetate-hexane (1:3, v/v). White crystals were obtained by recrystallization from ethyl acetate-diisopropyl ether. melting point: 104-105° C.

Reference Example 155

A mixture of methyl 4-[(5-methyl-2-phenyl-1,3-oxazol-4-yl)methoxy]benzoate (2.00 g), 1N aqueous sodium hydroxide solution (18.6 mL), tetrahydrofuran (30 mL) and methanol (20 mL) was stirred at room temperature for 2 hrs, and at 50-60° C. for 1 hr. The reaction mixture was acidified by adding 1N hydrochloric acid and concentrated. The residue was extracted with ethyl acetate. The extract was washed with saturated brine, dried over anhydrous magnesium sulfate and concentrated. The residue was filtered with diisopropyl ether to give 4-[(5-methyl-2-phenyl-1,3-oxazol-4-yl)methoxy]benzoic acid as a white solid (1.73 g, yield 85%). Recrystallization from ethyl acetate-diisopropyl ether gave needle crystals. melting point: 190-191° C.

Reference Example 156

To a mixture of 5-tert-butyldiphenylsilyloxymethyl-4-methoxymethoxymethyl-2-phenyl-1,3-oxazole (20.0 g) and chloroform (250 mL) added dropwise trimethylsilyl bromide (25.0 g) at −40° C. The reaction mixture was stirred at −40° C. for 30 min, and the mixture was further stirred at room temperature for 1 hr. The reaction mixture was poured into saturated aqueous sodium hydrogen carbonate, and extracted with chloroform. The organic layer was dried over magnesium sulfate and concentrated. The residue was subjected to silica gel column chromatography and eluted with ethyl acetate-hexane (1:2, v/v) to give [5-(tert-butyldiphenylsilyloxymethyl)-2-phenyl-1,3-oxazol-4-yl]methanol. Recrystallization from hexane-ethyl acetate gave colorless crystals (10.2 g, yield 56%). melting point: 95-96° C.

Reference Example 157

To a mixture of {3-[(4-{[2-(2-furyl)-5-methyl-1,3-oxazol-4-yl]methoxy}-3-methoxybenzyl)oxy]-1-phenyl-1H-pyrazol-4-yl}acetonitrile (0.86 g) and ethanol (30 mL) was added 2N aqueous sodium hydroxide solution (30 mL), and the mixture was heated under reflux for 6 hrs. The reaction mixture was neutralized by adding 1N hydrochloric acid and water; and the mixture was extracted with ethyl acetate. The organic layer was washed with saturated brine, dried over anhydrous magnesium sulfate and concentrated to give {3-[(4-{[2-(2-furyl)-5-methyl-1,3-oxazol-4-yl]methoxy}-3-methoxybenzyl)oxy]-1-phenyl-1H-pyrazol-4-yl}acetic acid as yellow crystals (0.80 g, yield 91%). Recrystallization from ethyl acetate-hexane gave yellow prism crystals. melting point: 179-180° C.

Reference Example 158

To a solution (300 mL) of methyl 5-formyl-2-hydroxybenzoate (5.79 g) in tetrahydrofuran was added sodium hydride (60% in oil, 1.41 g) at room temperature, and the mixture was stirred for 30 min. N-Phenyltrifluoromethanesulfonimide (14.90 g) was added to the reaction mixture, and the mixture was further stirred at room temperature for 15 hrs. Water was added to the reaction mixture, and the mixture was extracted with ethyl acetate. The organic layer was washed with saturated brine, dried over anhydrous magnesium sulfate and concentrated. The residue was subjected to silica gel column chromatography to give methyl 5-formyl-2-{[(trifluoromethyl)sulfonyl]oxy}benzoate as a colorless oil (5.99 g, yield 60%) from a fraction eluted with ethyl acetate-hexane (1:9, v/v).

NMR (CDCl$_3$) δ: 4.02 (3H, s), 7.50 (1H, d, J=8.4 Hz), 8.17 (1H, dd, J=8.4, 2.2 Hz), 8.61 (1H, d, J=2.2 Hz), 10.09 (1H, s).

Reference Example 159

A mixture of methyl 5-formyl-2-{[(trifluoromethyl)sulfonyl]oxy}benzoate (4.88 g), tetramethyltin (10.8 g), tetrakis(triphenylphosphine)palladium (1.85 g) and toluene (150 mL) was heated under reflux for 20 hrs. The reaction mixture was concentrated, and the residue was subjected to silica gel column chromatography to give methyl 5-formyl-2-methylbenzoate as colorless crystals (2.31 g, yield 83%) from a fraction eluted with ethyl acetate-hexane (1:8, v/v). Recrystallization from diethyl ether-hexane gave colorless prism crystals. melting point: 60-61° C.

Reference Example 160

A mixture of methyl 5-formyl-2-methylbenzoate (2.10 g), 2,3-butanedione-2-oxime (1.19 g) and 4N hydrogenchloride-ethyl acetate (50 mL) was stirred at room temperature for 3 days. The reaction mixture was concentrated, diethyl ether was added to the residue to allow precipitation of crystals, and crystals were collected by filtration. A mixture of the obtained crystal, tetrahydrofuran (50 mL) and thionyl chloride (2.11 g) was heated under reflux for 2 hrs. The reaction mixture was concentrated and ethyl acetate was added to the residue. The ethyl acetate layer was washed successively with saturated aqueous sodium hydrogen carbonate solution and saturated brine, dried over anhydrous magnesium sulfate and concentrated. The obtained residue was subjected to silica gel column chromatography to give methyl 5-(4-chloromethyl-5-methyl-1,3-oxazol-2-yl)-2-methylbenzoate as colorless crystals (1.34 g, yield 41%) from a fraction eluted with ethyl acetate-hexane (1:9, v/v). Recrystallization from ethyl acetate-hexane gave colorless prism crystals. melting point: 89-90° C.

Reference Example 161

A mixture of methyl 5-(4-chloromethyl-5-methyl-1,3-oxazol-2-yl)-2-methylbenzoate (1.21 g), vanillin (0.65 g), anhydrous potassium carbonate (0.59 g) and N,N-dimethylformamide (50 mL) was stirred at 90° C. for 2 hrs. Water was poured into the reaction mixture, and the mixture was extracted with ethyl acetate. The organic layer was washed with saturated brine, dried over anhydrous magnesium sulfate and concentrated to give methyl 5-{4-[(4-formyl-2-methoxyphenoxy)methyl]-5-methyl-1,3-oxazol-2-yl}-2-methylbenzoate as colorless crystals (1.45 g, yield 85%). Recrystallization from ethyl acetate-hexane gave colorless prism crystals. melting point: 136-137° C.

Reference Example 162

To a solution of methyl 5-{4-[(4-formyl-2-methoxyphenoxy)methyl]-5-methyl-1,3-oxazol-2-yl}-2-methylbenzoate (1.35 g) in tetrahydrofuran (30 mL)-ethanol (5 mL) was gradually added sodium borohydride 1 (65 mg) at 0° C. After stirring at room temperature for 1 hr, water was added to the reaction mixture, and the mixture was extracted with ethyl acetate. The organic layer was washed with saturated brine, dried over anhydrous magnesium sulfate and concentrated to give methyl 5-{4-[(4-hydroxymethyl-2-methoxyphenoxy)methyl]-5-methyl-1,3-oxazol-2-yl}-2-methylbenzoate as colorless crystals (1.30 g, yield 96%). Recrystallization from ethyl acetate-hexane gave colorless prism crystals. melting point: 145-146° C.

Reference Example 163

To a mixture of methyl 5-{4-[(4-hydroxymethyl-2-methoxyphenoxy)methyl]-5-methyl-1,3-oxazol-2-yl}-2-methylbenzoate (1.16 g) and toluene (50 mL) was added thionyl chloride (0.38 g), and the mixture was heated under reflux for 1 hr. The reaction mixture was concentrated and ethyl acetate was added to the residue. The organic layer was washed successively with saturated aqueous sodium hydrogen carbonate and saturated brine, dried over anhydrous magnesium sulfate and concentrated to give methyl 5-{4-[(4-chloromethyl-2-methoxyphenoxy)methyl]-5-methyl-1,3-oxazol-2-yl}-2-methylbenzoate (1.18 g, yield 98%) as colorless crystals. Recrystallization from ethyl acetate-hexane gave colorless prism crystals. melting point: 139-140° C.

Reference Example 164

To a solution (200 mL) of 1,1'-thiocarbonyldiimidazole (15.0 g) in tetrahydrofuran was added ethyl piperidine-4-carboxylate (12.59 g) at room temperature, and the mixture was stirred at room temperature for 3 hrs and then at 55° C. for 1 hr. Tetrahydrofuran (ca. 100 mL) was distilled off under reduced pressure and 2M ammonia methanol solution (150 mL) was added. After stirring the reaction mixture at room temperature for 15 hrs, the mixture was concentrated. The residue was diluted with ethyl acetate and washed successively with water and saturated brine. The organic layer was dried over anhydrous magnesium sulfate and concentrated. The residue was subjected to silica gel column chromatography and eluted with ethyl acetate-hexane (2:1, v/v) to give ethyl 1-(aminocarbonothioyl)piperidine-4-carboxylate as colorless crystals (4.76 g, yield 27%). The crystals were recrystallized from ethyl acetate-hexane. melting point: 97-98° C.

Reference Example 165

A mixture of ethyl 1-(aminocarbonothioyl)piperidine-4-carboxylate (5.85 g), 3-chloro-2-butanone (5.75 g) and 2-propanol (100 mL) was heated under reflux for 15 hrs, and concentrated. Ethyl acetate was added to the residue. The ethyl acetate layer was washed successively with saturated aqueous sodium hydrogen carbonate and saturated brine, dried ver anhydrous magnesium sulfate and concentrated. The residue was subjected to silica gel column chromatography and eluted with ethyl acetate-hexane (1:4, v/v) to give ethyl 1-(4,5-dimethyl-1,3-thiazol-2-yl)piperidine-4-carboxylate as a colorless oil (6.86 g, yield 95%).

NMR (CDCl$_3$) δ: 1.26 (3H, t, J=7.2 Hz), 1.77-2.05 (4H, m), 2.14 (3H, s), 2.19 (3H, s), 2.40-2.55 (1H, m), 2.92-3.06 (2H, m), 3.08-3.91 (2H, m), 4.15 (2H, q, J=7.2 Hz).

Reference Example 166

To a mixture of ethyl 1-(4,5-dimethyl-1,3-thiazol-2-yl) piperidine-4-carboxylate (6.51 g), acetonitrile (100 mL) was added N-chlorosuccinimide (3.24 g) at 0° C. The reaction mixture was stirred at 0° C. for 2 hrs. Saturated aqueous sodium hydrogen carbonate was added to the reaction mixture, and the mixture was extracted with ethyl acetate. The organic layer was washed with saturated brine, dried over anhydrous magnesium sulfate and concentrated. The residue was subjected to silica gel column chromatography and eluted with ethyl acetate-hexane (1:3, v/v) to give ethyl 1-(4-chloromethyl-5-methyl-1,3-thiazol-2-yl)piperidine-4-carboxylate as colorless crystals (1.93 g, yield 26%). The crystals were recrystallized from ethyl acetate-hexane. melting point: 76-77° C.

Reference Example 167

A mixture of ethyl 1-(4-chloromethyl-5-methyl-1,3-thiazol-2-yl)piperidine-4-carboxylate (1.48 g), vanillin (0.75 g), anhydrous potassium carbonate (0.68 g) and N,N-dimethylformamide (50 mL) was stirred at 90° C. for 2 hrs. Water was poured into the reaction mixture, and the mixture was extracted with ethyl acetate. The organic layer was washed with saturated brine, dried over anhydrous magnesium sulfate and concentrated. The residue was subjected to silica gel column chromatography and eluted with ethyl acetate-hexane (1:3, v/v) to give ethyl 1-{4-[(4-formyl-2-methoxyphenoxy)methyl]-5-methyl-1,3-thiazol-2-yl}piperidine-4-carboxylate as colorless crystals (1.70 g, yield 83%). Recrystallization from ethyl acetate-hexane gave colorless prism crystals. melting point: 97-98° C.

Reference Example 168

To a solution of ethyl 1-{4-[(4-formyl-2-methoxyphenoxy)methyl]-5-methyl-1,3-thiazol-2-yl}piperidine-4-carboxylate (1.56 g) in tetrahydrofuran (30 mL)-ethanol (5 mL) was gradually added sodium borohydride (70 mg) at 0° C. After stirring at 0° C. for 1 hr, water was added to the reaction mixture, and the mixture was extracted with ethyl acetate. The organic layer was washed with saturated brine, dried over anhydrous magnesium sulfate and concentrated to give ethyl 1-{4-[(4-hydroxymethyl-2-methoxyphenoxy)methyl]-5-methyl-1,3-thiazol-2-yl}piperidine-4-carboxylate as colorless crystals (1.48 g, yield 95%). Recrystallization from ethyl acetate-hexane gave colorless prism crystals. melting point: 84-85° C.

Reference Example 169

To a mixture of ethyl 1-{4-[(4-hydroxymethyl-2-methoxyphenoxy)methyl]-5-methyl-1,3-thiazol-2-yl}piperidine-4-carboxylate (1.35 g) and toluene (50 mL) was added thionyl chloride (0.42 g), and the mixture was heated under reflux for 2 hrs. The reaction mixture was concentrated and ethyl acetate was added to the residue. The organic layer was washed successively with saturated aqueous sodium hydrogen carbonate and saturated brine, dried over anhydrous magnesium sulfate and concentrated. The residue was subjected to silica gel column chromatography and eluted with ethyl acetate-hexane (1:4, v/v) to give ethyl 1-{4-[(4-chloromethyl-2-methoxyphenoxy)methyl]-5-methyl-1,3-thiazol-2-yl}piperidine-4-carboxylate as colorless crystals (0.45 g, yield 32%). Recrystallization from ethyl acetate-hexane gave colorless prism crystals. melting point: 98-99° C.

Reference Example 170

A mixture of ethyl 5-formylthiophene-2-carboxylate (14.6 g), 2,3-butanedione-2-oxime (8.02 g) and 4N hydrogenchloride-ethyl acetate (300 mL) was stirred at room temperature for 15 hrs. The reaction mixture was concentrated, diethyl ether was added to the residue to allow precipitation of crystals, and crystals were collected by filtration. A mixture of the obtained crystal, tetrahydrofuran (500 mL) and thionyl chloride (14.16 g) was heated under reflux for 2 hrs. The reaction mixture was concentrated and ethyl acetate was added to the residue. The ethyl acetate layer was washed successively with saturated aqueous sodium hydrogen carbonate solution and saturated brine, dried over anhydrous magnesium sulfate and concentrated. The obtained residue was subjected to silica gel column chromatography and eluted with ethyl acetate-hexane (1:6, v/v) to give ethyl 5-(4-chloromethyl-5-methyl-1,3-oxazol-2-yl)thiophene-2-carboxylate as colorless crystals (5.41 g, yield 24%). Recrystallization from ethyl acetate-hexane gave colorless prism crystals. melting point: 101-102° C.

Reference Example 171

A mixture of ethyl 5-(4-chloromethyl-5-methyl-1,3-oxazol-2-yl)thiophene-2-carboxylate (5.0 g), vanillin (2.66 g), anhydrous potassium carbonate (2.42 g) and N,N-dimethylformamide (50 mL) was stirred at 90° C. for 2 hrs. Water was poured into the reaction mixture, and the precipitated crystals were collected by filtration, and washed with diethyl ether. The obtained crystals were recrystallized from acetone-hexane to give ethyl 5-{4-[(4-formyl-2-methoxyphenoxy)methyl]-5-methyl-1,3-oxazol-2-yl}thiophene-2-carboxylate as colorless prism crystals (5.75 g, yield 82%). melting point: 155-156° C.

Reference Example 172

To a solution of ethyl 5-{4-[(4-formyl-2-methoxyphenoxy)methyl]-5-methyl-1,3-oxazol-2-yl}thiophene-2-carboxylate (5.60 g) in tetrahydrofuran (100 mL)-ethanol (10 mL) was gradually added sodium borohydride (0.26 g) at 0° C. After stirring at room temperature for 1 hr, water was added to the reaction mixture, and the mixture was extracted with ethyl acetate. The organic layer was washed with saturated brine, dried over anhydrous magnesium sulfate and concentrated to give ethyl 5-{4-[(4-hydroxymethyl-2-methoxyphenoxy)methyl]-5-methyl-1,3-oxazol-2-yl}thiophene-2-carboxylate as colorless crystals (5.22 g, yield 92%). Recrystallization from ethyl acetate-hexane gave colorless prism crystals. melting point: 108-109° C.

Reference Example 173

To a mixture of ethyl 5-{4-[(4-hydroxymethyl-2-methoxyphenoxy)methyl]-5-methyl-1,3-oxazol-2-yl}thiophene-2-carboxylate (5.00 g) and toluene (100 mL) was added thionyl chloride (1.62 g), and the mixture was heated under reflux for 1 hr. The reaction mixture was concentrated and ethyl acetate was added to the residue. The organic layer was washed successively with saturated aqueous sodium hydrogen carbonate and saturated brine, dried over anhydrous magnesium sulfate and concentrated to give ethyl 5-{4-[(4-chloromethyl-2-ethoxyphenoxy)methyl]-5-methyl-1,3-oxazol-2-yl}thiophene-2-carboxylate (4.98 g, yield 95%) as colorless crystals. Recrystallization from ethyl acetate-hexane gave colorless prism crystals. melting point: 157-158° C.

Reference Example 174

A mixture of 3-formylbenzonitrile (25.00 g), 2,3-butanedione-2-oxime (19.31 g) and 4N hydrogenchloride-ethyl acetate (300 mL) was stirred at room temperature for 15 hrs. The reaction mixture was concentrated and the obtained oily substance was decanted and washed with diethyl ether. A mixture of the obtained residue, tetrahydrofuran (500 mL) and thionyl chloride (34.14 g) was heated under reflux for 2 hrs. The reaction mixture was concentrated and ethyl acetate was added to the residue. The ethyl acetate layer was washed successively with saturated aqueous sodium hydrogen carbonate solution and saturated brine, dried over anhydrous magnesium sulfate and concentrated. The obtained residue was subjected to silica gel column chromatography and eluted with ethyl acetate-hexane (1:2, v/v) to obtain 3-(4-chloromethyl-5-methyl-1,3-oxazol-2-yl)benzonitrile as colorless crystals (12.01 g, yield 27%). Recrystallization from ethyl acetate-hexane gave colorless crystals. melting point: 100-101° C.

Reference Example 175

A mixture of 3-(4-chloromethyl-5-methyl-1,3-oxazol-2-yl)benzonitrile (26.3 g), vanillin (17.19 g), anhydrous potassium carbonate (15.62 g) and N,N-dimethylformamide (300 mL) was stirred at 90° C. for 2 hrs. Water was poured into the reaction mixture, and the precipitated crystals were collected by filtration to give 3-{4-[(4-formyl-2-methoxyphenoxy)methyl]-5-methyl-1,3-oxazol-2-yl}benzonitrile as colorless crystals (33.9 g, yield 86%). Recrystallization from ethyl acetate-hexane gave colorless prism crystals. melting point: 166-167° C.

Reference Example 176

To a solution of 3-{4-[(4-formyl-2-methoxyphenoxy)methyl]-5-methyl-1,3-oxazol-2-yl}benzonitrile (20.0 g) in tetrahydrofuran (300 mL)-ethanol (30 mL) was gradually added sodium borohydride (1.09 g) at 0° C. After stirring at room temperature for 1 hr, water was added to the reaction mixture, and the mixture was extracted with ethyl acetate. The organic layer was washed with saturated brine, dried over anhydrous magnesium sulfate and concentrated to give 3-{4-[(4-hydroxymethyl-2-methoxyphenoxy)methyl]-5-methyl-1,3-oxazol-2-yl}benzonitrile as colorless crystals (19.2 g, yield 96%). Recrystallization from ethyl acetate-hexane gave colorless prism crystals. melting point: 113-115° C.

Reference Example 177

N-Chlorosuccinimide (4.5 g) was added to a solution (100 ml) of tert-butyl 4-(4,5-dimethyl-1,3-thiazol-2-yl)piperazine-1-carboxylate (10 g) in acetonitrile at 0° C., and the mixture was stirred at 0° C. for 30 min. The reaction mixture was poured into water and the mixture was extracted with ethyl acetate. The organic layer was dried over anhydrous magnesium sulfate and concentrated. The residue was subjected to silica gel column chromatography and eluted with ethyl acetate-hexane (0:1-1:4-1:2, v/v) to give tert-butyl 4-(4-chloromethyl-5-methyl-1,3-thiazol-2-yl)piperazine-1-carboxylate as colorless crystals (6.2 g, yield 55%).

NMR (CDCl$_3$) δ: 1.47 (9H, s), 2.31 (3H, s), 3.37-3.41 (4H, m), 3.51-3.53 (4H, m), 4.47 (2H, s).

Reference Example 178

To a mixture of 3-{4-[(4-hydroxymethyl-2-methoxyphenoxy)methyl]-5-methyl-1,3-oxazol-2-yl}benzonitrile (10.0 g) and toluene (200 mL) was added thionyl chloride (3.74 g), and the mixture was heated under reflux for 1 hr. The reaction mixture was concentrated and ethyl acetate was added to the residue. The organic layer was washed successively with saturated aqueous sodium hydrogen carbonate and saturated brine, dried over anhydrous magnesium sulfate and concentrated to give 3-{4-[(4-chloromethyl-2-methoxyphenoxy)methyl]-5-methyl-1,3-oxazol-2-yl}benzonitrile (10.3 g, yield 98%) as colorless crystals. Recrystallization from ethyl acetate-hexane gave colorless prism crystals. melting point: 150-151° C.

Reference Example 179

A mixture of 3-{4-[(4-hydroxymethyl-2-methoxyphenoxy)methyl]-5-methyl-1,3-oxazol-2-yl}benzonitrile (0.40 g), triisopropylsilyl chloride (0.75 g), imidazole (0.27 g) and N,N-dimethylformamide (5 mL) was stirred at room temperature for 3 days. Water was poured into the reaction mixture, and the mixture was extracted with ethyl acetate. The organic layer was washed with saturated brine, dried over anhydrous magnesium sulfate and concentrated. The obtained residue was subjected to silica gel column chromatography to give 3-{4-[(2-methoxy-4-{[(triisopropylsilyl)oxy]methyl}phenoxy)methyl]-5-methyl-1,3-oxazol-2-yl}benzonitrile as a colorless oil (0.53 g, yield 95%) from a fraction eluted with ethyl acetate-hexane (1:4, v/v).

NMR (CDCl$_3$) δ: 1.00-1.26 (21H, m), 2.42 (3H, s), 3.86 (3H, s), 4.78 (2H, s), 5.03 (2H, s), 6.81-6.84 (1H, m), 6.96-6.99 (2H, m), 7.52-7.66 (1H, m), 7.66-7.69 (1H, m), 8.20-8.29 (2H, m).

Reference Example 180

A mixture of 3-{4-[(2-methoxy-4-{[(triisopropylsilyl)oxy]methyl}phenoxy)methyl]-5-methyl-1,3-oxazol-2-yl}benzonitrile (0.52 g), trimethyl tin azide (0.62 g) and toluene (10 mL) was heated under reflux for 15 hrs. The reaction mixture was concentrated, and the residue was subjected to silica gel column chromatography to give 5-(3-{4-[(2-methoxy-4-{[(triisopropylsilyl)oxy]methyl}phenoxy)methyl]-5-methyl-1,3-oxazol-2-yl}phenyl)-1H-tetrazole as colorless crystals (0.36 g, yield 65%), from a fraction eluted with ethyl acetate-methanol (95:5, v/v). Recrystallization from ethyl acetate-hexane gave colorless prism crystals. melting point: 152-153° C.

Reference Example 181

Under ice-cooling, 98% formic acid (12.75 g) was added to acetic anhydride (22.97 g) using an dropping funnel, the obtained mixture was stirred at 50-60° C. for 2 hrs, and cooled to room temperature. Tetrahydrofuran (25 mL) was added to the obtained mixture and a solution of ethyl 3-amino-1-phenyl-1H-pyrazole-4-carboxylate (20.00 g) in tetrahydrofuran (20 mL) was added. The obtained mixture was stirred at room temperature for 3 hrs and concentrated. The residue was recrystallized from ethyl acetate-hexane to give ethyl 3-(formylamino)-1-phenyl-1H-pyrazole-4-carboxylate as colorless needle crystals (20.89 g, yield 93%). melting point: 135-136° C.

Reference Example 182

Lithium aluminum hydride (7.50 g) was added to tetrahydrofuran (200 mL) under ice-cooling. To the obtained mixture was added dropwise a solution (100 mL) of ethyl 3-(formylamino)-1-phenyl-1H-pyrazole-4-carboxylate (20.50 g) in tetrahydrofuran, and the mixture was heated under reflux for 1.5 hrs. To the obtained mixture was added small portions of sodium sulfate decahydrate (50 g) on an ice bath, and the mixture was stirred for 2 hrs. while adding tetrahydrofuran (50 mL) as appropriate to allow stirring. Solids were filtered off and the filtrate was concentrated to give [3-(methylamino)-1-phenyl-1H-pyrazol-4-yl]methanol as a colorless oil (15.42 g, yield 96%).

NMR (CDCl$_3$) δ: 3.01 (3H, s), 3.96 (1H, br-s), 4.58 (2H, s), 7.11-7.19 (1H, m), 7.26-7.43 (2H,m), 7.54-7.64 (3H, m).

Reference Example 183

A mixture of [3-(methylamino)-1-phenyl-1H-pyrazol-4-yl]methanol (15.42 g), activated manganese dioxide (50 g) and tetrahydrofuran (150 mL) was stirred at room temperature for 16 hrs. The obtained mixture was filtered, and the filtrate was concentrated. The residue was subjected to silica gel column chromatography to give 3-(methylamino)-1-phenyl-1H-pyrazole-4-carbaldehyde as colorless crystals from a fraction eluted with ethyl acetate-hexane (1:4, v/v). Recrystallization from ethyl acetate-hexane gave colorless needle crystal (9.17 g, yield 60%). melting point: 83-84° C.

Reference Example 184

To a solution (5 mL) of tetraethyl methylenediphosphonate in N,N-dimethylformamide was added sodium hydride (60% in oil, 8.8 mg) at room temperature, and the mixture was stirred for 15 min. 3-(Methylamino)-1-phenyl-1H-pyrazole-4-carbaldehyde (1.00 g) was added to the reaction mixture, and the mixture was further stirred at room temperature for 2 hrs. Water was added to the reaction mixture and the mixture was stirred at room temperature for 2 hrs, and stood still for 16 hrs. The precipitated pale-yellow needle crystals were collected by filtration. The obtained crystals were recrystallized from ethyl acetate-hexane to give diethyl {(E)-2-[3-(methylamino)-1-phenyl-1H-pyrazol-4-yl]ethenyl}phosphonate as pale-yellow needle crystals (1.45 g, yield 87%). melting point: 132-133° C.

Reference Example 185

5-Chloromethyl-1-ethyl-1H-imidazole hydrochloride (6.00 g), triphenylphosphine (25.73 g) and acetonitrile (80 mL) were heated under reflux overnight. After cooling, the precipitated crystals were collected by filtration and washed with hexane to give [(1-ethyl-1H-imidazol-5-yl)methyl](triphenyl)phosphonium chloride hydrochloride as colorless crystals (10.50 g, yield 72%). melting point: 287-289° C.

Reference Example 186

To a mixture of lithium aluminum hydride (1.74 g) and tetrahydrofuran (100 mL) was added 1-ethyl-1H-imidazole-4-carbaldehyde (5.71 g) at 0° C. After stirring the reaction mixture for 1 hr, sodium sulfate decahydrate (15 g) was added and the mixture was further stirred at room temperature for 5 hrs. Insoluble materials were filtered off and the filtrate was concentrated to give (1-ethyl-1H-imidazol-4-yl)methanol as a colorless oil (5.83 g, yield 100%).

NMR(CDCl$_3$) δ: 1.45 (3H, t, J=7.5 Hz), 3.96 (2H, q, J=7.5 Hz), 4.59 (2H, s), 6.89 (1H, s), 7.45 (1H, d, J=7.4 Hz).

Reference Example 187

To a solution (100 mL) of (1-ethyl-1H-imidazol-4-yl)methanol (5.80 g) in tetrahydrofuran was added thionyl chloride (14.59 g). The reaction mixture was heated under reflux for 1 hr and concentrated. Diethyl ether was added to the residue to allow crystallization, and the obtained crystals were collected by filtration, and washed with diethyl ether. The obtained crystals were recrystallized from methanol-tetrahydrofuran to give 4-chloromethyl-1-ethyl-1H-imidazole hydrochloride as colorless crystals (8.35 g, yield 100%).

NMR(DMSO-d$_6$) δ: 1.42 (3H, t, J=7.3 Hz), 4.20 (2H, q, J=7.3 Hz), 4.89 (2H, s), 7.88 (1H, s), 9.23 (1H, s).

Reference Example 188

A mixture of 4-chloromethyl-1-ethyl-1H-imidazole hydrochloride (8.35 g), triphenylphosphine (12.1 g) and acetonitrile (200 mL) was heated under reflux for 16 hrs. After cooling, the obtained mixture was concentrated. Diethyl ether was added to the residue to allow crystallization, and the precipitated crystals were collected by filtration and washed successively with hexane and ethyl acetate. The obtained crystals were recrystallized from methanol-tetrahydrofuran to give [(1-ethyl-1H-imidazol-4-yl)methyl](triphenyl)phosphonium chloride hydrochloride as colorless crystals (14.09 g, yield 68%). melting point: 121-122° C.

Reference Example 189

Lithium aluminum hydride (7.19 g) was suspended in tetrahydrofuran (400 mL). To the obtained mixture were added a solution (100 mL) of ethyl 1-ethyl-1H-pyrazole-4-carboxylate (29.00 g) in tetrahydrofuran on an ice bath with stirring. After stirring the reaction mixture at room temperature for 1.5 hrs, sodium sulfate decahydrate (80 g) was added by small portions on an ice bath with stirring, and the mixture was further stirred at room temperature for 16 hrs. The solid was filtered, and the filtrate was concentrated under reduced pressure. The residue was subjected to silica gel chromatography to give (1-ethyl-1H-pyrazol-4-yl)methanol as a colorless oil (16.85 g, yield 78%) from a fraction eluted with ethyl acetate-methanol (1:0 to 49:1, v/v).

NMR (CDCl$_3$) δ: 1.48 (3H, t, J=7.2 Hz), 4.15 (2H, q, J=7.2 Hz), 4.58 (2H, s), 7.41 (1H, s), 7.48 (1H, s).

Reference Example 190

To a solution (400 mL) of (1-ethyl-1H-pyrazol-4-yl)methanol (16.80 g) in tetrahydrofuran was added thionyl chloride (40.0 g), and the mixture was stirred at room temperature for 4 hr. The mixture liquid was concentrated under reduced pressure to obtain 4-chloromethyl-1-ethyl-1H-pyrazole hydrochloride as a colorless oil (24.15 g, yield 100%).

NMR (DMSO-$d_6$) δ: 1.34 (3H, t, J=7.3 Hz), 4.09 (2H, q, J=7.3 Hz), 4.68 (2H, s), 7.48 (1H, s), 7.83 (1H, s), 8.28 (1H, brs).

Reference Example 191

A mixture of 4-chloromethyl-1-ethyl-1H-pyrazole hydrochloride (24.00 g), triphenylphosphine (34.10 g), acetonitrile (250 mL) was heated under reflux for 16 hrs. The reaction mixture was concentrated, and the residue was decanted and washed with diethyl ether (3 times with 200 mL). Toluene was added and the mixture was concentrated under reduced pressure to give [(1-ethyl-1H-pyrazol-4-yl)methyl](triphenyl)phosphonium chloride hydrochloride as amorphous form (57.47 g, yield 95%). NMR (DMSO-$d_6$) δ: 1.22 (3H, t, J=7.2 Hz), 4.01 (2H, q, J=7.2 Hz), 4.66 (1H,brs), 5.01 (2H, d, J=13.8 Hz), 6.93 (1H, s), 7.25 (1H, s), 7.68-7.79 (12H, m), 7.87-7.92 (3H, m).

Reference Example 192

A mixture of 3-hydroxy-1-phenyl-1H-pyrazole-4-carbaldehyde (1.88 g), chloromethyl methyl ether (0.835 mL), N,N-diisopropylethylamine (2.09 mL) and tetrahydrofuran (30 mL) was stirred at room temperature for 2 hrs. Saturated aqueous sodium hydrogen carbonate was poured into the reaction mixture, and the mixture was extracted with ethyl acetate. The ethyl acetate layer was washed with saturated brine, dried over anhydrous magnesium sulfate and concentrated. The residue was washed with diisopropyl ether-hexane to give 3-(methoxymethoxy)-1-phenyl-1H-pyrazole-4-carbaldehyde as white crystals (1.34 g, yield 58%). Recrystallization from ethyl acetate-hexane gave colorless prism crystals. melting point: 106-107° C.

Reference Example 193

To a solution of diethyl [(2-ethyl-1,3-thiazol-4-yl)methyl]phosphonate (4.64 g) in tetrahydrofuran (75 mL) was added sodium hydride (60% in oil, 0.96 g) at room temperature, and the mixture was stirred for 30 min. 3-(Methoxymethoxy)-1-phenyl-1H-pyrazole-4-carbaldehyde (6.32 g) was added to the reaction mixture, and the mixture was heated under reflux for 15 hrs. Water was poured into the reaction mixture, and the mixture was extracted with ethyl acetate. The ethyl acetate layer was washed with saturated brine, dried over anhydrous magnesium sulfate and concentrated. The residue was subjected to silica gel column chromatography and eluted with ethyl acetate-hexane (1:9-1:1, v/v) to give 2-ethyl-4-{(E)-2-[3-(methoxymethoxy)-1-phenyl-1H-pyrazol-4-yl]ethenyl}-1,3-thiazole as a pale-yellow oil (4.49 g, yield 66%).

NMR (CDCl$_3$) δ: 1.42 (3H, t, J=7.6 Hz), 3.06 (2H, q, J=7.5 Hz), 3.62 (3H, s), 5.55 (2H, s), 6.94 (1H, s), 7.10 (1H, d, J=16.0 Hz), 7.18-7.23 (1H, m), 7.30 (1H, d, J=15.9 Hz), 7.37-7.44 (2H, m), 7.57-7.61 (2H, m), 7.82 (1H, s).

Reference Example 194

A mixture of 4-chloromethyl-2-isopropyl-1,3-thiazole (1.90 g) and triethyl phosphite (3.49 g) was stirred at 160° C. for 16 hrs. Excess triethyl phosphite was evaporated under reduced pressure. The residue was subjected to silica gel column chromatography and eluted with ethyl acetate-hexane (1:1, v/v), ethyl acetate, then ethyl acetate-ethanol (10:1, v/v) to give diethyl [(2-isopropyl-1,3-thiazol-4-yl)methyl]phosphonate as a pale-yellow oil (2.48 g, yield 83%).

NMR (CDCl$_3$) δ: 1.28 (6H, t, J=7.1 Hz), 1.38 (6H, d, J=6.8 Hz), 3.25-3.32 (1H, m), 3.37 (2H, dd, J=20.9, 0.6 Hz), 4.04-4.14 (4H, m), 7.08 (1H, d, J=3.6 Hz).

Reference Example 195

To a solution of 2-isopropyl-4-{(E)-2-[3-(methoxymethoxy)-1-phenyl-1H-pyrazol-4-yl]ethenyl}-1,3-thiazole (1.47 g) in methanol (20 mL) was added concentrated hydrochloric acid (0.5 mL) at room temperature, and the mixture was stirred at room temperature for 20 hrs. The reaction mixture was evaporated under reduced pressure, and the residue was washed with ethyl acetate-hexane to give 4-[(E)-2-(2-isopropyl-1,3-thiazol-4-yl)ethenyl]-1-phenyl-1H-pyrazol-3-ol hydrochloride (1.43 g, yield 99%) as pale-yellow crystals. melting point: 137-139° C.

Reference Example 196

To a solution of diethyl ([(2-ethyl-1,3-oxazol-4-yl)methyl]phosphonate (2.97 g) in tetrahydrofuran (50 mL) was added sodium hydride (60% in oil, 0.48 g) at room temperature, and the mixture was stirred for 30 min. 3-(Methoxymethoxy)-1-phenyl-1H-pyrazole-4-carbaldehyde (2.32 g) was added to the reaction mixture and the mixture was heated under reflux for 1.5 hrs. Water was poured into the reaction mixture, and the mixture was extracted with ethyl acetate. The ethyl acetate layer was washed with saturated brine, dried over anhydrous magnesium sulfate and concentrated. The residue was subjected to silica gel column chromatography and eluted with ethyl acetate-hexane (1:9-3:7, v/v) to give 2-ethyl-4-{(Z)-2-[3-(methoxymethoxy)-1-phenyl-1H-pyrazol-4-yl]ethenyl}-1,3-oxazole as a pale-yellow oil (0.24 g, yield 7.4%).

NMR (CDCl$_3$) δ: 1.45 (3H, t, J=7.5 Hz), 2.86 (2H, q, J=7.7 Hz), 3.58 (3H, s), 5.49 (2H, s), 6.15 (1H, d, J=12.8 Hz), 6.36 (1H, d, J=13.0 Hz), 7.20 (1H, tt, J=7.4, 1.1 Hz), 7.37-7.44 (2H, m), 7.58 (1H, s), 7.64-7.67 (2H, m), 9.31 (1H, d, J=0.6 Hz).

In addition, 2-ethyl-4-{(E)-2-[3-(methoxymethoxy)-1-phenyl-1H-pyrazol-4-yl]ethenyl}-1,3-oxazole was obtained as a pale-yellow oil (2.57 g, yield 79%) from a fraction successively obtained by elution.

NMR (CDCl$_3$) δ: 1.36 (3H, t, J=7.6 Hz), 2.81 (2H, q, J=7.7 Hz), 3.61 (3H, s), 5.54 (2H, s), 6.94 (1H, d, J=16.0 Hz), 7.13 (1H, d, J=15.9 Hz), 7.20 (1H, t, J=7.4 Hz), 7.38-7.44 (2H, m), 7.50 (1H, s), 7.57-7.61 (2H, m), 7.79 (1H, s).

Reference Example 197

A mixture of 4-chloromethyl-2-isopropyl-1,3-oxazole (1.12 g) and triethyl phosphite (2.57 g) was stirred at 160° C. for 16 hrs. Excess triethyl phosphite was evaporated under reduced pressure. The residue was subjected to silica gel column chromatography and eluted with ethyl acetate-hexane (1:1, v/v), ethyl acetate, then ethyl acetate-ethanol (10:1, v/v) to give diethyl [(2-isopropyl-1,3-oxazol-4-yl)methyl]phosphonate as a colorless oil (1.67 g, yield 91%).

NMR (CDCl$_3$) δ: 1.29-1.34 (12H, m), 3.01-3.10 (1H, m), 3.09 (2H, dd, J=20.8, 1.0 Hz), 4.07-4.17 (4H, m), 7.52 (1H, dt, J=3.8, 1.0 Hz).

Reference Example 198

To a solution of 2-isopropyl-4-{(E)-2-[3-(methoxymethoxy)-1-phenyl-1H-pyrazol-4-yl]ethenyl}-1,3-oxazole (1.00 g) in methanol (12 mL) was added concentrated hydrochloric acid (0.52 mL) at room temperature, and the mixture was stirred at 50° C. for 1 hr. The reaction mixture was evaporated under reduced pressure, and the residue was washed with diethyl ether to give 4-[(E)-2-(2-isopropyl-1,3-oxazol-4-yl)ethenyl]-1-phenyl-1H-pyrazol-3-ol hydrochloride (0.95 g, yield 92%) as orange crystals. melting point: 205-209° C.

Reference Example 199

A mixture of 2-tert-butyl-4-chloromethyl-1,3-oxazole (10.42 g) and triethyl phosphite (19.94 g) was stirred at 160° C. for 16 hrs. Excess triethyl phosphite was evaporated under reduced pressure. The residue was subjected to silica gel column chromatography and eluted with ethyl acetate-hexane (1:1, v/v), ethyl acetate, then ethyl acetate-ethanol (10:1, v/v) to give diethyl [(2-tert-butyl-1,3-oxazol-4-yl)methyl]phosphonate as a colorless oil (16.51 g, yield 100%).

NMR (CDCl$_3$) δ: 1.31 (6H, t, J=7.1 Hz), 1.36 (9H, s), 3.10 (2H, dd, J=20.6, 1.0 Hz), 4.07-4.17 (4H, m), 7.52 (1H, dt, J=3.6, 1.1 Hz).

Reference Example 200

To a solution of 2-tert-butyl-4-{(E)-2-[3-(methoxymethoxy)-1-phenyl-1H-pyrazol-4-yl]ethenyl}-1,3-oxazole (2.15 g) in methanol (25 mL) was added concentrated hydrochloric acid (1.00 mL) at room temperature, and the mixture was stirred at 50° C. for 1 hr. The reaction mixture was evaporated under reduced pressure, and the residue was washed with diethyl ether to give 4-[(E)-2-(2-tert-butyl-1,3-oxazol-4-yl)ethenyl]-1-phenyl-1H-pyrazol-3-ol.hydrochloride (1.74 g, yield 83%) as orange crystals. melting point: 220-221° C.

Reference Example 201

To a solution of 2-ethyl-4-{(E)-2-[3-(methoxymethoxy)-1-phenyl-1H-pyrazol-4-yl]ethenyl}-1,3-thiazole (4.49 g) in methanol (50 mL) was added concentrated hydrochloric acid (2.17 mL) at room temperature, and the mixture was stirred at 50° C. for 1 hr. The reaction mixture was evaporated under reduced pressure and the residue was washed with ethyl acetate-diethyl ether to give 4-[(E)-2-(2-ethyl-1,3-thiazol-4-yl)ethenyl]-1-phenyl-1H-pyrazol-3-ol (4.18 g, yield 95%) as orange crystals. hydrochloride. melting point: 222-224° C.

Reference Example 202

To a solution of diethyl [(2-isopropyl-1,3-thiazol-4-yl)methyl]phosphonate (2.47 g) in tetrahydrofuran (100 mL) was added sodium hydride (60% in oil, 0.36 g) at room temperature, and the mixture was stirred for 30 min. 3-(Methoxymethoxy)-1-phenyl-1H-pyrazole-4-carbaldehyde (1.72 g) was added to the reaction mixture and the mixture was heated under reflux for 2 hrs. Water was poured into the reaction mixture, and the mixture was extracted with ethyl acetate. The ethyl acetate layer was washed with saturated brine, dried over anhydrous magnesium sulfate and concentrated. The residue was subjected to silica gel column chromatography and eluted with ethyl acetate-hexane (1:3, v/v) to give 2-isopropyl-4-{(E)-2-[3-(methoxymethoxy)-1-phenyl-1H-pyrazol-4-yl]ethenyl}-1,3-thiazole as pale-yellow oil (1.59 g, yield 60%).

NMR (CDCl$_3$) δ: 1.48 (6H, d, J=7.0 Hz), 3.26-3.41 (1H, m), 3.62 (3H, s), 5.55 (2H, s), 6.95 (1H, s), 7.04-7.46 (5H, m), 7.53-7.65 (2H, m), 7.83 (1H, s).

Reference Example 203

A mixture of 4-chloromethyl-2-ethyl-1,3-oxazole (3.26 g), triethyl phosphite (8.19 g) was stirred at 160° C. for 16 hrs. Excess triethyl phosphite was evaporated under reduced pressure. The residue was subjected to silica gel column chromatography and eluted with ethyl acetate-hexane (1:1, v/v), ethyl acetate, then ethyl acetate-ethanol (10:1, v/v) to give diethyl [(2-ethyl-1,3-oxazol-4-yl)methyl]phosphonate as a colorless oil (3.86 g, yield 70%).

NMR (CDCl$_3$) δ: 1.29-1.34 (9H, m), 2.76 (2H, q, J=7.7 Hz), 3.08 (2H, dd, J=20.7, 1.1 Hz), 4.07-4.17 (4H, m), 7.52 (1H, dt, J=3.7, 1.1 Hz).

Reference Example 204

To a solution of 2-ethyl-4-{(E)-2-[3-(methoxymethoxy)-1-phenyl-1H-pyrazol-4-yl]ethenyl}-1,3-oxazole (2.57 g) in methanol (30 mL) was added concentrated hydrochloric acid (1.33 mL) at room temperature, and the mixture was stirred at 50° C. for 1 hr. The reaction mixture was evaporated under reduced pressure, and the residue was washed with diethyl ether to give 4-[(E)-2-(2-ethyl-1,3-oxazol-4-yl)ethenyl]-1-phenyl-1H-pyrazol-3-ol.hydrochloride (2.00 g, yield 90%) as orange crystals. melting point: 157-159° C.

Reference Example 205

To a solution of diethyl [(2-isopropyl-1,3-oxazol-4-yl)methyl]phosphonate (1.16 g) in tetrahydrofuran (15 mL) was added sodium hydride (60% in oil, 0.24 g) at room temperature, and the mixture was stirred for 30 min. 3-(Methoxymethoxy)-1-phenyl-1H-pyrazole-4-carbaldehyde (1.57 g) was added to the reaction mixture and the mixture was heated under reflux for 1.5 hrs. Water was poured into the reaction mixture, and the mixture was extracted with ethyl acetate. The ethyl acetate layer was washed with saturated brine, dried over anhydrous magnesium sulfate and concentrated. The residue was subjected to silica gel column chromatography and eluted with ethyl acetate-hexane (1:9-1:2, v/v) to give 2-isopropyl-4-{(Z)-2-[3-(methoxymethoxy)-1-phenyl-1H-pyrazol-4-yl]ethenyl}-1,3-oxazole as a pale-yellow oil (0.02 g, yield 1.2%).

NMR (CDCl$_3$) δ: 1.45 (6H, d, J=7.0 Hz), 3.07-3.21 (1H, m), 3.59 (3H, s), 5.49 (2H, s), 6.15 (1H, d, J=13.0 Hz), 6.36 (1H, d, J=12.9 Hz), 7.20 (1H, tt, J=7.4, 1.1 Hz), 7.37-7.43 (2H, m), 7.58 (1H, s), 7.64-7.70 (2H, m), 9.40 (1H, d, J=0.4 Hz).

In addition, 2-isopropyl-4-{(E)-2-[3-(methoxymethoxy)-1-phenyl-1H-pyrazol-4-yl]ethenyl}-1,3-oxazole was obtained as a pale-yellow oil (1.00 g, yield 63%) from a fraction successively obtained by elution. NMR (CDCl$_3$) δ: 1.37 (6H, d, J=7.0 Hz), 3.07-3.16 (1H, m), 3.61 (3H, s), 5.54

(2H, s), 6.94 (1H, d, J=16.0 Hz), 7.13 (1H, d, J=16.2 Hz), 7.20 (1H, tt, J=7.4, 1.1 Hz), 7.37-7.44 (2H, m), 7.50 (1H, s), 7.57-7.61 (2H, m), 7.79 (1H, s).

Reference Example 206

A mixture of pivalamide (30 g) and 1,3-dichloro-2-propanone (37.66 g) was stirred at 160° C. for 1.5 hrs. Saturated aqueous sodium hydrogen carbonate and ethyl acetate were added to the reaction mixture, and insoluble materials were removed by filtration. The organic layer was separated, dried over anhydrous magnesium sulfate and concentrated. The residue was subjected to silica gel column chromatography and eluted with ethyl acetate-hexane (1:5-1:2, v/v). The obtained oily substance (a mixture (41 g) of 2-tert-butyl-4-chloromethyl-1,3-oxazole and 1,3-dichloro-2-propanone) was dissolved in tetrahydrofuran (500 mL) ethanol (50 mL), sodium borohydride (5 g) was added, and the mixture was stirred at room temperature for 16 hrs. Water was poured into the reaction mixture, and the mixture was extracted with ethyl acetate. The ethyl acetate layer was washed with saturated brine, dried over anhydrous magnesium sulfate and concentrated. The residue was subjected to silica gel column chromatography and eluted with ethyl acetate-hexane (1:20, v/v) to give 2-tert-butyl-4-(chloromethyl)-1,3-oxazole as a colorless oil (19.61 g, yield 38%).

NMR (CDCl$_3$) δ: 1.38 (9H, s), 4.50 (2H, d, J=0.9 Hz), 7.54 (1H, t, J=0.9 Hz).

Reference Example 207

To a solution of diethyl [(2-tert-butyl-1,3-oxazol-4-yl)methyl]phosphonate (2.32 g) in tetrahydrofuran (30 mL) was added sodium hydride (60% in oil, 0.48 g) at room temperature, and the mixture was stirred for 30 min. 3-(Methoxymethoxy)-1-phenyl-1H-pyrazole-4-carbaldehyde (3.30 g) was added to the reaction mixture, and the mixture was heated under reflux for 1.5 hrs. Water was poured into the reaction mixture, and the mixture was extracted with ethyl acetate. The ethyl acetate layer was washed with saturated brine, dried over anhydrous magnesium sulfate and concentrated. The residue was subjected to silica gel column chromatography and eluted with ethyl acetate-hexane (1:20-1:3, v/v) to give 2-tert-butyl-4-{(Z)-2-[3-(methoxymethoxy)-1-phenyl-1H-pyrazol-4-yl]ethenyl}-1,3-oxazole as a pale-yellow oil (0.02 g, yield 0.6%).

NMR (CDCl$_3$) δ: 1.47 (9H, s), 3.59 (3H, s), 5.49 (2H, s), 6.15 (1H, d, J=13.0 Hz), 6.36 (1H, d, J=13.2 Hz), 7.16-7.22 (1H, m), 7.36-7.43 (2H, m), 7.58 (1H, s), 7.66-7.68 (2H, m), 9.47 (1H, s).

In addition, 2-tert-butyl-4-{(E)-2-[3-(methoxymethoxy)-1-phenyl-1H-pyrazol-4-yl]ethenyl}-1,3-oxazole was obtained as a pale-yellow oil (2.15 g, yield 61%) from a fraction successively obtained by elution. NMR (CDCl$_3$) δ: 1.41 (9H, s), 3.61 (3H, s), 5.54 (2H, s), 6.94 (1H, d, J=16.0 Hz), 7.13 (1H, d, J=16.2 Hz), 7.20 (1H, tt, J=7.4, 1.1 Hz), 7.40 (2H, m), 7.50 (1H, s), 7.59 (2H, m), 7.80 (1H, s).

Reference Example 208

To a solution of diethyl [(2-methyl-1,3-thiazol-4-yl)methyl]phosphonate (2.32 g) in tetrahydrofuran (100 mL) was added sodium hydride (60% in oil, 0.48 g) at room temperature, and the mixture was stirred for 30 min. 3-(Methoxymethoxy)-1-phenyl-1H-pyrazole-4-carbaldehyde (2.32 g) was added to the reaction mixture, and the mixture was heated under reflux for 1.5 hrs. Water was poured into the reaction mixture, and the mixture was extracted with ethyl acetate. The ethyl acetate layer was washed with saturated brine, dried over anhydrous magnesium sulfate and concentrated. The residue was subjected to silica gel column chromatography and eluted with ethyl acetate-hexane (4:1, v/v) to give 2-methyl-4-{(E)-2-[3-(methoxymethoxy)-1-phenyl-1H-pyrazol-4-yl]ethenyl}-1,3-thiazole as a pale-yellow oil (2.72 g, yield 83%).

NMR (CDCl$_3$) δ: 2.74 (3H, s), 3.62 (3H, s), 5.55 (2H, s), 6.92 (1H, s), 7.03-7.49 (6H, m), 7.52-7.68 (1H, m), 7.81 (1H, m).

Reference Example 209

To a solution of diethyl [(2-tert-butyl-1,3-thiazol-4-yl)methyl]phosphonate (2.2 g) in tetrahydrofuran (100 mL) was added sodium hydride (60% in oil, 0.48 g) at room temperature, and the mixture was stirred for 30 min. 3-(Methoxymethoxy)-1-phenyl-1H-pyrazole-4-carbaldehyde (2.3 g) was added to the reaction mixture, and the mixture was heated under reflux for 3 hrs. Water was poured into the reaction mixture, and the mixture was extracted with ethyl acetate. The ethyl acetate layer was washed with saturated brine, dried over anhydrous magnesium sulfate and concentrated. The residue was subjected to silica gel column chromatography and eluted with ethyl acetate-hexane (4:1, v/v) to give 2-tert-butyl-4-{(E)-2-[3-(methoxymethoxy)-1-phenyl-1H-pyrazol-4-yl]ethenyl}-1,3-thiazole as pale-yellow crystals (2.6 g, yield 71%). melting point: 112-113° C.

Reference Example 210

A mixture of 2,2-dimethylpropanethioamide (6.36 g) 1,3-dichloro-2-propanone (7.60 g) and ethanol (100 mL) was heated under reflux for 2 hrs. The solvent was evaporated under reduced pressure, saturated aqueous sodium hydrogen carbonate was added to the residue and the mixture was extracted with ethyl acetate. The ethyl acetate layer was washed with saturated brine, dried over anhydrous magnesium sulfate and concentrated. The residue was subjected to silica gel column chromatography and eluted with ethyl acetate-hexane (1:10, v/v) to give 2-tert-butyl-4-chloromethyl-1,3-thiazole as a colorless oil (9.06 g, yield 88%).

NMR (CDCl$_3$) δ: 1.43 (9H, s), 4.68 (2H, s), 7.15 (1H, s).

Reference Example 211

A mixture of 2-amino-2-thioxoethyl benzoate (7.6 g), 1,3-dichloro-2-propanone (7.6 g) and ethanol (100 mL) was heated under reflux for 4 hrs. The solvent was evaporated under reduced pressure, saturated aqueous sodium hydrogen carbonate was added to the residue and the mixture was extracted with ethyl acetate. The ethyl acetate layer was washed with saturated brine, dried over anhydrous magnesium sulfate and concentrated. The residue was subjected to silica gel column chromatography and eluted with ethyl acetate-hexane (1:5, v/v) to give (4-chloromethyl-1,3-thiazol-2-yl)methyl benzoate as a brown oil (7.3 g, yield 45%).

NMR (CDCl$_3$) δ: 4.71 (2H, s), 5.62 (2H, s), 7.36 (1H, s), 7.41-7.53 (2H, m), 7.54-7.66 (1H, m), 8.02-8.17 (2H, m).

Reference Example 212

To a solution of methyl {4-[(diethoxyphosphoryl)methyl]-1,3-thiazol-2-yl}benzoate (4.7 g) in tetrahydrofuran (100 mL) was added sodium hydride (60% in oil, 1.1 g) at room temperature, and the mixture was stirred for 30 min. 3-(Methoxymethoxy)-1-phenyl-1H-pyrazole-4-carbaldehyde (2.8 g) was added to the reaction mixture, and the mixture was heated under reflux for 3 hrs. Water was poured into the reaction mixture, and the mixture was extracted with ethyl acetate. The ethyl acetate layer was washed with saturated brine, dried over anhydrous magnesium sulfate and concentrated. The residue was subjected to silica gel column chromatography and eluted with ethyl acetate-hexane (30:70-60:40, v/v) to give methyl (4-{(E)-2-[3-(methoxymethoxy)-1-phenyl-1H-pyrazol-4-yl]ethenyl}-1,3-thiazol-2-yl)benzoate as pale-yellow crystals (1.1 g, yield 20%). Recrystallization from ethyl acetate-hexane gave pale-yellow prism crystals. melting point: 134-135° C.

Reference Example 213

To a solution of 2-methyl-4-{(E)-2-[3-(methoxymethoxy)-1-phenyl-1H-pyrazol-4-yl]ethenyl}-1,3-thiazole (2.72 g) in methanol (30 mL) was added concentrated hydrochloric acid (1.00 mL) at room temperature, and the mixture was stirred at room temperature for 18 hrs. The reaction mixture was evaporated under reduced pressure, and the residue was washed with ethyl acetate-methanol to give 4-[(E)-2-(2-methyl-1,3-thiazol-4-yl)ethenyl]-1-phenyl-1H-pyrazol-3-ol.hydrochloride (2.30 g, yield 90%) as pale-yellow crystals. melting point: 211-212° C.

Reference Example 214

To a solution of 2-tert-butyl-4-{(E)-2-[3-(methoxymethoxy)-1-phenyl-1H-pyrazol-4-yl]ethenyl}-1,3-thiazole (2.4 g) in methanol (30 mL) was added concentrated hydrochloric acid (0.8 mL) at room temperature, and the mixture was stirred at room temperature for 24 hr. The reaction mixture was evaporated under reduced pressure, and the residue was washed with ethyl acetate-hexane to give 4-[(E)-2-(2-tert-butyl-1,3-thiazol-4-yl)ethenyl]-1-phenyl-1H-pyrazol-3-ol.hydrochloride (2.1 g, yield 91%) as pale-yellow crystals. melting point: 209-211° C.

Reference Example 215

A mixture of 2-tert-butyl-4-chloromethyl-1,3-thiazole (8.66 g) and triethyl phosphite (15.7 g) was stirred at 160° C. for 20 hrs. Excess triethyl phosphite was evaporated under reduced pressure. The residue was subjected to silica gel column chromatography and eluted with ethyl acetate-hexane (1:2 to 1:0, v/v) to give diethyl [(2-tert-butyl-1,3-thiazol-4-yl)methyl]phosphonate as a colorless oil (12.0 g, yield 90%).
NMR (CDCl$_3$) δ: 1.28 (6H, t, J=7.1 Hz), 1.42 (9H, s), 3.37 (2H, d, J=20.9 Hz), 4.02-4.15 (4H, m), 7.05 (1H, d, J=3.6 Hz).

Reference Example 216

A mixture of (4-chloromethyl-1,3-thiazol-2-yl)methyl benzoate (6.4 g), triethyl phosphite (8.7 g) was stirred at 150° C. for 17 hrs. Excess triethyl phosphite was evaporated under reduced pressure. The residue was subjected to silica gel column chromatography and eluted with ethyl acetate-hexane (1:2, v/v)-ethyl acetate to give {4-[(diethoxyphosphoryl)methyl]-1,3-thiazol-2-yl}methyl benzoate as a yellow oil (8.0 g, yield 91%).
NMR (CDCl$_3$) δ: 1.28 (6H, t, J=7.1 Hz), 3.41 (2H, d, J=20.9 Hz), 4.00-4.17 (4H, m), 5.60 (2H, s), 7.24-7.32 (1H, m), 7.41-7.53 (2H, m), 7.55-7.65 (1H, m), 8.03-8.15 (2H, m).

Reference Example 217

To a solution of (4-{(E)-2-[3-(methoxymethoxy)-1-phenyl-1H-pyrazol-4-yl]ethenyl}-1,3-thiazol-2-yl)methyl benzoate (1.02 g) in methanol (30 mL) was added concentrated hydrochloric acid (0.28 mL) at room temperature, and the mixture was stirred at 50° C. for 2 hrs. The reaction mixture was evaporated under reduced pressure, and the residue was washed with ethyl acetate-methanol to give {4-[(E)-2-(3-hydroxy-1-phenyl-1H-pyrazol-4-yl)ethenyl]-1,3-thiazol-2-yl}methyl benzoate (0.79 g, yield 79%) as colorless crystals. melting point: 215-216° C.

Reference Example 218

A mixture of 3-nitrobenzaldehyde (18.67 g), 2,3-butanedione-2-oxime (12.50 g) and 4N hydrogenchloride-ethyl acetate (400 mL) was stirred at room temperature for 16 hrs. The reaction mixture was concentrated. A mixture of the residue, tetrahydrofuran (400 mL) and thionyl chloride (13.6 mL) was heated under reflux for 2 hrs. The reaction mixture was concentrated and ethyl acetate was added to the residue. The ethyl acetate layer was washed successively with saturated aqueous sodium hydrogen carbonate solution and saturated brine, dried over anhydrous magnesium sulfate and concentrated. The residue was subjected to silica gel column chromatography and the crude product obtained from a fraction eluted with ethyl acetate-hexane (1:4-1:3, v/v) was washed with diethyl ether-hexane to give 4-chloromethyl-5-methyl-2-(3-nitrophenyl)-1,3-oxazole as colorless crystals (2.67 g, yield 8.6%). Recrystallization from ethyl acetate-hexane gave colorless prism crystals. melting point: 111-113° C.

Reference Example 219

A mixture of 4-chloromethyl-5-methyl-2-(3-nitrophenyl)-1,3-oxazole (2.67 g), vanillin (1.52 g), anhydrous potassium carbonate (1.38 g) and N,N-dimethylformamide (30 mL) was stirred at 90° C. for 2 hrs. Water was poured into the reaction mixture, and the mixture was extracted with ethyl acetate-tetrahydrofuran. The organic layer was dried over anhydrous magnesium sulfate, and filtered through a silica gel column. The filtrate was concentrated and the residue was washed with diethyl ether-hexane to give 3-methoxy-4-{[5-methyl-2-(3-nitrophenyl)-1,3-oxazol-4-yl]methoxy}benzaldehyde as colorless crystals (3.58 g, yield 97%). Recrystallization from ethyl acetate-hexane gave pale-yellow prism crystals. melting point: 179-180° C.

Reference Example 220

To a solution of 3-methoxy-4-{[5-methyl-2-(3-nitrophenyl)-1,3-oxazol-4-yl]methoxy}benzaldehyde (7.51 g) in tetrahydrofuran (100 mL)-ethanol (15 mL) was gradually added sodium borohydride (397 mg) at 0° C. After stirring at room temperature for 6 hrs, water was added to the reaction mixture, and the mixture was extracted with ethyl acetate. The organic layer was washed with saturated brine, dried over anhydrous magnesium sulfate and concentrated to give (3-methoxy-4-{[5-methyl-2-(3-nitrophenyl)-1,3-oxazol-4-yl]methoxy}phenyl)methanol as colorless crystals (5.92 g, yield 78%). Recrystallization from ethyl acetate-hexane gave colorless prism crystals. melting point: 134-135° C.

Reference Example 221

To a mixture of (3-methoxy-4-{[5-methyl-2-(3-nitrophenyl)-1,3-oxazol-4-yl]methoxy}phenyl)methanol (5.92 g) and toluene (250 ml) was added thionyl chloride (2.19 mL), and the mixture was heated under reflux for 1.5 hrs. The reaction mixture was concentrated and ethyl acetate was added to the residue. The organic layer was washed successively with saturated aqueous sodium hydrogen carbonate and saturated brine, dried over anhydrous magnesium sulfate and concentrated to give 4-[(4-chloromethyl-2-methoxyphenoxy)methyl]-5-methyl-2-(3-nitrophenyl)-1,3-oxazole (6.31 g, yield 100%) as colorless crystals. Recrystallization from ethyl acetate-hexane gave colorless prism crystals. melting point: 166-168° C.

Reference Example 222

A mixture of ethyl [4-(4-chloromethyl-5-methyl-1,3-oxazol-2-yl)phenyl]acetate (2.00 g), methyl 3-hydroxyisoxazole-5-carboxylate (0.974 g), anhydrous potassium carbonate (0.941 g) and N,N-dimethylformamide (40 mL) was stirred at 90° C. for 2 hrs. Water was poured into the reaction mixture, and the mixture was extracted with ethyl acetate. The organic layer was dried over anhydrous magnesium sulfate and filtered through silica gel. The filtrate was concentrated to give methyl 3-({2-[4-(2-ethoxy-2-oxoethyl)phenyl]-5-methyl-1,3-oxazol-4-yl}methoxy)isoxazole-5-carboxylate as colorless crystals (2.02 g, yield 81%). Recrystallization from ethyl acetate-hexane gave colorless prism crystals. melting point: 124-126° C.

Reference Example 223

To a solution of methyl 3-({2-[4-(2-ethoxy-2-oxoethyl)phenyl]-5-methyl-1,3-oxazol-4-yl}methoxy)isoxazole-5-carboxylate (2.02 g) in methanol (25 mL) was gradually added sodium borohydride (250 mg) at 0° C. After stirring at room temperature for 16 hrs, water was added to the reaction mixture, and the mixture was extracted with ethyl acetate. The organic layer was washed with saturated brine, dried over anhydrous magnesium sulfate and concentrated. The residue was subjected to silica gel column chromatography and eluted with ethyl acetate-hexane (1:9-1:1, v/v) to give ethyl (4-[4-({[5-(hydroxymethyl)isoxazol-3-yl]oxy}methyl)-5-methyl-1,3-oxazol-2-yl]phenyl)acetate as colorless crystals (0.95 g, yield 46%). Recrystallization from ethyl acetate-hexane gave colorless prism crystals. melting point: 116-117° C.

Reference Example 224

A mixture of 4-ethyl 1-tert-butyl 3-hydroxy-1H-pyrazole-1,4-dicarboxylate (30.75 g), chloromethyl methyl ether (4.56 mL), N,N-diisopropylethylamine (11.9 mL) and tetrahydrofuran (150 mL) was stirred at room temperature for 2 hrs. The reaction mixture was poured into saturated aqueous sodium hydrogen carbonate, and the mixture was extracted with ethyl acetate. The organic layer was washed with saturated brine, dried over anhydrous magnesium sulfate and concentrated. The residue was subjected to silica gel column chromatography and eluted with ethyl acetate-hexane (1:9-1:2, v/v) to give 4-ethyl 1-tert-butyl 3-(methoxymethoxy)-1H-pyrazole-1,4-dicarboxylate as a pale-yellow oil (3.52 g, yield 20%).
NMR (CDCl$_3$) δ: 1.36 (3H, t, J=7.2 Hz), 1.63 (9H, s), 3.58 (3H, s), 4.32 (2H, q, J=7.2 Hz), 5.51 (2H, s), 8.36 (1H, s).

Reference Example 225

A mixture of 4-ethyl 1-tert-butyl 3-(methoxymethoxy)-1H-pyrazole-1,4-dicarboxylate (3.52 g), lithium hydroxide monohydrate (1.47 g), tetrahydrofuran (60 mL), methanol (30 mL) and water (30 mL) was stirred at room temperature for hrs. Water was added to the reaction mixture, and the mixture was extracted with ethyl acetate. The organic layer was washed with saturated brine, dried over anhydrous magnesium sulfate and concentrated. The residue was subjected to silica gel column chromatography and eluted with ethyl acetate-hexane (1:9-4:1, v/v) to give ethyl 3-(methoxymethoxy)-1H-pyrazole-4-carboxylate as a colorless solid (1.80 g, yield 77%).
NMR (CDCl$_3$) δ: 1.34 (3H, t, J=7.2 Hz), 3.57 (3H, s), 4.30 (2H, q, J=7.2 Hz), 5.41 (2H, s), 7.26 (1H, s), 7.90 (1H, s).

Reference Example 226

A mixture of ethyl 3-(methoxymethoxy)-1H-pyrazole-4-carboxylate (1.80 g), 2-methylphenylboronic acid (2.45 g), pyridine (1.46 mL), copper(II) acetate (2.45 g) and dichloromethane (50 mL) was stirred at room temperature for 16 hrs. Water was poured into the reaction mixture, and the mixture was extracted with ethyl acetate. The organic layer was washed with saturated brine, dried over anhydrous magnesium sulfate and concentrated. The residue was subjected to silica gel column chromatography and eluted with ethyl acetate-hexane (1:9-1:1, v/v) to give ethyl 3-(methoxymethoxy)-1-(2-methylphenyl)-1H-pyrazole-4-carboxylate as a pale-yellow oil (2.39 g, yield 92%).
NMR (CDCl$_3$) δ: 1.36 (3H, t, J=7.2 Hz), 2.30 (3H, s), 3.60 (3H, s), 4.32 (2H, q, J=7.2 Hz), 5.46 (2H, s), 7.27-7.33 (4H, m), 7.91 (1H, s).

Reference Example 227

To a solution of ethyl 3-(methoxymethoxy)-1-(2-methylphenyl)-1H-pyrazole-4-carboxylate (2.39 g) in tetrahydrofuran (60 mL) was added lithium aluminum hydride (0.323 g) at 0° C. and the mixture was stirred at room temperature for 16 hrs. Sodium sulfate decahydrate (2.78 g) was added to the reaction mixture and the mixture was stirred at room temperature for 1 hr. After removing the precipitate by filtration, and the filtrate was concentrated. The residue was subjected to silica gel column chromatography and eluted with ethyl acetate-hexane (1:1-4:1, v/v) to give [3-(methoxymethoxy)-1-(2-methylphenyl)-1H-pyrazol-4-yl]methanol as a pale-yellow oil (1.84 g, yield 90%).
NMR (CDCl$_3$) δ: 1.89 (1H, t, J=5.6 Hz), 2.30 (3H, s), 3.59 (3H, s), 4.60 (2H, d, J=5.5 Hz), 5.39 (2H, s), 7.24-7.30 (4H, m), 7.44 (1H, s).

Reference Example 228

A mixture of [3-(methoxymethoxy)-1-(2-methylphenyl)-1H-pyrazol-4-yl]methanol (2.39 g), activated manganese dioxide (5.0 g) and toluene (30 mL) was stirred at room temperature for 8 hrs. Activated manganese dioxide (5.0 g) was added and the mixture was further stirred for 12 hrs. Manganese dioxide was removed by filtration, and the filtrate was concentrated. The residue was subjected to silica gel column chromatography and eluted with ethyl acetate-hexane (1:9-1:2, v/v) to give 3-(methoxymethoxy)-1-(2-methylphenyl)-1H-pyrazole-4-carbaldehyde as an orange oil (1.65 g, yield 81%).

NMR (CDCl$_3$) δ: 2.30 (3H, s), 3.60 (3H, s), 5.48 (2H, s), 7.28-7.35 (4H, m), 7.93 (1H, s), 9.91 (1H, s).

Reference Example 229

To a solution of diethyl [(2-ethyl-5-methyl-1,3-thiazol-4-yl)methyl]phosphonate (1.26 g) in tetrahydrofuran (40 mL) was added sodium hydride (60% in oil, 0.192 g) at room temperature, and the mixture was stirred for 30 min. 3-(Methoxymethoxy)-1-(2-methylphenyl)-1H-pyrazole-4-carbaldehyde (0.99 g) was added to the reaction mixture, and the mixture was heated under reflux for 1.5 hrs. Water was poured into the reaction mixture, and the mixture was extracted with ethyl acetate. The ethyl acetate layer was washed with saturated brine, dried over anhydrous magnesium sulfate and concentrated. The residue was subjected to silica gel column chromatography and eluted with ethyl acetate-hexane (1:20-1:3, v/v) to give 2-ethyl-4-{(E)-2-[3-(methoxymethoxy)-1-(2-methylphenyl)-1H-pyrazol-4-yl]ethenyl}-1,3-thiazole as a pale-yellow oil (0.81 g, yield 57%).

NMR (CDCl$_3$) δ: 1.42 (3H, t, J=7.5 Hz), 2.32 (3H, s), 3.06 (2H, q, J=7.5 Hz), 3.61 (3H, s), 5.49 (2H, s), 6.93 (1H, s), 7.09 (1H, d, J=16.0 Hz), 7.24-7.34 (5H, m), 7.50 (1H, s).

Reference Example 230

To a solution of 2-ethyl-4-{(E)-2-[3-(methoxymethoxy)-1-(2-methylphenyl)-1H-pyrazol-4-yl]ethenyl}-1,3-thiazole (0.81 g) in methanol (20 mL) was added concentrated hydrochloric acid (0.42 mL) at room temperature, and the mixture was stirred at 50° C. for 1 hr. The reaction mixture was evaporated under reduced pressure, saturated aqueous sodium hydrogen carbonate was added to the residue, and the mixture was extracted with ethyl acetate-tetrahydrofuran. The organic layer was washed with saturated brine, dried over anhydrous magnesium sulfate and concentrated. Recrystallization of the residue from tetrahydrofuran-hexane gave 4-[(E)-2-(2-ethyl-1,3-thiazol-4-yl)ethenyl]-1-(2-methylphenyl)-1H-pyrazol-3-ol (0.607 g, yield 86%) as colorless prism crystals. melting point: 174-176° C.

Reference Example 231

A mixture of methyl 3-bromo-2-oxobutanoate (16.2 g), propanethioamide (7.4 g) and ethanol (150 mL) was heated under reflux for 3 hrs. The solvent was evaporated under reduced pressure, saturated aqueous sodium hydrogen carbonate was added to the residue and the mixture was extracted with ethyl acetate. The ethyl acetate layer was washed with saturated brine, dried over anhydrous magnesium sulfate and concentrated. The residue was subjected to silica gel column chromatography and eluted with ethyl acetate-hexane (1:4, v/v) to give methyl 2-ethyl-5-methyl-1,3-thiazole-4-carboxylate as a yellow oil (8.1 g, yield 53%).

NMR (CDCl$_3$) δ: 1.36 (3H, t, J=7.6 Hz), 2.74 (3H, s), 3.00 (2H, q, J=7.6 Hz), 3.93 (3H, s).

Reference Example 232

To a solution of methyl 2-ethyl-5-methyl-1,3-thiazole-4-carboxylate (8.1 g) in tetrahydrofuran (400 mL) was added lithium aluminum hydride (1.8 g) at 0° C., and the mixture was stirred for 2 hrs. Sodium sulfate decahydrate (15.5 g) was added to the reaction mixture, and the mixture was stirred for 1 hr. The reaction mixture was filtered and concentrated. The residue was subjected to silica gel column chromatography and eluted with ethyl acetate-hexane (5:95-70:30, v/v) to give (2-ethyl-5-methyl-1,3-thiazol-4-yl) methanol as a yellow oil (3.7 g, yield 53%).

NMR (CDCl$_3$) δ: 1.34 (3H, t, J=7.6 Hz), 1.86 (1H, brs), 2.40 (3H, s), 2.93 (2H, q, J=7.6 Hz), 4.62 (2H, d, J=4.0 Hz).

Reference Example 233

To a solution of (2-ethyl-5-methyl-1,3-thiazol-4-yl) methanol (3.7 g) in toluene (200 mL) was added thionyl chloride (8.5 g) at room temperature, and the mixture was heated under reflux for 30 min. The solvent was evaporated under reduced pressure, saturated aqueous sodium hydrogen carbonate was added to the residue and the mixture was extracted with ethyl acetate. The ethyl acetate layer was washed with saturated brine, dried over anhydrous magnesium sulfate and concentrated. The residue was subjected to silica gel column chromatography and eluted with ethyl acetate-hexane (10:90-25:75, v/v) to give 4-chloromethyl-2-ethyl-5-methyl-1,3-thiazole as a yellow oil (3.5 g, yield 84%). NMR (CDCl$_3$) δ: 1.35 (3H, t, J=7.6 Hz), 2.44 (3H, s), 2.95 (2H, q, J=7.6 Hz), 4.63 (2H, s).

Reference Example 234

A mixture of 4-chloromethyl-2-ethyl-5-methyl-1,3-thiazole (3.2 g) and triethyl phosphite (6.7 g) was stirred at 160° C. for 16 hrs. Excess triethyl phosphite was evaporated under reduced pressure. The residue was subjected to silica gel column chromatography and eluted with ethyl acetate-hexane (1:2-1:1, v/v) to give diethyl [(2-ethyl-5-methyl-1,3-thiazol-4-yl)methyl]phosphonate as a colorless oil (4.9 g, yield 97%).

NMR (CDCl$_3$) δ: 1.23-1.39 (9H, m), 2.39 (3H, d, J=3.8 Hz), 2.92 (2H, q, J=7.7 Hz), 3.27 (2H, d, J=20.7 Hz), 3.90-4.21 (4H, m).

Reference Example 235

To a solution of diethyl [(2-ethyl-5-methyl-1,3-thiazol-4-yl)methyl]phosphonate (4.16 g) in tetrahydrofuran (100 mL) was added sodium hydride (60% in oil, 0.66 g) at room temperature, and the mixture was stirred for 30 min. 3-(Methoxymethoxy)-1-phenyl-1H-pyrazole-4-carbaldehyde (3.48 g) was added to the reaction mixture, and the mixture was heated under reflux for 2 hrs. Water was poured into the reaction mixture, and the mixture was extracted with ethyl acetate. The ethyl acetate layer was washed with saturated brine, dried over anhydrous magnesium sulfate and concentrated. The residue was subjected to silica gel column chromatography and eluted with ethyl acetate-hexane (5:95-25:75, v/v) to give 2-ethyl-4-{(E)-2-[3-(methoxymethoxy)-1-phenyl-1H-pyrazol-4-yl]ethenyl}-5-methyl-1,3-thiazole as a yellow oil (3.56 g, yield 68%). NMR (CDCl$_3$) δ: 1.38 (3H, t, J=7.6 Hz), 2.45 (3H, s), 2.98 (2H, q, J=7.6 Hz), 3.63 (3H, s), 5.55 (2H, s), 7.09 (1H, d, J=15.8 Hz), 7.14-7.33 (2H, m), 7.35-7.46 (2H, m), 7.55-7.65 (1H, m), 7.82 (1H, s).

Reference Example 236

To a solution of 2-ethyl-4-{(E)-2-[3-(methoxymethoxy)-1-phenyl-1H-pyrazol-4-yl]ethenyl}-5-methyl-1,3-thiazole (3.21 g) in methanol (75 mL) was added concentrated hydrochloric acid (1.5 mL) at room temperature, and the mixture was stirred at 50° C. for 2 hrs. The reaction mixture was evaporated under reduced pressure, and the residue was washed with ethyl acetate-methanol to give 4-[(E)-2-(2-ethyl-5-methyl-1,3-thiazol-4-yl)ethenyl]-1-phenyl-1H-pyrazol-3-ol.hydrochloride (3.02 g, yield 96%) as pale-yellow prism crystals. melting point: 184-186° C.

Reference Example 237

A mixture of tert-butyl 4-(4-chloromethyl-5-methyl-1,3-thiazol-2-yl)piperazine-1-carboxylate (2.91 g) and triethyl phosphite (3.20 g) was stirred at 160° C. for 15 hrs. Excess triethyl phosphite was evaporated under reduced pressure. The residue was subjected to silica gel column chromatography and eluted with ethyl acetate-hexane (1:2-4:1, v/v) to give tert-butyl 4-{4-[(diethoxyphosphoryl)methyl]-5-methyl-1,3-thiazol-2-yl}piperazine-1-carboxylate as a yellow oil (2.20 g, yield 58%).

NMR (CDCl$_3$) δ: 1.30 (6H, t, J=7.1 Hz), 1.47 (9H, s), 2.26 (3H, d, J=4.0 Hz), 3.11 (2H, d, J=20.9 Hz), 3.26-3.63 (8H, m), 3.99-4.20 (4H, m).

Reference Example 238

To a solution of tert-butyl 4-{4-[(diethoxyphosphoryl)methyl]-5-methyl-1,3-thiazol-2-yl}piperazine-1-carboxylate (2.0 g) in tetrahydrofuran (50 mL) was added sodium hydride (60% in oil, 0.20 g) at room temperature, and the mixture was stirred for 30 min. 3-(Methoxymethoxy)-1-phenyl-1H-pyrazole-4-carbaldehyde (1.1 g) was added to the reaction mixture, and the mixture was heated under reflux for 4 hrs. Water was poured into the reaction mixture, and the mixture was extracted with ethyl acetate. The ethyl acetate layer was washed with saturated brine, dried over anhydrous magnesium sulfate and concentrated. The residue was subjected to silica gel column chromatography and eluted with ethyl acetate-hexane (5:95-25:75, v/v) to give tert-butyl 4-(4-{(E)-2-[3-(methoxymethoxy)-1-phenyl-1H-pyrazol-4-yl]ethenyl}-5-methyl-1,3-thiazol-2-yl)piperazine-1-carboxylate as a yellow oil (1.3 g, yield 57%).

NMR (CDCl$_3$) δ: 1.49 (9H, s), 2.35 (3H, s), 3.42-3.60 (8H, m), 3.62 (3H, s), 5.54 (2H, s), 6.99 (1H, d, J=15.6 Hz), 7.08-7.24 (2H, m), 7.34-7.46 (2H, m), 7.54-7.65 (2H, m), 7.82 (1H, s).

Reference Example 239

To a solution of tert-butyl 4-(4-{(E)-2-[3-(methoxymethoxy)-1-phenyl-1H-pyrazol-4-yl]ethenyl}-5-methyl-1,3-thiazol-2-yl)piperazine-1-carboxylate (1.1 g) in methanol (20 mL) was added concentrated hydrochloric acid (0.3 mL) at room temperature, and the mixture was stirred at 50° C. for 2 hrs. The reaction mixture was evaporated under reduced pressure, and the residue was dissolved in ethyl acetate (15 mL), di-tert-butyl dicarbonate (1.4 g) and saturated aqueous sodium hydrogen carbonate (15 mL) were added, and the mixture was stirred for 30 min. Water was poured into the reaction mixture, and the mixture was extracted with ethyl acetate. The ethyl acetate layer was washed with saturated brine, dried over anhydrous magnesium sulfate and concentrated. The residue was washed with hexane to give tert-butyl 4-{4-[(E)-2-(3-hydroxy-1-phenyl-1H-pyrazol-4-yl)ethenyl]-5-methyl-1,3-thiazol-2-yl}piperazine-1-carboxylate (0.97 g, yield 88%) as pale-yellow prism crystals. melting point: 221-223° C.

Reference Example 240

A mixture of 1-(4-chloromethyl-5-methyl-1,3-thiazol-2-yl)piperidine (2.7 g) and triethyl phosphite (1.5 g) was stirred at 160° C. for 20 hrs. Excess triethyl phosphite was evaporated under reduced pressure. The residue was subjected to silica gel column chromatography and eluted with ethyl acetate-hexane (2:1, v/v), then ethyl acetate-methanol (10:1, v/v) to give diethyl {[5-methyl-2-(piperidin-1-yl)-1,3-thiazol-4-yl]methyl}phosphonate as a brown oil (1.4 g, yield 35%). NMR (CDCl$_3$) δ: 1.29 (6H, t, J=7.1 Hz), 1.53-1.74 (6H, m), 2.24 (3H, d, J=4.1 Hz), 3.10 (2H, d, J=20.9 Hz), 3.28-3.46 (4H, m), 4.00-4.21 (4H, m).

Reference Example 241

To a solution of diethyl {[5-methyl-2-(piperidin-1-yl)-1,3-thiazol-4-yl]methyl}phosphonate (1.26 g) in tetrahydrofuran (50 mL) was added sodium hydride (60% in oil, 0.17 g) at room temperature, and the mixture was stirred for 30 min. 3-(Methoxymethoxy)-1-phenyl-1H-pyrazole-4-carbaldehyde (0.88 g) was added to the reaction mixture, and the mixture was heated under reflux for 2.5 hrs. Water was poured into the reaction mixture, and the mixture was extracted with ethyl acetate. The ethyl acetate layer was washed with saturated brine, dried over anhydrous magnesium sulfate and concentrated. The residue was subjected to silica gel column chromatography and eluted with ethyl acetate-hexane (5:95-25:75, v/v) to give 1-(4-{(E)-2-[3-(methoxymethoxy)-1-phenyl-1H-pyrazol-4-yl]ethenyl}-5-methyl-1,3-thiazol-2-yl)piperidine as a yellow oil (0.69 g, yield 44%).

NMR (CDCl$_3$) δ: 1.62-1.75 (6H, m), 2.34 (3H, s), 3.40-3.51 (4H, m), 3.62 (3H, s), 5.54 (2H, s), 6.99 (1H, d, J=15.6 Hz), 7.07-7.25 (2H, m), 7.34-7.47 (2H, m), 7.54-7.65 (2H, m), 7.81 (1H, s).

Reference Example 242

To a solution of 1-(4-{(E)-2-[3-(methoxymethoxy)-1-phenyl-1H-pyrazol-4-yl]ethenyl}-5-methyl-1,3-thiazol-2-yl)piperidine (0.61 g) in methanol (30 mL) was added concentrated hydrochloric acid (0.3 mL) at room temperature, and the mixture was stirred at 50° C. for 1 hr. The reaction mixture was evaporated under reduced pressure, and the residue was washed with ethyl acetate-methanol to give 4-({E}-2-[5-methyl-2-(piperidin-1-yl)-1,3-thiazol-4-yl]ethenyl)-1-phenyl-1H-pyrazol-3-ol.hydrochloride (0.49 g, yield 81%) as yellow prism crystals. melting point: 224-226° C.

Reference Example 243

A mixture of 4-(4-chloromethyl-5-methyl-1,3-thiazol-2-yl)morpholine (1.2 g), triethyl phosphite (2.1 g) was stirred at 160° C. for 20 hrs. Excess triethyl phosphite was evaporated under reduced pressure. The residue was subjected to silica gel column chromatography and eluted with ethyl acetate-hexane (2:1, v/v), then ethyl acetate-methanol (10:1, v/v) to give diethyl {[5-methyl-2-(morpholin-4-yl)-1,3-thiazol-4-yl]methyl}phosphonate as a yellow oil (1.7 g, yield 95%). NMR (CDCl$_3$) δ: 1.30 (6H, t, J=7.1 Hz), 2.27 (3H, d, J=4.1 Hz), 3.11 (2H, d, J=20.9 Hz), 3.31-3.43 (4H, m), 3.72-3.85 (4H, m), 3.99-4.20 (4H, m).

Reference Example 244

To a solution of diethyl {[5-methyl-2-(morpholin-4-yl)-1,3-thiazol-4-yl]methyl}phosphonate (1.56 g) in tetrahydrofuran (50 mL) was added sodium hydride (60% in oil, 0.22 g) at room temperature, and the mixture was stirred for 30 min. 3-(Methoxymethoxy)-1-phenyl-1H-pyrazole-4-carbaldehyde (1.14 g) was added to the reaction mixture, and the mixture was heated under reflux for 1.5 hrs. Water was poured into the reaction mixture, and the mixture was extracted with ethyl acetate. The ethyl acetate layer was washed with saturated brine, dried over anhydrous magnesium sulfate and concentrated. The residue was subjected to silica gel column chromatography and eluted with acetone-hexane (1:5, v/v) to give 4-(4-{(E)-2-[3-(methoxymethoxy)-1-phenyl-1H-pyrazol-4-yl]ethenyl}-5-methyl-1,3-thiazol-2-yl)morpholine as pale-yellow crystals (1.05 g, yield 54%). melting point: 162-164° C.

Reference Example 245

To a solution of 4-(4-{(E)-2-[3-(methoxymethoxy)-1-phenyl-1H-pyrazol-4-yl]ethenyl}-5-methyl-1,3-thiazol-2-yl)morpholine (1.0 g) in methanol (20 mL) was added concentrated hydrochloric acid (0.4 mL) at room temperature, and stirred at 50° C. for 1.5 hrs. The reaction mixture was evaporated under reduced pressure, and the residue was washed with ethyl acetate-methanol to give 4-{(E)-2-[5-methyl-2-(morpholin-4-yl)-1,3-thiazol-4-yl]ethenyl}-1-phenyl-1H-pyrazol-3-ol.hydrochloride (0.98 g, yield 100%) as gray crystals. melting point: 278-279° C.

Reference Example 246 di-tert-Butyl dicarbonate (1.28 mL) was added to a solution (20 mL) of 1-(4,5-dimethyl-1,3-thiazol-2-yl)piperazine (1.0 g) in tetrahydrofuran at room temperature and the mixture was stirred at room temperature for 1 hr. The reaction mixture was concentrated under reduced pressure to give tert-butyl 4-(4,5-dimethyl-1,3-thiazol-2-yl)piperazine-1-carboxylate as colorless crystals (1.1 g, yield 73%). NMR (CDCl$_3$) δ: 1.47 (9H, s), 2.13 (3H, s), 2.20 (3H, s), 3.34-3.37 (4H, m), 3.51-3.54 (4H, m).

Example 1

A mixture of 4-(4-chloromethyl-2-methoxyphenoxy)methyl-5-methyl-2-phenyl-1,3-oxazole (2.30 g), ethyl 1-benzyl-3-hydroxy-1H-pyrazole-4-carboxylate (1.50 g), potassium carbonate (0.84 g) and N,N-dimethylformamide (50 mL) was stirred at 80° C. for 15 hrs. Water was poured into the reaction mixture, and the mixture was extracted with ethyl acetate. The ethyl acetate layer was washed with saturated brine, dried over anhydrous magnesium sulfate and concentrated to give ethyl 1-benzyl-3-({3-methoxy-4-[(5-methyl-2-phenyl-1,3-oxazol-4-yl)methoxy]benzyl}oxy)-1H-pyrazole-4-carboxylate (3.10 g, yield 92%) as colorless crystals. Recrystallization from ethyl acetate-hexane gave colorless prism crystals. melting point: 154-155° C.

Example 2

To a mixture of ethyl 1-benzyl-3-({3-methoxy-4-[(5-methyl-2-phenyl-1,3-oxazol-4-yl)methoxy]benzyl}oxy)-1H-pyrazole-4-carboxylate (1.80 g), tetrahydrofuran (10 mL) and ethanol (10 mL) was added 1N aqueous sodium hydroxide solution (15 mL), and the mixture was heated under reflux for 4 hrs. 1N Hydrochloric acid (15 mL) and water were added to the reaction mixture, and the precipitated crystals were collected by filtration to give 1-benzyl-3-({3-methoxy-4-[(5-methyl-2-phenyl-1,3-oxazol-4-yl)methoxy]benzyl}oxy)-1H-pyrazole-4-carboxylic acid as crystals (1.70 g, yield 98%). Recrystallization from ethyl acetate-hexane gave colorless prism crystals. melting point: 162-163° C.

Example 3

A mixture of 1-benzyl-3-({3-methoxy-4-[(5-methyl-2-phenyl-1,3-oxazol-4-yl)methoxy]benzyl}oxy)-1H-pyrazole-4-carboxylic acid (1.30 g), 1-hydroxybenzotriazole ammonia complex (0.58 g), 1-ethyl-3-(3-dimethylaminopropyl)carbodiimide hydrochloride (0.73 g) and N,N-dimethylformamide (50 mL) was stirred at room temperature for 15 hrs. Water was poured into the reaction mixture, and the mixture was extracted with ethyl acetate. The organic layer was washed with saturated brine, dried over anhydrous magnesium sulfate and concentrated to give 1-benzyl-3-({3-methoxy-4-[(5-methyl-2-phenyl-1,3-oxazol-4-yl)methoxy]benzyl}oxy)-1H-pyrazole-4-carboxamide as colorless crystals (1.29 g, yield 98%). Recrystallization from acetone-methanol gave colorless prism crystals. melting point: 164-165° C.

Example 4

To a solution of ethyl 1-benzyl-3-({3-methoxy-4-[(5-methyl-2-phenyl-1,3-oxazol-4-yl)methoxy]benzyl}oxy)-1H-pyrazole-4-carboxylate (0.90 g) in tetrahydrofuran (30 mL) was added lithium aluminum hydride (0.06 g) at 0° C. and the mixture was stirred at room temperature for 3 hrs. Sodium sulfate decahydrate (0.51 g) was added to the reaction mixture, and the mixture was stirred at room temperature for 30 min. The reaction mixture was diluted with ethyl acetate, the precipitate was filtered off and the filtrate was concentrated. The obtained crystals were collected by filtration to give [1-benzyl-3-({3-methoxy-4-[(5-methyl-2-phenyl-1,3-oxazol-4-yl)methoxy]benzyl}oxy)-1H-pyrazol-4-yl]methanol (0.63 g, yield 77%). Recrystallization from ethyl acetate-hexane gave colorless prism crystals. melting point: 90-91° C.

Example 5

A mixture of [1-benzyl-3-({3-methoxy-4-[(5-methyl-2-phenyl-1,3-oxazol-4-yl)methoxy]benzyl}oxy)-1H-pyrazol-4-yl]methanol (0.30 g), activated manganese dioxide (1.00 g) and tetrahydrofuran (50 mL) was stirred at room temperature for 20 hrs. Manganese dioxide was removed by filtration, and the filtrate was concentrated. The obtained crystals were collected by filtration to give 1-benzyl-3-({3-methoxy-4-[(5-methyl-2-phenyl-1,3-oxazol-4-yl)methoxy]benzyl}oxy)-1H-pyrazole-4-carbaldehyde (0.24 g, yield 80%). Recrystallization from ethyl acetate-hexane gave colorless prism crystals. melting point: 151-152° C.

Example 6

A mixture of 4-(4-chloromethylphenoxy)methyl-5-methyl-2-(2-furyl)-1,3-oxazole (2.04 g), ethyl 1-benzyl-3-hydroxy-1H-pyrazole-4-carboxylate (1.50 g), potassium carbonate (0.84 g) and N,N-dimethylformamide (50 mL) was stirred at 80° C. for 15 hrs. Water was poured into the reaction mixture, and the mixture was extracted with ethyl acetate. The ethyl acetate layer was washed with saturated brine, dried over anhydrous magnesium sulfate and concentrated to give ethyl 1-benzyl-3-[(4-{[2-(2-furyl)-5-methyl-1,3-oxazol-4-yl]methoxy}benzyl)oxy]-1H-pyrazole-4-carboxylate (3.00 g, yield 96%) as colorless crystals. Recrystallization from ethyl acetate-hexane gave colorless prism crystals. melting point: 101-102° C.

Example 7

To a mixture of ethyl 1-benzyl-3-[(4{[2-(2-furyl)-5-methyl-1,3-oxazol-4-yl]methoxy}benzyl)oxy]-1H-pyrazole-4-carboxylate (2.0 g), tetrahydrofuran (10 mL) and ethanol (10 mL) was added 1N aqueous sodium hydroxide solution (16 mL), and the mixture was heated under reflux for 7 hrs. 1N Hydrochloric acid (16 mL) and water were added to the reaction mixture, and the mixture was extracted with ethyl acetate. The ethyl acetate layer was washed with saturated brine, dried over anhydrous magnesium sulfate and concentrated to give 1-benzyl-3-[(4{[2-(2-furyl)-5-methyl-1,3-oxazol-4-yl]methoxy}benzyl)oxy]-1H-pyrazole-4-carboxylic acid as crystals (1.70 g, yield 90%). Recrystallization from ethyl acetate-hexane gave colorless prism crystals. melting point: 170-171° C.

Example 8

A mixture of 1-benzyl-3-[(4{[2-(2-furyl)-5-methyl-1,3-oxazol-4-yl]methoxy}benzyl)oxy]-1H-pyrazole-4-carboxylic acid (1.10 g), 1-hydroxybenzotriazole ammonia complex (0.53 g), 1-ethyl-3-(3-dimethylaminopropyl)carbodiimide hydrochloride (0.67 g) and N,N-dimethylformamide (50 mL) was stirred at room temperature for 3 days. Water was poured into the reaction mixture, and the mixture was extracted with ethyl acetate. The organic layer was washed with saturated brine, dried over anhydrous magnesium sulfate and concentrated to give 1-benzyl-3-[(4{[2-(2-furyl)-5-methyl-1,3-oxazol-4-yl]methoxy}benzyl)oxy]-1H-pyrazole-4-carboxamide as pale-yellow crystals (1.10 g, yield 99%). Recrystallization from ethyl acetate-hexane gave pale-yellow prism crystals. melting point: 139-140° C.

Example 9

A mixture of 1-benzyl-3-[(4{[2-(2-furyl)-5-methyl-1,3-oxazol-4-yl]methoxy}benzyl)oxy]-1H-pyrazole-4-carboxamide (0.50 g) and acetic anhydride (20 mL) was heated under reflux for 4 hrs. The reaction mixture was concentrated and ethyl acetate was added to the residue. The ethyl acetate layer was washed successively with saturated aqueous sodium hydrogen carbonate and saturated brine and concentrated to give N-acetyl-1-benzyl-3-[(4{[2-(2-furyl)-5-methyl-1,3-oxazol-4-yl]methoxy}benzyl)oxy]-1H-pyrazole-4-carboxamide as colorless crystals (0.25 g, yield 48%). Recrystallization from ethyl acetate-hexane gave colorless prism crystals. melting point: 193-194° C.

Example 10

To a solution of ethyl 1-benzyl-3-[(4{[2-(2-furyl)-5-methyl-1,3-oxazol-4-yl]methoxy}benzyl)oxy]-1H-pyrazole-4-carboxylate (0.80 g) in tetrahydrofuran (10 mL) was added lithium aluminum hydride (0.06 g) at 0° C. and the mixture was stirred at room temperature for 1 hr. Sodium sulfate decahydrate (0.51 g) was added to the reaction mixture and the mixture was stirred at room temperature for 30 min. The reaction mixture was diluted with ethyl acetate and the precipitate was filtered off and the filtrate was concentrated. The residue was subjected to silica gel column chromatography and eluted with ethyl acetate-hexane (1:2, v/v) to give {1-benzyl-3-[(4{[2-(2-furyl)-5-methyl-1,3-oxazol-4-yl]methoxy}benzyl)oxy]-1H-pyrazol-4-yl}methanol as a colorless oil (0.49 g, yield 65%).

NMR (CDCl$_3$) δ: 2.42 (3H, s), 4.44 (2H, d, J=5.6 Hz), 4.99 (2H, s), 5.11 (2H, s), 5.19 (2H, s), 6.51-6.53 (1H, m), 6.96-7.00 (3H, m), 7.16-7.39 (8H, m), 7.54 (1H, s)

Example 11

A mixture of {1-benzyl-3-[(4{[2-(2-furyl)-5-methyl-1,3-oxazol-4-yl]methoxy}benzyl)oxy]-1H-pyrazol-4-yl}methanol (0.38 g), activated manganese dioxide (1.20 g) and tetrahydrofuran (50 mL) was stirred at room temperature for 20 hrs. Manganese dioxide was removed by filtration, and the filtrate was concentrated. The obtained crystals were collected by filtration to give 1-benzyl-3-[(4{[2-(2-furyl)-5-methyl-1,3-oxazol-4-yl]methoxy}benzyl)oxy]-1H-pyrazole-4-carbaldehyde (0.35 g, yield 92%). Recrystallization from ethyl acetate-hexane gave colorless prism crystals. melting point: 118-119° C.

Example 12

A mixture of 4-(4-chloromethyl-2-methoxyphenoxy)methyl-5-methyl-2-(2-furyl)-1,3-oxazole (1.94 g), ethyl 1-benzyl-3-hydroxy-1H-pyrazole-4-carboxylate (1.31 g), potassium carbonate (0.73 g) and N,N-dimethylformamide (50 mL) was stirred at 80° C. for 15 hrs. Water was poured into the reaction mixture, and the mixture was extracted with ethyl acetate. The ethyl acetate layer was washed with saturated brine, dried over anhydrous magnesium sulfate and concentrated. The residue was subjected to silica gel column chromatography and eluted with ethyl acetate-hexane (1:1, v/v) to give ethyl 1-benzyl-3-[(4-{[2-(2-furyl)-5-methyl-1,3-oxazol-4-yl]methoxy}-3-methoxybenzyl)oxy]-1H-pyrazole-4-carboxylate (2.48 g, yield 86%) as colorless crystals. Recrystallization from ethyl acetate-hexane gave colorless prism crystals. melting point: 117-118° C.

Example 13

To a mixture of ethyl 1-benzyl-3-[(4-{[2-(2-furyl)-5-methyl-1,3-oxazol-4-yl]methoxy}-3-methoxybenzyl)oxy]-1H-pyrazole-4-carboxylate (0.70 g), tetrahydrofuran (5 mL) and ethanol (5 mL) was added 1N aqueous sodium hydroxide solution (5 mL) and the mixture was heated under reflux for 2 hrs. 1N Hydrochloric acid (5 mL) and water were added to the reaction mixture and the precipitated crystals were collected by filtration to give 1-benzyl-3-[(4-{[2-(2-furyl)-5-methyl-1,3-oxazol-4-yl]methoxy}-3-methoxybenzyl)oxy]-1H-pyrazole-4-carboxylic acid as crystals (0.56 g, yield 84%). Recrystallization from ethyl acetate-hexane gave colorless prism crystals. melting point: 167-168° C.

Example 14

A mixture of 1-benzyl-3-[(4-{[2-(2-furyl)-5-methyl-1,3-oxazol-4-yl]methoxy}-3-methoxybenzyl)oxy]-1H-pyrazole-4-carboxylic acid (0.25 g), 1-hydroxybenzotriazole ammonia complex (0.11 g), 1-ethyl-3-(3-dimethylaminopropyl)carbodiimide hydrochloride (0.14 g) and N,N-dimethylformamide (10 mL) was stirred at room temperature for 3 days. Water was poured into the reaction mixture, and the mixture was extracted with ethyl acetate. The organic layer was washed with saturated brine, dried over anhydrous magnesium sulfate and concentrated to give 1-benzyl-3-[(4-{[2-(2-furyl)-5-methyl-1,3-oxazol-4-yl]methoxy}-3-methoxybenzyl)oxy]-1H-pyrazole-4-carboxamide as colorless crystals (0.23 g, yield 92%). Recrystallization from ethyl acetate-hexane gave colorless prism crystals. melting point: 160-161° C.

Example 15

To a solution of ethyl 1-benzyl-3-[(4-{[2-(2-furyl)-5-methyl-1,3-oxazol-4-yl]methoxy}-3-methoxybenzyl)oxy]-1H-pyrazole-4-carboxylate (1.46 g) in tetrahydrofuran (50 mL) was added lithium aluminum hydride (0.10 g) at 0° C. and the mixture was stirred at room temperature for 3 hrs. Sodium sulfate decahydrate (0.87 g) was added to the reaction mixture and the mixture was stirred at room temperature for 30 min. The reaction mixture was diluted with ethyl acetate and the precipitate was filtered off. The filtrate was concentrated to give (1-benzyl-3-[(4-{[2-(2-furyl)-5-methyl-1,3-oxazol-4-yl]methoxy)-3-methoxybenzyl)oxy]-1H-pyrazol-4-yl}methanol as colorless crystals (1.30 g, yield 96%). Recrystallization from ethyl acetate-hexane gave colorless prism crystals. melting point: 104-105° C.

Example 16

A mixture of {1-benzyl-3-[(4-{[2-(2-furyl)-5-methyl-1,3-oxazol-4-yl]methoxy}-3-methoxybenzyl)oxy]-1H-pyrazol-4-yl}methanol (0.95 g), activated manganese dioxide (3.0 g) and tetrahydrofuran (100 mL) was stirred at room temperature for 20 hrs. Manganese dioxide was removed by filtration, and the filtrate was concentrated. The obtained crystals were collected by filtration to give 1-benzyl-3-[(4-{[2-(2-furyl)-5-methyl-1,3-oxazol-4-yl]methoxy}-3-methoxybenzyl)oxy]-1H-pyrazole-4-carbaldehyde (0.85 g, yield 89%). Recrystallization from ethyl acetate-hexane gave colorless prism crystals. melting point: 139-140° C.

Example 17

A mixture of 1-benzyl-3-[(4-{[2-(2-furyl)-5-methyl-1,3-oxazol-4-yl]methoxy}-3-methoxybenzyl)oxy]-1H-pyrazole-4-carbaldehyde (0.30 g), hydroxylamine hydrochloride (0.065 g), pyridine (0.12 g) and ethanol (20 mL) was heated under reflux for 1.5 hrs. Water was added to the reaction mixture, and the mixture was extracted with ethyl acetate. The organic layer was washed with saturated brine, dried over anhydrous magnesium sulfate and concentrated. Acetic anhydride (20 mL) was added to the residue, and the mixture was heated under reflux for 1 hr. After concentration of the reaction mixture, water was added to the residue, and the mixture was extracted with ethyl acetate. The organic layer was washed successively with saturated aqueous hydrogen carbonate solution and saturated brine, dried over anhydrous magnesium sulfate and concentrated. The residue was subjected to silica gel column chromatography and eluted with ethyl acetate-hexane (1:2, v/v) to give 1-benzyl-3-[(4-{[2-(2-furyl)-5-methyl-1,3-oxazol-4-yl]methoxy}-3-methoxybenzyl)oxy])-1H-pyrazole-4-carbonitrile as colorless crystals (0.21 g, yield 70%). Recrystallization from ethyl acetate-hexane gave colorless prism crystals. melting point: 158-159° C.

Example 18

To a solution of 1-benzyl-3-[(4-{[2-(2-furyl)-5-methyl-1,3-oxazol-4-yl]methoxy}-3-methoxybenzyl)oxy]-1H-pyrazole-4-carbaldehyde (0.30 g) in tetrahydrofuran (10 mL) was added methylmagnesium bromide (0.9 M tetrahydrofuran solution, 1.3 mL) at 0° C., and the mixture was stirred at the same temperature for 1 hr. Water was added to the reaction mixture, and the mixture was extracted with ethyl acetate. The organic layer was washed with saturated brine, dried over anhydrous magnesium sulfate and concentrated to give 1-{1-benzyl-3-[(4-{[2-(2-furyl)-5-methyl-1,3-oxazol-4-yl]methoxy}-3-methoxybenzyl)oxy]-1H-pyrazol-4-yl}-1-ethanol as colorless crystals (0.27 g, yield 87%). Recrystallization from ethyl acetate-hexane gave colorless prism crystals. melting point: 105-106° C.

Example 19

A mixture of 1-{1-benzyl-3-[(4-{[2-(2-furyl)-5-methyl-1,3-oxazol-4-yl]methoxy}-3-methoxybenzyl)oxy]-1H-pyrazol-4-yl}-1-ethanol (0.15 g), activated manganese dioxide (0.50 g) and tetrahydrofuran (50 mL) was stirred at room temperature for 4 days. Manganese dioxide was removed by filtration, and the filtrate was concentrated. The obtained crystals were collected by filtration to give 1-{1-benzyl-3-[(4-{[2-(2-furyl)-5-methyl-1,3-oxazol-4-yl]methoxy}-3-methoxybenzyl)oxy]-1H-pyrazol-4-yl}-1-ethanone (0.13 g, yield 87%). Recrystallization from ethyl acetate-hexane gave colorless prism crystals. melting point: 144-145° C.

Example 20

A mixture of 4-(4-chloromethylphenoxy)methyl-5-methyl-2-phenyl-1,3-oxazole (2.10 g), ethyl 1-benzyl-3-hydroxy-1H-pyrazole-4-carboxylate (1.50 g), potassium carbonate (0.84 g) and N,N-dimethylformamide (50 mL) was stirred at 80° C. for 15 hrs. Water was poured into the reaction mixture, and the mixture was extracted with ethyl acetate. The ethyl acetate layer was washed with saturated brine, dried over anhydrous magnesium sulfate and concentrated. The residue was subjected to silica gel column chromatography and eluted with ethyl acetate-hexane (1:2, v/v) to give ethyl 1-benzyl-3-({4-[(5-methyl-2-phenyl-1,3-oxazol-4-yl)methoxy]benzyl}oxy)-1H-pyrazole-4-carboxylate as colorless crystals (3.04 g, yield 95%). Recrystallization from ethyl acetate-hexane gave colorless prism crystals. melting point: 99-100° C.

Example 21

To a solution of ethyl 1-benzyl-3-({4-[(5-methyl-2-phenyl-1,3-oxazol-4-yl)methoxy]benzyl}oxy)-1H-pyrazole-4-carboxylate (1.50 g) in tetrahydrofuran (50 mL) was added lithium aluminum hydride (0.22 g) at 0° C. and the mixture was stirred at room temperature for 1 hr. To the reaction mixture was added sodium sulfate decahydrate (1.86 g) and the mixture was stirred at room temperature for 30 min. The reaction mixture was diluted with ethyl acetate and the precipitate was filtered off, and the filtrate was concentrated. The residue was subjected to silica gel column chromatography and eluted with ethyl acetate-hexane (1:1, v/v) to give {1-benzyl-3-({4-[(5-methyl-2-phenyl-1,3-oxazol-4-yl)methoxy]benzyl}oxy)-1H-pyrazol-4-yl}methanol as a colorless oil (1.13 g, yield 81%).

NMR (CDCl$_3$) δ: 1.58 (1H, t, J=5.6 Hz), 2.44 (3H, s), 4.44 (2H, d, J=5.6 Hz), 5.00 (2H, s), 5.11 (2H, s), 5.19 (2H, S), 6.98-7.02 (2H, m), 7.16-7.45 (11H, m), 7.99-8.04 (2H, m).

Example 22

A mixture of [1-benzyl-3-({4-[(5-methyl-2-phenyl-1,3-oxazol-4-yl)methoxy]benzyl}oxy)-1H-pyrazol-4-yl]methanol (0.40 g), activated manganese dioxide (1.0 g) and tetrahydrofuran (50 mL) was stirred at room temperature for 15 hrs. Manganese dioxide was removed by filtration and the filtrate was concentrated. The obtained crystals were collected by filtration to give 1-benzyl-3-[{4-[(5-methyl-2-phenyl-1,3-oxazol-4-yl)methoxy]benzyl}oxy]-1H-pyrazole-4-carbaldehyde (0.35 g, yield 88%). Recrystallization from ethyl acetate-hexane gave colorless prism crystals. melting point: 133-134° C.

Example 23

A mixture of 4-(3-chloromethylphenoxy)methyl-5-methyl-2-phenyl-1,3-oxazole (2.10 g), ethyl 1-benzyl-3-hydroxy-1H-pyrazole-4-carboxylate (1.50 g), potassium carbonate (0.84 g) and N,N-dimethylformamide (50 mL) was stirred at 80° C. for 15 hrs. Water was poured into the reaction mixture, and the mixture was extracted with ethyl acetate. The ethyl acetate layer was washed with saturated brine, dried over anhydrous magnesium sulfate and concentrated. The residue was subjected to silica gel column chromatography and eluted with ethyl acetate-hexane (1:2, v/v) to give ethyl 1-benzyl-3-({3-[(5-methyl-2-phenyl-1,3-oxazol-4-yl)methoxy]benzyl}oxy)-1H-pyrazole-4-carboxylate as colorless crystals (2.78 g, yield 87%). Recrystallization from ethyl acetate-hexane gave colorless prism crystals. melting point: 95-96° C.

Example 24

To a solution of ethyl 1-benzyl-3-({3-[(5-methyl-2-phenyl-1,3-oxazol-4-yl)methoxy]benzyl}oxy)-1H-pyrazole-4-carboxylate (1.50 g) in tetrahydrofuran (50 mL) was added lithium aluminum hydride (0.22 g) at 0° C. and the mixture was stirred at room temperature for 1 hr. Sodium sulfate decahydrate (1.86 g) was added to the reaction mixture, and the mixture was stirred at room temperature for 30 min. The reaction mixture was diluted with ethyl acetate and the precipitate was filtered off, and the filtrate was concentrated. The residue was subjected to silica gel column chromatography and eluted with ethyl acetate-hexane (1:1, v/v) to give (1-benzyl-3-({3-[(5-methyl-2-phenyl-1,3-oxazol-4-yl)methoxy]benzyl}oxy)-1H-pyrazol-4-yl)methanol as a colorless oil (1.25 g, yield 89%).

NMR (CDCl$_3$) δ: 1.81 (1H, t, J=5.6 Hz), 2.43 (3H, s), 4.47 (2H, d, J=5.6 Hz), 5.01 (2H, s), 5.10 (2H, s), 5.26 (2H, s), 6.94-7.45 (13H, m), 7.98-8.04 (2H, m).

Example 25

A mixture of {1-benzyl-3-({3-[(5-methyl-2-phenyl-1,3-oxazol-4-yl)methoxy]benzyl}oxy)-1H-pyrazol-4-yl}methanol (0.70 g), activated manganese dioxide (2.0 g) and tetrahydrofuran (50 mL) was stirred at room temperature for 15 hrs. Manganese dioxide was removed by filtration, and the filtrate was concentrated. The obtained crystals were collected by filtration to give 1-benzyl-3-({3-[(5-methyl-2-phenyl-1,3-oxazol-4-yl)methoxy]benzyl}oxy)-1H-pyrazole-4-carbaldehyde (0.56 g, yield 78%). Recrystallization from ethyl acetate-hexane gave colorless prism crystals. melting point: 131-132° C.

Example 26

A mixture of 4-(3-chloromethylphenoxy)methyl-2-(2-furyl)-5-methyl-1,3-oxazole (2.04 g), ethyl 1-benzyl-3-hydroxy-1H-pyrazole-4-carboxylate (1.50 g), potassium carbonate (0.84 g) and N,N-dimethylformamide (50 mL) was stirred at 80° C. for 15 hrs. Water was poured into the reaction mixture, and the mixture was extracted with ethyl acetate. The ethyl acetate layer was washed with saturated brine, dried over anhydrous magnesium sulfate and concentrated. The residue was subjected to silica gel column chromatography and eluted with ethyl acetate-hexane (1:2, v/v) to give ethyl 1-benzyl-3-[(3-{[2-(2-furyl)-5-methyl-1,3-oxazol-4-yl]methoxy}benzyl)oxy]-1H-pyrazole-4-carboxylate as colorless crystals (2.46 g, yield 79%). Recrystallization from ethyl acetate-hexane gave colorless prism crystals. melting point: 92-93° C.

Example 27

To a solution of ethyl 1-benzyl-3-[(3-{[2-(2-furyl)-5-methyl-1,3-oxazol-4-yl]methoxy}benzyl)oxy]-1H-pyrazole-4-carboxylate (1.0 g) in tetrahydrofuran (10 mL) was added lithium aluminum hydride (0.07 g) at 0° C. and the mixture was stirred at room temperature for 1 hr. Sodium sulfate decahydrate (0.61 g) was added to the reaction mixture, and the mixture was stirred at room temperature for 30 min. The reaction mixture was diluted with ethyl acetate and the precipitate was filtered off, and the filtrate was concentrated. The residue was subjected to silica gel column chromatography and eluted with ethyl acetate-hexane (1:1, v/v) to give {1-benzyl-3-[(3-{[2-(2-furyl)-5-methyl-1,3-oxazol-4-yl]methoxy}benzyl)oxy]-1H-pyrazol-4-yl}methanol as a colorless oil (0.81 g, yield 90%).

NMR (CDCl$_3$) δ: 1.87 (1H, brs), 2.41 (3H, s), 4.47 (2H, d, J=4.2 Hz), 4.99 (2H, s), 5.10 (2H, s), 5.25 (2H, s), 6.52 (1H, dd, J=3.4, 2.0 Hz), 6.91-7.38 (11H, m), 7.53 (1H, t, J=1.0 Hz).

Example 28

A mixture of {1-benzyl-3-[(3-{[2-(2-furyl)-5-methyl-1,3-oxazol-4-yl]methoxy}benzyl)oxy]-1H-pyrazol-4-yl}methanol (0.51 g), activated manganese dioxide (1.50 g) and tetrahydrofuran (50 mL) was stirred at room temperature for 3 days. Manganese dioxide was removed by filtration and the filtrate was concentrated. The obtained crystals were collected by filtration to give 1-benzyl-3-[(3-{[2-(2-furyl)-5-methyl-1,3-oxazol-4-yl]methoxy}benzyl)oxy]-1H-pyrazole-4-carbaldehyde (0.50 g, yield 96%). Recrystallization from ethyl acetate-hexane gave colorless prism crystals. melting point: 135-136° C.

Example 29

A mixture of 4-(4-chloromethyl-2-ethoxyphenoxy)methyl-5-methyl-2-(2-furyl)-1,3-oxazole (2.33 g), ethyl 1-benzyl-3-hydroxy-1H-pyrazole-4-carboxylate (1.50 g), potassium carbonate (0.84 g) and N,N-dimethylformamide (50 mL) was stirred at 90° C. for 2 hrs. Water was poured into the reaction mixture, and the mixture was extracted with ethyl acetate. The ethyl acetate layer was washed with saturated brine, dried over anhydrous magnesium sulfate and concentrated to give ethyl 1-benzyl-3-[(3-ethoxy-4-{[2-(2-furyl)-5-methyl-1,3-oxazol-4-yl]methoxy}benzyl)oxy]-1H-pyrazole-4-carboxylate as colorless crystals (3.02 g, yield 89%). Recrystallization from ethyl acetate-hexane gave colorless prism crystals. melting point: 121-122° C.

Example 30

To a solution of ethyl 1-benzyl-3-[(3-ethoxy-4-{[2-(2-furyl)-5-methyl-1,3-oxazol-4-yl]methoxy}benzyl)oxy]-1H-pyrazole-4-carboxylate (1.50 g) in tetrahydrofuran (50 mL) was added lithium aluminum hydride (0.10 g) at 0° C. and the mixture was stirred at room temperature for 1 hr. Sodium sulfate decahydrate (0.87 g) was added to the reaction mixture, and the mixture was stirred at room temperature for 30 min. The reaction mixture was diluted with ethyl acetate and the precipitate was filtered off. The filtrate was concentrated to give {1-benzyl-3-[(3-ethoxy-4-{[2-(2-furyl)-5-methyl-1,3-oxazol-4-yl]methoxy}benzyl)oxy]-1H-pyrazol-4-yl}methanol as colorless crystals (1.30 g, yield 94%). Recrystallization from ethyl acetate-hexane gave colorless prism crystals. melting point: 137-138° C.

Example 31

A mixture of {1-benzyl-3-[(3-ethoxy-4-{[2-(2-furyl)-5-methyl-1,3-oxazol-4-yl]methoxy}benzyl)oxy]-1H-pyrazol-4-yl}methanol (0.70 g), activated manganese dioxide (2.0 g) and tetrahydrofuran (100 mL) was stirred at room temperature for 15 hrs. Manganese dioxide was removed by filtration and the filtrate was concentrated. The obtained crystals were collected by filtration to give 1-benzyl-3-[(3-ethoxy-4-{[2-(2-furyl)-5-methyl-1,3-oxazol-4-yl]methoxy}benzyl)oxy]-1H-pyrazole-4-carbaldehyde (0.65 g, yield 90%). Recrystallization from ethyl acetate-hexane gave colorless prism crystals. melting point: 144-145° C.

Example 32

A mixture of 4-(5-chloromethyl-2-methoxyphenoxy)methyl-2-(2-furyl)-5-methyl-1,3-oxazole (2.24 g), ethyl 1-benzyl-3-hydroxy-1H-pyrazole-4-carboxylate (1.50 g), potassium carbonate (0.84 g) and N,N-dimethylformamide (50 mL) was stirred at 90° C. for 15 hrs. Water was poured into the reaction mixture, and the mixture was extracted with ethyl acetate. The ethyl acetate layer was washed with saturated brine, dried over anhydrous magnesium sulfate and concentrated. The residue was subjected to silica gel column chromatography and eluted with ethyl acetate-hexane (1:1, v/v) to give ethyl 1-benzyl-3-[(3-{[2-(2-furyl)-5-methyl-1,3-oxazol-4-yl]methoxy}-4-methoxybenzyl)oxy]-1H-pyrazole-4-carboxylate (2.51 g, yield 76%) as colorless crystals. Recrystallization from ethyl acetate-hexane gave colorless prism crystals. melting point: 147-148° C.

Example 33

To a solution of ethyl 1-benzyl-3-[(3-{[2-(2-furyl)-5-methyl-1,3-oxazol-4-yl]methoxy}-4-methoxybenzyl)oxy]-1H-pyrazole-4-carboxylate (1.50 g) in tetrahydrofuran (50 mL) was added lithium aluminum hydride (0.11 g) at 0° C. and the mixture was stirred at room temperature for 1 hr. Sodium sulfate decahydrate (0.90 g) was added to the reaction mixture, and the mixture was stirred at room temperature for 30 min. The reaction mixture was diluted with ethyl acetate and the precipitate was filtered off, and the filtrate was concentrated. The residue was subjected to silica gel column chromatography and eluted with ethyl acetate-hexane (1:1, v/v) to give {1-benzyl-3-[(3-{[2-(2-furyl)-5-methyl-1,3-oxazol-4-yl]methoxy}-4-methoxybenzyl)oxy]-1H-pyrazol-4-yl}methanol as colorless crystals (1.20 g, yield 86%). Recrystallization from ethyl acetate-hexane gave colorless prism crystals. melting point: 108-109° C.

Example 34

A mixture of {1-benzyl-3-[(3-{[2-(2-furyl)-5-methyl-1,3-oxazol-4-yl]methoxy}-4-methoxybenzyl)oxy]-1H-pyrazol-4-yl}methanol (0.60 g), activated manganese dioxide (2.0 g) and tetrahydrofuran (50 mL) was stirred at room temperature for 15 hrs. Manganese dioxide was removed by filtration and the filtrate was concentrated. The obtained crystals were collected by filtration to give 1-benzyl-3-[(3-{[2-(2-furyl)-5-methyl-1,3-oxazol-4-yl]methoxy}-4-methoxybenzyl)oxy]-1H-pyrazole-4-carbaldehyde (0.54 g, yield 90%). Recrystallization from ethyl acetate-hexane gave colorless prism crystals. melting point: 142-143° C.

Example 35

A mixture of 4-(2-chloro-4-chloromethylphenoxy)methyl-2-(2-furyl)-5-methyl-1,3-oxazole (2.00 g), ethyl 1-benzyl-3-hydroxy-1H-pyrazole-4-carboxylate (1.45 g), potassium carbonate (0.82 g) and N,N-dimethylformamide (50 mL) was stirred at 90° C. for 2 hrs. Water was poured into the reaction mixture, and the mixture was extracted with ethyl acetate. The ethyl acetate layer was washed with saturated brine, dried over anhydrous magnesium sulfate and concentrated to give ethyl 1-benzyl-3-[(3-chloro-4-{[2-(2-furyl)-5-methyl-1,3-oxazol-4-yl]methoxy}benzyl)oxy]-1H-pyrazole-4-carboxylate as colorless crystals (3.09 g, yield 96%). Recrystallization from ethyl acetate-hexane gave colorless prism crystals. melting point: 153-154° C.

Example 36

To a solution of ethyl 1-benzyl-3-[(3-chloro-4-{[2-(2-furyl)-5-methyl-1,3-oxazol-4-yl]methoxy}benzyl)oxy]-1H-pyrazole-4-carboxylate (1.30 g) in tetrahydrofuran (30 mL) was added lithium aluminum hydride (0.14 g) at 0° C. and the mixture was stirred at room temperature for 1 hr. Sodium sulfate decahydrate (1.16 g) was added to the reaction mixture, and the mixture was stirred at room temperature for 30 min. The reaction mixture was diluted with ethyl acetate and the precipitate was filtered off. The filtrate was concentrated to give {1-benzyl-3-[(3-chloro-4-{[2-(2-furyl)-5-methyl-1,3-oxazol-4-yl]methoxy}benzyl)oxy]-1H-pyrazol-4-yl}methanol as colorless crystals (1.11 g, yield 92%). Recrystallization from ethyl acetate-hexane gave colorless prism crystals. melting point: 119-120° C.

Example 37

A mixture of {1-benzyl-3-[(3-chloro-4-{[2-(2-furyl)-5-methyl-1,3-oxazol-4-yl]methoxy}benzyl)oxy]-1H-pyrazol-4-yl}methanol (0.61 g), activated manganese dioxide (2.0 g) and tetrahydrofuran (50 mL) was stirred at room temperature for 15 hrs. Manganese dioxide was removed by filtration and the filtrate was concentrated. The obtained crystals were collected by filtration to give 1-benzyl-3-[(3-chloro-4-{[2-(2-furyl)-5-methyl-1,3-oxazol-4-yl]methoxy}benzyl)oxy]-1H-pyrazole-4-carbaldehyde (0.53 g, yield 88%). Recrystallization from ethyl acetate-hexane gave colorless prism crystals. melting point: 158-159° C.

Example 38

To a mixture of ethyl 1-benzyl-3-[(3-chloro-4-{[2-(2-furyl)-5-methyl-1,3-oxazol-4-yl]methoxy}benzyl)oxy]-1H-pyrazole-4-carboxylate (0.40 g), tetrahydrofuran (3 mL) and ethanol (3 mL) was added 1N aqueous sodium hydroxide solution (3 mL), and the mixture was heated under reflux for 1 hr. The reaction mixture was neutralized by adding 1N hydrochloric acid and water, and the precipitated crystals were collected by filtration to give 1-benzyl-3-[(3-chloro-4-{[2-(2-furyl)-5-methyl-1,3-oxazol-4-yl]methoxy}benzyl)oxy]-1H-pyrazole-4-carboxylic acid as crystals (0.37 g, yield 97%). Recrystallization from ethyl acetate-hexane gave colorless prism crystals. melting point: 191-192° C.

Example 39

To a mixture of (4-{[2-(2-furyl)-5-methyl-1,3-oxazol-4-yl]methoxy}-3-(methoxymethoxy)phenyl)methanol (8.50 g), tributylphosphine (9.95 g), ethyl 1-benzyl-3-hydroxy-1H-pyrazole-4-carboxylate (6.06 g) and tetrahydrofuran (300 mL) was added 1,1'-(azodicarbonyl)dipiperidine (12.41 g) at room temperature, and the mixture was stirred for 2 hrs. The precipitated crystals were removed by filtration and the filtrate was concentrated. The residue was subjected to silica gel column chromatography to give ethyl 1-benzyl-3-[(4-{[2-(2-furyl)-5-methyl-1,3-oxazol-4-yl]methoxy}-3-(methoxymethoxy)benzyl)oxy]-1H-pyrazole-4-carboxylate as colorless crystals (12.42 g, yield 88%) from a fraction eluted with ethyl acetate-hexane (1:2, v/v). Recrystallization from ethyl acetate-hexane gave colorless needle crystals. melting point: 120-121° C.

Example 40

A mixture of 5-chloromethyl-2-{[2-(2-furyl)-5-methyl-1,3-oxazol-4-yl]methoxy}pyridine (1.30 g), ethyl 1-benzyl-3-hydroxy-1H-pyrazole-4-carboxylate (1.06 g), potassium carbonate (0.59 g) and N,N-dimethylformamide (50 mL) was stirred at 90° C. for 2 hrs. Water was poured into the reaction mixture, and the precipitated crystals were collected by filtration to give ethyl 1-benzyl-3-[(6-{[2-(2-furyl)-5-methyl-1,3-oxazol-4-yl]methoxy}-3-pyridinyl)methoxy]-1H-pyrazole-4-carboxylate as colorless crystals (2.00 g, yield 90%). Recrystallization from ethyl acetate-hexane gave colorless prism crystals. melting point: 140-141° C.

Example 41

To a solution of ethyl 1-benzyl-3-[(6-{[2-(2-furyl)-5-methyl-1,3-oxazol-4-yl]methoxy}-3-pyridinyl)methoxy]-1H-pyrazole-4-carboxylate (1.00 g) in tetrahydrofuran (30 mL) was added lithium aluminum hydride (0.15 g) at 0° C. and the mixture was stirred at room temperature for 2 hrs. Sodium sulfate decahydrate (1.25 g) was added to the reaction mixture, and the mixture was stirred at room temperature for 30 min. The reaction mixture was diluted with ethyl acetate and the precipitate was filtered off. The filtrate was concentrated to give {1-benzyl-3-[(6-{[2-(2-furyl)-5-methyl-1,3-oxazol-4-yl]methoxy}-3-pyridinyl)methoxy]-1H-pyrazol-4-yl}methanol as colorless crystals (0.87 g, yield 95%). Recrystallization from ethyl acetate-hexane gave colorless prism crystals. melting point: 94-95° C.

Example 42

A mixture of {1-benzyl-3-[(6-{[2-(2-furyl)-5-methyl-1,3-oxazol-4-yl]methoxy}-3-pyridinyl)methoxy]-1H-pyrazol-4-yl}methanol (0.50 g), activated manganese dioxide (1.50 g) and tetrahydrofuran (50 mL) was stirred at room temperature for 15 hrs. Manganese dioxide was removed by filtration and the filtrate was concentrated. The obtained crystals were collected by filtration to give 1-benzyl-3-[(6-{[2-(2-furyl)-5-methyl-1,3-oxazol-4-yl]methoxy}-3-pyridinyl)methoxy]-1H-pyrazole-4-carbaldehyde as colorless crystals (0.42 g, yield 84%). Recrystallization from ethyl acetate-hexane gave colorless prism crystals. melting point: 104-105° C.

Example 43

To a mixture of ethyl 1-benzyl-3-[(6-{[2-(2-furyl)-5-methyl-1,3-oxazol-4-yl]methoxy}-3-pyridinyl)methoxy]-1H-pyrazole-4-carboxylate (0.35 g), tetrahydrofuran (3 mL) and ethanol (3 mL) was added 1N aqueous sodium hydroxide solution (3 mL), and the mixture was heated under reflux for 2 hrs. The reaction mixture was neutralized by adding 1N hydrochloric acid and water, and the mixture was extracted with ethyl acetate. The ethyl acetate layer was washed with saturated brine, dried over anhydrous magnesium sulfate and concentrated to give 1-benzyl-3-[(6-{[2-(2-furyl)-5-methyl-1,3-oxazol-4-yl]methoxy}-3-pyridinyl)methoxy]-1H-pyrazole-4-carboxylic acid as crystals (0.31 g, yield 94%). Recrystallization from ethyl acetate-hexane gave colorless prism crystals. melting point: 151-152° C.

Example 44

To a solution of ethyl 1-benzyl-3-[(4-{[2-(2-furyl)-5-methyl-1,3-oxazol-4-yl]methoxy}-3-(methoxymethoxy)benzyl)oxy]-1H-pyrazole-4-carboxylate (1.50 g) in tetrahydrofuran (30 mL) was added lithium aluminum hydride (0.15 g) at 0° C. and the mixture was stirred at room temperature for 1 hr. Sodium sulfate decahydrate (1.26 g) was added to the reaction mixture, and the mixture was stirred at room temperature for 30 min. The reaction mixture was diluted with ethyl acetate and the precipitate was filtered off. The filtrate was concentrated to give {1-benzyl-3-([4-{[2-(2-furyl)-5-methyl-1,3-oxazol-4-yl]methoxy}-3-(methoxymethoxy)benzyl]oxy)-1H-pyrazol-4-yl}methanol as colorless crystals (1.34 g, yield 97%). Recrystallization from ethyl acetate-hexane gave colorless prism crystals. melting point: 98-99° C.

Example 45

A mixture of {1-benzyl-3-([4-{[2-(2-furyl)-5-methyl-1,3-oxazol-4-yl]methoxy}-3-(methoxymethoxy)benzyl]oxy)-1H-pyrazol-4-yl}methanol (0.80 g), activated manganese dioxide (2.50 g) and tetrahydrofuran (50 mL) was stirred at room temperature for 15 hrs. Manganese dioxide was removed by filtration and the filtrate was concentrated. The obtained crystals were collected by filtration to give 1-benzyl-3-([4-{[2-(2-furyl)-5-methyl-1,3-oxazol-4-yl]methoxy}-3-(methoxymethoxy)benzyl]oxy)-1H-pyrazole-4-carbaldehyde (0.70 g, yield 89%). Recrystallization from ethyl acetate-hexane gave colorless prism crystals. melting point: 141-142° C.

Example 46

A mixture of ethyl 1-benzyl-3-[(4-{[2-(2-furyl)-5-methyl-1,3-oxazol-4-yl]methoxy}-3-(methoxymethoxy)benzyl)oxy]-1H-pyrazole-4-carboxylate (8.65 g), 1N hydrochloric acid (50 mL), tetrahydrofuran (100 mL) and ethanol (100 mL) was stirred at 50° C. for 5 hrs. The reaction mixture was diluted with ethyl acetate, and washed successively with water and saturated brine. The organic layer was dried over anhydrous magnesium sulfate and concentrated. The residue was subjected to silica gel column chromatography and eluted with ethyl acetate-hexane (2:3, v/v) to give ethyl 1-benzyl-3-[(4-{[2-(2-furyl)-5-methyl-1,3-oxazol-4-yl]methoxy}-3-hydroxybenzyl)oxy]-1H-pyrazole-4-carboxylate as colorless crystals (5.37 g, yield 67%). Recrystallization from ethyl acetate-hexane gave colorless prism crystals. melting point: 134-135° C.

Example 47

To a solution of ethyl 1-benzyl-3-[(4-{[2-(2-furyl)-5-methyl-1,3-oxazol-4-yl]methoxy}-3-hydroxybenzyl)oxy]-1H-pyrazole-4-carboxylate (0.60 g) in tetrahydrofuran (10 mL) was added lithium aluminum hydride (0.07 g) at 0° C. and the mixture was stirred at room temperature for 1 hr. Sodium sulfate decahydrate (0.55 g) was added to the reaction mixture, and the mixture was stirred at room temperature for 30 min. The reaction mixture was diluted with ethyl acetate and the precipitate was filtered off, and the filtrate was concentrated. The residue was subjected to silica gel column chromatography, and eluted with tetrahydrofuran-hexane (1:1, v/v) to obtain {1-benzyl-3-[(4-{[2-(2-furyl)-5-methyl-1,3-oxazol-4-yl]methoxy}-3-hydroxybenzyl)oxy]-1H-pyrazol-4-yl}methanol as a colorless oil (0.35 g, yield 65%).

NMR (CDCl$_3$) δ: 2.38 (3H, s), 4.45 (2H, d, J=4.4 Hz), 4.99 (2H, s), 5.11 (2H, s), 5.16 (2H, s), 6.54 (1H, dd, J=3.8, 2.0 Hz), 6.84-7.06 (5H, m), 7.15-7.35 (6H, m), 7.55-7.56 (1H, m).

Example 48

A mixture of ethyl 1-benzyl-3-[(4-{[2-(2-furyl)-5-methyl-1,3-oxazol-4-yl]methoxy}-3-hydroxybenzyl)oxy]-1H-pyrazole-4-carboxylate (2.00 g), benzyl bromide (0.97 g) potassium carbonate (0.53 g) and N,N-dimethylformamide (30 mL) was stirred at 90° C. for 15 hrs. Water was poured into the reaction mixture, and the mixture was extracted with ethyl acetate. The ethyl acetate layer was washed with saturated brine, dried over anhydrous magnesium sulfate and concentrated. The residue was subjected to silica gel column chromatography and eluted with ethyl acetate-hexane (1:1, v/v) to give ethyl 1-benzyl-3-[(3-benzyloxy-4-{[2-(2-furyl)-5-methyl-1,3-oxazol-4-yl]methoxy}benzyl)oxy]-1H-pyrazole-4-carboxylate as colorless crystals (1.51 g, yield 64%). Recrystallization from ethyl acetate-hexane gave colorless prism crystals. melting point: 127-128° C.

Example 49

To a solution of ethyl 1-benzyl-3-[(3-benzyloxy-4-{[2-(2-furyl)-5-methyl-1,3-oxazol-4-yl]methoxy}benzyl)oxy]-1H-pyrazole-4-carboxylate (0.70 g) in tetrahydrofuran (20 mL) was added lithium aluminum hydride (0.085 g) at 0° C. and the mixture was stirred at room temperature for 1 hr. Sodium sulfate decahydrate (0.71 g) was added to the reaction mixture, and the mixture was stirred at room temperature for 30 min. The reaction mixture was diluted with ethyl acetate and the precipitate was filtered off. The filtrate was concentrated to give {1-benzyl-3-[(3-benzyloxy-4-{[2-(2-furyl)-5-methyl-1,3-oxazol-4-yl]methoxy}benzyl)oxy]-1H-pyrazol-4-yl}methanol as colorless crystals (0.52 g, yield 81%). Recrystallization from ethyl acetate-hexane gave colorless prism crystals. melting point: 145-146° C.

Example 50

A mixture of {1-benzyl-3-[(3-benzyloxy-4-{[2-(2-furyl)-5-methyl-1,3-oxazol-4-yl]methoxy}benzyl)oxy]-1H-pyrazol-4-yl}methanol (0.35 g), activated manganese dioxide (1.00 g) and tetrahydrofuran (50 mL) was stirred at room temperature for 15 hrs. Manganese dioxide was removed by filtration and the filtrate was concentrated. The obtained crystals were collected by filtration to give 1-benzyl-3-[(3-benzyloxy-4-{[2-(2-furyl)-5-methyl-1,3-oxazol-4-yl]methoxy}benzyl)oxy]-1H-pyrazole-4-carbaldehyde as colorless crystals (0.30 g, yield 86%). Recrystallization from ethyl acetate-hexane gave colorless prism crystals. melting point: 130-131° C.

Example 51

To a mixture of ethyl 1-benzyl-3-[(3-benzyloxy-4-{[2-(2-furyl)-5-methyl-1,3-oxazol-4-yl]methoxy}benzyl)oxy]-1H-pyrazole-4-carboxylate (0.55 g), tetrahydrofuran (3 mL) and ethanol (3 mL) was added 1N aqueous sodium hydroxide solution (3 mL), and the mixture was heated under reflux for 1 hr. The reaction mixture was neutralized by adding 1N hydrochloric acid and water, and the precipitated crystals were collected by filtration to give 1-benzyl-3-[(3-benzyloxy-4-{[2-(2-furyl)-5-methyl-1,3-oxazol-4-yl]methoxy}benzyl)oxy]-1H-pyrazole-4-carboxylic acid as crystals (0.45 g, yield 85%). Recrystallization from tetrahydrofuran-hexane gave colorless prism crystals. melting point: 184-185° C.

Example 52

To a mixture of (4-{[2-(2-furyl)-5-methyl-1,3-oxazol-4-yl]methoxy}-2-methoxyphenyl)methanol (1.04 g), tributylphosphine (1.34 g), ethyl 1-benzyl-3-hydroxy-1H-pyrazole-4-carboxylate (0.81 g) and tetrahydrofuran (100 mL) was added 1,1'-(azodicarbonyl)dipiperidine (1.67 g) at room temperature, and the mixture was stirred for 15 hrs. The precipitated crystals were removed by filtration and the filtrate was concentrated. The residue was subjected to silica gel column chromatography to give ethyl 1-benzyl-3-[(4-{[2-(2-furyl)-5-methyl-1,3-oxazol-4-yl]methoxy}-2-methoxybenzyl)oxy]-1H-pyrazole-4-carboxylate as crystals (0.41 g, yield 23%) from a fraction eluted with tetrahydrofuran-hexane (1:2, v/v). Recrystallization from ethyl acetate-hexane gave colorless prism crystals. melting point: 137-138° C.

Example 53

To a solution of ethyl 1-benzyl-3-[(4-{[2-(2-furyl)-5-methyl-1,3-oxazol-4-yl]methoxy}-2-methoxybenzyl)oxy]-1H-pyrazole-4-carboxylate (0.23 g) in tetrahydrofuran (10 mL) was added lithium aluminum hydride (0.03 g) at 0° C. and the mixture was stirred at room temperature for 1 hr. Sodium sulfate decahydrate (0.26 g) was added to the reaction mixture, and the mixture was stirred at room temperature for 30 min. The reaction mixture was diluted with ethyl acetate and the precipitate was filtered off, and the filtrate was concentrated. The residue was subjected to silica gel column chromatography to give {1-benzyl-3-[(4-{[2-(2-furyl)-5-methyl-1,3-oxazol-4-yl]methoxy}-2-methoxybenzyl)oxy]-1H-pyrazol-4-yl}methanol as a colorless oil (0.52 g, yield 81%) from a fraction eluted with ethyl acetate-hexane (1:1, v/v).

NMR (CDCl$_3$) δ: 1.80 (1H, brs), 2.43 (3H, s), 3.80 (3H, s), 4.44 (2H, d, J=5.0 Hz), 4.99 (2H, s), 5.13 (2H, s), 5.22 (2H, s), 6.51-6.59 (3H, m), 6.97-7.00 (1H, m), 7.13 (1H, s), 7.19-7.35 (6H, m), 7.53-7.55 (1H, m).

Example 54

A mixture of {1-benzyl-3-[(4-{[2-(2-furyl)-5-methyl-1,3-oxazol-4-yl]methoxy}-2-methoxybenzyl)oxy]-1H-pyrazol-4-yl}methanol (0.17 g), activated manganese dioxide (0.50 g) and tetrahydrofuran (10 mL) was stirred at room temperature for 2 hrs. Manganese dioxide was removed by filtration and the filtrate was concentrated. The obtained crystals were collected by filtration to give 1-benzyl-3-[(4-{[2-(2-furyl)-5-methyl-1,3-oxazol-4-yl]methoxy}-2-methoxybenzyl)oxy]-1H-pyrazole-4-carbaldehyde (0.12 g, yield 71%). Recrystallization from ethyl acetate-hexane gave colorless needle crystals. melting point: 147-148° C.

Example 55

A mixture of 4-{[2-bromo-4-(chloromethyl)phenoxy]methyl}-2-(2-furyl)-5-methyl-1,3-oxazole (3.52 g), ethyl 1-benzyl-3-hydroxy-1H-pyrazole-4-carboxylate (2.27 g), potassium carbonate (1.27 g) and N,N-dimethylformamide (100 mL) was stirred at 90° C. for 2 hrs. Water was poured into the reaction mixture, and the precipitated crystals were collected by filtration to give ethyl 1-benzyl-3-[(3-bromo-4-{[2-(2-furyl)-5-methyl-1,3-oxazol-4-yl]methoxy}benzyl)oxy]-1H-pyrazole-4-carboxylate as colorless crystals (5.17 g, yield 95%). Recrystallization from ethyl acetate-hexane gave colorless prism crystals. melting point: 158-159° C.

Example 56

Ethyl 1-benzyl-3-[(3-bromo-4-{[2-(2-furyl)-5-methyl-1,3-oxazol-4-yl]methoxy}benzyl)oxy]-1H-pyrazole-4-carboxylate (1.20 g), phenylboronic acid (0.37 g), tetrakis(triphenylphosphine)palladium (0.12 g), 2M aqueous sodium carbonate solution (3 mL), ethanol (5 mL) and toluene (20 mL) were stirred under an argon atmosphere while heating under reflux for 24 hrs. Ethyl acetate was added to the reaction mixture. The ethyl acetate layer was washed successively with saturated aqueous sodium hydrogen carbonate and saturated brine, dried over anhydrous magnesium sulfate and concentrated. The residue was subjected to silica gel column chromatography to give ethyl 1-benzyl-3-[(4-{[2-(2-furyl)-5-methyl-1,3-oxazol-4-yl]methoxy}-3-phenylbenzyl)oxy]-1H-pyrazole-4-carboxylate as colorless crystals (0.91 g, 77%) from a fraction eluted with ethyl acetate-hexane (1:1, v/v). Recrystallization from ethyl acetate-hexane gave colorless prism crystals. melting point: 134-135° C.

Example 57

To a mixture of ethyl 1-benzyl-3-[(4-{[2-(2-furyl)-5-methyl-1,3-oxazol-4-yl]methoxy}-3-phenylbenzyl)oxy]-1H-pyrazole-4-carboxylate (0.25 g), tetrahydrofuran (2 mL) and ethanol (2 mL) was added 1N aqueous sodium hydroxide solution (2 mL), and the mixture was heated under reflux for 1 hr. The reaction mixture was neutralized by adding 1N hydrochloric acid and water, and the mixture was extracted with ethyl acetate. The ethyl acetate layer was washed with saturated brine, dried over anhydrous magnesium sulfate and concentrated to give 1-benzyl-3-[(4-{[2-(2-furyl)-5-methyl-1,3-oxazol-4-yl]methoxy}-3-phenylbenzyl)oxy]-1H-pyrazole-4-carboxylic acid as crystals (0.20 g, yield 83%). Recrystallization from ethyl acetate-hexane gave colorless prism crystals. melting point: 181-182° C.

Example 58

To a solution of ethyl 1-benzyl-3-[(4-{[2-(2-furyl)-5-methyl-1,3-oxazol-4-yl]methoxy}-3-phenylbenzyl)oxy]-1H-pyrazole-4-carboxylate (0.50 g) in tetrahydrofuran (10 mL) was added lithium aluminum hydride (0.06 g) at 0° C. and the mixture was stirred at room temperature for 1 hr. Sodium sulfate decahydrate (0.55 g) was added to the reaction mixture, and the mixture was stirred at room temperature for 30 min. The reaction mixture was diluted with ethyl acetate and the precipitate was filtered off. The filtrate was concentrated to give {1-benzyl-3-(4-{[2-(2-furyl)-5-methyl-1,3-oxazol-4-yl]methoxy}-3-phenylbenzyl)oxy}-1H-pyrazol-4-yl]methanol as colorless crystals (0.36 g, yield 77%). Recrystallization from ethyl acetate-hexane gave colorless prism crystals. melting point: 93-94° C.

Example 59

A mixture of {1-benzyl-3-[(4-{[2-(2-furyl)-5-methyl-1,3-oxazol-4-yl]methoxy}-3-phenylbenzyl)oxy]-1H-pyrazol-4-yl}methanol (0.20 g), activated manganese dioxide (0.60 g) and tetrahydrofuran (10 mL) was stirred at room temperature for 5 hrs. Manganese dioxide was removed by filtration and the filtrate was concentrated. The obtained crystals were collected by filtration to give 1-benzyl-3-[(4-{[2-(2-furyl)-5-methyl-1,3-oxazol-4-yl]methoxy}-3-phenylbenzyl)oxy]-1H-pyrazole-4-carbaldehyde (0.19 g, yield 95%). Recrystallization from ethyl acetate-hexane gave colorless needle crystals. melting point: 122-123° C.

Example 60

Ethyl 1-benzyl-3-[(3-bromo-4-{[2-(2-furyl)-5-methyl-1,3-oxazol-4-yl]methoxy}benzyl)oxy]-1H-pyrazole-4-carboxylate ethyl (1.50 g), tetramethyltin (2.19 g), tetrakis(triphenylphosphine)palladium (0.15 g) and toluene (50 mL) were stirred under an argon atmosphere while heating under reflux for 3 days. After concentration of the reaction mixture, The residue was subjected to silica gel column chromatography to give ethyl 1-benzyl-3-[(4-{[2-(2-furyl)-5-methyl-1,3-oxazol-4-yl]methoxy}-3-methylbenzyl)oxy]-1H-pyrazole-4-carboxylate as colorless crystals (0.73 g, 55%) from a fraction eluted with ethyl acetate-hexane (1:2, v/v). Recrystallization from ethyl acetate-hexane gave colorless prism crystals. melting point: 120-121° C.

Example 61

To a mixture of ethyl 1-benzyl-3-[(4-{[2-(2-furyl)-5-methyl-1,3-oxazol-4-yl]methoxy}-3-methylbenzyl)oxy]-1H-pyrazole-4-carboxylate (0.15 g), tetrahydrofuran (2 mL) and ethanol (2 mL) was added 1N aqueous sodium hydroxide solution (2 mL), and the mixture was heated under reflux for 1 hr. The reaction mixture was neutralized by adding 1N hydrochloric acid and water, and the mixture was extracted with ethyl acetate. The ethyl acetate layer was washed with saturated brine, dried over anhydrous magnesium sulfate and concentrated to give 1-benzyl-3-[(4-{[2-(2-furyl)-5-methyl-1,3-oxazol-4-yl]methoxy}-3-methylbenzyl)oxy]-1H-pyrazole-4-carboxylic acid as crystals (0.10 g, yield 71%). Recrystallization from ethyl acetate-hexane gave colorless prism crystals. melting point: 176-177° C.

Example 62

To a solution of ethyl 1-benzyl-3-[(4-{[2-(2-furyl)-5-methyl-1,3-oxazol-4-yl]methoxy}-3-methylbenzyl)oxy]-1H-pyrazole-4-carboxylate (0.49 g) in tetrahydrofuran (10 mL) was added lithium aluminum hydride (0.06 g) at 0° C. and the mixture was stirred at room temperature for 1 hr. Sodium sulfate decahydrate (0.45 g) was added to the reaction mixture, and the mixture was stirred at room temperature for 30 min. The reaction mixture was diluted with ethyl acetate and the precipitate was filtered off. The filtrate was concentrated to give {1-benzyl-3-[(4-{[2-(2-furyl)-5-methyl-1,3-oxazol-4-yl]methoxy}-3-methylbenzyl)oxy]-1H-pyrazol-4-yl}methanol as colorless crystals (0.41 g, yield 91%). Recrystallization from ethyl acetate-hexane gave colorless prism crystals. melting point: 91-92° C.

Example 63

A mixture of {1-benzyl-3-[(4-{[2-(2-furyl)-5-methyl-1,3-oxazol-4-yl]methoxy}-3-methylbenzyl)oxy]-1H-pyrazol-4-yl}methanol (0.27 g), activated manganese dioxide (0.90 g) and tetrahydrofuran (20 mL) was stirred at room temperature for 3 hrs. Manganese dioxide was removed by filtration and the filtrate was concentrated. The obtained crystals were collected by filtration to give 1-benzyl-3-[(4-{[2-(2-furyl)-5-methyl-1,3-oxazol-4-yl]methoxy}-3-methylbenzyl)oxy]-1H-pyrazole-4-carbaldehyde as colorless crystals (0.22 g, yield 81%). Recrystallization from ethyl acetate-hexane gave colorless needle crystals. melting point: 121-122° C.

Example 64

A mixture of 4-({[2-(chloromethyl)-3-phenyl-1-benzofuran-6-yl]oxy}methyl)-5-methyl-2-phenyl-1,3-oxazole (1.16 g), ethyl 3-hydroxy-1-phenyl-1H-pyrazole-4-carboxylate (0.58 g), potassium carbonate (0.35 g) and N,N-dimethylformamide (30 mL) was stirred at 90° C. for 3 hrs. Water was poured into the reaction mixture, and the precipitated crystals were collected by filtration, and subjected to silica gel column chromatography to give ethyl 3-({6-[(5-methyl-2-phenyl-1,3-oxazol-4-yl)methoxy]-3-phenyl-1-benzofuran-2-yl}methoxy)-1-phenyl-1H-pyrazole-4-carboxylate as colorless crystals (1.19 g, 76%) from a fraction eluted with ethyl acetate-hexane (1:3, v/v). Recrystallization from ethyl acetate-hexane gave colorless prism crystals. melting point: 143-144° C.

Example 65

To a mixture of ethyl 3-({6-[(5-methyl-2-phenyl-1,3-oxazol-4-yl)methoxy]-3-phenyl-1-benzofuran-2-yl}methoxy)-1-phenyl-1H-pyrazole-4-carboxylate (0.40 g), tetrahydrofuran (3 mL) and ethanol (3 mL) was added 1N aqueous sodium hydroxide solution (3 mL), and the mixture was heated under reflux for 1 hr. The reaction mixture was neutralized by adding 1N hydrochloric acid and water, and the mixture was extracted with ethyl acetate. The ethyl acetate layer was washed with saturated brine, dried over anhydrous magnesium sulfate and concentrated to give 3-({6-[(5-methyl-2-phenyl-1,3-oxazol-4-yl)methoxy]-3-phenyl-1-benzofuran-2-yl}methoxy)-1-phenyl-1H-pyrazole-4-carboxylic acid as colorless crystals (0.35 g, yield 92%). Recrystallization from tetrahydrofuran-hexane gave colorless prism crystals. melting point: 200-201° C.

Example 66

To a solution of ethyl 3-({6-[(5-methyl-2-phenyl-1,3-oxazol-4-yl)methoxy]-3-phenyl-1-benzofuran-2-yl}methoxy)-1-phenyl-1H-pyrazole-4-carboxylate (0.60 g) in tetrahydrofuran (10 mL) was added lithium aluminum hydride (0.055 g) at 0° C., and the mixture was stirred at 0° C. for 1 hr. Sodium sulfate decahydrate (0.46 g) was added to the reaction mixture, and the mixture was stirred at room temperature for 30 min. The reaction mixture was diluted with ethyl acetate and the precipitate was filtered off. The filtrate was concentrated to give [3-({6-[(5-methyl-2-phenyl-1,3-oxazol-4-yl)methoxy]-3-phenyl-1-benzofuran-2-yl}methoxy)-1-phenyl-1H-pyrazol-4-yl]methanol as colorless crystals (0.45 g, yield 80%). Recrystallization from ethyl acetate-hexane gave colorless prism crystals. melting point: 118-119° C.

Example 67

A mixture of [3-({6-[(5-methyl-2-phenyl-1,3-oxazol-4-yl)methoxy]-3-phenyl-1-benzofuran-2-yl}methoxy)-1-phenyl-1H-pyrazol-4-yl]methanol (0.22 g), activated manganese dioxide (0.75 g) and tetrahydrofuran (10 mL) was stirred at room temperature for 3 hrs. Manganese dioxide was removed by filtration and the filtrate was concentrated. The obtained crystals were collected by filtration to give 3-({6-[(5-methyl-2-phenyl-1,3-oxazol-4-yl)methoxy]-3-phenyl-1-benzofuran-2-yl}methoxy)-1-phenyl-1H-pyrazole-4-carbaldehyde as colorless crystals (0.19 g, yield 86%). Recrystallization from ethyl acetate-hexane gave colorless needle crystals. melting point: 176-177° C.

Example 68

Ethyl 1-benzyl-3-[(3-bromo-4-{[2-(2-furyl)-5-methyl-1,3-oxazol-4-yl]methoxy}benzyl)oxy]-1H-pyrazole-4-carboxylate (2.07 g), tetraethyltin (2.07 g), tetrakis(triphenylphosphine)palladium (0.40 g) and toluene (50 mL) was stirred under an argon atmosphere while heating under reflux for 3 days. After concentration of the reaction mixture, the residue was subjected to silica gel column chromatography to give ethyl 1-benzyl-3-[(3-ethyl-4-{[2-(2-furyl)-5-methyl-1,3-oxazol-4-yl]methoxy}benzyl)oxy]-1H-pyrazole-4-carboxylate as colorless crystals (0.96 g, 51%) from a fraction eluted with ethyl acetate-hexane (1:2, v/v). Recrystallization from ethyl acetate-hexane gave colorless prism crystals. melting point: 125-126° C.

Example 69

To a mixture of ethyl 1-benzyl-3-[(3-ethyl-4-{[2-(2-furyl)-5-methyl-1,3-oxazol-4-yl]methoxy}benzyl)oxy]-1H-pyrazole-4-carboxylate (0.25 g), tetrahydrofuran (3 mL) and ethanol (3 mL) was added 1N aqueous sodium hydroxide solution (3 mL), and the mixture was heated under reflux for 2 hrs. The reaction mixture was neutralized by adding 1N hydrochloric acid and water, and the mixture was extracted with ethyl acetate. The ethyl acetate layer was washed with saturated brine, dried over anhydrous magnesium sulfate and concentrated to give 1-benzyl-3-[(3-ethyl-4-{[2-(2-furyl)-5-methyl-1,3-oxazol-4-yl]methoxy}benzyl)oxy]-1H-pyrazole-4-carboxylic acid as crystals (0.17 g, yield 71%). Recrystallization from ethyl acetate-hexane gave colorless prism crystals. melting point: 173-174° C.

Example 70

To a solution of ethyl 1-benzyl-3-[(3-ethyl-4-{[2-(2-furyl)-5-methyl-1,3-oxazol-4-yl]methoxy}benzyl)oxy]-1H-pyrazole-4-carboxylate (0.50 g) in tetrahydrofuran (10 mL) was added lithium aluminum hydride (0.050 g) at 0° C. and the mixture was stirred at room temperature for 1 hr. Sodium sulfate decahydrate (0.45 g) was added to the reaction mixture, and the mixture was stirred at room temperature for 30 min. The reaction mixture was diluted with ethyl acetate and the precipitate was filtered off. The filtrate was concentrated to give {1-benzyl-3-[(3-ethyl-4-{[2-(2-furyl)-5-methyl-1,3-oxazol-4-yl]methoxy}benzyl)oxy]-1H-pyrazol-4-yl}methanol as colorless crystals (0.35 g, yield 78%). Recrystallization from ethyl acetate-hexane gave colorless prism crystals. melting point: 116-117° C.

Example 71

A mixture of {1-benzyl-3-[(3-ethyl-4-{[2-(2-furyl)-5-methyl-1,3-oxazol-4-yl]methoxy}benzyl)oxy]-1H-pyrazol-4-yl}methanol (0.23 g), activated manganese dioxide (0.70 g) and tetrahydrofuran (10 mL) was stirred at room temperature for 3 hrs. Manganese dioxide was removed by filtration and the filtrate was concentrated. The obtained crystals were collected by filtration to give 1-benzyl-3-[(3-ethyl-4-{[2-(2-furyl)-5-methyl-1,3-oxazol-4-yl]methoxy}benzyl)oxy]-1H-pyrazole-4-carbaldehyde as colorless crystals (0.20 g, yield 87%). Recrystallization from ethyl acetate-hexane gave colorless prism crystals. melting point: 128-129° C.

Example 72

A mixture of 4-[(4-chloromethyl-2-methoxyphenoxy)methyl]-2-(2-furyl)-5-methyl-1,3-oxazole (3.07 g), ethyl 3-hydroxy-1-phenyl-1H-pyrazole-4-carboxylate (2.04 g), potassium carbonate (1.22 g) and N,N-dimethylformamide (50 mL) was stirred at 90° C. for 3 hrs. Water was poured into the reaction mixture, and the mixture was extracted with ethyl acetate. The ethyl acetate layer was washed with saturated brine, dried over anhydrous magnesium sulfate and concentrated. The residue was subjected to silica gel column chromatography to give ethyl 3-[(4-{[2-(2-furyl)-5-methyl-1,3-oxazol-4-yl]methoxy}-3-methoxybenzyl)oxy]-1-phenyl-1H-pyrazole-4-carboxylate as colorless crystals (3.20 g, 69%) from a fraction eluted with ethyl acetate-hexane (1:1, v/v). Recrystallization from ethyl acetate-hexane gave colorless prism crystals. melting point: 150-151° C.

Example 73

To a mixture of ethyl 3-[(4-{[2-(2-furyl)-5-methyl-1,3-oxazol-4-yl]methoxy}-3-methoxybenzyl)oxy])-1-phenyl-1H-pyrazole-4-carboxylate (0.40 g), tetrahydrofuran (5 mL) and ethanol (5 mL) was added 1N aqueous sodium hydroxide solution (5 mL), and the mixture was heated under reflux for 2 hrs. The reaction mixture was neutralized by adding 1N hydrochloric acid and water, and the precipitated crystals were collected by filtration to give 3-[(4-{[2-(2-furyl)-5-methyl-1,3-oxazol-4-yl]methoxy}-3-methoxybenzyl)oxy]-1-phenyl-1H-pyrazole-4-carboxylic acid as colorless crystals (0.37 g, yield 97%). Recrystallization from ethyl acetate-hexane gave colorless prism crystals. melting point: 184-185° C.

Example 74

A mixture of 3-[(4-{[2-(2-furyl)-5-methyl-1,3-oxazol-4-yl]methoxy}-3-methoxybenzyl)oxy]-1-phenyl-1H-pyrazole-4-carboxylic acid (0.17 g), 1-hydroxybenzotriazole ammonia complex (0.08 g), 1-ethyl-3-(3-dimethylaminopropyl)carbodiimide hydrochloride (0.10 g) and N,N-dimethylformamide (10 mL) was stirred at room temperature for 3 days. Water was poured into the reaction mixture, and the precipitated crystals were collected by filtration to give 3-[(4-{[2-(2-furyl)-5-methyl-1,3-oxazol-4-yl]methoxy}-3-methoxybenzyl)oxy]-1-phenyl-1H-pyrazole-4-carboxamide as colorless crystals (0.15 g, yield 88%). Recrystallization from ethyl acetate-hexane gave colorless prism crystals. melting point: 175-176° C.

Example 75

To a solution of ethyl 3-[(4-{[2-(2-furyl)-5-methyl-1,3-oxazol-4-yl]methoxy}-3-methoxybenzyl)oxy]-1-phenyl-1H-pyrazole-4-carboxylate (2.44 g) in tetrahydrofuran (50 mL) was added lithium aluminum hydride (0.17 g) at 0° C. and the mixture was stirred at room temperature for 1 hr. Sodium sulfate decahydrate (1.48 g) was added to the reaction mixture, and the mixture was stirred at room temperature for 30 min. The reaction mixture was diluted with ethyl acetate and the precipitate was filtered off. The filtrate was concentrated to give {3-[(4-{[2-(2-furyl)-5-methyl-1,3-oxazol-4-yl]methoxy}-3-methoxybenzyl)oxy]-1-phenyl-1H-pyrazol-4-yl}methanol as colorless crystals (2.20 g, yield 98%). Recrystallization from ethyl acetate-hexane gave colorless prism crystals. melting point: 127-128° C.

Example 76

A mixture of {3-[(4-{[2-(2-furyl)-5-methyl-1,3-oxazol-4-yl]methoxy}-3-methoxybenzyl)oxy]-1-phenyl-1H-pyrazol-4-yl}methanol (2.05 g), activated manganese dioxide (6.0 g) and tetrahydrofuran (100 mL) was stirred at room temperature for 15 hrs. Manganese dioxide was removed by filtration and the filtrate was concentrated. The obtained crystals were collected by filtration to give 3-[(4-{[2-(2-furyl)-5-methyl-1,3-oxazol-4-yl]methoxy}-3-methoxybenzyl)oxy]-1-phenyl-1H-pyrazole-4-carbaldehyde as colorless crystals (1.65 g, yield 81%). Recrystallization from ethyl acetate-hexane gave colorless prism crystals. melting point: 137-138° C.

Example 77

A mixture of 3-[(4-{[2-(2-furyl)-5-methyl-1,3-oxazol-4-yl]methoxy}-3-methoxybenzyl)oxy]-1-phenyl-1H-pyrazole-4-carbaldehyde (0.57 g), hydroxylamine hydrochloride (0.13 g), pyridine (0.24 g) and ethanol (20 mL) was heated under reflux for 2 hrs. Water was poured into the reaction mixture, and the mixture was extracted with ethyl acetate. The ethyl acetate layer was washed with saturated brine, dried over anhydrous magnesium sulfate and concentrated. Acetic anhydride (20 mL) was added to residue, and the mixture was heated under reflux for 2 hrs. The reaction mixture was concentrated and ethyl acetate was added to the residue. The ethyl acetate layer was washed successively with water and saturated brine, dried over anhydrous magnesium sulfate and concentrated. The residue was subjected to silica gel column chromatography to give 3-[(4-{[2-(2-furyl)-5-methyl-1,3-oxazol-4-yl]methoxy}-3-methoxybenzyl)oxy]-1-phenyl-1H-pyrazole-4-carbonitrile as colorless crystals (0.36 g, 62%) from a fraction eluted with ethyl acetate-hexane (1:1, v/v). Recrystallization from ethyl acetate-hexane gave colorless needle crystals. melting point: 167-168° C.

Example 78

To a mixture of 3-[(4-{[2-(2-furyl)-5-methyl-1,3-oxazol-4-yl]methoxy}-3-methoxybenzyl)oxy]-1-phenyl-1H-pyrazole-4-carbaldehyde (0.80 g), ethyl diethylphosphonoacetate (0.40 g) and N,N-dimethylformamide (20 mL) was added sodium hydride (60% in oil, 0.080 g) under ice-cooling. The mixture was stirred at room temperature for 3 hrs. The reaction mixture was poured into ice water and the precipitated solid was collected by filtration to give ethyl (2E)-3-{3-[(4-{[2-(2-furyl)-5-methyl-1,3-oxazol-4-yl]methoxy}-3-methoxybenzyl)oxy]-1-phenyl-1H-pyrazol-4-yl}-2-propenoate as pale-brown crystals (0.85 g, yield 96%). Recrystallization from ethyl acetate-hexane gave pale-yellow prism crystals. melting point: 177-178° C.

Example 79

To a mixture of ethyl (2E)-3-{3-[(4-{[2-(2-furyl)-5-methyl-1,3-oxazol-4-yl]methoxy}-3-methoxybenzyl)oxy]-1-phenyl-1H-pyrazol-4-yl}-2-propenoate (0.66 g), tetrahydrofuran (5 mL) and ethanol (5 mL) was added 1N aqueous sodium hydroxide solution (5 mL), and the mixture was heated under reflux for 2 hrs. The reaction mixture was neutralized by adding 1N hydrochloric acid and water, and the precipitated crystals were collected by filtration to give (2E)-3-{3-[(4-{[2-(2-furyl)-5-methyl-1,3-oxazol-4-yl]methoxy}-3-methoxybenzyl)oxy]-1-phenyl-1H-pyrazol-4-yl}-2-propenoic acid as pale-yellow crystals (0.56 g, yield 89%). Recrystallization from tetrahydrofuran-hexane gave pale-yellow prism crystals. melting point: 204-205° C.

Example 80

A mixture of 4-[(4-chloromethylphenoxy)methyl]-2-phenyl-5-methyl-1,3-oxazole (2.85 g), 3-hydroxy-1-phenyl-1H-pyrazole-4-carbaldehyde (1.64 g), potassium carbonate (1.20 g) and N,N-dimethylformamide (100 mL) was stirred at 90° C. for 2 hrs. Water was poured into the reaction mixture, and the mixture was extracted with ethyl acetate. The ethyl acetate layer was washed with saturated brine, dried over anhydrous magnesium sulfate and concentrated. The residue was subjected to silica gel column chromatography to give 3-({4-[(2-phenyl-5-methyl-1,3-oxazol-4-yl)methoxy]benzyl}oxy)-1-phenyl-1H-pyrazole-4-carbaldehyde as colorless crystals (3.49 g, 86%) from a fraction eluted with ethyl acetate-hexane (1:1, v/v). Recrystallization from ethyl acetate-hexane gave colorless prism crystals. melting point: 152-153° C.

Example 81

To a solution of 3-({4-[(2-phenyl-5-methyl-1,3-oxazol-4-yl)methoxy]benzyl}oxy)-1-phenyl-1H-pyrazole-4-carbaldehyde (0.50 g) in tetrahydrofuran (5 mL)-ethanol (10 mL) was gradually added sodium borohydride (0.040 g) at 0° C. After stirring the reaction mixture at room temperature for 1 hr, water was added, and the precipitated crystals were collected by filtration to give [3-({4-[(2-phenyl-5-methyl-1,3-oxazol-4-yl)methoxy]benzyl}oxy)-1-phenyl-1H-pyrazol-4-yl]methanol as colorless crystals (0.50 g, yield 98%). Recrystallization from ethyl acetate-hexane gave colorless prism crystals. melting point: 118-119° C.

Example 82

To a mixture of 3-[{4-[(2-phenyl-5-methyl-1,3-oxazol-4-yl)methoxy]benzyl}oxy]-1-phenyl-1H-pyrazole-4-carbaldehyde (0.50 g), ethyl diethylphosphonoacetate (0.27 g) and N,N-dimethylformamide (20 mL) was added sodium hydride (60% in oil, 0.050 g) under ice-cooling. The mixture was stirred at room temperature for 15 hrs. Water was poured into the reaction mixture, and the mixture was extracted with ethyl acetate. The ethyl acetate layer was washed with saturated brine, dried over anhydrous magnesium sulfate and concentrated to give ethyl (2E)-3-[3-({4-[(2-phenyl-5-methyl-1,3-oxazol-4-yl)methoxy]benzyl}oxy)-1-phenyl-1H-pyrazol-4-yl]-2-propenoate as colorless crystals (0.51 g, yield 86%). Recrystallization from ethyl acetate-hexane gave colorless prism crystals. melting point: 154-155° C.

Example 83

To a mixture of ethyl (2E)-3-[3-({4-[(2-phenyl-5-methyl-1,3-oxazol-4-yl)methoxy]benzyl}oxy)-1-phenyl-1H-pyrazol-4-yl]-2-propenoate (0.39 g), tetrahydrofuran (3 mL) and ethanol (3 mL) was added 1N aqueous sodium hydroxide solution (3 mL), and the mixture was heated under reflux for 2 hrs. The reaction mixture was neutralized by adding 1N hydrochloric acid and water, and the mixture was extracted with ethyl acetate. The ethyl acetate layer was washed with saturated brine, dried over anhydrous magnesium sulfate and concentrated to give (2E)-3-[3-({4-[(2-phenyl-5-methyl-1,3-oxazol-4-yl)methoxy]benzyl}oxy)-1-phenyl-1H-pyrazol-4-yl]-2-propenoic acid as colorless crystals (0.32 g, yield 86%). Recrystallization from ethyl acetate-hexane gave colorless prism crystals. melting point: 186-187° C.

Example 84

A mixture of 3-[{4-[(2-phenyl-5-methyl-1,3-oxazol-4-yl)methoxy]benzyl}oxy]-1-phenyl-1H-pyrazole-4-carbaldehyde (0.70 g), hydroxylamine hydrochloride (0.16 g), pyridine (0.30 g) and ethanol (30 mL) was heated under reflux for 2 hrs. Water was poured into the reaction mixture, and the mixture was extracted with ethyl acetate. The ethyl acetate layer was washed with saturated brine, dried over anhydrous magnesium sulfate and concentrated. Acetic anhydride (20 mL) was added to residue, and the mixture was heated under reflux for 2 hrs. The reaction mixture was concentrated and ethyl acetate was added to the residue. The ethyl acetate layer was washed successively with water and saturated brine, dried over anhydrous magnesium sulfate and concentrated. The residue was subjected to silica gel column chromatography to give 3-({4-[(2-phenyl-5-methyl-1,3-oxazol-4-yl)methoxy]benzyl}oxy)}-1-phenyl-1H-pyrazole-4-carbonitrile as colorless crystals (0.35 g, 51%) from a fraction eluted with ethyl acetate-hexane (1:1, v/v). Recrystallization from ethyl acetate-hexane gave colorless prism crystals. melting point: 162-163° C.

Example 85

A mixture of 4-[(4-chloromethylphenoxy)methyl]-2-(2-furyl)-5-methyloxazole (3.01 g), 3-hydroxy-1-phenyl-1H-pyrazole-4-carbaldehyde (1.70 g), potassium carbonate (1.24 g) and N,N-dimethylformamide (100 mL) was stirred at 90° C. for 2 hrs. Water was poured into the reaction mixture, and the mixture was extracted with ethyl acetate. The ethyl acetate layer was washed with saturated brine, dried over anhydrous magnesium sulfate and concentrated. The residue was subjected to silica gel column chromatography to give 3-[(4-{[2-(2-furyl)-5-methyl-1,3-oxazol-4-yl]methoxy}benzyl)oxy]-1-phenyl-1H-pyrazole-4-carbaldehyde as colorless crystals (2.66 g, 65%) from a fraction eluted with ethyl acetate-hexane (1:2, v/v). Recrystallization from ethyl acetate-hexane gave colorless prism crystals. melting point: 148-149° C.

Example 86

To a solution of 3-[(4-{[2-(2-furyl)-5-methyl-1,3-oxazol-4-yl]methoxy}benzyl)oxy]-1-phenyl-1H-pyrazole-4-carbaldehyde (0.50 g) in tetrahydrofuran (10 mL)-ethanol (5 mL) was gradually added sodium borohydride (0.040 g) at 0° C. After stirring at room temperature for 1 hr, water was added to the reaction mixture and the precipitated crystals were collected by filtration to give {3-[(4-{[2-(2-furyl)-5-methyl-1,3-oxazol-4-yl]methoxy}benzyl)oxy]-1-phenyl-1H-pyrazol-4-yl}methanol as colorless crystals (0.47 g, yield 94%). Recrystallization from ethyl acetate-hexane gave colorless prism crystals. melting point: 113-114° C.

Example 87

To a mixture of 3-[(4-{[2-(2-furyl)-5-methyl-1,3-oxazol-4-yl]methoxy}benzyl)oxy]-1-phenyl-1H-pyrazole-4-carbaldehyde (0.50 g), ethyl diethylphosphonoacetate (0.25 g) and N,N-dimethylformamide (20 mL) was added sodium hydride (60% in oil, 0.050 g) under ice-cooling. The mixture was stirred at room temperature for 15 hrs. Water was added to the reaction mixture and the precipitated crystals were collected by filtration to give ethyl (2E)-3-(3-[(4-{[2-(2-furyl)-5-methyl-1,3-oxazol-4-yl]methoxy}benzyl)oxy]-1-phenyl-1H-pyrazol-4-yl]-2-propenoate as colorless crystals (0.48 g, yield 83%). Recrystallization from ethyl acetate-hexane gave colorless prism crystals. melting point: 142-143° C.

Example 88

To a mixture of ethyl (2E)-3-{3-[(4-{[2-(2-furyl)-5-methyl-1,3-oxazol-4-yl]methoxy}benzyl)oxy]-1-phenyl-1H-pyrazol-4-yl}-2-propenoate (0.38 g), tetrahydrofuran (3 mL) and ethanol (3 mL) was added 1N aqueous sodium hydroxide solution (3 mL), and the mixture was heated under reflux for 2 hrs. The reaction mixture was neutralized by adding 1N hydrochloric acid and water, and the mixture was extracted with ethyl acetate. The ethyl acetate layer was washed with saturated brine, dried over anhydrous magnesium sulfate and concentrated to give (2E)-3-{3-[(4-{[2-(2-furyl)-5-methyl-1,3-oxazol-4-yl]methoxy}benzyl)oxy]-1-phenyl-1H-pyrazol-4-yl}-2-propenoic acid as colorless crystals (0.33 g, yield 92%). Recrystallization from ethyl acetate-hexane gave colorless prism crystals. melting point: 144-145° C.

Example 89

A mixture of 3-[(4-{[2-(2-furyl)-5-methyl-1,3-oxazol-4-yl]methoxy}benzyl)oxy]-1-phenyl-1H-pyrazole-4-carbaldehyde (0.60 g), hydroxylamine hydrochloride (0.14 g), pyridine (0.26 g) and ethanol (20 mL) was heated under reflux for 2 hrs. Water was poured into the reaction mixture, and the mixture was extracted with ethyl acetate. The ethyl acetate layer was washed with saturated brine, dried over anhydrous magnesium sulfate and concentrated. Acetic anhydride (20 mL) was added to residue, and the mixture was heated under reflux for 2 hrs. The reaction mixture was concentrated and ethyl acetate was added to the residue. The ethyl acetate layer was washed successively with water and saturated brine, dried over anhydrous magnesium sulfate and concentrated. The residue was subjected to silica gel column chromatography to give 3-[(4-{[2-(2-furyl)-5-methyl-1,3-oxazol-4-yl]methoxy}benzyl)oxy]-1-phenyl-1H-pyrazole-4-carbonitrile as colorless crystals (0.40 g, 68%) from a fraction eluted with ethyl acetate-hexane (1:1, v/v). Recrystallization from ethyl acetate-hexane gave colorless prism crystals. melting point: 158-159° C.

Example 90

To a mixture of [5-(tert-butyldiphenylsilyloxymethyl)-2-phenyl-1,3-oxazol-4-yl]methanol (1.11 g), tributylphosphine (1.01 g), 4-[(5-methyl-2-phenyl-1,3-oxazol-4-yl)methoxy]phenol (0.70 g) and tetrahydrofuran (80 mL) was added 1,1'-(azodicarbonyl)dipiperidine (1.26 g) at room temperature, and the mixture was stirred for 15 hrs. The precipitated crystals were removed by filtration and the filtrate was concentrated. The residue was subjected to silica gel column chromatography to give 5-(tert-butyldiphenylsilyloxymethyl)-4-[[4-[(5-methyl-2-phenyl-1,3-oxazol-4-yl)methoxy]phenoxy]methyl]-2-phenyl-1,3-oxazole as an oil (1.44 g, yield 81%) from a fraction eluted with ethyl acetate-hexane (1:4, v/v).

NMR (CDCl$_3$) δ: 1.05 (9H, s), 2.41 (3H, s), 4.73 (2H, s), 4.82 (2H, s), 4.94 (2H, s), 6.79-6.95 (4H, m), 7.31-7.49 (12H, m), 7.67-7.73 (4H, m), 7.99-8.05 (4H, m).

Example 91

To a mixture of 5-(tert-butyldiphenylsilyloxymethyl)-4-[[4-[(5-methyl-2-phenyl-1,3-oxazol-4-yl)methoxy]phenoxy]methyl]-2-phenyl-1,3-oxazole (1.44 g) and tetrahydrofuran (30 mL) was added tetrabutylammonium fluoride (1M tetrahydrofuran solution, 5 mL) at 0° C., and the mixture was stirred at room temperature for 30 min. Water was added to the reaction mixture and extracted with ethyl acetate. The ethyl acetate layer was washed with saturated brine, dried over anhydrous magnesium sulfate and concentrated. The residue was subjected to silica gel column chromatography to give [4-({4-[(5-methyl-2-phenyl-1,3-oxazol-4-yl)methoxy]phenoxy}methyl)-2-phenyl-1,3-oxazol-5-yl]methanol as colorless crystals (0.55 g, yield 59%) from a fraction eluted with ethyl acetate-hexane (2:1, v/v). Recrystallization from ethyl acetate-hexane gave colorless prism crystals. melting point: 157-158° C.

Example 92

To a mixture of 4-[(methoxymethoxy)methyl]-2-phenyl-1,3-oxazole-5-carbaldehyde (0.45 g), tributylphosphine (0.73 g), 4-[(5-methyl-2-phenyl-1,3-oxazol-4-yl)methoxy]phenol (0.50 g) and tetrahydrofuran (50 mL) was added 1,1'-(azodicarbonyl)dipiperidine (0.91 g) at room temperature, and the mixture was stirred for 15 hrs. The precipitated crystals were removed by filtration and the filtrate was concentrated. The residue was subjected to silica gel column chromatography to give 4-[(methoxymethoxy)methyl]-5-({4-[(5-methyl-2-phenyl-1,3-oxazol-4-yl)methoxy]phenoxy}methyl)-2-phenyl-1,3-oxazole as colorless crystals (0.52 g, yield 57%) from a fraction eluted with ethyl acetate-hexane (1:2, v/v). Recrystallization from ethyl acetate-hexane gave colorless prism crystals. melting point: 74-75° C.

Example 93

A mixture of 4-[(methoxymethoxy)methyl]-5-({4-[(5-methyl-2-phenyl-1,3-oxazol-4-yl)methoxy]phenoxy}methyl)-2-phenyl-1,3-oxazole (0.80 g), 1N hydrochloric acid (20 mL) and tetrahydrofuran (20 mL) was heated under reflux for 20 hrs. Water was added to the reaction mixture, and the mixture was extracted with ethyl acetate. The ethyl acetate layer was washed with saturated brine, dried over anhydrous magnesium sulfate and concentrated. The residue was subjected to silica gel column chromatography to give [5-({4-[(5-methyl-2-phenyl-1,3-oxazol-4-yl)methoxy]phenoxy}methyl)-2-phenyl-1,3-oxazol-4-yl]methanol as colorless crystals (0.22 g, yield 29%) from a fraction eluted with ethyl acetate-hexane (1:1, v/v). Recrystallization from ethyl acetate-hexane gave colorless prism crystals. melting point: 143-144° C.

Example 94

A mixture of (2E)-3-{3-[(4-{[2-(2-furyl)-5-methyl-4-oxazolyl]methoxy}-3-methoxybenzyl)oxy]-1-phenyl-1H-pyrazol-4-yl}-2-propenoic acid (0.30 g), 1-hydroxybenzotriazole ammonia complex (0.17 g), 1-ethyl-3-(3-dimethylaminopropyl)carbodiimide hydrochloride (0.22 g) and N,N-dimethylformamide (15 mL) was stirred at room temperature for 15 hrs. Water was poured into the reaction mixture, and the precipitated crystals were collected by filtration to give (2E)-3-{3-[(4-{[2-(2-furyl)-5-methyl-4-oxazolyl]methoxy}-3-methoxybenzyl)oxy]-1-phenyl-1H-pyrazol-4-yl}-2-propenamide as colorless crystals (0.25 g, yield 83%). Recrystallization from tetrahydrofuran-hexane gave colorless prism crystals. melting point: 187-188° C.

Example 95

To a mixture of 3-[(4-{[2-(2-furyl)-5-methyl-1,3-oxazol-4-yl]methoxy}-3-methoxybenzyl)oxy]-1-phenyl-1H-pyrazole-4-carbaldehyde (0.50 g), diethyl cyanomethylphosphonate (0.19 g) and N,N-dimethylformamide (10 mL) was added sodium hydride (60% in oil, 0.050 g) under ice-cooling. The mixture was stirred at room temperature for 15 hrs. Water was added to the reaction mixture, and the mixture was extracted with ethyl acetate. The ethyl acetate layer was washed with saturated brine, dried over anhydrous magnesium sulfate and concentrated. The residue was subjected to silica gel column chromatography to give (2E)-3-{3-[(4-{[2-(2-furyl)-5-methyl-1,3-oxazol-4-yl]methoxy}-3-methoxybenzyl)oxy]-1-phenyl-1H-pyrazol-4-yl}-2-propenenitrile as colorless crystals (0.040 g, yield 8%) from a fraction eluted with ethyl acetate-hexane (1:1, v/v). Recrystallization from ethyl acetate-hexane gave colorless prism crystals. melting point: 177-178° C.

Example 96

A mixture of 3-[(4-{[2-(2-furyl)-5-methyl-1,3-oxazol-4-yl]methoxy}-3-methoxybenzyl)oxy]-1-phenyl-1H-pyrazole-4-carbaldehyde (0.40 g), piperazine (0.02 g), malononitrile (0.065 g), benzoic acid (0.020 g) and toluene (30 mL) was heated under reflux for 2 hrs with azeotropic removal of water. Ethyl acetate was added to the reaction mixture. The ethyl acetate layer was washed successively with 1N hydrochloric acid, saturated aqueous sodium hydrogen carbonate and saturated brine, dried over anhydrous magnesium sulfate and concentrated. The residue was subjected to silica gel column chromatography to give ({3-[(4-{[2-(2-furyl)-5-methyl-1,3-oxazol-4-yl]methoxy}-3-methoxybenzyl)oxy]-1-phenyl-1H-pyrazol-4-yl)methylene) malononitrile as yellow crystals (0.35 g, yield 80%) from a fraction eluted with ethyl acetate-hexane (1:2, v/v). Recrystallization from ethyl acetate-hexane gave yellow prism crystals. melting point: 190-191° C.

Example 97

To a mixture of 3-[(4-{[2-(2-furyl)-5-methyl-1,3-oxazol-4-yl]methoxy}-3-methoxybenzyl)oxy]-1-phenyl-1H-pyrazole-4-carbaldehyde (0.50 g), nitromethane (0.07 g), methanol (5 mL) and tetrahydrofuran (10 mL) was added 2N aqueous sodium hydroxide solution (0.6 mL) at 0° C. The mixture was stirred at room temperature for 7 hrs. To the reaction mixture was added dilute hydrochloric acid, and the mixture was extracted with ethyl acetate. The organic layer was washed with saturated brine, dried over anhydrous magnesium sulfate and concentrated. The residue was subjected to silica gel column chromatography to give 2-(2-furyl)-4-({2-methoxy-4-[({4-[2-nitro-1-(nitromethyl)ethyl]-1-phenyl-1H-pyrazol-3-yl}oxy)methyl]phenoxy}methyl)-5-methyl-1,3-oxazole as yellow crystals (0.15 g, yield 25%) from a fraction eluted with ethyl acetate-hexane (1:2, v/v). Recrystallization from ethyl acetate-hexane gave yellow prism crystals. melting point: 126-127° C.

Example 98

A mixture of (2E)-3-{3-[(4-{[2-(2-furyl)-5-methyl-4-oxazolyl]methoxy}-3-methoxybenzyl)oxy]-1-phenyl-1H-pyrazol-4-yl}-2-propenoic acid (0.40 g), 1-hydroxybenzotriazole monohydrate (0.17 g), 1-ethyl-3-(3-dimethylaminopropyl)carbodiimide hydrochloride (0.22 g), morpholine (0.10 g) and N,N-dimethylformamide (10 mL) was stirred at room temperature for 15 hrs. Water was poured into the reaction mixture, and the mixture was extracted with ethyl acetate. The organic layer was washed with saturated brine, dried over anhydrous magnesium sulfate and concentrated to give 4-((2E)-3-{3-[(4-{[2-(2-furyl)-5-methyl-1,3-oxazol-4-yl]methoxy}-3-methoxybenzyl)oxy]-1-phenyl-1H-pyrazol-4-yl}-2-propenoyl)morpholine as yellow crystals (0.41 g, yield 91%). Recrystallization from ethyl acetate-hexane gave yellow prism crystals. melting point: 180-181° C.

Example 99

To a mixture of (2E)-{3-{3-[(4-([2-(2-furyl)-5-methyl-4-oxazolyl]methoxy}-3-methoxybenzyl)oxy]-1-phenyl-1H-pyrazol-4-yl}-2-propenoic acid (0.60 g), triethylamine (0.14 g) and tetrahydrofuran (30 mL) was added ethyl chlorocarbonate (0.15 g) at −30° C. The reaction mixture was stirred at the same temperature for 40 min and added to a mixture of 1-amino-2-chloroethane hydrochloride (0.66 g), triethylamine (0.58 g) and tetrahydrofuran (20 mL) at −30° C. After stirring the reaction mixture at room temperature for 1 hr, water was added, and the mixture was extracted with ethyl acetate. The organic layer was washed with saturated brine, dried over anhydrous magnesium sulfate and concentrated. A mixture of the obtained residue, potassium carbonate (0.19 g) and N,N-dimethylformamide (20 mL) was stirred at 90° C. for 2 hrs. Water was poured into the reaction mixture, and the mixture was extracted with ethyl acetate. The organic layer was washed with saturated brine, dried over anhydrous magnesium sulfate and concentrated. The residue was subjected to silica gel column chromatography to give 4-({4-[({4-[(E)-2-(4,5-dihydro-1,3-oxazol-2-yl)ethenyl]-1-phenyl-1H-pyrazol-3-yl}oxy)methyl]-2-methoxyphenoxy}methyl)-2-(2-furyl)-5-methyl-1,3-oxazole as pale-yellow crystals (0.22 g, yield 35%) from a fraction eluted with ethyl acetate-methanol (50:1, v/v). Recrystallization from ethyl acetate-hexane gave pale-yellow prism crystals. melting point: 162-163° C.

Example 100

To a mixture of 4-[(4-chloromethyl-2-methoxyphenoxy)methyl]-2-(2-furyl)-5-methyl-1,3-oxazole (0.38 g), diethyl 2-(3-hydroxy-1-phenyl-1H-pyrazol-4-yl)ethylphosphonate (0.47 g) and N,N-dimethylformamide (20 mL) was added sodium hydride (60% in oil, 0.050 g) at room temperature. The mixture was stirred at room temperature for 6 hrs. Water was poured into the reaction mixture, and the mixture was extracted with ethyl acetate. The ethyl acetate layer was washed with saturated brine, dried over anhydrous magnesium sulfate and concentrated. The residue was subjected to silica gel column chromatography to give diethyl 2-{3-[(4-{[2-(2-furyl)-5-methyl-1,3-oxazol-4-yl]methoxy}-3-methoxybenzyl)oxy]-1-phenyl-1H-pyrazol-4-yl}ethylphosphonate as a colorless oil (0.60 g, yield 80%) from a fraction eluted with ethyl acetate-hexane (3:1, v/v).

NMR (CDCl$_3$) δ: 1.28 (6H, t, =7.2 Hz), 1.98-2.15 (2H, m), 2.41 (3H, s), 2.66-2.81 (2H, m), 3.89 (3H, s), 4.04 (2H, q, J=7.2 Hz), 4.07 (2H, q, J=7.2 Hz), 5.07 (2H, s), 5.27 (2H, s), 6.52 (1H, dd, J=3.8, 1.8 Hz), 6.95-7.05 (4H, m), 7.13-7.21 (1H, m), 7.35-7.44 (2H, m), 7.53-7.62 (4H, m).

Example 101

To a mixture of {3-[(4-{[2-(2-furyl)-5-methyl-1,3-oxazol-4-yl]methoxy}-3-methoxybenzyl)oxy]-1-phenyl-1H-pyrazol-4-yl}methanol (0.30 g) and N,N-dimethylformamide (5 mL) was added sodium hydride (60% in oil, 0.030 g) at 0° C. After stirring the reaction mixture at 0° C. for 30 min, methyl iodide (0.11 g) was added to the reaction mixture, and the mixture was further stirred at room temperature for 3 hrs. The reaction mixture was poured into water and the mixture was extracted with ethyl acetate. The ethyl acetate layer was washed with saturated brine, dried over anhydrous magnesium sulfate and concentrated. The residue was subjected to silica gel column chromatography to give 2-(2-furyl)-4-{[2-methoxy-4-({[4-(methoxymethyl)-1-phenyl-1H-pyrazol-3-yl]oxy}methyl)phenoxy]methyl}-5-methyl-1,3-oxazole as colorless crystals (0.20 g, yield 65%) from a fraction eluted with ethyl acetate-hexane (1:2, v/v). Recrystallization from ethyl acetate-hexane gave colorless prism crystals. melting point: 121-122° C.

Example 102

A mixture of 3-[(4-{[2-(2-furyl)-5-methyl-1,3-oxazol-4-yl]methoxy}-3-methoxybenzyl)oxy]-1-phenyl-1H-pyrazole-4-carbaldehyde (1.0 g), methylamine (2M tetrahydrofuran solution, 3.2 mL), acetic acid (0.13 g), ethanol (20 mL) and tetrahydrofuran (20 mL) was stirred at room temperature for 2 hrs. Sodium cyanotrihydroborate (0.20 g) was added to the reaction mixture, and the mixture was further stirred at room temperature for 3 hrs. The reaction mixture was concentrated and ethyl acetate was added to the residue. The ethyl acetate layer was washed successively with saturated aqueous sodium hydrogen carbonate and saturated brine, dried over anhydrous magnesium sulfate and concentrated. The residue was subjected to silica gel column chromatography to give N-({3-[(4-{[2-(2-furyl)-5-methyl-1,3-oxazol-4-yl]methoxy}-3-methoxybenzyl)oxy]-1-phenyl-1H-pyrazol-4-yl}methyl)-N-methylamine as colorless crystals (0.15 g, yield 14%) from a fraction eluted with ethyl acetate-methanol (10:1, v/v). Recrystallization from ethyl acetate-hexane gave colorless prism crystals. melting point: 103-104° C.

Example 103

To a mixture of potassium tert-butoxide (0.94 g) and dimethoxyethane (30 mL) was added p-toluenesulfonyl methylisocyanide (0.86 g) at −78° C., and a solution of 3-[(4-{[2-(2-furyl)-5-methyl-1,3-oxazol-4-yl]methoxy}-3-methoxybenzyl)oxy]-1-phenyl-1H-pyrazole-4-carbaldehyde (1.96 g) in dimethoxyethane (50 mL)-tetrahydrofuran (10 mL) was added at −78° C. After stirring at the same temperature for 1 hr, the reaction mixture was heated to room temperature. Methanol (30 mL) was added to the obtained mixture, and the mixture was heated under reflux for 1 hr. After cooling, the reaction mixture was poured into water, and the mixture was extracted with ethyl acetate. The ethyl acetate layer was washed successively with saturated aqueous sodium hydrogen carbonate and saturated brine, dried over anhydrous magnesium sulfate and concentrated. The residue was subjected to silica gel column chromatography to give {3-[(4-{[2-(2-furyl)-5-methyl-1,3-oxazol-4-yl]methoxy}-3-methoxybenzyl)oxy]-1-phenyl-1H-pyrazol-4-yl}acetonitrile as colorless crystals (1.21 g, yield 61%) from a fraction eluted with ethyl acetate-hexane (1:1, v/v). Recrystallization from ethyl acetate-hexane gave colorless prism crystals. melting point: 153-154° C.

Example 104

To a mixture of {3-[(4-{[2-(2-furyl)-5-methyl-1,3-oxazol-4-yl]methoxy}-3-methoxybenzyl)oxy]-1-phenyl-1H-pyrazol-4-yl}acetic acid (0.52 g) and tetrahydrofuran (10 mL) was added borane-tetrahydrofuran (1.02 M tetrahydrofuran solution, 2.0 mL) at 0° C., and the mixture was stirred at room temperature for 1 hr. 1N Hydrochloric acid (5 mL) and water were added to the reaction mixture and the mixture was extracted with ethyl acetate. The ethyl acetate layer was washed successively with saturated aqueous sodium hydrogen carbonate and saturated brine, dried over anhydrous magnesium sulfate and concentrated. The residue was subjected to silica gel column chromatography to give 2-{3-[(4-{[2-(2-furyl)-5-methyl-1,3-oxazol-4-yl]methoxy}-3-methoxybenzyl)oxy]-1-phenyl-1H-pyrazol-4-yl}ethanol as colorless crystals (0.31 g, yield 62%) from a fraction eluted with ethyl acetate-hexane (2:1, v/v). Recrystallization from ethyl acetate-hexane gave colorless prism crystals. melting point: 123-124° C.

Example 105

To a mixture of (5Z)-5-({3-[(4-{[2-(2-furyl)-5-methyl-1,3-oxazol-4-yl]methoxy}-3-methoxybenzyl)oxy]-1-phenyl-1H-pyrazol-4-yl}methylene)-1,3-thiazolidine-2,4-dione (0.50 g) and N,N-dimethylformamide (10 mL) was added sodium hydride (60% in oil, 0.040 g) at room temperature. After stirring the reaction mixture at room temperature for 30 min, methyl iodide (0.16 g) was added, and the mixture was further stirred at room temperature for 30 hrs. The reaction mixture was poured into water, and the precipitated crystals were collected by filtration to give (5Z)-5-({3-[(4-{[2-(2-furyl)-5-methyl-1,3-oxazol-4-yl]methoxy}-3-methoxybenzyl)oxy]-1-phenyl-1H-pyrazol-4-yl}methylene)-3-methyl-1,3-thiazolidine-2,4-dione as yellow crystals (0.47 g, yield 92%). Recrystallization from tetrahydrofuran-hexane gave yellow prism crystals. melting point: 215-216° C.

Example 106

To a mixture of 4-[(4-chloromethyl-2-methoxyphenoxy)methyl]-2-(2-furyl)-5-methyl-1,3-oxazole (0.40 g), 5-[(3-hydroxy-1-phenyl-1H-pyrazol-4-yl)methyl]-1,3-thiazolidine-2,4-dione (0.30 g) and N,N-dimethylformamide (10 mL) was added sodium hydride (60% in oil, 0.050 g) at room temperature. The mixture was stirred at room temperature for 15 hrs. The reaction mixture was poured into water and the mixture was extracted with ethyl acetate. The ethyl acetate layer was washed with saturated brine, dried over anhydrous magnesium sulfate and concentrated. The residue was subjected to silica gel column chromatography to give 5-({3-[(4-{[2-(2-furyl)-5-methyl-1,3-oxazol-4-yl]methoxy}-3-methoxybenzyl)oxy]-1-phenyl-1H-pyrazol-4-yl}methyl)-3-methyl-1,3-thiazolidine-2,4-dione as pale-yellow crystals (0.22 g, yield 37%) from a fraction eluted with ethyl acetate-hexane (1:1, v/v). Recrystallization from ethyl acetate-hexane gave pale-yellow prism crystals. melting point: 111-112° C.

Example 107

A mixture of 3-[(4-{[2-(2-furyl)-5-methyl-1,3-oxazol-4-yl]methoxy}-3-methoxybenzyl)oxy]-1-phenyl-1H-pyrazole-4-carbaldehyde (0.60 g), p-toluenesulfonylmethylisocyanide (0.25 g), potassium carbonate (0.17 g) and methanol (30 mL) was heated under reflux for 3 hrs. Water was added to the reaction mixture, and the mixture was extracted with ethyl acetate. The ethyl acetate layer was washed with saturated brine, dried over anhydrous magnesium sulfate and concentrated. The residue was subjected to silica gel column chromatography to give 2-(2-furyl)-4-{[2-methoxy-4-({[4-(1,3-oxazol-5-yl)-1-phenyl-1H-pyrazol-3-yl]oxy}methyl)phenoxy]methyl}-5-methyl-1,3-oxazole as colorless crystals (0.34 g, yield 54%) from a fraction eluted with ethyl acetate-hexane (1:1, v/v). Recrystallization from ethyl acetate-hexane gave colorless prism crystals. melting point: 153-154° C.

Example 108

To a solution of ethyl (2E)-3-{3-[(4-{[2-(2-furyl)-5-methyl-1,3-oxazol-4-yl]methoxy}-3-methoxybenzyl)oxy]-1-phenyl-1H-pyrazol-4-yl}-2-propenoate (0.55 g) in tetrahydrofuran (50 mL) was added diisobutylaluminum hydride (0.95 M hexane solution, 6.3 mL) at 0° C., and the mixture was stirred at room temperature for 3 hrs. Sodium sulfate decahydrate (1.91 g) was added to the reaction mixture, and the mixture was stirred at room temperature for 30 min. The reaction mixture was diluted with ethyl acetate and the precipitate was filtered off, and the filtrate was concentrated. The residue was subjected to silica gel column chromatography to give (2E)-3-{3-[(4-{[2-(2-furyl)-5-methyl-1,3-oxazol-4-yl]methoxy}-3-methoxybenzyl)oxy]-1-phenyl-1H-pyrazol-4-yl}-2-propen-1-ol as colorless crystals (0.30 g, yield 59%) from a fraction eluted with ethyl acetate-hexane (1:1, v/v). Recrystallization from ethyl acetate-hexane gave colorless prism crystals. melting point: 120-121° C.

Example 109

A mixture of (2E)-3-{3-[(4-{[2-(2-furyl)-5-methyl-1,3-oxazol-4-yl]methoxy}-3-methoxybenzyl)oxy]-1-phenyl-1H-pyrazol-4-yl}-2-propen-1-ol (0.80 g), activated manganese dioxide (2.40 g) and tetrahydrofuran (100 mL) was stirred at room temperature for 15 hrs. Manganese dioxide was removed by filtration and the filtrate was concentrated. The obtained crystals were collected by filtration to give (2E)-3-{3-[(4-{[2-(2-furyl)-5-methyl-1,3-oxazol-4-yl]methoxy}-3-methoxybenzyl)oxy]-1-phenyl-1H-pyrazol-4-yl}-2-propenaldehyde (0.71 g, yield 87%). Recrystallization from ethyl acetate-hexane gave colorless prism crystals. melting point: 134-135° C.

Example 110

To a mixture of (2E)-3-{3-[(4-{[2-(2-furyl)-5-ethyl-1,3-oxazol-4-yl]methoxy}-3-methoxybenzyl)oxy]-1-phenyl-1H-pyrazol-4-yl}-2-propen-1-ol (1.00 g), tributylphosphine (0.77 g), 1H-1,2,4-triazole (0.26 g) and tetrahydrofuran (30 mL) was added 1,1'-(azodicarbonyl)dipiperidine (0.95 g) at room temperature, and the mixture was stirred for 15 hrs. The precipitated crystals were removed by filtration, and the filtrate was concentrated. The residue was subjected to silica gel column chromatography to give 1-(1-{3-[(4-{[2-(2-furyl)-5-methyl-1,3-oxazol-4-yl]methoxy}-3-methoxybenzyl)oxy]-1-phenyl-1H-pyrazol-4-yl}-2-propenyl)-1H-1,2,4-triazole as crystals (0.48 g, yield 45%) from a fraction eluted with ethyl acetate-hexane (2:1, v/v). Recrystallization from ethyl acetate-hexane gave colorless prism crystals. melting point: 115-116° C.

Example 111

A mixture of 3-[(4-{[2-(2-furyl)-5-methyl-1,3-oxazol-4-yl]methoxy}-3-methoxybenzyl)oxy]-1-phenyl-1H-pyrazole-4-carbaldehyde (1.00 g), [(1,3-thiazol-4-yl)methyl]triphenylphosphonium chloride (1.27 g), potassium carbonate (0.44 g) and N,N-dimethylformamide (50 mL) was stirred at room temperature for 15 hrs. Water was poured into the reaction mixture, and the mixture was extracted with ethyl acetate. The organic layer was washed with saturated brine, dried over anhydrous magnesium sulfate and concentrated. The obtained residue was subjected to silica gel column chromatography and eluted with ethyl acetate-hexane (2:3, v/v) to give 2-(2-furyl)-4-({2-methoxy-4-[({1-phenyl-4-[(Z)-2-(1,3-thiazol-4-yl)ethenyl]-1H-pyrazol-3-yl}oxy)methyl]phenoxy}methyl)-5-methyl-1,3-oxazole as colorless crystals (0.40 g, yield 34%). Recrystallization from ethyl acetate-hexane gave colorless prism crystals. melting point: 137-138° C.

In addition, 2-(2-furyl)-4-({2-methoxy-4-[({1-phenyl-4-[(E)-2-(1,3-thiazol-4-yl)ethenyl]-1H-pyrazol-3-yl}oxy)methyl]phenoxy}methyl)-5-methyl-1,3-oxazole was obtained as colorless crystals (0.63 g, yield 53%) from a fraction

Example 112

To a solution (5 mL) of tetraethyl methylenediphosphonate (265 mg) in N,N-dimethylformamide was added sodium hydride (60% in oil, 40 mg) and the mixture was stirred at room temperature for 20 min. A solution (5 mL) of N-(4-formyl-1-phenyl-1H-pyrazol-3-yl)-4-[(5-methyl-2-phenyl-1,3-oxazol-4-yl)methoxy]benzamide (400 mg) in N,N-dimethylformamide was added to the reaction mixture, and the mixture was stirred at room temperature for 2 hrs. Water was poured into the reaction mixture, and the mixture was extracted with ethyl acetate. The ethyl acetate layer was washed successively with distilled water and saturated brine, dried over anhydrous magnesium sulfate and concentrated. The residue was subjected to silica gel column chromatography and eluted with ethyl acetate-hexane (1:1 to 1:0, v/v) to give diethyl (E)-2-[3-({4-[(5-methyl-2-phenyl-1,3-oxazol-4-yl)methoxy]benzoyl}amino)-1-phenyl-1H-pyrazol-4-yl]ethenylphosphonate as colorless amorphous form (195 mg, yield 37%).

NMR(CDCl$_3$) δ: 1.29 (6H, t, J=6.9 Hz), 2.45 (3H, s), 4.04-4.13 (4H, m), 5.01 (2H,s), 5.95 (1H, dd, J=17.6, 18.5 Hz), 7.00-7.05 (2H, m), 7.26-7.33 (1H, m), 7.39-7.46 (6H, m), 7.57-7.60 (2H, m), 7.90-7.95 (2H,m), 7.98-8.02 (2H, m), 8.07 (1H, s), 8.76 (1H,s).

Example 113

A mixture of 3-[(4-{[2-(2-furyl)-5-methyl-1,3-oxazol-4-yl]methoxy}-3-methoxybenzyl)oxy]-1-phenyl-1H-pyrazole-4-carbaldehyde (0.80 g), [(2-pyridyl)methyl]triphenylphosphonium chloride (0.94 g), potassium carbonate (0.33 g) and N,N-dimethylformamide (50 mL) was stirred at room temperature for 15 hrs. Water was poured into the reaction mixture, and the mixture was extracted with ethyl acetate. The organic layer was washed with saturated brine, dried over anhydrous magnesium sulfate and concentrated. The residue was subjected to silica gel column chromatography and eluted with ethyl acetate-hexane (1:1, v/v) to give 2-((E)-2-{3-[(4-{[2-(2-furyl)-5-methyl-1,3-oxazol-4-yl]methoxy}-3-methoxybenzyl)oxy]-1-phenyl-1H-pyrazol-4-yl}ethenyl)pyridine as colorless crystals (0.68 g, yield 76%). Recrystallization from ethyl acetate-hexane gave colorless prism crystals. melting point: 135-136° C.

Example 114

A mixture of (2E)-3-{3-[(4-{[2-(2-furyl)-5-methyl-1,3-oxazol-4-yl]methoxy}-3-methoxybenzyl)oxy]-1-phenyl-1H-pyrazol-4-yl}-2-propenaldehyde (0.40 g), p-toluenesulfonylmethylisocyanide (0.17 g), potassium carbonate (0.11 g) and methanol (20 mL) was heated under 1 reflux for 30 min. Water was added to the reaction mixture, and the mixture was extracted with ethyl acetate. The ethyl acetate layer was washed with saturated brine, dried over anhydrous magnesium sulfate and concentrated. The residue was subjected to silica gel column chromatography to give 2-(2-furyl)-4-({2-methoxy-4-[({4-[(E)-2-(1,3-oxazol-5-yl)ethenyl]-1-phenyl-1H-pyrazol-3-yl}oxy)methyl]phenoxy}methyl)-5-methyl-1,3-oxazole as colorless crystals (0.23 g, yield 53%) from a fraction eluted with ethyl acetate-hexane (1:1, v/v). Recrystallization from ethyl acetate-hexane gave colorless prism crystals. melting point: 137-138° C.

Example 115

To a solution (80 mL) of (2E)-3-{3-[(4-{[2-(2-furyl)-5-methyl-1,3-oxazol-4-yl]methoxy}-3-methoxybenzyl)oxy]-1-phenyl-1H-pyrazol-4-yl}-2-propenoic acid (0.78 g) in tetrahydrofuran were successively added 4-methylmorpholine (0.20 g) and isobutyl chlorocarbonate (0.29 g) at 0° C. The reaction mixture was stirred at 0° C. for 1 hr, insoluble materials were removed by filtration, and the filtrate was added dropwise to a mixture of hydrazine monohydrate (0.38 g) and tetrahydrofuran (20 mL) at 0° C. After stirring at 0° C. for 1 hr, the reaction mixture was diluted with ethyl acetate. The ethyl acetate layer was washed successively with water, saturated aqueous ammonium chloride solution and saturated brine, dried over anhydrous magnesium sulfate and concentrated. A mixture of the obtained residue, trimethyl orthobutyrate (0.67 g), methanesulfonic acid (0.030 g) and 1,4-dioxane (50 mL) was stirred at 110° C. for 1 hr and concentrated. Ethyl acetate was added to the residue, and the mixture was washed successively with saturated aqueous sodium hydrogen carbonate and saturated brine, dried over anhydrous magnesium sulfate and concentrated. The residue was subjected to silica gel column chromatography to give 2-((E)-2-{3-[(4-{[2-(2-furyl)-5-methyl-1,3-oxazol-4-yl]methoxy}-3-methoxybenzyl)oxy]-1-phenyl-1H-pyrazol-4-yl}ethenyl)-5-propyl-1,3,4-oxadiazole as colorless crystals (0.41 g, yield 46%) from a fraction eluted with ethyl acetate-hexane (1:1, v/v). Recrystallization from ethyl acetate-hexane gave colorless prism crystals. melting point: 172-173° C.

Example 116

To a mixture of 3-[(4-{[2-(2-furyl)-5-methyl-1,3-oxazol-4-yl]methoxy}-3-methoxybenzyl)oxy]-1-phenyl-1H-pyrazole-4-carbaldehyde (28.0 g), tetraethyl methylenediphosphonate (17.5 g) and N,N-dimethylformamide (300 mL) was added sodium hydride (60% in oil, 2.43 g) at 0° C. The mixture was stirred at room temperature for 2 hrs. The reaction mixture was poured into water, 2N hydrochloric acid was added to acidify the solution, and the mixture was extracted with ethyl acetate. The organic layer was washed with water, dried over anhydrous magnesium sulfate and concentrated. The residue was subjected to silica gel column chromatography and eluted with acetone-hexane (2:3, v/v) to give diethyl (Z)-2-(3-[(4-{[2-(2-furyl)-5-methyl-1,3-oxazol-4-yl]methoxy}-3-methoxybenzyl)oxy]-1-phenyl-1H-pyrazol-4-yl}ethenylphosphonate as a colorless oil (1.94 g, yield 5%).

NMR (CDCl$_3$) δ: 1.31 (6H, t, J=7.2 Hz), 2.41 (3H, s), 3.89 (3H, s), 4.03-4.14 (4H, m), 5.07 (2H, s), 5.31 (2H, s), 5.43 (1H, dd, J=16.2, 14.4 Hz), 6.51-6.53 (1H, m), 6.96-7.07 (5H, m), 7.19-7.24 (1H, m), 7.39-7.45 (2H, m), 7.53-7.54 (1H, m), 7.67-7.71 (2H, m), 9.08 (1H, s).

In addition, by successive elution with acetone-hexane (1:1, v/v), diethyl (E)-2-{3-[(4-{[2-(2-furyl)-5-methyl-1,3-oxazol-4-yl]methoxy}-3-methoxybenzyl)oxy]-1-phenyl-1H-pyrazol-4-yl}ethenylphosphonate was obtained as crystals, which were recrystallization from ethyl acetate-hexane (32.2 g, yield 92%). Recrystallization from acetone-water gave colorless prism crystals. melting point: 60-63° C.

Example 117

To a solution of tetraethyl methylenediphosphonate (215 mg) in N,N-dimethylformamide (5 mL) was added sodium hydride (60% in oil, 38 mg), and the mixture was stirred at room temperature for 20 min. A solution of N-(4-formyl-1-phenyl-1H-pyrazol-3-yl)-3-methoxy-4-[(5-methyl-2-phenyl-1,3-oxazol-4-yl)methoxy]benzamide (433 mg) in N,N-dimethylformamide (5 mL) was added to the reaction mixture, and the mixture was stirred at room temperature for 2 hrs. Water was poured into the reaction mixture, and the mixture was extracted with ethyl acetate. The ethyl acetate layer was washed successively with distilled water and saturated brine, dried over anhydrous magnesium sulfate and concentrated. The residue was subjected to silica gel column chromatography to give diethyl (E)-2-[3-({3-methoxy-4-[(5-methyl-2-phenyl-1,3-oxazol-4-yl)methoxy]benzoyl}amino)-1-phenyl-1H-pyrazol-4-yl]ethenylphosphonate as colorless amorphous form (205 mg, yield 38%) from a fraction eluted with ethyl acetate-hexane (1:1 to 1:0, v/v).

NMR(CDCl$_3$) δ: 1.31 (6H, t, J=7.1 Hz), 2.45 (3H, s), 3.92 (3H, s), 4.07-4.18 (4H, m), 5.12 (2H, s), 5.97 (1H, t, J=18.1 Hz), 7.08-7.12 (1H, m), 7.32-7.36 (2H, m), 7.41-7.54 (6H, m), 7.55-7.66 (2H,m), 7.98-8.03 (3H, m), 8.11 (1H,s), 8.44 (1H, brs).

Example 118

To a solution (80 mL) of (2E)-3-{3-[(4-{[2-(2-furyl)-5-methyl-1,3-oxazol-4-yl]methoxy}-3-methoxybenzyl)oxy]-1-phenyl-1H-pyrazol-4-yl}-2-propenoic acid (0.50 g) in tetrahydrofuran were successively added 4-methylmorpholine (0.12 g) and isobutyl chlorocarbonate (0.18 g) at 0° C. The reaction mixture was stirred at 0° C. for 1 hr, and insoluble materials were removed by filtration. The filtrate was added dropwise to a mixture of hydrazine monohydrate (0.24 g) and tetrahydrofuran (20 mL) at 0° C. After stirring at 0° C. for 1 hr, the reaction mixture was diluted with ethyl acetate. The ethyl acetate layer was washed successively with water, saturated aqueous ammonium chloride solution and saturated brine, dried over anhydrous magnesium sulfate and concentrated. A mixture of the obtained residue, triethyl orthoformate (0.43 g), methanesulfonic acid (0.020 g) and tetrahydrofuran (80 mL) was heated under reflux for 1.5 hrs, and ethyl acetate was added to the reaction mixture. The ethyl acetate layer was washed successively with saturated aqueous sodium hydrogen carbonate and saturated brine, dried over anhydrous magnesium sulfate and concentrated. The residue was subjected to silica gel column chromatography to give 2-((E)-2-{3-[(4-{[2-(2-furyl)-5-methyl-1,3-oxazol-4-yl]methoxy}-3-methoxybenzyl)oxy]-1-phenyl-1H-pyrazol-4-yl}ethenyl)-1,3,4-oxadiazole as colorless crystals (0.28 g, yield 53%) from a fraction eluted with ethyl acetate-hexane (3:2, v/v). Recrystallization from ethyl acetate-hexane gave colorless prism crystals. melting point: 162-163° C.

Example 119

To a mixture of 4-[(4-chloromethyl-2-methoxyphenoxy)methyl]-2-(2-furyl)-5-methyl-1,3-oxazole (0.57 g), 1-phenyl-4-[2-(1,3-thiazol-4-yl)ethyl]-1H-pyrazol-3-ol (0.38 g) and N,N-dimethylformamide (20 mL) was added sodium hydride (60% in oil, 0.060 g) at room temperature, and the mixture was stirred at room temperature for 4 hrs. Water was poured into the reaction mixture, and the mixture was extracted with ethyl acetate. The ethyl acetate layer was washed with saturated brine, dried over anhydrous magnesium sulfate and concentrated. The residue was subjected to silica gel column chromatography to give 2-(2-furyl)-4-({2-methoxy-4-[({1-phenyl-4-[2-(1,3-thiazol-4-yl)ethyl]-1H-pyrazol-3-yl}oxy)methyl]phenoxy}methyl)-5-methyl-1,3-oxazole as colorless crystals (0.53 g, yield 66%) from a fraction eluted with ethyl acetate-hexane (1:1, v/v). Recrystallization from ethyl acetate-hexane gave colorless prism crystals. melting point: 127-128° C.

Example 120

To a solution (80 mL) of {3-[(4-{[2-(2-furyl)-5-methyl-1,3-oxazol-4-yl]methoxy}-3-methoxybenzyl)oxy]-1-phenyl-1H-pyrazol-4-yl}acetic acid (0.70 g) in tetrahydrofuran were successively added 4-methylmorpholine (0.18 g) and isobutyl chlorocarbonate (0.27 g) at 0° C. The reaction mixture was stirred at 0° C. for 1 hr, and insoluble materials were removed by filtration. The filtrate was added dropwise to a mixture of hydrazine monohydrate (0.35 g) and tetrahydrofuran (20 mL) at 0° C. After stirring at 0° C. for 1 hr, the reaction mixture was diluted with ethyl acetate. The ethyl acetate layer was washed successively with water, saturated aqueous ammonium chloride solution and saturated brine, dried over anhydrous magnesium sulfate and concentrated. A mixture of the obtained residue, trimethyl orthobutyrate (0.62 g), methanesulfonic acid (0.030 g) and 1,4-dioxane (80 mL) was stirred at 110° C. for 1 hr. The reaction mixture was concentrated and ethyl acetate was added to the residue. The ethyl acetate layer was washed successively with saturated aqueous sodium hydrogen carbonate and saturated brine, dried over anhydrous magnesium sulfate and concentrated. The residue was subjected to silica gel column chromatography to give 2-({3-[(4-{[2-(2-furyl)-5-methyl-1,3-oxazol-4-yl]methoxy}-3-methoxybenzyl)oxy]-1-phenyl-1H-pyrazol-4-yl}methyl)-5-propyl-1,3,4-oxadiazole as colorless crystals (0.51 g, yield 63%) from a fraction eluted with ethyl acetate-hexane (3:1, v/v). Recrystallization from ethyl acetate-hexane gave colorless prism crystals. melting point: 102-103° C.

Example 121

To a mixture of {3-[(4-{[2-(2-furyl)-5-methyl-1,3-oxazol-4-yl]methoxy}-3-methoxybenzyl)oxy]-1-phenyl-1H-pyrazol-4-yl}acetic acid (0.70 g), triethylamine (0.17 g) and tetrahydrofuran (30 mL) was added ethyl chlorocarbonate (0.18 g) at −30° C., and the mixture was stirred at the same temperature for 40 min. The reaction mixture was added to a mixture of 1-amino-2-chloroethane hydrochloride (0.81 g), triethylamine (0.71 g) and tetrahydrofuran (20 mL) at −30° C., and the mixture was stirred at room temperature for 1 hr. Water was added to the reaction mixture, and the mixture was extracted with ethyl acetate. The organic layer was washed with saturated brine, dried over anhydrous magnesium sulfate and concentrated. A mixture of the obtained residue, potassium carbonate (0.24 g) and N,N-dimethylformamide (20 mL) was stirred at 90° C. for 2 hrs. Water was poured into the reaction mixture, and the mixture was extracted with ethyl acetate. The organic layer was washed with saturated brine, dried over anhydrous magnesium sulfate and concentrated. The residue was subjected to silica gel column chromatography to give 4-{[4-({[4-(4,5-dihydro-1,3-oxazol-2-ylmethyl)-1-phenyl-1H-pyrazol-3-yl]oxy}methyl)-2-methoxyphenoxy]methyl}-2-(2-furyl)-5-methyl-1,3-oxazole as colorless crystals (0.14 g, yield 18%) from a fraction eluted with ethyl acetate-methanol (50:1, v/v). Recrystallization from ethyl acetate-hexane gave colorless prism crystals. melting point: 95-96° C.

Example 122

To a mixture of {3-[(4-{[2-(2-furyl)-5-methyl-1,3-oxazol-4-yl]methoxy}-3-methoxybenzyl)oxy]-1-phenyl-1H-pyrazol-4-yl}methanol (0.50 g), tributylphosphine (0.40 g), 1H-1,2,4-triazole (0.14 g) and tetrahydrofuran (50 mL) was added 1,1'-(azodicarbonyl)dipiperidine (0.50 g) at room temperature, and the mixture was stirred for 15 hrs. The precipitated crystals were removed by filtration, and the filtrate was concentrated. The residue was subjected to silica gel column chromatography to give 1-({3-[(4-{[2-(2-furyl)-5-methyl-1,3-oxazol-4-yl]methoxy}-3-methoxybenzyl)oxy]-1-phenyl-1H-pyrazol-4-yl}methyl)-1H-1,2,4-triazole as crystals (0.22 g, yield 41%) from a fraction eluted with ethyl acetate-methanol (50:1, v/v). Recrystallization from ethyl acetate-hexane gave colorless prism crystals. melting point: 149-150° C.

Example 123

To a solution (50 mL) of 3-[3-({3-methoxy-4-[(5-methyl-2-phenyl-1,3-oxazol-4-yl)methoxy]benzyl}oxy)-1-phenyl-1H-pyrazol-5-yl]propanoic acid (0.60 g) in tetrahydrofuran were successively added 4-methylmorpholine (0.14 g) and isobutyl chlorocarbonate (0.20 g) at 0° C. After stirring the reaction mixture at 0° C. for 1 hr., insoluble materials were removed by filtration. The filtrate was added dropwise to a mixture of hydrazine monohydrate (0.28 g) and tetrahydrofuran (20 mL) at 0° C. After stirring at 0° C. for 1 hr, the reaction mixture was diluted with ethyl acetate. The ethyl acetate layer was washed successively with water, saturated aqueous ammonium chloride solution and saturated brine, dried over anhydrous magnesium sulfate and concentrated. A mixture of the obtained residue, trimethyl orthobutyrate (0.49 g), methanesulfonic acid (0.020 g) and tetrahydrofuran (50 mL) was heated under reflux for 1.5 hrs. Ethyl acetate was added to the reaction mixture. The ethyl acetate layer was washed successively with saturated aqueous sodium hydrogen carbonate and saturated brine, dried over anhydrous magnesium sulfate and concentrated. The residue was subjected to silica gel column chromatography to give 2-{2-[3-({3-methoxy-4-[(5-methyl-2-phenyl-1,3-oxazol-4-yl)methoxy]benzyl}oxy)-1-phenyl-1H-pyrazol-5-yl]ethyl}-5-propyl-1,3,4-oxadiazole as colorless crystals (0.42 g, yield 63%) from a fraction eluted with ethyl acetate-hexane (1:1, v/v). Recrystallization from ethyl acetate-hexane gave colorless prism crystals. melting point: 85-86° C.

Example 124

A mixture of (2E)-3-{3-[(4-{[2-(2-furyl)-5-methyl-1,3-oxazol-4-yl]methoxy}-3-methoxybenzyl)oxy]-1-phenyl-1H-pyrazol-4-yl}-2-propenoic acid (0.60 g), 4-methylmorpholine (0.28 g), 1-ethyl-3-(3-dimethylaminopropyl)carbodiimide hydrochloride (0.21 g), 1-hydroxybenzotriazole monohydrate (0.17 g) and N,N-dimethylformamide (30 mL) was stirred at room temperature for 30 min, N'-hydroxybutanimidamide (0.14 g) was added, and the mixture was further stirred at room temperature for 15 hrs. Water was added to the reaction mixture, and the mixture was extracted with ethyl acetate. The organic layer was washed with saturated brine, dried over anhydrous magnesium sulfate and concentrated. Xylene (50 mL) was added to the residue, and the mixture was heated under reflux for 24 hrs. The reaction mixture was concentrated, and the obtained residue was subjected to silica gel column chromatography to give 5-((E)-2-{3-[(4-{[2-(2-furyl)-5-methyl-1,3-oxazol-4-yl]methoxy}-3-methoxybenzyl)oxy]-1-phenyl-1H-pyrazol-4-yl}ethenyl)-3-propyl-1,2,4-oxadiazole as colorless crystals (0.12 g, yield 18%) from a fraction eluted with ethyl acetate-hexane (1:2, v/v). Recrystallization from ethyl acetate-hexane gave colorless prism crystals. melting point: 192-193° C.

Example 125

To a solution (80 mL) of (2E)-3-{3-[(4-{[2-(2-furyl)-5-methyl-1,3-oxazol-4-yl]methoxy}-3-methoxybenzyl)oxy]-1-phenyl-1H-pyrazol-4-yl}-2-propenoic acid (0.50 g) in tetrahydrofuran were successively added 4-methylmorpholine (0.12 g) and isobutyl chlorocarbonate (0.18 g) at 0° C. After stirring the reaction mixture at 0° C. for 1 hr, insoluble materials were removed by filtration. The filtrate was added dropwise to a mixture of hydrazine monohydrate (0.24 g) and tetrahydrofuran (20 mL) at 0° C. After stirring at 0° C. for 1 hr, the reaction mixture was diluted with ethyl acetate. The ethyl acetate layer was washed successively with water, saturated aqueous ammonium chloride solution and saturated brine, dried over anhydrous magnesium sulfate and concentrated. A mixture of the obtained residue, triethyl orthoacetate (0.47 g), methanesulfonic acid (0.020 g) and tetrahydrofuran (50 mL) and the mixture was heated under reflux for 1.5 hrs. Ethyl acetate was added to the reaction mixture. The ethyl acetate layer was washed successively with saturated aqueous sodium hydrogen carbonate and saturated brine, dried over anhydrous magnesium sulfate and concentrated. The residue was subjected to silica gel column chromatography to give 2-((E)-2-{3-[(4-{[2-(2-furyl)-5-methyl-1,3-oxazol-4-yl]methoxy}-3-methoxybenzyl)oxy]-1-phenyl-1H-pyrazol-4-yl}ethenyl)-5-methyl-1,3,4-oxadiazole as colorless crystals (0.16 g, yield 30%) from a fraction eluted with ethyl acetate-hexane (2:1, v/v). Recrystallization from ethyl acetate-hexane gave colorless prism crystals. melting point: 186-187° C.

Example 126

To a solution (80 mL) of (2E)-3-{3-[(4-{[2-(2-furyl)-5-methyl-1,3-oxazol-4-yl]methoxy}-3-methoxybenzyl)oxy]-1-phenyl-1H-pyrazol-4-yl}-2-propenoic acid (0.50 g) in tetrahydrofuran were successively added 4-methylmorpholine (0.12 g) and isobutyl chlorocarbonate (0.18 g) at 0° C. After stirring the reaction mixture at 0° C. for 1 hr, insoluble materials were removed by filtration. The filtrate was added dropwise to a mixture of hydrazine monohydrate (0.24 g) and tetrahydrofuran (20 mL) at 0° C. After stirring the reaction mixture at 0° C. for 1 hr, the reaction mixture was diluted with ethyl acetate. The ethyl acetate layer was washed successively with water, saturated aqueous ammonium chloride solution and saturated brine, dried over anhydrous magnesium sulfate and concentrated. A mixture of the obtained residue, triethyl orthopropionate (0.50 g), methanesulfonic acid (0.020 g) and tetrahydrofuran (50 mL) was heated under reflux for 1.5 hrs. Ethyl acetate was added to the reaction mixture. The ethyl acetate layer was washed successively with saturated aqueous sodium hydrogen carbonate and saturated brine, dried over anhydrous magnesium sulfate and concentrated. The residue was subjected to silica gel column chromatography to give 2-ethyl-5-((E)-2-{3-[(4-{[2-(2-furyl)-5-methyl-1,3-oxazol-4-yl]methoxy}-3-methoxybenzyl)oxy]-1-phenyl-1H-pyrazol-4-yl}ethenyl)-1,3,4-oxadiazole as colorless crystals (0.23 g, yield 42%) from a fraction eluted with ethyl acetate-hexane (3:2, v/v). Recrystallization from ethyl acetate-hexane gave colorless prism crystals. melting point: 183-184° C.

Example 127

To a solution (80 mL) of (2E)-3-{3-[(4-{[2-(2-furyl)-5-methyl-1,3-oxazol-4-yl]methoxy}-3-methoxybenzyl)oxy]-1-phenyl-1H-pyrazol-4-yl}-2-propenoic acid (0.50 g) in tetrahydrofuran were successively added 4-methylmorpholine (0.12 g) and isobutyl chlorocarbonate (0.18 g) at 0° C. After stirring the reaction mixture at 0° C. for 1 hr, insoluble materials were removed by filtration. The filtrate was added dropwise to a mixture of hydrazine monohydrate (0.24 g) and tetrahydrofuran (20 mL) at 0° C. After stirring at 0° C. for 1 hr, the reaction mixture was diluted with ethyl acetate. The ethyl acetate layer was washed successively with water, saturated aqueous ammonium chloride solution and saturated brine, dried over anhydrous magnesium sulfate and concentrated. A mixture of the obtained residue, triethyl orthopentanoate (0.47 g), methanesulfonic acid (0.020 g) and tetrahydrofuran (50 mL), was heated under reflux for 15 hrs. Ethyl acetate was added to the reaction mixture. The ethyl acetate layer was washed successively with saturated aqueous sodium hydrogen carbonate and saturated brine, dried over anhydrous magnesium sulfate and concentrated. The residue was subjected to silica gel column chromatography to give 2-((E)-2-{3-[(4-{[2-(2-furyl)-5-methyl-1,3-oxazol-4-yl]methoxy}-3-methoxybenzyl)oxy]-1-phenyl-1H-pyrazol-4-yl}ethenyl)-5-propyl-1,3,4-oxadiazole as colorless crystals (0.39 g, yield 67%) from a fraction eluted with ethyl acetate-hexane (1:1, v/v). Recrystallization from ethyl acetate-hexane gave colorless prism crystals. melting point: 165-166° C.

Example 128

To a mixture of 3-[(4-{[2-(2-furyl)-5-methyl-1,3-oxazol-4-yl]methoxy}-3-methoxybenzyl)oxy]-1-phenyl-1H-pyrazole-4-carbaldehyde (2.0 g), diethyl (methylthio)methylphosphonate (0.89 g) and N,N-dimethylformamide (50 mL) was added sodium hydride (60% in oil, 0.20 g) at room temperature and the mixture was stirred at room temperature for 15 hrs. The reaction mixture was poured into ice water, and the mixture was extracted with ethyl acetate. The organic layer was washed with saturated brine, dried over anhydrous magnesium sulfate and concentrated. The residue was subjected to silica gel column chromatography and eluted with ethyl acetate-hexane (1:2, v/v) to give colorless crystals. To a mixture of the obtained crystal and tetrahydrofuran (50 mL) was added m-chloroperbenzoic acid (0.66 g) at room temperature, and the mixture was stirred at the same temperature for 2 hrs. Saturated sodium sulfite aqueous solution was added to the reaction mixture, and the mixture was stirred at room temperature for 10 min, and extracted with ethyl acetate. The organic layer was washed successively with saturated aqueous sodium hydrogen carbonate and saturated brine, dried over anhydrous magnesium sulfate and concentrated. The residue was subjected to silica gel column chromatography and eluted with ethyl acetate-methanol (100:1, v/v) to give 2-(2-furyl)-4-({2-methoxy-4-[({4-[(E)-2-(methylsulfinyl)ethenyl]-1-phenyl-1H-pyrazol-3-yl}oxy)methyl]phenoxy}methyl)-5-methyl-1,3-oxazole as colorless crystals (0.81 g, yield 36%). Recrystallization from ethyl acetate-hexane gave colorless prism crystals. melting point: 156-157° C.

In addition, 2-(2-furyl)-4-({2-methoxy-4-[({4-[(Z)-2-(methylsulfinyl)ethenyl]-1-phenyl-1H-pyrazol-3-yl}oxy)methyl]phenoxy}methyl)-5-methyl-1,3-oxazole was obtained as colorless crystals (0.33 g, yield 15%) from a fraction successively obtained by elution. Recrystallization from ethyl acetate-hexane gave colorless prism crystals. melting point: 180-181° C.

Example 129

To a solution of tetraethyl methylenediphosphonate (357 mg) in N,N-dimethylformamide (5 mL) was added sodium hydride (60% in oil, 54 mg), and the mixture was stirred at room temperature for 20 min. To the reaction mixture was added a solution of N-(4-formyl-1-phenyl-1H-pyrazol-3-yl)-2-{3-methoxy-4-[(5-methyl-2-phenyl-1,3-oxazol-4-yl)methoxy]phenyl}acetamide (590 mg) in N,N-dimethylformamide (5 mL), and the mixture was stirred at room temperature for 2 hrs. Water was poured into the reaction mixture, and the mixture was extracted with ethyl acetate. The ethyl acetate layer was washed successively with distilled water and saturated brine, dried over anhydrous magnesium sulfate and concentrated. The residue was subjected to silica gel column chromatography and eluted with ethyl acetate-hexane (1:1 to 1:0, v/v) to give diethyl (E)-2-{3-[({3-methoxy-4-[(5-methyl-2-phenyl-1,3-oxazol-4-yl)methoxy]phenyl}acetyl)amino]-1-phenyl-1H-pyrazol-4-yl}ethenylphosphonate as colorless amorphous form (159 mg, yield 21%).

NMR(CDCl$_3$) δ: 1.34 (6H, t, J=7.0 Hz), 2.43 (3H, s), 3.74 (2H, s), 3.87 (3H, s), 4.04-4.18 (4H, m), 5.04 (2H, s), 5.91 (1H, t, J=18.1 Hz), 6.86-6.90 (2H, m), 7.04-7.08 (1H, m), 7.25-7.47 (7H, m), 7.55-7.58 (2H, m), 7.78 (1H, s), 7.96-8.03 (2H, m), 8.06 (1H, s).

Example 130

To a mixture of 2-(2-furyl)-4-({2-methoxy-4-[({4-[(E)-2-(methylsulfinyl)ethenyl]-1-phenyl-1H-pyrazol-3-yl}oxy)methyl]phenoxy}methyl)-5-methyl-1,3-oxazole (0.47 g) and tetrahydrofuran (30 mL) was added m-chloroperbenzoic acid (0.18 g) at room temperature, and the mixture was stirred at the same temperature for 1 hr. Saturated aqueous sodium sulfite solution was added to the reaction mixture, and the mixture was stirred at room temperature for 10 min, and the mixture was extracted with ethyl acetate. The organic layer was washed successively with saturated aqueous sodium hydrogen carbonate and saturated brine, dried over anhydrous magnesium sulfate and concentrated. The residue was subjected to silica gel column chromatography and eluted with ethyl acetate-hexane (1:1, v/v) to give 2-(2-furyl)-4-({2-methoxy-4-[({4-[(E)-2-(methylsulfonyl)ethenyl]-1-phenyl-1H-pyrazol-3-yl}oxy)methyl]phenoxy}methyl)-5-methyl-1,3-oxazole as colorless crystals (0.41 g, yield 85%). Recrystallization from ethyl acetate-hexane gave colorless prism crystals. melting point: 152-153° C.

Example 131

To a mixture of 2-(2-furyl)-4-({2-methoxy-4-[({4-[(Z)-2-(methylsulfinyl)ethenyl]-1-phenyl-1H-pyrazol-3-yl}oxy)methyl]phenoxy}methyl)-5-methyl-1,3-oxazole (0.20 g) and tetrahydrofuran (20 mL) was added m-chloroperbenzoic acid (0.08 g) at room temperature, and the mixture was stirred at the same temperature for 1 hr. Saturated aqueous sodium sulfite solution was added to the reaction mixture, and the mixture was stirred at room temperature for 10 min, and the mixture was extracted with ethyl acetate. The organic layer was washed successively with saturated aqueous sodium hydrogen carbonate and saturated brine, dried over anhydrous magnesium sulfate and concentrated. The residue was subjected to silica gel column chromatography and eluted with ethyl acetate-hexane (1:1, v/v) to give 2-(2-furyl)-4-({2-methoxy-4-[({4-[(Z)-2-(methylsulfonyl) ethenyl]-1-phenyl-1H-pyrazol-3-yl}oxy)methyl] phenoxy}methyl)-5-methyl-1,3-oxazole as colorless crystals (0.15 g, yield 71%). Recrystallization from ethyl acetate-hexane gave colorless prism crystals. melting point: 158-159° C.

Example 132

To a solution (80 mL) of (2E)-3-{1-benzyl-3-[(4-{[2-(2-furyl)-5-methyl-1,3-oxazol-4-yl]methoxy}-3-methoxybenzyl)oxy]-1H-pyrazol-4-yl}-2-propenoic acid (0.51 g) in tetrahydrofuran were successively added 4-methylmorpholine (0.12 g) and isobutyl chlorocarbonate (0.18 g) at 0° C. After stirring the reaction mixture at 0° C. for 1 hr, insoluble materials were removed by filtration. The filtrate was added dropwise to a mixture of hydrazine monohydrate (0.24 g) and tetrahydrofuran (20 mL) at 0° C. After stirring at 0° C. for 1 hr, the reaction mixture was diluted with ethyl acetate. The ethyl acetate layer was washed successively with water, saturated aqueous ammonium chloride solution and saturated brine, dried over anhydrous magnesium sulfate and concentrated. A mixture of the obtained residue, trimethyl orthobutyrate (0.34 g), methanesulfonic acid (0.020 g) and tetrahydrofuran (50 mL) was heated under reflux for 1.5 hrs. Ethyl acetate was added to the reaction mixture. The ethyl acetate layer was washed successively with saturated aqueous sodium hydrogen carbonate and saturated brine, dried over anhydrous magnesium sulfate and concentrated. The residue was subjected to silica gel column chromatography to give 2-((E)-2-{1-benzyl-3-[(4-{[2-(2-furyl)-5-methyl-1,3-oxazol-4-yl]methoxy}-3-methoxybenzyl)oxy]-1H-pyrazol-4-yl}ethenyl)-5-propyl-1,3,4-oxadiazole as colorless crystals (0.34 g, yield 59%) from a fraction eluted with ethyl acetate-hexane (1:1, v/v). Recrystallization from ethyl acetate-hexane gave colorless prism crystals. melting point: 146-147° C.

Example 133

To a solution (20 mL) of (2E)-3-[5-({4-[(5-methyl-2-phenyl-1,3-oxazol-4-yl)methoxy]phenoxy}methyl)-2-phenyl-1,3-oxazol-4-yl]-2-propenoic acid (0.30 g) in tetrahydrofuran were successively added 4-methylmorpholine (0.08 g) and isobutyl chlorocarbonate (0.11 g) at 0° C. After stirring the reaction mixture at 0° C. for 1 hr, insoluble materials were removed by filtration. The filtrate was added dropwise to a mixture of hydrazine monohydrate (0.15 g) and tetrahydrofuran (20 mL) at 0° C. After stirring at 0° C. for 1 hr, the reaction mixture was diluted with ethyl acetate. The ethyl acetate layer was washed successively with water, saturated aqueous ammonium chloride solution and saturated brine, dried over anhydrous magnesium sulfate and concentrated. A mixture of the obtained residue, trimethyl orthobutyrate (0.27 g), methanesulfonic acid (0.020 g) and tetrahydrofuran (20 mL) was heated under reflux for 1.5 hrs. Ethyl acetate was added to the reaction mixture. The ethyl acetate layer was washed successively with saturated aqueous sodium hydrogen carbonate and saturated brine, dried over anhydrous magnesium sulfate and concentrated. The residue was subjected to silica gel column chromatography to give 2-{(E)-2-[5-({4-[(5-methyl-2-phenyl-1,3-oxazol-4-yl)methoxy]phenoxy}methyl)-2-phenyl-1,3-oxazol-4-yl]ethenyl}-5-propyl-1,3,4-oxadiazole as colorless crystals (0.27 g, yield 79%) from a fraction eluted with ethyl acetate-hexane (1:1, v/v). Recrystallization from ethyl acetate-hexane gave colorless prism crystals. melting point: 119-120° C.

Example 134

To a mixture of 5-({4-[(5-methyl-2-phenyl-1,3-oxazol-4-yl)methoxy]phenoxy}methyl)-2-phenyl-1,3-oxazole-4-carbaldehyde (0.50 g), tetraethyl methylenediphosphonate (0.35 g) and N,N-dimethylformamide (10 mL) was added sodium hydride (60% in oil, 0.05 g) at room temperature, and the mixture was stirred at the same temperature for 1 hr. The reaction mixture was poured into water and the mixture was extracted with ethyl acetate. The organic layer was washed with saturated brine, dried over anhydrous magnesium sulfate and concentrated. The residue was subjected to silica gel column chromatography to give diethyl (E)-2-[5-({4-[(5-methyl-2-phenyl-1,3-oxazol-4-yl)methoxy] phenoxy}methyl)-2-phenyl-1,3-oxazol-4-yl]ethenylphosphonate as colorless crystals (0.41 g, yield 62%) from a fraction eluted with ethyl acetate-hexane (2:1, v/v). Recrystallization from ethyl acetate-hexane gave colorless prism crystals. melting point: 124-125° C.

Example 135

To a mixture of 3-[(4-{[2-(2-furyl)-5-methyl-1,3-oxazol-4-yl]methoxy}-3-methoxybenzyl)oxy]-1-phenyl-1H-pyrazole-5-carbaldehyde (1.0 g), ethyl diethylphosphonoacetate (0.52 g) and N,N-dimethylformamide (30 mL) was added sodium hydride (60% in oil, 0.10 g) under ice-cooling, and the mixture was stirred at room temperature for 15 hrs. The reaction mixture was poured into ice water, and the mixture was extracted with ethyl acetate. The organic layer was washed with saturated brine, dried over anhydrous magnesium sulfate and concentrated to give ethyl (2E)-3-{3-[(4-{[2-(2-furyl)-5-methyl-1,3-oxazol-4-yl]methoxy}-3-methoxybenzyl)oxy]-1-phenyl-1H-pyrazol-5-yl}-2-propenoate as colorless crystals (0.87 g, yield 74%). Recrystallization from ethyl acetate-hexane gave colorless prism crystals. melting point: 127-128° C.

Example 136

To a mixture of ethyl (2E)-3-{3-[(4-{[2-(2-furyl)-5-methyl-1,3-oxazol-4-yl]methoxy}-3-methoxybenzyl)oxy]-1-phenyl-1H-pyrazol-5-yl}-2-propenoate (0.73 g), tetrahydrofuran (5 mL) and ethanol (5 mL) was added 1N aqueous sodium hydroxide solution (5 mL), and the mixture was heated under reflux for 1 hr. 1N Hydrochloric acid (5 mL) and water were added to neutralize the reaction mixture, and the precipitated crystals were collected by filtration to give (2E)-3-{3-[(4-{[2-(2-furyl)-5-methyl-1,3-oxazol-4-yl]methoxy}-3-methoxybenzyl)oxy]-1-phenyl-1H-pyrazol-5-yl}-2-propenoic acid as colorless crystals (0.65 g, yield 94%). Recrystallization from ethyl acetate-hexane gave colorless prism crystals. melting point: 191-192° C.

Example 137

To a mixture of 3-[(4-{[2-(2-furyl)-5-methyl-1,3-oxazol-4-yl]methoxy}-3-methoxybenzyl)oxy]-1-phenyl-1H-pyrazole-5-carbaldehyde (0.50 g), tetraethyl methylenediphosphonate (0.32 g) and N,N-dimethylformamide (10 mL) was added sodium hydride (60% in oil, 0.05 g) at room temperature, and the mixture was stirred at the same temperature for 1 hr. The reaction mixture was poured into water and the mixture was extracted with ethyl acetate. The organic layer was washed with saturated brine, dried over anhydrous magnesium sulfate and concentrated. The residue was subjected to silica gel column chromatography to give diethyl (E)-2-{3-[(4-{[2-(2-furyl)-5-methyl-1,3-oxazol-4-yl]methoxy}-3-methoxybenzyl)oxy]-1-phenyl-1H-pyrazol-5-yl}ethenylphosphonate as a colorless oil (0.43 g, yield 69%) from a fraction eluted with ethyl acetate-hexane (3:1, v/v).

NMR (CDCl$_3$) δ: 1.32 (6H, t, J=7.0 Hz), 2.41 (3H, s), 3.88 (3H, s), 4.01-4.17 (4H, m), 5.07 (2H, s), 5.20 (2H, s), 6.06-6.24 (2H, m), 6.52 (1H, dd, J=3.8, 1.8 Hz), 6.95-7.03 (4H, m), 7.25 (1H, dd, J=22.0, 17.4 Hz), 7.35-7.55 (6H, m).

Example 138

To a solution (50 mL) of (2E)-3-{3-[(4-{[2-(2-furyl)-5-methyl-1,3-oxazol-4-yl]methoxy}-3-methoxybenzyl)oxy]-1-phenyl-1H-pyrazol-5-yl}-2-propenoic acid (0.54 g) in tetrahydrofuran were successively added 4-methylmorpholine (0.13 g) and isobutyl chlorocarbonate (0.19 g) at 0° C. After stirring the reaction mixture at 0° C. for 1 hr, insoluble materials were removed by filtration. The filtrate was added dropwise to a mixture of hydrazine monohydrate (0.25 g) and tetrahydrofuran (50 mL) at 0° C. After stirring at 0° C. for 1 hr, the reaction mixture was diluted with ethyl acetate. The ethyl acetate layer was washed successively with water, saturated aqueous ammonium chloride solution and saturated brine, dried over anhydrous magnesium sulfate and concentrated. A mixture of the obtained residue, trimethyl orthobutyrate (0.44 g), methanesulfonic acid (0.020 g) and tetrahydrofuran (50 mL) was heated under reflux for 1.5 hrs. Ethyl acetate was added to the reaction mixture. The ethyl acetate layer was washed successively with saturated aqueous sodium hydrogen carbonate and saturated brine, dried over anhydrous magnesium sulfate and concentrated. The residue was subjected to silica gel column chromatography to give 2-((E)-2-{3-[(4-{[2-(2-furyl)-5-methyl-1,3-oxazol-4-yl]methoxy}-3-methoxybenzyl)oxy]-1-phenyl-1H-pyrazol-5-yl}ethenyl)-5-propyl-1,3,4-oxadiazole as colorless crystals (0.38 g, yield 64%) from a fraction eluted with ethyl acetate-hexane (1:1, v/v). Recrystallization from ethyl acetate-hexane gave colorless prism crystals. melting point: 107-108° C.

Example 139

A mixture of 3-[(4-{[2-(2-furyl)-5-methyl-1,3-oxazol-4-yl]methoxy}-3-methoxybenzyl)oxy]-1-phenyl-1H-pyrazole-5-carbaldehyde (1.00 g), [(1,3-thiazol-4-yl)methyl]triphenylphosphonium chloride (1.27 g), potassium carbonate (0.44 g) and N,N-dimethylformamide (50 mL) was stirred at room temperature for 15 hrs. Water was poured into the reaction mixture, and the mixture was extracted with ethyl acetate. The organic layer was washed with saturated brine, dried over anhydrous magnesium sulfate and concentrated. The residue was subjected to silica gel column chromatography and eluted with ethyl acetate-hexane (1:1, v/v) to give 2-(2-furyl)-4-({2-methoxy-4-[({1-phenyl-5-[(E)-2-(1,3-thiazol-4-yl)ethenyl]-1H-pyrazol-3-yl}oxy)methyl]phenoxy}methyl)-5-methyl-1,3-oxazole as colorless crystals (0.77 g, yield 78%). Recrystallization from ethyl acetate-hexane gave colorless prism crystals. melting point: 154-155° C.

Example 140

A mixture of 3-[(4-{[2-(2-furyl)-5-methyl-1,3-oxazol-4-yl]methoxy}-3-methoxybenzyl)oxy]-1-phenyl-1H-pyrazole-5-carbaldehyde (0.70 g), [(2-pyridyl)methyl]triphenylphosphonium chloride (0.82 g), potassium carbonate (0.29 g) and N,N-dimethylformamide (50 mL) was stirred at room temperature for 15 hrs. Water was poured into the reaction mixture, and the mixture was extracted with ethyl acetate. The organic layer was washed with saturated brine, dried over anhydrous magnesium sulfate and concentrated. The residue was subjected to silica gel column chromatography and eluted with ethyl acetate-hexane (1:1, v/v) to give 2-((E)-2-{3-[(4-{[2-(2-furyl)-5-methyl-1,3-oxazol-4-yl]methoxy}-3-methoxybenzyl)oxy]-1-phenyl-1H-pyrazol-5-yl}ethenyl)pyridine as colorless crystals (0.65 g, yield 74%). Recrystallization from ethyl acetate-hexane gave colorless prism crystals. melting point: 122-123° C.

Example 141

To a mixture of 4-[(4-chloromethyl-2-methoxyphenoxy)methyl]-2-(2-furyl)-5-methyl-1,3-oxazole (0.30 g), 1-phenyl-5-[2-(pyridin-2-yl)ethyl]-1H-pyrazol-3-ol (0.43 g) and N,N-dimethylformamide (20 mL) was added sodium hydride (60% in oil, 0.050 g) at room temperature, and the mixture was stirred at the same temperature for 15 hrs. Water was poured into the reaction mixture, and the mixture was extracted with ethyl acetate. The ethyl acetate layer was washed with saturated brine, dried over anhydrous magnesium sulfate and concentrated. The residue was subjected to silica gel column chromatography to give 2-(2-{3-[(4-{[2-(2-furyl)-5-methyl-1,3-oxazol-4-yl]methoxy}-3-methoxybenzyl)oxy]-1-phenyl-1H-pyrazol-5-yl}ethyl)pyridine as a colorless oil (0.47 g, yield 76%) from a fraction eluted with ethyl acetate-hexane (1:1, v/v). Recrystallization from ethyl acetate-hexane gave colorless prism crystals. melting point: 104-105° C.

Example 142

To a mixture of 4-[(4-chloromethyl-2-methoxyphenoxy)methyl]-2-(2-furyl)-5-methyl-1,3-oxazole (0.32 g), diethyl 2-(3-hydroxy-1-phenyl-1H-pyrazol-5-yl)ethylphosphonate (0.40 g) and N,N-dimethylformamide (20 mL) was added sodium hydride (60% in oil, 0.040 g) at room temperature, and the mixture was stirred at the same temperature for 15 hrs. Water was poured into the reaction mixture, and the mixture was extracted with ethyl acetate. The ethyl acetate layer was washed with saturated brine, dried over anhydrous magnesium sulfate and concentrated. The residue was subjected to silica gel column chromatography to give diethyl 2-{3-[(4-{[2-(2-furyl)-5-methyl-1,3-oxazol-4-yl]methoxy}-3-methoxybenzyl)oxy]-1-phenyl-1H-pyrazol-5-yl}ethylphosphonate as colorless crystals (0.29 g, yield 47%) from a fraction eluted with ethyl acetate-hexane (2:1, v/v). Recrystallization from ethyl acetate-hexane gave colorless prism crystals. melting point: 76-77° C.

Example 143

To a mixture of {3-[(4-{[2-(2-furyl)-5-methyl-1,3-oxazol-4-yl]methoxy}-3-methoxybenzyl)oxy]-1-phenyl-1H-pyrazol-5-yl}methanol (0.50 g), tributylphosphine (0.61 g), 1H-1,2,4-triazole (0.21 g) and tetrahydrofuran (80 mL) was added 1,1'-(azodicarbonyl)dipiperidine (0.75 g) at room temperature, and the mixture was stirred for 15 hrs. Ethyl acetate was added to the reaction mixture. The ethyl acetate layer was washed successively with 1N hydrochloric acid and saturated brine, dried over anhydrous magnesium sulfate and concentrated. The residue was subjected to silica gel column chromatography to give 1-({3-[(4-{[2-(2-furyl)-5-methyl-1,3-oxazol-4-yl]methoxy}-3-methoxybenzyl)oxy]-1-phenyl-1H-pyrazol-5-yl}methyl)-1H-1,2,4-triazole as crystals (0.47 g, yield 85%) from a fraction eluted with ethyl acetate-hexane (2:1, v/v). Recrystallization from ethyl acetate-hexane gave colorless prism crystals. melting point: 95-96° C.

Example 144

To a mixture of 3-[(4-{[2-(2-furyl)-5-methyl-1,3-oxazol-4-yl]methoxy}-3-methoxybenzyl)oxy]-1-phenyl-1H-pyrazole-4-carbaldehyde (0.60 g), tetramethyl. methylenediphosphonate (0.32 g) and N,N-dimethylformamide (20 mL) was added sodium hydride (60% in oil, 0.05 g) at room temperature, and the mixture was stirred at the same temperature for 15 hrs. The reaction mixture was poured into water and the mixture was extracted with ethyl acetate. The organic layer was washed with saturated brine, dried over anhydrous magnesium sulfate and concentrated. The residue was subjected to silica gel column chromatography to give dimethyl (E)-2-{3-[(4-{[2-(2-furyl)-5-methyl-1,3-oxazol-4-yl]methoxy}-3-methoxybenzyl)oxy]-1-phenyl-1H-pyrazol-4-yl}ethenylphosphonate as colorless crystals (0.56 g, yield 79%) from a fraction eluted with ethyl acetate-hexane (3:1, v/v). Recrystallization from ethyl acetate-hexane gave colorless prism crystals. melting point: 107-108° C.

Example 145

To a mixture of 3-[(4-{[2-(2-furyl)-5-methyl-1,3-oxazol-4-yl]methoxy}-3-methoxybenzyl)oxy]-1-phenyl-1H-pyrazole-4-carbaldehyde (0.70 g), tetraisopropyl methylenediphosphonate (0.59 g) and N,N-dimethylformamide (20 mL) was added sodium hydride (60% in oil, 0.06 g) at room temperature, and the mixture was stirred at the same temperature for 15 hrs. The reaction mixture was poured into water and the mixture was extracted with ethyl acetate. The organic layer was washed with saturated brine, dried over anhydrous magnesium sulfate and concentrated. The residue was subjected to silica gel column chromatography to give diisopropyl (E)-2-{3-[(4-{[2-(2-furyl)-5-methyl-1,3-oxazol-4-yl]methoxy}-3-methoxybenzyl)oxy]-1-phenyl-1H-pyrazol-4-yl}ethenylphosphonate as colorless crystals (0.61 g, yield 67%) from a fraction eluted with ethyl acetate-hexane (2:1, v/v). Recrystallization from ethyl acetate-hexane gave colorless prism crystals. melting point: 152-153° C.

Example 146

To a mixture of 3-({3-methoxy-4-[(5-methyl-2-phenyl-1,3-oxazol-4-yl)methoxy]benzyl}oxy)-1-phenyl-1H-pyrazole-4-carbaldehyde (0.50 g), tetraethyl methylenediphosphonate (0.32 g) and N,N-dimethylformamide (20 mL) was added sodium hydride (60% in oil, 0.05 g) at room temperature, and the mixture was stirred at the same temperature for 15 hrs. The reaction mixture was poured into water and the mixture was extracted with ethyl acetate. The organic layer was washed with saturated brine, dried over anhydrous magnesium sulfate and concentrated. The residue was subjected to silica gel column chromatography to give diethyl (E)-2-[3-({3-methoxy-4-[(5-methyl-2-phenyl-1,3-oxazol-4-yl)methoxy]benzyl}oxy)-1-phenyl-1H-pyrazol-4-yl]ethenylphosphonate as colorless crystals (0.43 g, yield 68%) from a fraction eluted with ethyl acetate-hexane (3:1, v/v). Recrystallization from ethyl acetate-hexane gave colorless prism crystals. melting point: 92-93° C.

Example 147

To a mixture of 3-({4-[(5-methyl-2-phenyl-1,3-oxazol-4-yl)methoxy]benzyl}oxy)-1-phenyl-1H-pyrazole-4-carbaldehyde (0.60 g), tetraethyl methylenediphosphonate (0.40 g) and N,N-dimethylformamide (20 mL) was added sodium hydride (60% in oil, 0.05 g) at room temperature, and the mixture was stirred at the same temperature for 15 hrs. The reaction mixture was poured into water and the mixture was extracted with ethyl acetate. The organic layer was washed with saturated brine, dried over anhydrous magnesium sulfate and concentrated. The residue was subjected to silica gel column chromatography to give diethyl (E)-2-[3-({4-[(5-methyl-2-phenyl-1,3-oxazol-4-yl)methoxy]benzyl}oxy)-1-phenyl-1H-pyrazol-4-yl]ethenylphosphonate as colorless crystals (0.51 g, yield 65%) from a fraction eluted with ethyl acetate-hexane (3:1, v/v). Recrystallization from ethyl acetate-hexane gave colorless prism crystals. melting point: 109-110° C.

Example 148

To a mixture of 3-[(4-{[2-(2-furyl)-5-methyl-1,3-oxazol-4-yl]methoxy}benzyl)oxy]-1-phenyl-1H-pyrazole-4-carbaldehyde (0.37 g), tetraethyl methylenediphosphonate (0.26 g) and N,N-dimethylformamide (20 mL) was added sodium hydride (60% in oil, 0.04 g) at room temperature, and the mixture was stirred at the same temperature for 15 hrs. The reaction mixture was poured into water and the mixture was extracted with ethyl acetate. The organic layer was washed with saturated brine, dried over anhydrous magnesium sulfate and concentrated. The residue was subjected to silica gel column chromatography to give diethyl (E)-2-{3-[(4-{[2-(2-furyl)-5-methyl-1,3-oxazol-4-yl]methoxy}benzyl)oxy]-1-phenyl-1H-pyrazol-4-yl}ethenylphosphonate as colorless crystals (0.31 g, yield 65%) from a fraction eluted with ethyl acetate-hexane (3:1, v/v). Recrystallization from ethyl acetate-hexane gave colorless prism crystals. melting point: 131-132° C.

Example 149

To a mixture of 3-[(3-ethoxy-4-{[2-(2-furyl)-5-methyl-1,3-oxazol-4-yl]methoxy}benzyl)oxy]-1-phenyl-1H-pyrazole-4-carbaldehyde (0.44 g), tetraethyl methylenediphosphonate (0.31 g) and N,N-dimethylformamide (20 mL) was added sodium hydride (60% in oil, 0.05 g) at room temperature, and the mixture was stirred at the same temperature for 15 hrs. The reaction mixture was poured into water and the mixture was extracted with ethyl acetate. The organic layer was washed with saturated brine, dried over anhydrous magnesium sulfate and concentrated. The residue was subjected to silica gel column chromatography to give diethyl (E)-2-{3-[(3-ethoxy-4-{[2-(2-furyl)-5-methyl-1,3-oxazol-4-yl]methoxy}benzyl)oxy]-1-phenyl-1H-pyrazol-4-yl}ethenylphosphonate as colorless crystals (0.34 g, yield 55%) from a fraction eluted with ethyl acetate-hexane (3:1, v/v). Recrystallization from ethyl acetate-hexane gave colorless prism crystals. melting point: 117-118° C.

Example 150

A mixture of 3-[(4-{[2-(2-furyl)-5-methyl-1,3-oxazol-4-yl]methoxy}-3-methoxybenzyl)oxy]-1-phenyl-1H-pyrazole-4-carbaldehyde (0.80 g), [(2-methyl-1,3-thiazol-4-yl)methyl]triphenylphosphonium chloride (0.98 g), potassium carbonate (0.33 g) and N,N-dimethylformamide (50 mL) was stirred at room temperature for 15 hrs. Water was poured into the reaction mixture, and the mixture was extracted with ethyl acetate. The organic layer was washed with saturated brine, dried over anhydrous magnesium sulfate and concentrated. The residue was subjected to silica gel column chromatography and eluted with ethyl acetate-hexane (2:3, v/v) to give 2-(2-furyl)-4-({2-methoxy-4-[({4-[(Z)-2-(2-methyl-1,3-thiazol-4-yl)ethenyl]-1-phenyl-1H-pyrazol-3-yl}oxy)methyl]phenoxy}methyl)-5-methyl-1,3-oxazole as colorless crystals (0.33 g, yield 35%). Recrystallization from ethyl acetate-hexane gave colorless prism crystals. melting point: 164-165° C.

In addition, 2-(2-furyl)-4-({2-methoxy-4-[({4-[(E)-2-(2-methyl-1,3-thiazol-4-yl)ethenyl]-1-phenyl-1H-pyrazol-3-yl}oxy)methyl]phenoxy}methyl)-5-methyl-1,3-oxazole was obtained as colorless crystals (0.45 g, yield 48%) from a fraction successively obtained by elution. Recrystallization from ethyl acetate-hexane gave colorless prism crystals. melting point: 111-112° C.

Example 151

To a solution of tetraethyl methylenediphosphonate (277 mg) in N,N-dimethylformamide (5 mL) was added sodium hydride (60% in oil, 38 mg), and the mixture was stirred at room temperature for 20 min. To the reaction mixture was added a solution of N-(4-formyl-1-phenyl-1H-pyrazol-3-yl)-4-{[2-(2-furyl)-5-methyl-1,3-oxazol-4-yl]methoxy}-3-methoxybenzamide (400 mg) in N,N-dimethylformamide (5 mL), and the mixture was stirred at room temperature for 2 hrs. Water was poured into the reaction mixture, and the mixture was extracted with ethyl acetate. The ethyl acetate layer was washed successively with distilled water and saturated brine, dried over anhydrous magnesium sulfate and concentrated. The residue was subjected to silica gel column chromatography and eluted with ethyl acetate-hexane (1:1 to 1:0, v/v), then methanol-ethyl acetate (0:1 to 0.5:9.5, v/v) to give diethyl (E)-2-{3-[(4-{[2-(2-furyl)-5-methyl-1,3-oxazol-4-yl]methoxy}-3-methoxybenzoyl)amino]-1-phenyl-1H-pyrazol-4-yl}ethenylphosphonate as colorless amorphous form (380 mg, yield 75%).

NMR(CDCl$_3$) δ: 1.30 (6H, t, J=7.1 Hz), 2.43 (3H, s), 3.89 (3H, s), 4.02-4.17 (4H, m), 5.10 (2H, m), 5.96 (1H, t=18.0 Hz), 6.51-6.53 (1H, m), 6.96-7.06 (2H, m), 7.31-7.34 (1H, m), 7.40-7.55 (6H, m), 7.59-7.64 (2H, m), 8.10 (1H, s), 8.73 (1H, s).

Example 152

A mixture of 3-[(4-{[2-(2-furyl)-5-methyl-1,3-oxazol-4-yl]methoxy}-3-methoxybenzyl)oxy]-1-phenyl-1H-pyrazole-4-carbaldehyde (0.60 g), [(2-ethyl-1,3-thiazol-4-yl)methyl]triphenylphosphonium chloride (0.76 g), potassium carbonate (0.25 g) and N,N-dimethylformamide (30 mL) was stirred at room temperature for 15 hrs. Water was poured into the reaction mixture, and the mixture was extracted with ethyl acetate. The organic layer was washed with saturated brine, dried over anhydrous magnesium sulfate and concentrated. The residue was subjected to silica gel column chromatography and eluted with ethyl acetate-hexane (1:2, v/v) to give 4-({4-[({4-[(Z)-2-(2-ethyl-1,3-thiazol-4-yl)ethenyl]-1-phenyl-1H-pyrazol-3-yl}oxy)methyl]-2-methoxyphenoxy}methyl)-2-(2-furyl)-5-methyl-1,3-oxazole as colorless crystals (0.15 g, yield 21%). Recrystallization from ethyl acetate-hexane gave colorless prism crystals. melting point: 132-133° C.

In addition, 4-({4-[({4-[(E)-2-(2-ethyl-1,3-thiazol-4-yl)ethenyl]-1-phenyl-1H-pyrazol-3-yl}oxy)methyl]-2-methoxyphenoxy}methyl)-2-(2-furyl)-5-methyl-1,3-oxazole was obtained as colorless crystals (0.25 g, yield 35%) from a fraction successively obtained by elution. Recrystallization from ethyl acetate-hexane gave colorless prism crystals. melting point: 108-109° C.

Example 153

To a solution of tetraethyl methylenediphosphonate (186 mg) in N,N-dimethylformamide (5 mL) was added sodium hydride (60% in oil, 28 mg), and the mixture was stirred at room temperature for 20 min. To the reaction mixture was added a solution of N-(4-formyl-1-phenyl-1H-pyrazol-3-yl)-2-(4-{[2-(2-furyl)-5-methyl-1,3-oxazol-4-yl]methoxy}-3-methoxyphenyl)acetamide (300 mg) in N,N-dimethylformamide (5 mL), and the mixture was stirred at room temperature for 2 hrs. Water was poured into the reaction mixture, and the mixture was extracted with ethyl acetate. The ethyl acetate layer was washed successively with distilled water and saturated brine, dried over anhydrous magnesium sulfate and concentrated. The residue was subjected to silica gel column chromatography and eluted with ethyl acetate-hexane (1:1 to 1:0, v/v) then methanol ethyl acetate (0:1 to 0.5:9.5, v/v) to give diethyl (E)-2-{3-[(4-{[2-(2-furyl)-5-methyl-1,3-oxazol-4-yl]methoxy}-3-methoxybenzoyl)amino]-1-phenyl-1H-pyrazol-4-yl}ethenylphosphonate as a colorless oil (240 mg, yield 63%).

NMR(CDCl$_3$) δ: 1.35 (6H, t, J=7.2 Hz), 2.42 (3H, s), 3.75 (2H,s), 3.89 (3H, s), 4.04-4.19 (4H, m), 5.05 (2H, m), 5.90 (1H, t=18.2 Hz), 6.51-6.53 (1H, m), 6.91-7.07 (4H, m), 7.23-7.60 (8H, m), 8.05 (1H, s).

Example 154

To a mixture of 4-(4-chloromethyl-2-ethoxyphenoxy)methyl-5-methyl-2-(2-furyl)-1,3-oxazole (0.56 g), 3-hydroxy-1-phenyl-1H-pyrazole-4-carbaldehyde (0.25 g) and N,N-dimethylformamide (20 mL) was added sodium hydride (60% in oil, 0.06 g) at room temperature. After stirring the reaction mixture at room temperature for 30 min, the mixture was stirred at 90° C. for 2 hrs. The reaction mixture was poured into water and the mixture was extracted with ethyl acetate. The organic layer was washed with saturated brine, dried over anhydrous magnesium sulfate and concentrated. The residue was subjected to silica gel column chromatography to give 3-[(3-ethoxy-4-{[2-(2-furyl)-5-methyl-1,3-oxazol-4-yl]methoxy}benzyl)oxy]-1-phenyl-1H-pyrazole-4-carbaldehyde as colorless crystals (0.56 g, yield 86%) from a fraction eluted with tetrahydrofuran-hexane (1:1, v/v). Recrystallization from ethyl acetate-hexane gave colorless prism crystals. melting point: 149-150° C.

Example 155

To a mixture of (2E)-3-{3-[(4-{[2-(2-furyl)-5-methyl-1,3-oxazol-4-yl]methoxy}-3-methoxybenzyl)oxy]-1-phenyl-1H-pyrazol-4-yl}-N-methoxy-N-methyl-2-propenamide (0.40 g) and tetrahydrofuran (30 mL) was added dropwise methylmagnesium bromide (1M tetrahydrofuran solution, 2.8 mL) at 0° C. and the mixture was stirred at room temperature for 2 hrs. 1N Hydrochloric acid was added to the reaction mixture, and the mixture was extracted with ethyl acetate. The organic layer was washed with saturated brine, dried over anhydrous magnesium sulfate and concentrated. The residue was subjected to silica gel column chromatography to give (3E)-4-{3-[(4-{[2-(2-furyl)-5-methyl-1,3-oxazol-4-yl]methoxy}-3-methoxybenzyl)oxy]-1-phenyl-1H-pyrazol-4-yl}-3-buten-2-one as colorless crystals (0.25 g, yield 68%) from a fraction eluted with ethyl acetate-hexane (1:2, v/v). Recrystallization from ethyl acetate-hexane gave colorless prism crystals. melting point: 177-178° C.

Example 156

To a mixture of (2E)-3-{3-[(4-{[2-(2-furyl)-5-methyl-1,3-oxazol-4-yl]methoxy}-3-methoxybenzyl)oxy]-1-phenyl-1H-pyrazol-4-yl}-N-methoxy-N-methyl-2-propenamide (0.40 g) and tetrahydrofuran (30 mL) was added dropwise ethylmagnesium bromide (1M tetrahydrofuran solution, 4.2 mL) at 0° C. and the mixture was stirred at room temperature for 2 hrs. 1N Hydrochloric acid was added to the reaction mixture, and the mixture was extracted with ethyl acetate. The organic layer was washed with saturated brine, dried over anhydrous magnesium sulfate and concentrated. The residue was subjected to silica gel column chromatography to give (1E)-1-{3-[(4-{[2-(2-furyl)-5-methyl-1,3-oxazol-4-yl]methoxy}-3-methoxybenzyl)oxy]-1-phenyl-1H-pyrazol-4-yl}-1-penten-3-one as colorless crystals (0.13 g, yield 34%) from a fraction eluted with ethyl acetate-hexane (1:1, v/v). Recrystallization from ethyl acetate-hexane gave colorless prism crystals. melting point: 167-168° C.

Example 157

To a mixture of (2E)-3-{3-[(4-{[2-(2-furyl)-5-methyl-1,3-oxazol-4-yl]methoxy}-3-methoxybenzyl)oxy]-1-phenyl-1H-pyrazol-4-yl}-N-methoxy-N-methyl-2-propenamide (0.80 g) and tetrahydrofuran (30 mL) was added dropwise propylmagnesium bromide (2M tetrahydrofuran solution, 4.2 mL) at 0° C. and the mixture was stirred at room temperature for 2 hrs. 1N Hydrochloric acid was added to the reaction mixture, and the mixture was extracted with ethyl acetate. The organic layer was washed with saturated brine, dried over anhydrous magnesium sulfate and concentrated. The residue was subjected to silica gel column chromatography to give (1E)-1-{3-[(4-{[2-(2-furyl)-5-methyl-1,3-oxazol-4-yl]methoxy}-3-methoxybenzyl)oxy]-1-phenyl-1H-pyrazol-4-yl}-1-hexen-3-one as colorless crystals (0.32 g, yield 41%) from a fraction eluted with ethyl acetate-hexane (1:1, v/v). Recrystallization from ethyl acetate-hexane gave colorless prism crystals. melting point: 167-168° C.

Example 158

To a mixture of diethyl (E)-2-{3-[(4-{[2-(2-furyl)-5-methyl-1,3-oxazol-4-yl]methoxy}-3-methoxybenzyl)oxy]-1-phenyl-1H-pyrazol-4-yl}ethenylphosphonate (0.40 g) and acetonitrile (20 mL) was added trimethylsilyl bromide (0.40 g) at room temperature. After stirring the reaction mixture at room temperature for 1 hr, trimethylsilyl bromide (0.30 g) was added again, and the mixture was further stirred for 1 hr. Water was added to the reaction mixture, and the mixture was extracted with ethyl acetate. The organic layer was washed with saturated brine, dried over anhydrous magnesium sulfate and concentrated to give (E)-2-{3-[(4-{[2-(2-furyl)-5-methyl-1,3-oxazol-4-yl]methoxy}-3-methoxybenzyl)oxy]-1-phenyl-1H-pyrazol-4-yl}ethenylphosphonic acid as pale-yellow crystals (0.28 g, yield 76%). Recrystallization from tetrahydrofuran-hexane gave pale-yellow prism crystals. melting point: 138-140° C.

Example 159

To a mixture of methyl 5-{[(4-formyl-1-phenyl-1H-pyrazol-3-yl)oxy]methyl}-2-{[2-(2-furyl)-5-methyl-1,3-oxazol-4-yl]methoxy}benzoic acid (0.83 g), tetraethyl methylenediphosphonate (0.52 g) and N,N-dimethylformamide (20 mL) was added sodium hydride (60% in oil, 0.080 g) at room temperature, and the mixture was stirred at the same temperature for 15 hrs. Water was poured into the reaction mixture, and the mixture was extracted with ethyl acetate. The organic layer was washed with saturated brine, dried over anhydrous magnesium sulfate and concentrated. The residue was subjected to silica gel column chromatography and eluted with ethyl acetate-hexane (3:2 to 9:1, v/v) to give methyl 5-[({4-[(E)-2-(diethoxyphosphoryl)ethenyl]-1-phenyl-1H-pyrazol-3-yl}oxy)methyl]-2-{[2-(2-furyl)-5-methyl-1,3-oxazol-4-yl]methoxy}benzoate as colorless crystals (0.55 g, yield 53%). Recrystallization from ethyl acetate-hexane gave colorless prism crystals. melting point: 92-93° C.

Example 160

To a mixture of methyl 5-[({4-[(E)-2-(diethoxyphosphoryl)ethenyl]-1-phenyl-1H-pyrazol-3-yl}oxy)methyl]-2-{[2-(2-furyl)-5-methyl-1,3-oxazol-4-yl]methoxy}benzoate (0.40 g), tetrahydrofuran (2 mL) and ethanol (2 mL) was added 1N aqueous sodium hydroxide solution (1 mL), and the mixture was stirred at 50° C. for 1 hr. 1N Hydrochloric acid (1 mL) and water were added to the reaction mixture, and the precipitated crystals were collected by filtration to give 5-[({4-[(E)-2-(diethoxyphosphoryl)ethenyl]-1-phenyl-1H-pyrazol-3-yl}oxy)methyl]-2-{[2-(2-furyl)-5-methyl-1,3-oxazol-4-yl]methoxy}benzoic acid as colorless crystals (0.29 g, yield 74%). Recrystallization from tetrahydrofuran-hexane gave colorless prism crystals. melting point: 169-170° C.

Example 161

To a mixture of 3-[(6-{[2-(2-furyl)-5-methyl-1,3-oxazol-4-yl]methoxy}pyridin-3-yl)methoxy]-1-phenyl-1H-pyrazole-4-carbaldehyde (0.40 g), tetraethyl methylenediphosphonate (0.28 g) and N,N-dimethylformamide (20 mL) was added sodium hydride (60% in oil, 0.040 g) at room temperature, and the mixture was stirred at the same temperature for 15 hrs. Water was poured into the reaction mixture, and the mixture was extracted with ethyl acetate. The organic layer was washed with saturated brine, dried over anhydrous magnesium sulfate and concentrated. The residue was subjected to silica gel column chromatography and eluted with ethyl acetate-hexane (3:1, v/v) to give diethyl (E)-2-{3-[(6-{[2-(2-furyl)-5-methyl-1,3-oxazol-4-yl]methoxy}pyridin-3-yl)methoxy]-1-phenyl-1H-pyrazol-4-yl}ethenylphosphonate as colorless crystals (0.38 g, yield 71%). Recrystallization from ethyl acetate-hexane gave colorless prism crystals. melting point: 134-135° C.

Example 162

To a mixture of N,O-dimethylhydroxylamine hydrochloride (0.56 g) and N,N-dimethylformamide (30 mL) was added triethylamine (0.69 g) at room temperature, and the mixture was stirred for 15 min. To the reaction mixture were added (2E)-3-{3-[(4-{[2-(2-furyl)-5-methyl-1,3-oxazol-4-yl]methoxy}-3-methoxybenzyl)oxy]-1-phenyl-1H-pyrazol-4-yl}-2-propenoic acid (2.0 g), 1-ethyl-3-(3-dimethylaminopropyl)carbodiimide hydrochloride (1.09 g) and 1-hydroxybenzotriazole monohydrate (0.87 g), and the mixture was further stirred at room temperature for 20 hr. Water was added to the reaction mixture and the precipitated crystals were collected by filtration to give (2E)-3-{3-[(4-{[2-(2-furyl)-5-methyl-1,3-oxazol-4-yl]methoxy}-3-methoxybenzyl)oxy]-1-phenyl-1H-pyrazol-4-yl}-N-methoxy-N-methyl-2-propenamide as colorless crystals (1.92 g, yield 88%). Recrystallization from ethyl acetate-hexane gave colorless prism crystals. melting point: 173-174° C.

Example 163

To a mixture of methyl 5-(chloromethyl)-2-{[2-(2-furyl)-5-methyl-1,3-oxazol-4-yl]methoxy}benzoate (1.16 g), 3-hydroxy-1-phenyl-1H-pyrazole-4-carbaldehyde (0.50 g) and N,N-dimethylformamide (30 mL) was added sodium hydride (60% in oil, 0.12 g) at room temperature, and the mixture was stirred at 90° C. for 2 hrs. Water was poured into the reaction mixture, and the mixture was extracted with ethyl acetate. The organic layer was washed with saturated brine, dried over anhydrous magnesium sulfate and concentrated to give methyl 5-{[(4-formyl-1-phenyl-1H-pyrazol-3-yl)oxy]methyl}-2-{[2-(2-furyl)-5-methyl-1,3-oxazol-4-yl]methoxy}benzoate as colorless crystals (1.07 g, yield 77%). Recrystallization from ethyl acetate-hexane gave colorless prism crystals. melting point: 173-174° C.

Example 164

To a mixture of 5-chloromethyl-2-{[2-(2-furyl)-5-methyl-1,3-oxazol-4-yl]methoxy}pyridine (0.58 g), 3-hydroxy-1-phenyl-1H-pyrazole-4-carbaldehyde (0.30 g) and N,N-dimethylformamide (20 mL) was added sodium hydride (60% in oil, 0.07 g) at room temperature, and the mixture was stirred at 90° C. for 2 hrs. Water was poured into the reaction mixture, and the mixture was extracted with ethyl acetate. The organic layer was washed with saturated brine, dried over anhydrous magnesium sulfate and concentrated. The residue was subjected to silica gel column chromatography and eluted with ethyl acetate-hexane (1:3, v/v) to give 3-[(6-{[2-(2-furyl)-5-methyl-1,3-oxazol-4-yl]methoxy}pyridin-3-yl)methoxy]-1-phenyl-1H-pyrazole-4-carbaldehyde as colorless crystals (0.56 g, yield 77%). Recrystallization from ethyl acetate-hexane gave colorless prism crystals. melting point: 122-123° C.

Example 165

To a mixture of 3-[(4-{[2-(2-furyl)-5-methyl-1,3-oxazol-4-yl]methoxy}-3-methoxybenzyl)oxy]-1-methyl-1H-pyrazole-4-carbaldehyde (1.50 g), ethyl diethylphosphonoacetate (0.87 g) and N,N-dimethylformamide (50 mL) was added sodium hydride (60% in oil, 0.17 g) at room temperature, and the mixture was stirred at the same temperature for 15 hrs. Water was poured into the reaction mixture, and the precipitated crystals were collected by filtration to give ethyl (2E)-3-{3-[(4-([2-(2-furyl)-5-methyl-1,3-oxazol-4-yl]methoxy}-3-methoxybenzyl)oxy]-1-methyl-1H-pyrazol-4-yl)-2-propenoate as colorless crystals (1.60 g, yield 92%). Recrystallization from ethyl acetate-hexane gave colorless prism crystals. melting point: 135-136° C.

Example 166

To a mixture of 3-[(4-{[2-(2-furyl)-5-methyl-1,3-oxazol-4-yl]methoxy}-3-methoxybenzyl)oxy]-1-methyl-1H-pyrazole-4-carbaldehyde (0.60 g), tetraethyl methylenediphosphonate (0.43 g) and N,N-dimethylformamide (20 mL) was added sodium hydride (60% in oil, 0.070 g) at room temperature, and the mixture was stirred at the same temperature for 15 hrs. Water was poured into the reaction mixture, and the mixture was extracted with ethyl acetate. The organic layer was washed with saturated brine, dried over anhydrous magnesium sulfate and concentrated. The residue was subjected to silica gel column chromatography and eluted with ethyl acetate-hexane (4:1 to 9:1, v/v) to give diethyl (E)-2-{3-[(4-{[2-(2-furyl)-5-methyl-1,3-oxazol-4-yl]methoxy}-3-methoxybenzyl)oxy]-1-methyl-1H-pyrazol-4-yl}ethenylphosphonate as colorless crystals (0.43 g, yield 55%). Recrystallization from ethyl acetate-hexane gave colorless prism crystals. melting point: 72-73° C.

Example 167

A mixture of 3-[(4-{[2-(2-furyl)-5-methyl-1,3-oxazol-4-yl]methoxy}-3-methoxybenzyl)oxy]-1-methyl-1H-pyrazole-4-carbaldehyde (0.50 g), [(1,3-thiazol-4-yl)methyl]triphenylphosphonium chloride (0.95 g), potassium carbonate (0.33 g) and N,N-dimethylformamide (20 mL) was stirred at room temperature for 15 hrs, and further stirred at 50° C. for 3 hrs. Water was poured into the reaction mixture, and the mixture was extracted with ethyl acetate. The organic layer was washed with saturated brine, dried over anhydrous magnesium sulfate and concentrated. The residue was subjected to silica gel column chromatography and eluted with ethyl acetate-hexane (1:1 to 3:1, v/v) to give 2-(2-furyl)-4-({2-methoxy-4-[({1-methyl-4-[(Z)-2-(1,3-thiazol-4-yl)ethenyl]-1H-pyrazol-3-yl}oxy)methyl]phenoxy}methyl)-5-methyl-1,3-oxazole as colorless crystals (0.16 g, yield 26%). Recrystallization from ethyl acetate-hexane gave colorless prism crystals. melting point: 97-98° C.

In addition, 2-(2-furyl)-4-({2-methoxy-4-[({1-methyl-4-[(E)-2-(1,3-thiazol-4-yl)ethenyl]-1H-pyrazol-3-yl}oxy)methyl]phenoxy}methyl)-5-methyl-1,3-oxazole was obtained as colorless crystals (0.22 g, yield 36%) from a fraction successively obtained by elution. Recrystallization from ethyl acetate-diisopropyl ether gave colorless prism crystals. melting point: 134-135° C.

Example 168

To a mixture of 1-ethyl-3-[(4-{[2-(2-furyl)-5-methyl-1,3-oxazol-4-yl]methoxy}-3-methoxybenzyl)oxy]-1H-pyrazole-4-carbaldehyde (0.50 g), ethyl diethylphosphonoacetate (0.27 g) and N,N-dimethylformamide (10 mL) was added sodium hydride (60% in oil, 0.05 g) at room temperature, and the mixture was stirred at the same temperature for 15 hrs. Water was poured into the reaction mixture, and the precipitated crystals were collected by filtration to give ethyl (2E)-3-{1-ethyl-3-[(4-{[2-(2-furyl)-5-methyl-1,3-oxazol-4-yl]methoxy}-3-methoxybenzyl)oxy]-1H-pyrazol-4-yl}-2-propenoate as colorless crystals (0.51 g, yield 91%).

Example 169

To a mixture of 1-ethyl-3-[(4-{[2-(2-furyl)-5-methyl-1,3-oxazol-4-yl]methoxy}-3-methoxybenzyl)oxy]-1H-pyrazole-4-carbaldehyde (0.50 g), tetraethyl methylenediphosphonate (0.35 g) and N,N-dimethylformamide (10 mL) was added sodium hydride (60% in oil, 0.050 g) at room temperature, and the mixture was stirred at the same temperature for 15 hrs. Water was poured into the reaction mixture, and the mixture was extracted with ethyl acetate. The organic layer was washed with saturated brine, dried over anhydrous magnesium sulfate and concentrated. The residue was subjected to silica gel column chromatography and eluted with ethyl acetate-hexane (9:1, v/v) to give diethyl (E)-2-{1-ethyl-3-[(4-{[2-(2-furyl)-5-methyl-1,3-oxazol-4-yl]methoxy}-3-methoxybenzyl)oxy]-1H-pyrazol-4-yl}ethenylphosphonate as colorless crystals (0.41 g, yield 65%). Recrystallization from ethyl acetate-hexane gave colorless prism crystals. melting point: 82-84° C.

Example 170

To a mixture of 3-[(4-{[2-(2-furyl)-5-methyl-1,3-oxazol-4-yl]methoxy}-3-methoxybenzyl)oxy]-1-(2-hydroxyethyl)-1H-pyrazole-4-carbaldehyde (0.50 g), tetraethyl methylenediphosphonate (0.30 g) and N,N-dimethylformamide (15 mL) was added sodium hydride (60% in oil, 0.060 g) at room temperature, and the mixture was stirred at the same temperature for 15 hrs. Water was poured into the reaction mixture, and the mixture was extracted with ethyl acetate. The organic layer was washed with saturated brine, dried over anhydrous magnesium sulfate and concentrated. The residue was subjected to silica gel column chromatography and eluted with ethyl acetate-methanol (100:1, v/v) to give diethyl (E)-2-[3-[(4-{[2-(2-furyl)-5-methyl-1,3-oxazol-4-yl]methoxy}-3-methoxybenzyl)oxy]-1-(2-hydroxyethyl)-1H-pyrazol-4-yl]ethenylphosphonate as colorless crystals (0.06 g, yield 15%). Recrystallization from ethyl acetate-hexane gave colorless prism crystals. melting point: 95-96° C.

Example 171

To a mixture of 4-[(4-chloromethyl-2-methoxyphenoxy)methyl]-2-(2-furyl)-5-methyl-1,3-oxazole (7.63 g), ethyl 3-hydroxy-1-methyl-1H-pyrazole-4-carboxylate (3.0 g) and N,N-dimethylformamide (50 mL) was added sodium hydride (60% in oil, 0.78 g) at room temperature, and the mixture was stirred at 90° C. for 2 hrs. Water was poured into the reaction mixture, and the mixture was extracted with ethyl acetate. The organic layer was washed with saturated brine, dried over anhydrous magnesium sulfate and concentrated to give ethyl 3-[(4-{[2-(2-furyl)-5-methyl-1,3-oxazol-4-yl]methoxy}-3-methoxybenzyl)oxy]-1-methyl-1H-pyrazole-4-carboxylate as pale-brown crystals (8.03 g, yield 98%). Recrystallization from acetone-hexane gave colorless prism crystals. melting point: 117-118° C.

Example 172

To a mixture of 4-[(4-chloromethyl-2-methoxyphenoxy)methyl]-2-(2-furyl)-5-methyl-1,3-oxazole (3.50 g), ethyl 1-ethyl-3-hydroxy-1H-pyrazole-4-carboxylate (1.50 g) and N,N-dimethylformamide (30 mL) was added sodium hydride (60% in oil, 0.36 g) at room temperature, and the mixture was stirred at 90° C. for 2 hrs. Water was poured into the reaction mixture, and the mixture was extracted with ethyl acetate. The organic layer was washed with saturated brine, dried over anhydrous magnesium sulfate and concentrated. The residue was subjected to silica gel column chromatography to give ethyl 1-ethyl-3-[(4-{[2-(2-furyl)-5-methyl-1,3-oxazol-4-yl]methoxy}-3-methoxybenzyl)oxy]-1H-pyrazole-4-carboxylate as colorless crystals (2.94 g, yield 75%) from a fraction eluted with ethyl acetate-hexane (2:1, v/v). Recrystallization from ethyl acetate-hexane gave colorless prism crystals. melting point: 114-115° C.

Example 173

To a mixture of diethyl (E)-2-[3-({4-[(5-methyl-2-phenyl-1,3-oxazol-4-yl)methoxy]benzoyl}amino)-1-phenyl-1H-pyrazol-4-yl]ethenylphosphonate (50 mg), sodium hydride (60% in oil, 3.9 mg) and N,N-dimethylformamide (2 mL) was added methyl iodide (14 mg) with stirring, and the mixture was further stirred at room temperature for 2 hrs. Water was poured into the reaction mixture, and the mixture was extracted with ethyl acetate. The ethyl acetate layer was washed successively with distilled water and saturated brine, dried over anhydrous magnesium sulfate and concentrated. The residue was purified by reverse phase partition-high performance liquid chromatography (elution with distilled water containing 0.1% trifluoroacetic acid/acetonitrile) to give a colorless oil. To remove remaining trifluoroacetic acid, water was added to the oil, and the mixture was extracted with ethyl acetate. The ethyl acetate layer was dried over anhydrous magnesium sulfate and concentrated to give diethyl (E)-2-[3-(methyl{4-[(5-methyl-2-phenyl-1,3-oxazol-4-yl)methoxy]benzoyl}amino)-1-phenyl-1H-pyrazol-4-yl]ethenylphosphonate as a colorless oil (42.5 mg, yield 83%)

NMR(CDCl$_3$) δ: 1.36 (6H, t, J 7.1 Hz), 2.39 (3H, s), 3.49 (3H, s), 4.03-4.16 (4H, m), 4.91 (2H, s), 5.90 (1H, t, J=17.9 Hz), 6.80 (2H, d, J=9.0 Hz), 7.04-7.60 (11H, m), 7.93-8.00 (3H, m)

Example 174

To a solution of ethyl 3-[(4-{[2-(2-furyl)-5-methyl-1,3-oxazol-4-yl]methoxy}-3-methoxybenzyl)oxy]-1-methyl-1H-pyrazole-4-carboxylate (7.54 g) in tetrahydrofuran (100 mL) was added lithium aluminum hydride (0.61 g) at 0° C. and the mixture was stirred at room temperature for 1 hr. Sodium sulfate decahydrate (5.19 g) was added to the reaction mixture and the mixture was stirred at room temperature for 30 min. The reaction mixture was diluted with ethyl acetate and the precipitate was filtered off, and the filtrate was concentrated. The residue was subjected to silica gel column chromatography to give {3-[(4-{[2-(2-furyl)-5-methyl-1,3-oxazol-4-yl]methoxy}-3-methoxybenzyl)oxy]-1-methyl-1H-pyrazol-4-yl}methanol as colorless crystals (4.15 g, yield 61%) from a fraction eluted with ethyl acetate-hexane (5:1, v/v). Recrystallization from ethyl acetate-hexane gave colorless prism crystals. melting point: 132-133° C.

Example 175

To a solution of ethyl 1-ethyl-3-[(4-{[2-(2-furyl)-5-methyl-1,3-oxazol-4-yl]methoxy}-3-methoxybenzyl)oxy]-1H-pyrazole-4-carboxylate (2.80 g) in tetrahydrofuran (50 mL) was added lithium aluminum hydride (0.22 g) at 0° C. and the mixture was stirred at room temperature for 1 hr. Sodium (continued: Recrystallization from ethyl acetate-hexane gave colorless prism crystals. melting point: 149-150° C.)

sulfate decahydrate (1.87 g) was added to the reaction mixture, and the mixture was stirred at room temperature for 30 min. The reaction mixture was diluted with ethyl acetate and the precipitate was filtered off. The filtrate was concentrated to give {1-ethyl-3-[(4-{[2-(2-furyl)-5-methyl-1,3-oxazol-4-yl]methoxy}-3-methoxybenzyl)oxy]-1H-pyrazol-4-yl}methanol as colorless crystals (2.32 g, yield 91%). Recrystallization from ethyl acetate-hexane gave colorless prism crystals. melting point: 117-118° C.

Example 176

To a solution of ethyl {4-ethoxycarbonyl-3-[(4-{[2-(2-furyl)-5-methyl-1,3-oxazol-4-yl]methoxy}-3-methoxybenzyl)oxy]-1H-pyrazol-1-yl}acetate (1.24 g) in tetrahydrofuran (30 mL) was added lithium aluminum hydride (0.17 g) at 0° C. and the mixture was stirred at room temperature for 1 hr. Sodium sulfate decahydrate (1.48 g) was added to the reaction mixture, and the mixture was stirred at room temperature for 30 min. The reaction mixture was diluted with ethyl acetate and the precipitate was filtered off. The filtrate was concentrated to give 2-[3-[(4-{[2-(2-furyl)-5-methyl-1,3-oxazol-4-yl]methoxy}-3-methoxybenzyl)oxy]-4-(hydroxymethyl)-1H-pyrazol-1-yl]ethanol as colorless crystals (0.73 g, yield 70%). Recrystallization from ethyl acetate-hexane gave colorless prism crystals. melting point: 120-122° C.

Example 177

A mixture of {3-[(4-{[2-(2-furyl)-5-methyl-1,3-oxazol-4-yl]methoxy}-3-methoxybenzyl)oxy]-1-methyl-1H-pyrazol-4-yl}methanol (3.80 g), activated manganese dioxide (12.0 g) and tetrahydrofuran (150 mL) was stirred at room temperature for 15 hrs. Manganese dioxide was removed by filtration and the filtrate was concentrated. The obtained crystals were collected by filtration to give 3-[(4-{[2-(2-furyl)-5-methyl-1,3-oxazol-4-yl]methoxy}-3-methoxybenzyl)oxy]-1-methyl-1H-pyrazole-4-carbaldehyde (3.64 g, yield 97%). Recrystallization from ethyl acetate-hexane gave colorless prism crystals. melting point: 155-156° C.

Example 178

A mixture of {1-ethyl-3-[(4-{[2-(2-furyl)-5-methyl-1,3-oxazol-4-yl]methoxy}-3-methoxybenzyl)oxy]-1H-pyrazol-4-yl}methanol (2.19 g), activated manganese dioxide (6.0 g) and tetrahydrofuran (100 mL) was stirred at room temperature for 15 hrs. Manganese dioxide was removed by filtration and the filtrate was concentrated. The obtained crystals were collected by filtration to give 1-ethyl-3-[(4-{[2-(2-furyl)-5-methyl-1,3-oxazol-4-yl]methoxy}-3-methoxybenzyl)oxy]-1H-pyrazole-4-carbaldehyde (1.95 g, yield 89%). Recrystallization from ethyl acetate-hexane gave colorless prism crystals. melting point: 103-104° C.

Example 179

A mixture of 2-[3-[(4-{[2-(2-furyl)-5-methyl-1,3-oxazol-4-yl]methoxy}-3-methoxybenzyl)oxy]-4-(hydroxymethyl)-1H-pyrazol-1-yl]ethanol (0.63 g), activated manganese dioxide (1.5 g) and tetrahydrofuran (100 mL) was stirred at room temperature for 15 hrs. Manganese dioxide was removed by filtration and the filtrate was concentrated. The obtained crystals were collected by filtration to give 3-[(4-{[2-(2-furyl)-5-methyl-1,3-oxazol-4-yl]methoxy}-3-methoxybenzyl)oxy]-1-(2-hydroxyethyl)-1H-pyrazole-4-carbaldehyde (0.61 g, yield 97%). Recrystallization from ethyl acetate-hexane gave colorless prism crystals. melting point: 149-150° C.

Example 180

To a mixture of {3-[(4-{[2-(2-furyl)-5-methyl-1,3-oxazol-4-yl]methoxy}-3-methoxybenzyl)oxy]-1-phenyl-1H-pyrazol-4-yl}acetic acid (0.20 g), N,N-dimethylformamide (0.02 mL) and tetrahydrofuran (5 mL) was added oxalyl chloride (0.06 g) at room temperature. The reaction mixture was stirred at room temperature for 1 hr. and concentrated. Triethyl phosphite (1.0 mL) was added to the residue, and the mixture was stirred at room temperature for 1 hr. Diethyl ether was added to the reaction mixture, and the precipitated crystals were collected by filtration to give diethyl (E)-2-{3-[(4-{[2-(2-furyl)-5-methyl-1,3-oxazol-4-yl]methoxy}-3-methoxybenzyl)oxy]-1-phenyl-1H-pyrazol-4-yl}-1-hydroxyethenylphosphonate as pale-yellow crystals (0.14 g, yield 56%). Recrystallization from ethyl acetate-diethyl ether gave colorless prism crystals. melting point: 147-149° C.

Example 181

To a mixture of potassium tert-butoxide (0.19 g) and tetrahydrofuran (10 mL) added dropwise a solution of toluenesulfonylmethylisocyanide (0.23 g) in tetrahydrofuran (5 mL) at −30° C., and the mixture was stirred at the same temperature for 10 min. To the reaction mixture was added dropwise a solution of (2E)-3-{3-[(4-{[2-(2-furyl)-5-methyl-1,3-oxazol-4-yl]methoxy}-3-methoxybenzyl)oxy]-1-phenyl-1H-pyrazol-4-yl}-2-propenaldehyde (0.60 g) in tetrahydrofuran (5 mL) at −40° C., and the mixture was stirred at the same temperature for 1 hr. The reaction mixture was poured into ice water, acetic acid was added for neutralization, and the mixture was extracted with ethyl acetate. The organic layer was washed with saturated brine, dried over anhydrous magnesium sulfate and concentrated. The residue was subjected to silica gel column chromatography to give yellow crystal from a fraction eluted with ethyl acetate-hexane (2:1, v/v). To a mixture of the crystal and tetrahydrofuran (30 mL) was added triethylamine (0.61 g) at −10° C. To the reaction mixture was added a solution of phosphorous oxychloride (0.21 g) in tetrahydrofuran (10 mL), and stirred at −10° C. for 30 min. The reaction mixture was poured into water and the mixture was extracted with ethyl acetate. The organic layer was washed with saturated brine, dried over anhydrous magnesium sulfate and concentrated. A mixture of the obtained residue, methylamine (2M tetrahydrofuran solution, 15 mL) and methanol (15 mL) was stirred at room temperature for 1 hr. The reaction mixture was concentrated, and the obtained residue was subjected to silica gel column chromatography to give 2-(2-furyl)-4-({2-methoxy-4-[({4-[(E)-2-(1-methyl-1H-imidazol-5-yl)ethenyl]-1-phenyl-1H-pyrazol-3-yl}oxy)methyl]phenoxy}methyl)-5-methyl-1,3-oxazole as colorless crystals (0.19 g, yield 28%) from a fraction eluted with ethyl acetate-methanol (10:1, v/v). Recrystallization from ethyl acetate-hexane gave colorless prism crystals. melting point: 144-145° C.

Example 182

To a mixture of potassium tert-butoxide (0.27 g) and tetrahydrofuran (10 mL) was added dropwise a solution of toluenesulfonylmethylisocyanide. (0.31 g) in tetrahydrofuran (10 mL) at −30° C., and the mixture was stirred at the same temperature for 10 min. To the reaction mixture was added dropwise a solution of (2E)-3-{3-[(4-{[2-(2-furyl)-5-methyl-1,3-oxazol-4-yl]methoxy}-3-methoxybenzyl)oxy]-1-phenyl-1H-pyrazol-4-yl}-2-propenaldehyde (0.83 g) in tetrahydrofuran (10 mL) at −40° C., and the mixture was stirred at the same temperature for 1 hr. The reaction mixture was poured into ice water, acetic acid was added for neutralization, and the mixture was extracted with ethyl acetate. The organic layer was washed with saturated brine, dried over anhydrous magnesium sulfate and concentrated. The residue was subjected to silica gel column chromatography to give yellow crystals from a fraction eluted with ethyl acetate-hexane (2:1, v/v). To a mixture of the crystal and tetrahydrofuran (50 mL) was added triethylamine (0.81 g) at −10° C. A solution of phosphorous oxychloride (0.29 g) in tetrahydrofuran (50 mL) was added to the reaction mixture, and the mixture was stirred at −10° C. for 30 min. The reaction mixture was poured into water and the mixture was extracted with ethyl acetate. The organic layer was washed with saturated brine, dried over anhydrous magnesium sulfate and concentrated. A mixture of the obtained residue, ethylamine (70% aqueous solution, 3 mL) and methanol (10 mL) was stirred at room temperature for 1 hr. The reaction mixture was concentrated. The residue was subjected to silica gel column chromatography to give 4-({4-[({4-[(E)-2-(1-ethyl-1H-imidazol-5-yl)ethenyl]-1-phenyl-1H-pyrazol-3-yl}oxy)methyl]-2-methoxyphenoxy}methyl)-2-(2-furyl)-5-methyl-1,3-oxazole as pale-yellow crystals (0.19 g, yield 21%) from a fraction eluted with ethyl acetate-methanol (10:1, v/v). Recrystallization from ethyl acetate-hexane gave pale-yellow needle crystals. melting point: 130-132° C.

Example 183

To a mixture of (2E)-3-{3-[(4-{[2-(2-furyl)-5-methyl-1,3-oxazol-4-yl]methoxy}-3-methoxybenzyl)oxy]-1-phenyl-1H-pyrazol-4-yl}-2-propenaldehyde (0.51 g), tetraethyl methylenediphosphonate (0.32 g) and N,N-dimethylformamide (10 mL) was added sodium hydride (60% in oil, 0.050 g) at room temperature, and the mixture was stirred at the same temperature for 15 hrs. Water was poured into the reaction mixture, and the mixture was extracted with ethyl acetate. The organic layer was washed with saturated brine, dried over anhydrous magnesium sulfate and concentrated. The residue was subjected to silica gel column chromatography to give diethyl (1E,3E)-4-{3-[(4-{[2-(2-furyl)-5-methyl-1,3-oxazol-4-yl]methoxy}-3-methoxybenzyl)oxy]-1-phenyl-1H-pyrazol-4-yl}-1,3-butadienylphosphonate as colorless crystals (0.53 g, yield 82%) from a fraction eluted with ethyl acetate-hexane (8:1, v/v). Recrystallization from ethyl acetate-hexane gave colorless prism crystals. melting point: 143-144° C.

Example 184

A mixture of (2E)-3-{3-[(4-{[2-(2-furyl)-5-methyl-1,3-oxazol-4-yl]methoxy}-3-methoxybenzyl)oxy]-1-phenyl-1H-pyrazol-4-yl}-2-propenamide (2.50 g), Lawesson's reagent (2.26 g) and pyridine (15 mL) was heated under reflux for 30 min. After concentration of the reaction mixture, water was added to the residue, and the mixture was extracted with ethyl acetate. The organic layer was washed with saturated brine, dried over anhydrous magnesium sulfate and concentrated. The residue was subjected to silica gel column chromatography to give (2E)-3-{3-[(4-{[2-(2-furyl)-5-methyl-1,3-oxazol-4-yl]methoxy}-3-methoxybenzyl)oxy]-1-phenyl-1H-pyrazol-4-yl}-2-propenethioamide as yellow crystals (0.56 g, yield 22%) from a fraction eluted with ethyl acetate-hexane (1:1, v/v). Recrystallization from ethyl acetate-diethyl ether gave yellow prism crystals. melting point: 129-131° C.

Example 185

A mixture of (2E)-3-{3-[(4-{[2-(2-furyl)-5-methyl-1,3-oxazol-4-yl]methoxy}-3-methoxybenzyl)oxy]-1-phenyl-1H-pyrazol-4-yl}-2-propenethioamide (0.46 g), 1-bromo-2-propanone (0.13 g) and ethanol (30 mL) was heated under reflux for 1 hr. After concentration of the reaction mixture, saturated aqueous sodium hydrogen carbonate was added to the residue, and the mixture was extracted with ethyl acetate. The organic layer was washed with saturated brine, dried over anhydrous magnesium sulfate and concentrated. The residue was subjected to silica gel column chromatography to give 2-(2-furyl)-4-({2-methoxy-4-[({4-[(E)-2-(4-methyl-1,3-thiazol-2-yl)ethenyl]-1-phenyl-1H-pyrazol-3-yl}oxy)methyl]phenoxy}methyl)-5-methyl-1,3-oxazole as pale-yellow crystals (0.25 g, yield 51%) from a fraction eluted with ethyl acetate-hexane (1:1, v/v). Recrystallization from ethyl acetate-hexane gave pale-yellow prism crystals. melting point: 130-131° C.

Example 186

A mixture of (2E)-3-{3-[(4-{[2-(2-furyl)-5-methyl-1,3-oxazol-4-yl]methoxy}-3-methoxybenzyl)oxy]-1-phenyl-1H-pyrazol-4-yl}-2-propenethioamide (0.45 gmmol), ethyl bromopyruvate (0.20 g) and ethanol (30 mL) was heated under reflux for 1 hr. The reaction mixture was concentrated and ethyl acetate was added to the residue. The organic layer was washed successively with saturated aqueous sodium hydrogen carbonate and saturated brine, dried over anhydrous magnesium sulfate and concentrated. The residue was subjected to silica gel column chromatography to give ethyl 2-((E)-2-{3-[(4-{[2-(2-furyl)-5-methyl-1,3-oxazol-4-yl]methoxy}-3-methoxybenzyl)oxy]-1-phenyl-1H-pyrazol-4-yl}ethenyl)-1,3-thiazole-4-carboxylate as yellow crystals (0.35 g, yield 66%) from a fraction eluted with ethyl acetate-hexane (2:1, v/v). Recrystallization from ethyl acetate-hexane gave yellow prism crystals. melting point: 156-157° C.

Example 187

To a mixture of ethyl 2-((E)-2-{3-[(4-{[2-(2-furyl)-5-methyl-1,3-oxazol-4-yl]methoxy}-3-methoxybenzyl)oxy]-1-phenyl-1H-pyrazol-4-yl}ethenyl)-1,3-thiazole-4-carboxylate (0.13 g), tetrahydrofuran (1 mL) and ethanol (1 mL) was added 1N aqueous sodium hydroxide solution (1 mL), and the mixture was heated under reflux for 1 hr. To the reaction mixture were added 1N hydrochloric acid (1 mL) and water, and the precipitated crystals were collected by filtration to give 2-((E)-2-{3-[(4-{[2-(2-furyl)-5-methyl-1,3-oxazol-4-yl]methoxy}-3-methoxybenzyl)oxy]-1-phenyl-1H-pyrazol-4-yl}ethenyl)-1,3-thiazole-4-carboxylic acid as yellow crystals (0.08 g, yield 67%). Recrystallization from tetrahydrofuran-hexane gave yellow prism crystals. melting point: 170-172° C.

Example 188

To a mixture of (2E)-3-{3-[(4-{[2-(2-furyl)-5-methyl-1,3-oxazol-4-yl]methoxy}-3-methoxybenzyl)oxy]-1-phenyl- 1H-pyrazol-4-yl}-2-propenoic acid (1.0 g), 4-methylmorpholine (0.25 g) and tetrahydrofuran (80 mL) was added dropwise isobutyl chlorocarbonate (0.37 g) at 0° C., and the mixture was stirred at room temperature for 1 hr. The precipitate was filtered off, and the filtrate was added to a mixture of hydrazine monohydrate (0.48 g) and tetrahydrofuran (20 mL). The obtained mixture was stirred at room temperature for 1 hr and diluted with ethyl acetate. The ethyl acetate layer was washed successively with water, saturated aqueous ammonium chloride solution and saturated brine, dried over anhydrous magnesium sulfate and concentrated. A mixture of the obtained residue, ethyl acetimidate hydrochloride (0.28 g), triethylamine (0.26 g) and tetrahydrofuran (100 mL) was stirred at room temperature for 15 hrs and ethyl acetate was added. The ethyl acetate layer was washed successively with saturated aqueous sodium hydrogen carbonate and saturated brine, dried over anhydrous magnesium sulfate and concentrated. Xylene (100 mL) was added to the residue and the mixture was heated under reflux for 15 hrs. After concentration of the reaction mixture, the residue was subjected to silica gel column chromatography to give 3-((E)-2-{3-[(4-{[2-(2-furyl)-5-methyl-1,3-oxazol-4-yl]methoxy}-3-methoxybenzyl)oxy]-1-phenyl-1H-pyrazol-4-yl}ethenyl)-5-methyl-4H-1,2,4-triazole as pale-yellow crystals (0.18 g, yield 17%) from a fraction eluted with ethyl acetate-methanol (100:1, v/v). Recrystallization from ethyl acetate-hexane gave pale-yellow prism crystals. melting point: 165-166° C.

Example 189

To a mixture of (2E)-3-{3-[(4-{[2-(2-furyl)-5-methyl-1,3-oxazol-4-yl]methoxy}-3-methoxybenzyl)oxy]-1-phenyl-1H-pyrazol-4-yl}-2-propenoic acid (1.0 g), 4-methylmorpholine (0.25 g) and tetrahydrofuran (80 mL) was added dropwise isobutyl chlorocarbonate (0.37 g) at 0° C., and the mixture was stirred at room temperature for 1 hr. The precipitate was filtered off, and the filtrate was added to a mixture of hydrazine monohydrate (0.48 g) and tetrahydrofuran (20 mL). The obtained mixture was stirred at 0° C. for 1 hr and diluted with ethyl acetate. The ethyl acetate layer was washed successively with water, saturated aqueous ammonium chloride solution and saturated brine, dried over anhydrous magnesium sulfate and concentrated. A mixture of the obtained residue, acetic acid (0.14 g), triethylamine (0.49 g), 1-hydroxybenzotriazole monohydrate (0.32 g) and N,N-dimethylformamide (30 mL) was stirred at room temperature for 5 min. To the reaction mixture was added 1-ethyl-3-(3-dimethylaminopropyl)carbodiimide hydrochloride (0.44 g), and the mixture was stirred at room temperature for 15 hrs. Water was added to the reaction mixture, and the mixture was extracted with a mixed solvent of ethyl acetate and tetrahydrofuran. The organic layer was washed with saturated brine, dried over anhydrous magnesium sulfate and concentrated. The obtained crystals were washed with diethyl ether to give (2E)-N'-acetyl-3-{3-[(4-{[2-(2-furyl)-5-methyl-1,3-oxazol-4-yl]methoxy}-3-methoxybenzyl)oxy]-1-phenyl-1H-pyrazol-4-yl}-2-propenohydrazide as colorless crystals (0.65 g, yield 59%). Recrystallization from tetrahydrofuran-hexane gave colorless prism crystals. melting point: 221-222° C.

Example 190

To a mixture of 3-[(3-methoxy-4-{[2-(piperidin-1-yl)-1,3-thiazol-4-yl]methoxy}benzyl)oxy]-1-phenyl-1H-pyrazole-4-carbaldehyde. (0.40 g), tetraethyl methylenediphosphonate (0.25 g) and N,N-dimethylformamide (10 mL) was added sodium hydride (60% in oil, 0.040 g) at room temperature, and the mixture was stirred at the same temperature for 15 hrs. Water was poured into the reaction mixture, and the mixture was extracted with ethyl acetate. The organic layer was washed with saturated brine, dried over anhydrous magnesium sulfate and concentrated. The residue was subjected to silica gel column chromatography to give diethyl [(E)-2-(3-{[3-methoxy-4-{[2-(piperidin-1-yl)-1,3-thiazol-4-yl]methoxy}benzyl]oxy}-1-phenyl-1H-pyrazol-4-yl)ethenylphosphonate as colorless crystals (0.36 g, yield 72%) from a fraction eluted with ethyl acetate-hexane (4:1, v/v). Recrystallization from ethyl acetate-hexane gave colorless prism crystals. melting point: 99-100° C.

Example 191

To a mixture of 3-[(3-methoxy-4-{[2-(morpholin-4-yl)-1,3-thiazol-4-yl]methoxy}benzyl)oxy]-1-phenyl-1H-pyrazole-4-carbaldehyde (0.40 g), tetraethyl methylenediphosphonate (0.25 g) and N,N-dimethylformamide (10 mL) was added sodium hydride (60% in oil, 0.040 g) at room temperature, and the mixture was stirred at the same temperature for 15 hrs. Water was poured into the reaction mixture, and the mixture was extracted with ethyl acetate. The organic layer was washed with saturated brine, dried over anhydrous magnesium sulfate and concentrated. The residue was subjected to silica gel column chromatography to give diethyl (E)-2-{3-[(3-methoxy-4-{[2-(morpholin-4-yl)-1,3-thiazol-4-yl]methoxy}benzyl)oxy]-1-phenyl-1H-pyrazol-4-yl}ethenylphosphonate as colorless crystals (0.36 g, yield 71%) from a fraction eluted with ethyl acetate-hexane (4:1, v/v). Recrystallization from ethyl acetate-hexane gave colorless prism crystals. melting point: 93-94° C.

Example 192

To a mixture of 3-[(3-methoxy-4-{[5-methyl-2-(piperidin-1-yl)-1,3-thiazol-4-yl]methoxy}benzyl)oxy]-1-phenyl-1H-pyrazole-4-carbaldehyde (0.15 g), tetraethyl methylenediphosphonate (0.09 g) and N,N-dimethylformamide (5 mL) was added sodium hydride (60% in oil, 0.015 g) at room temperature, and the mixture was stirred at the same temperature for 15 hrs. Water was poured into the reaction mixture, and the mixture was extracted with ethyl acetate. The organic layer was washed with saturated brine, dried over anhydrous magnesium sulfate and concentrated. The residue was subjected to silica gel column chromatography to give diethyl (E)-2-{3-[(3-methoxy-4-{[5-methyl-2-(piperidin-1-yl)-1,3-thiazol-4-yl]methoxy}benzyl)oxy]-1-phenyl-1H-pyrazol-4-yl}ethenylphosphonate as colorless crystals (0.11 g, yield 58%) from a fraction eluted with ethyl acetate-hexane (4:1, v/v). Recrystallization from ethyl acetate-hexane gave colorless prism crystals. melting point: 95-96° C.

Example 193

A mixture of 3-[(3-methoxy-4-{[2-(piperidin-1-yl)-1,3-thiazol-4-yl]methoxy}benzyl)oxy]-1-phenyl-1H-pyrazole-4-carbaldehyde (0.60 g), [(2-ethyl-1,3-thiazol-4-yl)methyl]triphenylphosphonium chloride (0.76 g), potassium carbonate (0.17 g) and N,N-dimethylformamide (20 mL) was stirred at room temperature for 15 hrs. Water was poured into the reaction mixture, and the mixture was extracted with ethyl acetate. The organic layer was washed with saturated brine, dried over anhydrous magnesium sulfate and concentrated. The residue was subjected to silica gel column chromatography and eluted with ethyl acetate-hexane (1:2, v/v) to give 1-[4-({4-[({4-[(Z)-2-(2-ethyl-1,3-thiazol-4-yl)ethenyl]-1-phenyl-1H-pyrazol-3-yl}oxy)methyl]-2-methoxyphenoxy}methyl)-1,3-thiazol-2-yl]piperidine as colorless crystals (0.13 g, yield 18%). The crystals were recrystallized from ethyl acetate-hexane. melting point: 93-94° C.

In addition, 1-[4-({4-[({4-[(E)-2-(2-ethyl-1,3-thiazol-4-yl)ethenyl]-1-phenyl-1H-pyrazol-3-yl}oxy)methyl]-2-methoxyphenoxy}methyl)-1,3-thiazol-2-yl]piperidine was obtained as a colorless oil (0.30 g, yield 41%) from a fraction successively obtained by elution.

NMR(CDCl$_3$) δ: 1.41 (3H, t, J=7.5 Hz), 1.60-1.75 (6H, m), 3.05 (2H, q, J=7.5 Hz), 3.43-3.46 (4H, m), 3.92 (3H, s), 5.10 (2H, d, J=1.2 Hz), 5.38 (2H, s), 6.52 (1H, s), 6.86 (1H, s), 6.96-7.31 (6H, m), 7.39-7.45 (2H, m), 7.59-7.63 (2H, m), 7.82 (1H, s).

Example 194

To a mixture of diethyl (E)-2-[3-({3-methoxy-4-[(5-ethyl-2-phenyl-1,3-oxazol-4-yl)methoxy]benzoyl}amino)-1-phenyl-1H-pyrazol-4-yl]ethenylphosphonate (50 mg), sodium hydride (60% in oil, 3.9 mg) and N,N-dimethylformamide (2 mL) was added methyl iodide (14 mg) with stirring, and the mixture was further stirred at room temperature for 2 hrs. Water was poured into the reaction mixture, and the mixture was extracted with ethyl acetate. The ethyl acetate layer was washed successively with distilled water and saturated brine, dried over anhydrous magnesium sulfate and concentrated. The residue was purified by reverse phase partition-high performance liquid chromatography (elution with distilled water containing 0.1% trifluoroacetic acid/acetonitrile) to give a colorless oil compound. To remove remaining trifluoroacetic acid, water was added to the oil compound, and the mixture was extracted with ethyl acetate. The ethyl acetate layer was dried over anhydrous magnesium sulfate and concentrated to give diethyl (E)-2-{3-[{3-methoxy-4-[(5-methyl-2-phenyl-1,3-oxazol-4-yl)methoxy]benzoyl}(methyl)amino]-1-phenyl-1H-pyrazol-4-yl}ethenylphosphonate as a colorless oil (20.8 mg, yield 41%).

NMR(CDCl$_3$) δ: 1.34 (6H, t, J=7.1 Hz), 2.36 (3H, s), 3.48 (3H, s), 3.70 (3H, s), 4.02-4.13 (4H, m), 4.97 (2H, s), 5.92 (1H, t, J=17.6 Hz), 6.81 (1H, d, J=8.4 Hz), 6.99 (1H, dd, J=8.4, 2.1 Hz), 7.07-7.20 (2H, m), 7.32-7.49 (6H, m), 7.55-7.58 (2H, m), 7.91 (1H, s), 7.95-7.98 (2H, m).

Example 195

To a mixture of 3-[(4-{[2-(2-furyl)-5-methyl-1,3-oxazol-4-yl]methoxy}-3-methoxybenzyl)oxy]-1-(pyridin-3-ylmethyl)-1H-pyrazole-4-carbaldehyde (0.17 g), tetraethyl methylenediphosphonate (0.11 g) and N,N-dimethylformamide (5 mL) was added sodium hydride (60% in oil, 0.015 g) at room temperature, and the mixture was stirred at the same temperature for 15 hrs. Water was poured into the reaction mixture, and the mixture was extracted with ethyl acetate. The organic layer was washed with saturated brine, dried over anhydrous magnesium sulfate and concentrated. The residue was subjected to silica gel column chromatography to give diethyl (E)-2-[3-[(4-{[2-(2-furyl)-5-methyl-1,3-oxazol-4-yl]methoxy}-3-methoxybenzyl)oxy]-1-(pyridin-3-ylmethyl)-1H-pyrazol-4-yl]ethenylphosphonate as a colorless oil (0.19 g, yield 86%) from a fraction eluted with ethyl acetate-hexane (4:1, v/v).

NMR(CDCl$_3$) δ: 1.30 (6H, t, J=7.2 Hz), 2.42 (3H, s), 3.85 (3H, s), 3.98-4.18 (4H, m), 5.07 (2H, s), 5.14 (2H, s), 5.22 (2H, s), 6.14 (1H, dd, J=20.0, 17.2 Hz), 6.52 (1H, dd, J=3.4, 1.8 Hz), 6.91-7.03 (4H, m), 7.18-7.38 (3H, m), 7.48-7.54 (2H, m), 8.54-8.59 (2H, m).

Example 196

To a mixture of {3-methoxy-4-[(2-piperidin-1-yl-1,3-thiazol-4-yl)methoxy]phenyl}methanol (1.15 g), 3-hydroxy-1-phenyl-1H-pyrazole-4-carbaldehyde (0.70 g), tributylphosphine (1.03 g) and tetrahydrofuran (100 mL) was added 1,1'-(azodicarbonyl)dipiperidine (1.29 g) at room temperature, and the mixture was stirred for 15 hrs. The precipitated crystals were removed by filtration and the filtrate was concentrated. The residue was subjected to silica gel column chromatography to give 3-({3-methoxy-4-[(2-piperidin-1-yl-1,3-thiazol-4-yl)methoxy]benzyl}oxy)-1-phenyl-1H-pyrazole-4-carbaldehyde as crystals (1.15 g, yield 67%) from a fraction eluted with ethyl acetate-hexane (2:3, v/v). Recrystallization from ethyl acetate-hexane gave colorless prism crystals. melting point: 123-124° C.

Example 197

To a mixture of {3-methoxy-4-[(2-morpholin-4-yl-1,3-thiazol-4-yl)methoxy]phenyl}methanol (0.93 g), 3-hydroxy-1-phenyl-1H-pyrazole-4-carbaldehyde (0.58 g), tributylphosphine (0.85 g) and tetrahydrofuran (100 mL) was added 1,1'-(azodicarbonyl)dipiperidine (1.06 g) at room temperature, and the mixture was stirred for 15 hrs. The precipitated crystals were removed by filtration and the filtrate was concentrated. The residue was subjected to silica gel column chromatography to give 3-({3-methoxy-4-[(2-morpholin-4-yl-1,3-thiazol-4-yl)methoxy]benzyl}oxy)-1-phenyl-1H-pyrazole-4-carbaldehyde as crystals (0.83 g, yield 58%) from a fraction eluted with ethyl acetate-hexane (2:3, v/v). Recrystallization from ethyl acetate-hexane gave colorless prism crystals. melting point: 128-129° C.

Example 198

To a mixture of {3-methoxy-4-[(5-methyl-2-piperidin-1-yl-1,3-thiazol-4-yl)methoxy]phenyl}methanol (0.36 g), 3-hydroxy-1-phenyl-1H-pyrazole-4-carbaldehyde (0.21 g), tributylphosphine (0.30 g) and tetrahydrofuran (50 mL) was added 1,1'-(azodicarbonyl)dipiperidine (0.38 g) at room temperature, and the mixture was stirred for 15 hrs. The precipitated crystals were removed by filtration and the filtrate was concentrated. The residue was subjected to silica gel column chromatography to give 3-({3-methoxy-4-[(5-methyl-2-piperidin-1-yl-1,3-thiazol-4-yl)methoxy]benzyl}oxy)-1-phenyl-1H-pyrazole-4-carbaldehyde as crystals (0.23 g, yield 44%) from a fraction eluted with ethyl acetate-hexane (2:1, v/v). Recrystallization from ethyl acetate-hexane gave colorless prism crystals. melting point: 180-181° C.

Example 199

To a mixture of 4-{[4-(chloromethyl)-2-methoxyphenoxy]methyl}-2-(2-furyl)-5-methyl-1,3-oxazole (0.94 g), ethyl 3-hydroxy-1-(pyridin-3-ylmethyl)-1H-pyrazole-4-carboxylate (0.55 g) and N,N-dimethylformamide (20 mL) was added sodium hydride (60% in oil, 0.10 g) at room temperature. After stirring the reaction mixture at room temperature for 1 hr, the mixture was further stirred at 90° C. for

Example 200

To a solution of ethyl 3-[(4-{[2-(2-furyl)-5-methyl-1,3-oxazol-4-yl]methoxy}-3-methoxybenzyl)oxy]-1-(pyridin-3-ylmethyl)-1H-pyrazole-4-carboxylate (0.71 g) in tetrahydrofuran (30 mL) was added lithium aluminum hydride (0.08 g) at 0° C. and the mixture was stirred at room temperature for 2 hrs. Sodium sulfate decahydrate (0.65 g) was added to the reaction mixture, and the mixture was stirred at room temperature for 30 min. The reaction mixture was diluted with ethyl acetate and the precipitate was filtered off, and the filtrate was concentrated. The residue was subjected to silica gel column chromatography to give [3-[(4-{[2-(2-furyl)-5-methyl-1,3-oxazol-4-yl]methoxy}-3-methoxybenzyl)oxy]-1-(pyridin-3-ylmethyl)-1H-pyrazol-4-yl]methanol as colorless crystals (0.34 g, yield 52%) from a fraction eluted with ethyl acetate-methanol (10:1, v/v). Recrystallization from ethyl acetate-hexane gave colorless prism crystals. melting point: 90-91° C.

Example 201

To a mixture of 3-[(4-{[2-(2-furyl)-5-methyl-1,3-oxazol-4-yl]methoxy}-3-methoxybenzyl)oxy]-1-(pyridin-3-ylmethyl)-1H-pyrazole-4-carbaldehyde (0.17 g), tetraethyl methylenediphosphonate (0.11 g) and N,N-dimethylformamide (5 mL) was added sodium hydride (60% in oil, 0.015 g) at room temperature, and the mixture was stirred at the same temperature for 15 hrs. Water was poured into the reaction mixture, and the mixture was extracted with ethyl acetate. The organic layer was washed with saturated brine, dried over anhydrous magnesium sulfate and concentrated. The residue was subjected to silica gel column chromatography to give diethyl (E)-2-[3-[(4-{[2-(2-furyl)-5-methyl-1,3-oxazol-4-yl]methoxy}-3-methoxybenzyl)oxy]-1-(pyridin-3-ylmethyl)-1H-pyrazol-4-yl]ethenylphosphonate as a colorless oil (0.19 g, yield 86%) from a fraction eluted with ethyl acetate-hexane (4:1, v/v).

NMR(CDCl$_3$) δ: 1.30 (6H, t, J=7.2 Hz), 2.42 (3H, s), 3.85 (3H, s), 3.98-4.18 (4H, m), 5.07 (2H, s), 5.14 (2H, s), 5.22 (2H, s), 6.14 (1H, dd, J=20.0, 17.2 Hz), 6.52 (1H, dd, J=3.4, 1.8 Hz), 6.91-7.03 (4H, m), 7.18-7.38 (3H, m), 7.48-7.54 (2H, m), 8.54-8.59 (2H, m).

Example 202

To a mixture of methyl 2-[4-({4-[({4-[(E)-2-(diethoxyphosphoryl)ethenyl]-1-phenyl-1H-pyrazol-3-yl}oxy)methyl]-2-methoxyphenoxy}methyl)-5-methyl-1,3-oxazol-2-yl]benzoate (0.40 g), tetrahydrofuran (2 mL) and ethanol (2 mL) was added 1N aqueous sodium hydroxide solution (2 mL), and the mixture was heated under reflux for 1 hr. To the reaction mixture were added 1N hydrochloric acid (2 mL) and water, and the mixture was extracted with ethyl acetate. The organic layer was washed with saturated brine, dried over anhydrous magnesium sulfate and concentrated to give 2-[4-({4-[({4-[(E)-2-(diethoxyphosphoryl)ethenyl]-1-phenyl-1H-pyrazol-3-yl}oxy)methyl]-2-methoxyphenoxy}methyl)-5-methyl-1,3-oxazol-2-yl]benzoic acid as colorless amorphous form (0.26 g, yield 67%).

NMR(CDCl$_3$) δ: 1.32 (6H, t, J=7.2 Hz), 2.47 (3H, s), 3.91 (3H, s), 4.02-4.17 (4H, m), 5.10 (2H, s), 5.36 (2H, s), 6.26 (1H, dd, J=19.8, 17.6 Hz), 6.98-7.02 (3H, m), 7.26-7.48 (4H, m), 7.59-7.65 (4H, m), 7.86 (1H, s), 8.06-8.11 (1H, m), 8.46-8.52 (1H, m).

Example 203

To a mixture of methyl 3-[4-({4-[({4-[(E)-2-(diethoxyphosphoryl)ethenyl]-1-phenyl-1H-pyrazol-3-yl}oxy)methyl]-2-methoxyphenoxy}methyl)-5-methyl-1,3-oxazol-2-yl]benzoate (0.38 g), tetrahydrofuran (2 mL) and methanol (2 mL) was added 1N aqueous sodium hydroxide solution (2 mL), and the mixture was heated under reflux for 1 hr. To the reaction mixture were added 1N hydrochloric acid (2 mL) and water, and the mixture was extracted with ethyl acetate. The organic layer was washed with saturated brine, dried over anhydrous magnesium sulfate and concentrated. The residue was subjected to silica gel column chromatography to give 3-[4-({4-[({4-[(E)-2-(diethoxyphosphoryl)ethenyl]-1-phenyl-1H-pyrazol-3-yl}oxy)methyl]-2-methoxyphenoxy}methyl)-5-methyl-1,3-oxazol-2-yl]benzoic acid as colorless crystals (0.25 g, yield 68%) from a fraction eluted with ethyl acetate-hexane (4:1, v/v). Recrystallization from ethyl acetate-hexane gave colorless prism crystals. melting point: 148-149° C.

Example 204

To a mixture of methyl 4-[4-({4-[({4-[(E)-2-(diethoxyphosphoryl)ethenyl]-1-phenyl-1H-pyrazol-3-yl}oxy)methyl]-2-methoxyphenoxy}methyl)-5-methyl-1,3-oxazol-2-yl]benzoate (0.34 g), tetrahydrofuran (5 mL) and methanol (5 mL) was added 1N aqueous sodium hydroxide solution (2 mL), and the mixture was heated under reflux for 1 hr. To the reaction mixture were added 1N hydrochloric acid (2 mL) and water, and tetrahydrofuran and methanol were evaporated under reduced pressure. The precipitated crystals were collected by filtration to give 4-[4-({4-[({4-[(E)-2-(diethoxyphosphoryl)ethenyl]-1-phenyl-1H-pyrazol-3-yl}oxy)methyl]-2-methoxyphenoxy}methyl)-5-methyl-1,3-oxazol-2-yl]benzoic acid as colorless crystals (0.31 g, yield 94%). Recrystallization from tetrahydrofuran-hexane gave colorless prism crystals. melting point: 194-195° C.

Example 205

A mixture of 4-[4-({4-[({4-[(E)-2-(diethoxyphosphoryl)ethenyl]-1-phenyl-1H-pyrazol-3-yl}oxy)methyl]-2-methoxyphenoxy}methyl)-5-methyl-1,3-oxazol-2-yl]benzoic acid (0.18 g), 1-hydroxybenzotriazole ammonia complex (0.06 g), 1-ethyl-3-(3-dimethylaminopropyl)carbodiimide hydrochloride (0.08 g) and N,N-dimethylformamide (5 mL) was stirred at room temperature for 15 hrs. Water was poured into the reaction mixture, and the mixture was extracted with ethyl acetate. The organic layer was washed with saturated brine, dried over anhydrous magnesium sulfate and concentrated to give diethyl (E)-2-(3-{[4-({2-[4-(carbamoyl)phenyl]-5-methyl-1,3-oxazol-4-yl}methoxy)-3-methoxybenzyl]oxy}-1-phenyl-1H-pyrazol-4-yl)ethenylphosphonate as colorless crystals (0.15 g, yield (Page begins with continuation:)

1 hr. Water was poured into the reaction mixture, and the mixture was extracted with ethyl acetate. The organic layer was washed with saturated brine, dried over anhydrous magnesium sulfate and concentrated. The residue was subjected to silica gel column chromatography to give ethyl 3-[(4-{[2-(2-furyl)-5-methyl-1,3-oxazol-4-yl]methoxy}-3-methoxybenzyl)oxy]-1-(pyridin-3-ylmethyl)-1H-pyrazole-4-carboxylate as colorless crystals (0.81 g, yield 68%) from a fraction eluted with ethyl acetate-methanol (20:1, v/v). Recrystallization from ethyl acetate-hexane gave colorless prism crystals. melting point: 131-132° C.

83%). Recrystallization from ethyl acetate-hexane gave colorless prism crystals. melting point: 146-148° C.

Example 206

To a mixture of 3-({3-methoxy-4-[(5-methyl-2-phenyl-1,3-thiazol-4-yl)methoxy]benzyl}oxy)-1-phenyl-1H-pyrazole-4-carbaldehyde (0.30 g), tetraethyl methylenediphosphonate (0.19 g) and N,N-dimethylformamide (10 mL) was added sodium hydride (60% in oil, 0.03 g) at room temperature, and the mixture was stirred at the same temperature for 15 hrs. Water was poured into the reaction mixture, and the mixture was extracted with ethyl acetate. The organic layer was washed with saturated brine, dried over anhydrous magnesium sulfate and concentrated. The residue was subjected to silica gel column chromatography to give diethyl (E)-2-[3-({3-methoxy-4-[(5-methyl-2-phenyl-1,3-thiazol-4-yl)methoxy]benzyl}oxy)-1-phenyl-1H-pyrazol-4-yl]ethenylphosphonate as colorless crystals (0.21 g, yield 55%) from a fraction eluted with ethyl acetate-hexane (9:1, v/v). Recrystallization from ethyl acetate-hexane gave colorless prism crystals. melting point: 110-111° C.

Example 207

To a mixture of methyl 2-{4-[(4-hydroxymethyl-2-methoxyphenoxy)methyl]-5-methyl-1,3-oxazol-2-yl}benzoate (1.06 g), 3-hydroxy-1-phenyl-1H-pyrazole-4-carbaldehyde (0.58 g), tributylphosphine (0.85 g) and tetrahydrofuran (100 mL) was added 1,1'-(azodicarbonyl)dipiperidine (1.06 g) at room temperature, and the mixture was stirred for 15 hrs. The precipitated crystals were removed by filtration and the filtrate was concentrated. The residue was subjected to silica gel column chromatography to give methyl 2-{4-[(4-{[(4-formyl-1-phenyl-1H-pyrazol-3-yl)oxy]methyl}-2-methoxyphenoxy)methyl]-5-methyl-1,3-oxazol-2-yl}benzoate as colorless crystals (0.99 g, yield 64%) from a fraction eluted with ethyl acetate-hexane (1:1, v/v). Recrystallization from ethyl acetate-hexane gave colorless prism crystals. melting point: 134-135° C.

Example 208

To a mixture of methyl 3-{4-[(4-chloromethyl-2-methoxyphenoxy)methyl]-5-methyl-1,3-oxazol-2-yl}benzoate (1.00 g), 3-hydroxy-1-phenyl-1H-pyrazole-4-carbaldehyde (0.45 g), and N,N-dimethylformamide (30 mL) was added sodium hydride (60% in oil, 0.10 g) at room temperature, and the mixture was stirred at 90° C. for 1 hr. Water was poured into the reaction mixture, and the mixture was extracted with ethyl acetate. The organic layer was washed with saturated brine, dried over anhydrous magnesium sulfate and concentrated. The residue was subjected to silica gel column chromatography to give methyl 3-{4-[(4-{[(4-formyl-1-phenyl-1H-pyrazol-2-yl)oxy]methyl}-2-methoxyphenoxy)methyl]-5-methyl-1,3-oxazol-2-yl}benzoate as colorless crystals (1.03 g, yield 77%) from a fraction eluted with ethyl acetate-hexane (1:1, v/v). Recrystallization from ethyl acetate-hexane gave colorless prism crystals. melting point: 164-165° C.

Example 209

To a mixture of methyl 4-{4-[(4-hydroxymethyl-2-methoxyphenoxy)methyl]-5-methyl-1,3-oxazol-2-yl}benzoate (0.77 g), 3-hydroxy-1-phenyl-1H-pyrazole-4-carbaldehyde (0.41 g), tributylphosphine (0.61 g) and tetrahydrofuran (100 mL) was added 1,1-(azodicarbonyl)dipiperidine (0.76 g) at room temperature, and the mixture was stirred for 15 hrs. The precipitated crystals were removed by filtration and the filtrate was concentrated. The residue was subjected to silica gel column chromatography to give methyl 4-{4-[(4-{[(4-formyl-1-phenyl-1H-pyrazol-3-yl)oxy]methyl}-2-methoxyphenoxy)methyl]-5-methyl-1,3-oxazol-2-yl}benzoate as colorless crystals (0.64 g, yield 58%) from a fraction eluted with ethyl acetate-hexane (2:1, v/v). Recrystallization from ethyl acetate-hexane gave colorless prism crystals. melting point: 190-191° C.

Example 210

To a mixture of methyl 2-{4-[(4-{[(4-formyl-1-phenyl-1H-pyrazol-3-yl)oxy]methyl}-2-methoxyphenoxy)methyl]-5-methyl-1,3-oxazol-2-yl}benzoate (0.65 g), tetraethyl methylenediphosphonate (0.37 g) and N,N-dimethylformamide (20 mL) was added sodium hydride (60% in oil, 0.060 g) at room temperature, and the mixture was stirred at the same temperature for 15 hrs. Water was poured into the reaction mixture, and the mixture was extracted with ethyl acetate. The organic layer was washed with saturated brine, dried over anhydrous magnesium sulfate and concentrated. The residue was subjected to silica gel column chromatography to give methyl 2-[4-({4-[({4-[(E)-2-(diethoxyphosphoryl)ethenyl]-1-phenyl-1H-pyrazol-3-yl}oxy)methyl]-2-methoxyphenoxy}methyl)-5-methyl-1,3-oxazol-2-yl]benzoate as a colorless oil (0.41 g, yield 49%) from a fraction eluted with ethyl acetate-hexane (4:1, v/v).

NMR(CDCl$_3$) δ: 1.32 (6H, t, J=7.2 Hz), 2.40 (3H, s), 3.82 (3H, s), 3.89 (3H, s), 4.03-4.13 (4H, m), 5.07 (2H, s), 5.36 (2H, s), 6.25 (1H, dd, J=19.8, 17.4 Hz), 7.01 (3H, m), 7.22-7.68 (9H, m), 7.84-7.91 (2H, m).

Example 211

To a mixture of methyl 3-{4-[(4-{[(4-formyl-1-phenyl-1H-pyrazol-2-yl)oxy]methyl}-2-methoxyphenoxy)methyl]-5-methyl-1,3-oxazol-2-yl}benzoate (0.85 g), tetraethyl methylenediphosphonate (0.49 g) and N,N-dimethylformamide (30 mL) was added sodium hydride (60% in oil, 0.07 g) at room temperature, and the mixture was stirred at the same temperature for 15 hrs. Water was poured into the reaction mixture, and the mixture was extracted with ethyl acetate. The organic layer was washed with saturated brine, dried over anhydrous magnesium sulfate and concentrated. The residue was subjected to silica gel column chromatography to give methyl 3-[4-({4-[({4-[(E)-2-(diethoxyphosphoryl)ethenyl]-1-phenyl-1H-pyrazol-3-yl}oxy)methyl]-2-methoxyphenoxy}methyl)-5-methyl-1,3-oxazol-2-yl]benzoate as colorless crystals (0.59 g, yield 57%) from a fraction eluted with ethyl acetate-hexane (4:1, v/v). Recrystallization from ethyl acetate-hexane gave colorless prism crystals. melting point: 141-142° C.

Example 212

To a mixture of methyl 4-{4-[(4-{[(4-formyl-1-phenyl-1H-pyrazol-2-yl)oxy]methyl}-2-methoxyphenoxy)methyl]-5-methyl-1,3-oxazol-2-yl}benzoate (0.57 g), tetraethyl methylenediphosphonate (0.32 g) and N,N-dimethylformamide (20 mL) was added sodium hydride (60% in oil, 0.05 g) at room temperature, and the mixture was stirred at the same temperature for 15 hrs. Water was poured into the reaction mixture, and the mixture was extracted with ethyl acetate. The organic layer was washed with saturated brine, dried over anhydrous magnesium sulfate and concentrated. The residue was subjected to silica gel column chromatography to give methyl 4-[4-({4-[({4-[(E)-2-(diethoxyphosphoryl)ethenyl]-1-phenyl-1H-pyrazol-3-yl}oxy)methyl]-2-methoxyphenoxy}methyl)-5-methyl-1,3-oxazol-2-yl]benzoate as colorless crystals (0.45 g, yield 65%) from a fraction eluted with ethyl acetate-hexane (5:1, v/v). Recrystallization from ethyl acetate-hexane gave colorless prism crystals. melting point: 129-130° C.

Example 213

To a mixture of {3-methoxy-4-[(5-methyl-2-phenyl-1,3-thiazol-4-yl)methoxy]phenyl}methanol (0.95 g), 3-hydroxy-1-phenyl-1H-pyrazole-4-carbaldehyde (0.58 g), tributylphosphine (0.85 g) and tetrahydrofuran (100 mL) was added 1,1'-(azodicarbonyl)dipiperidine (1.06 g) at room temperature, and the mixture was stirred for 15 hrs. The precipitated crystals were removed by filtration and the filtrate was concentrated. The residue was subjected to silica gel column chromatography to give 3-({3-methoxy-4-[(5-methyl-2-phenyl-1,3-thiazol-4-yl)methoxy]benzyl}oxy)-1-phenyl-1H-pyrazole-4-carbaldehyde as colorless crystals (0.83 g, yield 58%) from a fraction eluted with ethyl acetate-hexane (2:1, v/v). Recrystallization from ethyl acetate-hexane gave colorless prism crystals. melting point: 164-165° C.

Example 214

To a mixture of 3-[(4-{[2-(2-furyl)-1,3-oxazol-4-yl]methoxybenzyl}oxy)-1-phenyl-1H-pyrazole-4-carbaldehyde (0.80 g), tetraethyl methylenediphosphonate (0.55 g) and N,N-dimethylformamide (30 mL) was added sodium hydride (60% in oil, 0.08 g) at room temperature, and the mixture was stirred at the same temperature for 15 hrs. Water was poured into the reaction mixture, and the mixture was extracted with ethyl acetate. The organic layer was washed with saturated brine, dried over anhydrous magnesium sulfate and concentrated. The residue was subjected to silica gel column chromatography to give diethyl (E)-2-{3-[(4-{[2-(2-furyl)-1,3-oxazol-4-yl]methoxy}-3-methoxybenzyl)oxy]-1-phenyl-1H-pyrazol-4-yl}ethenylphosphonate as colorless crystals (0.78 g, yield 76%) from a fraction eluted with ethyl acetate-hexane (8:1, v/v). Recrystallization from ethyl acetate-hexane gave colorless prism crystals. melting point: 96-97° C.

Example 215

To a mixture of 3-({3-methoxy-4-[(4-methyl-2-phenyl-1,3-thiazol-5-yl)methoxy]benzyl}oxy)-1-phenyl-1H-pyrazole-4-carbaldehyde (0.60 g), tetraethyl methylenediphosphonate (0.37 g) and N,N-dimethylformamide (20 mL) was added sodium hydride (60% in oil, 0.060 g) at room temperature, and the mixture was stirred at the same temperature for 15 hrs. Water was poured into the reaction mixture, and the mixture was extracted with ethyl acetate. The organic layer was washed with saturated brine, dried over anhydrous magnesium sulfate and concentrated. The residue was subjected to silica gel column chromatography to give diethyl (E)-2-[3-({3-methoxy-4-[(4-methyl-2-phenyl-1,3-thiazol-5-yl)methoxy]benzyl}oxy)-1-phenyl-1H-pyrazol-4-yl]ethenylphosphonate as colorless crystals (0.45 g, yield 58%) from a fraction eluted with ethyl acetate-hexane (5:1, v/v). Recrystallization from ethyl acetate-hexane gave colorless prism crystals. melting point: 113-114° C.

Example 216

To a mixture of 3-({3-methoxy-4-[(3-methyl-1-pyridin-2-yl-1H-pyrazol-4-yl)methoxy]benzyl}oxy)-1-phenyl-1H-pyrazole-4-carbaldehyde (0.28 g), tetraethyl methylenediphosphonate (0.18 g) and N,N-dimethylformamide (10 mL) was added sodium hydride (60% in oil, 0.030 g) at room temperature, and the mixture was stirred at the same temperature for 15 hrs. Water was poured into the reaction mixture, and the mixture was extracted with ethyl acetate. The organic layer was washed with saturated brine, dried over anhydrous magnesium sulfate and concentrated. The residue was subjected to silica gel column chromatography to give diethyl (E)-2-[3-({3-methoxy-4-[(3-methyl-1-pyridin-2-yl-1H-pyrazol-4-yl)methoxy]benzyl}oxy)-1-phenyl-1H-pyrazol-4-yl]ethenylphosphonate as colorless crystals (0.24 g, yield 67%) from a fraction eluted with ethyl acetate-hexane (5:1, v/v). Recrystallization from ethyl acetate-hexane gave colorless prism crystals. melting point: 103-104° C.

Example 217

To a mixture of 3-({3-methoxy-4-[(1-methyl-4-phenyl-1H-imidazol-2-yl)methoxy]benzyl}oxy)-1-phenyl-1H-pyrazole-4-carbaldehyde (0.65 g), tetraethyl methylenediphosphonate (0.40 g) and N,N-dimethylformamide (30 mL) was added sodium hydride (60% in oil, 0.060 g) at room temperature, and the mixture was stirred at the same temperature for 15 hrs. Water was poured into the reaction mixture, and the mixture was extracted with ethyl acetate. The organic layer was washed with saturated brine, dried over anhydrous magnesium sulfate and concentrated. The residue was subjected to silica gel column chromatography to give diethyl (E)-2-[3-({3-methoxy-4-[(1-methyl-4-phenyl-1H-imidazol-2-yl)methoxy]benzyl}oxy)-1-phenyl-1H-pyrazol-4-yl]ethenylphosphonate as colorless crystals (0.58 g, yield 71%) from a fraction eluted with ethyl acetate-hexane (8:1, v/v). Recrystallization from ethyl acetate-hexane gave colorless prism crystals. melting point: 144-145° C.

Example 218

To a mixture of 4-[(4-chloromethyl-2-methoxyphenoxy)methyl]-2-(2-furyl)-1,3-oxazole (0.80 g), 3-hydroxy-1-phenyl-1H-pyrazole-4-carbaldehyde (0.45 g) and N,N-dimethylformamide (30 mL) was added sodium hydride (60% in oil, 0.10 g) at room temperature, and the mixture was stirred at 90° C. for 2 hrs. Water was added to the reaction mixture, and the precipitated crystals were collected by filtration to give 3-[(4-{[2-(2-furyl)-1,3-oxazol-4-yl]methoxy}-3-methoxybenzyl)oxy]-1-phenyl-1H-pyrazole-4-carbaldehyde as pale-yellow crystals (0.93 g, yield 82%). Recrystallization from ethyl acetate-hexane gave pale-yellow prism crystals. melting point: 162-163° C.

Example 219

To a mixture of {3-methoxy-4-[(4-methyl-2-phenyl-1,3-thiazol-5-yl)methoxy]phenyl}methanol (2.35 g), 3-hydroxy-1-phenyl-1H-pyrazole-4-carbaldehyde (1.43 g), tributylphosphine (1.43 g) and tetrahydrofuran (50 mL) was added 1,1'-(azodicarbonyl)dipiperidine (2.62 g) at room temperature, and the mixture was stirred for 15 hrs. The precipitated crystals were removed by filtration and the filtrate was concentrated. The residue was subjected to silica gel column chromatography to give 3-({3-methoxy-4-[(4-methyl-2-phenyl-1,3-thiazol-5-yl)methoxy]benzyl}oxy)-1-phenyl-1H-pyrazole-4-carbaldehyde as pale-yellow crystals (2.60 g, yield 74%) from a fraction eluted with ethyl acetate-hexane (3:2, v/v). Recrystallization from ethyl acetate-hexane gave colorless prism crystals. melting point: 171-172° C.

Example 220

To a mixture of {3-methoxy-4-[(3-methyl-1-pyridin-2-yl-1H-pyrazol-4-yl)methoxy]phenyl}methanol (0.73 g), 3-hydroxy-1-phenyl-1H-pyrazole-4-carbaldehyde (0.45 g), tributylphosphine (0.67 g) and tetrahydrofuran (80 mL) was added 1,1'-(azodicarbonyl)dipiperidine (0.83 g) at room temperature, and the mixture was stirred for 15 hrs. The precipitated crystals were removed by filtration and the filtrate was concentrated. The residue was subjected to silica gel column chromatography to give 3-({3-methoxy-4-[(3-methyl-1-pyridin-2-yl-1H-pyrazol-4-yl)methoxy]benzyl}oxy)-1-phenyl-1H-pyrazole-4-carbaldehyde as pale-yellow crystals (0.35 g, yield 32%) from a fraction eluted with ethyl acetate-hexane (1:1, v/v). Recrystallization from ethyl acetate-hexane gave pale-yellow prism crystals. melting point: 179-180° C.

Example 221

To a mixture of {3-methoxy-4-[(1-methyl-4-phenyl-1H-imidazol-2-yl)methoxy]phenyl}methanol (1.00 g), 3-hydroxy-1-phenyl-1H-pyrazole-4-carbaldehyde (0.64 g), tributylphosphine (0.95 g) and tetrahydrofuran (100 mL) was added 1,1'-(azodicarbonyl)dipiperidine (1.19 g) at room temperature, and the mixture was stirred for 15 hrs. The precipitated crystals were removed by filtration and the filtrate was concentrated. The residue was subjected to silica gel column chromatography to give 3-({3-methoxy-4-[(1-methyl-4-phenyl-1H-imidazol-2-yl)methoxy]benzyl}oxy)-1-phenyl-1H-pyrazole-4-carbaldehyde as colorless crystals (0.78 g, yield 51%) from a fraction eluted with ethyl acetate-hexane (1:1, v/v). Recrystallization from ethyl acetate-hexane gave colorless prism crystals. melting point: 126-127° C.

Example 222

To a mixture of 3-({3-methoxy-4-[(5-methyl-2-pyridin-3-yl-1,3-oxazol-4-yl)methoxy]benzyl}oxy)-1-phenyl-1H-pyrazole-4-carbaldehyde (0.55 g), tetraethyl methylenediphosphonate (0.35 g) and N,N-dimethylformamide (30 mL) was added sodium hydride (60% in oil, 0.050 g) at room temperature, and the mixture was stirred at the same temperature for 15 hrs. Water was poured into the reaction mixture, and the mixture was extracted with ethyl acetate. The organic layer was washed with saturated brine, dried over anhydrous magnesium sulfate and concentrated. The residue was subjected to silica gel column chromatography to give diethyl (E)-2-[3-({3-methoxy-4-[(5-methyl-2-pyridin-3-yl-1,3-oxazol-4-yl)methoxy]benzyl}oxy)-1-phenyl-1H-pyrazol-4-yl]ethenylphosphonate as colorless crystals (0.53 g, yield 77%) from a fraction eluted with ethyl acetate-hexane (19:1, v/v). Recrystallization from ethyl acetate-hexane gave colorless prism crystals. melting point: 128-129° C.

Example 223

To a mixture of 3-{4-[(4-{[(4-formyl-1-phenyl-1H-pyrazol-3-yl)oxy]methyl}-2-methoxyphenoxy)methyl]-5-methyl-1,3-oxazol-2-yl}phenyl methanesulfonate (0.30 g), tetraethyl methylenediphosphonate (0.16 g) and N,N-dimethylformamide (10 mL) was added sodium hydride (60% in oil, 0.025 g) at room temperature, and the mixture was stirred at the same temperature for 15 hrs. Water was poured into the reaction mixture, and the mixture was extracted with ethyl acetate. The organic layer was washed with saturated brine, dried over anhydrous magnesium sulfate and concentrated. The residue was subjected to silica gel column chromatography to give crystals from a fraction eluted with ethyl acetate-hexane (5:1, v/v). To a mixture of the obtained crystal, tetrahydrofuran (2 mL) and ethanol (2 mL) was added 1N aqueous sodium hydroxide solution (2 mL), and the mixture was stirred at 60° C. for 1 hr. To the reaction mixture was added dilute hydrochloric acid to acidify the solution, and the mixture was extracted with ethyl acetate. The organic layer was washed with saturated brine, dried over anhydrous magnesium sulfate and concentrated. The residue was subjected to silica gel column chromatography to give diethyl (E)-2-{3-[(4-{[2-(3-hydroxyphenyl)-5-methyl-1,3-oxazol-4-yl]methoxy}-3-methoxybenzyl)oxy]-1-phenyl-1H-pyrazol-4-yl}ethenylphosphonate as colorless crystals (0.050 g, yield 15%) from a fraction eluted with ethyl acetate-hexane (8:1, v/v). Recrystallization from ethyl acetate-hexane gave colorless prism crystals. melting point: 127-128° C.

Example 224

To a mixture of methyl 3-[4-({4-[({4-[(E)-2-(2-ethyl-1,3-thiazol-4-yl)ethenyl]-1-phenyl-1H-pyrazol-3-yl}oxy)methyl]-2-methoxyphenoxy}methyl)-5-methyl-1,3-oxazol-2-yl]benzoate (0.28 g), tetrahydrofuran (2 mL) and ethanol (2 mL) was added 1N aqueous sodium hydroxide solution (2 mL), and the mixture was heated under reflux for 2 hrs. To the reaction mixture were added 1N hydrochloric acid (2 mL) and water for neutralization, and the precipitated crystals were collected by filtration to give 3-[4-({4-[({4-[(E)-2-(2-ethyl-1,3-thiazol-4-yl)ethenyl]-1-phenyl-1H-pyrazol-3-yl}oxy)methyl]-2-methoxyphenoxy}methyl)-5-methyl-1,3-oxazol-2-yl]benzoic acid as colorless crystals (0.23 g, yield 85%). Recrystallization from tetrahydrofuran-hexane gave colorless prism crystals. melting point: 190-191° C.

Example 225

A mixture of methyl 3-{4-[(4-{[(4-formyl-1-phenyl-1H-pyrazol-2-yl)oxy]methyl}-2-methoxyphenoxy)methyl]-5-methyl-1,3-oxazol-2-yl}benzoate (0.80 g), [(2-ethyl-1,3-thiazol-4-yl)methyl]triphenylphosphonium chloride (0.89 g), potassium carbonate (0.29 g) and N,N-dimethylformamide (30 mL) was stirred at room temperature for 15 hrs. Water was poured into the reaction mixture, and the mixture was extracted with ethyl acetate. The organic layer was washed with saturated brine, dried over anhydrous magnesium sulfate and concentrated. The residue was subjected to silica gel column chromatography and eluted with ethyl acetate-hexane (2:3, v/v) to give methyl 3-[4-({4-[({4-[(Z)-2-(2-ethyl-1,3-thiazol-4-yl)ethenyl]-1-phenyl-1H-pyrazol-3-yl}oxy)methyl]-2-methoxyphenoxy}methyl)-5-methyl-1,3-oxazol-2-yl]benzoate as colorless crystals (0.32 g, yield 34%). The crystals were recrystallized from ethyl acetate-hexane. melting point: 125-126° C.

In addition, methyl 3-[4-({4-[({4-[(E)-2-(2-ethyl-1,3-thiazol-4-yl)ethenyl]-1-phenyl-1H-pyrazol-3-yl}oxy)methyl]-2-methoxyphenoxy}methyl)-5-methyl-1,3-oxazol-2-yl]benzoate was obtained as colorless crystals (0.41 g, yield 44%) from a fraction successively obtained by elution. The crystals were recrystallized from ethyl acetate-hexane. melting point: 132-133° C.

Example 226

To a mixture of diethyl (E)-2-{3-[(4-{[2-(2-furyl)-5-methyl-1,3-oxazol-4-yl]methoxy)-3-methoxybenzoyl)amino]-1-phenyl-1H-pyrazol-4-yl}ethenylphosphonate (50 mg), sodium hydride (60% in oil, 3.9 mg) and N,N-dimethylformamide (2 mL) was added methyl iodide (14 mg) with stirring, and the mixture was further stirred at room temperature for 2 hrs. Water was poured into the reaction mixture, and the mixture was extracted with ethyl acetate. The ethyl acetate layer as washed successively with distilled water and saturated brine, dried over anhydrous magnesium sulfate and concentrated. The residue was purified by reverse phase partition-high performance liquid chromatography (elution with distilled water containing 0.1% trifluoroacetic acid/acetonitrile) to give a colorless oil compound. To remove remaining trifluoroacetic acid, water was added to the oil compound, and the mixture was extracted with ethyl acetate. The ethyl acetate layer was dried over anhydrous magnesium sulfate and concentrated to give diethyl (E)-2-{3-[(4-([2-(2-furyl)-5-methyl-1,3-oxazol-4-yl]methoxy}-3-methoxybenzoyl)(methyl)amino]-1-phenyl-1H-pyrazol-4-yl}ethenylphosphonate as a colorless oil (39.8 mg, yield 78%).

NMR(CDCl$_3$)δ: 1.34(6H, t, J=7.1 Hz), 2.35 (3H, s), 3.48(3H, s), 3.70(3H, s), 4.00-4.16(4H, m), 4.96(2H, s), 5.91(1H, t, J=17.6 Hz), 6.50-6.53(1H, m), 6.78(1H, d, J=8.4 Hz), 6.94-7.16(4H, m), 7.25-7.60(6H, m), 7.95(1H, s).

Example 227

To a mixture of {3-methoxy-4-[(5-methyl-2-pyridin-3-yl-1,3-oxazol-4-yl)methoxy]phenyl}methanol (1.00 g), 3-hydroxy-1-phenyl-1H-pyrazole-4-carbaldehyde (0.58 g), tributylphosphine (0.95 g) and tetrahydrofuran (100 mL) was added 1,1'-(azodicarbonyl)dipiperidine (1.19 g) at room temperature, and the mixture was stirred for 15 hrs. The precipitated crystals were removed by filtration and the filtrate was concentrated. The residue was subjected to silica gel column chromatography to give 3-({3-methoxy-4-[(5-methyl-2-pyridin-3-yl-1,3-oxazol-4-yl)methoxy]benzyl}oxy)-1-phenyl-1H-pyrazole-4-carbaldehyde as colorless crystals (0.72 g, 47%) from a fraction eluted with ethyl acetate-hexane (4:1, v/v). Recrystallization from ethyl acetate-hexane gave colorless prism crystals. melting point: 161-162° C.

Example 228

To a mixture of 3-{4-[(4-chloromethyl-2-methoxyphenoxy)methyl]-5-methyl-1,3-oxazol-2-yl}phenyl methanesulfonate (2.00 g), 3-hydroxy-1-phenyl-1H-pyrazole-4-carbaldehyde (0.81 g) and N,N-dimethylformamide (50 mL) was added sodium hydride (60% in oil, 0.19 g) at room temperature, and the mixture was stirred at 90° C. for 2 hrs. Water was poured into the reaction mixture, and the mixture was extracted with ethyl acetate. The organic layer was washed with saturated brine, dried over anhydrous magnesium sulfate and concentrated. The residue was subjected to silica gel column chromatography to give 3-{4-[(4-{[(4-formyl-1-phenyl-1H-pyrazol-3-yl)oxy]methyl}-2-methoxyphenoxy)methyl]-5-methyl-1,3-oxazol-2-yl}phenyl methanesulfonate as colorless crystals (1.43 g, yield 56%) from a fraction eluted with ethyl acetate-hexane (2:1, v/v). Recrystallization from ethyl acetate-hexane gave colorless prism crystals. melting point: 146-148° C.

Example 229

To a mixture of methyl {3-[4-({4-[({4-[(E)-2-(diethoxyphosphoryl)ethenyl]-1-phenyl-1H-pyrazol-3-yl}oxy)methyl]-2-methoxyphenoxy}methyl)-5-methyl-1,3-oxazol-2-yl]phenoxy}acetate (0.25 g), tetrahydrofuran (2 mL) and ethanol (2 mL) was added 1N aqueous sodium hydroxide solution (1 mL), and the mixture was stirred at 60° C. for 1 hr. To the reaction mixture was added dilute hydrochloric acid to acidify the solution, and the precipitated crystals were collected by filtration to give {3-[4-({4-[({4-[(E)-2-(diethoxyphosphoryl)ethenyl]-1-phenyl-1H-pyrazol-3-yl}oxy)methyl]-2-methoxyphenoxy}methyl)-5-methyl-1,3-oxazol-2-yl]phenoxy}acetic acid as colorless crystals (0.18 g, yield 72%). Recrystallization from tetrahydrofuran-hexane gave colorless prism crystals. melting point: 166-168° C.

Example 230

To a mixture of methyl 3-{4-[(4-{[(4-formyl-1-phenyl-1H-pyrazol-3-yl)oxy]methyl}phenoxy)methyl]-5-methyl-1,3-oxazol-2-yl}benzoate (0.29 g), tetraethyl methylenediphosphonate (0.18 g) and N,N-dimethylformamide (10 mL) was added sodium hydride (60% in oil, 0.03 g) at room temperature, and the mixture was stirred at the same temperature for 15 hrs. Water was poured into the reaction mixture, and the mixture was extracted with ethyl acetate. The organic layer was washed with saturated brine, dried over anhydrous magnesium sulfate and concentrated. The residue was subjected to silica gel column chromatography to give an oily substance (0.28 g) from a fraction eluted with ethyl acetate-hexane (8:1, v/v). To a mixture of the oily substance, tetrahydrofuran (2 mL) and methanol (2 mL) was added 1N aqueous sodium hydroxide solution (2 mL), and the mixture was stirred at 60° C. for 1 hr. To the reaction mixture was added dilute hydrochloric acid to acidify the solution, and the mixture was extracted with ethyl acetate. The organic layer was washed with saturated brine, dried over anhydrous magnesium sulfate and concentrated to give 3-[4-({4-[({4-[(E)-2-(diethoxyphosphoryl)ethenyl]-1-phenyl-1H-pyrazol-3-yl}oxy)methyl]phenoxy}methyl)-5-methyl-1,3-oxazol-2-yl]benzoic acid as colorless crystals (0.23 g, yield 88%). Recrystallization from ethyl acetate-hexane gave colorless prism crystals. melting point: 153-155° C.

Example 231

To a mixture of 3-({3-methoxy-4-[(5-methyl-2-morpholin-4-yl-1,3-thiazol-4-yl)methoxy]benzyl}oxy)-1-phenyl-1H-pyrazole-4-carbaldehyde (0.52 g), tetraethyl methylenediphosphonate (0.32 g) and N,N-dimethylformamide (10 mL) was added sodium hydride (60% in oil, 0.050 g) at room temperature, and the mixture was stirred at the same temperature for 15 hrs. Water was poured into the reaction mixture, and the mixture was extracted with ethyl acetate. The organic layer was washed with saturated brine, dried over anhydrous magnesium sulfate and concentrated. The residue was subjected to silica gel column chromatography to give diethyl (E)-2-[3-({3-methoxy-4-[(5-methyl-2-morpholin-4-yl-1,3-thiazol-4-yl)methoxy]benzyl}oxy)-1-phenyl-1H-pyrazol-4-yl]ethenylphosphonate as colorless crystals (0.33 g, yield 51%) from a fraction eluted with ethyl acetate-hexane (9:1, v/v). Recrystallization from ethyl acetate-hexane gave colorless prism crystals. melting point: 88-90° C.

Example 232

A mixture of 3-({3-methoxy-4-[(5-methyl-2-morpholin-4-yl-1,3-thiazol-4-yl)methoxy]benzyl}oxy)-1-phenyl-1H-pyrazole-4-carbaldehyde (0.75 g), [(2-ethyl-1,3-thiazol-4-yl)methyl]triphenylphosphonium chloride (0.89 g), potassium carbonate (0.29 g) and N,N-dimethylformamide (30 mL) was stirred at room temperature for 15 hrs. Water was poured into the reaction mixture, and the mixture was extracted with ethyl acetate. The organic layer was washed with saturated brine, dried over anhydrous magnesium sulfate and concentrated. The residue was subjected to silica gel column chromatography and eluted with ethyl acetate-hexane (1:3, v/v) to give 4-[4-({4-[({4-[(Z)-2-(2-ethyl-1,3-thiazol-4-yl)ethenyl]-1-phenyl-1H-pyrazol-3-yl}oxy)methyl]-2-methoxyphenoxy}methyl)-5-methyl-1,3-thiazol-2-yl]morpholine as colorless crystals (0.25 g, yield 28%). The crystals were recrystallized from ethyl acetate-hexane. melting point: 112-114° C.

In addition, 4-[4-({4-[({4-[(E)-2-(2-ethyl-1,3-thiazol-4-yl)ethenyl]-1-phenyl-1H-pyrazol-3-yl}oxy)methyl]-2-methoxyphenoxy}methyl)-5-methyl-1,3-thiazol-2-yl]morpholine was obtained as colorless crystals (0.33 g, yield 38%) from a fraction successively obtained by elution. The crystals were recrystallized from ethyl acetate-hexane. melting point: 76-78° C.

Example 233

A solution (15 mL) of 4-[(5-methyl-2-phenyl-1,3-oxazol-4-yl)methoxy]benzoic acid (909 mg), oxalyl chloride (407 mg) and N,N-dimethylformamide (0.05 mL) in tetrahydrofuran was stirred at room temperature for 15 min. The reaction mixture was concentrated and a solution (10 mL) of 3-amino-1-phenyl-1H-pyrazole-4-carbaldehyde (500 mg) in N,N-dimethylacetamide was added to the residue. The mixture was stirred at room temperature for 2 hrs. Water was poured into the reaction mixture, and the mixture was extracted with ethyl acetate. The ethyl acetate layer was washed with saturated brine, dried over anhydrous magnesium sulfate and concentrated. The residue was subjected to silica gel column chromatography and eluted with ethyl acetate-hexane (1:9 to 4:1, v/v) to give N-(4-formyl-1-phenyl-1H-pyrazol-3-yl)-4-[(5-methyl-2-phenyl-1,3-oxazol-4-yl)methoxy]benzamide. Recrystallization from ethyl acetate-hexane gave pale-yellow crystal (698 mg, yield 50%). melting point: 185-186° C.

Example 234

To a mixture of 3-{4-[(4-{[(4-formyl-1-phenyl-1H-pyrazol-3-yl)oxy]methyl}-2-methoxyphenoxy)methyl]-5-ethyl-1,3-oxazol-2-yl}phenyl methanesulfonate (0.20 g), tetrahydrofuran (2 mL) and ethanol (2 mL) was added 1N aqueous sodium hydroxide solution (2 mL), and the mixture was stirred at 60° C. for 1 hr. To the reaction mixture was added dilute hydrochloric acid to acidify the solution, and the precipitated crystals were collected by filtration to give 3-[(4-{[2-(3-hydroxyphenyl)-5-methyl-1,3-oxazol-4-yl]methoxy}-3-methoxybenzyl)oxy]-1-phenyl-1H-pyrazole-4-carbaldehyde as colorless crystals (0.10 g, yield 59%). Recrystallization from ethyl acetate-hexane gave colorless prism crystals. melting point: 193-194° C.

Example 235

A mixture of 3-[(4-{[2-(3-hydroxyphenyl)-5-methyl-1,3-oxazol-4-yl]methoxy}-3-methoxybenzyl)oxy]-1-phenyl-1H-pyrazole-4-carbaldehyde (0.80 g), methyl bromoacetate (0.37 g), potassium carbonate (0.33 g) and N,N-dimethylformamide (30 mL) was stirred at 90° C. for 1 hr. Water was poured into the reaction mixture, and the mixture was extracted with ethyl acetate. The organic layer was washed with saturated brine, dried over anhydrous magnesium sulfate and concentrated. The residue was subjected to silica gel column chromatography to give methyl (3-{4-[(4-{[(4-formyl-1-phenyl-1H-pyrazol-3-yl)oxy]methyl}-2-methoxyphenoxy)methyl]-5-methyl-1,3-oxazol-2-yl}phenoxy)acetate as colorless crystals (0.38 g, yield 41%) from a fraction eluted with ethyl acetate-hexane (1:2, v/v). Recrystallization from ethyl acetate-hexane gave colorless prism crystals. melting point: 107-109° C.

Example 236

To a mixture of methyl ((3-{4-[(4-{[(4-formyl-1-phenyl-1H-pyrazol-3-yl)oxy]methyl}-2-methoxyphenoxy)methyl]-5-methyl-1,3-oxazol-2-yl}phenoxy)acetate (0.30 g), tetraethyl methylenediphosphonate (0.16 g) and N,N-dimethylformamide (10 mL) was added sodium hydride (60% in oil, 0.025 g) at room temperature, and the mixture was stirred at the same temperature for 4 hrs. Water was poured into the reaction mixture, and the mixture was extracted with ethyl acetate. The organic layer was washed with saturated brine, dried over anhydrous magnesium sulfate and concentrated. The residue was subjected to silica gel column chromatography to give methyl {3-[4-({4-[({4-[(E)-2-(diethoxyphosphoryl)ethenyl]-1-phenyl-1H-pyrazol-3-yl}oxy)methyl]-2-methoxyphenoxy}methyl)-5-methyl-1,3-oxazol-2-yl]phenoxy}acetate as a colorless oil from a fraction eluted with ethyl acetate-hexane (9:1, v/v) (0.25 g, yield 68%).

NMR(CDCl$_3$) δ: 1.32 (6H, t, J=7.0 Hz), 2.42 (3H, s), 3.82 (3H, s), 3.89 (3H, s), 4.01-4.16 (4H, m), 4.71 (2H, s), 5.07 (2H, s), 5.36 (2H, s), 6.26 (1H, dd, J=19.8, 17.6 Hz), 6.99-7.08 (4H, m), 7.25-7.67 (9H, m), 7.85 (1H, s).

Example 237

To a mixture of methyl 3-(4-{[4-(hydroxymethyl)phenoxy]methyl}-5-methyl-1,3-oxazol-2-yl)benzoate (1.34 g), 3-hydroxy-1-phenyl-1H-pyrazole-4-carbaldehyde (0.50 g), tributylphosphine (0.77 g) and tetrahydrofuran (100 mL) was added 1,1'-(azodicarbonyl)dipiperidine (0.96 g) was added at room temperature, and the mixture was stirred for 15 hrs. The precipitated crystals were removed by filtration and the filtrate was concentrated. The residue was subjected to silica gel column chromatography to give methyl 3-{4-[(4-{[(4-formyl-1-phenyl-1H-pyrazol-3-yl)oxy]methyl}phenoxy)methyl]-5-methyl-1,3-oxazol-2-yl}benzoate as crystals (0.62 g, yield 47%) from a fraction eluted with ethyl acetate-hexane (1:2, v/v). Recrystallization from ethyl acetate-hexane gave colorless prism crystals. melting point: 161-162° C.

Example 238

To a mixture of {3-methoxy-4-[(5-methyl-2-morpholin-4-yl-1,3-thiazol-4-yl)methoxy]phenyl}methanol (2.00 g), 3-hydroxy-1-phenyl-1H-pyrazole-4-carbaldehyde (1.19 g), tributylphosphine (1.74 g) and tetrahydrofuran (100 mL) was added 1,1'-(azodicarbonyl)dipiperidine (2.17 g) at room temperature, and the mixture was stirred for 15 hrs. The precipitated crystals were removed by filtration and the filtrate was concentrated. The residue was subjected to silica gel column chromatography to give 3-({3-methoxy-4-[(5-methyl-2-morpholin-4-yl-1,3-thiazol-4-yl)methoxy]benzyl}oxy)-1-phenyl-1H-pyrazole-4-carbaldehyde as colorless crystals (1.68 g, yield 57%) from a fraction eluted with ethyl acetate-hexane (1:1, v/v). Recrystallization from ethyl acetate-hexane gave colorless prism crystals. melting point: 149-150° C.

Example 239

A mixture of 3-[4-({4-[({4-[(E)-2-(diethoxyphosphoryl)ethenyl]-1-phenyl-1H-pyrazol-3-yl}oxy)methyl]-2-methoxyphenoxy}methyl)-5-methyl-1,3-oxazol-2-yl]benzoic acid (1.09 g), 1-hydroxybenzotriazole ammonia complex (0.37 g), 1-ethyl-3-(3-dimethylaminopropyl)carbodiimide hydrochloride (0.46 g) and N,N-dimethylformamide (50 mL) was stirred at room temperature for 15 hrs. Water was poured into the reaction mixture, and the mixture was extracted with ethyl acetate. The organic layer was washed with saturated brine, dried over anhydrous magnesium sulfate and concentrated to give diethyl (E)-2-(3-{[4-({2-[3-(carbamoyl)phenyl]-5-methyl-1,3-oxazol-4-yl}methoxy)-3-methoxybenzyl]oxy}-1-phenyl-1H-pyrazol-4-yl)ethenylphosphonate as colorless crystals (0.82 g, yield 76%). Recrystallization from acetone-hexane gave colorless prism crystals. melting point: 127-128° C.

Example 240

To a mixture of ethyl (5-[4-({4-[({4-[(E)-2-(diethoxyphosphoryl)ethenyl]-1-phenyl-1H-pyrazol-3-yl}oxy)methyl]-2-methoxyphenoxy}methyl)-5-methyl-1,3-oxazol-2-yl]-2-furancarboxylate (0.33 g), tetrahydrofuran (2 mL) and ethanol (2 mL) was added 1N aqueous sodium hydroxide solution (1 mL), and the mixture was stirred at 50° C. for 1 hr. To the reaction mixture were added 1N hydrochloric acid (1 mL) and water, and the precipitated crystals were collected by filtration to give (5-[4-({4-[({4-[(E)-2-(diethoxyphosphoryl)ethenyl]-1-phenyl-1H-pyrazol-3-yl}oxy)methyl]-2-methoxyphenoxy}methyl)-5-methyl-1,3-oxazol-2-yl]-2-furancarboxylic acid as colorless crystals (0.33 g, yield 94%). Recrystallization from acetone-hexane gave colorless prism crystals. melting point: 171-172° C.

Example 241

To a mixture of ethyl {4-[4-({4-[({4-[(E)-2-(diethoxyphosphoryl)ethenyl]-1-phenyl-1H-pyrazol-3-yl}oxy)methyl]-2-methoxyphenoxy}methyl)-5-methyl-1,3-oxazol-2-yl]phenyl}acetate (0.28 g), tetrahydrofuran (2 mL) and ethanol (2 mL) was added 1N aqueous sodium hydroxide solution (1 mL), and the mixture was stirred at 50° C. for 1 hr. To the reaction mixture were added 1N hydrochloric acid (1 mL) and water, and the mixture was extracted with ethyl acetate. The organic layer was washed with saturated brine, dried over anhydrous magnesium sulfate and concentrated to give {4-[4-({4-[({4-[(E)-2-(diethoxyphosphoryl)ethenyl]-1-phenyl-1H-pyrazol-3-yl}oxy)methyl]-2-methoxyphenoxy}methyl)-5-methyl-1,3-oxazol-2-yl]phenyl}acetic acid as colorless crystals (0.15 g, yield 56%). Recrystallization from acetone-hexane gave colorless prism crystals. melting point: 119-120° C.

Example 242

To a mixture of ethyl 5-[4-({4-[({4-[(E)-2-(2-ethyl-1,3-thiazol-4-yl)ethenyl]-1-phenyl-1H-pyrazol-3-yl}oxy)methyl]-2-methoxyphenoxy}methyl)-5-methyl-1,3-oxazol-2-yl]-2-furancarboxylate (0.46 g), tetrahydrofuran (2 mL) and ethanol (2 mL) was added 1N aqueous sodium hydroxide solution (1.5 mL), and the mixture was stirred at 60° C. for 1 hr. To the reaction mixture were added 1N hydrochloric acid (2 mL) and water, and the precipitated crystals were collected by filtration to give 5-[4-({4-[({4-[(E)-2-(2-ethyl-1,3-thiazol-4-yl)ethenyl]-1-phenyl-1H-pyrazol-3-yl}oxy)methyl]-2-methoxyphenoxy}methyl)-5-methyl-1,3-oxazol-2-yl]-2-furancarboxylic acid as colorless crystals (0.31 g, yield 84%). Recrystallization from acetone-hexane gave colorless prism crystals. melting point: 154-155° C.

Example 243

To a mixture of ethyl 5-(4-{[(4-chloromethyl-2-methoxyphenoxy)methyl]-5-methyl-1,3-oxazol-2-yl}-2-furancarboxylate (2.33 g), 3-hydroxy-1-phenyl-1H-pyrazole-4-carbaldehyde (1.02 g) and N,N-dimethylformamide (50 mL) was added sodium hydride (60% in oil, 0.24 g) at room temperature, and the mixture was stirred at 90° C. for 1 hr. Water was poured into the reaction mixture, and the mixture was extracted with ethyl acetate. The organic layer was washed with saturated brine, dried over anhydrous magnesium sulfate and concentrated. The residue was subjected to silica gel column chromatography to give ethyl 5-{4-[(4-{[(4-formyl-1-phenyl-1H-pyrazol-3-yl)oxy]methyl}-2-methoxyphenoxy)methyl]-5-methyl-1,3-oxazol-2-yl}-2-furancarboxylate as colorless crystals (2.20 g, yield 73%) from a fraction eluted with ethyl acetate-hexane (1:1, v/v). Recrystallization from ethyl acetate-hexane gave colorless prism crystals. melting point: 143-145° C.

Example 244

A mixture of ethyl 5-{4-[(4-{[(4-formyl-1-phenyl-1H-pyrazol-2-yl)oxy]methyl}-2-methoxyphenoxy)methyl]-5-methyl-1,3-oxazol-2-yl}-2-furancarboxylate (1.39 g), [(2-ethyl-1,3-thiazol-4-yl)methyl]triphenylphosphonium chloride (1.61 g), potassium carbonate (0.53 g) and N,N-dimethylformamide (30 mL) was stirred at room temperature for 15 hrs. Water was poured into the reaction mixture, and the mixture was extracted with ethyl acetate. The organic layer was washed with saturated brine, dried over anhydrous magnesium sulfate and concentrated. The residue was subjected to silica gel column chromatography and eluted with ethyl acetate-hexane (1:1, v/v) to give ethyl 5-[4-({4-[({4-[(Z)-2-(2-ethyl-1,3-thiazol-4-yl)ethenyl]-1-phenyl-1H-pyrazol-3-yl}oxy)methyl]-2-methoxyphenoxy}methyl)-5-methyl-1,3-oxazol-2-yl]-2-furancarboxylate as colorless crystals (0.54 g, yield 32%). Recrystallization from ethyl acetate-hexane gave colorless prism crystals. melting point: 133-135° C.

In addition, ethyl 5-[4-({4-[({4-[(E)-2-(2-ethyl-1,3-thiazol-4-yl)ethenyl]-1-phenyl-1H-pyrazol-3-yl}oxy)methyl]-2-methoxyphenoxy}methyl)-5-methyl-1,3-oxazol-2-yl]-2-furancarboxylate was obtained as colorless crystals (0.74 g, yield 44%) from a fraction successively obtained by elution. Recrystallization from ethyl acetate-hexane gave colorless prism crystals. melting point: 150-151° C.

Example 245

A solution (15 mL) of 3-methoxy-4-[(5-methyl-2-phenyl-1,3-oxazol-4-yl)methoxy]benzoic acid (998 mg), oxalyl chloride (407 mg) and N,N-dimethylformamide (0.05 mL) in tetrahydrofuran was stirred at room temperature for 15 min. The reaction mixture was concentrated and to the residue was added a solution (10 mL) of 3-amino-1-phenyl-1H-pyrazole-4-carbaldehyde (500 mg) in N,N-dimethylacetamide and the mixture was stirred at room temperature for 2 hrs. Water was poured into the reaction mixture, and the mixture was extracted with ethyl acetate. The ethyl acetate layer was washed with saturated brine, dried over anhydrous magnesium sulfate and concentrated. The residue was subjected to silica gel column chromatography and eluted with ethyl acetate-hexane (1:9 to 4:1, v/v) to give N-(4-formyl-1-phenyl-1H-pyrazol-3-yl)-3-methoxy-4-[(5-methyl-2-phenyl-1,3-oxazol-4-yl)methoxy]benzamide. Recrystallization from ethyl acetate-hexane gave pale-yellow crystal (536 mg, yield 40%). melting point: 234-235° C.

Example 246

A mixture of ethyl (4-{4-[(4-chloromethyl-2-methoxyphenoxy)methyl]-5-methyl-1,3-oxazol-2-yl}phenyl)acetate (0.51 g), 3-hydroxy-1-phenyl-1H-pyrazole-4-carbaldehyde (0.21 g), potassium carbonate (0.15 g) and N,N-dimethylformamide (20 mL) was stirred at 90° C. for 1 hr. Water was poured into the reaction mixture, and the mixture was extracted with ethyl acetate. The organic layer was washed with saturated brine, dried over anhydrous magnesium sulfate and concentrated. The residue was subjected to silica gel column chromatography to give ethyl (4-{4-[(4-{[(4-formyl-1-phenyl-1H-pyrazol-3-yl)oxy]methyl}-2-methoxyphenoxy)methyl]-5-methyl-1,3-oxazol-2-yl}phenyl)acetate as colorless crystals (0.55 g, yield 86%) from a fraction eluted with ethyl acetate-hexane (1:1, v/v). Recrystallization from ethyl acetate-hexane gave colorless prism crystals. melting point: 157-158° C.

Example 247

To a mixture of ethyl (4-{4-[(4-{[(4-formyl-1-phenyl-1H-pyrazol-3-yl)oxy]methyl}-2-methoxyphenoxy)methyl]-5-methyl-1,3-oxazol-2-yl}phenyl)acetate (0.45 g), tetraethyl methylenediphosphonate (0.25 g) and N,N-dimethylformamide (10 mL) was added sodium hydride (60% in oil, 0.04 g) at room temperature, and the mixture was stirred at the same temperature for 1 hr. Water was poured into the reaction mixture, and the mixture was extracted with ethyl acetate. The organic layer was washed with saturated brine, dried over anhydrous magnesium sulfate and concentrated. The residue was subjected to silica gel column chromatography to give ethyl {4-[4-({4-[({4-[(E)-2-(diethoxyphosphoryl)ethenyl]-1-phenyl-1H-pyrazol-3-yl}oxy)methyl]-2-methoxyphenoxy}methyl)-5-methyl-1,3-oxazol-2-yl]phenyl}acetate as a colorless oil (0.28 g, yield 51%) from a fraction eluted with ethyl acetate-hexane (6:1, v/v).

NMR(CDCl$_3$) δ: 1.26 (3H, t, J=7.2 Hz), 1.32 (6H, t, J=7.0 Hz), 2.42 (3H, s), 3.65 (2H, s), 3.90 (3H, s), 4.01-4.16 (4H, m), 4.17 (2H, q, J=7.2 Hz), 5.07 (2H, s), 5.36 (2H, s), 6.25 (1H, dd, J=19.8, 17.6 Hz), 7.00-7.09 (3H, m), 7.22-7.49 (6H, m), 7.59-7.65 (2H, m), 7.86 (1H, s), 7.94-7.99 (2H, m).

Example 248

To a mixture of ethyl 5-{4-[(4-{[(4-formyl-1-phenyl-1H-pyrazol-3-yl)oxy]methyl}-2-methoxyphenoxy)methyl]-5-methyl-1,3-oxazol-2-yl}-2-furancarboxylate (0.70 g), tetraethyl methylenediphosphonate (0.40 g) and N,N-dimethylformamide (20 mL) was added sodium hydride (60% in oil, 0.06 g) at room temperature, and the mixture was stirred at the same temperature for 2 hrs. Water was poured into the reaction mixture, and the mixture was extracted with ethyl acetate. The organic layer was washed with saturated brine, dried over anhydrous magnesium sulfate and concentrated. The residue was subjected to silica gel column chromatography to give ethyl 5-[4-({4-[({4-[(E)-2-(diethoxyphosphoryl)ethenyl]-1-phenyl-1H-pyrazol-3-yl}oxy)methyl]-2-methoxyphenoxy}methyl)-5-methyl-1,3-oxazol-2-yl]-2-furancarboxylate as colorless crystals (0.41 g, yield 46%) from a fraction eluted with acetate-hexane (9:1, v/v). Recrystallization from ethyl ethyl acetate-hexane gave colorless prism crystals. melting point: 129-130° C.

Example 249

To a mixture of ethyl {3-[4-({4-[({4-[(E)-2-(diethoxyphosphoryl)ethenyl]-1-phenyl-1H-pyrazol-3-yl}oxy)methyl]-2-methoxyphenoxy}methyl)-5-methyl-1,3-oxazol-2-yl]phenyl}acetate (1.87 g), tetrahydrofuran (10 mL) and ethanol (10 mL) was added 1N aqueous sodium hydroxide solution (5 mL), and the mixture was stirred at 50° C. for 1 hr. To the reaction mixture were added 1N hydrochloric acid (5 mL) and water, and the precipitated crystals were collected by filtration to give {3-[4-({4-[({4-[(E)-2-(diethoxyphosphoryl)ethenyl]-1-phenyl-1H-pyrazol-3-yl}oxy)methyl]-2-methoxyphenoxy}methyl)-5-methyl-1,3-oxazol-2-yl]phenyl}acetic acid as colorless crystals (1.67 g, yield 93%). Recrystallization from acetone-hexane gave colorless prism crystals. melting point: 174-175° C.

Example 250

To a mixture of ethyl {3-[4-({4-[({4-[(E)-2-(2-ethyl-1,3-thiazol-4-yl)ethenyl]-1-phenyl-1H-pyrazol-3-yl}oxy)methyl]-2-methoxyphenoxy}methyl)-5-methyl-1,3-oxazol-2-yl]phenyl}acetate (0.36 g), tetrahydrofuran (2 mL) and ethanol (2 mL) was added 1N aqueous sodium hydroxide solution (1 mL), and the mixture was stirred at 50° C. for 1 hr. To the reaction mixture were added 1N hydrochloric acid (1 mL) and water, and the mixture was extracted with ethyl acetate. The organic layer was washed with saturated brine, dried over anhydrous magnesium sulfate and concentrated to give {3-[4-({4-[({4-[(E)-2-(2-ethyl-1,3-thiazol-4-yl)ethenyl]-1-phenyl-1H-pyrazol-3-yl}oxy)methyl]-2-methoxyphenoxy}methyl)-5-methyl-1,3-oxazol-2-yl]phenyl}acetic acid as colorless crystals (0.29 g, 85%). Recrystallization from acetone-hexane gave pale-yellow prism crystals. melting point: 154-155° C.

Example 251

A mixture of {3-[4-({4-[({4-[(E)-2-(diethoxyphosphoryl)ethenyl]-1-phenyl-1H-pyrazol-3-yl}oxy)methyl]-2-methoxyphenoxy}methyl)-5-methyl-1,3-oxazol-2-yl]phenyl}acetic acid (0.66 g), 1-hydroxybenzotriazole ammonia complex (0.21 g), 1-ethyl-3-(3-dimethylaminopropyl)carbodiimide hydrochloride (0.27 g) and N,N-dimethylformamide (30 mL) was stirred at room temperature for 15 hrs. Water was poured into the reaction mixture, and the precipitated crystals were collected by filtration to give ethyl (E)-2-{3-[(4-{[2-(3-carbamoylmethylphenyl)-5-methyl-1,3-oxazol-4-yl]methoxy}-3-methoxybenzyl)oxy]-1-phenyl-1H-pyrazol-4-yl}ethenylphosphonate as colorless crystals (0.56 g, yield 85%). Recrystallization from acetone-hexane gave colorless prism crystals. melting point: 112-113° C.

Example 252

To a mixture of methyl 5-{4-({4-[({4-[(E)-2-(diethoxyphosphoryl)ethenyl]-1-phenyl-1H-pyrazol-3-yl}oxy)methyl]-2-methoxyphenoxy}methyl)-5-methyl-1,3-oxazol-2-yl}-2-methoxybenzoate (0.10 g), tetrahydrofuran (1 mL) and ethanol (1 mL) was added 1N aqueous sodium hydroxide solution (0.5 mL); and the mixture was stirred at 50° C. for 1 hr. To the reaction mixture were added 1N hydrochloric acid (1 mL) and water, and the mixture was extracted with ethyl acetate. The organic layer was washed with saturated brine, dried over anhydrous magnesium sulfate and concentrated to give 5-{4-({4-[({4-[(E)-2-(diethoxyphosphoryl)ethenyl]-1-phenyl-1H-pyrazol-3-yl}oxy)methyl]-2-methoxyphenoxy}methyl)-5-methyl-1,3-oxazol-2-yl}-2-methoxybenzoic acid as colorless crystals (0.08 g, yield 80%). Recrystallization from acetone-hexane gave colorless prism crystals. melting point: 171-172° C.

Example 253

A mixture of ethyl (3-{4-[(4-chloromethyl-2-methoxyphenoxy)methyl]-5-methyl-1,3-oxazol-2-yl}phenyl)acetate (7.20 g), 3-hydroxy-1-phenyl-1H-pyrazole-4-carbaldehyde (3.01 g), potassium carbonate (2.21 g) and N,N-dimethylformamide (100 mL) was stirred at 80° C. for 1 hr. Water was poured into the reaction mixture, and the mixture was extracted with ethyl acetate. The organic layer was washed with saturated brine, dried over anhydrous magnesium sulfate and concentrated. The residue was subjected to silica gel column chromatography to give ethyl (3-{4-[(4-{[(4-formyl-1-phenyl-1H-pyrazol-3-yl)oxy]methyl}-2-methoxyphenoxy)methyl]-5-methyl-1,3-oxazol-2-yl}phenyl)acetate as colorless crystals (6.84 g, yield 73%) from a fraction eluted with ethyl acetate-hexane (3:2, v/v). Recrystallization from ethyl acetate-hexane gave colorless prism crystals. melting point: 145-146° C.

Example 254

To a mixture of ethyl (3-{4-[(4-{[(4-formyl-1-phenyl-1H-pyrazol-3-yl)oxy]methyl}-2-ethoxyphenoxy)methyl]-5-methyl-1,3-oxazol-2-yl}phenyl)acetate (2.0 g), tetraethyl methylenediphosphonate (1.07 g) and N,N-dimethylformamide (50 mL) was added sodium hydride (60% in oil, 0.16 g) at room temperature, and the mixture was stirred at the same temperature for 3 hrs. Water was poured into the reaction mixture, and the mixture was extracted with ethyl acetate. The organic layer was washed with saturated brine, dried over anhydrous magnesium sulfate and concentrated. The residue was subjected to silica gel column chromatography to give ethyl {3-[4-({4-[({4-[(E)-2-(diethoxyphosphoryl)ethenyl]-1-phenyl-1H-pyrazol-3-yl}oxy)methyl]-2-methoxyphenoxy}methyl)-5-methyl-1,3-oxazol-2-yl]phenyl}acetate as a colorless oil from a fraction eluted with ethyl acetate-hexane (9:1, v/v) (1.87 g, yield 77%).

NMR(CDCl$_3$) δ: 1.26 (3H, t, J=7.2 Hz), 1.32 (6H, t, J=7.0 Hz), 2.42 (3H, s), 3.67 (2H, s), 3.90 (3H, s), 4.01-4.16 (4H, m), 4.17 (2H, q, J=7.2 Hz), 5.08 (2H, s), 5.36 (2H, s), 6.26 (1H, dd, J=19.8, 17.6 Hz), 7.03-7.09 (3H, m), 7.22-7.49 (6H, m), 7.59-7.65 (2H, m), 7.86-7.95 (3H, m).

Example 255

A mixture of methyl 5-{4-[(4-chloromethyl-2-methoxyphenoxy)methyl]-5-methyl-1,3-oxazol-2-yl}-2-(methanesulfonyloxy)benzoate (1.50 g), 3-hydroxy-1-phenyl-1H-pyrazole-4-carbaldehyde (0.56 g), potassium carbonate (0.41 g) and N,N-dimethylformamide (30 mL) was stirred at room temperature for 2 hrs. The reaction mixture was acidified by adding 1N hydrochloric acid, and the mixture was extracted with ethyl acetate. The organic layer was washed with saturated brine, dried over anhydrous magnesium sulfate and concentrated. The residue was subjected to silica gel column chromatography and eluted with ethyl acetate-hexane (1:3 to 1:1, v/v) to give methyl 5-{4-[(4-{[(4-formyl-1-phenyl-1H-pyrazol-3-yl)oxy]methyl}-2-methoxyphenoxy)methyl]-5-methyl-1,3-oxazol-2-yl}-2-(methanesulfonyloxy)benzoate as pale-yellow crystals (0.80 g, yield 41%). Recrystallization from ethyl acetate-hexane gave pale-yellow prism crystals. melting point: 136-137° C.

Example 256

To a mixture of methyl 5-{4-[(4-{[(4-formyl-1-phenyl-1H-pyrazol-3-yl)oxy]methyl}2-methoxyphenoxy)methyl]-5-methyl-1,3-oxazol-2-yl}-2-(methanesulfonyloxy)benzoate (0.50 g), tetrahydrofuran (3 mL) and ethanol (3 mL) was added 1N aqueous sodium hydroxide solution (3 mL), and the mixture was stirred at 50° C. for 1 hr. To the reaction mixture were added 1N hydrochloric acid (3 mL) and water, and the mixture was extracted with ethyl acetate. The organic layer was washed with saturated brine, dried over anhydrous magnesium sulfate and concentrated to give pale-yellow crystal. A mixture of the crystal, potassium carbonate (0.21 g), methyl iodide (0.55 g) and N,N-dimethylformamide (10 mL) was stirred at room temperature for 3 hrs. Water was added to the reaction mixture, and the mixture was extracted with ethyl acetate. The organic layer was washed with saturated brine, dried over anhydrous magnesium sulfate and concentrated to give methyl 5-{4-[(4-{[(4-formyl-1-phenyl-1H-pyrazol-3-yl)oxy]methyl}2-methoxyphenoxy)methyl]-5-methyl-1,3-oxazol-2-yl}-2-methoxybenzoate as pale-yellow crystals (0.30 g, yield 67%). Recrystallization from ethyl acetate-hexane gave colorless prism crystals. melting point: 165-166° C.

Example 257

To a mixture of methyl 5-{4-[(4-{[(4-formyl-1-phenyl-1H-pyrazol-3-yl)oxy]methyl)}2-methoxyphenoxy)methyl]-5-methyl-1,3-oxazol-2-yl}-2-methoxybenzoate (0.26 g), tetraethyl methylenediphosphonate (0.14 g) and N,N-dimethylformamide (5 mL) was added sodium hydride (60% in oil, 0.02 g) at room temperature, and the mixture was stirred at the same temperature for 2 hrs. Water was poured into the reaction mixture, and the mixture was extracted with ethyl acetate. The organic layer was washed with saturated brine, dried over anhydrous magnesium sulfate and concentrated. The residue was subjected to silica gel column chromatography to give methyl 5-{4-({4-[({4-[(E)-2-(diethoxyphosphoryl)ethenyl]-1-phenyl-1H-pyrazol-3-yl}oxy)methyl]-2-methoxyphenoxy}methyl)-5-methyl-1,3-oxazol-2-yl}-2-methoxybenzoate as colorless crystals (0.13 g, yield 41%) from a fraction eluted with ethyl acetate-hexane (9:1, v/v). Recrystallization from ethyl acetate-hexane gave colorless prism crystals. melting point: 144-145° C.

Example 258

To a mixture of 5-({4-[(5-methyl-2-phenyl-1,3-oxazol-4-yl)methoxy]phenoxy}methyl)-2-phenyl-1,3-oxazole-4-carbaldehyde (1.0 g), ethyl diethylphosphonoacetate (0.52 g) and N,N-dimethylformamide (20 mL) was added sodium hydride (60% in oil, 0.10 g) at room temperature, and the mixture was stirred at the same temperature for 3 hrs. The reaction mixture was poured into water and the mixture was extracted with ethyl acetate. The organic layer was washed with saturated brine, dried over anhydrous magnesium sulfate and concentrated. The residue was subjected to silica gel column chromatography to give ethyl (2E)-3-[5-({4-[(5-methyl-2-phenyl-1,3-oxazol-4-yl)methoxy]phenoxy}methyl)-2-phenyl-1,3-oxazol-4-yl]-2-propenoate as colorless crystals (0.55 g, yield 49%) from a fraction eluted with ethyl acetate-hexane (1:4, v/v). Recrystallization from ethyl acetate-hexane gave colorless prism crystals. melting point: 107-108° C.

Example 259

To a mixture of 1-benzyl-3-[(4-{[2-(2-furyl)-5-methyl-1,3-oxazol-4-yl]methoxy}-3-methoxybenzyl)oxy]-1H-pyrazole-4-carbaldehyde (1.50 g), ethyl diethylphosphonoacetate (0.74 g) and N,N-dimethylformamide (30 mL) was added sodium hydride (60% in oil, 0.14 g) at room temperature, and the mixture was stirred at the same temperature for 15 hrs. The reaction mixture was poured into water and the mixture was extracted with ethyl acetate. The organic layer was washed with saturated brine, dried over anhydrous magnesium sulfate and concentrated to give ethyl (2E)-3-{1-benzyl-3-[(4-{[2-(2-furyl)-5-methyl-1,3-oxazol-4-yl]methoxy}-3-methoxybenzyl)oxy]-1H-pyrazol-4-yl}-2-propenoate as colorless crystals (1.50 g, yield 88%). Recrystallization from ethyl acetate-hexane gave colorless prism crystals. melting point: 147-148° C.

Example 260

To a mixture of ethyl (2E)-3-{1-benzyl-3-[(4-{[2-(2-furyl)-5-methyl-1,3-oxazol-4-yl]methoxy}-3-methoxybenzyl)oxy]-1H-pyrazol-4-yl}-2-propenoate (1.20 g), tetrahydrofuran (5 mL) and ethanol (5 mL) was added 1N aqueous sodium hydroxide solution (5 mL), and the mixture was heated under reflux for 3 hrs. To the reaction mixture were added 1N hydrochloric acid (5 mL) and water, and the precipitated crystals were collected by filtration to give (2E)-3-{1-benzyl-3-[(4-{[2-(2-furyl)-5-methyl-1,3-oxazol-4-yl]methoxy}-3-methoxybenzyl)oxy]-1H-pyrazol-4-yl}-2-propenoic acid as colorless crystals (1.12 g, yield 98%). Recrystallization from ethyl acetate-hexane gave colorless prism crystals. melting point: 175-176° C.

Example 261

To a mixture of ethyl (2E)-3-[5-({4-[(5-methyl-2-phenyl-1,3-oxazol-4-yl)methoxy]phenoxy}methyl)-2-phenyl-1,3-oxazol-4-yl]-2-propenoate (0.40 g), tetrahydrofuran (2 mL) and ethanol (2 mL) was added 1N aqueous sodium hydroxide solution (2 mL), and the mixture was heated under reflux for 1 hr. To the reaction mixture were added 1N hydrochloric acid (2 mL) and water, and the precipitated crystals were collected by filtration to give (2E)-3-[5-({4-[(5-methyl-2-phenyl-1,3-oxazol-4-yl)methoxy]phenoxy}methyl)-2-phenyl-1,3-oxazol-4-yl]-2-propenoic acid as colorless crystals (0.37 g, yield 97%). Recrystallization from tetrahydrofuran-hexane gave colorless prism crystals. melting point: 209-210° C.

Example 262

A mixture of 3-[(4-{[2-(2-furyl)-5-methyl-1,3-oxazol-4-yl]methoxy}-3-methoxybenzyl)oxy]-1-phenyl-1H-pyrazole-4-carbaldehyde (1.10 g), 1,3-thiazolidine-2,4-dione (0.27 g), piperidine (0.04 g) and ethanol (30 mL) was heated under reflux for 3 hrs. The reaction mixture was concentrated, and the obtained crystals were washed with ethanol to give (5Z)-5-({3-[(4-{[2-(2-furyl)-5-methyl-1,3-oxazol-4-yl]methoxy}-3-methoxybenzyl)oxy]-1-phenyl-1H-pyrazol-4-yl}methylene)-1,3-thiazolidine-2,4-dione as yellow crystals (1.13 g, yield 84%). Recrystallization from tetrahydrofuran-hexane gave yellow prism crystals. melting point: 252-253° C.

Example 263

A mixture of 4-(4-chloromethyl-2-methoxyphenoxy)methyl-5-methyl-2-(2-furyl)-1,3-oxazole (2.25 g), ethyl 4-hydroxy-2-phenylpyrimidine-5-carboxylate (1.50 g), potassium carbonate (1.27 g) and N,N-dimethylformamide (50 mL) was stirred at 90° C. for 2 hrs. The reaction mixture was poured into water and the mixture was extracted with ethyl acetate. The ethyl acetate layer was washed successively with 0.2N aqueous sodium hydroxide solution and water, dried over anhydrous magnesium sulfate and concentrated. The obtained crystals were recrystallized from tetrahydrofuran-ethyl acetate to give ethyl 4-[(4-{[2-(2-furyl)-5-methyl-1,3-oxazol-4-yl]methoxy}-3-methoxybenzyl)oxy]-2-phenylpyrimidine-5-carboxylate as colorless prism crystals (2.50 g, yield 75%). melting point: 142-143° C.

Example 264

A mixture of ethyl 3-hydroxy-1-methyl-1H-pyrazole-4-carboxylate (1.93 g), 4-(4-chloromethyl-2-methoxyphenoxymethyl)-5-methyl-2-phenyl-1,3-oxazole (3.89 g), potassium carbonate (3.15 g) and N,N-dimethylformamide (30 mL) was stirred overnight at 60° C. The reaction mixture was poured into dilute hydrochloric acid, and the mixture was extracted with ethyl acetate. The ethyl acetate layer was washed with saturated brine, dried over anhydrous magnesium sulfate and concentrated. The obtained colorless crystals were collected by filtration to give ethyl 3-{[3-methoxy-4-(5-methyl-2-phenyl-1,3-oxazol-4-ylmethoxy)benzyl]oxy}-1-methyl-1H-pyrazole-4-carboxylate (5.23 g, yield 97%). The crystals were recrystallized from acetone-hexane. melting point: 134-135° C.

Example 265

A mixture of ethyl 3-{[3-methoxy-4-(5-methyl-2-phenyl-1,3-oxazol-4-ylmethoxy)benzyl]oxy}-1-methyl-1H-pyrazole-4-carboxylate (400 mg), 1N aqueous sodium hydroxide solution (3 mL), tetrahydrofuran (5 mL) and ethanol (5 mL) was stirred at 60° C. for 5 hrs. To the reaction mixture was added 1N hydrochloric acid (3 mL), and the mixture was extracted with ethyl acetate. The ethyl acetate layer was washed with saturated brine, dried over anhydrous magnesium sulfate and concentrated. The obtained colorless crystals were collected by filtration to give 3-{[3-methoxy-4-(5-methyl-2-phenyl-1,3-oxazol-4-ylmethoxy)benzyl]oxy}-1- methyl-1H-pyrazole-4-carboxylic acid (350 mg, yield 93%). The crystals were recrystallized from acetone-hexane. melting point: 169-170° C.

Example 266

To a solution of ethyl 3-{[3-methoxy-4-(5-methyl-2-phenyl-1,3-oxazol-4-ylmethoxy)benzyl]oxy}-1-methyl-1H-pyrazole-4-carboxylate (4.40 g) in tetrahydrofuran (20 mL) was gradually added lithium aluminum hydride (350 mg) at 0° C., and the mixture was stirred for 30 min. Sodium sulfate decahydrate (3.54 g) was added to the reaction mixture, the precipitate was filtered off, and the filtrate was concentrated. The residue was subjected to silica gel column chromatography to give (3-{[3-methoxy-4-(5-methyl-2-phenyl-1,3-oxazol-4-ylmethoxy)benzyl]oxy}-1-methyl-1H-pyrazol-4-yl)methanol (3.88 g, yield 97%) as colorless crystals from a fraction eluted with ethyl acetate-hexane (1:1, volume ratio). The crystals were recrystallized from ethyl acetate-hexane. melting point: 108-109° C.

Example 267

A mixture of (3-{[3-methoxy-4-(5-methyl-2-phenyl-1,3-oxazol-4-ylmethoxy)benzyl]oxy}-1-methyl-1H-pyrazol-4-yl)methanol (3.40 g), activated manganese dioxide (10.03 g) and tetrahydrofuran (50 mL) was stirred overnight at room temperature. Manganese dioxide was removed by filtration, and the filtrate was concentrated to give 3-{[3-methoxy-4-(5-methyl-2-phenyl-1,3-oxazol-4-ylmethoxy)benzyl]oxy}-1-methyl-1H-pyrazole-4-carbaldehyde (3.25 g, yield 96%) as colorless crystals. The crystals were recrystallized from acetone-hexane. melting point: 123-124° C.

Example 268

A mixture of 3-{[3-methoxy-4-(5-methyl-2-phenyl-1,3-oxazol-4-ylmethoxy)benzyl]oxy}-1-methyl-1H-pyrazole-4-carboxylic acid (0.90 g), 1-hydroxy-1H-1,2,3-benzotriazole ammonia complex (0.35 g), 1-ethyl-3-(3-dimethylaminopropyl)carbodiimide hydrochloride (0.45 g) and N,N-dimethylformamide (10 mL) was stirred overnight at room temperature. The reaction mixture was poured into water and the mixture was extracted with ethyl acetate. The ethyl acetate layer was washed successively with dilute hydrochloric acid, saturated aqueous sodium hydrogen carbonate and saturated brine, dried over anhydrous magnesium sulfate and concentrated to give 3-{[3-methoxy-4-(5-methyl-2-phenyl-1,3-oxazol-4-ylmethoxy)benzyl]oxy}-1-methyl-1H-pyrazole-4-carboxamide (0.71 g, yield 79%) as colorless crystals. The crystals were recrystallized from acetone-hexane. melting point: 168-169° C.

Example 269

A mixture of methoxymethylamine hydrochloride (0.85 g), triethylamine (1.3 mL) and N,N-dimethylformamide (20 mL) was stirred at room temperature for 30 min. To the reaction mixture were added 3-{[3-methoxy-4-(5-methyl-2-phenyl-1,3-oxazol-4-ylmethoxy)benzyl]oxy}-1-methyl-1H-pyrazole-4-carboxylic acid (3.45 g), 1-hydroxy-1H-1,2,3-benzotriazole monohydrate (1.22 g) and 1-ethyl-3-(3-dimethylaminopropyl)carbodiimide hydrochloride (1.60 g), and the mixture was stirred overnight at room temperature. The reaction mixture was poured into water and the mixture was extracted with ethyl acetate. The ethyl acetate layer was washed successively with dilute hydrochloric acid, saturated aqueous sodium hydrogen carbonate and saturated brine, dried over anhydrous magnesium sulfate and concentrated to give N-methoxy-N-methyl-3-{[3-methoxy-4-(5-methyl-2-phenyl-1,3-oxazol-4-ylmethoxy)benzyl]oxy}-1-methyl-1H-pyrazole-4-carboxamide (3.63 g, yield 96%) as colorless crystals. The crystals were recrystallized from acetone-hexane. melting point: 138-139° C.

Example 270

To a solution of N-methoxy-N-methyl-3-{[3-methoxy-4-(5-methyl-2-phenyl-1,3-oxazol-4-ylmethoxy)benzyl]oxy}-1-methyl-1H-pyrazole-4-carboxamide (3.00 g) in tetrahydrofuran (30 mL) was slowly added methylmagnesium bromide (1.0 M tetrahydrofuran solution, 15 mL) at 0° C., and the mixture was stirred at room temperature for 2 hrs. The reaction mixture was poured into dilute hydrochloric acid, and the mixture was extracted with ethyl acetate. The ethyl acetate layer was washed with saturated brine, dried over anhydrous magnesium sulfate and concentrated to give 1-(3-{[3-methoxy-4-(5-methyl-2-phenyl-1,3-oxazol-4-ylmethoxy)benzyl]oxy}-1-methyl-1H-pyrazol-4-yl)ethanone (2.65 g, yield 97%) as colorless crystals. The crystals were recrystallized from acetone-hexane. melting point: 170-171° C.

Example 271

To a solution of 3-{[3-methoxy-4-(5-methyl-2-phenyl-1,3-oxazol-4-ylmethoxy)benzyl]oxy}-1-methyl-1H-pyrazole-4-carbaldehyde (0.45 g) in tetrahydrofuran (10 mL) was slowly added methylmagnesium bromide (3.0 M diethyl ether solution, 0.5 mL) at 0° C., and the mixture was stirred for 1 hr. The reaction mixture was poured into dilute hydrochloric acid, and the mixture was extracted with ethyl acetate. The ethyl acetate layer was washed with saturated brine, dried over anhydrous magnesium sulfate and concentrated to give 1-(3-{[3-methoxy-4-(5-methyl-2-phenyl-1,3-oxazol-4-ylmethoxy)benzyl]oxy}-1-methyl-1H-pyrazol-4-yl)ethanol (0.38 g, yield 81%) as colorless crystals. The crystals were recrystallized from ethyl acetate-hexane. melting point: 94-95° C.

Example 272

A mixture of ethyl 3-hydroxy-1-phenyl-1H-pyrazole-4-carboxylate (6.00 g), 4-(4-chloromethyl-2-methoxyphenoxymethyl)-5-methyl-2-phenyl-1,3-oxazole (8.96 g), potassium carbonate (7.20 g) and N,N-dimethylformamide (100 mL) was stirred overnight at 60° C. The reaction mixture was poured into dilute hydrochloric acid, and the mixture was extracted with ethyl acetate. The ethyl acetate layer was washed with saturated brine, dried over anhydrous magnesium sulfate and concentrated. The obtained colorless crystals were collected by filtration to give ethyl 3-{[3-methoxy-4-(5-methyl-2-phenyl-1,3-oxazol-4-ylmethoxy)benzyl]oxy}-1-phenyl-1H-pyrazole-4-carboxylate (13.15 g, yield 95%). The crystals were recrystallized from acetone-hexane. melting point: 160-161° C.

Example 273

A mixture of ethyl 3-{[3-methoxy-4-(5-methyl-2-phenyl-1,3-oxazol-4-ylmethoxy)benzyl]oxy}-1-phenyl-1H-pyrazole-4-carboxylate (3.00 g), 1N aqueous sodium hydroxide solution (10 mL), tetrahydrofuran (30 mL) and ethanol (30 mL) was stirred at 60° C. for 5 hrs. 1N Hydrochloric acid (10 mL) was added to the reaction mixture, and the mixture was extracted with ethyl acetate. The ethyl acetate layer was washed with saturated brine, dried over anhydrous magnesium sulfate and concentrated. The obtained colorless crystals were collected by filtration to give 3-{[3-methoxy-4-(5-methyl-2-phenyl-1,3-oxazol-4-ylmethoxy)benzyl]oxy}-1-phenyl-1H-pyrazole-4-carboxylic acid (2.63 g, yield 92%). The crystals were recrystallized from acetone-hexane. melting point: 209-210° C.

Example 274

To a solution of ethyl 3-{[3-methoxy-4-(5-methyl-2-phenyl-1,3-oxazol-4-ylmethoxy)benzyl]oxy}-1-phenyl-1H-pyrazole-4-carboxylate (9.02 g) in tetrahydrofuran (50 mL) was slowly added lithium aluminum hydride (650 mg) at 0° C., and the mixture was stirred for 30 min. Sodium sulfate decahydrate (6.88 g) was added to the reaction mixture, the precipitate was filtered off, and the filtrate was concentrated. The residue was subjected to silica gel column chromatography to give (3-{[3-methoxy-4-(5-methyl-2-phenyl-1,3-oxazol-4-ylmethoxy)benzyl]oxy})-1-phenyl-1H-pyrazol-4-yl"methanol (8.11 g, yield 98%) as colorless crystals from a fraction eluted with ethyl acetate-hexane (1:1, v/v). The crystals were recrystallized from acetone-hexane. melting point: 144-145° C.

Example 275

A mixture of (3-{[3-methoxy-4-(5-methyl-2-phenyl-1,3-oxazol-4-ylmethoxy)benzyl]oxy}-1-phenyl-1H-pyrazol-4-yl)methanol (7.05 g), activated manganese dioxide (20.09 g) and tetrahydrofuran (50 mL) was stirred overnight at room temperature. Manganese dioxide was removed by filtration, and the filtrate was concentrated to give 3-{[3-methoxy-4-(5-methyl-2-phenyl-1,3-oxazol-4-ylmethoxy)benzyl]oxy}-1-phenyl-1H-pyrazole-4-carbaldehyde (6.80 g, yield 96%) as colorless crystals. The crystals were recrystallized from acetone-hexane. melting point: 142-143° C.

Example 276

A mixture of 3-{[3-methoxy-4-(5-methyl-2-phenyl-1,3-oxazol-4-ylmethoxy)benzyl]oxy}-1-phenyl-1H-pyrazole-4-carboxylic acid (0.80 g), 1-hydroxy-1H-1,2,3-benzotriazole ammonia complex (0.27 g), 1-ethyl-3-(3-dimethylaminopropyl)carbodiimide hydrochloride (0.34 g) and N,N-dimethylformamide (10 mL) was stirred overnight at room temperature. The reaction mixture was poured into water and the mixture was extracted with ethyl acetate. The ethyl acetate layer was washed successively with dilute hydrochloric acid, saturated aqueous sodium hydrogen carbonate and saturated brine, dried over anhydrous magnesium sulfate and concentrated to give 3-{[3-methoxy-4-(5-methyl-2-phenyl-1,3-oxazol-4-ylmethoxy)benzyl]oxy}-1-phenyl-1H-pyrazole-4-carboxamide (0.78 g, yield 98%) as colorless crystals. The crystals were recrystallized from acetone-hexane. melting point: 190-191° C.

Example 277

A solution (10 mL) of {3-methoxy-4-[(5-methyl-2-phenyl-1,3-oxazol-4-yl)methoxy]phenyl}acetic acid (1.04 g), oxalyl chloride (403 mg) and N,N-dimethylformamide (0.05 mL) in tetrahydrofuran was stirred at room temperature for 15 min. The reaction mixture was concentrated and to the residue was added a solution (10 mL) of 3-amino-1-phenyl-1H-pyrazole-4-carbaldehyde (500 mg) in N,N-dimethylacetamide, and the mixture was stirred at room temperature for 2 hrs. Water was poured into the reaction mixture, and the mixture was extracted with a mixed solution of ethyl acetate-tetrahydrofuran (1:1). The organic layer was washed successively with distilled water and saturated brine, dried over anhydrous magnesium sulfate and concentrated. The residue was subjected to silica gel column chromatography and eluted with ethyl acetate-hexane (1:4 to 7:3, v/v) to give N-(4-formyl-1-phenyl-1H-pyrazol-3-yl)-2-{3-methoxy-4-[(5-methyl-2-phenyl-1,3-oxazol-4-yl)methoxy]phenyl}acetamide. Recrystallization from ethyl acetate-hexane gave pale-yellow crystal (750 mg, yield 49%). melting point: 156-158° C.

Example 278

A mixture of 3-{[3-methoxy-4-(5-methyl-2-phenyl-1,3-oxazol-4-ylmethoxy)benzyl]oxy}-1-phenyl-1H-pyrazole-4-carbaldehyde (950 mg), hydroxylamine hydrochloride (150 mg), pyridine (1 mL) and ethanol (20 mL) was refluxed for 3 hrs. After concentration of the reaction mixture, dilute hydrochloric acid was added to the residue, and the mixture was extracted with ethyl acetate. The ethyl acetate layer was washed with saturated brine, dried over anhydrous magnesium sulfate and concentrated. The residue was dissolved in acetic anhydride (20 mL), and the mixture was refluxed for 5 hrs. After concentration of the reaction mixture, the residue was subjected to silica gel column chromatography to give 3-{[3-methoxy-4-(5-methyl-2-phenyl-1,3-oxazol-4-ylmethoxy)benzyl]oxy}-1-phenyl-1H-pyrazole-4-carbonitrile (850 mg, yield 90%) as colorless crystals from a fraction eluted with ethyl acetate-hexane (1:2, v/v). The crystals were recrystallized from acetone-hexane. melting point: 174-175° C.

Example 279

To a solution of ethyl 4-[(4-{[2-(2-furyl)-5-methyl-1,3-oxazol-4-yl]methoxy}-3-methoxybenzyl)oxy]-2-phenylpyrimidine-5-carboxylate (3.40 g) in tetrahydrofuran (100 mL) was added lithium aluminum hydride (0.24 g) at room temperature, and the mixture was stirred at room temperature for 1 hr. The reaction mixture was diluted with ethyl acetate (100 mL), and sodium sulfate decahydrate (2.0 g) was further added. After removing the precipitate by filtration, the filtrate was concentrated. The obtained crystals were recrystallized from ethyl acetate to give {4-[(4-{[2-(2-furyl)-5-methyl-1,3-oxazol-4-yl]methoxy}-3-methoxybenzyl)oxy]-2-phenylpyrimidin-5-yl}methanol as colorless prism crystals (2.20 g, yield 70%). melting point: 150-151° C.

Example 280

A mixture of {4-[(4-{[2-(2-furyl)-5-methyl-1,3-oxazol-4-yl]methoxy}-3-methoxybenzyl)oxy]-2-phenylpyrimidin-5-yl}methanol (2.10 g), activated manganese dioxide (8.40 g) and tetrahydrofuran (80 mL) was stirred at room temperature for 3 hrs. Manganese dioxide was removed by filtration, and the filtrate was concentrated. Recrystallization of the obtained crystal from ethyl acetate-hexane gave 4-[(4-{[2-(2-furyl)-5-methyl-1,3-oxazol-4-yl]methoxy}-3-methoxybenzyl)oxy]-2-phenylpyrimidine-5-carbaldehyde as colorless prism crystals (1.50 g, yield 72%). melting point: 143-144° C.

Example 281

A mixture of ethyl (E)-3-(3-{[3-methoxy-4-(5-methyl-2-phenyl-1,3-oxazol-4-ylmethoxy)benzyl]oxy}-1-phenyl-1H-pyrazol-4-yl)-2-propenoate (800 mg), 1N aqueous sodium hydroxide solution (3 mL), tetrahydrofuran (10 mL) and ethanol (10 mL) was stirred at 60° C. for 5 hrs. 1N Hydrochloric acid (3 mL) was added to the reaction mixture, and the mixture was extracted with ethyl acetate. The ethyl acetate layer was washed with saturated brine, dried over anhydrous magnesium sulfate and concentrated. The obtained colorless crystals were collected by filtration to give (E)-3-(3-{[3-methoxy-4-(5-methyl-2-phenyl-1,3-oxazol-4-ylmethoxy)benzyl]oxy}-1-phenyl-1H-pyrazol-4-yl)-2-propenoic acid (720 mg, yield 95%). The crystals were recrystallized from ethyl acetate-hexane. melting point: 188-189° C.

Example 282

To a mixture of 3-{[3-methoxy-4-(5-methyl-2-phenyl-1,3-oxazol-4-ylmethoxy)benzyl]oxy}-1-phenyl-1H-pyrazole-4-carbaldehyde (580 mg), diethylphosphonoacetonitrile (230 mg) and N,N-dimethylformamide (10 mL) was added sodium hydride (60% in oil, 56.0 mg) at 0° C., and the mixture was stirred at room temperature for 5 hrs. The reaction mixture was poured into water and the mixture was extracted with ethyl acetate. The ethyl acetate layer was washed successively with dilute hydrochloric acid and saturated brine, dried over anhydrous magnesium sulfate and concentrated. The residue was subjected to silica gel column chromatography to give (E)-3-(3-{[3-methoxy-4-(5-methyl-2-phenyl-1,3-oxazol-4-ylmethoxy)benzyl]oxy}-1-phenyl-1H-pyrazol-4-yl)-2-propenonitrile (460 mg, yield 76%) as colorless crystals from a fraction eluted with ethyl acetate-hexane (1:2, v/v). The crystals were recrystallized from acetone-hexane. melting point: 184-185° C.

Example 283

To a mixture of potassium tert-butoxide (700 mg) and dimethoxyethane (10 mL) was added a solution of p-toluenesulfonylmethylisocyanide (650 mg) in dimethoxyethane (10 mL) at −78° C., and the mixture was stirred for 5 min. To the reaction mixture was added a solution of 3-{[3-methoxy-4-(5-methyl-2-phenyl-1,3-oxazol-4-ylmethoxy)benzyl]oxy}-1-phenyl-1H-pyrazole-4-carbaldehyde (1.46 g) in dimethoxyethane (10 mL). After stirring at the same temperature for 1 hr, the mixture was stirred for 1 hr while warming to room temperature. To the reaction mixture was added methanol (20 mL), and the mixture was refluxed for 1 hr. After cooling, the reaction mixture was poured into saturated aqueous ammonium chloride solution, and the mixture was extracted with ethyl acetate. The ethyl acetate layer was washed with saturated brine, dried over anhydrous magnesium sulfate and concentrated. The residue was subjected to silica gel column chromatography to give (3-{[3-methoxy-4-(5-methyl-2-phenyl-1,3-oxazol-4-ylmethoxy)benzyl]oxy}-1-phenyl-1H-pyrazol-4-yl)acetonitrile (700 mg, yield 47%) as colorless crystals from a fraction eluted with ethyl acetate-hexane (1:2, v/v). The crystals were recrystallized from ethyl acetate-hexane. melting point: 137-138° C.

Example 284

To a mixture of 3-{[3-methoxy-4-(5-methyl-2-phenyl-1,3-oxazol-4-ylmethoxy)benzyl]oxy}-1-phenyl-1H-pyrazole-4-carbaldehyde (1.00 g), ethyl diethylphosphonoacetate (0.50 g) and N,N-dimethylformamide (15 mL) was added sodium hydride (60% in oil, 100 mg) at 0° C., and the mixture was stirred overnight at room temperature. The reaction mixture was poured into water and the mixture was extracted with ethyl acetate. The ethyl acetate layer was washed successively with dilute hydrochloric acid and saturated brine, dried over anhydrous magnesium sulfate and concentrated. The residue was subjected to silica gel column chromatography to give ethyl (E)-3-(3-{[3-methoxy-4-(5-methyl-2-phenyl-1,3-oxazol-4-ylmethoxy)benzyl]oxy}-1-phenyl-1H-pyrazol-4-yl)-2-propenoate (1.08 g, yield 95%) as colorless crystals from a fraction eluted with ethyl acetate-hexane (1:4, v/v). The crystals were recrystallized from tetrahydrofuran-hexane. melting point: 194-195° C.

Example 285

A mixture of ethyl 3-hydroxy-1-(4-trifluoromethyl)phenyl-1H-pyrazole-4-carboxylate (2.86 g), 4-(4-chloromethyl-2-methoxyphenoxymethyl)-5-methyl-2-phenyl-1,3-oxazole (3.28 g), potassium carbonate (2.66 g) and N,N-dimethylformamide (30 mL) was stirred overnight at 80° C. The reaction mixture was poured into dilute hydrochloric acid, and the mixture was extracted with ethyl acetate. The ethyl acetate layer was washed with saturated brine, dried over anhydrous magnesium sulfate and concentrated. The obtained colorless crystals were collected by filtration to give ethyl 3-{[3-methoxy-4-(5-methyl-2-phenyl-1,3-oxazol-4-ylmethoxy)benzyl]oxy}]-1-(4-trifluoromethyl)phenyl-1H-pyrazole-4-carboxylate (5.16 g, yield 89%). The crystals were recrystallized from tetrahydrofuran-hexane. melting point: 211-212° C.

Example 286

A mixture of ethyl 3-{[3-methoxy-4-(5-methyl-2-phenyl-1,3-oxazol-4-ylmethoxy)benzyl]oxy}-1-(4-trifluoromethyl)phenyl-1H-pyrazole-4-carboxylate (500 mg), 1N aqueous sodium hydroxide solution (3 mL), tetrahydrofuran (3 mL) and ethanol (3 mL) was stirred at 60° C. for 5 hrs. 1N Hydrochloric acid (3 mL) was added to the reaction mixture, and the mixture was extracted with ethyl acetate. The ethyl acetate layer was washed with saturated brine, dried over anhydrous magnesium sulfate and concentrated. The obtained colorless crystals were collected by filtration to give 3-{[3-methoxy-4-(5-methyl-2-phenyl-1,3-oxazol-4-ylmethoxy)benzyl]oxy}-1-(4-trifluoromethyl)phenyl-1H-pyrazole-4-carboxylic acid (390 mg, yield 82%). The crystals were recrystallized from tetrahydrofuran-hexane. melting point: 171-172° C.

Example 287

To a solution of ethyl 3-{[3-methoxy-4-(5-methyl-2-phenyl-1,3-oxazol-4-ylmethoxy)benzyl]oxy}-1-(4-trifluoromethyl)phenyl-1H-pyrazole-4-carboxylate (3.00 g) in tetrahydrofuran (15 mL) was slowly added lithium aluminum hydride (150 mg) at 0° C., and the mixture was stirred for 30 min. Sodium sulfate decahydrate (1.93 g) was added to the reaction mixture, the precipitate was filtered off, and the filtrate was concentrated. The residue was subjected to silica gel column chromatography to give (3-{[3-methoxy-4-(5-methyl-2-phenyl-1,3-oxazol-4-ylmethoxy)benzyl]oxy}-1-(4-trifluoromethyl)phenyl-1H-pyrazol-4-yl)methanol (2.54 g, yield 91%) as colorless crystals from a fraction eluted

Example 288

A mixture of (3-{[3-methoxy-4-(5-methyl-2-phenyl-1,3-oxazol-4-ylmethoxy)benzyl]oxy}-1-(4-trifluoromethyl)phenyl-1H-pyrazol-4-yl)methanol (1.50 g) activated manganese dioxide (4.82 g) and tetrahydrofuran (20 mL) was stirred overnight at room temperature. Manganese dioxide was removed by filtration, the filtrate was concentrated to give 3-{[3-methoxy-4-(5-methyl-2-phenyl-1,3-oxazol-4-ylmethoxy)benzyl]oxy}-1-(4-trifluoromethyl)phenyl-1H-pyrazole-4-carbaldehyde (1.35 g, yield 91%) as colorless crystals. The crystals were recrystallized from tetrahydrofuran-hexane. melting point: 190-191° C.

Example 289

To a mixture of 3-{[3-methoxy-4-(5-methyl-2-phenyl-1,3-oxazol-4-ylmethoxy)benzyl]oxy}-1-(4-trifluoromethyl)phenyl-1H-pyrazole-4-carbaldehyde (850 mg), ethyl diethylphosphonoacetate (370 mg), tetrahydrofuran (5 mL) and N,N-dimethylformamide (10 mL) was added sodium hydride (60% in oil, 70 mg) at 0° C., and the mixture was stirred overnight at room temperature. The reaction mixture was poured into water and the mixture was extracted with ethyl acetate. The ethyl acetate layer was washed successively with dilute hydrochloric acid and saturated brine, dried over anhydrous magnesium sulfate and concentrated. The residue was subjected to silica gel column chromatography to give colorless oil from a fraction eluted with ethyl acetate-hexane (1:4, v/v). A mixture of the oily substance, 1N aqueous sodium hydroxide solution (3 mL), tetrahydrofuran (10 mL) and ethanol (3 mL) was refluxed for 5 hrs. 1N Hydrochloric acid (3 mL) was added to the reaction mixture, and the mixture was extracted with ethyl acetate. The ethyl acetate layer was washed with saturated brine, dried over anhydrous magnesium sulfate and concentrated. The obtained colorless crystals were collected by filtration to give (E)-3-(3-{[3-methoxy-4-(5-methyl-2-phenyl-1,3-oxazol-4-ylmethoxy)benzyl]oxy}-1-(4-trifluoromethyl)phenyl-1H-pyrazol-4-yl)-2-propenoic acid (780 mg, yield 85%). The crystals were recrystallized from acetone-isopropyl ether. melting point: 178-179° C.

Example 290

A solution (15 mL) of 4-{[2-(2-furyl)-5-methyl-1,3-oxazol-4-yl]methoxy}-3-methoxybenzoic acid (968 mg), oxalyl chloride (407 mg) and N,N-dimethylformamide (0.05 mL) in tetrahydrofuran was stirred at room temperature for 15 min. The reaction mixture was concentrated and to the residue was added a solution (5 mL) of 3-amino-1-phenyl-1H-pyrazole-4-carbaldehyde (500 mg) in N,N-dimethylacetamide, and the mixture was stirred at room temperature for 2 hrs. Water was poured into the reaction mixture, and the mixture was extracted with a mixture of ethyl acetate-tetrahydrofuran (1:1). The organic layer was washed successively with distilled water and saturated brine, dried over anhydrous magnesium sulfate and concentrated. The residue was subjected to column chromatography and eluted with ethyl acetate-hexane (1:4 to 1:0, v/v) to give N-(4-formyl-1-phenyl-1H-pyrazol-3-yl)-4-{[2-(2-furyl)-5-methyl-1,3-oxazol-4-yl]methoxy}-3-methoxybenzamide. Recrystallization from ethyl acetate-hexane gave pale-yellow crystal (650 mg, yield 44%). melting point: 212-213.

Example 291

A mixture of methyl 3-hydroxy-1-phenyl-1H-pyrazole-5-carboxylate (3.36 g), 4-(4-chloromethyl-2-methoxyphenoxymethyl)-5-methyl-2-phenyl-1,3-oxazole (5.30 g), potassium carbonate (4.25 g) and N,N-dimethylformamide (50 mL) was stirred at 80° C. for 5 hrs. The reaction mixture was poured into dilute hydrochloric acid, and the mixture was extracted with ethyl acetate. The ethyl acetate layer was washed with saturated brine, dried over anhydrous magnesium sulfate and concentrated. The obtained colorless crystals were collected by filtration to give methyl 3-{[3-methoxy-4-(5-methyl-2-phenyl-1,3-oxazol-4-ylmethoxy)benzyl]oxy}-1-phenyl-1H-pyrazole-5-carboxylate (7.53 g, yield 93%). The crystals were recrystallized from acetone-isopropyl ether. melting point: 143-144° C.

Example 292

A mixture of methyl 3-{[3-methoxy-4-(5-methyl-2-phenyl-1,3-oxazol-4-ylmethoxy)benzyl]oxy}-1-phenyl-1H-pyrazole-5-carboxylate (700 mg), 1N aqueous sodium hydroxide solution (3 mL), tetrahydrofuran (5 mL) and ethanol (3 mL) was stirred at 60° C. for 5 hrs. 1N Hydrochloric acid (3 mL) was added to the reaction mixture, and the mixture was extracted with ethyl acetate. The ethyl acetate layer was washed with saturated brine, dried over anhydrous magnesium sulfate and concentrated. The obtained colorless crystals were collected by filtration to give 3-{[3-methoxy-4-(5-methyl-2-phenyl-1,3-oxazol-4-ylmethoxy)benzyl]oxy}-1-phenyl-1H-pyrazole-5-carboxylic acid (610 mg, yield 90%). The crystals were recrystallized from tetrahydrofuran-hexane. melting point: 192-193° C.

Example 293

To a solution of methyl 3-{[3-methoxy-4-(5-methyl-2-phenyl-1,3-oxazol-4-ylmethoxy)benzyl]oxy}-1-phenyl-1H-pyrazole-5-carboxylate (6.00 g) in tetrahydrofuran (20 mL) was slowly added lithium aluminum hydride (400 mg) at 0° C., and the mixture was stirred for 30 min. Sodium sulfate decahydrate (4.16 g) was added to the reaction mixture, the precipitate was filtered off, and the filtrate was concentrated. The residue was subjected to silica gel column chromatography to give (3-{[3-methoxy-4-(5-methyl-2-phenyl-1,3-oxazol-4-ylmethoxy)benzyl]oxy}-1-phenyl-1H-pyrazol-5-yl)methanol (5.19 g, yield 92%) as colorless crystals from a fraction eluted with ethyl acetate-hexane (1:1, v/v). The crystals were recrystallized from ethyl acetate-hexane. melting point: 146-147° C.

Example 294

A mixture of (3-{[3-methoxy-4-(5-methyl-2-phenyl-1,3-oxazol-4-ylmethoxy)benzyl]oxy}-1-phenyl-1H-pyrazol5-yl)methanol (4.50 g), activated manganese dioxide (14.11 g) and tetrahydrofuran (100 mL) was stirred overnight at room temperature. Manganese dioxide was removed by filtration, and the filtrate was concentrated to give 3-{[3-methoxy-4-(5-methyl-2-phenyl-1,3-oxazol-4-ylmethoxy)benzyl]oxy}-1-phenyl-1H-pyrazole-5-carbaldehyde (4.01 g, yield 90%) as colorless crystals. The crystals were recrystallized from acetone-hexane. melting point: 119-120° C.

with ethyl acetate-hexane (1:1, v/v). The crystals were recrystallized from tetrahydrofuran-hexane. melting point: 147-148° C.

Example 295

To a mixture of 3-({3-methoxy-4-[(5-methyl-2-phenyl-1,3-oxazol-4-yl)methoxy]benzyl}oxy)-1-[4-(trifluoromethyl)phenyl]-1H-pyrazole-4-carbaldehyde (3.30 g), ethyl diethylphosphonoacetate (1.32 g) and N,N-dimethylformamide (50 mL) was added sodium hydride (60% in oil, 0.236 g) at room temperature, and the mixture was stirred for 30 min at the same temperature. The reaction mixture was poured into water, and the precipitated crystals were collected by filtration, and recrystallized from tetrahydrofuran to give ethyl (2E)-3-{3-({3-methoxy-4-[(5-methyl-2-phenyl-1,3-oxazol-4-yl)methoxy]benzyl}oxy)-1-[4-(trifluoromethyl)phenyl]-1H-pyrazol-4-yl}-2-propenoate as a colorless powder (2.59 g, yield 69%). melting point: 205-206° C.

Example 296

To a solution of ethyl (2E)-3-{3-({3-methoxy-4-[(5-methyl-2-phenyl-1,3-oxazol-4-yl)methoxy]benzyl}oxy)-1-[4-(trifluoromethyl)phenyl]-1H-pyrazol-4-yl}-2-propenoate (0.507 g) in tetrahydrofuran (50 mL) was added diisobutylaluminum hydride (0.95 M hexane solution, 7.0 mL) at room temperature, and the mixture was stirred at room temperature for 1 hr. Sodium sulfate decahydrate (2.14 g) was added to the reaction mixture, and the mixture was further stirred for 2 hrs. After removing the precipitate by filtration, the filtrate was concentrated. The residue was subjected to silica gel column chromatography to give (2E)-3-{3-({3-methoxy-4-[(5-methyl-2-phenyl-1,3-oxazol-4-yl)methoxy]benzyl}oxy)-1-[4-(trifluoromethyl)phenyl]-1H-pyrazol-4-yl}-2-propen-1-ol as colorless crystals from a fraction eluted with tetrahydrofuran-hexane (1:1, v/v). Recrystallization from ethyl acetate-hexane gave colorless powder (0.300 g, yield 63%). melting point: 118-119° C.

Example 297

A mixture of (2E)-3-{3-({3-methoxy-4-[(5-methyl-2-phenyl-1,3-oxazol-4-yl)methoxy]benzyl}oxy)-1-[4-(trifluoromethyl)phenyl]-1H-pyrazol-4-yl}-2-propenoic acid (0.303 g), chloromethyl pivalate (0.075 g), potassium carbonate (0.138 g) and N,N-dimethylformamide (5 mL) was stirred at 60° C. for 1 hr. The reaction mixture was poured into water and the mixture was extracted with ethyl acetate. The ethyl acetate layer was washed successively with water and saturated brine, dried over anhydrous magnesium sulfate and concentrated. Recrystallization of the obtained crystal from hexane-ethyl acetate gave [(2,2-dimethylpropanoyl)oxy]methyl (2E)-3-{3-({3-methoxy-4-[(5-methyl-2-phenyl-1,3-oxazol-4-yl)methoxy]benzyl}oxy)-1-[4-(trifluoromethyl)phenyl]-1H-pyrazol-4-yl}-2-propenoate as a colorless powder (0.271 g, yield 75%). melting point: 131-132° C.

Example 298

A mixture of 3-{[3-methoxy-4-(5-methyl-2-phenyl-1,3-oxazol-4-ylmethoxy)benzyl]oxy}-1-phenyl-1H-pyrazole-5-carbaldehyde (990 mg), hydroxylamine hydrochloride (200 mg), pyridine (1 mL) and ethanol (10 mL) was refluxed for 3 hrs. After concentration of the reaction mixture, dilute hydrochloric acid was added to the residue, and the mixture was extracted with ethyl acetate. The ethyl acetate layer was washed with saturated brine, dried over anhydrous magnesium sulfate and concentrated. The residue was dissolved in acetic anhydride (20 mL), and the mixture was refluxed for 5 hrs. After concentration of the reaction mixture, The residue was subjected to silica gel column chromatography to give 3-{[3-methoxy-4-(5-methyl-2-phenyl-1,3-oxazol-4-ylmethoxy)benzyl]oxy}-1-phenyl-1H-pyrazole-5-carbonitrile (850 mg, yield 86%) as colorless crystals from a fraction eluted with ethyl acetate-hexane (1:2, v/v). The crystals were recrystallized from tetrahydrofuran-hexane. melting point: 120-121° C.

Example 299

To a mixture of 3-{[3-methoxy-4-(5-methyl-2-phenyl-1,3-oxazol-4-ylmethoxy)benzyl]oxy}-1-phenyl-1H-pyrazole-5-carbaldehyde (600 mg), ethyl diethylphosphonoacetate (300 mg) and N,N-dimethylformamide (10 mL) was added sodium hydride (60% in oil, 52.0 mg) at 0° C., and the mixture was stirred overnight at room temperature. The reaction mixture was poured into water and the mixture was extracted with ethyl acetate. The ethyl acetate layer was washed successively with dilute hydrochloric acid and saturated brine, dried over anhydrous magnesium sulfate and concentrated. The residue was subjected to silica gel column chromatography to give ethyl (E)-3-(3-{[3-methoxy-4-(5-methyl-2-phenyl-1,3-oxazol-4-ylmethoxy)benzyl]oxy}-1-phenyl-1H-pyrazol5-yl)-2-propenoate (590 mg, yield 86%) as colorless crystals from a fraction eluted with ethyl acetate-hexane (1:4, v/v). The crystals were recrystallized from ethyl acetate-hexane. melting point: 121-122° C.

Example 300

A mixture of ethyl (E)-3-(3-{[3-methoxy-4-(5-methyl-2-phenyl-1,3-oxazol-4-ylmethoxy)benzyl]oxy}-1-phenyl-1H-pyrazol5-yl)-2-propenoate (300 mg), 1N aqueous sodium hydroxide solution (3 mL), tetrahydrofuran (5 mL) and ethanol (3 mL) was stirred at 60° C. for 5 hrs. 1N Hydrochloric acid (3 mL) was added to the reaction mixture, and the mixture was extracted with ethyl acetate. The ethyl acetate layer was washed with saturated brine, dried over anhydrous magnesium sulfate and concentrated. The obtained colorless crystals were collected by filtration to give (E)-3-(3-{[3-methoxy-4-(5-methyl-2-phenyl-1,3-oxazol-4-ylmethoxy)benzyl]oxy}-1-phenyl-1H-pyrazol5-yl)-2-propenoic acid (270 mg, yield 95%). The crystals were recrystallized from tetrahydrofuran-hexane. melting point: 194-195° C.

Example 301

To a mixture of 2-[(4-{[2-(2-furyl)-5-methyl-1,3-oxazol-4-yl]methoxy}-3-methoxybenzyl)oxy]nicotinaldehyde (0.30 g), tetraethyl methylenediphosphonate (0.21 g) and N,N-dimethylformamide (15 mL) was added sodium hydride (60% in oil, 0.040 g) at room temperature, and the mixture was stirred at the same temperature for 15 hrs. Water was poured into the reaction mixture, and the mixture was extracted with ethyl acetate. The organic layer was washed with saturated brine, dried over anhydrous magnesium sulfate and concentrated. The residue was subjected to silica gel column chromatography and eluted with ethyl acetate-hexane (3:1, v/v) to give diethyl (E)-2-[2-[(4-{[2-(2-furyl)-5-methyl-1,3-oxazol-4-yl]methoxy}-3-methoxybenzyl)oxy]pyridin-3-yl}ethenylphosphonate as a colorless oil (0.25 g, yield 64%).

NMR(CDCl$_3$) δ: 1.30 (3H, t, J=7.0 Hz), 1.31 (3H, t, J=7.0 Hz), 2.41 (3H, s), 3.87 (3H, s), 3.88-4.18 (4H, m), 5.06 (2H, s), 5.41 (2H, s), 6.41-6.60 (2H, m), 6.91-7.04 (5H, m), 7.50-7.76 (3H, m), 8.15-8.19 (1H, m).

Example 302

To a mixture of 4-[(4-{[2-(2-furyl)-5-methyl-1,3-oxazol-4-yl]methoxy}-3-methoxybenzyl)oxy]-2-phenylpyrimidine-5-carbaldehyde (1.00 g), tetraethyl methylenediphosphonate (0.58 g) and N,N-dimethylformamide (20 mL) was added sodium hydride (60% in oil, 0.090 g) at 0° C., and the mixture was stirred at room temperature for 1 hr. The reaction mixture was poured into water, 2N hydrochloric acid was added to acidify the solution, and the mixture was extracted with ethyl acetate. The organic layer was washed with water, dried over anhydrous magnesium sulfate and concentrated. The residue was subjected to silica gel column chromatography and eluted with acetone-hexane (2:3, v/v) to give diethyl (Z)-2-(4-[(4-{[2-(2-furyl)-5-methyl-1,3-oxazol-4-yl]methoxy}-3-methoxybenzyl)oxy]-2-phenylpyrimidin-5-yl)ethenylphosphonate as crystals (0.095 g, yield 7%). Recrystallization from acetone-hexane gave colorless needle crystals. melting point: 154-155° C.

In addition, the crystals were successively eluted with acetone-hexane (1:1, v/v) to give diethyl (E)-2-{4-[(4-{[2-(2-furyl)-5-methyl-1,3-oxazol-4-yl]methoxy}-3-methoxybenzyl)oxy]-2-phenylpyrimidin-5-yl}ethenylphosphonate as crystals (0.87 g, yield 69%). Recrystallized from ethyl acetate-diisopropyl ether gave colorless needle crystals. melting point: 103-104° C.

Example 303

A solution (20 mL) of (4-{[2-(2-furyl)-5-methyl-1,3-oxazol-4-yl]methoxy}-3-methoxyphenyl)acetic acid (1.01 g), oxalyl chloride (407 mg) and N,N-dimethylformamide (0.05 mL) in tetrahydrofuran was stirred at room temperature for 15 min. The reaction mixture was concentrated, 3-amino-1-phenyl-1H-pyrazole-4-carbaldehyde (500 mg) in N,N-dimethylacetamide a solution (20 mL) was added to the obtained white solid, and the mixture was stirred at room temperature for 2 hrs. Water was poured into the reaction mixture, and the mixture was extracted with a mixture of ethyl acetate-tetrahydrofuran (1:1). The organic layer was washed successively with distilled water and saturated brine, dried over anhydrous magnesium sulfate and concentrated. The residue was subjected to silica gel column chromatography and eluted with ethyl acetate-hexane (1:1 to 1:0, v/v) to give N-(4-formyl-1-phenyl-1H-pyrazol-3-yl)-2-(4-{[2-(2-furyl)-5-methyl-1,3-oxazol-4-yl]methoxy}-3-methoxyphenyl)acetamide. Recrystallization from ethyl acetate-hexane gave pale-yellow crystal (0.54 g, yield 39%). melting point: 190-191° C.

Example 304

A mixture of [5-({4-[(5-methyl-2-phenyl-1,3-oxazol-4-yl)methoxy]phenoxy}methyl)-2-phenyl-1,3-oxazol-4-yl]methanol (3.10 g), activated manganese dioxide (10.0 g) and tetrahydrofuran (300 mL) was stirred at room temperature for 15 hrs. Manganese dioxide was removed by filtration, and the filtrate was concentrated. The obtained crystals were collected by filtration and washed with hexane to give 5-({4-[(5-methyl-2-phenyl-1,3-oxazol-4-yl)methoxy]phenoxy}methyl)-2-phenyl-1,3-oxazole-4-carbaldehyde (2.75 g, yield 89%). Recrystallization from ethyl acetate-hexane gave colorless prism crystals. melting point: 127-128° C.

Example 305

To a mixture of ethyl 4-[(4-{[2-(2-furyl)-5-methyl-1,3-oxazol-4-yl]methoxy}-3-methoxybenzyl)oxy]-2-phenylpyrimidine-5-carboxylate (0.47 g), tetrahydrofuran (10 mL) and ethanol (10 mL) was added 1N aqueous sodium hydroxide solution (3 mL), and the mixture was stirred at 60° C. for 1 hr. The reaction mixture was poured into water, 2N hydrochloric acid was added to acidify the solution, and the precipitated crystals were collected by filtration. Recrystallized from methanol-ethyl acetate gave 4-[(4-{[2-(2-furyl)-5-methyl-1,3-oxazol-4-yl]methoxy}-3-methoxybenzyl)oxy]-2-phenylpyrimidine-5-carboxylic acid as pale-yellow needle crystals (0.18 g, yield 40%). melting point: 163-164° C.

Example 306

A mixture of methyl 3-{4-[(4-{([(4-formyl-1-phenyl-1H-pyrazol-3-yl)oxy]methyl}-2-methoxyphenoxy)methyl]-5-methyl-1,3-oxazol-2-yl}benzoate (1.50 g), [(2-ethyl-1,3-oxazol-4-yl)methyl]triphenylphosphonium chloride (1.67 g), potassium carbonate (0.57 g) and N,N-dimethylformamide (50 mL) was stirred at room temperature for 15 hrs. Water was poured into the reaction mixture, and the mixture was extracted with ethyl acetate. The organic layer was washed with saturated brine, dried over anhydrous magnesium sulfate and concentrated. The residue was subjected to silica gel column chromatography and eluted with ethyl acetate-hexane (1:2, v/v) to give methyl 3-{4-[(4-{[(4-[(Z)-2-(2-ethyl-1,3-oxazol-4-yl)ethenyl-1-phenyl-1H-pyrazol-3-yl]oxy)methyl]-2-methoxyphenoxy}methyl)-5-methyl-1,3-oxazol-2-yl]benzoate as colorless crystals (1.29 g, yield 74%). The crystals were recrystallized from ethyl acetate-hexane. melting point: 149-150° C.

In addition, methyl 3-{4-[(4-{[(4-[(E)-2-(2-ethyl-1,3-oxazol-4-yl)ethenyl-1-phenyl-1H-pyrazol-3-yl]oxy)methyl]-2-methoxyphenoxy}methyl)-5-methyl-1,3-oxazol-2-yl]benzoate was obtained as pale-yellow crystals (0.40 g, yield 23%) from a fraction successively obtained by elution. The crystals were recrystallized from ethyl acetate-hexane. melting point: 105-107° C.

Example 307

To a mixture of methyl 3-{4-[(4-{[(4-[(E)-2-(2-ethyl-1,3-oxazol-4-yl)ethenyl-1-phenyl-1H-pyrazol-3-yl]oxy)methyl]-2-methoxyphenoxy}methyl)-5-methyl-1,3-oxazol-2-yl]benzoate (0.31 g), tetrahydrofuran (2 mL) and methanol (2 mL) was added 1N aqueous sodium hydroxide solution (2 mL), and the mixture was stirred at 50° C. for 2 hrs. To the reaction mixture were added 1N hydrochloric acid (3 mL) and water to acidify the solution, and the mixture was extracted with ethyl acetate. The organic layer was washed with saturated brine, dried over anhydrous magnesium sulfate and concentrated to give 3-(4-[(4-{[(4-[(E)-2-(2-ethyl-1,3-oxazol-4-yl)ethenyl-1-phenyl-1H-pyrazol-3-yl]oxy)methyl]-2-methoxyphenoxy}methyl)-5-methyl-1,3-oxazol-2-yl]benzoic acid as pale-yellow crystals (0.24 g, yield 80%). Recrystallization from acetone-hexane gave pale-yellow prism crystals. melting point: 169-171° C.

Example 308

To a mixture of methyl 3-{4-[(4-{[(4-[(Z)-2-(2-ethyl-1,3-thiazol-4-yl)ethenyl-1-phenyl-1H-pyrazol-3-yl]oxy)methyl]-2-methoxyphenoxy}methyl)-5-methyl-1,3-oxazol-2- yl]benzoate (0.65 g), tetrahydrofuran (4 mL) and methanol (4 mL) was added 1N aqueous sodium hydroxide solution (4 mL), and the mixture was stirred at 50° C. for 2 hrs. 1N Hydrochloric acid (4 mL) and water were added to the reaction mixture, and the mixture was extracted with ethyl acetate. The organic layer was washed with saturated brine, dried over anhydrous magnesium sulfate and concentrated to give 3-{4-[(4-{[(4-[(Z)-2-(2-ethyl-1,3-thiazol-4-yl)ethenyl-1-phenyl-1H-pyrazol-3-yl]oxy)methyl]-2-methoxyphenoxy}methyl)-5-methyl-1,3-oxazol-2-yl]benzoic acid as pale-yellow crystals (0.62 g, yield 97%). Recrystallization from acetone-hexane gave pale-yellow prism crystals. melting point: 196-198° C.

Example 309

A mixture of methyl 3-{4-[(4-{[(4-formyl-1-phenyl-1H-pyrazol-3-yl)oxy]methyl}-2-methoxyphenoxy)methyl]-5-methyl-1,3-oxazol-2-yl}benzoate (1.05 g), (5-methyl-2-morpholin-4-yl-1,3-thiazol-4-yl)triphenylphosphonium chloride (1.40 g), potassium carbonate (0.39 g) and N,N-dimethylformamide (50 mL) was stirred at room temperature for 15 hrs. Water was poured into the reaction mixture, and the mixture was extracted with ethyl acetate. The organic layer was washed with saturated brine, dried over anhydrous magnesium sulfate and concentrated. The residue was subjected to silica gel column chromatography and eluted with ethyl acetate-hexane (1:3, v/v) to give methyl 3-[4-({2-methoxy-4-[({4-[(E)-2-(5-methyl-2-morpholin-4-yl-1,3-thiazol-4-yl)ethenyl]-1-phenyl-1H-pyrazol-3-yl}oxy)methyl]phenoxy}methyl)-5-methyl-1,3-oxazol-2-yl]benzoate as pale-yellow crystals (0.55 g, yield 40%). The crystals were recrystallized from ethyl acetate-hexane. melting point: 183-184° C.

Example 310

To a mixture of methyl 3-[4-({2-methoxy-4-[({4-[(E)-2-(5-methyl-2-morpholin-4-yl-1,3-thiazol-4-yl)ethenyl]-1-phenyl-1H-pyrazol-3-yl}oxy)methyl]phenoxy}methyl)-5-methyl-1,3-oxazol-2-yl]benzoate (0.35 g), tetrahydrofuran (50 mL) and methanol (20 mL) was added 1N aqueous sodium hydroxide solution (20 mL), and the mixture was heated under reflux for 2 hrs. 1N Hydrochloric acid and water were added to acidify the reaction mixture, and the precipitated crystals were collected by filtration and washed with diethyl ether to give 3-[4-({2-methoxy-4-[({4-[(E)-2-(5-methyl-2-morpholin-4-yl-1,3-thiazol-4-yl)ethenyl]-1-phenyl-1H-pyrazol-3-yl}oxy)methyl]phenoxy)methyl)-5-methyl-1,3-oxazol-2-yl]benzoic acid as brown crystals (0.25 g, yield 71%). Recrystallization from acetone-hexane gave brown prism crystals. melting point: 215-217 (dec) ° C.

Example 311

A mixture of methyl 3-{4-[(4-{[(4-formyl-1-phenyl-1H-pyrazol-3-yl)oxy]methyl}-2-methoxyphenoxy)methyl]-5-methyl-1,3-oxazol-2-yl]benzoate (1.00 g), [(2-isopropyl-1,3-thiazol-4-yl)methyl]triphenylphosphonium chloride (1.18 g), potassium carbonate (0.37 g) and N,N-dimethylformamide (50 mL) was stirred at room temperature for 15 hrs. Water was poured into the reaction mixture, and the mixture was extracted with ethyl acetate. The organic layer was washed with saturated brine, dried over anhydrous magnesium sulfate and concentrated. The residue was subjected to silica gel column chromatography and eluted with acetone-hexane (1:4, v/v) to give methyl 3-{4-[(4-{[(4-[(E)-2-(2-isopropyl-1,3-thiazol-4-yl)ethenyl-1-phenyl-1H-pyrazol-3-yl]oxy)methyl]-2-methoxyphenoxy}methyl)-5-methyl-1,3-oxazol-2-yl]benzoate as colorless crystals (0.30 g, yield 25%). The crystals were recrystallized from ethyl acetate-hexane. melting point: 126-127° C.

Example 312

To a mixture of methyl 3-{4-[(4-{[(4-[(E)-2-(2-isopropyl-1,3-thiazol-4-yl)ethenyl-1-phenyl-1H-pyrazol-3-yl]oxy)methyl]-2-methoxyphenoxy}methyl)-5-methyl-1,3-oxazol-2-yl]benzoate (0.21 g), tetrahydrofuran (2 mL) and methanol (2 mL) was added 1N aqueous sodium hydroxide solution (2 mL), and the mixture was stirred at 50° C. for 2 hrs. To the reaction mixture were added 1N hydrochloric acid (3 mL) and water to acidify the solution, and the mixture was extracted with ethyl acetate. The organic layer was washed with saturated brine, dried over anhydrous magnesium sulfate and concentrated to give 3-{4-[(4-{[(4-[(E)-2-(2-isopropyl-1,3-thiazol-4-yl)ethenyl-1-phenyl-1H-pyrazol-3-yl]oxy)methyl]-2-methoxyphenoxy}methyl)-5-methyl-1,3-oxazol-2-yl]benzoic acid as colorless crystals (0.16 g, yield 76%). Recrystallization from acetone-hexane gave colorless prism crystals. melting point: 194-195° C.

Example 313

A mixture of ethyl (2E)-3-{4[(4-chloromethyl-2-methoxyphenoxy)methyl]-5-methyl-1,3-oxazol-2-yl}-2-propenoate (2.50 g), 3-hydroxy-1-phenyl-1H-pyrazole-4-carbaldehyde (1.22 g), potassium carbonate (0.90 g) and N,N-dimethylformamide (50 mL) was stirred at room temperature for 5 hrs. Water was poured into the reaction mixture, and the mixture was extracted with ethyl acetate. The organic layer was washed with saturated brine, dried over anhydrous magnesium sulfate and concentrated. The residue was subjected to silica gel column chromatography to give ethyl (2E)-3-{4-[(4-{[(4-formyl-1-phenyl-1H-pyrazol-3-yl)oxy]methyl}-2-methoxyphenoxy)methyl]-5-methyl-1,3-oxazol-2-yl}-2-propenoate as colorless crystals (1.81 g, yield 54%) from a fraction eluted with ethyl acetate-hexane (1:1, v/v). Recrystallization from ethyl acetate-hexane gave colorless prism crystals. melting point: 150-151° C.

Example 314

To a mixture of ethyl (2E)-3-{4-[(4-{[(4-formyl-1-phenyl-1H-pyrazol-3-yl)oxy]methyl}-2-methoxyphenoxy)methyl]-5-methyl-1,3-oxazol-2-yl}-2-propenoate (0.80 g), tetraethyl methylenediphosphonate (0.49 g) and N,N-dimethylformamide (10 mL) was added sodium hydride (60% in oil, 0.07 g) at room temperature, and the mixture was stirred at the same temperature for 2 hrs. Water was poured into the reaction mixture, and the mixture was extracted with ethyl acetate. The organic layer was washed with saturated brine, dried over anhydrous magnesium sulfate and concentrated. The residue was subjected to silica gel column chromatography to give ethyl (2E)-3-[4-({4-[({4-[(E)-2-(diethoxyphosphoryl)ethenyl]-1-phenyl-1H-pyrazol-3-yl}oxy)methyl]-2-methoxyphenoxy}methyl)-5-methyl-1,3-oxazol-2-yl]-2-propenoate as colorless crystals (0.70 g, yield 71%) from a fraction eluted with ethyl acetate-hexane (4:1, v/v). Recrystallization from ethyl acetate-hexane gave colorless prism crystals. melting point: 130-131° C.

Example 315

To a mixture of ethyl (2E)-3-[4-({4-[({4-[(E)-2-(diethoxyphosphoryl)ethenyl]-1-phenyl-1H-pyrazol-3-yl}oxy)methyl]-2-methoxyphenoxy}methyl)-5-methyl-1,3-oxazol-2-yl]-2-propenoate (0.62 g), tetrahydrofuran (2 mL) and ethanol (2 mL) was added 1N aqueous sodium hydroxide solution (2 mL), and the mixture was stirred at 50° C. for 1 hr. To the reaction mixture were added 1N hydrochloric acid (2 mL) and water, and the precipitated crystals were collected by filtration to give (2E)-3-[4-({4-[({4-[(E)-2-(diethoxyphosphoryl)ethenyl]-1-phenyl-1H-pyrazol-3-yl}oxy)methyl]-2-methoxyphenoxy}methyl)-5-methyl-1,3-oxazol-2-yl]-2-propenoic acid as colorless crystals (0.50 g, yield 85%). Recrystallization from acetone-hexane gave colorless prism crystals. melting point: 89-90° C.

Example 316

A mixture of ethyl 3-{4[(4-chloromethyl-2-methoxyphenoxy)methyl]-5-methyl-1,3-oxazol-2-yl}-2-propionate (2.00 g), 3-hydroxy-1-phenyl-1H-pyrazole-4-carbaldehyde (1.02 g), potassium carbonate (0.75 g) and N,N-dimethylformamide (50 mL) was stirred at room temperature for 4 hr. Water was poured into the reaction mixture, and the mixture was extracted with ethyl acetate. The organic layer was washed with saturated brine, dried over anhydrous magnesium sulfate and concentrated. The residue was subjected to silica gel column chromatography to give ethyl 3-{4-[(4-([(4-formyl-1-phenyl-1H-pyrazol-3-yl)oxy]methyl}-2-methoxyphenoxy)methyl]-5-methyl-1,3-oxazol-2-yl}-2-propionate as colorless crystals (1.05 g, yield 37%) from a fraction eluted with ethyl acetate-hexane (1:1, v/v). Recrystallization from ethyl acetate-hexane gave colorless prism crystals. melting point: 106-108° C.

Example 317

To a mixture of ethyl 3-{4-[(4-{[(4-formyl-1-phenyl-1H-pyrazol-3-yl)oxy]methyl}-2-methoxyphenoxy)methyl]-5-methyl-1,3-oxazol-2-yl}-2-propionate (0.52 g), tetraethyl methylenediphosphonate (0.32 g) and N,N-dimethylformamide (10 mL) was added sodium hydride (60% in oil, 0.05 g) at room temperature, and the mixture was stirred at the same temperature for 15 hrs. Water was poured into the reaction mixture, and the mixture was extracted with ethyl acetate. The organic layer was washed with saturated brine, dried over anhydrous magnesium sulfate and concentrated. The residue was subjected to silica gel column chromatography to give ethyl 3-[4-({4-[({4-[(E)-2-(diethoxyphosphoryl)ethenyl]-1-phenyl-1H-pyrazol-3-yl}oxy)methyl]-2-methoxyphenoxy}methyl)-5-methyl-1,3-oxazol-2-yl]-2-propionate as a colorless oil (0.38 g, yield 58%) from a fraction eluted with ethyl acetate-hexane (9:1, v/v)).

NMR(CDCl$_3$) δ: 1.26 (3H, t, J=7.0 Hz), 1.32 (6H, t, J=7.0 Hz), 2.30 (3H, s), 2.75-2 83 (2H, m), 2 99-3.07 (2H, m), 3.88 (3H, s), 4.01-4.16 (4H, m), 4.16 (2H, q, J=7.0 Hz), 4.94 (2H, s), 5.35 (2H, s), 6.25 (1H, dd, J=20.0, 17.4 Hz), 7.01-7.07 (3H, m), 7.22-7.48 (4H, m), 7.59-7.64 (2H, m), 7.86 (1H, s).

Example 318

To a mixture of ethyl 3-[4-({4-[({4-[(E)-2-(diethoxyphosphoryl)ethenyl]-1-phenyl-1H-pyrazol-3-yl}oxy)methyl]-2-methoxyphenoxy}methyl)-5-methyl-1,3-oxazol-2-yl]-2-propionate (0.37 g), tetrahydrofuran (2 mL) and ethanol (2 mL) was added 1N aqueous sodium hydroxide solution (1 mL) and the mixture was stirred at 50° C. for 30 min. To the reaction mixture were added 1N hydrochloric acid (2 mL) and water, and the precipitated crystals were collected by filtration to give 3-[4-({4-[({4-[(E)-2-(diethoxyphosphoryl)ethenyl]-1-phenyl-1H-pyrazol-3-yl}oxy)methyl]-2-methoxyphenoxy}methyl)-5-methyl-1,3-oxazol-2-yl]-2-propionic acid as colorless crystals (0.34 g, yield 94%). Recrystallization from acetone-hexane gave colorless prism crystals. melting point: 125-126° C.

Example 319

A mixture of methyl 5-{4-[(4-chloromethyl-2-methoxyphenoxy)methyl]-5-methyl-1,3-oxazol-2-yl}-2-methylbenzoate (1.04 g), 3-hydroxy-1-phenyl-1H-pyrazole-4-carbaldehyde (0.45 g), anhydrous potassium carbonate (0.33 g) and N,N-dimethylformamide (30 mL) was stirred at 90° C. for 2 hrs. Water was poured into the reaction mixture, and the precipitated crystals were collected by filtration to give methyl 5-{4-[(4-{[(4-formyl-1-phenyl-1H-pyrazol-3-yl)oxy]methyl}-2-methoxyphenoxy)methyl]-5-methyl-1,3-oxazol-2-yl}-2-methylbenzoate as colorless crystals (1.25 g, yield 92%). Recrystallization from ethyl acetate-hexane gave colorless prism crystals. melting point: 195-196° C.

Example 320

To a mixture of methyl 5-{4-[(4-{[(4-formyl-1-phenyl-1H-pyrazol-3-yl)oxy]methyl}-2-methoxyphenoxy)methyl]-5-methyl-1,3-oxazol-2-yl}-2-methylbenzoate (1.13 g), tetraethyl methylenediphosphonate (0.63 g) and N,N-dimethylformamide (30 mL) was added sodium hydride (60% in oil, 0.10 g) at room temperature. The mixture was stirred at room temperature for 2 hrs. Water was poured into the reaction mixture, and the mixture was extracted with ethyl acetate. The organic layer was washed with saturated brine, dried over anhydrous magnesium sulfate and concentrated. The residue was subjected to silica gel column chromatography to give methyl 5-[4-({4-[({4-[(E)-2-(diethoxyphosphoryl)ethenyl]-1-phenyl-1H-pyrazol-3-yl}oxy)methyl]-2-methoxyphenoxy}methyl)-5-methyl-1,3-oxazol-2-yl]-2-methylbenzoate as colorless crystals (0.57 g, yield 41%) from a fraction eluted with ethyl acetate-hexane (4:1, v/v). Recrystallization from ethyl acetate-hexane gave colorless prism crystals. melting point: 121-122° C.

Example 321

To a mixture of methyl 5-[4-({4-[({4-[(E)-2-(diethoxyphosphoryl)ethenyl]-1-phenyl-1H-pyrazol-3-yl}oxy)methyl]-2-methoxyphenoxy}methyl)-5-methyl-1,3-oxazol-2-yl]-2-methylbenzoate (0.46 g), tetrahydrofuran (2 mL) and ethanol (2 mL) was added 1N aqueous sodium hydroxide solution (2 mL), and the mixture was stirred at 60° C. for 1 hr. To the reaction mixture were added 1N hydrochloric acid (2 mL) and water, and the mixture was extracted with ethyl acetate. The organic layer was washed with saturated brine, dried over anhydrous magnesium sulfate and concentrated to give 5-[4-({4-[({4-[(E)-2-(diethoxyphosphoryl)ethenyl]-1-phenyl-1H-pyrazol-3-yl}oxy)methyl]-2-methoxyphenoxy}methyl)-5-ethyl-1,3-oxazol-2-yl]-2-methylbenzoic acid as colorless crystals (0.39 g, yield 87%). Recrystallization from acetone-hexane gave colorless prism crystals. melting point: 165-166° C.

Example 322

A mixture of ethyl (2E)-3-{4-[(4-([(4-formyl-1-phenyl-1H-pyrazol-3-yl)oxy]methyl}-2-methoxyphenoxy)methyl]-5-methyl-1,3-oxazol-2-yl}-2-propenoate (0.87 g), [(2-ethyl-1,3-thiazol-4-yl)methyl]triphenylphosphonium chloride (1.06 g), anhydrous potassium carbonate (0.36 g) and N,N-dimethylformamide (50 mL) was stirred at room temperature for 15 hrs. Water was poured into the reaction mixture, and the mixture was extracted with ethyl acetate. The organic layer was washed with saturated brine, dried over anhydrous magnesium sulfate and concentrated. The residue was subjected to silica gel column chromatography and eluted with ethyl acetate-hexane (1:3, v/v) to give ethyl (2E)-3-[4-({4-[({4-[(Z)-2-(2-ethyl-1,3-thiazol-4-yl)ethenyl]-1-phenyl-1H-pyrazol-3-yl}oxy)methyl]-2-methoxyphenoxy}methyl)-5-methyl-1,3-oxazol-2-yl]-2-propenoate as colorless crystals (0.14 g, yield 17%). Recrystallization from ethyl acetate-hexane gave colorless prism crystals. melting point: 119-120° C.

In addition, ethyl (2E)-3-[4-({4-[({4-[(E)-2-(2-ethyl-1,3-thiazol-4-yl)ethenyl]-1-phenyl-1H-pyrazol-3-yl}oxy)methyl]-2-methoxyphenoxy}methyl)-5-methyl-1,3-oxazol-2-yl]-2-propenoate was obtained as colorless crystals (0.35 g, yield 33%) from a fraction successively obtained by elution. Recrystallization from ethyl acetate-hexane gave colorless prism crystals. melting point: 95-96° C.

Example 323

To a mixture of ethyl (2E)-3-[4-({4-[({4-[(E)-2-(2-ethyl-1,3-thiazol-4-yl)ethenyl]-1-phenyl-1H-pyrazol-3-yl}oxy)methyl]-2-methoxyphenoxy}methyl)-5-methyl-1,3-oxazol-2-yl]-2-propenoate (0.25 g), tetrahydrofuran (2 mL) and ethanol (2 mL) was added 1N aqueous sodium hydroxide solution (2 mL), and the mixture was stirred at 50° C. for 2 hrs. 1N hydrochloric acid and water were added to the reaction mixture to acidify the solution, and the precipitated crystals were collected by filtration to give (2E)-3-[4-({4-[({4-[(E)-2-(2-ethyl-1,3-thiazol-4-yl)ethenyl]-1-phenyl-1H-pyrazol-3-yl}oxy)methyl]-2-methoxyphenoxy}methyl)-5-methyl-1,3-oxazol-2-yl]-2-propenoic acid as colorless crystals (0.21 g, yield 88%). Recrystallization from acetone-hexane gave colorless prism crystals. melting point: 125-126° C.

Example 324

A mixture of ethyl 1-{4-[(4-chloromethyl-2-methoxyphenoxy)methyl]-5-methyl-1,3-thiazol-2-yl}piperidine-4-carboxylate (0.40 g), 3-hydroxy-1-phenyl-1H-pyrazole-4-carbaldehyde (0.18 g), anhydrous potassium carbonate (0.13 g), and N,N-dimethylformamide (10 mL) was stirred at 90° C. for 2 hrs. Water was poured into the reaction mixture, and the mixture was extracted with ethyl acetate. The organic layer was washed with saturated brine, dried over anhydrous magnesium sulfate and concentrated. The residue was subjected to silica gel column chromatography and eluted with ethyl acetate-hexane (1:2, v/v) to give ethyl 1-(4-[(4-{[(4-formyl-1-phenyl-1H-pyrazol-3-yl)oxy]methyl}-2-methoxyphenoxy)methyl]-5-methyl-1,3-thiazol-2-yl}piperidine-4-carboxylate as colorless crystals (0.37 g, yield 69%). Recrystallization from ethyl acetate-hexane gave colorless prism crystals. melting point: 126-127° C.

Example 325

To a mixture of ethyl 1-{4-[(4-{[(4-formyl-1-phenyl-1H-pyrazol-3-yl)oxy]methyl}-2-methoxyphenoxy)methyl]-5-methyl-1,3-thiazol-2-yl}piperidine-4-carboxylate (0.30 g), tetraethyl methylenediphosphonate (0.16 g) and N,N-dimethylformamide (10 mL) was added sodium hydride (60% in oil, 25 mg) at room temperature. The mixture was stirred at room temperature for 2 hrs. Water was poured into the reaction mixture, and the mixture was extracted with ethyl acetate. The organic layer was washed with saturated brine, dried over anhydrous magnesium sulfate and concentrated. The residue was subjected to silica gel column chromatography to give ethyl 1-[4-({4-[({4-[(E)-2-(diethoxyphosphoryl)ethenyl]-1-phenyl-1H-pyrazol-3-yl}oxy)methyl]-2-methoxyphenoxy}methyl)-5-methyl-1,3-thiazol-2-yl]piperidine-4-carboxylate as a colorless oil (0.29 g, yield 78%) from a fraction eluted with ethyl acetate-hexane (9:1, v/v).

NMR (CDCl$_3$) δ: 1.26 (3H, t, J=7.2 Hz), 1.32 (6H,t, J=7.2 Hz), 1.77-2.04 (4H, m), 2.31 (3H, s), 2.43-2.54 (1H, m), 2.95-3.09 (2H, m), 3.85-3.92 (5H, m), 4.01-4.21 (6H, m), 4.97 (2H, s), 5.35 (2H, s), 6.26 (1H, dd, J=19.6, 17.2 Hz), 6.98-7.08 (3H, m), 7.21-7.48 (4H, m), 7.59-7.64 (2H, m), 7.86 (1H, s).

Example 326

To a mixture of ethyl 1-[4-({4-[({4-[(E)-2-(diethoxyphosphoryl)ethenyl]-1-phenyl-1H-pyrazol-3-yl}oxy)methyl]-2-methoxyphenoxy}methyl)-5-methyl-1,3-thiazol-2-yl]piperidine-4-carboxylate (0.28 g), tetrahydrofuran (2 mL) and ethanol (2 mL) was added 1N aqueous sodium hydroxide solution (1 mL), and the mixture was stirred at 50° C. for 1 hr. To the reaction mixture were added 1N hydrochloric acid (1 mL) and water, and the mixture was extracted with ethyl acetate. The organic layer was washed with saturated brine, dried over anhydrous magnesium sulfate and concentrated to give 1-[4-({4-[({4-[(E)-2-(diethoxyphosphoryl)ethenyl]-1-phenyl-1H-pyrazol-3-yl}oxy)methyl]-2-methoxyphenoxy}methyl)-5-methyl-1,3-thiazol-2-yl]piperidine-4-carboxylic acid as colorless crystals (0.23 g, yield 85%). Recrystallized from acetone-hexane gave colorless prism crystals. melting point: 159-160° C.

Example 327

A mixture of ethyl 5-{4-[(4-chloromethyl-2-methoxyphenoxy)methyl]-5-methyl-1,3-oxazol-2-yl}thiophene-2-carboxylate (4.63 g), 3-hydroxy-1-phenyl-1H-pyrazole-4-carbaldehyde (2.07 g), anhydrous potassium carbonate (1.52 g) and N,N-dimethylformamide (100 mL) was stirred at 90° C. for 1 hr. Water was poured into the reaction mixture, and the mixture was extracted with ethyl acetate. The organic layer was washed with saturated brine, dried over anhydrous magnesium sulfate and concentrated to give ethyl 5-{4-[(4-{[(4-formyl-1-phenyl-1H-pyrazol-3-yl)oxy]methyl}-2-methoxyphenoxy)methyl]-5-methyl-1,3-oxazol-2-yl}thiophene-2-carboxylate as colorless crystals (5.50 g, yield 87%). Recrystallization from tetrahydrofuran-hexane gave colorless prism crystals. melting point: 156-157° C.

Example 328

To a mixture of ethyl 5-{4-[(4-{[(4-formyl-1-phenyl-1H-pyrazol-3-yl)oxy]methyl}-2-methoxyphenoxy)methyl]-5-methyl-1,3-oxazol-2-yl}thiophene-2-carboxylate (1.50 g), tetraethyl methylenediphosphonate (0.84 g) and N,N-dimethylformamide (50 mL) was added sodium hydride (60% in oil, 0.12 g) at room temperature. The mixture was stirred at room temperature for 15 hrs. Water was poured into the reaction mixture, and the mixture was extracted with ethyl acetate. The organic layer was washed with saturated brine, dried over anhydrous magnesium sulfate and concentrated. The residue was subjected to silica gel column chromatography to give ethyl 5-[4-({4-[({4-[(E)-2-(diethoxyphosphoryl)ethenyl]-1-phenyl-1H-pyrazol-3-yl}oxy)methyl]-2-methoxyphenoxy}methyl)-5-methyl-1,3-oxazol-2-yl]thiophene-2-carboxylate as colorless crystals (1.20 g, yield 65%) from a fraction eluted with ethyl acetate-hexane (4:1 to 9:1, v/v). Recrystallization from ethyl acetate-hexane gave colorless prism crystals. melting point: 114-115° C.

Example 329

To a mixture of ethyl 5-[4-({4-[({4-[(E)-2-(diethoxyphosphoryl)ethenyl]-1-phenyl-1H-pyrazol-3-yl}oxy)methyl]-2-methoxyphenoxy}methyl)-5-methyl-1,3-oxazol-2-yl]thiophene-2-carboxylate (1.05 g), tetrahydrofuran (5 mL) and ethanol (5 mL) was added 1N aqueous sodium hydroxide solution (5 mL), and the mixture was heated under reflux for 30 min. To the reaction mixture were added 1N hydrochloric acid (5 mL) and water, and the mixture was extracted with ethyl acetate. The organic layer was washed with saturated brine, dried over anhydrous magnesium sulfate and concentrated. The residue was subjected to silica gel column chromatography to give 5-[4-({4-[({4-[(E)-2-(diethoxyphosphoryl)ethenyl]-1-phenyl-1H-pyrazol-3-yl}oxy)methyl]-2-methoxyphenoxy}methyl)-5-methyl-1,3-oxazol-2-yl]thiophene-2-carboxylic acid as colorless crystals (0.26 g, yield 25%) from a fraction eluted with ethyl acetate-methanol (6:1, v/v). Recrystallization from ethyl acetate-hexane gave colorless prism crystals. Melting point: 165-166° C.

Example 330

A mixture of ethyl 5-{4-[(4-[{(4-formyl-1-phenyl-1H-pyrazol-3-yl)oxy}methyl]-2-methoxyphenoxy)methyl]-5-methyl-1,3-oxazol-2-yl}thiophene-2-carboxylate (1.80 g), [(2-ethyl-1,3-thiazol-4-yl)methyl]triphenylphosphonium chloride (1.99 g), anhydrous potassium carbonate (0.65 g) and N,N-dimethylformamide (50 mL) was stirred at room temperature for 15 hrs. Water was poured into the reaction mixture, and the mixture was extracted with ethyl acetate. The organic layer was washed with saturated brine, dried over anhydrous magnesium sulfate and concentrated. The residue was subjected to silica gel column chromatography and eluted with ethyl acetate-hexane (2:3, v/v) to give ethyl 5-[4-({4-[({4-[(Z)-2-(2-ethyl-1,3-thiazol-4-yl)ethenyl]-1-phenyl-1H-pyrazol-3-yl}oxy)methyl]-2-methoxyphenoxy}methyl)-5-methyl-1,3-oxazol-2-yl]thiophene-2-carboxylate as colorless crystals (0.60 g, yield 28%). Recrystallization from ethyl acetate-hexane gave colorless prism crystals. melting point: 118-119° C.

In addition, ethyl 5-[4-({4-[({4-[(E)-2-(2-ethyl-1,3-thiazol-4-yl)ethenyl]-1-phenyl-1H-pyrazol-3-yl}oxy)methyl]-2-methoxyphenoxy}methyl)-5-methyl-1,3-oxazol-2-yl]thiophene-2-carboxylate was obtained as pale-yellow crystals (0.73 g, yield 35%) from a fraction successively obtained by elution. Recrystallization from ethyl acetate-hexane gave colorless prism crystals. melting point: 145-146° C.

Example 331

To a mixture of ethyl 5-[4-({4-[({4-[(E)-2-(2-ethyl-1,3-thiazol-4-yl)ethenyl]-1-phenyl-1H-pyrazol-3-yl}oxy)methyl]-2-methoxyphenoxy}methyl)-5-methyl-1,3-oxazol-2-yl]thiophene-2-carboxylate (0.63 g), tetrahydrofuran (3 mL) and ethanol (3 mL) was added 1N aqueous sodium hydroxide solution (3 mL), and the mixture was stirred at 60° C. for 1 hr. To the reaction mixture were added 1N hydrochloric acid (5 mL) and water, and the precipitated crystals were collected by filtration to give 5-[4-({4-[({4-[(E)-2-(2-ethyl-1,3-thiazol-4-yl)ethenyl]-1-phenyl-1H-pyrazol-3-yl}oxy)methyl]-2-methoxyphenoxy}methyl)-5-methyl-1,3-oxazol-2-yl]thiophene-2-carboxylic acid as colorless crystals (0.51 g, yield 85%). Recrystallization from acetone-hexane gave colorless prism crystals. melting point: 150-151° C.

Example 332

A mixture of 3-[4-{(4-chloromethyl-2-methoxyphenoxy)methyl}-5-methyl-1,3-oxazol-2-yl]benzonitrile (4.32 g), 3-hydroxy-1-phenyl-1H-pyrazole-4-carbaldehyde (2.0 g), anhydrous potassium carbonate (1.47 g) and N,N-dimethylformamide (100 mL) was stirred at 80° C. for 2 hrs. Water was poured into the reaction mixture, and the mixture was extracted with ethyl acetate-tetrahydrofuran. The organic layer was washed with saturated brine, dried over anhydrous magnesium sulfate and concentrated to give 3-{4-[(4-{[(4-formyl-1-phenyl-1H-pyrazol-3-yl)oxy]methyl)-2-methoxyphenoxy}methyl]-5-methyl-1,3-oxazol-2-yl}benzonitrile (5.30 g, yield 96%) as colorless crystals. Recrystallization from ethyl acetate-hexane gave colorless prism crystals. melting point: 161-162° C.

Example 333

To a mixture of 3-{4-[(4-{[(4-formyl-1-phenyl-1H-pyrazol-3-yl)oxy]methyl}-2-methoxyphenoxy)methyl]-5-methyl-1,3-oxazol-2-yl}benzonitrile (2.50 g), tetraethyl methylenediphosphonate (1.53 g) and N,N-dimethylformamide (50 mL) was added sodium hydride (60% in oil, 0.23 g) at room temperature. The mixture was stirred at room temperature for 2 hrs. Water was poured into the reaction mixture, and the mixture was extracted with ethyl acetate. The organic layer was washed with saturated brine, dried over anhydrous magnesium sulfate and concentrated. The residue was subjected to silica gel column chromatography to give diethyl [(E)-2-{3-[(4-{[2-(3-cyanophenyl)-5-methyl-1,3-oxazol-4-yl]methoxy}-3-methoxybenzyl)oxy]-1-phenyl-1H-pyrazol-4-yl}ethenyl]phosphonate as colorless crystals (2.20 g, yield 70%) from a fraction eluted with ethyl acetate-hexane (4:1 to 9:1, v/v). Recrystallization from ethyl acetate-hexane gave colorless prism crystals. melting point: 147-148° C.

Example 334

To a mixture of methyl 3-{4-[(4-{[(4-formyl-1-phenyl-1H-pyrazol2-yl)oxy]methyl}-2-methoxyphenoxy)methyl]-5-methyl-1,3-oxazol-2-yl}benzoate (33.0 g), tetraethyl methylenediphosphonate (18.91 g) and N,N-dimethylformamide (300 mL) was added sodium hydride (60% in oil, 2.86 g) at 0° C., and the mixture was stirred at room temperature for 15 hrs. Water was poured into the reaction mixture, and the mixture was extracted with ethyl acetate. The organic layer was washed successively with water and saturated brine, dried over anhydrous magnesium sulfate and concentrated. The residue was subjected to silica gel column chromatography to give methyl 3-[4-({4-[({4-[(Z)-2-(diethoxyphosphoryl)ethenyl]-1-phenyl-1H-pyrazol-3-yl}oxy)methyl]-2-methoxyphenoxy}methyl)-5-methyl-1,3-oxazol-2-yl]benzoate as colorless crystals (1.82 g, yield 4.4%) from a fraction eluted with acetone-hexane (1:1, v/v). Recrystallization from ethyl acetate-hexane gave colorless prism crystals. melting point: 112-113° C.

In addition, methyl 3-[4-({4-[({4-[(E)-2-(diethoxyphosphoryl)ethenyl]-1-phenyl-1H-pyrazol-3-yl}oxy)methyl]-2-methoxyphenoxy}methyl)-5-methyl-1,3-oxazol-2-yl]benzoate was obtained as colorless crystals (24.74 g, yield 60%) from a fraction successively obtained by elution.

Example 335

To a mixture of methyl 3-[4-({4-[({4-[(Z)-2-(diethoxyphosphoryl)ethenyl]-1-phenyl-1H-pyrazol-3-yl}oxy)methyl]-2-methoxyphenoxy}methyl)-5-methyl-1,3-oxazol-2-yl]benzoate (1.38 g), tetrahydrofuran (10 mL) and methanol (10 mL) was added 1N aqueous sodium hydroxide solution (5 mL), and the mixture was stirred at 50° C. for 1 hr. To the reaction mixture were added 1N hydrochloric acid (5 mL) and water, and the mixture was extracted with ethyl acetate. The organic layer was washed with saturated brine, dried over anhydrous magnesium sulfate and concentrated to give 3-[4-({4-[({4-[(Z)-2-(diethoxyphosphoryl)ethenyl]-1-phenyl-1H-pyrazol-3-yl}oxy)methyl]-2-methoxyphenoxy}methyl)-5-methyl-1,3-oxazol-2-yl]benzoic acid as colorless crystals (1.26 g, yield 93%). Recrystallization from acetone-hexane gave colorless prism crystals. melting point: 158-159° C.

Example 336

A mixture of 5-(3-{4-[(2-methoxy-4-{[(triisopropylsilyl)oxy]methyl}phenoxy)methyl]-5-methyl-1,3-oxazol-2-yl}phenyl)-1H-tetrazole (0.20 g), triphenylchloromethane (0.12 g), triethylamine (0.04 g) and acetonitrile (10 mL) was stirred at room temperature for 15 hrs. The reaction mixture was concentrated, water was added to the residue, and the mixture was extracted with ethyl acetate. The organic layer was washed with saturated brine, dried over anhydrous magnesium sulfate and concentrated. The residue was subjected to silica gel column chromatography to give N-tritylated 5-(3-{4-[(2-methoxy-4-{[(triisopropylsilyl)oxy]methyl}phenoxy)methyl]-5-methyl-1,3-oxazol-2-yl}phenyl)-1H-tetrazole as a colorless oil. (0.24 g, yield 83%) from a fraction eluted with ethyl acetate-hexane (1:4, v/v).

NMR (CDCl$_3$) δ: 0.97-1.30 (21H, m), 2.41 (3H, s), 3.86 (3H, s), 4.79 (2H, s), 5.05 (2H, s), 6.80-6.85 (1H, m), 6.97-7.01 (2H, m), 7.15-7.40 (15H, m), 7.49-7.58 (1H, m), 7.57-7.82 (2H, m), 8.74-8.75 (1H, m).

A solution (48.6 mL) of tetrabutylammonium fluoride in 1M tetrahydrofuran was added dropwise to a solution (200 mL) of the obtained oily substance (12.8 g) in tetrahydrofuran at room temperature. After stirring the reaction mixture at room temperature for 1 hr, water was added, and the mixture was extracted with ethyl acetate. The organic layer was washed with saturated brine, dried over anhydrous magnesium sulfate and concentrated to give N-tritylated [3-methoxy-4-({5-methyl-2-[3-(1H-tetrazol-5-yl)phenyl]-1,3-oxazol-4-yl}methoxy)phenyl]methanol as colorless crystals. (10.0 g, yield 97%). Recrystallization from ethyl acetate-hexane gave colorless prism crystals. melting point: 186-187° C.

To a mixture of the obtained crystal (5.40 g), 3-hydroxy-1-phenyl-1H-pyrazole-4-carbaldehyde (1.77 g), tributylphosphine (5.26 g) and tetrahydrofuran (200 mL) was added 1,1'-(azodicarbonyl)dipiperidine (6.56 g) at room temperature, and the mixture was stirred for 15 hrs. The reaction mixture was concentrated and ethyl acetate was added to the residue. The precipitated crystals were removed by filtration and the filtrate was concentrated. The residue was subjected to silica gel column chromatography to give N-tritylated 3-{[3-methoxy-4-({5-methyl-2-[3-(1H-tetrazol-5-yl)phenyl]-1,3-oxazol-4-yl}methoxy)benzyl]oxy}-1-phenyl-1H-pyrazole-4-carbaldehyde as colorless crystals (2.60 g, yield 38%) from a fraction eluted with ethyl acetate-hexane (1:2, v/v). Recrystallization from ethyl acetate-hexane gave colorless prism crystals. melting point: 132-133° C.

To a mixture of the obtained crystal (1.70 g), tetraethyl methylenediphosphonate (0.66 g) and N,N-dimethylformamide (20 mL) was added sodium hydride (60% in oil, 0.10 g) at room temperature. The reaction mixture was stirred at room temperature for 2 hrs. Water was poured into the reaction mixture, and the mixture was extracted with ethyl acetate. The organic layer was washed with saturated brine, dried over anhydrous magnesium sulfate and concentrated. The residue was subjected to silica gel column chromatography to give N-tritylated diethyl {(E)-2-(3-{[3-methoxy-4-({5-methyl-2-[3-(1H-tetrazol-5-yl)phenyl]-1,3-oxazol-4-yl}methoxy)benzyl]oxy}-1-phenyl-1H-pyrazol-4-yl)ethenyl}phosphonate as colorless crystals (1.53 g, yield 78%) from a fraction eluted with ethyl acetate-hexane (4:1, v/v). Recrystallization from ethyl acetate-hexane gave colorless prism crystals. melting point: 148-149° C.

A mixture of the obtained crystal (820 mg), 1N hydrochloric acid (10 mL) and tetrahydrofuran (50 mL) was stirred at 60° C. for 2 hrs. Water was poured into the reaction mixture, and the mixture was extracted with ethyl acetate. The organic layer was washed with saturated brine, dried over anhydrous magnesium sulfate and concentrated. The residue was crystallized from ethyl acetate-hexane to give {(E)-2-(3-{[3-methoxy-4-({5-methyl-2-[3-(1H-tetrazol-5-yl)phenyl]-1,3-oxazol-4-yl}methoxy)benzyl]oxy}-1-phenyl-1H-pyrazol-4-yl)ethenyl}phosphonate diethyl as colorless crystals (0.52 g, yield 85%). Recrystallization from acetone-hexane gave colorless prism crystals. melting point: 156-157° C.

Example 337

A mixture of ethyl {4-[4-({4-[({4-[(E)-2-(2-ethyl-1,3-thiazol-4-yl)ethenyl]-1-phenyl-1H-pyrazol-3-yl}oxy)methyl]-2-methoxyphenoxy}methyl)-5-methyl-1,3-oxazol-2-yl]phenyl}acetate (800 mg), 1N aqueous sodium hydroxide solution (5 mL), tetrahydrofuran (10 mL) and ethanol (10 mL) was heated under reflux for 30 min. After cooling, the reaction mixture was neutralized with 1N hydrochloric acid, and the mixture was extracted with ethyl acetate. The organic layer was washed with saturated brine, dried over anhydrous magnesium sulfate and concentrated. Recrystallization of the obtained crystal from ethyl acetate-hexane gave {4-[4-({4-[({4-[(E)-2-(2-ethyl-1,3-thiazol-4-yl)ethenyl]-1-phenyl-1H-pyrazol-3-yl}oxy)methyl]-2-methoxyphenoxy}methyl)-5-methyl-1,3-oxazol-2-yl]phenyl}acetic acid as colorless crystals (704 mg, yield 92%). melting point: 123-124° C.

Example 338

A mixture of ethyl (4-{4-[(4-{[(4-formyl-1-phenyl-1H-pyrazol-3-yl)oxy]methyl}-2-methoxyphenoxy)methyl]-5-methyl-1,3-oxazol-2-yl}phenyl)acetate (2.00 g), [(2-ethyl-1,3-thiazol-4-yl)methyl]triphenylphosphonium chloride (2.19 g), anhydrous potassium carbonate (713 mg) and N,N-dimethylformamide (30 mL) was stirred at room temperature for 16 hrs. The reaction mixture was poured into water and the mixture was extracted with ethyl acetate. The organic layer was washed with saturated brine, dried over anhydrous magnesium sulfate and concentrated. The residue was subjected to silica gel column chromatography and eluted with ethyl acetate-hexane (1:4 to 1:1, v/v) to give ethyl {4-[4-({4-[({4-[(Z)-2-(2-ethyl-1,3-thiazol-4-yl)ethenyl]-1-phenyl-1H-pyrazol-3-yl}oxy)methyl]-2-methoxyphenoxy}methyl)-5-methyl-1,3-oxazol-2-yl]phenyl}acetate as colorless crystals (0.71 g, yield 31%). The crystals were recrystallized from tetrahydrofuran-hexane. melting point: 136-137° C.

In addition, ethyl {4-[4-({4-[({4-[(E)-2-(2-ethyl-1,3-thiazol-4-yl)ethenyl]-1-phenyl-1H-pyrazol-3-yl}oxy)methyl]-2-methoxyphenoxy}methyl)-5-methyl-1,3-oxazol-2-yl]phenyl}acetate was obtained as colorless crystals (0.69 g, yield 30%) from a fraction successively obtained by elution. The crystals were recrystallized from tetrahydrofuran-hexane. melting point: 140-141° C.

Example 339

A mixture of ethyl {4-[4-({4-[({4-[(Z)-2-(2-ethyl-1,3-thiazol-4-yl)ethenyl]-1-phenyl-1H-pyrazol-3-yl}oxy)methyl]-2-methoxyphenoxy}methyl)-5-methyl-1,3-oxazol-2-yl]phenyl}acetate (650 mg), 1N aqueous sodium hydroxide solution (5 mL), tetrahydrofuran (10 mL) and ethanol (10 mL) was heated under reflux for 30 min. After cooling, the reaction mixture was neutralized with 1N hydrochloric acid, and the mixture was extracted with ethyl acetate. The organic layer was washed with saturated brine, dried over anhydrous magnesium sulfate and concentrated. Recrystallization of the obtained crystal from ethyl acetate-hexane gave {4-[4-({4-[({4-[(Z)-2-(2-ethyl-1,3-thiazol-4-yl)ethenyl]-1-phenyl-1H-pyrazol-3-yl}oxy)methyl]-2-methoxyphenoxy}methyl)-5-methyl-1,3-oxazol-2-yl]phenyl}acetic acid as colorless crystals (524 mg, yield 81%). melting point: 168-169° C.

Example 340

A mixture of ethyl (4-{4-[(4-{[(4-formyl-1-phenyl-1H-pyrazol-3-yl)oxy]methyl}-2-methoxyphenoxy)methyl]-5-ethyl-1,3-oxazol-2-yl}phenyl)acetate (2.00 g), [(1-ethyl-1H-imidazol-5-yl)methyl](triphenyl)phosphonium chloride hydrochloride (2.29 g), anhydrous potassium carbonate (1.78 g) and N,N-dimethylformamide (30 mL) was stirred at room temperature for 16 hrs. The reaction mixture was poured into water and the mixture was extracted with ethyl acetate. The organic layer was washed with saturated brine, dried over magnesium sulfate and concentrated. The residue was subjected to silica gel column chromatography and eluted with ethyl acetate-hexane (9:1 to 1:0, v/v) to give ethyl {4-[4-({4-[({4-[(Z)-2-(1-ethyl-1H-imidazol-5-yl)ethenyl]-1-phenyl-1H-pyrazol-3-yl}oxy)methyl]-2-methoxyphenoxy}methyl)-5-methyl-1,3-oxazol-2-yl]phenyl}acetate as colorless crystals (0.459 g, yield 20%). The crystals were recrystallized from tetrahydrofuran-hexane. melting point: 85-86° C.

In addition, ethyl {4-[4-({4-[({4-[(E)-2-(1-ethyl-1H-imidazol-5-yl)ethenyl]-1-phenyl-1H-pyrazol-3-yl}oxy)methyl]-2-methoxyphenoxy}methyl)-5-methyl-1,3-oxazol-2-yl]phenyl}acetate as colorless crystals (0.198 g, yield 9%) was obtained from a fraction successively obtained by elution. The crystals were recrystallized from tetrahydrofuran-hexane. melting point: 134-135° C.

Example 341

A mixture of ethyl {4-[4-({4-[({4-[(E)-2-(1-ethyl-1H-imidazol-5-yl)ethenyl]-1-phenyl-1H-pyrazol-3-yl}oxy)methyl]-2-methoxyphenoxy}methyl)-5-methyl-1,3-oxazol-2-yl]phenyl}acetate (156 mg), 1N aqueous sodium hydroxide solution (5 mL), tetrahydrofuran (10 mL) and ethanol (10 mL) was heated under reflux for 30 min. After cooling, the reaction mixture was neutralized with 1N hydrochloric acid, and the mixture was extracted with ethyl acetate. The organic layer was washed with saturated brine, dried over anhydrous magnesium sulfate and concentrated. Recrystallization of the obtained crystal from ethyl acetate-hexane gave {4-[4-({4-[({4-[(E)-2-(1-ethyl-1H-imidazol-5-yl)ethenyl]-1-phenyl-1H-pyrazol-3-yl}oxy)methyl]-2-methoxyphenoxy}methyl)-5-methyl-1,3-oxazol-2-yl]phenyl}acetic acid as colorless crystals (109 mg, yield 73%). melting point: 149-150° C.

Example 342

A mixture of ethyl {4-[4-({4-[({4-[(Z)-2-(1-ethyl-1H-imidazol-5-yl)ethenyl]-1-phenyl-1H-pyrazol-3-yl}oxy)methyl]-2-methoxyphenoxy}methyl)-5-methyl-1,3-oxazol-2-yl]phenyl}acetate (385 mg), 1N aqueous sodium hydroxide solution (5 mL), tetrahydrofuran (10 mL) and ethanol (10 mL) was heated under reflux for 30 min. After cooling, the reaction mixture was neutralized with 1N hydrochloric acid, and the mixture was extracted with ethyl acetate. The organic layer was washed with saturated brine, dried over anhydrous magnesium sulfate and concentrated. Recrystallization of the obtained crystal from ethyl acetate-hexane gave {4-[4-({4-[({4-[(Z)-2-(1-ethyl-1H-imidazol-5-yl)ethenyl]-1-phenyl-1H-pyrazol-3-yl}oxy)methyl]-2-methoxyphenoxy}methyl)-5-methyl-1,3-oxazol-2-yl]phenyl}acetic acid as colorless crystals (202 mg, yield 55%). melting point: 148-149° C.

Example 343

A mixture of ethyl (4-{4-[(4-{[(4-formyl-1-phenyl-1H-pyrazol-3-yl)oxy]methyl}-2-methoxyphenoxy)methyl]-5-methyl-1,3-oxazol-2-yl}phenyl)acetate (3.00 g), [(1-ethyl-1H-imidazol-4-yl)methyl](triphenyl)phosphonium chloride hydrochloride (3.43 g), anhydrous potassium carbonate (1.07 g) and N,N-dimethylformamide (30 mL) was stirred at room temperature for 16 hrs. To the reaction mixture were added [(1-ethyl-1H-imidazol-4-yl)methyl](triphenyl)phosphonium chloride hydrochloride (1.14 g) and anhydrous potassium carbonate (356 mg) and the mixture was stirred at room temperature for 2 days. The reaction mixture was poured into water and the mixture was extracted with ethyl acetate. The organic layer was washed with saturated brine, dried over anhydrous magnesium sulfate and concentrated. The residue was subjected to silica gel column chromatography and eluted with ethyl acetate-hexane (9:1 to 1:0, v/v) to give ethyl (4-{4-[(4-[({4-[(E)-2-(1-ethyl-1H-imidazol-4-yl)ethenyl]-1-phenyl-1H-pyrazol-3-yl}oxy)methyl]-2-methoxyphenoxy)methyl]-5-methyl-1,3-oxazol-2- yl}phenyl)acetate as colorless crystals. Recrystallization from ethyl acetate-hexane gave colorless crystals (352 mg, yield 10%). melting point: 140-141° C.

Example 344

A mixture of ethyl (4-{4-[(4-[({4-[(E)-2-(1-ethyl-1H-imidazol-4-yl)ethenyl]-1-phenyl-1H-pyrazol-3-yl}oxy)methyl]-2-methoxyphenoxy)methyl]-5-methyl-1,3-oxazol-2-yl}phenyl)acetate (485 mg), 8N aqueous sodium hydroxide solution (1 mL), tetrahydrofuran (5 mL) and ethanol (5 mL) was heated under reflux for 30 min. After cooling, to the reaction mixture was added 1N hydrochloric acid (8 mL) and the mixture was left standing overnight. The precipitated crystals were collected by filtration and recrystallized from methanol-diethyl ether to give (4-{4-[(4-[({4-[(E)-2-(1-ethyl-1H-imidazol-4-yl)ethenyl]-1-phenyl-1H-pyrazol-3-yl}oxy)methyl]-2-methoxyphenoxy)methyl]-5-methyl-1,3-oxazol-2-yl}phenyl)acetic acid as colorless crystals (472 mg, yield 100%). melting point: 194-196° C.

Example 345

A mixture of 3-[(4-{[2-(2-furyl)-5-methyl-1,3-oxazol-4-yl]methoxy}-3-methoxybenzyl)oxy]-1-phenyl-1H-pyrazole-4-carbaldehyde (1.50 g), [(1-ethyl-1H-imidazol-4-yl)methyl](triphenyl)phosphonium chloride hydrochloride (2.05 g), anhydrous potassium carbonate (1.07 g) and N,N-dimethylformamide (50 mL) was stirred at room temperature for 16 hrs. To the reaction mixture were added [(1-ethyl-1H-imidazol-4-yl)methyl](triphenyl)phosphonium chloride hydrochloride (2.05 g) and anhydrous potassium carbonate (1.07 g), and the mixture was further stirred at room temperature for 16 hrs. The reaction mixture was poured into water and the mixture was extracted with ethyl acetate. The organic layer was washed with saturated brine, dried over anhydrous magnesium sulfate and concentrated. The residue was subjected to silica gel column chromatography and eluted with ethyl acetate-hexane (1:1 to 1:0, v/v) to give an oily substance, which was then subjected to silica gel column chromatography and eluted with acetone-hexane (1:1 to 6:4, v/v) to give [4-({4-[({4-[(E)-2-(1-ethyl-1H-imidazol-4-yl)ethenyl]-1-phenyl-1H-pyrazol-3-yl}oxy)methyl]-2-methoxyphenoxy}methyl)-2-(2-furyl)-5-methyl-1,3-oxazole as a pale-yellow oil (335 mg, yield 19%).

NMR (CDCl$_3$) δ: 1.45 (3H, t, J=7.3 Hz), 2.41 (3H, s), 3.89(3H, s), 3.95 (2H, q, J=7.3 Hz), 5.08 (2H, s), 5.37 (2H, s), 6.51-6.53 (1H, m), 6.85 (1H, d, J=1.4 Hz), 6.96-7.26 (7H, m), 7.37-7.45 (3H, m), 7.53-7.64 (3H, m), 7.78 (1H, s).

Example 346

A mixture of ethyl (4-{4-[(4-{[(4-formyl-1-phenyl-1H-pyrazol-3-yl)oxy]methyl}-2-methoxyphenoxy)methyl]-5-methyl-1,3-oxazol-2-yl}phenyl)acetate (1.50 g), [(1-ethyl-1H-pyrazol-4-yl)methyl]triphenylphosphonium chloride hydrochloride (2.29 g), anhydrous potassium carbonate (1.42 g) and N,N-dimethylformamide (30 mL) was stirred overnight at room temperature. The reaction mixture was poured into water and the mixture was extracted with ethyl acetate. The organic layer was washed with saturated brine, dried over anhydrous magnesium sulfate and concentrated. The residue was subjected to silica gel column chromatography and eluted with ethyl acetate-hexane (3:7 to 1:1, v/v) to give ethyl {4-[4-({4-[({4-[(Z)-2-(1-ethyl-1H-pyrazol-4-yl)ethenyl]-1-phenyl-1H-pyrazol-3-yl}oxy)methyl]-2-methoxy phenoxy}methyl)-5-methyl-1,3-oxazol-2-yl] phenyl}acetate as colorless crystals (446 mg, yield 26%). The crystals were recrystallized from tetrahydrofuran-hexane. melting point: 140-141° C.

In addition, ethyl {4-[4-({4-[({4-[(E)-2-(1-ethyl-1H-pyrazol-4-yl)ethenyl]-1-phenyl-1H-pyrazol-3-yl}oxy)methyl]-2-methoxyphenoxy}methyl)-5-methyl-1,3-oxazol-2-yl] phenyl}acetate was obtained as a colorless oil (62.6 mg, yield 3.6%) from a fraction successively obtained by elution.

NMR (CDCl$_3$) δ: 1.25 (3H, t, J=7.1 Hz), 1.45 (3H, t, J=7.4 Hz), 2.41 (3H, s), 3.65 (2H, s), 3.88 (3H, s), 4.10-4.20 (4H, m), 5.06 (2H, s), 5.36 (2H, s), 6.63 (1H, d, J=16.2 Hz), 6.92 (1H, d, J=16.2 Hz), 7.05-7.21(4H, m), 7.34-7.43(5H, m), 7.59-7.62 (3H, m), 7.77 (1H, s), 7.94-7.98 (2H, m).

Example 347

A mixture of ethyl {4-[4-({4-[({4-[(E)-2-(1-ethyl-1H-pyrazol-4-yl)ethenyl]-1-phenyl-1H-pyrazol-3-yl}oxy)methyl]-2-methoxyphenoxy}methyl)-5-methyl-1,3-oxazol-2-yl]phenyl}acetate (52 mg), 1N aqueous sodium hydroxide solution (2 mL), tetrahydrofuran (4 mL) and ethanol (4 mL) was heated under reflux for 30 min. After cooling, 1N hydrochloric acid was added to the reaction mixture for neutralization, and the mixture was extracted with ethyl acetate. The organic layer was washed with saturated brine; dried over anhydrous magnesium sulfate and concentrated. Recrystallization of the obtained crystal from tetrahydrofuran-hexane gave {4-[4-({4-[({4-[(E)-2-(1-ethyl-1H-pyrazol-4-yl)ethenyl]-1-phenyl-1H-pyrazol-3-yl}oxy)methyl]-2-methoxyphenoxy}methyl)-5-methyl-1,3-oxazol-2-yl] phenyl}acetic acid as colorless crystals (37.6 mg, yield 77%). melting point: 165-166° C.

Example 348

A mixture of ethyl {4-[4-({4-[({4-[(Z)-2-(1-ethyl-1H-pyrazol-4-yl)ethenyl]-1-phenyl-1H-pyrazol-3-yl}oxy)methyl]-2-methoxyphenoxy}methyl)-5-methyl-1,3-oxazol-2-yl]phenyl}acetate (350 mg), 1N aqueous sodium hydroxide solution (10 mL), tetrahydrofuran (20 mL) and ethanol (20 mL) was heated under reflux for 30 min. After cooling, the reaction mixture was acidified by adding 1N hydrochloric acid, and the mixture was extracted with ethyl acetate. The organic layer was washed with saturated brine, dried over anhydrous magnesium sulfate and concentrated. Recrystallization of the obtained crystal from tetrahydrofuran-hexane gave {4-[4-({4-[({4-[(Z)-2-(1-ethyl-1H-pyrazol-4-yl)ethenyl]-1-phenyl-1H-pyrazol-3-yl}oxy)methyl]-2-methoxyphenoxy}methyl)-5-methyl-1,3-oxazol-2-yl] phenyl}acetic acid as colorless crystals (300 mg, yield 89%). melting point: 146-147° C.

Example 349

To a solution of 3-(methylamino)-1-phenyl-1H-pyrazole-4-carbaldehyde (150 mg) in N,N-dimethylformamide (5 mL) was added sodium hydride (60% in oil, 36 mg) on an ice bath, and the mixture was stirred for 30 min. To the reaction mixture was added 4-[(4-chloromethyl-2-methoxyphenoxy)methyl]-2-(2-furyl)-5-methyl-1,3-oxazole (227 mg), and the mixture was further stirred at room temperature for 1 hr. Ice water was added to the reaction mixture, and the mixture was extracted with ethyl acetate. The organic layer was washed with saturated brine, dried over anhydrous magnesium sulfate and concentrated. The residue was subjected to flash silica gel column chromatography and eluted with ethyl acetate-hexane (1:9 to 6:4, v/v) to give 3-([4-{

[2-(2-furyl)-5-methyl-1,3-oxazol-4-yl]methoxy}-3-methoxybenzyl](methyl)amino)-1-phenyl-1H-pyrazole-4-carbaldehyde as colorless crystals (170.4 mg, yield 46%). melting point: 101-102° C.

Example 350

To a solution of tetraethyl methylenediphosphonate (63 mg) in N,N-dimethylformamide (3 mL) was added sodium hydride (60% in oil, 8.8 mg) at room temperature, and the mixture was stirred for 30 min. To the reaction mixture was added 3-([4-{[2-(2-furyl)-5-methyl-1,3-oxazol-4-yl]methoxy}-3-methoxybenzyl](methyl)amino)-1-phenyl-1H-pyrazole-4-carbaldehyde (100 mg) and the mixture was further stirred at room temperature for 2 hrs. Water was added to the reaction mixture, and the mixture was extracted with ethyl acetate. The organic layer was washed with saturated brine, dried over anhydrous magnesium sulfate and concentrated. The residue was subjected to flash silica gel column chromatography and eluted with ethyl acetate-hexane (1:1 to 4:1, v/v) to give diethyl ((E)-2-{3-[(4-{[2-(2-furyl)-5-methyl-1,3-oxazol-4-yl]methoxy}-3-methoxybenzyl)(methyl) amino]-1-phenyl-1H-pyrazol-4-yl}ethenyl)phosphonate as a colorless oil (84.9 mg, yield 67%).

NMR (CDCl$_3$) δ: 1.30 (6H, t, J=7.1 Hz), 2.40(3H, s), 2.82 (3H, s), 3.85 (3H, s), 3.99-4.14 (4H, m), 4.32 (2H, s), 5.04 (2H, s), 6.04 (1H, dd, J=19.2, 17.4 Hz), 6.51-6.53 (1H, m), 6.85-6.99 (4H, m), 7.21-7.29 (1H, m), 7.37-7.64 (6H, m), 7.96 (1H, s).

Example 351

To a solution (15 mL) of {3-methoxy-4-[(5-methyl-2-phenyl-1,3-oxazol-4-yl)methoxy]phenyl}acetic acid (964 mg) in tetrahydrofuran were added oxalyl chloride (258 µL) and N,N-dimethylformamide (0.05 mL) and the mixture was stirred at room temperature for 15 min. After concentration, N,N-dimethylacetamide (5 mL) was added to the residue and 3-(methylamino)-1-phenyl-1H-pyrazole-4-carbaldehyde (500 mg) was added to the obtained solution. The obtained mixed solution was stirred at room temperature for 16 hrs, water was added, and the mixture was extracted with ethyl acetate. The organic layer was washed with saturated brine, dried over anhydrous magnesium sulfate and concentrated. The residue was subjected to flash silica gel column chromatography and eluted with ethyl acetate-hexane (2:3 to 3:2, v/v) to give N-(4-formyl-1-phenyl-1H-pyrazol-3-yl)-2-{3-methoxy-4-[(5-methyl-2-phenyl-1,3-oxazol-4-yl)methoxy]phenyl}-N-methylacetamide as colorless amorphous form (380.4 mg, yield 29%).

NMR (CDCl$_3$) δ: 2.41 (3H, s), 3.35 (3H, s), 3.69 (2H, s), 3.72(3H, s), 4.98 (2H, s), 6.43-6.46 (1H, m), 6.61 (1H, m), 6.80-6.84 (1H, m), 7.42-7.55 (6H, m), 7.64-7.69 (2H, m), 7.98-8.03 (2H, m), 8.27 (1H, m), 9.62 (1H, s).

Example 352

To a solution (15 mL) of (4-{[2-(2-furyl)-5-methyl-1,3-oxazol-4-yl]methoxy}-3-methoxyphenyl)acetic acid (937 mg) in tetrahydrofuran were added oxalyl chloride (258 µL) and N,N-dimethylformamide (0.05 mL) and the mixture was stirred at room temperature for 15 min. After concentration, N,N-dimethylacetamide (2 mL) was added to the residue, and 3-(methylamino)-1-phenyl-1H-pyrazole-4-carbaldehyde (500 mg) was added to the obtained solution. After stirring the obtained mixture at room temperature for 16 hrs, water was added, and the mixture was extracted with ethyl acetate. The organic layer was washed with saturated brine, dried over anhydrous magnesium sulfate and concentrated. The residue was subjected to flash silica gel column chromatography and eluted with ethyl acetate-hexane (1:1 to 7:3, v/v) to give N-(4-formyl-1-phenyl-1H-pyrazol-3-yl)-2-(4-{[2-(2-furyl)-5-methyl-1,3-oxazol-4-yl]methoxy}-3-methoxyphenyl)-N-methylacetamide as a colorless oil (275.6 mg, yield 21%).

NMR (CDCl$_3$) δ: 2.40 (3H, s), 3.35 (3H, s), 3.69 (2H, s), 3.72(3H, s), 4.97 (2H, s), 6.40-6.42 (1H, m), 6.51-6.54 (1H, m), 6.60 (1H, m), 6.77-6.81 (1H, m), 6.96-6.98 (1H, m), 7.42-7.56 (4H, m), 7.66-7.71 (2H, m), 8.30 (1H, m), 9.62 (1H, s).

Example 353

To a solution (10 mL) of (4-{[2-(2-furyl)-5-methyl-1,3-oxazol-4-yl]methoxy}-3-methoxyphenyl)acetic acid (0.65 g) in tetrahydrofuran were added oxalyl chloride (179 µL) and N,N-dimethylformamide (0.05 mL) and the mixture was stirred at room temperature for 15 min. After concentration, N,N-dimethylacetamide (5 mL) was added to the residue and diethyl {(E)-2-[3-(methylamino)-1-phenyl-1H-pyrazol-4-yl]ethenyl}phosphonate (576 mg) was added to the obtained solution. After stirring the obtained mixture at room temperature for 16 hrs, water was added, and the mixture was extracted with ethyl acetate. The organic layer was washed with saturated brine, dried over anhydrous magnesium sulfate and concentrated. The residue was subjected to flash silica gel column chromatography and eluted with ethyl acetate-hexane (1:1 to 4:1, v/v) to give diethyl [(E)-2-(3-{[(4-{[2-(2-furyl)-5-methyl-1,3-oxazol-4-yl] methoxy}-3-methoxyphenyl)acetyl](methyl)amino}-1-phenyl-1H-pyrazol-4-yl)ethenyl]phosphonate as a pale-brown oil (0.95 g, yield 84%).

NMR (CDCl$_3$) δ: 1.34 (6H, t, J=7.0 Hz), 2.38(3H, s), 3.28 (3H, s), 3.55 (2H, s), 4.02 (3H, s), 4.02-4.17 (4H, m), 4.97 (2H, s), 5.93 (1H, t, J=17.6 Hz), 6.47-6.53 (2H, m), 6.69 (1H,d, J=1.8 Hz), 6.82 (1H, d, J=8.0 Hz), 6.95 (1H, m), 7.12-7.53 (5H, m), 7.62-7.67 (2H, m), 8.06 (1H, s).

Example 354

To a solution (10 mL) of {3-methoxy-4-[(5-methyl-2-phenyl-1,3-oxazol-4-yl)methoxy]phenyl}acetic acid (0.80 g) in tetrahydrofuran were added oxalyl chloride (311 mg) and N,N-dimethylformamide (0.05 mL) and the mixture was stirred at room temperature for 15 min. After concentration, N,N-dimethylacetamide (5 mL) was added to the residue and diethyl {(E)-2-[3-(methylamino)-1-phenyl-1H-pyrazol-4-yl]ethenyl}phosphonate (687 mg) was added to the obtained solution. After stirring the obtained mixture at room temperature for 16 hrs, water was added, and the mixture was extracted with ethyl acetate. The organic layer was washed with saturated brine, dried over anhydrous magnesium sulfate and concentrated. The residue was subjected to flash silica gel column chromatography and eluted with ethyl acetate-hexane (1:1 to 4:1, v/v) to give diethyl ((E)-2-{3-[({3-methoxy-4-[(5-methyl-2-phenyl-1,3-oxazol-4-yl)methoxy]phenyl}acetyl)(methyl)amino]-1-phenyl-1H-pyrazol-4-yl}ethenyl)phosphonate as a colorless oil (1.13 g, yield 84%).

NMR (CDCl$_3$) δ: 1.34 (6H, t, J=7.2 Hz), 2.39 (3H, s), 3.27 (3H, s), 3.55(2H, s), 3.75 (3H, s), 4.04-4.14 (4H, m), 4.97 (2H, s), 5.92 (1H, t, J=17.6 Hz), 6.47-6.53 (1H, dd, J=8.1, 1.8 Hz), 6.68 (1H,d, J=1.8 Hz), 6.85 (1H, d, J=8.1 Hz), 7.21

(1H, dd, J=23.2, 17.6 Hz), 7.35-7.51 (6H, m), 7.61-7.65 (2H, m), 7.97-8.00 (2H, m), 8.05 (1H, s).

Example 355

Ethyl {4-[4-({4-[({4-[(E)-2-(diethoxyphosphoryl)ethenyl]-1-phenyl-1H-pyrazol-3-yl}oxy)methyl]-2-methoxyphenoxy}methyl)-5-methyl-1,3-oxazol-2-yl]phenyl}acetate (700 mg) was dissolved in methanol (5.0 mL) and 1N aqueous sodium hydroxide solution (f=0.998, 1.02 mL) was added. The obtained mixture was stirred for 15 min and concentrated.

Methanol (0.05 mL) was added to the residue, diethyl ether (50 mL) was added, and the mixture was stirred for 6 hrs. The precipitated crystals were collected by filtration and the crystals were washed with diethyl ether and dried to give sodium {4-[4-({4-[({4-[(E)-2-(diethoxyphosphoryl)ethenyl]-1-phenyl-1H-pyrazol-3-yl}oxy)methyl]-2-methoxyphenoxy}methyl)-5-methyl-1,3-oxazol-2-yl]phenyl}acetate as a white solid (649 mg, yield 85%).

melting point: 109-110° C.

Example 356

A mixture of ethyl (4-{4-[(4-chloromethyl-2-methoxyphenoxy)methyl]-5-methyl-1,3-oxazol-2-yl}phenyl)acetate (1.49 g), 4-[(E)-2-(2-methyl-1,3-thiazol-4-yl)ethenyl]-1-phenyl-1H-pyrazol-3-ol.hydrochloride (1.05 g), potassium carbonate (1.01 g) and N,N-dimethylformamide (20 mL) was stirred at 90° C. for 2 hrs. Water was poured into the reaction mixture, and the mixture was extracted with ethyl acetate. The ethyl acetate layer was washed with saturated brine, dried over anhydrous magnesium sulfate and concentrated to give ethyl {4-[4-({2-methoxy-4-[({4-[(E)-2-(2-methyl-1,3-thiazol-4-yl)ethenyl]-1-phenyl-1H-pyrazol-3-yl}oxy)methyl]phenoxy}methyl)-5-methyl-1,3-oxazol-2-yl]phenyl}acetate (1.25 g, yield 53%) as pale-yellow crystals. melting point: 153-155° C.

Example 357

To a mixture of ethyl {4-[4-({2-methoxy-4-[({4-[(E)-2-(2-methyl-1,3-thiazol-4-yl)ethenyl]-1-phenyl-1H-pyrazol-3-yl}oxy)methyl]phenoxy}methyl)-5-methyl-1,3-oxazol-2-yl]phenyl}acetate (0.48 g), tetrahydrofuran (12 mL) and ethanol (3 mL) was added 1N aqueous sodium hydroxide solution (2 mL), and the mixture was stirred at 50° C. for 2 hrs. To the reaction mixture were added 1N hydrochloric acid (2 mL) and water, and the precipitated crystals were collected by filtration to give {4-[4-({2-methoxy-4-[({4-[(E)-2-(2-methyl-1,3-thiazol-4-yl)ethenyl]-1-phenyl-1H-pyrazol-3-yl}oxy)methyl]phenoxy}methyl)-5-methyl-1,3-oxazol-2-yl]phenyl}acetic acid as crystals (0.44 g, yield 96%). Recrystallization from ethyl acetate-hexane gave colorless prism crystals. melting point: 181-182° C.

Example 358

A mixture of ethyl (4-{4-[(4-chloromethyl-2-methoxyphenoxy)methyl]-5-methyl-1,3-oxazol-2-yl}phenyl)acetate (1.49 g), 4-[(E)-2-(2-tert-butyl-1,3-thiazol-4-yl)ethenyl]-1-phenyl-1H-pyrazol-3-ol hydrochloride (1.32 g), potassium carbonate (1.00 g) and N,N-dimethylformamide (20 mL) was stirred at 90° C. for 2 hrs. Water was poured into the reaction mixture, and the mixture was extracted with ethyl acetate. The ethyl acetate layer was washed with saturated brine, dried over anhydrous magnesium sulfate and concentrated to give ethyl {4-[4-({4-[({4-[(E)-2-(2-tert-butyl-1,3-thiazol-4-yl)ethenyl]-1-phenyl-1H-pyrazol-3-yl}oxy)methyl]-2-methoxyphenoxy}methyl)-5-methyl-1,3-oxazol-2-yl]phenyl}acetate (1.11 g, yield 45%) as a yellow oil.

NMR (CDCl$_3$) δ: 1.25 (3H, t, J=7.2 Hz), 1.46 (9H, s), 2.41 (3H, s), 3.65 (2H, s), 3.90 (3H, s), 4.16 (2H, q, J=7.2 Hz), 5.07 (2H, s), 5.39 (2H, s), 6.86 (1H, s), 7.03-7.24 (5H, m), 7.27-7.47 (5H, m), 7.58-7.65 (2H, m), 7.85 (1H, s), 7.93-8.00 (2H, m).

Example 359

To a mixture of ethyl {4-[4-({4-[({4-[(E)-2-(2-tert-butyl-1,3-thiazol-4-yl)ethenyl]-1-phenyl-1H-pyrazol-3-yl}oxy)methyl]-2-methoxyphenoxy}methyl)-5-methyl-1,3-oxazol-2-yl]phenyl}acetate (0.77 g), tetrahydrofuran (9 mL) and ethanol (3 mL) was added 1N aqueous sodium hydroxide solution (2 mL), and the mixture was stirred at 50° C. for 1 hr. To the reaction mixture were added 1N hydrochloric acid (2 mL) and water, and the mixture was extracted with ethyl acetate. The ethyl acetate layer was washed with saturated brine, dried over anhydrous magnesium sulfate and concentrated to give {4-[4-({4-[({4-[(E)-2-(2-tert-butyl-1,3-thiazol-4-yl)ethenyl]-1-phenyl-1H-pyrazol-3-yl}oxy)methyl]-2-methoxyphenoxy}methyl)-5-methyl-1,3-oxazol-2-yl]phenyl}acetic acid as crystals (0.59 g, yield 80%). Recrystallization from ethyl acetate-hexane gave colorless prism crystals. melting point: 113-115° C.

Example 360

A mixture of ethyl (4-{4-[(4-{[(4-formyl-1-phenyl-1H-pyrazol-3-yl)oxy]methyl}-2-methoxyphenoxy)methyl]-5-methyl-1,3-oxazol-2-yl}phenyl)acetate (1.60 g), [(2-isopropyl-1,3-thiazol-4-yl)methyl]triphenylphosphonium chloride (1.7 g), potassium carbonate (0.57 g) and N,N-dimethylformamide (30 mL) was stirred at room temperature for 17 hrs. Water was poured into the reaction mixture, and the mixture was extracted with ethyl acetate. The organic layer was washed with saturated brine, dried over anhydrous magnesium sulfate and concentrated. The residue was subjected to silica gel column chromatography, and eluted with ethyl acetate-hexane (1:4, v/v) to give ethyl {4-[4-({4-[({4-[(Z)-2-(2-isopropyl-1,3-thiazol-4-yl)ethenyl]-1-phenyl-1H-pyrazol-3-yl}oxy)methyl]-2-methoxyphenoxy}methyl)-5-methyl-1,3-oxazol-2-yl]phenyl}acetate as colorless crystals (0.22 g, yield 11%). Recrystallization from ethyl acetate-hexane gave colorless prism crystals. melting point: 126-127° C.

In addition, ethyl {4-[4-({4-[({4-[(E)-2-(2-isopropyl-1,3-thiazol-4-yl)ethenyl]-1-phenyl-1H-pyrazol-3-yl}oxy)methyl]-2-methoxyphenoxy}methyl)-5-methyl-1,3-oxazol-2-yl]phenyl}acetate was obtained as colorless crystals (0.26 g, yield 13%) from a fraction successively obtained by elution. Recrystallization from ethyl acetate-hexane gave colorless prism crystals. melting point: 89-90° C.

Example 361

To a mixture of ethyl {4-{4-({4-[({4-(E)-2-(2-isopropyl-1,3-thiazol-4-yl)ethenyl}-1-phenyl-1H-pyrazol-3-yl)oxy]methyl}-2-methoxyphenoxy)methyl}-5-methyl-1,3-oxazol-2-yl}phenyl}acetate (0.18 g), tetrahydrofuran (2 mL) and ethanol (1 mL) was added 1N aqueous sodium hydroxide solution (0.52 mL) and the mixture was stirred at 50° C. for 1.5 hrs. To the reaction mixture were added 1N hydrochloric acid (0.52 mL) and water, and the mixture was extracted with ethyl acetate. The ethyl acetate layer was washed with saturated brine, dried over anhydrous magnesium sulfate and concentrated to give {4-[4-({4-[({4-[(E)-2-(2-isopropyl-1,3-thiazol-4-yl)ethenyl]-1-phenyl-1H-pyrazol-3-yl}oxy)methyl]-2-methoxyphenoxy}methyl)-5-methyl-1,3-oxazol-2-yl]phenyl}acetic acid as crystals (0.15 g, yield 87%). Recrystallization from ethyl acetate-hexane gave colorless prism crystals. melting point: 107-109° C.

Example 362

To a mixture of ethyl {4-[4-({4-[({4-[(Z)-2-(2-isopropyl-1,3-thiazol-4-yl)ethenyl]-1-phenyl-1H-pyrazol-3-yl}oxy)methyl]-2-methoxyphenoxy}methyl)-5-methyl-1,3-oxazol-2-yl]phenyl}acetate (0.11 g), tetrahydrofuran (2 mL) and ethanol (0.64 mL) was added 1N aqueous sodium hydroxide solution (0.60 mL), and the mixture was stirred at 50° C. for 3 hrs. To the reaction mixture were added 1N hydrochloric acid (0.60 mL) and water, and the mixture was extracted with ethyl acetate. The ethyl acetate layer was washed with saturated brine, dried over anhydrous magnesium sulfate and concentrated to give {4-[4-({4-[({4-[(Z)-2-(2-isopropyl-1,3-thiazol-4-yl)ethenyl]-1-phenyl-1H-pyrazol-3-yl}oxy)methyl]-2-methoxyphenoxy}methyl)-5-methyl-1,3-oxazol-2-yl]phenyl}acetic acid as crystals (0.10 g, yield 92%). Recrystallization from ethyl acetate-hexane gave colorless prism crystals. melting point: 156-157° C.

Example 363

A mixture of 3-[4-({4-[{4-[(E)-2-(2-ethyl-1,3-thiazol-4-yl)ethenyl]-1-phenyl-1H-pyrazol-3-yl}oxy]methyl}-2-methoxyphenoxy)methyl]-5-methyl-1,3-oxazol-2-yl]-N'-hydroxybenzenecarboximideamide (140 mg), thionyl chloride (0.018 mL) and N,N-dimethylacetamide (2 mL) was stirred at 80° C. for 2 hrs. Water was poured into the reaction mixture, and the mixture was extracted with ethyl acetate-tetrahydrofuran. The organic layer was washed with saturated brine, dried over anhydrous magnesium sulfate and concentrated. The residue was subjected to silica gel column chromatography and eluted with ethyl acetate-hexane (1:5-1:2, v/v). The residue was washed with diethyl ether-hexane to give 4-{3-[4-({4-[({4-[(E)-2-(2-ethyl-1,3-thiazol-4-yl)ethenyl]-1-phenyl-1H-pyrazol-3-yl}oxy)methyl]-2-methoxyphenoxy}methyl)-5-methyl-1,3-oxazol-2-yl]phenyl}-3H-1,2,3,5-oxathiadiazole 2-oxide (40 mg, yield 27%) as colorless amorphous form.

NMR (CDCl$_3$) δ: 1.39 (3H, t, J=7.5 Hz), 2.35 (3H, s), 3.03 (2H, q, J=7.7 Hz) 3.87 (3H, s), 5.01 (2H, s), 5.39 (2H, s), 6.86 (1H, s), 7.15 (6H, m), 7.43 (3H, m), 7.61 (2H, m), 7.82 (1H, s), 7.86 (1H, m), 7.99 (1H, m), 8.24 (1H, t, J=1.4 Hz).

Example 364

A mixture of ethyl (4-{4-[(4-chloromethyl-2-methoxyphenoxy)methyl]-5-methyl-1,3-oxazol-2-yl}phenyl)acetate (0.68 g), {4-[(E)-2-(3-hydroxy-1-phenyl-1H-pyrazol-4-yl)ethenyl]-1,3-thiazol-2-yl}methyl benzoate hydrochloride (0.73 g), potassium carbonate (0.45 g) and N,N-dimethylformamide (15 mL) was stirred at 90° C. for 10 min. Water was poured into the reaction mixture, and the mixture was extracted with ethyl acetate. The ethyl acetate layer was washed with saturated brine, and dried over anhydrous magnesium sulfate and concentrated. The residue was subjected to silica gel column chromatography and eluted with ethyl acetate-hexane (10:90-30:70, v/v) to give {4-[(E)-2-(3-{[4-({2-[4-(2-ethoxy-2-oxoethyl)phenyl]-5-methyl-1,3-oxazol-4-yl}methoxy)-3-methoxybenzyl]oxy}-1-phenyl-1H-pyrazol-4-yl)ethenyl]-1,3-thiazol-2-yl}methyl benzoate as colorless crystals (0.55 g, yield 44%). Recrystallization from ethyl acetate-hexane gave colorless prism crystals. melting point: 116-117° C.

Example 365

To a mixture of {4-[(E)-2-(3-{[4-({2-[4-(2-ethoxy-2-oxoethyl)phenyl]-5-methyl-1,3-oxazol-4-yl}methoxy)-3-methoxybenzyl]oxy}-1-phenyl-1H-pyrazol-4-yl)ethenyl]-1,3-thiazol-2-yl}methyl benzoate (0.5 g), tetrahydrofuran (6 mL) and ethanol (3 mL) was added 1N aqueous sodium hydroxide solution (3 mL), and the mixture was stirred at 50° C. for 20 hrs. To the reaction mixture were added 1N hydrochloric acid (3 mL) and water, and the mixture was extracted with ethyl acetate. The ethyl acetate layer was washed with saturated brine, dried over anhydrous magnesium sulfate and concentrated to give (4-{4-[(4-{[(4-{(E)-2-[2-(hydroxymethyl)-1,3-thiazol-4-yl]ethenyl}-1-phenyl-1H-pyrazol-3-yl)oxy]methyl}-2-methoxyphenoxy)methyl]-5-methyl-1,3-oxazol-2-yl}phenyl)acetic acid as crystals (0.4 g, yield 90%). Recrystallization twice from tetrahydrofuran-hexane gave colorless prism crystals. melting point: 204-205° C.

Example 366

A mixture of ethyl (4-{4-[(4-chloromethyl-2-methoxyphenoxy)methyl]-5-methyl-1,3-oxazol-2-yl}phenyl)acetate (1.48 g), 4-[(E)-2-(2-ethyl-1,3-oxazol-4-yl)ethenyl]-1-phenyl-1H-pyrazol-3-ol.hydrochloride (1.07 g), potassium carbonate (1.05 g) and N,N-dimethylformamide (30 mL) was stirred at 90° C. for 2 hrs. Water was poured into the reaction mixture, and the mixture was extracted with ethyl acetate-tetrahydrofuran. The organic layer was washed with saturated brine, dried over anhydrous magnesium sulfate and concentrated. The residue was subjected to silica gel column chromatography and eluted with acetone-hexane (1:5-1:4-1:3, v/v) to give ethyl {4-[4-({4-[({4-[(E)-2-(2-ethyl-1,3-oxazol-4-yl)ethenyl]-1-phenyl-1H-pyrazol-3-yl}oxy)methyl]-2-methoxyphenoxy}methyl)-5-methyl-1,3-oxazol-2-yl]phenyl}acetate (480 mg, yield 20%) as colorless crystals. Recrystallization from ethyl acetate-hexane gave colorless prism crystals. melting point: 155-157° C.

Example 367

A mixture of ethyl (4-{4-[(4-chloromethyl-2-methoxyphenoxy)methyl]-5-methyl-1,3-oxazol-2-yl}phenyl)acetate (0.976 g), 4-[(E)-2-(2-isopropyl-1,3-oxazol-4-yl)ethenyl]-1-phenyl-1H-pyrazol-3-ol hydrochloride (0.83 g), potassium carbonate (0.691 g) and N,N-dimethylformamide (20 mL) was stirred at 90° C. for 1.5 hrs. Water was poured into the reaction mixture, and the mixture was extracted with ethyl acetate-tetrahydrofuran. The organic layer was washed with saturated brine, dried over anhydrous magnesium sulfate and concentrated. The residue was subjected to silica gel column chromatography and eluted with acetone-hexane (1:5-1:4-1:3, v/v) to give ethyl {4-[4-({4-[({4-[(E)-2-(2-isopropyl-1,3-oxazol-4-yl)ethenyl]-1-phenyl-1H-pyrazol-3-yl}oxy)methyl]-2-methoxyphenoxy}methyl)-5-methyl-1,3-oxazol-2-yl]phenyl}acetate (244 mg, yield 16%) as colorless crystals. Recrystallization from acetone-hexane gave colorless prism crystals. melting point: 106-108° C.

Example 368

A mixture of ethyl (4-{4-[(4-chloromethyl-2-methoxyphenoxy)methyl]-5-methyl-1,3-oxazol-2-yl}phenyl)acetate (1.29 g), 4-[(E)-2-(2-tert-butyl-1,3-oxazol-4-yl)ethenyl]-1-phenyl-1H-pyrazol-3-ol.hydrochloride (1.24 g), potassium carbonate (0.995 g) and N,N-dimethylformamide (30 mL) was stirred at 90° C. for 1.5 hrs. Water was poured into the reaction mixture, and the mixture was extracted with ethyl acetate-tetrahydrofuran. The organic layer was washed with saturated brine, dried over anhydrous magnesium sulfate and concentrated. The residue was subjected to aminopropyl silica gel column chromatography and eluted with ethyl acetate-hexane (1:5-1:4-1:3, v/v) to give ethyl {4-[4-({4-[({4-[(E)-2-(2-tert-butyl-1,3-oxazol-4-yl)ethenyl]-1-phenyl-1H-pyrazol-3-yl}oxy)methyl]-2-methoxyphenoxy}methyl)-5-methyl-1,3-oxazol-2-yl]phenyl}acetate (430 mg, yield 20%) as colorless crystals. Recrystallization from ethyl acetate-hexane gave colorless prism crystals. melting point: 126-129° C.

Example 369

To a mixture of ethyl {4-[4-({4-[({4-[(E)-2-(2-ethyl-1,3-oxazol-4-yl)ethenyl]-1-phenyl-1H-pyrazol-3-yl}oxy)methyl]-2-methoxyphenoxy}methyl)-5-methyl-1,3-oxazol-2-yl]phenyl}acetate (360 mg), tetrahydrofuran (5 mL) and ethanol (5 mL) was added 1N aqueous sodium hydroxide solution (1.6 mL) and the mixture was stirred at 50° C. for 1 hr. 1N Hydrochloric acid was added to the reaction mixture for neutralization, and the mixture was extracted with ethyl acetate. The residue was recrystallized from ethyl acetate-hexane and the precipitated crystals were collected by filtration to give {4-[4-({4-[({4-[(E)-2-(2-ethyl-1,3-oxazol-4-yl)ethenyl]-1-phenyl-1H-pyrazol-3-yl}oxy)methyl]-2-methoxyphenoxy}methyl)-5-methyl-1,3-oxazol-2-yl]phenyl}acetic acid (196 mg, yield 37%) as colorless crystals. melting point: 117-119° C.

Example 370

To a mixture of ethyl {4-[4-({4-[({4-[(E)-2-(2-isopropyl-1,3-oxazol-4-yl)ethenyl]-1-phenyl-1H-pyrazol-3-yl}oxy)methyl]-2-methoxyphenoxy}methyl)-5-methyl-1,3-oxazol-2-yl]phenyl}acetate (180 mg), tetrahydrofuran (3 mL) and ethanol (3 mL) was added 1N aqueous sodium hydroxide solution (0.8 mL), and the mixture was stirred at 50° C. for 1 hr. 1N Hydrochloric acid was added to the reaction mixture for neutralization, and the mixture was extracted with ethyl acetate. The residue was recrystallized from ethyl acetate-hexane and the precipitated crystals were collected by filtration to give {4-[4-({4-[({4-[(E)-2-(2-isopropyl-1,3-oxazol-4-yl)ethenyl]-1-phenyl-1H-pyrazol-3-yl}oxy)methyl]-2-methoxyphenoxy}methyl)-5-methyl-1,3-oxazol-2-yl]phenyl}acetic acid (47 mg, yield 27%) as colorless crystals. melting point: 116-118° C.

Example 371

To a mixture of ethyl {4-[4-({4-[({4-[(E)-2-(2-tert-butyl-1,3-oxazol-4-yl)ethenyl]-1-phenyl-1H-pyrazol-3-yl}oxy)methyl]-2-methoxyphenoxy}methyl)-5-methyl-1,3-oxazol-2-yl]phenyl}acetate (320 mg), tetrahydrofuran (5 mL) and ethanol (5 mL) was added 1N aqueous sodium hydroxide solution (1.5 mL), and the mixture was stirred at 50° C. for 1 hr. 1N Hydrochloric acid was added to the reaction mixture for neutralization, and the mixture was extracted with ethyl acetate. The residue was recrystallized from ethyl acetate-hexane and the precipitated crystals were collected by filtration to give {4-[4-({4-[({4-[(E)-2-(2-tert-butyl-1,3-oxazol-4-yl)ethenyl]-1-phenyl-1H-pyrazol-3-yl}oxy)methyl]-2-methoxyphenoxy}methyl)-5-methyl-1,3-oxazol-2-yl]phenyl}acetic acid (181 mg, yield 59%) as colorless prism crystals. melting point: 104-106° C.

Example 372

A mixture of 3-{4-[(4-chloromethyl-2-methoxyphenoxy)methyl]-5-methyl-1,3-oxazol-2-yl}benzonitrile (3.32 g), 4-[(E)-2-(2-ethyl-1,3-thiazol-4-yl)ethenyl]-1-phenyl-1H-pyrazol-3-ol (2.95 g), potassium carbonate (1.37 g) and N,N-dimethylformamide (100 mL) was stirred at 90° C. for 2 hrs. Water was poured into the reaction mixture, and the mixture was extracted with ethyl acetate-tetrahydrofuran. The organic layer was washed with saturated brine, dried over anhydrous magnesium sulfate and concentrated. The residue was subjected to silica gel column chromatography and eluted with acetone-hexane (1:5-1:4, v/v) to give 3-[4-({4-[({4-[(E)-2-(2-ethyl-1,3-thiazol-4-yl)ethenyl]-1-phenyl-1H-pyrazol-3-yl}oxy)methyl]-2-methoxyphenoxy}methyl)-5-methyl-1,3-oxazol-2-yl]benzonitrile (4.10 g, yield 72%) as colorless crystals. Recrystallization from ethyl acetate-hexane gave colorless prism crystals. melting point: 138-140° C.

Example 373

A mixture of 3-[4-({4-[({4-[(E)-2-(2-ethyl-1,3-thiazol-4-yl)ethenyl]-1-phenyl-1H-pyrazol-3-yl}oxy)methyl]-2-methoxyphenoxy}methyl)-5-methyl-1,3-oxazol-2-yl]benzonitrile (350 mg), sodium azide (55 mg), ammonium chloride (59 mg) and N,N-dimethylformamide (10 mL) was stirred at 120° C. for 6 hrs. Water was poured into the reaction mixture, and the mixture was extracted with ethyl acetate-tetrahydrofuran. The organic layer was washed with saturated brine, dried over anhydrous magnesium sulfate and concentrated. The residue was subjected to silica gel column chromatography and eluted with ethyl acetate-hexane (1:5-1:2-1:1, v/v) to give 5-{3-[4-({4-[({4-[(E)-2-(2-ethyl-1,3-thiazol-4-yl)ethenyl]-1-phenyl-1H-pyrazol-3-yl}oxy)methyl]-2-methoxyphenoxy}methyl)-5-methyl-1,3-oxazol-2-yl]phenyl}-1H-tetrazole (106 mg, yield 28%) as colorless crystals. Recrystallization from ethyl acetate-diethyl ether gave colorless prism crystals. melting point: 144-147° C.

Example 374

A mixture of 3-[4-({4-[({4-[(E)-2-(2-ethyl-1,3-thiazol-4-yl)ethenyl]-1-phenyl-1H-pyrazol-3-yl}oxy)methyl]-2-methoxyphenoxy}methyl)-5-methyl-1,3-oxazol-2-yl]benzonitrile (1:26 g), hydroxylammonium chloride (0.695 g), sodium methoxide (0.54 g) and dimethyl sulfoxide (20 mL) was stirred at 80° C. for 6 hrs. Water was poured into the reaction mixture, and the mixture was extracted with ethyl acetate-tetrahydrofuran. The organic layer was washed with saturated brine, dried over anhydrous magnesium sulfate and concentrated. The residue was subjected to silica gel column chromatography and eluted with ethyl acetate-hexane (1:5-1:2-2:1, v/v) to give 3-[4-({4-[({4-[(E)-2-(2-ethyl-1,3-thiazol-4-yl)ethenyl]-1-phenyl-1H-pyrazol-3-yl}oxy)methyl]-2-methoxyphenoxy}methyl)-5-methyl-1,3-oxazol-2-yl]-N'-hydroxybenzenecarboximideamide (0.52 g, yield

Example 375

A mixture of 3-[4-({4-[({4-[(E)-2-(2-ethyl-1,3-thiazol-4-yl)ethenyl]-1-phenyl-1H-pyrazol-3-yl}oxy)methyl]-2-methoxyphenoxy}methyl)-5-methyl-1,3-oxazol-2-yl]-N'-hydroxybenzenecarboximideamide (200 mg), 1,1'-carbonyldiimidazole (54 mg) and N,N-dimethylformamide (1.5 mL) was stirred at 80° C. for 1 hr. Water was poured into the reaction mixture, and the mixture was extracted with ethyl acetate-tetrahydrofuran. The organic layer was washed with saturated brine, dried over anhydrous magnesium sulfate and concentrated. Recrystallization of the residue from tetrahydrofuran-hexane gave 3-{3-[4-({4-[({4-[(E)-2-(2-ethyl-1,3-thiazol-4-yl)ethenyl]-1-phenyl-1H-pyrazol-3-yl}oxy)methyl]-2-methoxyphenoxy}methyl)-5-methyl-1,3-oxazol-2-yl]phenyl}-1,2,4-oxadiazol-5(4H)-one (146 mg, yield 70%) as colorless prism crystals. melting point: 139-140° C.

Example 376

A mixture of 3-[4-({4-[({4-[(E)-2-(2-ethyl-1,3-thiazol-4-yl)ethenyl]-1-phenyl-1H-pyrazol-3-yl}oxy)methyl]-2-methoxyphenoxy}methyl)-5-methyl-1,3-oxazol-2-yl]benzoic acid (200 mg), methanesulfonamide (57 mg), O-(7-azabenzotriazol-1-yl)-1,1,3,3-tetramethyluromium hexafluorophosphate (HATU, 228 mg), N,N-diisopropylethylamine (0.105 mL) and N,N-dimethylformamide (1.5 mL) was stirred at 80° C. for 16 hrs. Water was poured into the reaction mixture, and the mixture was extracted with ethyl acetate-tetrahydrofuran.

The organic layer was washed with saturated brine, dried over anhydrous magnesium sulfate and concentrated. The residue was subjected to reversed phase HPLC and eluted with acetonitrile-water (10:90-100:0, v/v) to give 3-[4-({4-[({4-[(E)-2-(2-ethyl-1,3-thiazol-4-yl)ethenyl]-1-phenyl-1H-pyrazol-3-yl}oxy)methyl]-2-methoxyphenoxy}methyl)-5-methyl-1,3-oxazol-2-yl]-N-(methylsulfonyl)benzamide (104 mg, yield 47%) as colorless crystals. Recrystallization from ethyl acetate-hexane gave colorless prism crystals. melting point: 211-213° C.

Example 377

A mixture of 3-[4-({4-[({4-[(E)-2-(2-ethyl-1,3-thiazol-4-yl)ethenyl]-1-phenyl-1H-pyrazol-3-yl}oxy)methyl]-2-methoxyphenoxy}methyl)-5-methyl-1,3-oxazol-2-yl]-N'-hydroxybenzenecarboximideamide (140 mg), 1,1'-thiocarbonyldiimidazole (45 mg), 1,8-diazabicyclo[5.4.0]-7-undecene (0.038 mL) and tetrahydrofuran (1.5 mL) was stirred at 80° C. for 1 hr. Water was poured into the reaction mixture, and the mixture was extracted with ethyl acetate-tetrahydrofuran. The organic layer was washed with saturated brine, dried over anhydrous magnesium sulfate and concentrated. The residue was subjected to silica gel column chromatography and eluted with acetone-hexane (1:5-1:4, v/v). The residue was washed with ethyl acetate-hexane to give 3-{3-[4-({4-[({4-[(E)-2-(2-ethyl-1,3-thiazol-4-yl)ethenyl]-1-phenyl-1H-pyrazol-3-yl}oxy)methyl]-2-methoxyphenoxy}methyl)-5-methyl-1,3-oxazol-2-yl]phenyl}-1,2,4-oxadiazole-5(4H)-thione (93 mg, yield 63%) as colorless amorphous form.

NMR (DMSO-$d_6$) δ: 1.31 (3H, t, J=7.5 Hz), 2.46 (3H, s), 2.98 (2H, d, J=7.5 Hz), 3.79 (3H, s), 5.01 (2H, s), 5.36 (2H, s), 7.04 (1H, d, J=16.0 Hz), 7.18 (6H, m), 7.33 (1H, s), 7.49 (2H, m), 7.60 (1H, t, J=7.8 Hz), 7.77 (2H, m), 7.99 (2H, m), 8.44 (1H, t, J=1.5 Hz), 8.64 (1H, s).

Example 378

A mixture of ethyl (4-{4-[(4-chloromethyl-2-methoxyphenoxy)methyl]-5-methyl-1,3-oxazol-2-yl}phenyl)acetate (1.72 g), 4-[(E)-2-(2-ethyl-5-methyl-1,3-thiazol-4-yl)ethenyl]-1-phenyl-1H-pyrazol-3-ol hydrochloride (1.39 g), potassium carbonate (1.11 g) and N,N-dimethylformamide (30 mL) was stirred at 90° C. for 2.5 hrs. Water was poured into the reaction mixture, and the mixture was extracted with ethyl acetate. The ethyl acetate layer was washed with saturated brine, dried over anhydrous magnesium sulfate and concentrated. The residue was subjected to silica gel column chromatography, tetrahydrofuran-hexane (1:5, v/v) to give ethyl {4-[4-({4-[({4-[(E)-2-(2-ethyl-5-methyl-1,3-thiazol-4-yl)ethenyl]-1-phenyl-1H-pyrazol-3-yl}oxy)methyl]-2-methoxyphenoxy}methyl)-5-methyl-1,3-oxazol-2-yl]phenyl}acetate (0.80 g, yield 28%) as crystals. Recrystallization from tetrahydrofuran-hexane gave colorless prism crystals. melting point: 127-128° C.

Example 379

To a mixture of ethyl {4-[4-({4-[({4-[(E)-2-(2-ethyl-5-methyl-1,3-thiazol-4-yl)ethenyl]-1-phenyl-1H-pyrazol-3-yl}oxy)methyl]-2-methoxyphenoxy}methyl)-5-methyl-1,3-oxazol-2-yl]phenyl}acetate (0.30 g), tetrahydrofuran (6 mL) and ethanol (3 mL) was added 1N aqueous sodium hydroxide solution (1 mL), and the mixture was stirred at 50° C. for 2 hrs. To the reaction mixture were added 1N hydrochloric acid (2 mL) and water, and the precipitated crystals were collected by filtration to give {4-[4-({4-[({4-[(E)-2-(2-ethyl-5-methyl-1,3-thiazol-4-yl)ethenyl]-1-phenyl-1H-pyrazol-3-yl}oxy)methyl]-2-methoxyphenoxy}methyl)-5-methyl-1,3-oxazol-2-yl]phenyl}acetic acid as crystals (0.19 g, yield 66%). Recrystallization from tetrahydrofuran-hexane gave pale-yellow prism crystals. melting point: 198-199° C.

Example 380

A mixture of ethyl (4-{4-[(4-chloromethyl-2-methoxyphenoxy)methyl]-5-methyl-1,3-oxazol-2-yl}phenyl)acetate (0.66 g), tert-butyl 4-{4-[(E)-2-(3-hydroxy-1-phenyl-1H-pyrazol-4-yl)ethenyl]-5-methyl-1,3-thiazol-2-yl}piperazine-1-carboxylate (0.81 g), potassium carbonate (0.22 g) and N,N-dimethylformamide (20 mL) was stirred at 90° C. for 1 hr. Water was poured into the reaction mixture, and the mixture was extracted with ethyl acetate. The ethyl acetate layer was washed with saturated brine, dried over anhydrous magnesium sulfate and concentrated. The residue was subjected to silica gel column chromatography and eluted with tetrahydrofuran-hexane (1:5, v/v) to give tert-butyl 4-{4-[(E)-2-(3-{[4-({2-[4-(2-ethoxy-2-oxoethyl)phenyl]-5-methyl-1,3-oxazol-4-yl}methoxy)-3-methoxybenzyl]oxy}-1-phenyl-1H-pyrazol-4-yl)ethenyl]-5-methyl-1,3-thiazol-2-yl}piperazine-1-carboxylate as crystals (0.53 g, yield 41%). Recrystallization from ethyl acetate-hexane gave pale-yellow prism crystals. melting point: 112-114° C.

Example 381

To a mixture of tert-butyl 4-{4-[(E)-2-(3-{[4-({2-[4-(2-ethoxy-2-oxoethyl)phenyl]-5-methyl-1,3-oxazol-4-yl}methoxy)-3-methoxybenzyl]oxy}-1-phenyl-1H-pyrazol-4-yl)ethenyl]-5-methyl-1,3-thiazol-2-yl}piperazine-1-carboxylate (0.30 g), tetrahydrofuran (6 mL) and ethanol (3 mL) was added 1N aqueous sodium hydroxide solution (1 mL), and the mixture was stirred at 50° C. for 1 hr. To the reaction mixture were added 1N hydrochloric acid (1 mL) and water, and the mixture was extracted with ethyl acetate. The ethyl acetate layer was washed with saturated brine, dried over anhydrous magnesium sulfate and concentrated to give [4-(4-{[4-({[4-((E)-2-{2-[4-(tert-butoxycarbonyl)piperazin-1-yl]-5-methyl-1,3-thiazol-4-yl}ethenyl)-1-phenyl-1H-pyrazol-3-yl]oxy}methyl)-2-methoxyphenoxy]methyl}-5-methyl-1,3-oxazol-2-yl)phenyl]acetic acid as crystals (0.14 g, yield 50%). Recrystallization from ethyl acetate-hexane gave brown prism crystals. melting point: 119-120° C.

Example 382

A mixture of ethyl (4-{4-[(4-chloromethyl-2-methoxyphenoxy)methyl]-5-methyl-1,3-oxazol-2-yl}phenyl)acetate (0.66 g), 4-{(E)-2-[5-methyl-2-(piperidin-1-yl)-1,3-thiazol-4-yl]ethenyl}-1-phenyl-1H-pyrazol-3-ol hydrochloride (0.44 g), potassium carbonate (0.30 g) and N,N-dimethylformamide (20 mL) was stirred at 90° C. for 2 hrs. Water was poured into the reaction mixture, and the mixture was extracted with ethyl acetate. The ethyl acetate layer was washed with saturated brine, dried over anhydrous magnesium sulfate and concentrated to give ethyl [4-{4-[(2-methoxy-4-{[(4-{(E)-2-[5-methyl-2-(piperidin-1-yl)-1,3-thiazol-4-yl]ethenyl}-1-phenyl-1H-pyrazol-3-yl)oxy]methyl}phenoxy)methyl]-5-methyl-1,3-oxazol-2-yl}phenyl]acetate (0.59 g, yield 72%) as crystals. Recrystallization from ethyl acetate-hexane gave yellow prism crystals. melting point: 131-132° C.

Example 383

To a mixture of ethyl [4-{4-[(2-methoxy-4-{[(4-{(E)-2-[5-methyl-2-(piperidin-1-yl)-1,3-thiazol-4-yl]ethenyl}-1-phenyl-1H-pyrazol-3-yl)oxy]methyl}phenoxy)methyl]-5-methyl-1,3-oxazol-2-yl}phenyl]acetate (0.36 g), tetrahydrofuran (9 mL) and ethanol (3 mL) was added 1N aqueous sodium hydroxide solution (1 mL), and the mixture was stirred at 50° C. for 1.5 hrs. To the reaction mixture were added 1N hydrochloric acid (1 mL) and water, and the mixture was extracted with ethyl acetate. The ethyl acetate layer was washed with saturated brine, dried over anhydrous magnesium sulfate and concentrated to give [4-{4-[(2-methoxy-4-{[(4-{(E)-2-[5-methyl-2-(piperidin-1-yl)-1,3-thiazol-4-yl]ethenyl}-1-phenyl-1H-pyrazol-3-yl)oxy]methyl}phenoxy)methyl]-5-methyl-1,3-oxazol-2-yl}phenyl]acetic acid as crystals (0.20 g, yield 58%). Recrystallization from ethyl acetate-hexane gave brown prism crystals. melting point: 146-148° C.

Example 384

A mixture of ethyl (4-{4-[(4-chloromethyl-2-ethoxyphenoxy)methyl]-5-methyl-1,3-oxazol-2-yl}phenyl)acetate (1.37 g), 4-{(E)-2-[5-methyl-2-(morpholin-4-yl)-1,3-thiazol-4-yl]ethenyl}-1-phenyl-1H-pyrazol-3-ol.hydrochloride (0.86 g), potassium carbonate (0.59 g) and N,N-dimethylformamide (30 mL) was stirred at 90° C. for 2 hrs. Water was poured into the reaction mixture, and the mixture was extracted with ethyl acetate. The ethyl acetate layer was washed with saturated brine, dried over anhydrous magnesium sulfate and concentrated to give ethyl [4-(4-{[2-methoxy-4-({[4-{(E)-2-[5-methyl-2-(morpholin-4-yl)-1,3-thiazol-4-yl]ethenyl}-1-phenyl-1H-pyrazol-3-yl)oxy]methyl}phenoxy)methyl]-5-methyl-1,3-oxazol-2-yl}phenyl)acetate as crystals (0.52 g, yield 32%). Recrystallization from tetrahydrofuran-hexane gave pale-yellow prism crystals. melting point: 151-153° C.

Example 385

To a mixture of ethyl (4-{4-[(2-methoxy-4-{[(4-{(E)-2-[5-methyl-2-(morpholin-4-yl)-1,3-thiazol-4-yl]ethenyl}-1-phenyl-1H-pyrazol-3-yl)oxy]methyl}phenoxy)methyl]-5-methyl-1,3-oxazol-2-yl}phenyl)acetate (0.43 g), tetrahydrofuran (12 mL) and ethanol (3 mL) was added 1N aqueous sodium hydroxide solution (1.5 mL), and the mixture was stirred at 50° C. for 2 hrs. To the reaction mixture were added 1N hydrochloric acid (1.5 mL) and water, and the mixture was extracted with ethyl acetate. The ethyl acetate layer was washed with saturated brine, dried over anhydrous magnesium sulfate and concentrated to give [4-(4-{[2-methoxy-4-({[4-{(E)-2-[5-methyl-2-(morpholin-4-yl)-1,3-thiazol-4-yl]ethenyl}-1-phenyl-1H-pyrazol-3-yl]oxy}methyl)phenoxy]methyl)-5-methyl-1,3-oxazol-2-yl}phenyl]acetic acid as crystals (0.22 g, yield 53%). Recrystallization from tetrahydrofuran-hexane gave orange prism crystals. melting point: 171-173° C.

Example 386

A mixture of 4-[(4-chloromethyl-2-methoxyphenoxy)methyl]-5-methyl-2-(3-nitrophenyl)-1,3-oxazole (1.17 g), 4-[(E)-2-(2-ethyl-1,3-thiazol-4-yl)ethenyl]-1-phenyl-1H-pyrazol-3-ol (0.892 g), potassium carbonate (0.415 g) and N,N-dimethylformamide (20 mL) was stirred at 90° C. for 2 hrs. Water was poured into the reaction mixture, and the mixture was extracted with ethyl acetate. The ethyl acetate layer was washed with saturated brine, dried over anhydrous magnesium sulfate and concentrated. The residue was subjected to silica gel column chromatography and eluted with acetone-hexane (1:5-1:4-1:3, v/v) to give {4-({4-[({4-[(E)-2-(2-ethyl-1,3-thiazol-4-yl)ethenyl]-1-phenyl-1H-pyrazol-3-yl}oxy)methyl]-2-methoxyphenoxy}methyl)-5-methyl-2-(3-nitrophenyl)-1,3-oxazole (0.742 g, yield 38%) as colorless crystals. Recrystallization from ethyl acetate-diethyl ether gave pale-yellow prism crystals. melting point: 127-129° C.

Example 387

A mixture of {4-({4-[({4-[(E)-2-(2-ethyl-1,3-thiazol-4-yl)ethenyl]-1-phenyl-1H-pyrazol-3-yl}oxy)methyl]-2-methoxyphenoxy}methyl)-5-methyl-2-(3-nitrophenyl)-1,3-oxazole (650 mg), iron (reduced) (284 mg), calcium chloride (11 mg) and 80% ethanol (8 mL) was heated under reflux for 2 hrs. Insoluble materials were removed by celite filtration, and the filtrate was concentrated. The residue was subjected to silica gel column chromatography and eluted with ethyl acetate to give {3-[4-({4-[({4-[(E)-2-(2-ethyl-1,3-thiazol-4-yl)ethenyl]-1-phenyl-1H-pyrazol-3-yl}oxy)methyl]-2-methoxyphenoxy}methyl)-5-methyl-1,3-oxazol-2-yl]phenyl}amine as yellow amorphous form (150 mg, yield 38%).

NMR (CDCl$_3$) δ: 1.41 (3H, t, J=7.5 Hz), 2.40 (3H, s), 3.05 (2H, q, J=7.5 Hz) 3.89 (3H, s), 5.07 (2H, s), 5.39 (2H, s), 6.74 (1H, ddd, J=8.0, 2.3, 0.9 Hz), 6.86 (1H, s), 7.06-7.14 (4H, m), 7.18-7.24 (2H, m), 7.32-7.45 (5H, m), 7.60-7.63 (2H, m), 7.82 (1H, s).

Example 388

A mixture of {3-[4-({4-[({4-[(E)-2-(2-ethyl-1,3-thiazol-4-yl)ethenyl]-1-phenyl-1H-pyrazol-3-yl}oxy)methyl]-2-methoxyphenoxy}methyl)-5-methyl-1,3-oxazol-2-yl]phenyl}amine (100 mg), methanesulfonyl chloride (0.013 mL), triethylamine (0.024 mL) and tetrahydrofuran (1 mL) was stirred at room temperature for 1 hr. The reaction mixture was added to saturated aqueous sodium hydrogen carbonate, and the mixture was extracted with ethyl acetate-tetrahydrofuran. The organic layer was dried over anhydrous magnesium sulfate and concentrated. The eluate was subjected to reversed phase HPLC and eluted with acetonitrile-water (10:90-100:0, v/v). The obtained fraction was concentrated, and saturated aqueous sodium hydrogen carbonate was added to the residue. The mixture was extracted with ethyl acetate-tetrahydrofuran. The organic layer was washed with saturated brine, dried over anhydrous magnesium sulfate and concentrated to give N-{3-[4-({4-[({4-[(E)-2-(2-ethyl-1,3-thiazol-4-yl)ethenyl]-1-phenyl-1H-pyrazol-3-yl}oxy)methyl]-2-methoxyphenoxy}methyl)-5-methyl-1,3-oxazol-2-yl]phenyl}methanesulfonamide (37 mg, yield 33%). Recrystallization from ethyl acetate-hexane gave pale-yellow prism crystals. melting point: 113-115° C.

Example 389

A mixture of ethyl {4-[4-({[5-(hydroxymethyl)isoxazol-3-yl]oxy}methyl)-5-methyl-1,3-oxazol-2-yl]phenyl}acetate (500 mg), 4-[(E)-2-(2-ethyl-1,3-thiazol-4-yl)ethenyl]-1-phenyl-1H-pyrazol-3-ol (389 mg), 1,1'-(azodicarbonyl)dipiperidine (440 mg), tributylphosphine (0.501 mL) and tetrahydrofuran (20 mL) was stirred at 50° C. for 1 hr. After cooling, the resulting precipitate was removed by filtration, and the filtrate was concentrated. The residue was subjected to silica gel column chromatography and eluted with acetone-hexane (1:5-1:4-1:3, v/v). The obtained eluate was subjected to reversed phase HPLC and eluted with acetonitrile-water (10:90-100:0, v/v). The obtained fraction was concentrated, and saturated aqueous sodium hydrogen carbonate was added to the residue. The mixture was extracted with ethyl acetate-tetrahydrofuran. The organic layer was washed with saturated brine, dried over anhydrous magnesium sulfate and concentrated to give ethyl (4-{4-[({5-[({4-[(E)-2-(2-ethyl-1,3-thiazol-4-yl)ethenyl]-1-phenyl-1H-pyrazol-3-yl}oxy)methyl]isoxazol-3-yl}oxy)methyl]-5-methyl-1,3-oxazol-2-yl}phenyl)acetate (257 mg, yield 30%) as pale-yellow amorphous form.

NMR (CDCl$_3$) δ: 1.25 (3H, t, J=7.2 Hz), 1.41 (3H, t, J=7.5 Hz), 2.47 (3H, s), 3.05 (2H, q, J=7.5 Hz), 3.65 (2H, s), 4.16 (2H, q, J=7.2 Hz), 5.21 (2H, s), 5.43 (2H, s), 6.13 (1H, s), 6.93 (1H, s), 7.04 (1H, d, J=16.0 Hz), 7.19-7.28 (2H, m), 7.34-7.44 (4H, m), 7.58 (2H, d, J=7.7 Hz), 7.81 (1H, s), 7.97 (2H, d, J=8.1 Hz).

Example 390

To a mixture of ethyl (4-{4-[({5-[({4-[(E)-2-(2-ethyl-1,3-thiazol-4-yl)ethenyl]-1-phenyl-1H-pyrazol-3-yl}oxy)methyl]isoxazol-3-yl}oxy)methyl]-5-methyl-1,3-oxazol-2-yl}phenyl)acetate (193 mg), tetrahydrofuran (3 mL) and ethanol (3 mL) was added 1N aqueous sodium hydroxide solution (0.9 mL), and the mixture was stirred at 50° C. for 1 hr. To the reaction mixture were added 1N hydrochloric acid (0.9 mL) and water, and the mixture was extracted with ethyl acetate. The organic layer was washed with saturated brine, dried over anhydrous magnesium sulfate and concentrated. The residue was recrystallized from ethyl acetate-diethyl ether gave (4-{4-[({5-[({4-[(E)-2-(2-ethyl-1,3-thiazol-4-yl)ethenyl]-1-phenyl-1H-pyrazol-3-yl}oxy)methyl]isoxazol-3-yl}oxy)methyl]-5-methyl-1,3-oxazol-2-yl}phenyl)acetic acid as colorless prism crystals (112 mg, yield 61%). melting point: 156-158° C.

Example 391

A mixture of methyl 3-[4-({4-[({4-[(E)-2-(2-ethyl-1,3-thiazol-4-yl)ethenyl]-1-phenyl-1H-pyrazol-3-yl}oxy)methyl]-2-methoxyphenoxy}methyl)-5-methyl-1,3-oxazol-2-yl]benzoate (212 mg), lithium borohydride (74 mg) and tetrahydrofuran (40 mL) was stirred at room temperature for 12 hrs. Water was poured into the reaction mixture, and the mixture was extracted with ethyl acetate-tetrahydrofuran. The organic layer was washed with saturated brine, dried over anhydrous magnesium sulfate and concentrated. The residue was subjected to silica gel column chromatography and eluted with acetone-hexane (1:5-1:4, v/v) to give {3-[4-({4-[({4-[(E)-2-(2-ethyl-1,3-thiazol-4-yl)ethenyl]-1-phenyl-1H-pyrazol-3-yl}oxy)methyl]-2-methoxyphenoxy}methyl)-5-methyl-1,3-oxazol-2-yl]phenyl}methanol (143 mg, yield 62%) as colorless crystals. Recrystallization from ethyl acetate-hexane gave colorless prism crystals. melting point: 130-132° C.

Example 392

A mixture of ethyl (4-{4-[(4-chloromethyl-2-methoxyphenoxy)methyl]-5-methyl-1,3-oxazol-2-yl}phenyl)acetate (552 mg), 4-[(E)-2-(2-ethyl-1,3-thiazol-4-yl)ethenyl]-1-(2-methylphenyl)-1H-pyrazol-3-ol (400 mg), anhydrous potassium carbonate (177 mg) and N,N-dimethylformamide (10 mL) was stirred at 90° C. for 1.5 hrs. Water was poured into the reaction mixture, and the mixture was extracted with ethyl acetate. The ethyl acetate layer was washed with saturated brine, dried over anhydrous magnesium sulfate and concentrated. The residue was subjected to silica gel column chromatography and eluted with acetone-hexane (1:4-1:3-1:2, v/v). The obtained eluate was subjected to reversed phase HPLC and eluted with acetonitrile-water (10:90-100:0, v/v). The obtained fraction was concentrated, and saturated aqueous sodium hydrogen carbonate was added to the residue. The mixture was extracted with ethyl acetate-tetrahydrofuran. The organic layer was washed with saturated brine, dried over anhydrous magnesium sulfate and concentrated. The residue was washed with ethyl acetate-hexane to give ethyl [4-(4-{[4-({[4-[(E)-2-(2-ethyl-1,3-thiazol-4-yl)ethenyl]-1-(2-methylphenyl)-1H-pyrazol-3-yl]oxy}methyl)-2-methoxyphenoxy]methyl}-5-methyl-1,3-oxazol-2-yl)phenyl]acetate as pale-yellow amorphous form (173 mg, yield 19%).

NMR (CDCl$_3$) δ: 1.25 (3H, t, J=7.2 Hz), 1.41 (3H, t, J=7.6 Hz), 2.31 (3H, s), 2.41 (3H, s), 3.04 (2H, q, J=7.5 Hz), 3.65 (2H, s), 3.89 (3H, s), 4.16 (2H, q, J=7.2 Hz), 5.07 (2H, s), 5.34 (2H, s), 6.85 (1H, s), 7.08 (4H, m), 7.30 (7H, m), 7.50 (1H, s), 7.97 (2H, dd, J=6.9, 1.5 Hz).

Example 393

To a mixture of ethyl 4-(4-{[4-({[4-[(E)-2-(2-ethyl-1,3-thiazol-4-yl)ethenyl]-1-(2-methylphenyl)-1H-pyrazol-3-yl]oxy}methyl)-2-methoxyphenoxy]methyl}-5-methyl-1,3-oxazol-2-yl)phenyl]acetate (120 mg), tetrahydrofuran (2 mL) and ethanol (2 mL) was added 1N aqueous sodium hydroxide solution (0.9 mL), and the mixture was stirred at 50° C. for 1 hr. To the reaction mixture were added 1N hydrochloric acid (0.9 mL) and water, and the mixture was extracted with ethyl acetate. The organic layer was washed with saturated brine, dried over anhydrous magnesium sulfate and concentrated. The residue was washed with acetone-diethyl ether to give 4-(4-{[4-({[4-[(E)-2-(2-ethyl-1,3-thiazol-4-yl)ethenyl]-1-(2-methylphenyl)-1H-pyrazol-3-yl]oxy}methyl)-2-methoxyphenoxy]methyl}-5-methyl-1,3-oxazol-2-yl)phenyl]acetic acid as colorless amorphous form (81 mg, yield 70%).

NMR (DMSO-$d_6$) δ: 1.29 (3H, t, J=7.5 Hz), 2.30 (3H, s), 2.41 (3H, s), 2.97 (2H, q, J=7.6 Hz), 3.33 (2H, s), 3.76 (3H, s), 4.96 (2H, s), 5.27 (2H, s), 7.12 (5H, m), 7.33 (7H, m), 7.81 (2H, d, J=7.9 Hz), 8.15 (1H, s).

| Formulation Example 1 (production of capsules) | |
|---|---|
| (1) Compound of Example 1 | 30 mg |
| (2) Microcrystalline cellulose | 10 mg |
| (3) Lactose | 19 mg |
| (4) Magnesium stearate | 1 mg |
| total | 60 mg |

(1), (2) and (3) and (4) are admixed and filled in a gelatin capsule.

| Formulation Example 2 (production of tablets) | | |
|---|---|---|
| (1) Compound of Example 1 | | 30 g |
| (2) Lactose | | 50 g |
| (3) Corn starch | | 15 g |
| (4) Carboxymethylcellulose calcium | | 44 g |
| (5) Magnesium stearate | | 1 g |
| 1000 tablets | total | 140 g |

The entire amount of (1), (2) and (3) and 30 g of (4) are admixed with water. After drying in vacuo, the mixture is granulated. Thereto are added 14 g of (4) and 1 g of (5) and the mixture is tableted with a tableting machine. In this way, 1,000 tablets containing 30 mg of the compound of Example 1 per tablet are obtained.

INDUSTRIAL APPLICABILITY

The compound of the present invention is superior in an adipose tissue weight decreasing action, a hypoglycemic action, a hypolipidemic action, a hypoinsulinemic action, an insulin resistance improving action, an insulin sensitizing action, and a retinoid-related receptor function regulating action, and can be used as, for example, an agent for the prophylaxis or treatment of diabetes mellitus (e.g., type 1 diabetes mellitus, type 2 diabetes mellitus, gestational diabetes mellitus, etc.); an agent for the prophylaxis or treatment of hyperlipidemia (e.g., hypertriglyceridemia, hypercholesterolemia, hypo-high-density-lipoproteinemia, postprandial hyperlipemia etc.); an agent for improving insulin resistance; an insulin sensitizer; an agent for the prophylaxis or treatment of impaired glucose tolerance (IGT); an agent for the prophylaxis or treatment of obesity; an agent for the prophylaxis or treatment of hypertension; and an agent for preventing progress from impaired glucose tolerance to diabetes mellitus.

The invention claimed is:
1. A compound represented by the formula:

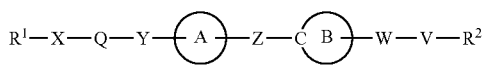 (I)

wherein
$R^1$ is an optionally substituted oxazolyl group;
X, Y and V
are the same or different and each is a bond, an oxygen atom, a sulfur atom, —CO—, —CS—, —SO—, —SO$_2$—, —CR$^3$(OR$^4$)—, —NR$^5$—, —CONR$^6$—, —NR$^6$CO—, —CSNR$^6$—, —NR$^6$CS— or —CONR$^6$NR$^7$— ($R^3$ is a hydrogen atom or an optionally substituted hydrocarbon group, $R^4$ is a hydrogen atom or a hydroxyl-protecting group, $R^5$ is a hydrogen atom, an optionally substituted hydrocarbon group or an amino-protecting group, and $R^6$ and $R^7$ are the same or different and each is a hydrogen atom or an optionally substituted hydrocarbon group);
Q is a divalent hydrocarbon group having 1 to 20 carbon atoms;
ring A is a benzene ring optionally further having 1 to 3 substituents;
Z is —(CH$_2$)$_n$-Z$^1$- or -Z$^1$-(CH$_2$)$_n$— (n is an integer of 1 to 8 and $Z^1$ is an oxygen atom);
ring B is a pyrazole ring optionally further having 1 to 3 substituents;
W is a bond or a divalent hydrocarbon group having 1 to 20 carbon atoms; and
$R^2$ is —PO(OR$^9$)(OR$^{10}$) ($R^9$ and $R^{10}$ are the same or different and each is a hydrogen atom or an optionally substituted hydrocarbon group, or $R^9$ and $R^{10}$ are optionally bonded to form an optionally substituted ring) or an optionally substituted thiazolyl group,
provided that
1) ring A and ring B do not have a substituent represented by the formula: -Wa-(C=O)—R$^a$ [Wa is a saturated divalent hydrocarbon group having 1 to 20 carbon atoms and $R^a$ is —OR$^b$ ($R^b$ is a hydrogen atom or an optionally substituted hydrocarbon group) or —NR$^c$R$^d$ ($R^c$ and $R^d$ are the same or different and each is a hydrogen atom, an optionally substituted hydrocarbon group, an optionally substituted heterocyclic group or an acyl group, and $R^c$ and $R^d$ are optionally bonded to form an optionally substituted ring together with the adjacent nitrogen atom)],
2) ring B does not have, on a ring-constituting N atom, a substituent represented by the formula:

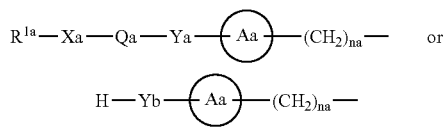

wherein
$R^{1a}$ is an optionally substituted hydrocarbon group or an optionally substituted heterocyclic group;
Xa and Ya
are the same or different and each is a bond, an oxygen atom, a sulfur atom, —CO—, —CS—, —SO—, —SO$_2$—, —CR$^{3a}$(OR$^{4a}$)—, —NR$^{5a}$—, —CONR$^{6a}$— or —NR$^{6a}$CO— ($R^{3a}$ is a hydrogen atom or an optionally substituted hydrocarbon group, $R^{4a}$ is a hydrogen atom or a hydroxyl-protecting group, $R^{5a}$ is a hydrogen atom, an optionally substituted hydrocarbon group or an amino-protecting group, $R^{6a}$ is a hydrogen atom or an optionally substituted hydrocarbon group);
Qa is a divalent hydrocarbon group having 1 to 20 carbon atoms;
ring Aa is an aromatic ring optionally further having 1 to 3 substituents;
na is an integer of 1 to 8; and
Yb is an oxygen atom, a sulfur atom or —NR$^{6a}$— ($R^{6a}$ is as defined above),
3) —X-Q-Y— is not —(CH$_2$)na- (na is an integer of 1 to 8),
4) when $R^1$ has a substituent represented by the formula: -Wa-(C=O)—R$^a$ (Wa and $R^a$ are as defined above), W is a divalent hydrocarbon group having 1 to 20 carbon atoms and V is a bond,
or a salt thereof.
2. The compound of claim 1, wherein X is a bond.
3. The compound of claim 1, wherein Q is a $C_{1-6}$ alkylene or a $C_{2-6}$ alkenylene.
4. The compound of claim 1, wherein Y is an oxygen atom.
5. The compound of claim 1, wherein the substituent that ring B may further have is a hydrocarbon group.
6. The compound of claim 5, wherein the hydrocarbon group is a $C_{1-10}$ alkyl group, a $C_{7-13}$ aralkyl group or a $C_{6-14}$ aryl group.
7. The compound of claim 1, wherein V is a bond.
8. The compound of claim 1, wherein W is a $C_{1-6}$ alkylene or a $C_{2-6}$ alkenylene; and V is a bond.
9. A pharmaceutical composition comprising the compound represented by the formula:

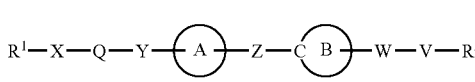 (I)

wherein
$R^1$ is an optionally substituted oxazolyl group;
X, Y and V
are the same or different and each is a bond, an oxygen atom, a sulfur atom, —CO—, —OS—, —SO—, —SO$_2$—, —CR$^3$(OR$^4$)—, —NR$^5$—, —CONR$^6$—, —NR$^6$CO—, —CSNR$^6$—, —NR$^6$CS— or —CONR$^6$NR$^7$— ($R^3$ is a hydrogen atom or an optionally substituted hydrocarbon group, $R^4$ is a hydrogen atom or a hydroxyl-protecting group, $R^5$ is a hydrogen atom, an optionally substituted hydrocarbon group or an amino-protecting group, and $R^6$ and $R^7$ are the same or different and each is a hydrogen atom or an optionally substituted hydrocarbon group);
Q is a divalent hydrocarbon group having 1 to 20 carbon atoms;
ring A is a benzene ring optionally further having 1 to 3 substituents;
Z is —(CH$_2$)$_n$-Z$^1$- or -Z$^1$-(CH$_2$)$_n$— (n is an integer of 1 to 8 and $Z^1$ is an oxygen atom);
ring B is a pyrazole ring optionally further having 1 to 3 substituents;

W is a bond or a divalent hydrocarbon group having 1 to 20 carbon atoms; and $R^2$ is —PO(OR$^9$)(OR$^{10}$) ($R^9$ and $R^{10}$ are the same or different and each is a hydrogen atom or an optionally substituted hydrocarbon group, or $R^9$ and $R^{10}$ are optionally bonded to form an optionally substituted ring) or an optionally substituted thiazolyl group, provided that 1) ring A and ring B do not have a substituent represented by the formula: -Wa-(C=O)—$R^a$ [Wa is a saturated divalent hydrocarbon group having 1 to 20 carbon atoms and $R^a$ is —OR$^b$ ($R^b$ is a hydrogen atom or an optionally substituted hydrocarbon group) or —NR$^c$R$^d$ ($R^c$ and $R^d$ are the same or different and each is a hydrogen atom, an optionally substituted hydrocarbon group, an optionally substituted heterocyctic group or an acyl group, and $R^c$ and $R^d$ are optionally bonded to form an optionally substituted ring together with the adjacent nitrogen atom)], 2) ring B does not have, on a ring-constituting N atom, a substituent represented by the formula:

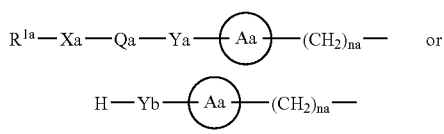

wherein $R^{1a}$ is an optionally substituted hydrocarbon group or an optionally substituted heterocyclic group;

Xa and Ya
are the same or different and each is a bond, an oxygen atom, a sulfur atom, —CO—, —CS—, —SO—, —SO$_2$—, —CR$^{3a}$(OR$^{4a}$)—, —NR$^{5a}$—, —CONR$^{6a}$ or —NR$^{6a}$CO—($R^{3a}$ is a hydrogen atom or an optionally substituted hydrocarbon group, $R^{4a}$ is a hydrogen atom or a hydroxyl-protecting group, $R^{5a}$ is a hydrogen atom, an optionally substituted hydrocarbon group or an amino-protecting group, $R^{6a}$ is a hydrogen atom or an optionally substituted hydrocarbon group);

Qa is a divalent hydrocarbon group having 1 to 20 carbon atoms;

ring Aa is an aromatic ring optionally further having 1 to 3 substituents;

na is an integer of 1 to 8; and

Yb is an oxygen atom, a sulfur atom or —NR$^{6a}$— ($R^{6a}$ is as defined above), 3) —X-Q-Y— is not —(CH$_2$)na- (na is an integer of 1 to 8), 4) when $R^1$ has a substituent represented by the formula: -Wa-(C=O)—$R^a$ (Wa and $R^a$ are as defined above), W is a divalent hydrocarbon group having 1 to 20 carbon atoms and V is a bond, or a salt thereof or a prodrug thereof.

10. The pharmaceutical composition of claim 9, which is an agent for the treatment of diabetes mellitus.

11. The pharmaceutical composition of claim 9, which is an agent for the treatment of obesity.

12. An agent for improving insulin resistance, which comprises the compound represented by the formula:

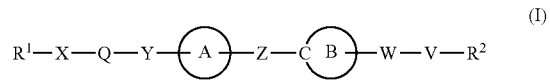

wherein $R^1$ is an optionally substituted oxazolyl group;

X, Y and V
are the same or different and each is a bond, an oxygen atom, a sulfur atom, —CO—, —CS—, —SO—, —SO$_2$—, —CR$^3$(OR$^4$)—, —NR$^5$—, —CONR$^6$—, —NR$^6$CO—, —CSNR$^6$—, —NR$^6$CS— or —CONR$^6$NR$^7$— ($R^3$ is a hydrogen atom or an optionally substituted hydrocarbon group, $R^4$ is a hydrogen atom or a hydroxyl-protecting group, $R^5$ is a hydrogen atom, an optionally substituted hydrocarbon group or an amino-protecting group. and $R^6$ and $R^7$ are the same or different and each is a hydrogen atom or an optionally substituted hydrocarbon group);

Q is a divalent hydrocarbon group having 1 to 20 carbon atoms;

ring A is a benzene ring optionally further having 1 to 3 substituents;

Z is —(CH$_2$)$_n$-Z$^1$- or -Z$^1$-(CH$^2$)$_n$- (n is an integer of 1 to 8 and $Z^1$ is an oxygen atom);

ring B is a pyrazole ring opbonally further having 1 to 3 substituents;

W is a bond or a divalent hydrocarbon group having 1 to 20 carbon atoms; and $R^2$ is —PO(OR$^9$)(OR$^{10}$) ($R^9$ and $R^{10}$ are the same or different and each is a hydrogen atom or an optionally substituted hydrocarbon group, or $R^9$ and $R^{10}$ are optionally bonded to form an optionally substituted ring) or an optionally substituted thiazolyl group, provided that 1) ring A and ring B do not have a substituent represented by the formula: -Wa-(C=O)—$R^a$ [Wa is a saturated divalent hydrocarbon group having 1 to 20 carbon atoms and $R^a$ is —OR$^b$ ($R^b$ is a hydrogen atom or an optionally substitued hydrocarbon group) or —NR$^c$R$^d$ ($R^c$ and $R^d$ are the same or different and each is a hydrogen atom, an optionally substituted hydrocarbon group, an optionally substituted heterocyclic group or an acyl group, and $R^c$ and $R^d$ are optionally bonded to form an optionally substituted ring together with the adjacent nitrogen atom)], 2) ring B does not have, on a ring-constituting N atom, a substituent represented by the formula:

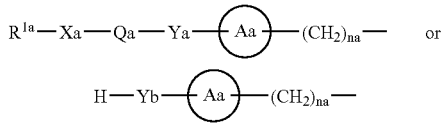

wherein $R^{1a}$ is an optionally substituted hydrocarbon group or an optionally substituted heterocyclic group;

Xa and Ya
are the same or different and each is a bond, an oxygen atom, a sulfur atom, —CO—, —CS—, —SO—, —SO$_2$—, —CR$^{3a}$(OR$^{4a}$)—, —NR$^{5a}$—, —CONR$^{6a}$— or —NR$^{6a}$CO— ($R^{3a}$ is a hydrogen atom or an optionally substituted hydrocarbon group, $R^{4a}$ is a hydrogen atom or a hydroxyl-protecting group, $R^{5a}$ is a hydrogen atom, an optionally substituted hydrocarbon group or an amino-protecting group, $R^{6a}$ is a hydrogen atom or an optionally substituted hydrocarbon group);

Qa is a divalent hydrocarbon group having 1 to 20 carbon atoms;

ring Aa is an aromatic ring optionally further having 1 to 3 substituents;

na is an integer of 1 to 8; and

Yb is an oxygen atom, a sulfur atom or —$NR^{6a}$— ($R^{6a}$ is as defined above), 3) —X-Q-Y— is not —$(CH_2)$na- (na is an integer of 1 to 8), 4) when $R^1$ has a substituent represented by the formula: -Wa-(C=O)—$R^a$ (Wa and $R^a$ are as defined above), W is a divalent hydrocarbon group having 1 to 20 carbon atoms and V is a bond, or a salt thereof or a prodrug thereof.

* * * * *

SEQUENCE LISTING

```
<160> NUMBER OF SEQ ID NOS: 8

<210> SEQ ID NO 1
<211> LENGTH: 33
<212> TYPE: DNA
<213> ORGANISM: Artificial Sequence
<220> FEATURE:
<223> OTHER INFORMATION: Primer XRA-U

<400> SEQUENCE: 1
ttagaattcg acatggacac caaacatttc ctg                           33

<210> SEQ ID NO 2
<211> LENGTH: 33
<212> TYPE: DNA
<213> ORGANISM: Artificial Sequence
<220> FEATURE:
<223> OTHER INFORMATION: Primer XRA-L

<400> SEQUENCE: 2
cccctcgagc taagtcattt ggtgcggcgc ctc                           33
```

```
<210> SEQ ID NO 3
<211> LENGTH: 36
<212> TYPE: DNA
<213> ORGANISM: Artificial Sequence
<220> FEATURE:
<223> OTHER INFORMATION: DNA fragment containing PPRE (PPRE-U)

<400> SEQUENCE: 3
tcgacagggg accaggacaa aggtcacgtt cgggag                             36

<210> SEQ ID NO 4
<211> LENGTH: 36
<212> TYPE: DNA
<213> ORGANISM: Artificial Sequence
<220> FEATURE:
<223> OTHER INFORMATION: DNA fragment containing PPRE (PPRE-L)

<400> SEQUENCE: 4
tcgactcccg aacgtgacct ttgtcctggt cccctg                             36

<210> SEQ ID NO 5
<211> LENGTH: 28
<212> TYPE: DNA
<213> ORGANISM: Artificial Sequence
<220> FEATURE:
<223> OTHER INFORMATION: Primer TK-U

<400> SEQUENCE: 5
cccagatctc cccagcgtct tgtcattg                                      28

<210> SEQ ID NO 6
<211> LENGTH: 28
<212> TYPE: DNA
<213> ORGANISM: Artificial Sequence
<220> FEATURE:
<223> OTHER INFORMATION: Primer TK-L

<400> SEQUENCE: 6
tcaccatggt caagctttta agcgggtc                                      28

<210> SEQ ID NO 7
<211> LENGTH: 33
<212> TYPE: DNA
<213> ORGANISM: Artificial Sequence
<220> FEATURE:
<223> OTHER INFORMATION: Primer PAG-U

<400> SEQUENCE: 7
gtgggtaccg aaatgaccat ggttgacaca gag                                33

<210> SEQ ID NO 8
<211> LENGTH: 33
<212> TYPE: DNA
<213> ORGANISM: Artificial Sequence
<220> FEATURE:
<223> OTHER INFORMATION: Primer PAG-L

<400> SEQUENCE: 8
ggggtcgacc aggactctct gctagtacaa gtc                                33
```